United States Patent
Lo et al.

(10) Patent No.: US 9,622,477 B2
(45) Date of Patent: *Apr. 18, 2017

(54) PESTICIDAL COMPOSITIONS AND PROCESSES RELATED THERETO

(71) Applicant: Dow AgroSciences LLC, Indianapolis, IN (US)

(72) Inventors: William C. Lo, Fishers, IN (US); James E. Hunter, Indianapolis, IN (US); Gerald B. Watson, Zionsville, IN (US); Akshay Patny, Waltham, MA (US); Pravin S. Iyer, Secunderabad (IN); Joshodeep Boruwa, Hyderabad (IN)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/880,790

(22) Filed: Oct. 12, 2015

(65) Prior Publication Data

US 2016/0029636 A1    Feb. 4, 2016

Related U.S. Application Data

(63) Continuation of application No. 14/133,094, filed on Dec. 18, 2013, now Pat. No. 9,226,501.
(Continued)

(51) Int. Cl.
*A01N 43/84* (2006.01)
*A01N 43/50* (2006.01)
(Continued)

(52) U.S. Cl.
CPC ............ *A01N 47/32* (2013.01); *A01N 25/08* (2013.01); *A01N 33/04* (2013.01); *A01N 37/10* (2013.01); *A01N 37/18* (2013.01); *A01N 37/28* (2013.01); *A01N 37/32* (2013.01); *A01N 37/34* (2013.01); *A01N 37/46* (2013.01); *A01N 41/10* (2013.01); *A01N 43/08* (2013.01); *A01N 43/16* (2013.01); *A01N 43/20* (2013.01); *A01N 43/36* (2013.01); *A01N 43/38* (2013.01); *A01N 43/40* (2013.01); *A01N 43/50* (2013.01); *A01N 43/54* (2013.01); *A01N 43/58* (2013.01); *A01N 43/60* (2013.01); *A01N 43/653* (2013.01); *A01N 43/78* (2013.01); *A01N 43/82* (2013.01); *A01N 43/84* (2013.01); *A01N 47/18* (2013.01); *A01N 47/28* (2013.01); *A01N 47/36* (2013.01); *A01N 47/38* (2013.01); *A01N 53/00* (2013.01); *C07C 63/70* (2013.01); *C07C 211/27* (2013.01); *C07C 211/29* (2013.01); *C07C 211/42* (2013.01); *C07C 233/13* (2013.01); *C07C 233/14* (2013.01); *C07C 233/56* (2013.01); *C07C 233/59* (2013.01); *C07C 233/65* (2013.01); *C07C 233/66* (2013.01); *C07C 233/76* (2013.01); *C07C 233/83* (2013.01); *C07C 237/22* (2013.01); *C07C 243/36* (2013.01); *C07C 243/38* (2013.01); *C07C 255/57* (2013.01); *C07C 259/06* (2013.01); *C07C 259/08* (2013.01); *C07C 271/14* (2013.01); *C07C 275/24* (2013.01); *C07C 317/44* (2013.01); *C07C 323/60* (2013.01); *C07C 323/62* (2013.01); *C07C 327/42* (2013.01); *C07C 327/46* (2013.01); *C07C 327/48* (2013.01); *C07C 335/12* (2013.01); *C07C 335/14* (2013.01); *C07D 207/16* (2013.01); *C07D 207/27* (2013.01); *C07D 209/50* (2013.01); *C07D 211/58* (2013.01); *C07D 213/61* (2013.01); *C07D 233/64* (2013.01); *C07D 237/32* (2013.01); *C07D 239/26* (2013.01);
(Continued)

(58) Field of Classification Search
None
See application file for complete search history.

(56) References Cited

U.S. PATENT DOCUMENTS 4,833,158 A    5/1989  Twydell et al.
4,873,329 A   10/1989  Hughes et al.
(Continued)

FOREIGN PATENT DOCUMENTS

EP    2723729 A1    4/2014
EP    2012043418    2/2015
(Continued)

OTHER PUBLICATIONS

Taylor et al. (editor, "Pesticide Residues in Coastal Tropical Ecosystems: Distribution, Fate, and Effects" p. 204, 2003).*
(Continued)

*Primary Examiner* — Mina Haghighatian
*Assistant Examiner* — Erin Hirt
(74) *Attorney, Agent, or Firm* — Carl D. Corvin

(57) ABSTRACT

This document discloses molecules having the following formula ("Formula One"):

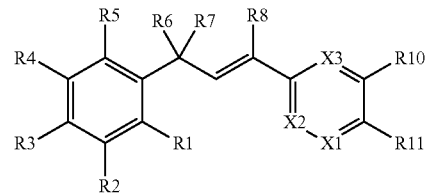

Formula One and processes associated therewith.

35 Claims, No Drawings

Related U.S. Application Data

(60) Provisional application No. 61/739,025, filed on Dec. 19, 2012.

(51) Int. Cl.

| | |
|---|---|
| C07D 331/04 | (2006.01) |
| C07D 241/12 | (2006.01) |
| C07D 209/50 | (2006.01) |
| C07D 277/64 | (2006.01) |
| A01N 43/60 | (2006.01) |
| C07D 249/08 | (2006.01) |
| A01N 43/08 | (2006.01) |
| C07D 211/58 | (2006.01) |
| A01N 43/653 | (2006.01) |
| A01N 43/38 | (2006.01) |
| C07D 233/64 | (2006.01) |
| C07D 309/14 | (2006.01) |
| C07D 277/30 | (2006.01) |
| A01N 43/58 | (2006.01) |
| A01N 43/36 | (2006.01) |
| A01N 43/20 | (2006.01) |
| A01N 25/08 | (2006.01) |
| C07D 295/192 | (2006.01) |
| A01N 43/16 | (2006.01) |
| A01N 43/54 | (2006.01) |
| C07D 207/27 | (2006.01) |
| A01N 37/18 | (2006.01) |
| C07C 211/29 | (2006.01) |
| C07D 213/61 | (2006.01) |
| C07D 271/10 | (2006.01) |
| C07C 63/70 | (2006.01) |
| A01N 33/04 | (2006.01) |
| C07D 239/26 | (2006.01) |
| C07C 233/59 | (2006.01) |
| C07D 237/32 | (2006.01) |
| A01N 43/40 | (2006.01) |
| C07D 307/16 | (2006.01) |
| C07C 255/57 | (2006.01) |
| A01N 37/34 | (2006.01) |
| A01N 43/78 | (2006.01) |
| A01N 43/82 | (2006.01) |
| A01N 47/32 | (2006.01) |
| A01N 37/10 | (2006.01) |
| C07C 233/65 | (2006.01) |
| C07C 233/66 | (2006.01) |
| C07D 207/16 | (2006.01) |
| C07D 401/10 | (2006.01) |
| A01N 53/00 | (2006.01) |
| C07C 259/06 | (2006.01) |
| C07C 259/08 | (2006.01) |
| C07C 271/14 | (2006.01) |
| C07C 275/24 | (2006.01) |
| C07C 211/27 | (2006.01) |
| C07C 211/42 | (2006.01) |
| C07C 233/13 | (2006.01) |
| C07C 233/14 | (2006.01) |
| C07C 233/56 | (2006.01) |
| C07C 233/76 | (2006.01) |
| C07C 233/83 | (2006.01) |
| C07C 237/22 | (2006.01) |
| C07C 243/36 | (2006.01) |
| C07C 243/38 | (2006.01) |
| C07C 317/44 | (2006.01) |
| C07C 323/60 | (2006.01) |
| C07C 323/62 | (2006.01) |
| C07C 327/42 | (2006.01) |
| C07C 327/46 | (2006.01) |
| C07C 327/48 | (2006.01) |
| C07C 335/12 | (2006.01) |
| C07C 335/14 | (2006.01) |
| A01N 37/28 | (2006.01) |
| A01N 37/32 | (2006.01) |
| A01N 37/46 | (2006.01) |
| A01N 41/10 | (2006.01) |
| A01N 47/18 | (2006.01) |
| A01N 47/28 | (2006.01) |
| A01N 47/36 | (2006.01) |
| A01N 47/38 | (2006.01) |

(52) U.S. Cl.
CPC ......... *C07D 241/12* (2013.01); *C07D 249/08* (2013.01); *C07D 271/10* (2013.01); *C07D 277/30* (2013.01); *C07D 277/64* (2013.01); *C07D 295/192* (2013.01); *C07D 307/16* (2013.01); *C07D 309/14* (2013.01); *C07D 331/04* (2013.01); *C07D 401/10* (2013.01); *C07C 2101/02* (2013.01); *C07C 2102/08* (2013.01); *C07C 2102/10* (2013.01)

(56) References Cited

U.S. PATENT DOCUMENTS

| | | | |
|---|---|---|---|
| 6,013,836 | A | 1/2000 | Hsu et al. |
| 7,375,232 | B2 | 5/2008 | Clark et al. |
| 7,951,828 | B1 | 5/2011 | Mita et al. |
| 2002/0068838 | A1 | 6/2002 | Demassey et al. |
| 2007/0027034 | A1 | 2/2007 | Tank et al. |
| 2007/0207093 | A1 | 9/2007 | Bryant et al. |
| 2008/0063678 | A1 | 3/2008 | von Deyn et al. |
| 2010/0093707 | A1 | 4/2010 | Nakamura et al. |
| 2010/0254959 | A1 | 10/2010 | Lahm et al. |
| 2010/0292253 | A1 | 11/2010 | Trullinger et al. |
| 2011/0144334 | A1 | 6/2011 | Mita et al. |
| 2011/0160054 | A1 | 6/2011 | Breuningger et al. |
| 2012/0053146 | A1 | 3/2012 | Parker et al. |
| 2012/0329649 | A1 | 12/2012 | Hunter et al. |
| 2014/0171308 | A1 | 6/2014 | Lo et al. |
| 2014/0171309 | A1 | 6/2014 | Lo et al. |
| 2014/0171310 | A1 | 6/2014 | Lo et al. |
| 2014/0171311 | A1 | 6/2014 | Lo et al. |
| 2014/0171312 | A1 | 6/2014 | Lo et al. |
| 2014/0171313 | A1 | 6/2014 | Lo et al. |
| 2014/0171314 | A1 | 6/2014 | Lo et al. |
| 2014/0171315 | A1 | 6/2014 | Lo et al. |
| 2014/0206537 | A1 | 7/2014 | Hunter et al. |

FOREIGN PATENT DOCUMENTS

| | | |
|---|---|---|
| WO | 8607590 A1 | 12/1986 |
| WO | 2010078300 A1 | 7/2010 |
| WO | 2012004326 A1 | 1/2012 |
| WO | 2012148772 A1 | 11/2012 |
| WO | 2012043418 | 12/2012 |
| WO | 2012177813 A1 | 12/2012 |
| WO | 2014100163 | 6/2014 |
| WO | 2014100163 A1 | 6/2014 |
| WO | 2014100166 | 6/2014 |
| WO | 2014100166 A1 | 6/2014 |
| WO | 2014100170 | 6/2014 |
| WO | 2014100170 A1 | 6/2014 |
| WO | 2014100190 | 6/2014 |
| WO | 2014100190 A1 | 6/2014 |
| WO | 2014100206 | 6/2014 |
| WO | 2014100206 A1 | 6/2014 |
| WO | 2014120355 | 8/2014 |
| WO | 2014120355 A1 | 8/2014 |

(56) References Cited

OTHER PUBLICATIONS

Cornell Environmental Backgrounder: Pesticides and Food Safety (http://psep.cce.cornell.edu/issues/foodsafety-issues.aspx, cached Jun. 29, 2010).
Peter Ertl Cheminformatics Analysis of Organic Substituents: Identification of the Most Common Substituents, Calculation of Substituent Properties, and Automatic Identification of Drug-like Bioisosteric Groups. Journal of Chemical Information and Computer Sciences 2003, 43(2), 374-380.
S. Kagabu et al. Insecticidal and Neuroblocking Activities of Thiamethoxam-Type Compounds in the American Cockroach (*Periplaneta americana* L.), Journal of Pesticide Science, 2005.
Andreas Unsinn et al. Steroselective synthesis of tetrasubstituted alkenes via a sequential carbocupration and a new sulfur-lithium exchange. Beilstein J. Org. Chem. vol. 8, Dec. 18 ,2012 (Dec. 18, 2012), pp. 2202-2206, XP55166411, DOI: 10.3762/bjoc.8.248 [retrieved on Mar. 25, 2012]. Retrieved from the Internet. <URL: http://www. beilstein-journals.org/bjoc/content/pdf/1860-5397-8-248.pdf>.
Y. Shiga et al. Synthesis and Acaricidal Activity of N-(1,2,4-Thiadiazol-2-yl)carboxamides. Journal of Pesticide Science, 2003.
Konno et al., "A first high enantiocontrol of an asymmetric tertiary carbon center attached with a fluoroalkyl group vis Rh(I)-catalyzed conjugate addition reaction", Tetrahedron Letters, Pergamon, GB, vol. 49, No. 13, Feb. 1, 2008, pp. 2106-2110, XP022502910, ISSN:0040-4039, DOI: 10.1016/J. Tetlet.2008.01.12, *abstract* p. 2109; examples Scheme 3, 4*.

\* cited by examiner

PESTICIDAL COMPOSITIONS AND PROCESSES RELATED THERETO

CROSS REFERENCE TO RELATED APPLICATIONS

This application is a continuation of, and claims the benefit of, U.S. patent application Ser. No. 14/133,094, which was filed on Dec. 18, 2013, the entire disclosure of which is hereby expressly incorporated by reference, and which claims the benefit of U.S. provisional patent application Ser. No. 61/739,025 filed Dec. 19, 2012, the disclosure of which is expressly incorporated herein by reference.

FIELD OF THE DISCLOSURE

The invention disclosed in this document is related to the field of processes to produce molecules that are useful as pesticides (e.g., acaricides, insecticides, molluscicides, and nematicides), such molecules, and processes of using such molecules to control pests.

BACKGROUND OF THE DISCLOSURE

Pests cause millions of human deaths around the world each year. Furthermore, there are more than ten thousand species of pests that cause losses in agriculture. The world-wide agricultural losses amount to billions of U.S. dollars each year.

Termites cause damage to all kinds of private and public structures. The world-wide termite damage losses amount to billions of U.S. dollars each year.

Stored food pests eat and adulterate stored food. The world-wide stored food losses amount to billions of U.S. dollars each year, but more importantly, deprive people of needed food.

There is an acute need for new pesticides. Certain pests are developing resistance to pesticides in current use. Hundreds of pest species are resistant to one or more pesticides. The development of resistance to some of the older pesticides, such as DDT, the carbamates, and the organophosphates, is well known. But resistance has even developed to some of the newer pesticides, for example, imidacloprid.

Therefore, for many reasons, including the above reasons, a need exists for new pesticides.

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, $(C_3)$alkyl which represents n-propyl and isopropyl), $(C_4)$alkyl which represents n-butyl, sec-butyl, isobutyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"$(C_x$-$C_y)$" where the subscripts "x" and "y" are integers such as 1, 2, or 3, means the range of carbon atoms for a substituent—for example, $(C_1$-$C_4)$alkyl means methyl, ethyl, n-propyl, isopropyl, n-butyl, sec-butyl, isobutyl, and tert-butyl, each individually.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. In the case of sulfur, that atom can be in other oxidation states such as a sulfoxide and sulfone. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, imidazolyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, oxetanyl, tetrahydrofuranyl, tetrahydrothienyl and tetrahydropyranyl. Examples of partially unsaturated heterocyclyls include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

Additional examples include the following

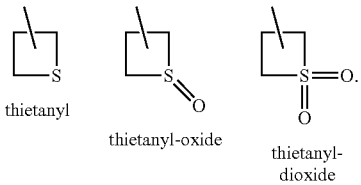

DETAILED DESCRIPTION OF THE DISCLOSURE

This document discloses molecules having the following formula ("Formula One"):

Formula One

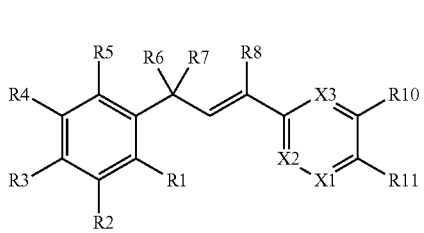

wherein:

(a) R1 is selected from
(1) H, F, Cl, Br, I, CN, $NO_2$, $(C_1-C_8)$alkyl, halo$(C_1-C_8)$alkyl, $(C_1-C_8)$alkoxy, halo$(C_1-C_8)$alkoxy, $S(C_1-C_8)$alkyl, S(halo$(C_1-C_8)$alkyl), $S(O)(C_1-C_8)$alkyl, $S(O)$(halo$(C_1-C_8)$alkyl), $S(O)_2(C_1-C_8)$alkyl, $S(O)_2$(halo$(C_1-C_8)$alkyl), N(R14)(R15),
(2) substituted $(C_1-C_8)$alkyl, wherein said substituted $(C_1-C_8)$alkyl has one or more substituents selected from CN and $NO_2$,
(3) substituted halo$(C_1-C_8)$alkyl, wherein said substituted halo$(C_1-C_8)$alkyl, has one or more substituents selected from CN and $NO_2$,
(4) substituted $(C_1-C_8)$alkoxy, wherein said substituted $(C_1-C_8)$alkoxy has one or more substituents selected from CN and $NO_2$, and
(5) substituted halo$(C_1-C_8)$alkoxy, wherein said substituted halo$(C_1-C_8)$alkoxy has one or more substituents selected from CN and $NO_2$;

(b) R2 is selected from
(1) H, F, Cl, Br, I, CN, $NO_2$, $(C_1-C_8)$alkyl, halo$(C_1-C_8)$alkyl, $(C_1-C_8)$alkoxy, halo$(C_1-C_8)$alkoxy, $S(C_1-C_8)$alkyl, S(halo$(C_1-C_8)$alkyl), $S(O)(C_1-C_8)$alkyl, $S(O)$(halo$(C_1-C_8)$alkyl), $S(O)_2(C_1-C_8)$alkyl, $S(O)_2$(halo$(C_1-C_8)$alkyl), N(R14)(R15),
(2) substituted $(C_1-C_8)$alkyl, wherein said substituted $(C_1-C_8)$alkyl has one or more substituents selected from CN and $NO_2$,
(3) substituted halo$(C_1-C_8)$alkyl, wherein said substituted halo$(C_1-C_8)$alkyl, has one or more substituents selected from CN and $NO_2$,
(4) substituted $(C_1-C_8)$alkoxy, wherein said substituted $(C_1-C_8)$alkoxy has one or more substituents selected from CN and $NO_2$, and
(5) substituted halo$(C_1-C_8)$alkoxy, wherein said substituted halo$(C_1-C_8)$alkoxy has one or more substituents selected from CN and $NO_2$;

(c) R3 is selected from
(1) H, F, Cl, Br, I, CN, $NO_2$, $(C_1-C_8)$alkyl, halo$(C_1-C_8)$alkyl, $(C_1-C_8)$alkoxy, halo$(C_1-C_8)$alkoxy, $S(C_1-C_8)$alkyl, S(halo$(C_1-C_8)$alkyl), $S(O)(C_1-C_8)$alkyl, $S(O)$(halo$(C_1-C_8)$alkyl), $S(O)_2(C_1-C_8)$alkyl, $S(O)_2$(halo$(C_1-C_8)$alkyl), N(R14)(R15),
(2) substituted $(C_1-C_8)$alkyl, wherein said substituted $(C_1-C_8)$alkyl has one or more substituents selected from CN and $NO_2$,
(3) substituted halo$(C_1-C_8)$alkyl, wherein said substituted halo$(C_1-C_8)$alkyl, has one or more substituents selected from CN and $NO_2$,
(4) substituted $(C_1-C_8)$alkoxy, wherein said substituted $(C_1-C_8)$alkoxy has one or more substituents selected from CN and $NO_2$, and
(5) substituted halo$(C_1-C_8)$alkoxy, wherein said substituted halo$(C_1-C_8)$alkoxy has one or more substituents selected from CN and $NO_2$;

(d) R4 is selected from
(1) H, F, Cl, Br, I, CN, $NO_2$, $(C_1-C_8)$alkyl, halo$(C_1-C_8)$alkyl, $(C_1-C_8)$alkoxy, halo$(C_1-C_8)$alkoxy, $S(C_1-C_8)$alkyl, S(halo$(C_1-C_8)$alkyl), $S(O)(C_1-C_8)$alkyl, $S(O)$(halo$(C_1-C_8)$alkyl), $S(O)_2(C_1-C_8)$alkyl, $S(O)_2$(halo$(C_1-C_8)$alkyl), N(R14)(R15),
(2) substituted $(C_1-C_8)$alkyl, wherein said substituted $(C_1-C_8)$alkyl has one or more substituents selected from CN and $NO_2$,
(3) substituted halo$(C_1-C_8)$alkyl, wherein said substituted halo$(C_1-C_8)$alkyl, has one or more substituents selected from CN and $NO_2$,
(4) substituted $(C_1-C_8)$alkoxy, wherein said substituted $(C_1-C_8)$alkoxy has one or more substituents selected from CN and $NO_2$, and
(5) substituted halo$(C_1-C_8)$alkoxy, wherein said substituted halo$(C_1-C_8)$alkoxy has one or more substituents selected from CN and $NO_2$;

(e) R5 is selected from
(1) H, F, Cl, Br, I, CN, $NO_2$, $(C_1-C_8)$alkyl, halo$(C_1-C_8)$alkyl, $(C_1-C_8)$alkoxy, halo$(C_1-C_8)$alkoxy, $S(C_1-C_8)$alkyl, S(halo$(C_1-C_8)$alkyl), $S(O)(C_1-C_8)$alkyl, $S(O)$(halo$(C_1-C_8)$alkyl), $S(O)_2(C_1-C_8)$alkyl, $S(O)_2$(halo$(C_1-C_8)$alkyl), N(R14)(R15),
(2) substituted $(C_1-C_8)$alkyl, wherein said substituted $(C_1-C_8)$alkyl has one or more substituents selected from CN and $NO_2$,
(3) substituted halo$(C_1-C_8)$alkyl, wherein said substituted halo$(C_1-C_8)$alkyl, has one or more substituents selected from CN and $NO_2$,
(4) substituted $(C_1-C_8)$alkoxy, wherein said substituted $(C_1-C_8)$alkoxy has one or more substituents selected from CN and $NO_2$, and
(5) substituted halo$(C_1-C_8)$alkoxy, wherein said substituted halo$(C_1-C_8)$alkoxy has one or more substituents selected from CN and $NO_2$;

(f) R6 is a $(C_1-C_8)$haloalkyl;
(g) R7 is selected from H, F, Cl, Br, I, OH, $(C_1-C_8)$alkoxy, and halo$(C_1-C_8)$alkoxy;
(h) R8 is selected from H, $(C_1-C_8)$alkyl, halo$(C_1-C_8)$alkyl, OR14, and N(R14)(R15);
(i) R9 is selected from H, F, Cl, Br, I, $(C_1-C_8)$alkyl, halo$(C_1-C_8)$alkyl, $(C_1-C_8)$alkoxy, halo$(C_1-C_8)$alkoxy, OR14, and N(R14)(R15);

(j) R10 is selected from
  (1) H, F, Cl, Br, I, CN, NO$_2$, (C$_1$-C$_8$)alkyl, halo(C$_1$-C$_8$)alkyl, (C$_1$-C$_8$)alkoxy, halo(C$_1$-C$_8$)alkoxy, cyclo(C$_3$-C$_6$)alkyl, S(C$_1$-C$_8$)alkyl, S(halo(C$_1$-C$_8$)alkyl), S(O)(C$_1$-C$_8$)alkyl, S(O)(halo(C$_1$-C$_8$)alkyl), S(O)$_2$(C$_1$-C$_8$)alkyl, S(O)$_2$(halo(C$_1$-C$_8$)alkyl), NR14R15, C(=O)H, C(=O)N(R14)(R15), CN(R14)(R15)(=NOH), (C=O)O(C$_1$-C$_8$)alkyl, (C=O)OH, heterocyclyl, (C$_2$-C$_8$)alkenyl, halo(C$_2$-C$_8$)alkenyl, (C$_2$-C$_8$)alkynyl,
  (2) substituted (C$_1$-C$_8$)alkyl, wherein said substituted (C$_1$-C$_8$)alkyl has one or more substituents selected from OH, (C$_1$-C$_8$)alkoxy, S(C$_1$-C$_8$)alkyl, S(O)(C$_1$-C$_8$)alkyl, S(O)$_2$(C$_1$-C$_8$)alkyl, NR14R15, and
  (3) substituted halo(C$_1$-C$_8$)alkyl, wherein said substituted halo(C$_1$-C$_8$)alkyl, has one or more substituents selected from (C$_1$-C$_8$)alkoxy, S(C$_1$-C$_8$)alkyl, S(O)(C$_1$-C$_8$)alkyl, S(O)$_2$(C$_1$-C$_8$)alkyl, and N(R14)(R15);

(k) R11 is selected from C(=X5)N(R14)((C$_1$-C$_8$)alkylC(=X5)N(R14)(R15)) wherein each X5 is independently selected from 0, or S;

(l) R12 is selected from (v), H, F, Cl, Br, I, CN, (C$_1$-C$_8$)alkyl, halo(C$_1$-C$_8$)alkyl, (C$_1$-C$_8$)alkoxy, halo(C$_1$-C$_8$)alkoxy, and cyclo(C$_3$-C$_6$)alkyl;

(m) R13 is selected from (v), H, F, Cl, Br, I, CN, (C$_1$-C$_8$)alkyl, halo(C$_1$-C$_8$)alkyl, (C$_1$-C$_8$)alkoxy, and halo(C$_1$-C$_8$)alkoxy;

(n) each R14 is independently selected from H, (C$_1$-C$_8$)alkyl, (C$_2$-C$_8$)alkenyl, substituted (C$_1$-C$_8$)alkyl, halo(C$_1$-C$_8$)alkyl, substituted halo(C$_1$-C$_8$)alkyl), (C$_1$-C$_8$)alkoxy, cyclo(C$_3$-C$_6$)alkyl, aryl, substituted-aryl, (C$_1$-C$_8$)alkyl-aryl, (C$_1$-C$_8$)alkyl-(substituted-aryl), O—(C$_1$-C$_8$)alkyl-aryl, O—(C$_1$-C$_8$)alkyl-(substituted-aryl), heterocyclyl, substituted-heterocyclyl, (C$_1$-C$_8$)alkyl-heterocyclyl, (C$_1$-C$_8$)alkyl-(substituted-heterocyclyl), O—(C$_1$-C$_8$)alkyl-heterocyclyl, O—(C$_1$-C$_8$)alkyl-(substituted-heterocyclyl), N(R16)(R17), (C$_1$-C$_8$)alkyl-C(=O)N(R16)(R17), C(=O)(C$_1$-C$_8$)alkyl, C(=O)(halo(C$_1$-C$_8$)alkyl), C(=O)(C$_3$-C$_6$)cycloalkyl, (C$_1$-C$_8$)alkyl-C(=O)O(C$_1$-C$_8$)alkyl, C(=O)H
  wherein each said substituted (C$_1$-C$_8$)alkyl has one or more substituents selected from CN, and NO$_2$,
  wherein each said substituted halo(C$_1$-C$_8$)alkyl), has one or more substituents selected from CN, and NO$_2$,
  wherein each said substituted-aryl has one or more substituents selected from F, Cl, Br, I, CN, NO$_2$, (C$_1$-C$_8$)alkyl, halo(C$_1$-C$_8$)alkyl, (C$_1$-C$_8$)alkoxy, halo(C$_1$-C$_8$)alkoxy, S(C$_1$-C$_8$)alkyl, S(halo(C$_1$-C$_8$)alkyl), N((C$_1$-C$_8$)alkyl)$_2$ (wherein each (C$_1$-C$_8$)alkyl is independently selected), and oxo, and
  wherein each said substituted-heterocyclyl has one or more substituents selected from F, Cl, Br, I, CN, NO$_2$, (C$_1$-C$_8$)alkyl, halo(C$_1$-C$_8$)alkyl, (C$_1$-C$_8$)alkoxy, halo(C$_1$-C$_8$)alkoxy, (C$_3$-C$_6$)cycloalkyl S(C$_1$-C$_8$)alkyl, S(halo(C$_1$-C$_8$)alkyl), N((C$_1$-C$_8$)alkyl)$_2$ (wherein each (C$_1$-C$_8$)alkyl is independently selected), heterocyclyl, C(=O)(C$_1$-C$_8$)alkyl, C(=O)O(C$_1$-C$_8$)alkyl, and oxo, (wherein said alkyl, alkoxy, and heterocyclyl, may be further substituted with one or more of F, Cl, Br, I, CN, and NO$_2$);

(o) each R15 is independently selected from H, (C$_1$-C$_8$)alkyl, (C$_2$-C$_8$)alkenyl, substituted (C$_1$-C$_8$)alkyl, halo(C$_1$-C$_8$)alkyl, substituted halo(C$_1$-C$_8$)alkyl), (C$_1$-C$_8$)alkoxy, cyclo(C$_3$-C$_6$)alkyl, aryl, substituted-aryl, (C$_1$-C$_8$)alkyl-aryl, (C$_1$-C$_8$)alkyl-(substituted-aryl), O—(C$_1$-C$_8$)alkyl-aryl, O—(C$_1$-C$_8$)alkyl-(substituted-aryl), heterocyclyl, substituted-heterocyclyl, (C$_1$-C$_8$)alkyl-heterocyclyl, (C$_1$-C$_8$)alkyl-(substituted-heterocyclyl), O—(C$_1$-C$_8$)alkyl-heterocyclyl, O—(C$_1$-C$_8$)alkyl-(substituted-heterocyclyl), N(R16)(R17), (C$_1$-C$_8$)alkyl-C(=O)N(R16)(R17), C(=O)(C$_1$-C$_8$)alkyl, C(=O)(halo(C$_1$-C$_8$)alkyl), C(=O)(C$_3$-C$_6$)cycloalkyl, (C$_1$-C$_8$)alkyl-C(=O)O(C$_1$-C$_8$)alkyl, C(=O)H
  wherein each said substituted (C$_1$-C$_8$)alkyl has one or more substituents selected from CN, and NO$_2$,
  wherein each said substituted halo(C$_1$-C$_8$)alkyl), has one or more substituents selected from CN, and NO$_2$,
  wherein each said substituted-aryl has one or more substituents selected from F, Cl, Br, I, CN, NO$_2$, (C$_1$-C$_8$)alkyl, halo(C$_1$-C$_8$)alkyl, (C$_1$-C$_8$)alkoxy, halo(C$_1$-C$_8$)alkoxy, S(C$_1$-C$_8$)alkyl, S(halo(C$_1$-C$_8$)alkyl), N((C$_1$-C$_8$)alkyl)$_2$ (wherein each (C$_1$-C$_8$)alkyl is independently selected), and oxo, and
  wherein each said substituted-heterocyclyl has one or more substituents selected from F, Cl, Br, I, CN, NO$_2$, (C$_1$-C$_8$)alkyl, halo(C$_1$-C$_8$)alkyl, (C$_1$-C$_8$)alkoxy, halo(C$_1$-C$_8$)alkoxy, (C$_3$-C$_6$)cycloalkyl S(C$_1$-C$_8$)alkyl, S(halo(C$_1$-C$_8$)alkyl), N((C$_1$-C$_8$)alkyl)$_2$ (wherein each (C$_1$-C$_8$)alkyl is independently selected), heterocyclyl, C(=O)(C$_1$-C$_8$)alkyl, C(=O)O(C$_1$-C$_8$)alkyl, and oxo, (wherein said alkyl, alkoxy, and heterocyclyl, may be further substituted with one or more of F, Cl, Br, I, CN, and NO$_2$);

(p) each R16 is independently selected from H, (C$_1$-C$_8$)alkyl, substituted-(C$_1$-C$_8$)alkyl, halo(C$_1$-C$_8$)alkyl, substituted-halo(C$_1$-C$_8$)alkyl, cyclo(C$_3$-C$_6$)alkyl, aryl, substituted-aryl, (C$_1$-C$_8$)alkyl-aryl, (C$_1$-C$_8$)alkyl-(substituted-aryl), O—(C$_1$-C$_8$)alkyl-aryl, O—(C$_1$-C$_8$)alkyl-(substituted-aryl), heterocyclyl, substituted-heterocyclyl, (C$_1$-C$_8$)alkyl-heterocyclyl, (C$_1$-C$_8$)alkyl-(substituted-heterocyclyl), O—(C$_1$-C$_8$)alkyl-heterocyclyl, O—(C$_1$-C$_8$)alkyl-(substituted-heterocyclyl), O—(C$_1$-C$_8$)alkyl
  wherein each said substituted (C$_1$-C$_8$)alkyl has one or more substituents selected from CN, and NO$_2$,
  wherein each said substituted halo(C$_1$-C$_8$)alkyl), has one or more substituents selected from CN, and NO$_2$,
  wherein each said substituted-aryl has one or more substituents selected from F, Cl, Br, I, CN, NO$_2$, (C$_1$-C$_8$)alkyl, halo(C$_1$-C$_8$)alkyl, (C$_1$-C$_8$)alkoxy, halo(C$_1$-C$_8$)alkoxy, S(C$_1$-C$_8$)alkyl, S(halo(C$_1$-C$_8$)alkyl), N((C$_1$-C$_8$)alkyl)$_2$ (wherein each (C$_1$-C$_8$)alkyl is independently selected), and oxo, and
  wherein each said substituted-heterocyclyl has one or more substituents selected from F, Cl, Br, I, CN, NO$_2$, (C$_1$-C$_8$)alkyl, halo(C$_1$-C$_8$)alkyl, (C$_1$-C$_8$)alkoxy, halo(C$_1$-C$_8$)alkoxy, S(C$_1$-C$_8$)alkyl, S(halo(C$_1$-C$_8$)alkyl), N((C$_1$-C$_8$)alkyl)$_2$ (wherein each (C$_1$-C$_8$)alkyl is independently selected), and oxo;

(q) each R17 is independently selected from H, (C$_1$-C$_8$)alkyl, substituted-(C$_1$-C$_8$)alkyl, halo(C$_1$-C$_8$)alkyl, substituted-halo(C$_1$-C$_8$)alkyl, cyclo(C$_3$-C$_6$)alkyl, aryl, substituted-aryl, (C$_1$-C$_8$)alkyl-aryl, (C$_1$-C$_8$)alkyl-(substituted-aryl), O—(C$_1$-C$_8$)alkyl-aryl, O—(C$_1$-C$_8$)alkyl-(substituted-aryl), heterocyclyl, substituted-heterocyclyl, (C$_1$-C$_8$)alkyl-heterocyclyl, (C$_1$-C$_8$)alkyl-(substituted-heterocyclyl), O—(C$_1$-C$_8$)alkyl-heterocyclyl, O—(C$_1$-C$_8$)alkyl-(substituted-heterocyclyl), O—(C$_1$-C$_8$)alkyl
  wherein each said substituted (C$_1$-C$_8$)alkyl has one or more substituents selected from CN, and NO$_2$,
  wherein each said substituted halo(C$_1$-C$_8$)alkyl), has one or more substituents selected from CN, and NO$_2$,
  wherein each said substituted-aryl has one or more substituents selected from F, Cl, Br, I, CN, NO$_2$, (C$_1$-C$_8$)alkyl, halo(C$_1$-C$_8$)alkyl, (C$_1$-C$_8$)alkoxy, halo(C$_1$-C$_8$)alkoxy, S(C$_1$-C$_8$)alkyl, S(halo(C$_1$-C$_8$)alkyl), N((C$_1$-C$_8$)alkyl)$_2$ (wherein each (C$_1$-C$_8$)alkyl is independently selected), and oxo, and wherein each said substituted-heterocyclyl has one or more substituents selected from F, Cl, Br, I, CN, NO$_2$, $(C_1-C_8)$alkyl, halo$(C_1-C_8)$alkyl, $(C_1-C_8)$alkoxy, halo$(C_1-C_8)$alkoxy, S$(C_1-C_8)$alkyl, S(halo$(C_1-C_8)$alkyl), N$((C_1-C_8)$alkyl$)_2$ (wherein each $(C_1-C_8)$alkyl is independently selected), and oxo;

(r) X1 is selected from N and CR12;

(s) X2 is selected from N, CR9, and CR13;

(t) X3 is selected from N and CR9; and (v) R12 and R13 together form a linkage containing 3 to 4 atoms selected from C, N, O, and S, wherein said linkage connects back to the ring to form a 5 to 6 member saturated or unsaturated cyclic ring, wherein said linkage has at least one substituent X4 wherein X4 is selected from R14, N(R14)(R15), N(R14)(C(=O)R14), N(R14)(C(=S)R14), N(R14)(C(=O)N(R14)(R14)), N(R14)(C(=S)N(R14)(R14)), N(R14)(C(=O)N(R14)$((C_2-C_8)$alkenyl)), N(R14)(C(=S)N(R14)$((C_2-C_8)$alkenyl)), wherein each R14 is independently selected.

In another embodiment of this invention R1 may be selected from any combination of one or more of the following—H, F, Cl, Br, I, CN, NO$_2$, methyl, ethyl, $(C_3)$alkyl, $(C_4)$alkyl, $(C_5)$alkyl, $(C_6)$alkyl, $(C_7)$alkyl, $(C_8)$alkyl, halomethyl, haloethyl, halo$(C_3)$alkyl, halo$(C_4)$alkyl, halo$(C_5)$alkyl, halo$(C_6)$alkyl, halo$(C_7)$alkyl, halo$(C_8)$alkyl, methoxy, ethoxy, $(C_3)$alkoxy, $(C_4)$alkoxy, $(C_5)$alkoxy, $(C_6)$alkoxy, $(C_7)$alkoxy, $(C_8)$alkoxy, halomethoxy, haloethoxy, halo$(C_3)$alkoxy, halo$(C_4)$alkoxy, halo$(C_5)$alkoxy, halo$(C_6)$alkoxy, halo$(C_7)$alkoxy, and halo$(C_8)$alkoxy.

In another embodiment of this invention R2 may be selected from any combination of one or more of the following—H, F, Cl, Br, I, CN, NO$_2$, methyl, ethyl, $(C_3)$alkyl, $(C_4)$alkyl, $(C_5)$alkyl, $(C_6)$alkyl, $(C_7)$alkyl, $(C_8)$alkyl, halomethyl, haloethyl, halo$(C_3)$alkyl, halo$(C_4)$alkyl, halo$(C_5)$alkyl, halo$(C_6)$alkyl, halo$(C_7)$alkyl, halo$(C_8)$alkyl, methoxy, ethoxy, $(C_3)$alkoxy, $(C_4)$alkoxy, $(C_5)$alkoxy, $(C_6)$alkoxy, $(C_7)$alkoxy, $(C_8)$alkoxy, halomethoxy, haloethoxy, halo$(C_3)$alkoxy, halo$(C_4)$alkoxy, halo$(C_5)$alkoxy, halo$(C_6)$alkoxy, halo$(C_7)$alkoxy, and halo$(C_8)$alkoxy.

In another embodiment of this invention R3 may be selected from any combination of one or more of the following—H, F, Cl, Br, I, CN, NO$_2$, methyl, ethyl, $(C_3)$alkyl, $(C_4)$alkyl, $(C_5)$alkyl, $(C_6)$alkyl, $(C_7)$alkyl, $(C_8)$alkyl, halomethyl, haloethyl, halo$(C_3)$alkyl, halo$(C_4)$alkyl, halo$(C_5)$alkyl, halo$(C_6)$alkyl, halo$(C_7)$alkyl, halo$(C_8)$alkyl, methoxy, ethoxy, $(C_3)$alkoxy, $(C_4)$alkoxy, $(C_5)$alkoxy, $(C_6)$alkoxy, $(C_7)$alkoxy, $(C_8)$alkoxy, halomethoxy, haloethoxy, halo$(C_3)$alkoxy, halo$(C_4)$alkoxy, halo$(C_5)$alkoxy, halo$(C_6)$alkoxy, halo$(C_7)$alkoxy, and halo$(C_8)$alkoxy.

In another embodiment of this invention R4 may be selected from any combination of one or more of the following—H, F, Cl, Br, I, CN, NO$_2$, methyl, ethyl, $(C_3)$alkyl, $(C_4)$alkyl, $(C_5)$alkyl, $(C_6)$alkyl, $(C_7)$alkyl, $(C_8)$alkyl, halomethyl, haloethyl, halo$(C_3)$alkyl, halo$(C_4)$alkyl, halo$(C_5)$alkyl, halo$(C_6)$alkyl, halo$(C_7)$alkyl, halo$(C_8)$alkyl, methoxy, ethoxy, $(C_3)$alkoxy, $(C_4)$alkoxy, $(C_5)$alkoxy, $(C_6)$alkoxy, $(C_7)$alkoxy, $(C_8)$alkoxy, halomethoxy, haloethoxy, halo$(C_3)$alkoxy, halo$(C_4)$alkoxy, halo$(C_5)$alkoxy, halo$(C_6)$alkoxy, halo$(C_7)$alkoxy, and halo$(C_8)$alkoxy.

In another embodiment of this invention R5 may be selected from any combination of one or more of the following—H, F, Cl, Br, I, CN, NO$_2$, methyl, ethyl, $(C_3)$alkyl, $(C_4)$alkyl, $(C_5)$alkyl, $(C_6)$alkyl, $(C_7)$alkyl, $(C_8)$alkyl, halomethyl, haloethyl, halo$(C_3)$alkyl, halo$(C_4)$alkyl, halo$(C_5)$alkyl, halo$(C_6)$alkyl, halo$(C_7)$alkyl, halo$(C_8)$alkyl, methoxy, ethoxy, $(C_3)$alkoxy, $(C_4)$alkoxy, $(C_5)$alkoxy, $(C_6)$alkoxy, $(C_7)$alkoxy, $(C_8)$alkoxy, halomethoxy, haloethoxy, halo$(C_3)$alkoxy, halo$(C_4)$alkoxy, halo$(C_5)$alkoxy, halo$(C_6)$alkoxy, halo$(C_7)$alkoxy, and halo$(C_8)$alkoxy.

In another embodiment of this invention R2 and R4 are selected from F, Cl, Br, I, CN, and NO$_2$ and R1, R3, and R5 are H.

In another embodiment of this invention R2, R3, and R4 are selected from F, Cl, Br, I, CN, and NO$_2$ and R1, and R5 are H.

In another embodiment of this invention R2, R3, and R4 are independently selected from F and Cl and R1 and R5 are H.

In another embodiment of this invention R1 is selected from Cl and H.

In another embodiment of this invention R2 is selected from CF$_3$, CH$_3$, Cl, F, and H.

In another embodiment of this invention R3 is selected from OCH$_3$, CH$_3$, F, Cl, or H.

In another embodiment of this invention R4 is selected from CF$_3$, CH$_3$, Cl, F, and H.

In another embodiment of this invention R5 is selected from F, Cl, and H.

In another embodiment of this invention R6 may be selected from any combination of one or more of the following—halomethyl, haloethyl, halo$(C_3)$alkyl, halo$(C_4)$alkyl, halo$(C_5)$alkyl, halo$(C_6)$alkyl, halo$(C_7)$alkyl, and halo$(C_8)$alkyl.

In another embodiment of this invention R6 is trifluoromethyl.

In another embodiment of this invention R7 may be selected from any combination of one or more of the following—H, F, Cl, Br, and I.

In another embodiment of this invention R7 is selected from H, OCH$_3$, and OH.

In another embodiment of this invention R8 may be selected from any combination of one or more of the following—H, methyl, ethyl, $(C_3)$alkyl, $(C_4)$alkyl, $(C_5)$alkyl, $(C_6)$alkyl, $(C_7)$alkyl, $(C_8)$alkyl, halomethyl, haloethyl, halo$(C_3)$alkyl, halo$(C_4)$alkyl, halo$(C_5)$alkyl, halo$(C_6)$alkyl, halo$(C_7)$alkyl, and halo$(C_8)$alkyl.

In another embodiment of this invention R8 is selected from CH$_3$ and H.

In another embodiment of this invention R9 may be selected from any combination of one or more of the following—H, F, Cl, Br, I, methyl, ethyl, $(C_3)$alkyl, $(C_4)$alkyl, $(C_5)$alkyl, $(C_6)$alkyl, $(C_7)$alkyl, $(C_8)$alkyl, halomethyl, haloethyl, halo$(C_3)$alkyl, halo$(C_4)$alkyl, halo$(C_5)$alkyl, halo$(C_6)$alkyl, halo$(C_7)$alkyl, halo$(C_8)$alkyl, methoxy, ethoxy, $(C_3)$alkoxy, $(C_4)$alkoxy, $(C_5)$alkoxy, $(C_6)$alkoxy, $(C_7)$alkoxy, $(C_8)$alkoxy, halomethoxy, haloethoxy, halo$(C_3)$alkoxy, halo$(C_4)$alkoxy, halo$(C_5)$alkoxy, halo$(C_6)$alkoxy, halo$(C_7)$alkoxy, and halo$(C_8)$alkoxy.

In another embodiment of this invention R10 may be selected from any combination of one or more of the following—H, F, Cl, Br, I, CN, methyl, ethyl, $(C_3)$alkyl, $(C_4)$alkyl, $(C_5)$alkyl, $(C_6)$alkyl, $(C_7)$alkyl, $(C_8)$alkyl, halomethyl, haloethyl, halo$(C_3)$alkyl, halo$(C_4)$alkyl, halo$(C_5)$alkyl, halo$(C_6)$alkyl, halo$(C_7)$alkyl, halo$(C_8)$alkyl, methoxy, ethoxy, $(C_3)$alkoxy, $(C_4)$alkoxy, $(C_5)$alkoxy, $(C_6)$alkoxy, $(C_7)$alkoxy, $(C_8)$alkoxy, halomethoxy, haloethoxy, halo$(C_3)$alkoxy, halo$(C_4)$alkoxy, halo$(C_5)$alkoxy, halo$(C_6)$alkoxy, halo$(C_7)$alkoxy, halo$(C_8)$alkoxy, cyclopropyl, cyclobutyl, cyclopentyl, and cyclohexyl.

In another embodiment of this invention R10 may be selected from any combination of one or more of the following—H, Cl, Br, CH$_3$, and CF$_3$.

In another embodiment of this invention R10 is selected from Br, C(=NOH)NH$_2$, C(=O)H, C(=O)NH$_2$, C(=O)

OCH$_2$CH$_3$, C(=O)OH, CF$_3$, CH$_2$CH$_3$, CH$_2$OH, CH3, Cl, CN, F, H, NH$_2$, NHC(=O)H, NHCH$_3$, NO$_2$, OCH$_3$, OCHF$_2$, and pyridyl.

In another embodiment of this invention R11 may be selected from any combination of one or more of the following—C(=O)N(H)(C((CH$_3$)$_2$)C(=O)N(H)(CH$_2$CF$_3$)), C(=O)N(H)(CH(CH$_3$)C(=O)N(H)(CH$_2$CF$_3$)), C(=O)N(H)(CH(CH$_2$CH$_3$)C(=O)N(H)(CH$_2$CF$_3$)), C(=O)N(H)(CH(CH$_3$)C(=S)N(H)(CH$_2$CF$_3$)), C(=O)N(H)(C((CH$_3$)$_2$)C(=S)N(H)(CH$_2$CF$_3$)), and C(=S)N(H)(C((CH$_3$)$_2$)C(=S)N(H)(CH$_2$CF$_3$)).

In another embodiment of this invention R11 is C(=O or S))N(H)(((C$_1$-C$_8$)alkyl)C(=O or S))N(H)(halo(C$_1$-C$_8$)alkyl)), which may be used in combination with any embodiment of R1 through R10 and X1 through X3.

In another embodiment of this invention R12 may be selected from any combination of one or more of the following—H, F, Cl, Br, I, methyl, ethyl, (C$_3$)alkyl, (C$_4$)alkyl, (C$_5$)alkyl, (C$_6$)alkyl, (C$_7$)alkyl, (C$_8$)alkyl, halomethyl, haloethyl, halo(C$_3$)alkyl, halo(C$_4$)alkyl, halo(C$_5$)alkyl, halo(C$_6$)alkyl, halo(C$_7$)alkyl, halo(C$_8$)alkyl, halomethoxy, haloethoxy, halo(C$_3$)alkoxy, halo(C$_4$)alkoxy, halo(C$_5$)alkoxy, halo(C$_6$)alkoxy, halo(C$_7$)alkoxy, and halo(C$_8$)alkoxy.

In another embodiment of this invention R12 is selected from CH3, and H.

In another embodiment of this invention R13 may be selected from any combination of one or more of the following—H, F, Cl, Br, I, methyl, ethyl, (C$_3$)alkyl, (C$_4$)alkyl, (C$_5$)alkyl, (C$_6$)alkyl, (C$_7$)alkyl, (C$_8$)alkyl, halomethyl, haloethyl, halo(C$_3$)alkyl, halo(C$_4$)alkyl, halo(C$_5$)alkyl, halo(C$_6$)alkyl, halo(C$_7$)alkyl, halo(C$_8$)alkyl, halomethoxy, haloethoxy, halo(C$_3$)alkoxy, halo(C$_4$)alkoxy, halo(C$_5$)alkoxy, halo(C$_6$)alkoxy, halo(C$_7$)alkoxy, and halo(C$_8$)alkoxy.

In another embodiment of this invention R13 is selected from CH$_3$, Cl and H.

In another embodiment of this invention R12-R13 are a hydrocarbyl linkage containing CH=CHCH=CH.

In another embodiment of this invention R14 may be selected from any combination of one or more of the following—H, methyl, ethyl, (C$_3$)alkyl, (C$_4$)alkyl, (C$_5$)alkyl, (C$_6$)alkyl, (C$_7$)alkyl, (C$_8$)alkyl, halomethyl, haloethyl, halo(C$_3$)alkyl, halo(C$_4$)alkyl, halo(C$_5$)alkyl, halo(C$_6$)alkyl, halo(C$_7$)alkyl, halo(C$_8$)alkyl, methyl-aryl, ethyl-aryl, (C$_3$)alkyl-aryl, (C$_4$)alkyl-aryl, (C$_5$)alkyl-aryl, (C$_6$)alkyl-aryl, (C$_7$)alkyl-aryl, (C$_8$)alkyl-aryl, methyl-(substituted-aryl), ethyl-(substituted-aryl), (C$_3$)alkyl-(substituted-aryl), (C$_4$)alkyl-(substituted-aryl), (C$_5$)alkyl-(substituted-aryl), (C$_6$)alkyl-(substituted-aryl), (C$_7$)alkyl-(substituted-aryl), (C$_8$)alkyl-(substituted-aryl), O-methyl-aryl, O-ethyl-aryl, O—(C$_3$)alkyl-aryl, O—(C$_4$)alkyl-aryl, O—(C$_5$)alkyl-aryl, O—(C$_6$)alkyl-aryl, O—(C$_7$)alkyl-aryl, O—(C$_8$)alkyl-aryl, O-methyl-(substituted-aryl), O-ethyl-(substituted-aryl), O—(C$_3$)alkyl-(substituted-aryl), O—(C$_4$)alkyl-(substituted-aryl), O—(C$_5$)alkyl-(substituted-aryl), O—(C$_6$)alkyl-(substituted-aryl), O—(C$_7$)alkyl-(substituted-aryl), O—(C$_8$)alkyl-(substituted-aryl), methyl-heterocyclyl, ethyl-heterocyclyl, (C$_3$)alkyl-heterocyclyl, (C$_4$)alkyl-heterocyclyl, (C$_5$)alkyl-heterocyclyl, (C$_6$)alkyl-heterocyclyl, (C$_7$)alkyl-heterocyclyl, (C$_8$)alkyl-heterocyclyl, methyl-(substituted-heterocyclyl), ethyl-(substituted-heterocyclyl), (C$_3$)alkyl-(substituted-heterocyclyl), (C$_4$)alkyl-(substituted-heterocyclyl), (C$_5$)alkyl-(substituted-heterocyclyl), (C$_6$)alkyl-(substituted-heterocyclyl), (C$_7$)alkyl-(substituted-heterocyclyl), (C$_8$)alkyl-(substituted-heterocyclyl), O-methyl-heterocyclyl, O-ethyl-heterocyclyl, O—(C$_3$)alkyl-heterocyclyl, O—(C$_4$)alkyl-heterocyclyl, O—(C$_5$)alkyl-heterocyclyl, O—(C$_6$)alkyl-heterocyclyl, O—(C$_7$)alkyl-heterocyclyl, O—(C$_8$)alkyl-heterocyclyl, O-methyl-(substituted-heterocyclyl), O-ethyl-(substituted-heterocyclyl), O—(C$_3$)alkyl-(substituted-heterocyclyl), O—(C$_4$)alkyl-(substituted-heterocyclyl), O—(C$_5$)alkyl-(substituted-heterocyclyl), O—(C$_6$)alkyl-(substituted-heterocyclyl), O—(C$_7$)alkyl-(substituted-heterocyclyl), O—(C$_8$)alkyl-(substituted-heterocyclyl), methyl-C(=O)N(R16)(R17), ethyl-C(=O)N(R16)(R17), (C$_3$)alkyl-C(=O)N(R16)(R17), (C$_4$)alkyl-C(=O)N(R16)(R17), (C$_5$)alkyl-C(=O)N(R16)(R17), (C$_6$)alkyl-C(=O)N(R16)(R17), (C$_7$)alkyl-C(=O)N(R16)(R17), and (C$_8$)alkyl-C(=O)N(R16)(R17).

In another embodiment of this invention R14 may be selected from any combination of one or more of the following—H, CH$_3$, CH$_2$CF$_3$, CH$_2$-halopyridyl, oxo-pyrrolidinyl, halophenyl, thietanyl, CH$_2$-phenyl, CH$_2$-pyridyl, thietanyl-dioxide, CH$_2$-halothiazolyl, C((CH$_3$)$_2$)-pyridyl, N(H)(halophenyl), CH$_2$-pyrimidinyl, CH$_2$-tetrahydrofuranyl, CH$_2$-furanyl, O—CH$_2$-halopyridyl, and CH$_2$C(=O)N(H)(CH$_2$CF$_3$).

In another embodiment of this invention R15 may be selected from any combination of one or more of the following—H, methyl, ethyl, (C$_3$)alkyl, (C$_4$)alkyl, (C$_5$)alkyl, (C$_6$)alkyl, (C$_7$)alkyl, (C$_8$)alkyl, halomethyl, haloethyl, halo(C$_3$)alkyl, halo(C$_4$)alkyl, halo(C$_5$)alkyl, halo(C$_6$)alkyl, halo(C$_7$)alkyl, halo(C$_8$)alkyl, methyl-aryl, ethyl-aryl, (C$_3$)alkyl-aryl, (C$_4$)alkyl-aryl, (C$_5$)alkyl-aryl, (C$_6$)alkyl-aryl, (C$_7$)alkyl-aryl, (C$_8$)alkyl-aryl, methyl-(substituted-aryl), ethyl-(substituted-aryl), (C$_3$)alkyl-(substituted-aryl), (C$_4$)alkyl-(substituted-aryl), (C$_5$)alkyl-(substituted-aryl), (C$_6$)alkyl-(substituted-aryl), (C$_7$)alkyl-(substituted-aryl), (C$_8$)alkyl-(substituted-aryl), O-methyl-aryl, O-ethyl-aryl, O—(C$_3$)alkyl-aryl, O—(C$_4$)alkyl-aryl, O—(C$_5$)alkyl-aryl, O—(C$_6$)alkyl-aryl, O—(C$_7$)alkyl-aryl, O—(C$_8$)alkyl-aryl, O-methyl-(substituted-aryl), O-ethyl-(substituted-aryl), O—(C$_3$)alkyl-(substituted-aryl), O—(C$_4$)alkyl-(substituted-aryl), O—(C$_5$)alkyl-(substituted-aryl), O—(C$_6$)alkyl-(substituted-aryl), O—(C$_7$)alkyl-(substituted-aryl), O—(C$_8$)alkyl-(substituted-aryl), methyl-heterocyclyl, ethyl-heterocyclyl, (C$_3$)alkyl-heterocyclyl, (C$_4$)alkyl-heterocyclyl, (C$_5$)alkyl-heterocyclyl, (C$_6$)alkyl-heterocyclyl, (C$_7$)alkyl-heterocyclyl, (C$_8$)alkyl-heterocyclyl, methyl-(substituted-heterocyclyl), ethyl-(substituted-heterocyclyl), (C$_3$)alkyl-(substituted-heterocyclyl), (C$_4$)alkyl-(substituted-heterocyclyl), (C$_5$)alkyl-(substituted-heterocyclyl), (C$_6$)alkyl-(substituted-heterocyclyl), (C$_7$)alkyl-(substituted-heterocyclyl), (C$_8$)alkyl-(substituted-heterocyclyl), O-methyl-heterocyclyl, O-ethyl-heterocyclyl, O—(C$_3$)alkyl-heterocyclyl, O—(C$_4$)alkyl-heterocyclyl, O—(C$_5$)alkyl-heterocyclyl, O—(C$_6$)alkyl-heterocyclyl, O—(C$_7$)alkyl-heterocyclyl, O—(C$_8$)alkyl-heterocyclyl, O-methyl-(substituted-heterocyclyl), O-ethyl-(substituted-heterocyclyl), O—(C$_3$)alkyl-(substituted-heterocyclyl), O—(C$_4$)alkyl-(substituted-heterocyclyl), O—(C$_5$)alkyl-(substituted-heterocyclyl), O—(C$_6$)alkyl-(substituted-heterocyclyl), O—(C$_7$)alkyl-(substituted-heterocyclyl), O—(C$_8$)alkyl-(substituted-heterocyclyl), methyl-C(=O)N(R16)(R17), ethyl-C(=O)N(R16)(R17), (C$_3$)alkyl-C(=O)N(R16)(R17), (C$_4$)alkyl-C(=O)N(R16)(R17), (C$_5$)alkyl-C(=O)N(R16)(R17), (C$_6$)alkyl-C(=O)N(R16)(R17), (C$_7$)alkyl-C(=O)N(R16)(R17), and (C$_8$)alkyl-C(=O)N(R16)(R17).

In another embodiment of this invention R15 may be selected from any combination of one or more of the following—H, CH$_3$, CH$_2$CF$_3$, CH$_2$-halopyridyl, oxo-pyrrolidinyl, halophenyl, thietanyl, CH$_2$-phenyl, CH$_2$-pyridyl, thietanyl-dioxide, CH$_2$-halothiazolyl, C((CH$_3$)$_2$)-pyridyl, N(H)(halophenyl), CH$_2$-pyrimidinyl, CH$_2$-tetrahydrofuranyl, CH$_2$-furanyl, O—CH$_2$-halopyridyl, and CH$_2$C(=O)N(H)(CH$_2$CF$_3$).

In another embodiment of this invention R16 may be selected from any combination of one or more of the following—H, methyl, ethyl, (C$_3$)alkyl, (C$_4$)alkyl, (C$_5$)alkyl, (C$_6$)alkyl, (C$_7$)alkyl, (C$_8$)alkyl, halomethyl, haloethyl, halo(C$_3$)alkyl, halo(C$_4$)alkyl, halo(C$_5$)alkyl, halo(C$_6$)alkyl, halo(C$_7$)alkyl, halo(C$_8$)alkyl, methyl-aryl, ethyl-aryl, (C$_3$)alkyl-aryl, (C$_4$)alkyl-aryl, (C$_5$)alkyl-aryl, (C$_6$)alkyl-aryl, (C$_7$)alkyl-aryl, (C$_8$)alkyl-aryl, methyl-(substituted-aryl), ethyl-(substituted-aryl), (C$_3$)alkyl-(substituted-aryl), (C$_4$)alkyl-(substituted-aryl), (C$_5$)alkyl-(substituted-aryl), (C$_6$)alkyl-(substituted-aryl), (C$_7$)alkyl-(substituted-aryl), (C$_8$)alkyl-(substituted-aryl), O-methyl-aryl, O-ethyl-aryl, O—(C$_3$)alkyl-aryl, O—(C$_4$)alkyl-aryl, O—(C$_5$)alkyl-aryl, O—(C$_6$)alkyl-aryl, O—(C$_7$)alkyl-aryl, O—(C$_8$)alkyl-aryl, O-methyl-(substituted-aryl), O-ethyl-(substituted-aryl), O—(C$_3$)alkyl-(substituted-aryl), O—(C$_4$)alkyl-(substituted-aryl), O—(C$_5$)alkyl-(substituted-aryl), O—(C$_6$)alkyl-(substituted-aryl), O—(C$_7$)alkyl-(substituted-aryl), O—(C$_8$)alkyl-(substituted-aryl), methyl-heterocyclyl, ethyl-heterocyclyl, (C$_3$)alkyl-heterocyclyl, (C$_4$)alkyl-heterocyclyl, (C$_5$)alkyl-heterocyclyl, (C$_6$)alkyl-heterocyclyl, (C$_7$)alkyl-heterocyclyl, (C$_8$)alkyl-heterocyclyl, methyl-(substituted-heterocyclyl), ethyl-(substituted-heterocyclyl), (C$_3$)alkyl-(substituted-heterocyclyl), (C$_4$)alkyl-(substituted-heterocyclyl), (C$_5$)alkyl-(substituted-heterocyclyl), (C$_6$)alkyl-(substituted-heterocyclyl), (C$_7$)alkyl-(substituted-heterocyclyl), (C$_8$)alkyl-(substituted-heterocyclyl), O-methyl-heterocyclyl, O-ethyl-heterocyclyl, O—(C$_3$)alkyl-heterocyclyl, O—(C$_4$)alkyl-heterocyclyl, O—(C$_5$)alkyl-heterocyclyl, O—(C$_6$)alkyl-heterocyclyl, O—(C$_7$)alkyl-heterocyclyl, O—(C$_8$)alkyl-heterocyclyl, O-methyl-(substituted-heterocyclyl), O-ethyl-(substituted-heterocyclyl), O—(C$_3$)alkyl-(substituted-heterocyclyl), O—(C$_4$)alkyl-(substituted-heterocyclyl), O—(C$_5$)alkyl-(substituted-heterocyclyl), O—(C$_6$)alkyl-(substituted-heterocyclyl), O—(C$_7$)alkyl-(substituted-heterocyclyl), and O—(C$_8$)alkyl-(substituted-heterocyclyl).

In another embodiment of this invention R16 may be selected from any combination of one or more of the following—H, CH$_2$CF$_3$, cyclopropyl, thietanyl, thietanyl dioxide, and halophenyl.

In another embodiment of this invention R17 may be selected from any combination of one or more of the following—H, methyl, ethyl, (C$_3$)alkyl, (C$_4$)alkyl, (C$_5$)alkyl, (C$_6$)alkyl, (C$_7$)alkyl, (C$_8$)alkyl, halomethyl, haloethyl, halo(C$_3$)alkyl, halo(C$_4$)alkyl, halo(C$_5$)alkyl, halo(C$_6$)alkyl, halo(C$_7$)alkyl, halo(C$_8$)alkyl, methyl-aryl, ethyl-aryl, (C$_3$)alkyl-aryl, (C$_4$)alkyl-aryl, (C$_5$)alkyl-aryl, (C$_6$)alkyl-aryl, (C$_7$)alkyl-aryl, (C$_8$)alkyl-aryl, methyl-(substituted-aryl), ethyl-(substituted-aryl), (C$_3$)alkyl-(substituted-aryl), (C$_4$)alkyl-(substituted-aryl), (C$_5$)alkyl-(substituted-aryl), (C$_6$)alkyl-(substituted-aryl), (C$_7$)alkyl-(substituted-aryl), (C$_8$)alkyl-(substituted-aryl), O-methyl-aryl, O-ethyl-aryl, O—(C$_3$)alkyl-aryl, O—(C$_4$)alkyl-aryl, O—(C$_5$)alkyl-aryl, O—(C$_6$)alkyl-aryl, O—(C$_7$)alkyl-aryl, O—(C$_8$)alkyl-aryl, O-methyl-(substituted-aryl), O-ethyl-(substituted-aryl), O—(C$_3$)alkyl-(substituted-aryl), O—(C$_4$)alkyl-(substituted-aryl), O—(C$_5$)alkyl-(substituted-aryl), O—(C$_6$)alkyl-(substituted-aryl), O—(C$_7$)alkyl-(substituted-aryl), O—(C$_8$)alkyl-(substituted-aryl), methyl-heterocyclyl, ethyl-heterocyclyl, (C$_3$)alkyl-heterocyclyl, (C$_4$)alkyl-heterocyclyl, (C$_5$)alkyl-heterocyclyl, (C$_6$)alkyl-heterocyclyl, (C$_7$)alkyl-heterocyclyl, (C$_8$)alkyl-heterocyclyl, methyl-(substituted-heterocyclyl), ethyl-(substituted-heterocyclyl), (C$_3$)alkyl-(substituted-heterocyclyl), (C$_4$)alkyl-(substituted-heterocyclyl), (C$_5$)alkyl-(substituted-heterocyclyl), (C$_6$)alkyl-(substituted-heterocyclyl), (C$_7$)alkyl-(substituted-heterocyclyl), (C$_8$)alkyl-(substituted-heterocyclyl), O-methyl-heterocyclyl, O-ethyl-heterocyclyl, O—(C$_3$)alkyl-heterocyclyl, O—(C$_4$)alkyl-heterocyclyl, O—(C$_5$)alkyl-heterocyclyl, O—(C$_6$)alkyl-heterocyclyl, O—(C$_7$)alkyl-heterocyclyl, O—(C$_8$)alkyl-heterocyclyl, O-methyl-(substituted-heterocyclyl), O-ethyl-(substituted-heterocyclyl), O—(C$_3$)alkyl-(substituted-heterocyclyl), O—(C$_4$)alkyl-(substituted-heterocyclyl), O—(C$_5$)alkyl-(substituted-heterocyclyl), O—(C$_6$)alkyl-(substituted-heterocyclyl), O—(C$_7$)alkyl-(substituted-heterocyclyl), and O—(C$_8$)alkyl-(substituted-heterocyclyl).

In another embodiment of this invention R17 may be selected from any combination of one or more of the following—H, CH$_2$CF$_3$, cyclopropyl, thietanyl, thietanyl dioxide, and halophenyl.

In another embodiment of this invention X1 is CR12, X2 is CR13, and X3 is CR9.

In another embodiment of this invention a heterocyclyl has preferably about 6 to 10 atoms in the ring structure, more preferably, 6 to 8 atoms.

The molecules of Formula One will generally have a molecular mass of about 100 Daltons to about 1200 Daltons. However, it is generally preferred if the molecular mass is from about 120 Daltons to about 900 Daltons, and it is even more generally preferred if the molecular mass is from about 140 Daltons to about 600 Daltons.

The benzyl alcohol of Formula IV, wherein R1, R2, R3, R4, R5, R6, and R7 are as previously disclosed, can be synthesized in two ways. One way, disclosed in step a of Scheme I, is by treatment of the ketone of Formula II, wherein R1, R2, R3, R4, R5, and R6 are as previously disclosed, with a reducing agent, such as sodium borohydride (NaBH$_4$), under basic conditions, such as aqueous sodium hydroxide (NaOH), in a polar protic solvent, such as methyl alcohol (MeOH) at 0° C. Alternatively, an aldehyde of Formula III, wherein R1, R2, R3, R4, R5, and R7 are as previously disclosed, is allowed to react with trifluorotrimethylsilane in the presence of a catalytic amount of tetrabutylammonium fluoride (TBAF) in a polar aprotic solvent, such as tetrahydrofuran (THF), as in step b of Scheme I. The compound of Formula IV can be transformed into the compound of Formula V, wherein Y is selected from Br, Cl or I, and R1, R2, R3, R4, R5, R6, and R7 are as previously disclosed, by reaction with a halogenating reagent, such as N-bromosuccinimide (NBS) and triethyl phosphite in a non-reactive solvent, such as dichloromethane (CH$_2$Cl$_2$) at reflux temperature to provide Y=Br, or such as thionyl chloride and pyridine in a hydrocarbon solvent, such as toluene at reflux temperature to provide Y=Cl, as in step c of Scheme I.

Scheme I

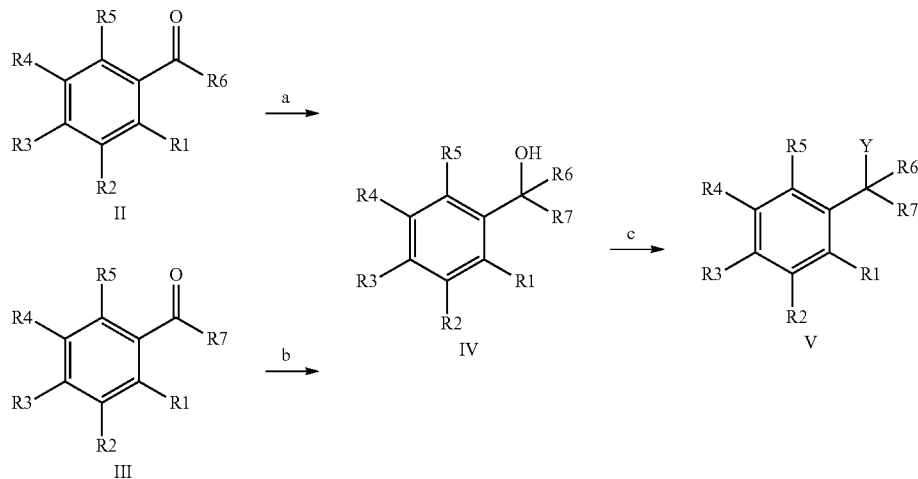

Formation of the styrene coupling partners can be accomplished as in Schemes II, III IV and V.

In Scheme II, a vinylbenzoic acid of Formula VI, wherein R11 is (C=O)OH and R8, R9, R10, R12, R13, X1, X2, and X3 are as previously disclosed, can be converted in two steps to the vinylbenzamide of Formula VIIa, wherein R11 is (C=O)N(R14)(R15), and R8, R9, R10, R12, R13, R14, R15, and X are as previously disclosed. As in step d of Scheme II, the benzoic acid of Formula VI is treated with oxalyl chloride in the presence of a catalytic amount of N,N-dimethylformamide (DMF) in a non-reactive solvent such as $CH_2Cl_2$ to form the acid chloride, which is subsequently allowed to react with an amine (HN(R14)(R15)), wherein R14 and R15 are as previously disclosed, in the presence of a base, such as triethylamine (TEA), in a polar aprotic solvent, such as THF, to provide the vinyl benzamide of Formula VIIa, wherein R11 is (C=O)N(R14)(R15), and R8, R9, R10, R12, R13, R14, R15, X1, X2, and X3 are as previously disclosed, as in step e of Scheme II.

Scheme II

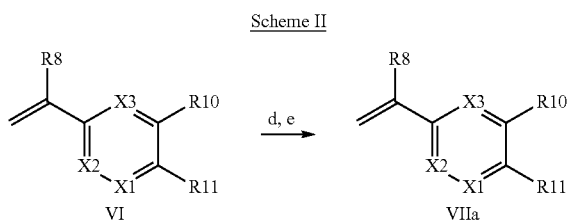

In Schemes III and IV, a halobenzoic acid of Formula VIII, wherein R18 is Br or I, R11 is (C=O)OH and R9, R10, R12, R13, X1, X2, and X3 are as previously disclosed can be converted to a vinylbenzoic acid ester of Formula VIIb1 or Formula VIIb2, wherein R18 is Br or I, R11 is (C=O)O($C_1$-$C_6$ alkyl), and R8, R9, R10, R12, R13, X1, X2, and X3 are as previously disclosed. In step f of Scheme III, the halobenzoic acid of Formula VIII, wherein R18 is Br, is treated with a base, such as n-butyllithium (n-BuLi), and DMF in a polar, aprotic solvent, such as THF, at a temperature of about −78° C. The resulting formyl benzoic acid is allowed to react with an acid, such as sulfuric acid ($H_2SO_4$), in the presence of an alcohol, such as ethyl alcohol (EtOH), as in step g, to provide the formyl benzoic acid ethyl ester of Formula IX, wherein R11 is (C=O)O($C_1$-$C_6$ alkyl), and R9, R10, R12, R13, X1, X2, and X3 are as previously disclosed. The vinyl benzoic acid ester of Formula VIIb1 is accessed via reaction of the compounds of Formula IX, with a base, such as potassium carbonate ($K_2CO_3$), and methyl triphenyl phosphonium bromide in a polar aprotic solvent, such as 1,4-dioxane, at ambient temperature, as in step h of Scheme III.

Scheme III

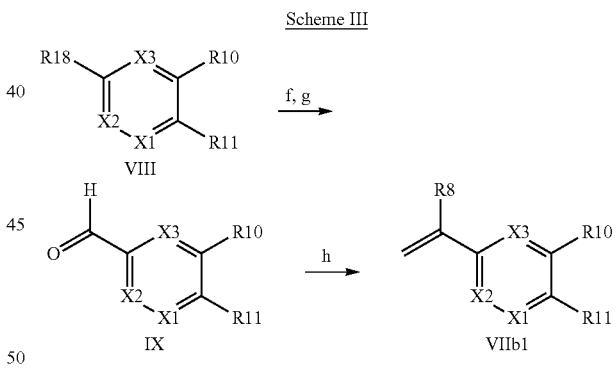

In step i of Scheme IV, the halobenzoic acid of Formula VIII, wherein R18 is Br, R11 is (C=O)OH, and R8, R9, R10, R12, R13, X1, X2, and X3 are as previously disclosed, is treated with di-tert-butyl dicarbonate in the presence of a base, such as TEA and a catalytic amount of 4-(dimethylamino)pyridine (DMAP) in a polar aprotic solvent, such as THF, at ambient temperature. The resulting benzoic acid tert-butyl ester is allowed to react with vinyl boronic anhydride pyridine complex in the presence of a palladium catalyst, such a tetrakis(triphenylphospine)palladium(0) (Pd (PPh$_3$)$_4$), and a base, such as $K_2CO_3$, in a non-reactive solvent such as toluene at reflux temperature, as in step j, to provide the vinyl benzoic acid ester of Formula VIIb2, wherein R11 is (C=O)O($C_1$-$C_6$ alkyl), and R8, R9, R10, R12, R13, X1, X2, and X3 are as previously disclosed.

Scheme IV

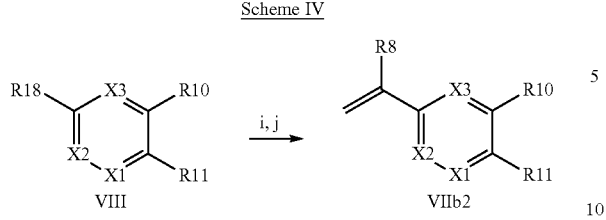

In step k of Scheme V, the vinyl benzoic acid ester of Formula VIIb2, wherein R10 is Br, R11 is (C=O)O(C₁-C₆ alkyl), and R8, R9, R12, R13, X1, X2, and X3 are as previously defined, can be further transformed into the corresponding vinyl benzoic acid ester of Formula VIIb3, wherein R10 is CN, R11 is (C=O)O(C₁-C₆ alkyl), and R8, R9, R12, R13, X1, X2, and X3 are as previously disclosed, by reaction with copper(I) cyanide (CuCN) in a polar aprotic solvent, such as DMF, at 140° C.

Scheme V

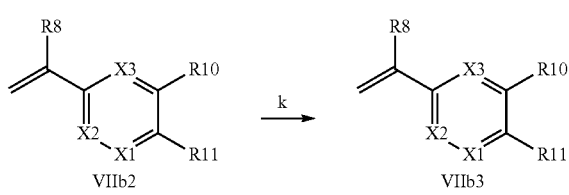

Coupling of the compounds of Formula V with the compounds of Formula VIIa, VIIb1, VIIb2 and VIIb3 can be accomplished as in Schemes VI, VII, and VIII. In step l of Scheme VI, a compound of Formula V, wherein Y, R1, R2, R3, R4, R5, R6, and R7 are as previously disclosed, and the vinylbenzamide of Formula VIIa, wherein R11 is (C=O)N(R14)(R15), and R8, R9, R10, R12, R13, R14, R15, X1, X2, and X3 are as previously disclosed, are allowed to react in the presence of copper(I) chloride (CuCl) and 2,2-bipyridyl in a solvent, such as 1,2-dichlorobenzene, at a temperature of about 180° C. to provide the molecules of Formula One, wherein R11 is (C=O)N(R14)(R15), and R1, R2, R3, R4, R5, R6, R7, R8, R9, R10, R12, R13, R14, R15, X1, X2, and X3 are as previously disclosed.

Scheme VI

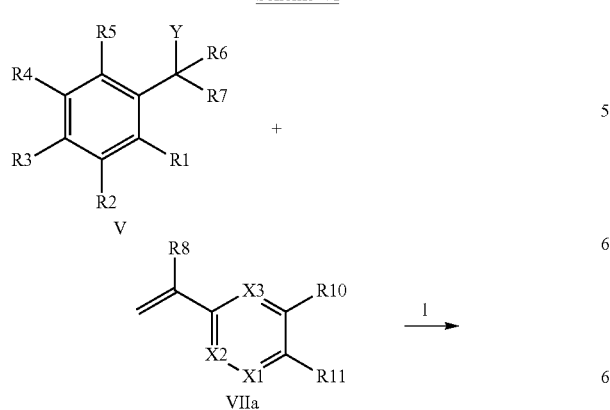

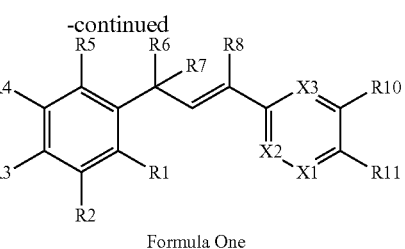

Formula One

In step l of Scheme VII, the compound of Formula V, wherein Y, R1, R2, R3, R4, R5, R6, and R7 are as previously disclosed, and the vinylbenzoic acid ester of Formula VIIb1, wherein R11 is (C=O)O(C₁-C₆ alkyl), and R8, R9, R10, R12, R13, X1, X2, and X3 are as previously disclosed, are allowed to react in the presence of CuCl and 2,2-bipyridyl in a solvent, such as 1,2-dichlorobenzene, at a temperature of about 180° C. to provide the compounds of Formula Xa, wherein R11 is (C=O)O(C₁-C₆ alkyl), and R1, R2, R3, R4, R5, R6, R7, R8, R9, R10, R12, R13, X1, X2, and X3 are as previously disclosed. The compounds of Formula Xa are then converted to the molecules of Formula One, wherein R11 is (C=O)N(R14)(R15), and R1, R2, R3, R4, R5, R6, R7, R8, R9, R10, R12, R13, R14, R15, X1, X2, and X3 are as previously disclosed, by either a two-step process as disclosed in steps m and n or in one step as disclosed in step o. In step m of Scheme VII, the ester of Formula Xa is saponified to the corresponding acid under acidic conditions, such as about 11 Normal (N) hydrochloric acid (HCl), in a polar aprotic solvent, such as 1,4-dioxane, at about 100° C. The acid can subsequently be coupled to an amine (HN(R14)(R15)), wherein R14 and R15 are as previously disclosed using peptide coupling reagents, such as 1-hydroxy-benzotriazole (HOBt), N-(3-dimethylaminopropyl)-N'-ethyl-carbodiimide hydrochloride (EDC.HCl), benzotriazol-1-yl-oxytripyrrolidinophosphonium hexafluorophosphate (PyBOP), 2-chloro-1,3-dimethylimidazolidinium hexafluorophosphate (CIP), 1-hydroxy-7-azabenzotriazole (HOAt), or O-benzotriazole-N,N,N',N'-tetramethyl-uronium-hexafluoro-phosphate (HBTU) in the presence of a base, such as N,N-diisopropylethylamine (DIPEA) or DMAP to give the molecules of Formula One, wherein R11 is (C=O)N(R14)(R15), and R1, R2, R3, R4, R5, R6, R7, R8, R9, R10, R12, R13, R14, R15, X1, X2, and X3 are as previously disclosed. Alternatively, the ester of Formula Xa is allowed to react with an amine (HN(R14)(R15)) in the presence of a solution of trimethylaluminum in toluene in a non-reactive solvent, such as CH₂Cl₂, at ambient temperature, as in step o of Scheme VII, to access the molecules of Formula One, wherein R11 is (C=O)N(R14)(R15), and R1, R2, R3, R4, R5, R6, R7, R8, R9, R10, R12, R13, R14, R15, X1, X2, and X3 are as previously disclosed.

Scheme VII

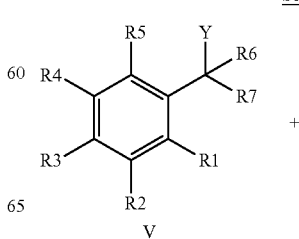

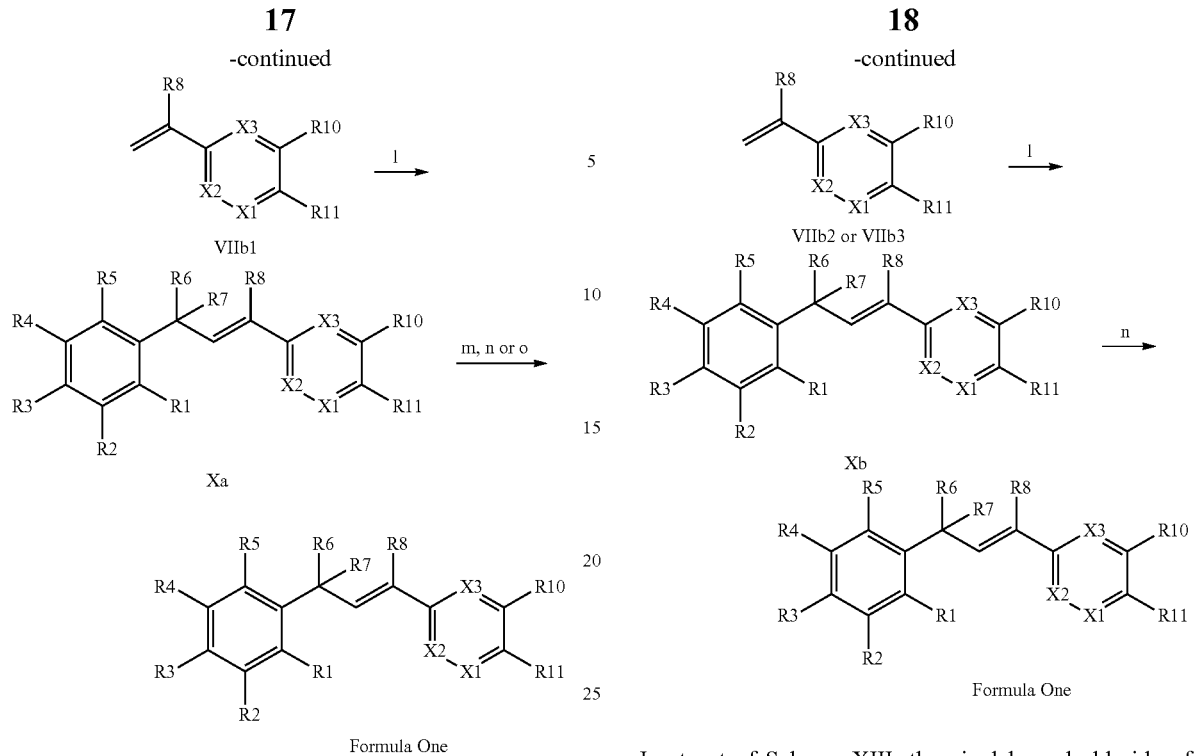

In step l of Scheme VIII, the compound of Formula V, wherein Y, R1, R2, R3, R4, R5, R6, and R7 are as previously disclosed, and the vinylbenzoic acid ester of Formula VIIb2 or VIIb3, wherein R11 is (C=O)O($C_1$-$C_6$ alkyl), and R8, R9, R10, R12, R13, X1, X2, and X3 are as previously disclosed, are allowed to react in the presence of CuCl and 2,2-bipyridyl in a solvent, such as 1,2-dichlorobenzene, at a temperature of about 180° C. to provide the compounds of Formula Xb, wherein R11 is (C=O)OH, and R1, R2, R3, R4, R5, R6, R7, R8, R9, R10, R12, R13, R14, R15, X1, X2, and X3 are as previously disclosed. The compounds of Formula Xb are then converted to the molecules of Formula One, wherein R11 is (C=O)N(R14)(R15), and R1, R2, R3, R4, R5, R6, R7, R8, R9, R10, R12, R13, R14, R15, X1, X2, and X3 are as previously disclosed, in one step as disclosed in step n. In step n of Scheme VIII, the acid of Formula Xb can be coupled to an amine (HN(R14)(R15)), wherein R14 and R15 are as previously disclosed, using peptide coupling reagents, such as HOBt, EDC.HCl, PyBOP, CIP, HOAt, or HBTU in the presence of a base, such as DIPEA or DMAP to give the molecules of Formula One, wherein R11 is (C=O)N(R14)(R15), and R1, R2, R3, R4, R5, R6, R7, R8, R9, R10, R12, R13, R14, R15, X1, X2, and X3 are as previously disclosed.

Scheme VIII

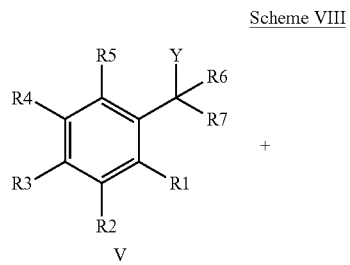

In step t of Scheme XIII, the vinyl benzyl chloride of Formula XIa, wherein R11 is —$CH_2Cl$ and R8, R9, R10, R12, R13, X1, X2, and X3 are as previously defined, can be transformed into the corresponding phthalimide-protected benzyl amine of Formula XIIa, wherein R11 is $CH_2N$(Phthalimide), and R8, R9, R10, R12, R13, X1, X2, and X3 are as previously disclosed, by reaction with potassium phthalimide in a polar aprotic solvent, such as DMF, at 70° C.

Scheme XIII

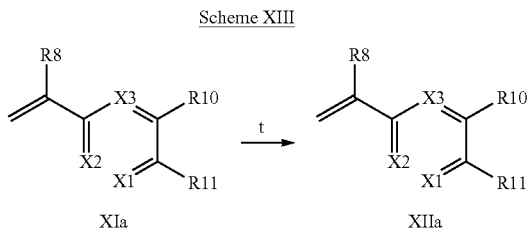

In step u of Scheme XIV, the 4-methylbenzonitrile of Formula XIIIa, wherein R11 is $CH_3$ and R9, R10, R12, R13, X1, X2, and X3 are as previously defined, can be transformed into the corresponding benzyl bromide of Formula XIVa, wherein R11 is $CH_2Br$ and R8, R9, R10, R12, R13, X1, X2, and X3 are as previously disclosed, by reaction with NBS and azobisisobutyronitrile (AIBN) in a non-reactive solvent, such as carbon tetrachloride ($CCl_4$) at 77° C. The nitrile group (CN) of Formula XIVa can be reduced to the corresponding aldehyde of Formula XVa, wherein R11 is $CH_2Br$ and R9, R10, R12, R13, X1, X2, and X3 are as previously defined via reaction with diisobutylaluminum hydride (DIBAL-H) in an aprotic solvent, such as toluene, at 0° C., followed by quenching with 1.0 M HCl as in step v of Scheme XIV. The compound of Formula XVa can be further transformed to the corresponding phthalimide-protected benzyl amine of Formula XVIa, wherein R11 is $CH_2N$(Phthalimide) and R9, R10, R12, R13, X1, X2, and X3 are as previously disclosed, by reaction with potassium phthalimide in a polar aprotic solvent, such as DMF, at 60° C. as in step t of Scheme XIV. In step w of Scheme XIV, the aldehyde of Formula XVIa can be converted to the olefin of Formula XIIb, wherein R11 is CH$_2$N(Phthalimide) and R8, R9, R10, R12, R13, X1, X2, and X3 are as previously disclosed, by reaction with methyl triphenyl phosphonium bromide in a polar aprotic solvent, such as 1,4-dioxane, in the presence of a base, such as K$_2$CO$_3$, at ambient temperature.

Scheme XIV

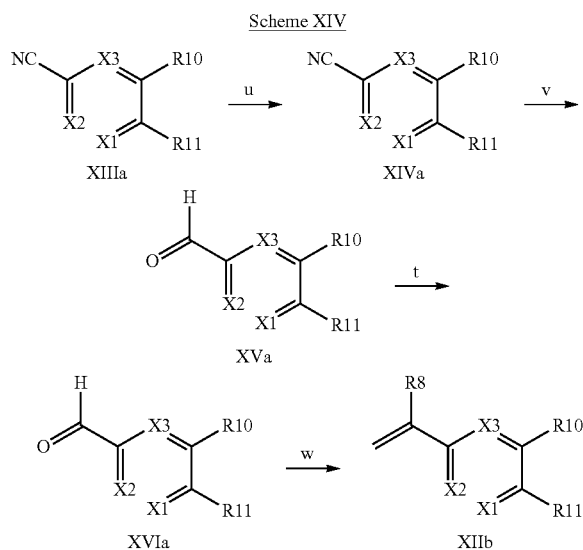

The aldehyde of Formula XVa, wherein R11 is CH$_2$Br and R9, R10, R12, R13, X1, X2, and X3 are as previously defined, can be reacted with a nucleophile, such as 2-aminopyridine, in a polar aprotic solvent, such as N,N-dimethylacetamide (DMA), in the presence of a base, such as K$_2$CO$_3$, at ambient temperature to provide the compound of Formula XVII, wherein R11 is CH$_2$NH(2-pyridine) and R9, R10, R12, R13, X1, X2, and X3 are as previously disclosed, as in step x of Scheme XV. In step w of Scheme XV, the compound of Formula XVII can be converted to the olefin of Formula XVIII, wherein R11 is CH$_2$NH(2-pyridine) and R8, R9, R10, R12, R13, X1, X2, and X3 are as previously disclosed.

Scheme XV

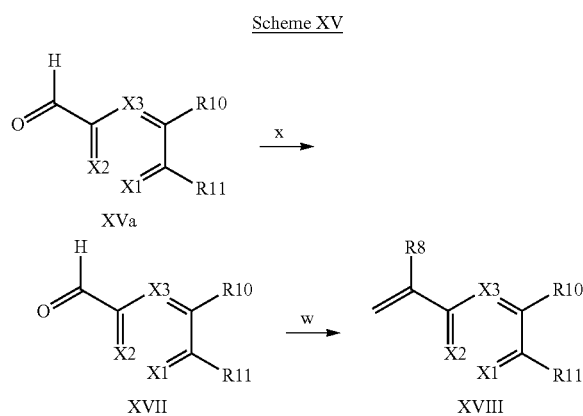

In a two-step, one-pot reaction as in steps y and z of Scheme XVI, the compound of Formula XIX can be reacted with the compounds of Formula XX, wherein R10 and R11 are Cl, X1 is N, and R9, R13, X2, and X3 are as previously disclosed, in the presence of a base, such as sodium hydride (NaH), and a polar aprotic solvent, such as DMF, at ambient temperature to provide the compounds of Formula XXI, wherein R10 is Cl, R11 is (CH)NH$_2$CO$_2$CH$_2$CH$_3$, X1 is N, and R9, R13, X2, and X3 are as previously defined. Hydrolysis and decarboxylation of the compounds of Formula XXI can be accomplished by reaction under acidic conditions, such as with 3 N HCl, at reflux temperature, to afford the compounds of Formula XXII, wherein R10 is Cl, R11 is CH$_2$NH$_2$.HCl, X1 is N, and R9, R13, X2, and X3 are as previously disclosed, as in step aa in Scheme XVI. The compounds of Formula XXII can be further transformed to the corresponding phthalimide-protected benzyl amines of Formula XXIIIa, wherein R10 is Cl, R11 is CH$_2$N(Phthalimide), X1 is N, and R9, R13, X1, X2, and X3 are as previously disclosed, by reaction with phthalic anhydride in the presence of a base, such as TEA, and an aprotic solvent, such as toluene, at reflux temperature as in step ab of Scheme XVI. The bromide of Formula XXIIIa can be converted to the olefin of Formula XIIc, wherein R10 is Cl, R11 is CH$_2$N(Phthalimide), X1 is N, and R8, R9, R13, X2 and X3 are as previously disclosed, by reaction with vinyl boronic anhydride pyridine complex in the presence of a palladium catalyst, such as Pd(PPh$_3$)$_4$, and a base, such as K$_2$CO$_3$, in a non-reactive solvent such as toluene at reflux temperature, as in step ac of Scheme XVI.

Scheme XVI

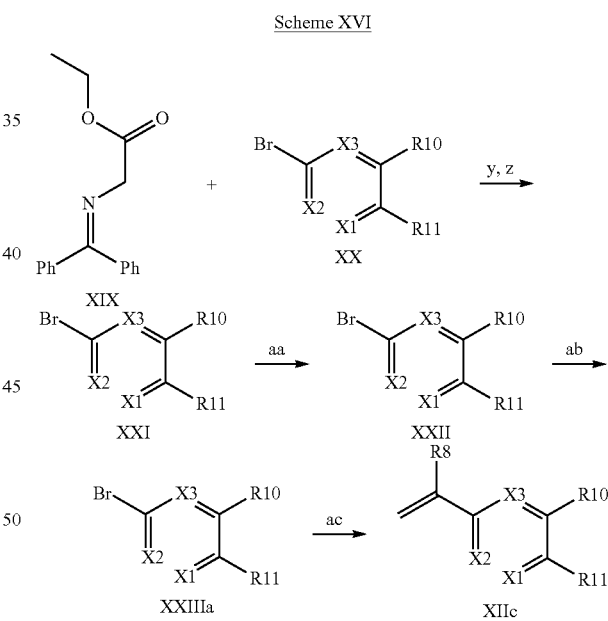

In step u of Scheme XVII, the 4-methylnaphthonitrile of Formula XIIIb, wherein X3 is CR9, R10 and X3 together form a linkage having 4 carbon atoms and with the ring carbon atoms form a 6-membered aromatic ring, R11 is CH$_3$, and R12, R13, X1 and X2 are as previously defined, can be transformed into the corresponding naphthyl bromide of Formula XIVb, wherein X3 is CR9, R10 and X3 together form a linkage having 4 carbon atoms and with the ring carbon atoms form a 6-membered aromatic ring, R11 is CH$_2$Br, and R12, R13, X1 and X2 are as previously disclosed, by reaction with NBS and AIBN in a non-reactive solvent, such as CCl$_4$ at 77° C. The nitrile group (CN) of Formula XIVb can be reduced to the corresponding aldehyde of Formula XVb, wherein X3 is CR9, R10 and X3 together form a linkage having 4 carbon atoms and with the ring carbon atoms form a 6-membered aromatic ring (or if desired a non-aromatic ring), R11 is CH$_2$Br, and R12, R13, X1 and X2 are as previously defined via reaction with diisobutylaluminum hydride (DIBAL-H) in an aprotic solvent, such as toluene, at 0° C., followed by quenching with 1.0 M HCl as in step v of Scheme XVII. The compound of Formula XVb can be further transformed to the corresponding phthalimide-protected benzyl amine of Formula XVIb, wherein X3 is CR9, R10 and X3 together form a linkage having 4 carbon atoms and with the ring carbon atoms form a 6-membered aromatic ring, R11 is CH$_2$N(Phthalimide), and R12, R13, X1 and X2 are as previously disclosed, by reaction with potassium phthalimide in a polar aprotic solvent, such as DMF, at 60° C. as in step t of Scheme XVII. In step w of Scheme XVII, the aldehyde of Formula XVIb can be converted to the olefin of Formula XIId, wherein X3 is CR9, R10 and X3 together form a linkage having 4 carbon atoms and with the ring carbon atoms form a 6-membered aromatic ring, R11 is CH$_2$N(Phthalimide), and R8, R12, R13, X1 and X2 are as previously disclosed, by reaction with methyl triphenyl phosphonium bromide in a polar aprotic solvent, such as 1,4-dioxane, in the presence of a base, such as K$_2$CO$_3$, at ambient temperature.

Scheme XVIII

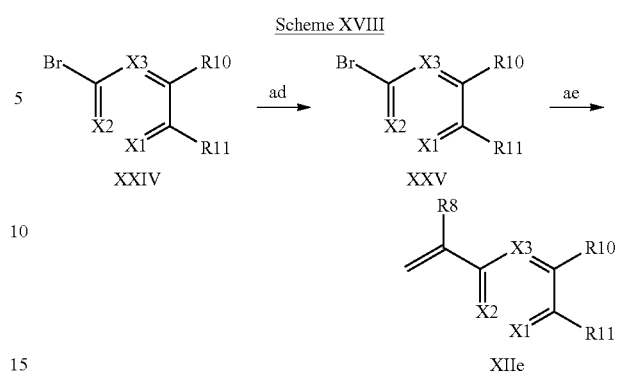

In step af of Scheme XIX, the compound of Formula XXVI, wherein R11 is B(OH)$_2$, and R8, R9, R10, R12, R13, X1, X2, and X3 are as previously disclosed, are allowed to react with 2-hydroxyisoindoline-1,3-dione in the presence of CuCl and pyridine in a solvent, such as 1,2-dichlorobenzene, at ambient temperature to provide the compound of Formula XIIf, wherein R11 is ON(Phthalimide) and R8, R9, R10, R12, R13, X1, X2, and X3 are as previously disclosed.

Scheme XVII

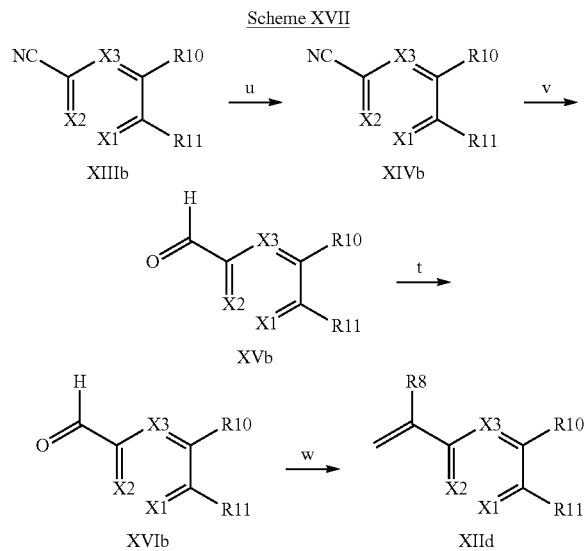

Scheme XIX

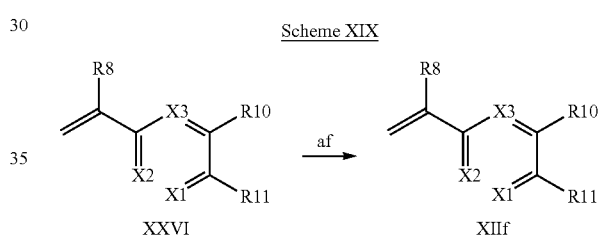

The compound of Formula XXIV, wherein R11 is NHNH$_2$.HCl and R9, R10, R12, R13, X1, X2, and X3 are as previously disclosed, can be transformed into the corresponding phthalimide-protected hydrazine of Formula XXV, wherein R11 is NHN(Phthalimide) and R9, R10, R12, R13, X1, X2, and X3 are as previously disclosed, by reaction with phthalic anhydride in glacial acetic acid (AcOH) at reflux temperature as in step ad of Scheme XVIII. The bromide of Formula XXV can be converted to the olefin of Formula XIIe, wherein R11 is NHN(Phthalimide) and R8, R9, R10, R13, X1, X2 and X3 are as previously disclosed, by reaction with vinyl boronic anhydride pyridine complex in the presence of a palladium catalyst, such as Pd(PPh$_3$)$_4$, and a base, such as K$_2$CO$_3$, in a polar aprotic solvent such as 1,2-dimethoxyethane at 150° C. under microwave conditions, as in step ae of Scheme XVIII.

In step l of Scheme XX, the compound of Formula V, wherein Y, R1, R2, R3, R4, R5, R6, and R7 are as previously disclosed, and the compounds of Formula XIIa, wherein R11 is CH$_2$N(Phthalimide) and R8, R9, R10, R12, R13, X1, X2, and X3 are as previously disclosed, are allowed to react in the presence of CuCl and 2,2-bipyridyl in a solvent, such as 1,2-dichlorobenzene, at a temperature of about 180° C. to provide the corresponding compounds of Formula XXVIIa, wherein R11 is CH$_2$N(Phthalimide) and R1, R2, R3, R4, R5, R6, R7, R8, R9, R10, R12, R13, X1, X2, and X3 are as previously disclosed. The phthalimide protecting group in the compounds of Formula XXVIIa is removed as in step ag of Scheme XX by reaction with hydrazine hydrate in a polar protic solvent such as EtOH at 90° C. to provide the compounds of Formula XXVIIIa, wherein R11 is CH$_2$NH$_2$ and R1, R2, R3, R4, R5, R6, R7, R8, R9, R10, R12, R13, X1, X2, and X3 are as previously disclosed. The compounds of Formula XXVIIIa can be transformed into the compounds of Formula One, wherein R11 is CH$_2$N(C═O)(R14) and R1, R2, R3, R4, R5, R6, R7, R8, R9, R10, R12, R13, X1, X2, and X3 are as previously disclosed, by acylation with an anhydride, such as acetic anhydride, and a base, such as TEA, in a non-reactive solvent such as CH$_2$Cl$_2$ at 0° C. as in step ah$_1$ of Scheme XX.

Scheme XX

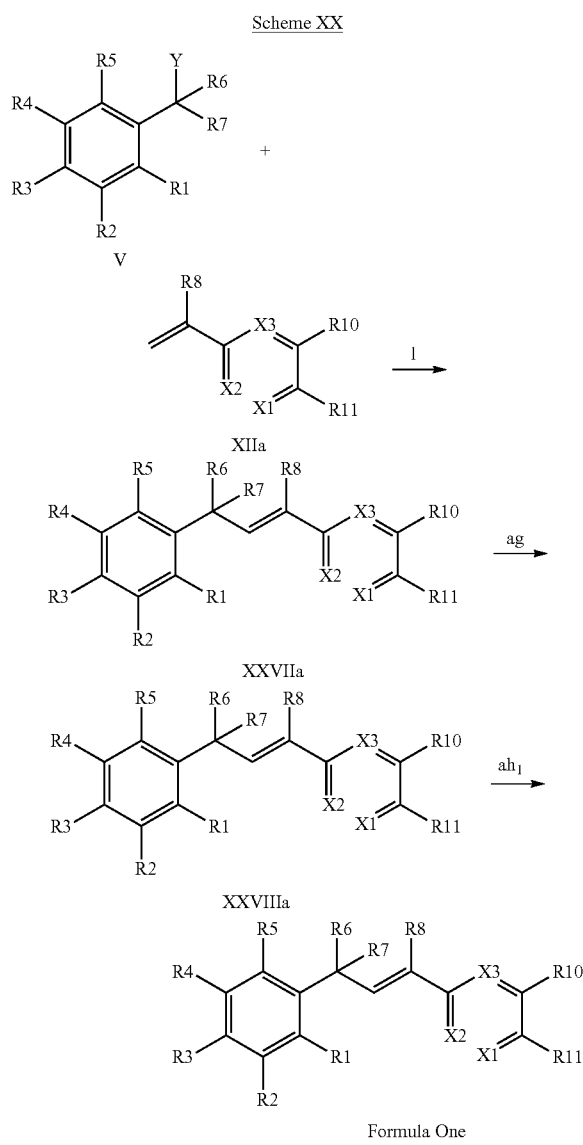

Formula One

In step 1 of Scheme XXI, the compound of Formula V, wherein Y, R1, R2, R3, R4, R5, R6, and R7 are as previously disclosed, and the compounds of Formula XIIb, wherein R11 is CH$_2$N(Phthalimide) and R8, R9, R10, R12, R13, X1, X2, and X3 are as previously disclosed, are allowed to react in the presence of CuCl and 2,2-bipyridyl in a solvent, such as 1,2-dichlorobenzene, at a temperature of about 180° C. to provide the corresponding compounds of Formula XXVIIb, wherein R11 is CH$_2$N(Phthalimide) and R1, R2, R3, R4, R5, R6, R7, R8, R9, R10, R12, R13, X1, X2, and X3 are as previously disclosed. The phthalimide protecting group in the compounds of Formula XXVIIb is removed as in step ag of Scheme XXI by reaction with hydrazine hydrate in a polar protic solvent such as EtOH at 90° C. to provide the compounds of Formula XXVIIIb, wherein R11 is CH$_2$NH$_2$ and R1, R2, R3, R4, R5, R6, R7, R8, R9, R10, R12, R13, X1, X2, and X3 are as previously disclosed. The compounds of Formula XXVIIIb can be transformed into the compounds of Formula One, wherein R11 is CH$_2$N(C=O)(R14) and R1, R2, R3, R4, R5, R6, R7, R8, R9, R10, R12, R13, X1, X2, and X3 are as previously disclosed, by reaction with an acid in the presence of HOBt.H$_2$O, EDC.HCl and a base, such as DIPEA, in a polar aprotic solvent, such as DMF, as in step ah$_a$ of Scheme XXI.

In another embodiment, the compounds of Formula XXVIIIb can be transformed into the compounds of Formula One, wherein R11 is CH$_2$N(C=S)(R14) and R1, R2, R3, R4, R5, R6, R7, R8, R9, R10, R12, R13, X1, X2, and X3 are as previously disclosed, by reaction with a thioacid in the presence of HOBt.H$_2$O, EDC.HCl and a base, such as DIPEA, in a polar aprotic solvent, such as DMF, as in step ah$_2$ of Scheme XXI.

In another embodiment, the compounds of Formula XXVIIIb can be transformed into the compounds of Formula One, wherein R11 is CH$_2$N(C=O)N(R14)(R15) and R1, R2, R3, R4, R5, R6, R7, R8, R9, R10, R12, R13, X1, X2, and X3 are as previously disclosed, in two steps. The first step (step ah$_{3a}$ of Scheme XXI) involves reaction with an aldehyde in a polar protic solvent such as MeOH, followed by reaction with NaBH$_4$. The second step (step ah$_{3b}$ of Scheme XXI) involves acylation with an acid chloride, such as cyclopropylcarbonyl chloride, and a base, such as TEA, in a non-reactive solvent such as CH$_2$Cl$_2$ at ambient temperature of Scheme XXI.

In another embodiment, the compounds of Formula XXVIIIb can be transformed into the compounds of Formula One, wherein R11 is CH$_2$N(C=O)N(R14)(R15) and R1, R2, R3, R4, R5, R6, R7, R8, R9, R10, R12, R13, X1, X2, and X3 are as previously disclosed, by reaction with an isocyanate (step ai$_1$ of Scheme XXI) or a carbamoyl chloride (step ai$_2$ of Scheme XXI) in the presence of a base such as TEA and in a non-reactive solvent such as CH$_2$Cl$_2$ at 0° C.

In another embodiment, the compounds of Formula XXVIIIb can be transformed into the compounds of Formula One, wherein R11 is CH$_2$N(C=S)N(R14)(R15) and R1, R2, R3, R4, R5, R6, R7, R8, R9, R10, R12, R13, X1, X2, and X3 are as previously disclosed, by reaction with an isothiocyanate in the presence of a base such as TEA and in a non-reactive solvent such as CH$_2$Cl$_2$ at 0° C., as in steps aj of Scheme XXI.

In another embodiment, the compounds of Formula XXVIIIb can be transformed into the compounds of Formula One, wherein R11 is CH$_2$N(C=O)O(R14) and R1, R2, R3, R4, R5, R6, R7, R8, R9, R10, R12, R13, X1, X2, and X3 are as previously disclosed, by reaction with a dicarbonate, such as di-tert-butyl dicarbonate in the presence of a base such as TEA and in a non-reactive solvent such as CH$_2$Cl$_2$ at ambient temperature, as in steps ak of Scheme XXI.

In yet another embodiment, the compounds of Formula XXVIIIb can be transformed into the compounds of Formula One, wherein R11 is CH$_2$N(C=O)(C=O)O(R14) and R1, R2, R3, R4, R5, R6, R7, R8, R9, R10, R12, R13, X1, X2, and X3 are as previously disclosed, by reaction with a chlorooxalic acid ester, such as 2-chloro-2-oxoacetate in the presence of a base such as TEA and in a non-reactive solvent such as CH$_2$Cl$_2$ at 0° C., as in steps al of Scheme XXI.

Scheme XXI

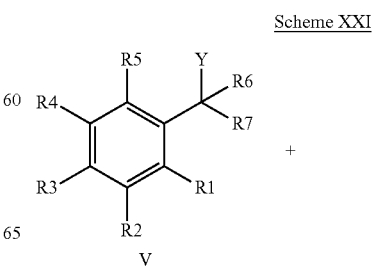

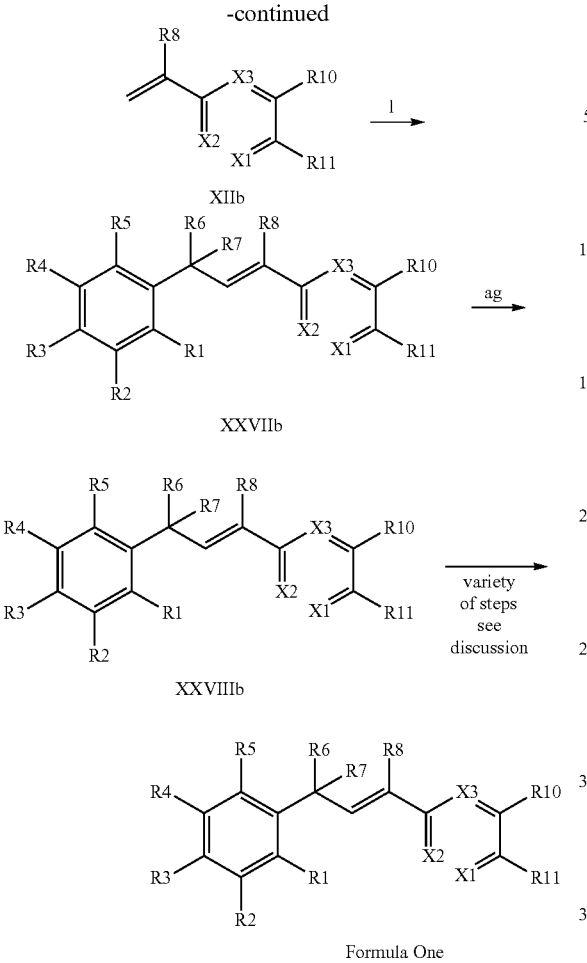

Formula One

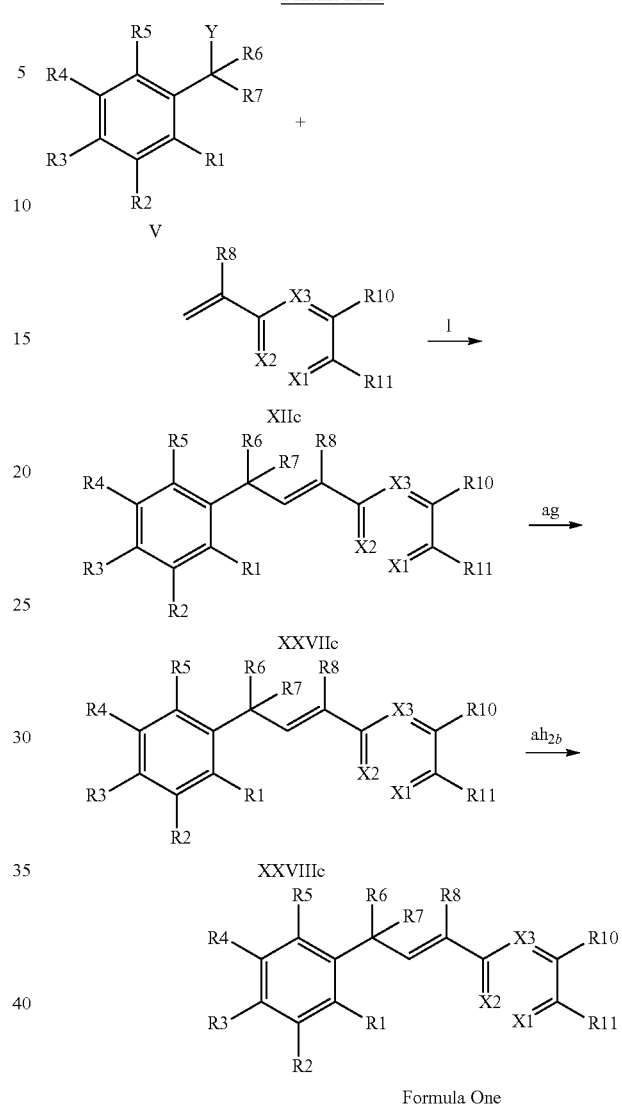

Formula One

In step 1 of Scheme XXII, the compound of Formula V, wherein Y, R1, R2, R3, R4, R5, R6, and R7 are as previously disclosed, and the compounds of Formula XIIc, wherein R10 is Cl, R11 is $CH_2N(Phthalimide)$, X1 is N, and R8, R9, R12, R13, X2, and X3 are as previously disclosed, are allowed to react in the presence of CuCl and 2,2-bipyridyl in a solvent, such as 1,2-dichlorobenzene, at a temperature of about 180° C. to provide the corresponding compounds of Formula XXVIIc, wherein R10 is Cl, R11 is $CH_2N(Phthalimide)$, X1 is N, and R1, R2, R3, R4, R5, R6, R7, R8, R9, R12, R13, X2, and X3 are as previously disclosed. The phthalimide protecting group in the compounds of Formula XXVIIc is removed as in step ag of Scheme XXII by reaction with hydrazine hydrate in a polar protic solvent such as EtOH at 90° C. to provide the compounds of Formula XXVIIIc, wherein R10 is Cl, R11 is $CH_2NH_2$, X1 is N, and R1, R2, R3, R4, R5, R6, R7, R8, R9, R12, R13, X2, and X3 are as previously disclosed. The compounds of Formula XXVIIIc can be transformed into the compounds of Formula One, wherein R10 is Cl, R11 is $CH_2N(C=O)$ (R14), X1 is N, and R1, R2, R3, R4, R5, R6, R7, R8, R9, R12, R13, X2, and X3 are as previously disclosed, by reaction with an acid in the presence of $HOBt.H_2O$, EDC.HCl and a base, such as DIPEA, in a polar aprotic solvent, such as $CH_2Cl_2$, as in step $ah_{2b}$ of Scheme XXII.

In step 1 of Scheme XXIII, the compound of Formula V, wherein Y, R1, R2, R3, R4, R5, R6, and R7 are as previously disclosed, and the compounds of Formula XIId, wherein X3 is CR9, R10 and X3 together form a linkage having 4 carbon atoms and with the ring carbon atoms form a 6-membered aromatic ring (or if desired a non-aromatic ring), R11 is $CH_2N(Phthalimide)$ and R8, R9, R12, R13, X1 and X2 are as previously disclosed, are allowed to react in the presence of CuCl and 2,2-bipyridyl in a solvent, such as 1,2-dichlorobenzene, at a temperature of about 180° C. to provide the corresponding compounds of Formula XXVIId, wherein X3 is CR9, R10 and X3 together form a linkage having 4 carbon atoms and with the ring carbon atoms form a 6-membered aromatic ring, R11 is $CH_2N(Phthalimide)$ and R1, R2, R3, R4, R5, R6, R7, R8, R9, R12, R13, X1 and X2 are as previously disclosed. The phthalimide protecting group in the compounds of Formula XXVIId is removed as in step ag of Scheme XXIII by reaction with hydrazine hydrate in a polar protic solvent such as EtOH at 90° C. to provide the compounds of Formula XXVIIId, wherein X3 is CR9, R10 and X3 together form a linkage having 4 carbon atoms and with the ring carbon atoms form a 6-membered aromatic ring, R11 is CH$_2$NH$_2$ and R1, R2, R3, R4, R5, R6, R7, R8, R9, R12, R13, X1 and X2 are as previously disclosed. The compounds of Formula XXVIIId can be transformed into the compounds of Formula One, wherein X3 is CR9, R10 and X3 together form a linkage having 4 carbon atoms and with the ring carbon atoms form a 6-membered aromatic ring, R11 is CH$_2$N(C=O)(R14) and R1, R2, R3, R4, R5, R6, R7, R8, R9, R12, R13, X1 and X2 are as previously disclosed, by reaction with an acid in the presence of HOBt.H$_2$O, EDC.HCl and a base, such as DIPEA, in a polar aprotic solvent, such as CH$_2$Cl$_2$, as in step ah$_{2b}$ of Scheme XXIII.

In another embodiment, the compounds of Formula XXVIIId can be transformed into the compounds of Formula One, wherein X3 is CR9, R10 and X3 together form a linkage having 4 carbon atoms and with the ring carbon atoms form a 6-membered aromatic ring, R11 is CH$_2$N(C=O)N(R14)(R15) and R1, R2, R3, R4, R5, R6, R7, R8, R9, R10, R12, R13, X1 and X2 are as previously disclosed, by reaction with an isocyanate in the presence of a base such as TEA and in a non-reactive solvent such as CH$_2$Cl$_2$ at 0° C. as in step ai$_1$ of Scheme XXIII.

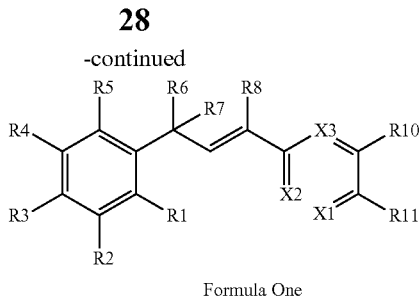

Formula One

In step 1 of Scheme XXIV, the compound of Formula V, wherein Y, R1, R2, R3, R4, R5, R6, and R7 are as previously disclosed, and the compounds of Formula XIIe, wherein R11 is NHN(Phthalimide) and R8, R9, R12, R13, X1, X2, and X3 are as previously disclosed, are allowed to react in the presence of CuCl and 2,2-bipyridyl in a solvent, such as 1,2-dichlorobenzene, at a temperature of about 180° C. to provide the corresponding compounds of Formula XXVIIe, wherein R11 is NHN(Phthalimide) and R1, R2, R3, R4, R5, R6, R7, R8, R9, R12, R13, X1, X2, and X3 are as previously disclosed. The phthalimide protecting group in the compounds of Formula XXVIIe is removed as in step ag of Scheme XXIV by reaction with hydrazine hydrate in a polar protic solvent such as EtOH at 90° C. to provide the compounds of Formula XXVIIIe, wherein R11 is NHNH$_2$ and R1, R2, R3, R4, R5, R6, R7, R8, R9, R12, R13, X1, X2, and X3 are as previously disclosed. The compounds of Formula XXVIIIe can be transformed into the compounds of Formula One, wherein R11 is NHN(C=O)(R14) and R1, R2, R3, R4, R5, R6, R7, R8, R9, R12, R13, X1, X2, and X3 are as previously disclosed, by reaction with an acid in the presence of HOBt.H$_2$O, EDC.HCl and a base, such as DIPEA, in a polar aprotic solvent, such as CH$_2$Cl$_2$, as in step ah$_{2b}$ of Scheme XXIV.

Scheme XXIII

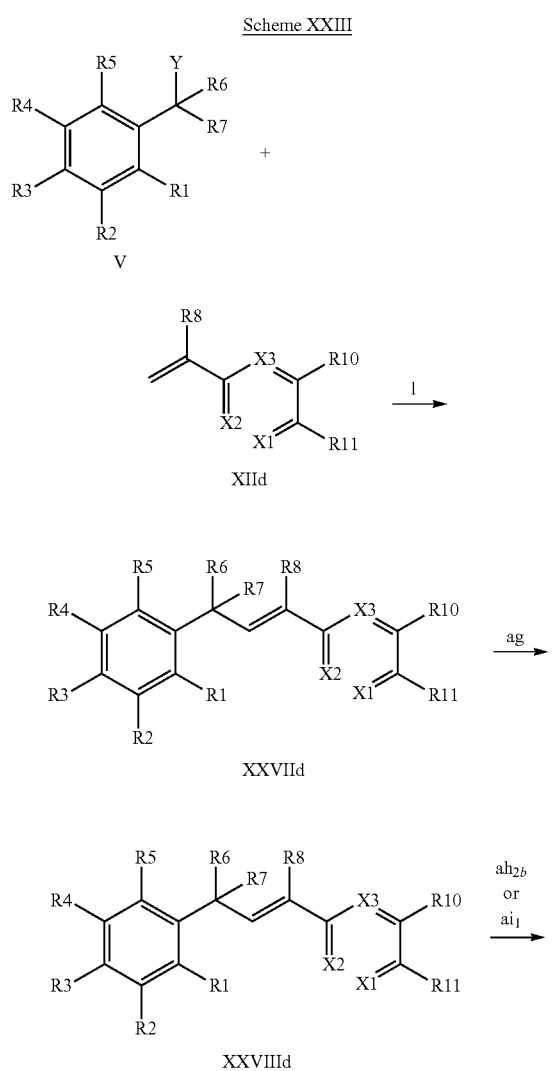

Scheme XXIV

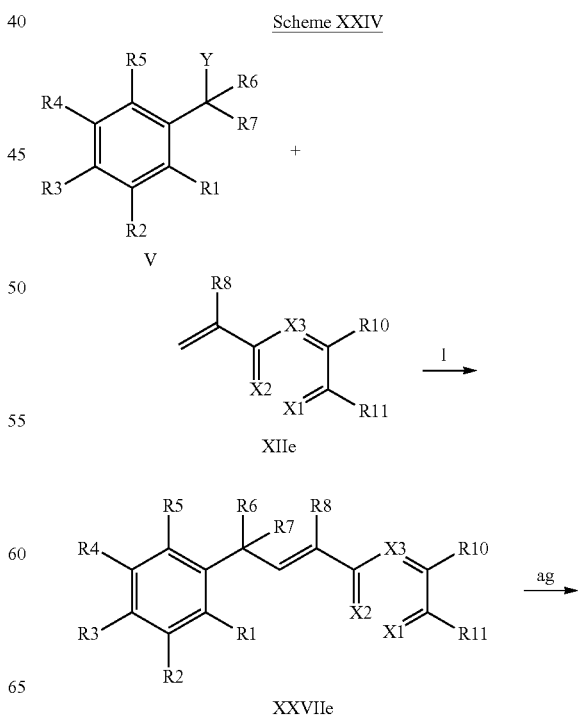

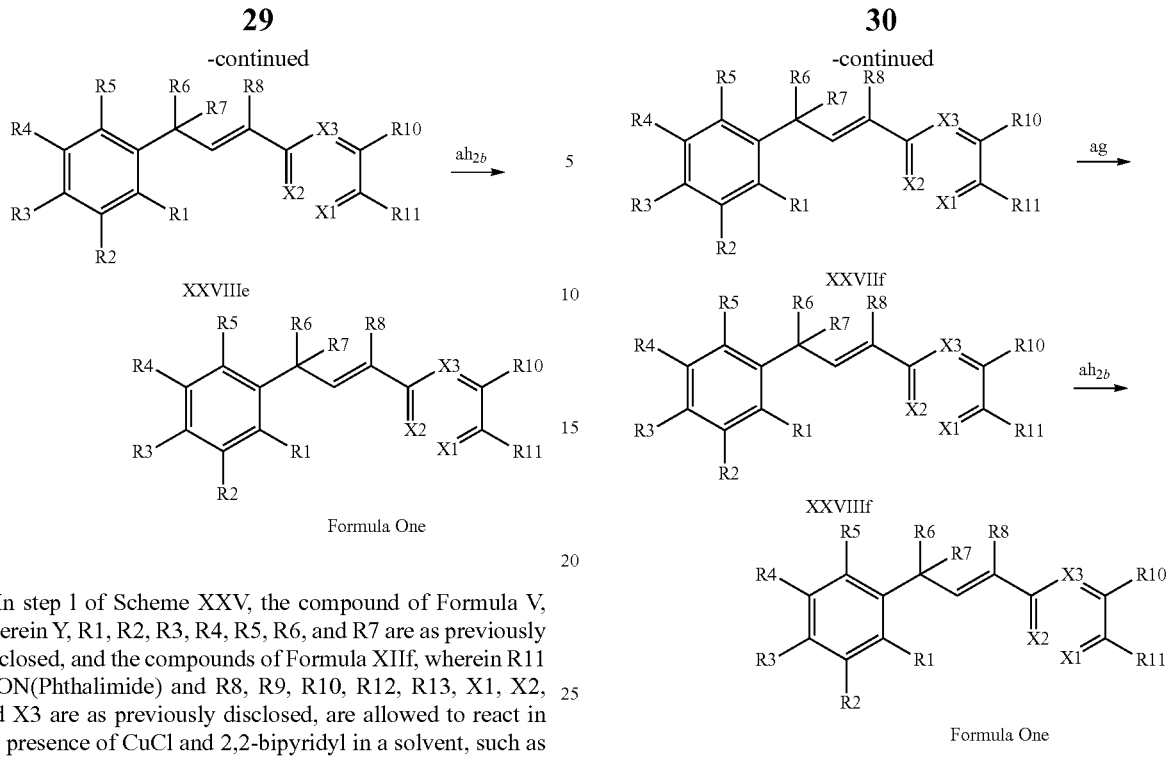

In step 1 of Scheme XXV, the compound of Formula V, wherein Y, R1, R2, R3, R4, R5, R6, and R7 are as previously disclosed, and the compounds of Formula XIIf, wherein R11 is ON(Phthalimide) and R8, R9, R10, R12, R13, X1, X2, and X3 are as previously disclosed, are allowed to react in the presence of CuCl and 2,2-bipyridyl in a solvent, such as 1,2-dichlorobenzene, at a temperature of about 180° C. to provide the corresponding compounds of Formula XXVIIf, wherein R11 is ON(Phthalimide) and R1, R2, R3, R4, R5, R6, R7, R8, R9, R10, R12, R13, X1, X2, and X3 are as previously disclosed. The phthalimide protecting group in the compounds of Formula XXVIIf is removed as in step ag of Scheme XXV by reaction with hydrazine hydrate in a polar protic solvent such as EtOH at 90° C. to provide the compounds of Formula XXVIIIf, wherein R11 is $ONH_2$ and R1, R2, R3, R4, R5, R6, R7, R8, R9, R10, R12, R13, X1, X2, and X3 are as previously disclosed. The compounds of Formula XXVIIIf can be transformed into the compounds of Formula One, wherein R11 is ON(C=O)(R14) and R1, R2, R3, R4, R5, R6, R7, R8, R9, R10, R12, R13, X1, X2, and X3 are as previously disclosed, by reaction with an acid in the presence of HOBt.$H_2O$, EDC.HCl and a base, such as DIPEA, in a polar aprotic solvent, such as $CH_2Cl_2$, as in step $ah_{2b}$ of Scheme XXV.

In step 1 of Scheme XXVI, the compound of Formula V, wherein Y, R1, R2, R3, R4, R5, R6, and R7 are as previously disclosed, and the compounds of Formula XVIII, wherein R11 is $CH_2NH$(2-pyridine) and R8, R9, R10, R12, R13, X1, X2, and X3 are as previously disclosed, are allowed to react in the presence of CuCl and 2,2-bipyridyl in a solvent, such as 1,2-dichlorobenzene, at a temperature of about 180° C. to provide the corresponding compounds of Formula One, wherein R11 is $CH_2NH$(2-pyridine), and R1, R2, R3, R4, R5, R6, R7, R8, R9, R10, R12, R13, X1, X2, and X3 are as previously disclosed.

The compounds of Formula One can be further elaborated by standard methods. For example, when R11 contains a thioether, the thioether can be oxidized to the sulfone by treatment with oxone in the presence of an acetone:water mixture at ambient temperature. When R11 contains an oxalate ester, the compound of Formula One can be transformed into the corresponding oxalamide by reaction with an amine hydrochloride and a solution of trimethylaluminum in toluene in a non-reactive solvent such as $CH_2Cl_2$.

Scheme XXV

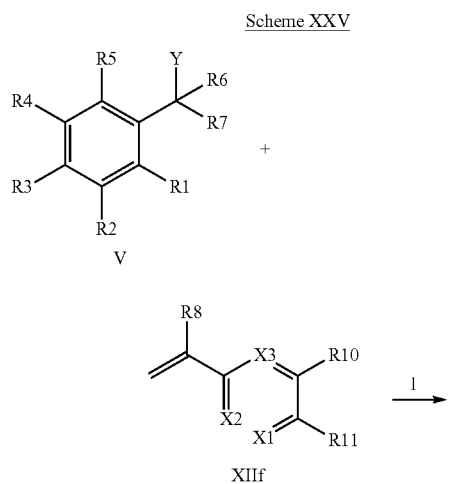

Scheme XXVI

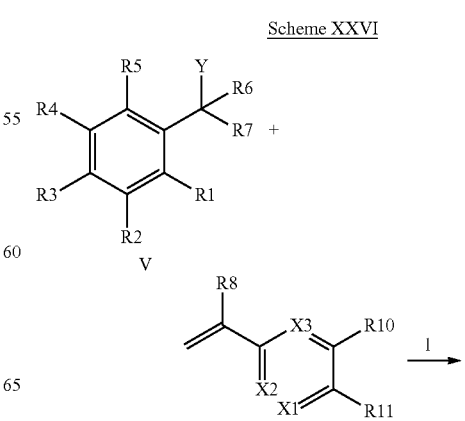

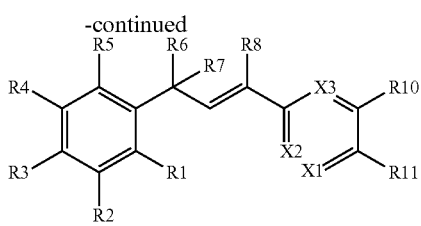

Formula One

In Scheme XXVII, a fluorobenzaldehyde of Formula XXIX, wherein R10, X1, X2, and X3 are as previously disclosed can be converted to a (1,2,4-triazol-1-yl)benzaldehyde of Formula XXX, wherein R11 is a substituted or unsubstituted 1,2,4-triazol-1-yl group, and R10, X1, X2, and X3 are as previously disclosed by reaction with a substituted or unsubstituted 1,2,4-triazole in the presence of a base, such as K$_2$CO$_3$, in a solvent such as DMF as in step aj. In step ak, the (1,2,4-triazol-1-yl)benzaldehyde of Formula XXX is converted to a (1,2,4-triazol-1-yl)vinyl benzene of Formula XXXIa wherein R11 is a substituted or unsubstituted 1,2,4-triazol-1-yl group, and R8, R10, X1, X2, and X3 are as previously disclosed by reaction with triphenyl phosphonium bromide in the presence of a base, such as K$_2$CO$_3$, in an aprotic solvent, such as 1,4-dioxane.

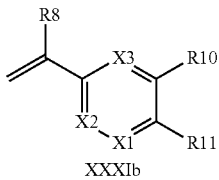

XXXIb

Coupling of the compounds of Formula V with compounds of Formula XXXIa and XXXIb can be accomplished as in Schemes XXIX. In step l, a compound of Formula V, wherein Y is Br, R1, R2, R3, R4, R5, R6, and R7 are as previously disclosed, and a vinylbenzene of Formula XXXIa or XXXIb, wherein R11 is a substituted or unsubstituted 1,2,4-triazol-1-yl group, and R8, R9, R10, X1, X2, and X3 are as previously disclosed, are allowed to react in the presence of CuCl and 2,2-bipyridyl in a solvent, such as 1,2-dichlorobenzene, at a temperature of about 180° C. to provide the molecules of Formula One, wherein R11 is a substituted or unsubstituted 1,2,4-triazol-1-yl group, and R1, R2, R3, R4, R5, R6, R7, R8, R10, X1, X2, and X3 are as previously disclosed.

Scheme XXVII

[Structure: XXIX → (aj) → XXX → (ak) → XXXIa]

In Scheme XXVIII, a bromofluorobenzene of Formula XXXII, wherein R10, X1, X2, and X3 are as previously disclosed can be converted to a (1,2,4-triazol-1-yl)vinylbenzene of Formula XXXIb, wherein R11 is a substituted or unsubstituted 1,2,4-triazol-1-yl group, and R8, R10, X1, X2, and X3 are as previously disclosed in two steps. In step al, the bromofluorobenzene is reacted with a substituted or unsubstituted 1,2,4-triazole in the presence of a base, such as K$_2$CO$_3$, in a solvent such as DMF to generate the (1,2,4-triazol-1-yl)bromobenzene. In step cl, the (1,2,4-triazol-1-yl)bromobenzene is reacted with vinyl boronic anhydride pyridine complex in the presence of a catalyst, such as Pd(PPh$_3$)$_4$, and a base, such as K$_2$CO$_3$ in a solvent such as toluene.

Scheme XXVIII

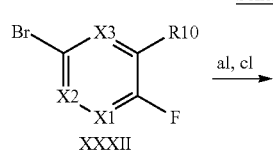

Scheme XXIX

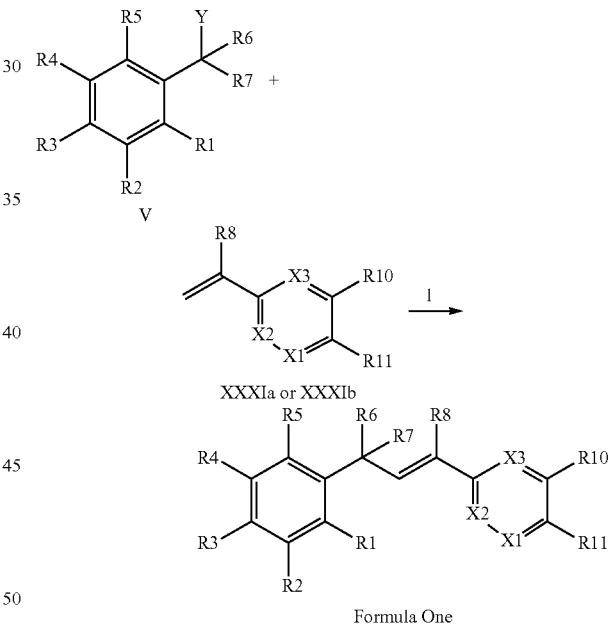

Formula One

In Scheme XXX, compounds of Formula XXXIII wherein R11 is a 3-nitro-1,2,4-triazol-1-yl group, and R1, R2, R3, R4, R5, R6, R7, R8, R10, X1, X2, and X3 are as previously disclosed can be converted to compounds of Formula One, wherein R11 is a 3-amido-1,2,4-triazol-1-yl group, and R1, R2, R3, R4, R5, R6, R7, R8, R10, X1, X2, and X3 are as previously disclosed by a two-step process. In step am, the 3-nitro-1,2,4-triazol-1-yl group is reduced to a 3-amino-1,2,4-triazol-1-yl group in the presence of zinc dust and ammonium chloride (NH$_4$Cl) in a protic solvent, such as MeOH. In step an, the 3-amino-1,2,4-triazol-1-yl group is acylated with an acid chloride, such as cyclopropylcarbonyl chloride or acetyl chloride, in the presence of a base, such as TEA, in a solvent such as CH$_2$Cl$_2$.

Scheme XXX

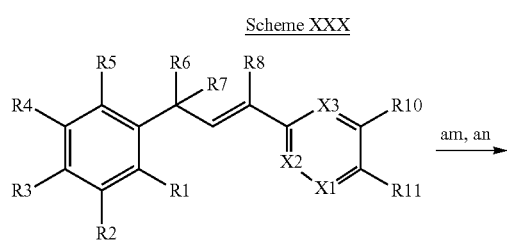

XXXIII

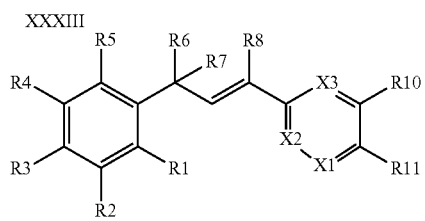

Formula One

In step ao of Scheme XXXI, a bromophenyl methyl ketone of Formula XXXIV wherein R10, X1, X2, and X3 are as previously disclosed is converted to an phenyl methyl ketone of the Formula XXXV wherein R11 is a 1,2,4-triazol-1-yl group, and R10, X1, X2, and X3 are as previously disclosed by treatment with 1,2,4-triazole in the presence of a base, such as cesium carbonate ($Cs_2CO_3$), and a catalyst, such as copper iodide (CuI), in a solvent, such as DMF. In step ap, the 1,2,4-triazolylacetophenone of Formula XXXV is converted to the trimethylsilyl enol ether of Formula XXXVI by treatment with trimethylsilyl trifluoromethanesulfonate in the presence of a base, such as TEA, in an aprotic solvent, such as $CH_2Cl_2$. In step aq, the silyl enol ether is reacted with a compound of Formula V, wherein Y is Br, R1, R2, R3, R4, R5, R6, and R7 are as previously disclosed in the presence of CuCl and 2,2-bipyridyl in a solvent, such as 1,2-dichlorobenzene at a temperature of about 180° C. to generate a ketone of the Formula XXXVII, wherein R11 is a 1,2,4-triazol-1-yl group, and R1, R2, R3, R4, R5, R6, R7, R10, X1, X2, and X3 are as previously disclosed. In step ar, the ketone of the Formula XXXVII is treated with methylmagnesium bromide in an aprotic solvent, such as THF to generate the tertiary alcohol. The tertiary alcohol then undergoes an elimination reaction when treated with a catalytic amount of p-toluenesulfonic acid in a solvent, such as toluene, when heated to a temperature to allow azeotropic removal of water to produce compounds of Formula One wherein R11 is a 1,2,4-triazol-1-yl group, R8 is methyl, and R1, R2, R3, R4, R5, R6, R7, R10, X1, X2, and X3 are as previously disclosed, as in step as.

Scheme XXXI

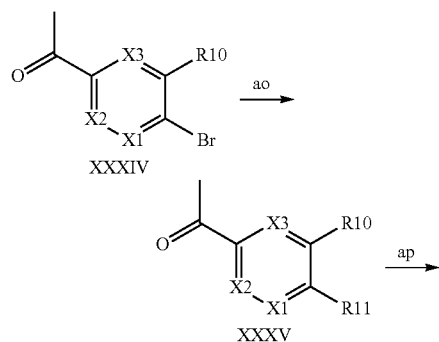

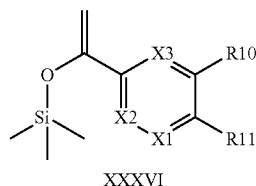

XXXVI

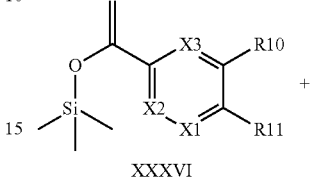

XXXVI

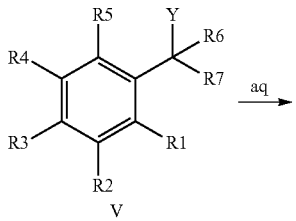

V

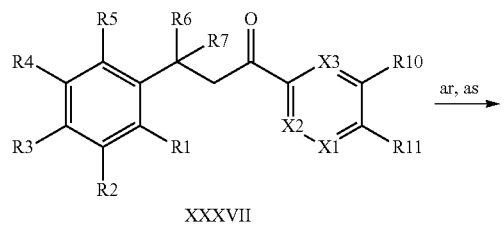

XXXVII

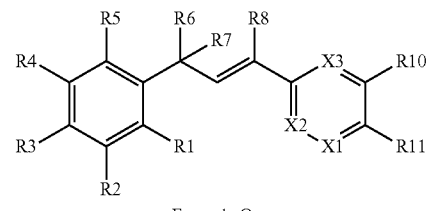

Formula One

In Scheme XXXII, a compound of Formula XXXVIII, wherein R10 and R11 together form a linkage, having 3-4 carbon atoms and an oxo substituent and with the ring carbon atoms form a 5- or 6-membered cyclic ring, and R1, R2, R3, R4, R5, R6, R7, R8, X1, X2, and X3 are as previously disclosed is converted to a molecule of Formula One, wherein R10 and R11 together form a linkage, having 3-4 carbon atoms and an alkylamine substituent with the ring carbon atoms form a 5- or 6-membered cyclic ring and R1, R2, R3, R4, R5, R6, R7, R8, X1, X2, and X3 are as previously disclosed, by treatment with an alkylamine, such as 3,3,3-trifluoropropylamine, in the presence of a reducing agent, such as sodium cyanoborohydride ($NaBH_3CN$), in a solvent, such as 1,2-dichloroethane (DCE).

Scheme XXXII

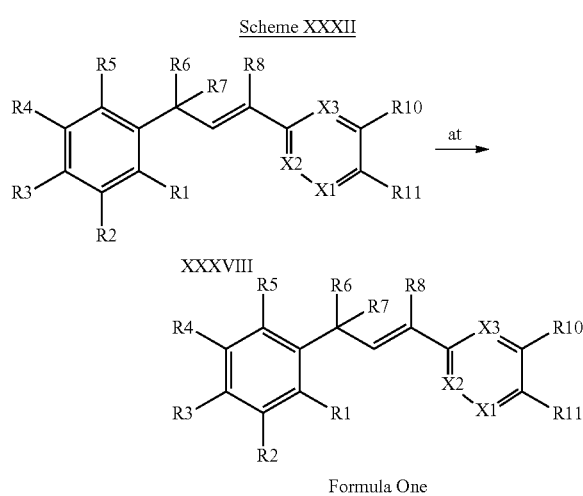

Formula One

In Scheme XXXIII, a compound of Formula XXXIX, wherein X1, X2, and X3 are as previously disclosed is converted to a molecule of Formula XL, wherein X1, X2, and X3 are as previously disclosed, by treatment with a reducing agent, such as NaBH$_3$CN, in a solvent, such as AcOH, as in step au. In step av, the nitrogen atom is protected with a tert-butyloxycarbonyl (BOC) group by reaction with di-tert-butyl dicarbonate in the presence of a catalyst, such as DMAP, in a solvent, such as acetonitrile (MeCN). The bromide of Formula XL can be converted to the olefin of Formula XLI, wherein R8, X1, X2 and X3 are as previously disclosed, by reaction with potassium vinyl trifluoroborate in the presence of a palladium catalyst, such as PdCl$_2$(dppf), and a base, such as K$_2$CO$_3$, in a polar aprotic solvent such as dimethylsulfoxide (DMSO) at 100° C., as in step aw.

Scheme XXXIII

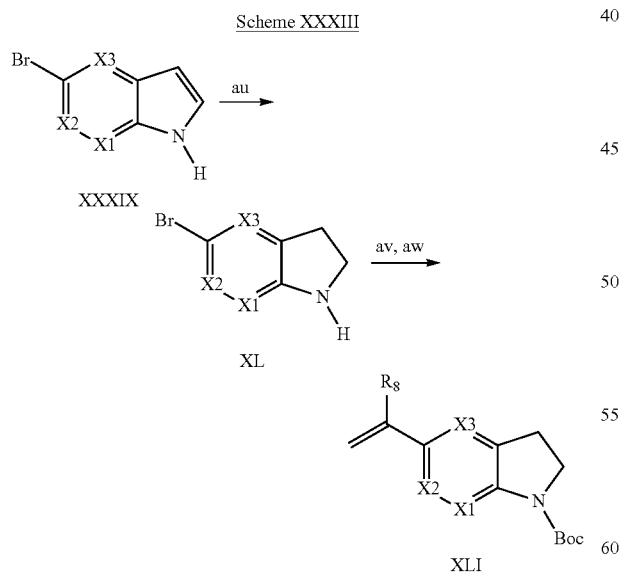

In Scheme XXXIV, a compound of Formula XXXIX, wherein X1, X2, and X3 are as previously disclosed is converted to a molecule of Formula XLII, wherein X1, X2, and X3 are as previously disclosed in two steps. In step ax, the olefin is formed by treatment of the bromide with potassium vinyl trifluoroborate in the presence of a palladium catalyst, such as PdCl$_2$, and a ligand, such as triphenylphosphine, and a base, such as Cs$_2$CO$_3$, in a solvent mixture such as THF/water. In step ay, the nitrogen atom is protected with a BOC group by reaction with di-tert-butyl dicarbonate in the presence of a catalyst, such as DMAP, in a solvent, such as MeCN.

Scheme XXXIV

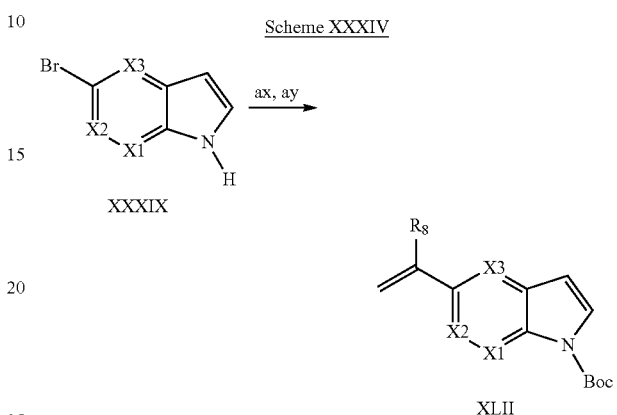

In step 1 of Scheme XXXV, the compound of Formula V, wherein Y, R1, R2, R3, R4, R5, R6, and R7 are as previously disclosed, and the compounds of Formula XLI or XLII, wherein R8, X1, X2 and X3 are as previously disclosed, are allowed to react in the presence of CuCl and 2,2-bipyridyl in a solvent, such as 1,2-dichlorobenzene, at a temperature of about 150° C. to provide the corresponding compounds of Formula XLIIIa or XLIIIb, wherein R1, R2, R3, R4, R5, R6, R7, R8, X1, X2, and X3 are as previously disclosed.

Scheme XXXV

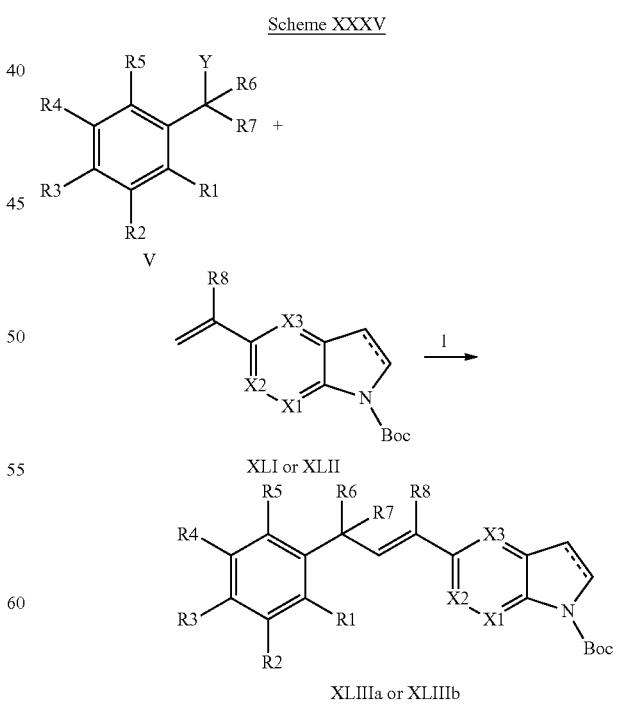

In Scheme XXXVI, a compound of Formula XLIIIa, wherein R1, R2, R3, R4, R5, R6, R7, R8, X1, X2, and X3 are as previously disclosed is converted to a molecule of Formula XLIV, wherein R1, R2, R3, R4, R5, R6, R7, R8, X1, X2, and X3 are as previously disclosed by treatment with trifluoroacetic acid (TFA), in a solvent such as CH$_2$Cl$_2$, as in step az. Compounds of the Formula XLIV can then be transformed into compounds of the Formula XLV wherein R1, R2, R3, R4, R5, R6, R7, R8, X1, X2, and X3 are as previously disclosed, in two steps. In step ba, the indoline is treated with sodium nitrite (NaNO$_2$), in an acid, such as concentrated HCl, at a temperature around 5° C., to form the nitrosoindole. In step bb, the nitrosoindole is reacted with NH$_4$Cl in the presence of zinc powder in a protic solvent, such as MeOH. In step bc, compounds of the Formula XLV are transformed into compounds of the Formula XLVI, wherein X4 is N(R14)(C(=O)R14) and R1, R2, R3, R4, R5, R6, R7, R8, X1, X2, and X3 are as previously disclosed, by treatment with and acid, such as 3,3,3-trifluoropropanoic acid, PyBOP, and a base, such as DIPEA, in a polar aprotic solvent, such as CH$_2$Cl$_2$.

by reaction with 4-nitrophenyl-2-((tert-butoxycarbonyl)amino)acetate in the presence of potassium fluoride (KF) and a crown ether, such as 18-crown-6-ether, in a solvent, such as MeCN, as in step be. Compounds of the Formula XLVIII can be transformed into compounds of the Formula XLIX, wherein R1, R2, R3, R4, R5, R6, R7, R8, X1, X2, and X3 are as previously disclosed in two steps. In step bf, the Boc group is removed by treatment with TFA, in a solvent such as CH$_2$Cl$_2$. In step bg, the amine is treated with 3,3,3-trifluoropropanoic acid, PyBOP, and a base, such as DIPEA, in a polar aprotic solvent, such as CH$_2$Cl$_2$.

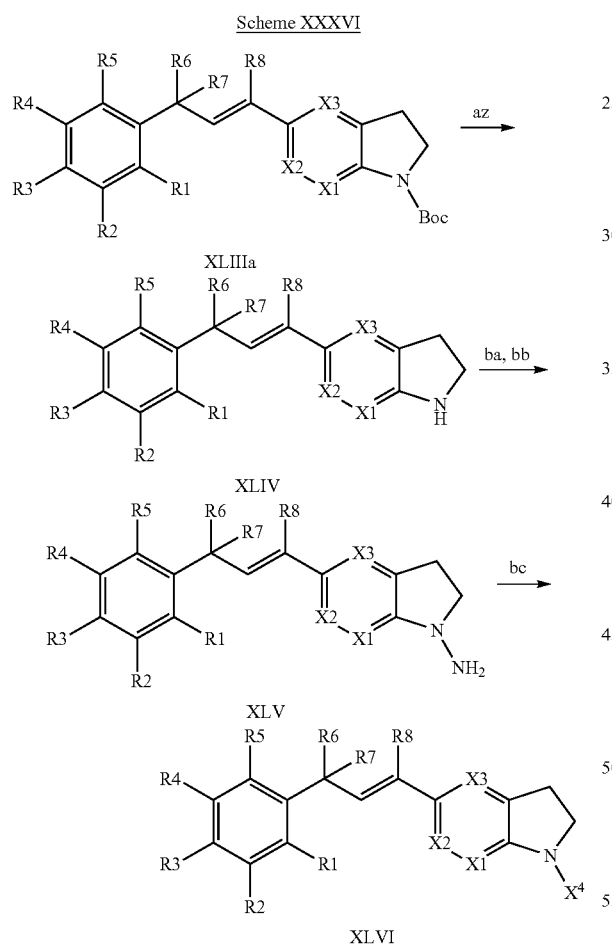

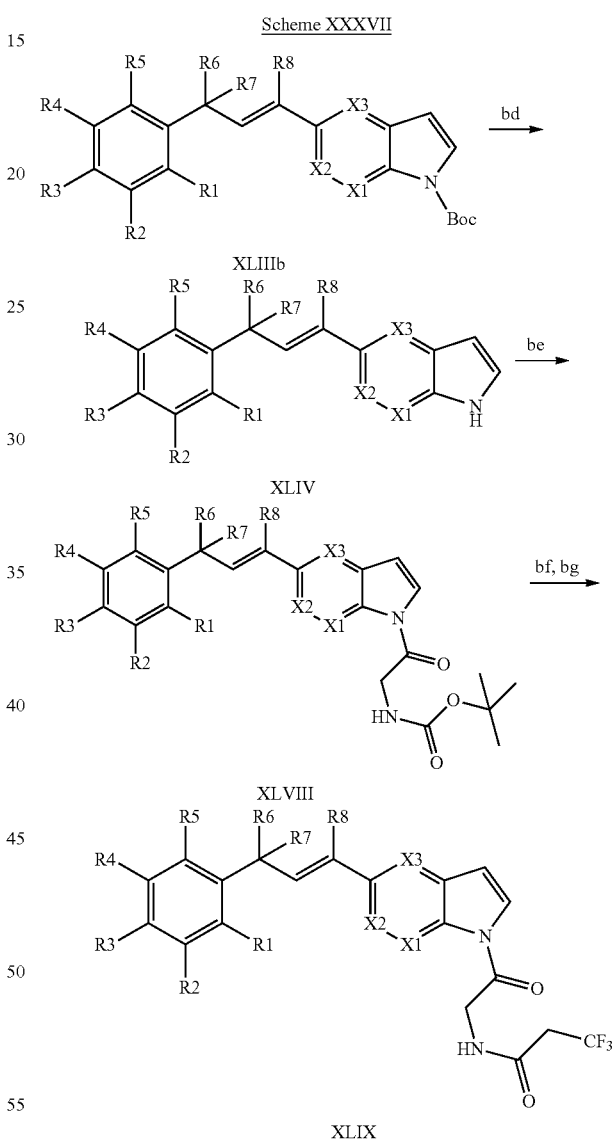

In Scheme XXXVII, a compound of Formula XLIIIb, wherein R1, R2, R3, R4, R5, R6, R7, R8, X1, X2, and X3 are as previously disclosed is converted to an indole of Formula XLVII, wherein R1, R2, R3, R4, R5, R6, R7, R8, X1, X2, and X3 are as previously disclosed by treatment with TFA, in a solvent such as CH$_2$Cl$_2$, as in step bd. Compounds of the Formula XLVII can be transformed into compounds of the Formula XLVIII wherein R1, R2, R3, R4, R5, R6, R7, R8, X1, X2, and X3 are as previously disclosed, In Scheme XXXVIII, a compound of Formula L, wherein X1, X2, and X3 are as previously disclosed is converted to a compound of the Formula LI, wherein X1, X2, and X3 are as previously disclosed by treatment with copper (II) sulfate pentahydrate and Zn powder in a base, such as NaOH as in step bh. Compounds of the Formula LI can be transformed into compounds of the Formula LII wherein X1, X2, and X3 are as previously disclosed, by reaction with hydrazine, in a solvent such as water, at a temperature around 95° C., as in step bi. In step bj, the olefin of the Formula LIII wherein X1, X2, and X3 are as previously disclosed is formed by treatment of the bromide with potassium vinyl trifluoroborate in the presence of a palladium catalyst, such as PdCl$_2$(dppf), and a base, such as K$_2$CO$_3$, in a solvent mixture such as DMSO. Compounds of the Formula LIV, wherein X1, X2, and X3 are as previously disclosed, can be formed from compounds of the Formula LIII by reaction with ethyl bromoacetate, in the presence of a base, such as Cs$_2$CO$_3$, in a solvent, such as DMF.

ester is hydrolyzed to the acid in the presence of HCl and AcOH, at a temperature of about 100° C. In step bm, the acid is treated with an amine, such as 2,2,2-trifluoroethylamine, PyBOP, and a base, such as DIPEA, in a polar aprotic solvent, such as CH$_2$Cl$_2$.

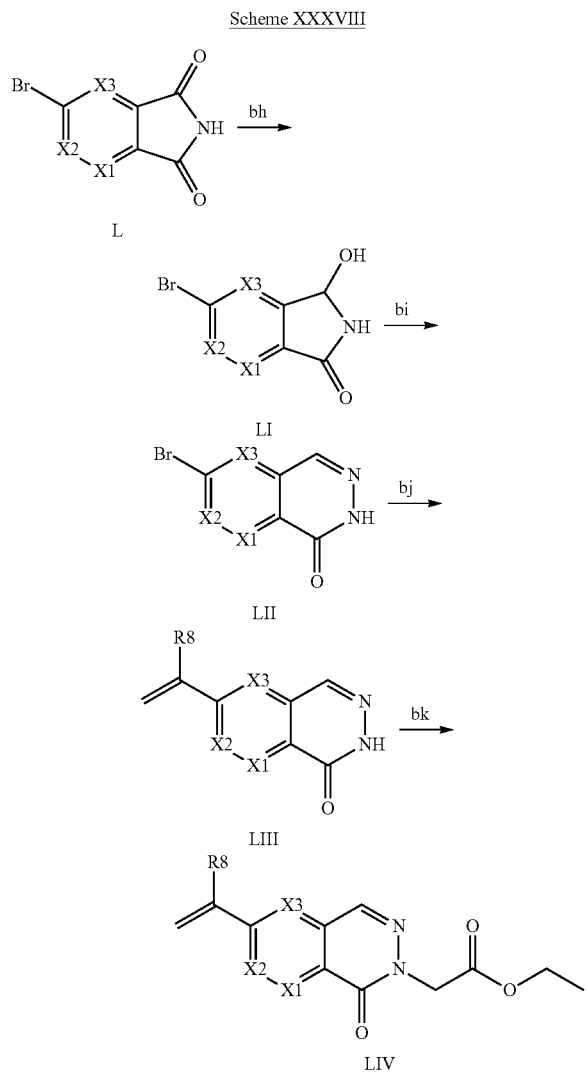

Scheme XXXVIII

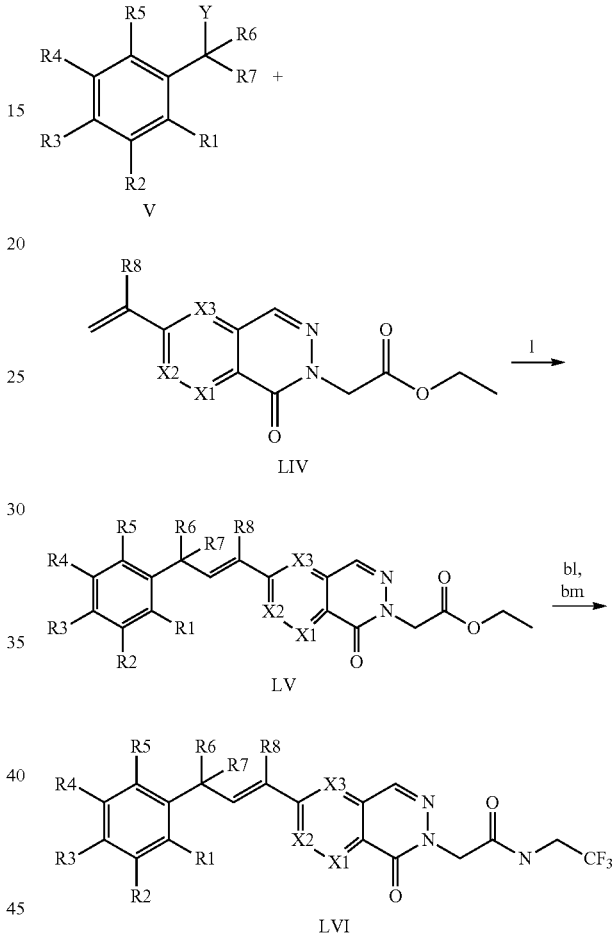

Scheme XXXIX

In step l of Scheme XXXIX, the compound of Formula V, wherein Y, R1, R2, R3, R4, R5, R6, and R7 are as previously disclosed, and the compound of Formula LIV, wherein R8, X1, X2 and X3 are as previously disclosed, are allowed to react in the presence of CuCl and 2,2-bipyridyl in a solvent, such as 1,2-dichlorobenzene, at a temperature of about 180° C. to provide the corresponding compound of Formula LV, wherein R1, R2, R3, R4, R5, R6, R7, R8, X1, X2, and X3 are as previously disclosed. The compound of Formula LV can be further transformed into a compound of the Formula LVI, wherein R1, R2, R3, R4, R5, R6, R7, R8, X1, X2, and X3 are as previously disclosed, in two steps. In step bl, the In step bn of Scheme XL, carboxylic acids of the Formula LVII, wherein R11 is C(=O)OH and R8, R10, X1, X2, and X3 are as previously disclosed and compounds of the Formula V, wherein Y is Br and R1, R2, R3, R4, R5, R6, and R7 are as previously disclosed are allowed to react in the presence of CuCl and 2,2-bipyridyl in a solvent, such as N-methyl pyrrolidine, at a temperature of about 150° C. to afford compounds of Formula LVIII, wherein R11 is (C=O)OH and R1, R2, R3, R4, R5, R6, R7, R8, R9, R10, X1, X2, and X3 are as previously disclosed. Compounds of the Formula LVIII can be further transformed to the corresponding benzamides of Formula LIX, wherein R11 is (C=O)N(R14)(R15), and R1, R2, R3, R4, R5, R6, R7, R8, R9, R10, X1, X2, and X3 are as previously disclosed, by treatment with an amine, such as 2-amino-N-(2,2,2-trifluoroethyl) acetamide, PyBOP, and a base, such as DIPEA, in a polar aprotic solvent, such as CH$_2$Cl$_2$, as in step bo.

Scheme XL

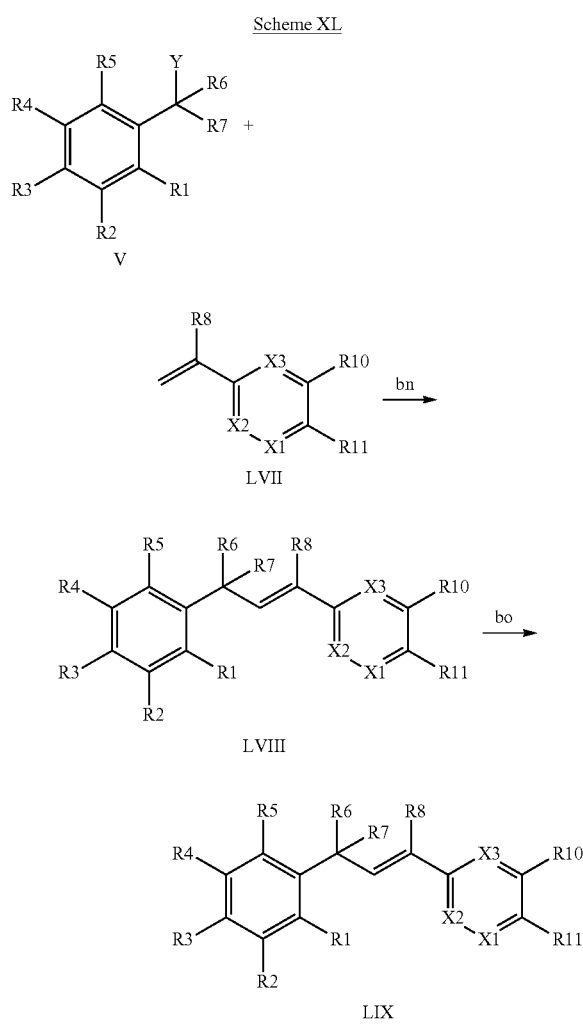

EXAMPLES

The examples are for illustration purposes and are not to be construed as limiting the invention disclosed in this document to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within ISIS Draw, ChemDraw, or ACD Name Pro. If such programs are unable to name a molecule, the molecule is named using conventional naming rules. $^1$H NMR spectral data are in ppm ($\delta$) and were recorded at 300, 400, or 600 MHz, and $^{13}$C NMR spectral data are in ppm ($\delta$) and were recorded at 75, 100, or 150 MHz, unless otherwise stated.

Example 1

Preparation of 1-(1-Bromo-2,2,2-trifluoroethyl)-3,5-dichlorobenzene (AI1)

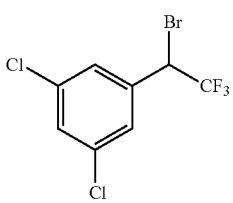 [SMILES: FC(F)(F)C(Br)c1cc(Cl)cc(Cl)c1]

Step 1 Method A.
1-(3,5-Dichlorophenyl)-2,2,2-trifluoroethanol (AI2)

To a stirred solution of 1-(3,5-dichlorophenyl)-2,2,2-trifluoroethanone (procured from Rieke Metals, UK; 5.0 grams (g), 20.5 millimoles (mmol)) in MeOH (100 milliliters (mL)) at 0° C. were added NaBH$_4$ (3.33 g, 92.5 mL) and 1 N aqueous NaOH solution (10 mL). The reaction mixture was warmed to 25° C. and stirred for 2 hours (h). After the reaction was deemed complete by thin layer chromatography (TLC), saturated aqueous NH$_4$Cl solution was added to the reaction mixture, and the mixture was concentrated under reduced pressure. The residue was diluted with diethyl ether (Et$_2$O) and washed with water (3×50 mL). The organic layer was dried over sodium sulfate (Na$_2$SO$_4$) and concentrated under reduced pressure to afford the title compound as a liquid (4.0 g, 79%): $^1$H NMR (400 MHz, CDCl$_3$) $\delta$ 7.41 (m, 3H), 5.00 (m, 2H), 2.74 (s, 1H); ESIMS m/z 242.97 ([M−H]$^−$).

Step 1 Method B.
1-(3,5-Dichlorophenyl)-2,2,2-trifluoroethanol (AI2)

To a stirred solution of 3,5-dichlorobenzaldehyde (10 g, 57 mmol) in THF (250 mL) were added trifluoromethyltrimethylsilane (9.79 g, 69.2 mmol) and a catalytic amount of TBAF. The reaction mixture was stirred at 25° C. for 8 h. After the reaction was deemed complete by TLC, the reaction mixture was diluted with 3 N HCl and then was stirred for 16 h. The reaction mixture was diluted with water and was extracted with ethyl acetate (EtOAc; 3×). The combined organic extracts were washed with brine, dried over Na$_2$SO$_4$, and concentrated under reduced pressure to afford the title compound as a liquid (8.41 g, 60%).

The following compounds were made in accordance with the procedures disclosed in Step 1 Method A of Example 1 above.

2,6-Difluoro-4-(2,2,2-trifluoro-1-hydroxyethyl)benzonitrile

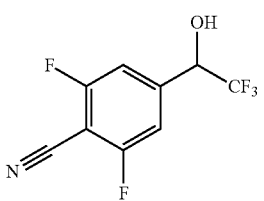 [SMILES: N#Cc1c(F)cc(C(O)C(F)(F)F)cc1F]

The product was isolated as a brown solid: mp 83-87° C.; $^1$H NMR (300 MHz, CDCl$_3$) δ 7.26 (d, J=9.0 Hz, 2H), 5.12 (d, J=6.0 Hz, 1H), 3.06 (s, 1H); ESIMS m/z 237.1 ([M+H]$^+$).

1-(3,5-Difluoro-4-methoxyphenyl)-2,2,2-trifluoroethanol

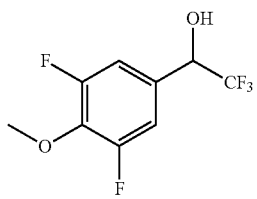 [SMILES: COc1c(F)cc(C(O)C(F)(F)F)cc1F]

The product was isolated as a pale yellow liquid: $^1$H NMR (300 MHz, CDCl$_3$) δ 7.06 (d, J=8.4 Hz, 2H), 4.97-4.94 (m, 1H), 4.03 (s, 3H), 2.64 (s, 1H); EIMS m/z 242.1 ([M]$^+$); IR (thinfilm) 3459, 1135 cm$^{-1}$.

1-(3,4-Dichlorophenyl)-2,2-difluoropropan-1-ol

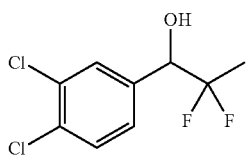

The product was isolated as a colorless liquid: $^1$H NMR (300 MHz, DMSO-d$_6$) δ 7.65-7.62 (m, 2H), 7.41 (d, J=8.4 Hz, 1H), 6.49 (d, J=5.1 Hz, 1H), 4.87-4.78 (m, 1H), 1.53 (t, J=18.9 Hz, 3H); EIMS m/z 240.0 ([M]$^+$); IR (thinfilm) 3434, 1131, 801, 512 cm$^{-1}$.

The following compounds were made in accordance with the procedures disclosed in Step 1 Method B of Example 1 above.

2,2,2-Trifluoro-1-(3,4,5-trichlorophenyl)ethanol (AI3)

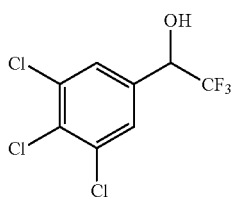 [SMILES: OC(c1cc(Cl)c(Cl)c(Cl)c1)C(F)(F)F]

The product was isolated as a pale yellow liquid (500 mg, 65%): $^1$H NMR (400 MHz, CDCl$_3$) δ 7.45 (s, 2H), 5.00 (m, 1H), 2.80 (s, 1H); ESIMS m/z 278 ([M+H]$^+$); IR (thin film) 3420, 1133, 718 cm$^{-1}$.

1-(3,5-Dichloro-4-fluorophenyl)-2,2,2-trifluoroethanol (AI4)

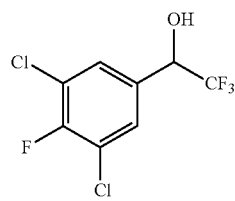 [SMILES: OC(c1cc(Cl)c(F)c(Cl)c1)C(F)(F)F]

The product was isolated as a pale yellow liquid (500 mg, 65%): $^1$H NMR (400 MHz, CDCl$_3$) δ 7.41 (s, 2H), 5.00 (m, 1H), 2.80 (s, 1H); ESIMS m/z 262 ([M+H]$^+$); IR (thin film) 3420, 1133, 718 cm$^{-1}$.

1-(3,4-Dichlorophenyl)-2,2,2-trifluoroethanol (AI5)

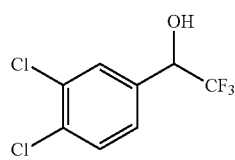 [SMILES: OC(c1ccc(Cl)c(Cl)c1)C(F)(F)F]

The product was isolated as a pale yellow liquid (500 mg, 65%): $^1$H NMR (400 MHz, CDCl$_3$) δ 7.60 (s, 1H), 7.51 (m, 1H), 7.35 (m, 1H), 5.01 (m, 1H), 2.60 (s, 1H); EIMS m/z 244 ([M]$^+$).

1-(3,5-Dibromophenyl)-2,2,2-trifluoroethanol

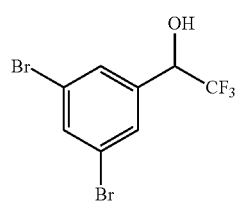

The title molecule was isolated as a colorless liquid: $^1$H NMR (300 MHz, CDCl$_3$) δ 7.67 (s, 1H), 7.58 (s, 2H), 5.08-5.02 (m, 1H), 4.42 (bs, 1H); EIMS m/z 333.7 ([M]$^+$); IR (thin film) 3417, 2966, 1128, 531 cm$^{-1}$.

2,2,2-Trifluoro-1-(3-fluoro-5-(trifluoromethyl)phenyl)ethanol

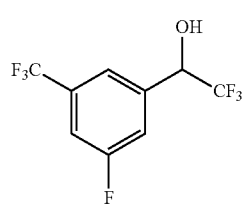 [SMILES: OC(c1cc(F)cc(C(F)(F)F)c1)C(F)(F)F]

The title molecule was isolated as a clear, colorless oil: $^1$H NMR (400 MHz, CDCl$_3$) δ 7.56 (s, 1H), 7.45-7.37 (m, 2H), 5.11 (q, J=6.4 Hz, 1H), 3.22 (bs, 1H); $^{13}$C NMR (101 MHz, CDCl$_3$) δ 162.42 (d, J=249.5 Hz), 137.46 (d, J=7.8 Hz), 132.89 (qd, J=33.5, 7.9 Hz), 123.67 (q, J=283.8 Hz), 122.92 (q, J=270.68 Hz), 120.10 (t, J=4.1 Hz), 118.13 (d, J=23.0 Hz), 113.94 (dq, J=24.2, 3.9 Hz), 71.57 (q, J=32.4 Hz); EIMS m/z 262 ([M]$^+$).

1-(3-Chloro-5-(trifluoromethyl)phenyl)-2,2,2-trifluoroethanol

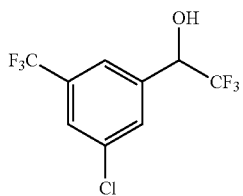 [SMILES: OC(c1cc(Cl)cc(C(F)(F)F)c1)C(F)(F)F]

The product was isolated as a white solid (4.98 g, 77%): mp 42-46° C.; $^1$H NMR (400 MHz, CDCl$_3$) δ 7.83-7.50 (m, 3H), 5.10 (p, J=6.2 Hz, 1H), 2.88 (d, J=4.3 Hz, 1H); $^{13}$C NMR (101 MHz, CDCl$_3$) δ 137.12, 135.84, 131.4, 133.03 (q, J=33.3 Hz), 127.15 (q, J=3.8 Hz), 124.50 (q, J=308.0 Hz), 123.45 (q, J=301.8 Hz), 123.04, 72.06 (q, J=32.5 Hz); $^{19}$F NMR (376 MHz, CDCl$_3$) δ −62.93, −78.43; EIMS m/z 278 ([M]$^+$).

2,2,2-Trifluoro-1-(4-fluoro-3-(trifluoromethyl)phenyl)ethanol

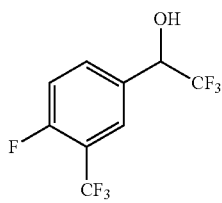 [SMILES: OC(c1ccc(F)c(C(F)(F)F)c1)C(F)(F)F]

The product was isolated as a brown liquid: $^1$H NMR (400 MHz, CDCl$_3$) δ 7.76 (d, J=6.8 Hz, 1H), 7.69-7.67 (m, 1H), 7.28-7.23 (m, 1H), 5.05-5.02 (m, 1H); ESIMS m/z 261.1 ([M−H]$^−$); IR (thin film) 3418, 1131 cm$^{-1}$.

2,2,2-Trifluoro-1-(3,4,5-trifluorophenyl)ethanol

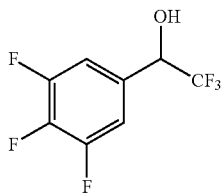 [SMILES: OC(c1cc(F)c(F)c(F)c1)C(F)(F)F]

The product was isolated as a colorless liquid: $^1$H NMR (300 MHz, CDCl$_3$) δ 7.19-7.10 (m, 2H), 5.03-4.96 (m, 1H), 2.85 (bs, 1H); EIMS m/z 230.1 ([M]$^+$).

2,2,2-Trifluoro-1-(2,3,4-trifluorophenyl)ethanol

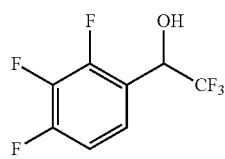

The product was isolated as a clear colorless liquid (4.61 g 66%): $^1$H NMR (400 MHz, CDCl$_3$) δ 7.23 (qd, J=7.4, 6.1, 4.2 Hz, 1H), 6.93 (tdd, J=9.2, 6.9, 2.2 Hz, 1H), 5.25 (q, J=6.3 Hz, 1H), 3.02-2.74 (m, 1H); $^{13}$C NMR (101 MHz, CDCl$_3$) δ 151.79 (ddd, J=254.5, 9.8, 3.4 Hz), 149.52 (ddd, J=253.5, 11.0, 3.5 Hz), 139.67 (dt, J=252.5, 15.3 Hz), 123.68 (q, J=282.2 Hz), 122.48 (dt, J=8.2, 4.1 Hz), 118.95 (dd, J=10.6, 3.6 Hz), 112.73 (dd, J=17.7, 3.9 Hz), 66.58-64.42 (m); $^{19}$F NMR (376 MHz, CDCl$_3$) δ −78.95 (d, J=6.2 Hz), −132.02 (dd, J=20.0, 8.2 Hz), −137.89 (m), 159.84 (t, J=20.3 Hz); EIMS m/z 230 ([M]$^+$).

2,2,2-Trifluoro-1-(2,4,5-trichlorophenyl)ethanol

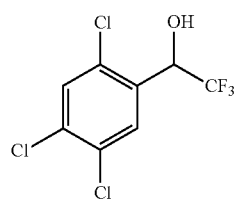 [SMILES: OC(c1cc(Cl)c(Cl)cc1Cl)C(F)(F)F]

The product was isolated as a white solid (3.37 g, 73%): mp 70-73° C.; $^1$H NMR (400 MHz, CDCl$_3$) δ 7.63 (d, J=2.5 Hz, 1H), 7.54 (d, J=2.5 Hz, 1H), 5.72-5.57 (m, 1H), 2.85 (d, J=4.8 Hz, 1H); $^{19}$F NMR (376 MHz, CDCl$_3$) δ −77.84.

1-(4-Chloro-3-nitrophenyl)-2,2,2-trifluoroethanol

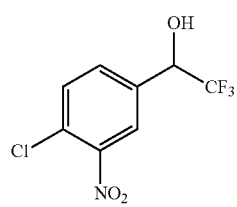

The product was isolated as a yellow oil (6.52 g, 73%): $^1$H NMR (400 MHz, CDCl$_3$) δ 8.04 (d, J=2.0 Hz, 1H), 7.75-7.51 (m, 2H), 5.16 (m, 1H), 3.41 (d, J=4.3 Hz, 1H); $^{13}$C NMR (101 MHz, CDCl3) δ 147.65, 134.44, 132.23, 132.17, 128.11, 124.66, 123.60 (q, J=283.8 Hz), 70.99 (q, J=32.6 Hz); $^{19}$F NMR (376 MHz, CDCl$_3$) δ −78.47; EIMS m/z 230 ([M]$^+$).

2,2,2-Trifluoro-1-(4-fluoro-3,5-dimethylphenyl)ethanol

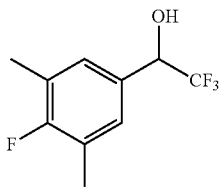

The product was isolated as a white solid (6.49 g, 84%): mp 45-49° C.; ¹H NMR (400 MHz, CDCl₃) δ 7.10 (d, J=6.8 Hz, 2H), 4.89 (m, 1H), 2.63 (d, J=4.3 Hz, 1H), 2.27 (d, J=2.2 Hz, 6H); ¹³C NMR (101 MHz, CDCl₃) δ 160.45 (d, J=246.0 Hz), 128.73, 127.97, 124.92 (d, J=18.6 Hz), 124.19 (q, J=279.1 Hz), 72.36 (q, J=32.0 Hz), 14.61 (d, J=4.1 Hz). ¹⁹F NMR (376 MHz, CDCl₃) δ −78.48, −120.14; EIMS m/z 222 ([M]⁺).

2,2,2-Trifluoro-1-(4-fluoro-3-methylphenyl)ethanol

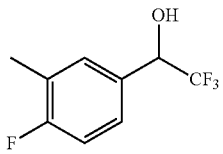

The product was isolated as a white solid (2.12 g, 33%): mp 40-46° C.; ¹H NMR (400 MHz, CDCl₃) δ 7.28 (d, J=7.4 Hz, 1H), 7.25-7.14 (m, 1H), 7.01 (t, J=8.9 Hz, 1H), 5.05-4.63 (m, 1H), 3.03 (d, J=4.2 Hz, 1H); ¹³C NMR (101 MHz, CDCl₃) δ 161.91 (d, J=247.0 Hz), 130.62 (d, J=5.6 Hz), 129.41 (d, J=3.5 Hz), 126.55 (d, J=8.5 Hz), 115.19 (d, J=22.9 Hz), 72.23 (q, J=32.1 Hz), 14.44 (d, J=3.6 Hz); ¹⁹F NMR (376 MHz, CDCl₃) δ −78.57, −116.15; EIMS m/z 208 ([M]⁺).

1-(3-Chloro-4-methylphenyl)-2,2,2-trifluoroethanol

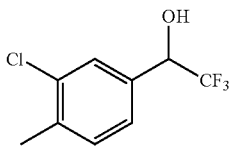

The product was isolated as a clear colorless oil (4.99 g, 75%): ¹H NMR (400 MHz, CDCl3) δ 7.31 (s, 1H), 7.10 (m, 2H), 4.79 (q, J=6.1 Hz, 1H), 2.89 (bs, 1H), 2.25 (s, 3H); ¹³C NMR (101 MHz, CDCl3) δ 137.64, 134.67, 132.99, 131.09, 128.01, 125.58, 124.02 (q, J=284.8 Hz), 72.08 (q, J=32.3 Hz); ¹⁹F NMR (376 MHz, CDCl₃) δ −78.39; EIMS m/z 224.5 ([M]⁺).

1-(3,4-Dibromophenyl)-2,2,2-trifluoroethanol

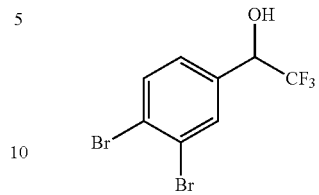

The product was isolated as a clear colorless oil (5.92 g, 88%): ¹H NMR (400 MHz, CDCl₃) δ 7.76 (d, J=2.0 Hz, 1H), 7.66 (d, J=8.3 Hz, 1H), 7.29 (dd, J=8.3, 2.0 Hz, 1H), 4.99 (qd, J=6.4, 4.2 Hz, 1H), 2.75 (d, J=4.3 Hz, 1H); ¹³C NMR (101 MHz, CDCl₃) δ 134.52, 133.81, 132.60, 127.45, 126.19, 125.16, 123.71 (q, J=283.8 Hz), 71.57 (q, J=32.5 Hz); ¹⁹F NMR (376 MHz, CDCl₃) δ −78.44; EIMS m/z 334 ([M]⁺).

2,2,2-Trifluoro-1-(3-(trifluoromethoxy)phenyl)ethanol

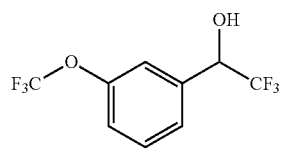 [SMILES: OC(c1cccc(OC(F)(F)F)c1)C(F)(F)F]

The product was isolated as a clear colorless oil (20.9 g, 79%): ¹H NMR (400 MHz, CDCl₃) δ 7.55-7.36 (m, 3H), 7.33-7.14 (m, 1H), 5.06 (m, 1H), 2.80 (br m, 1H); ¹³C NMR (101 MHz, CDCl₃) δ 149.36 (q, J=2.0 Hz), 136.04, 129.99, 125.78, 123.91 (q, J=282.8 Hz), 121.90, 120.31 (q, J=258.6 Hz), 120.12, 72.04 (q, J=32.3 Hz); ¹⁹F NMR (376 MHz, CDCl₃) δ −57.92, −78.49; EIMS m/z 260 ([M]⁺).

2-Fluoro-5-(2,2,2-trifluoro-1-hydroxyethyl)benzonitrile

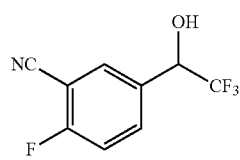 [SMILES: N#Cc1cc(C(O)C(F)(F)F)ccc1F]

The product was isolated as a clear colorless oil (5.47 g, 58%): ¹H NMR (400 MHz, CDCl₃) δ 7.80 (dd, J=5.9, 2.2 Hz, 1H), 7.76 (ddd, J=7.8, 5.0, 2.3 Hz, 1H), 7.30 (d, J=8.6 Hz, 1H), δ 5.09 (qd, J=6.3, 4.2 Hz, 1H), 3.12 (bm, 1H); ¹³C NMR (101 MHz, CDCl₃) δ 163.49 (d, J=261.7 Hz), 134.23 (d, J=8.6 Hz), 132.67, 131.17, 123.66 (q, J=282.4 Hz), 116.79 (d, J=20.1 Hz), 113.39, 100.96 (d, J=194.9), 71.07 (q, J=32.5 Hz); ¹⁹F NMR (376 MHz, CDCl₃) δ −78.70, −105.22; EIMS m/z 219 ([M]⁺).

1-(3-Bromo-5-chlorophenyl)-2,2,2-trifluoroethanol

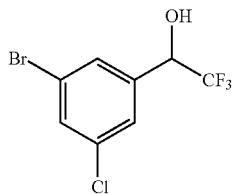 [SMILES: OC(c1cc(Cl)cc(Br)c1)C(F)(F)F]

The product was isolated as a yellow liquid: $^1$H NMR (300 MHz, DMSO-$d_6$) δ 7.78 (s, 1H), 7.67 (s, 1H), 7.57 (s, 1H), 7.15 (d, J=5.7 Hz, 1H); EIMS m/z 288 ([M]$^+$); IR (thin film) 3435, 1175, 750 cm$^{-1}$.

1-(3-Bromo-5-fluorophenyl)-2,2,2-trifluoroethanol

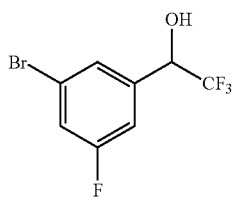 [SMILES: OC(c1cc(F)cc(Br)c1)C(F)(F)F]

The product was isolated as a pale yellow liquid: $^1$H NMR (400 MHz, CDCl$_3$) δ 7.43 (s, 1H), 7.29-7.26 (m, 1H), 7.18 (d, J=8.8 Hz, 1H), 5.03-4.98 (m, 1H), 3.60 (bs, 1H). EIMS m/z 272.0 ([M]$^+$); IR (thin film) 3400, 1176, 520 cm$^{-1}$.

1-(3,5-Dichlorophenyl)-2,2,3,3,3-pentafluoropropan-1-ol

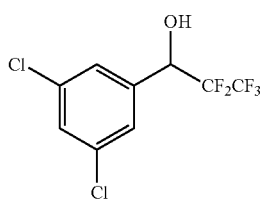

Using pentafluoroethyltrimethylsilane, the product was isolated as a white solid (6.22 g, 88%): mp 71-73° C.; $^1$H NMR (400 MHz, CDCl$_3$) δ 7.42 (t, J=1.9 Hz, 1H), 7.37 (d, J=1.8 Hz, 2H), 5.11 (dt, J=16.2, 5.7 Hz, 1H), 2.62 (d, J=4.9 Hz, 1H); $^{13}$C NMR (101 MHz, CDCl$_3$) δ 136.90, 135.31, 129.84, 126.38, 70.94 (dd, J=28.2, 23.1 Hz); $^{19}$F NMR (376 MHz, CDCl$_3$) δ -81.06, -120.94 (d, J=277.5 Hz), -129.18 (d, J=277.5 Hz); EIMS m/z 295 ([M]$^+$).

2,2,3,3,3-Pentafluoro-1-(3,4,5-trichlorophenyl)propan-1-ol

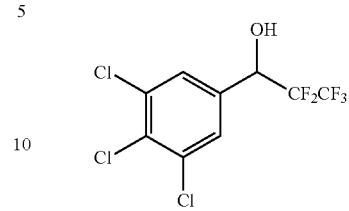

Using pentafluoroethyltrimethylsilane, the product was isolated as an off white semi solid: $^1$H NMR (300 MHz, DMSO-$d_6$) δ 7.78 (s, 2H), 7.29 (d, J=5.4 Hz), 5.50-5.40 (m, 1H); EIMS m/z 328.0 ([M]$^+$); IR (thin film) 3459, 1188, 797 cm$^{-1}$.

2,2,2-Trifluoro-1-(3-(trifluoromethyl)phenyl)ethanol

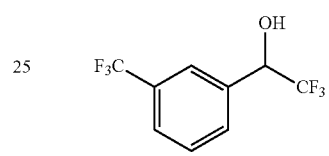

The product was isolated as a light yellow (13.8 g, 89%): $^1$H NMR (400 MHz, CDCl$_3$) δ 7.77 (s, 1H), 7.70-7.67 (m, 2H), 7.55 (t, J=7.8 Hz, 1H), 5.12 (q, J=6.6 Hz, 1H), 2.76 (s, 1H); $^{19}$F NMR (376 MHz, CDCl$_3$) δ -62.8, -78.5; EIMS m/z 244 ([M]$^+$).

1-(3,4-Dichloro-5-methylphenyl)-2,2,2-trifluoroethanol

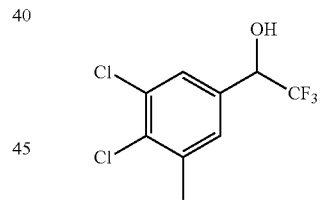

The product was isolated as an off pale yellow solid: $^1$H NMR (400 MHz, CDCl$_3$) δ 7.44 (s, 1H), 7.26 (s, 1H), 4.98-4.95 (m, 1H), 2.61 (d, J=4.4 Hz, 1H), 2.44 (s, 3H). EIMS m/z 258.1 ([M]$^+$); IR (thin film) 3421, 2926, 1129, 748 cm$^{-1}$.

1-(3-Chloro-5-ethylphenyl)-2,2,2-trifluoroethanol

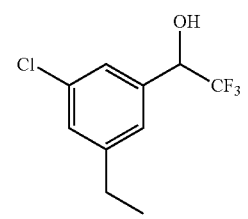

The product was isolated as an off brown liquid (0.43 g, 85%): ¹H NMR (300 MHz, DMSO-$d_6$) δ 7.34 (s, 1H), 7.31-7.30 (m, 2H), 6.99 (d, J=5.7 Hz, 1H), 5.23-5.16 (m, 1H), 2.67 (m, 2H), 1.19 (t, J=7.8 Hz, 3H); EIMS m/z 238.0 ([M]⁺); IR (thin film) 3361, 1172, 749 cm⁻¹.

1-(4-Bromo-3,5-dichlorophenyl)-2,2,2-trifluoroethanol

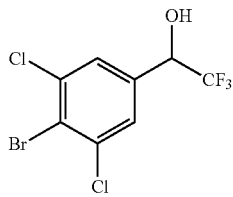

The product was isolated as a colorless liquid: ¹H NMR (300 MHz, DMSO-$d_6$) δ 7.75 (s, 2H), 7.24 (d, J=6.0 Hz, 1H), 5.34-5.29 (m, 1H); EIMS m/z 321.88 ([M]⁺); IR (thin film) 3420, 1706, 1267, 804, 679 cm⁻¹.

1-(3,5-Dibromo-4-chlorophenyl)-2,2,2-trifluoroethanol

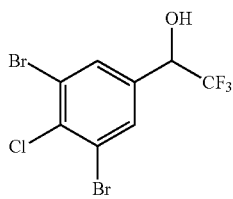 [SMILES: OC(c1cc(Br)c(Cl)c(Br)c1)C(F)(F)F]

The product was isolated as a pale yellow gum: ¹H NMR (300 MHz, DMSO-$d_6$) δ 7.89 (s, 2H), 7.20 (d, J=6.0 Hz, 1H) 5.34-5.30 (m, 1H); EIMS m/z 366.0 ([M]⁺).

Step 2. 1-(1-Bromo-2,2,2-trifluoroethyl)-3,5-dichlorobenzene (AI1)

To a stirred solution of 1-(3,5-dichlorophenyl)-2,2,2-trifluoroethanol (4.0 g, 16.3 mmol) in CH₂Cl₂ (50 mL), were added NBS (2.9 g, 16.3 mmol) and triphenyl phosphite (5.06 g, 16.3 mmol), and the resultant reaction mixture was heated at reflux for 18 h. After the reaction was deemed complete by TLC, the reaction mixture was cooled to 25° C. and was concentrated under reduced pressure. Purification by flash column chromatography (SiO₂, 100-200 mesh; eluting with 100% pentane) afforded the title compound as a liquid (2.0 g, 40%): ¹H NMR (400 MHz, CDCl₃) δ 7.41 (s, 3H), 5.00 (m, 1H); EIMS m/z 306 ([M]⁺).

The following compounds were made in accordance with the procedures disclosed in Step 2 of Example 1.

5-(1-Bromo-2,2,2-trifluoroethyl)-1,2,3-trichlorobenzene (AI6)

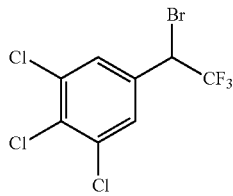 [SMILES: FC(F)(F)C(Br)c1cc(Cl)c(Cl)c(Cl)c1]

The product was isolated as a colorless oil (300 mg, 60%): ¹H NMR (400 MHz, CDCl₃) δ 7.59 (s, 2H), 5.00 (m, 1H); EIMS m/z 340.00 ([M]⁺).

5-(1-Bromo-2,2,2-trifluoroethyl)-1,3-dichloro-2-fluorobenzene (AI7)

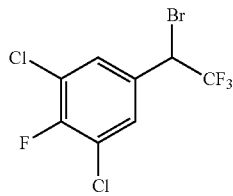 [SMILES: Fc1c(Cl)cc(C(Br)C(F)(F)F)cc1Cl]

The product was isolated as a colorless oil (320 mg, 60%): ¹H NMR (400 MHz, CDCl₃) δ 7.45 (s, 2H), 5.00 (m, 2H); EIMS m/z 324.00 ([M]⁺).

4-(1-Bromo-2,2,2-trifluoroethyl)-1,2-dichlorobenzene (AI8)

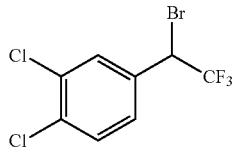 [SMILES: FC(F)(F)C(Br)c1ccc(Cl)c(Cl)c1]

The product was isolated as a colorless oil (300 mg, 60%): ¹H NMR (400 MHz, CDCl₃) δ 7.63 (s, 1H), 7.51 (m, 1H), 7.35 (m, 1H), 5.01 (m, 1H); EIMS m/z 306.00 ([M]⁺).

1,3-Dibromo-5-(1-bromo-2,2,2-trifluoroethyl)benzene

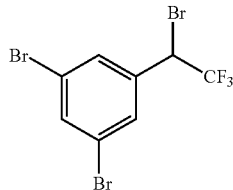

The title molecule was isolated as a colorless liquid: ¹H NMR (300 MHz, CDCl₃) δ 7.71 (s, 1H), 7.59 (s, 2H), 5.04-4.97 (m, 1H); EIMS m/z 394.6 ([M]⁺); IR (thin film) 1114, 535 cm⁻¹.

1-(1-Bromo-2,2,2-trifluoroethyl)-3-fluoro-5-(trifluoromethyl)benzene

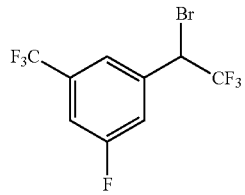

The title molecule was isolated as a colorless liquid: ¹H NMR (400 MHz, DMSO-d₆) δ 7.90 (d, J=8.4 Hz, 1H), 7.79-7.77 (m, 2H), 6.40-6.34 (m, 1H); EIMS m/z 324.00 ([M]⁺); IR (thin film) 1175, 525 cm⁻¹.

1-(1-Bromo-2,2,2-trifluoroethyl)-3-chloro-5-(trifluoromethyl)benzene

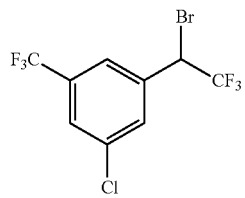

The title molecule was isolated as a colorless liquid: ¹H NMR (400 MHz, CDCl3) δ 7.71 (s, 1H), 7.67 (s, 1H), 7.64 (s, 1H), 5.15-5.09 (m, 1H); EIMS m/z 340.00 ([M]⁺); IR (thin film) 1178, 750, 540 cm⁻¹.

4-(1-Bromo-2,2,2-trifluoroethyl)-1-fluoro-2-(trifluoromethyl)benzene

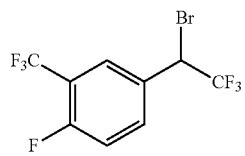

The title molecule was isolated as a colorless liquid: ¹H NMR (400 MHz, CDCl₃) δ 7.75-7.72 (m, 2H), 7.28-7.24 (m, 1H), 5.19-5.16 (m, 1H); EIMS m/z 326.0 ([M]⁺); IR (thin film) 1114, 571 cm⁻¹.

5-(1-Bromo-2,2,2-trifluoroethyl)-1,2,3-trifluorobenzene

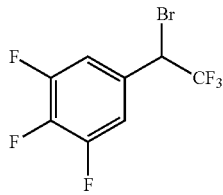 [SMILES: Fc1cc(C(Br)C(F)(F)F)cc(F)c1F]

The title molecule was isolated as a brown liquid: ¹H NMR (300 MHz, CDCl₃) δ 7.23-7.12 (m, 2H), 5.05-4.98 (m, 1H); EIMS m/z 292.0 ([M]⁺); IR (thin film) 1116, 505 cm⁻¹.

1-(1-Bromo-2,2,2-trifluoroethyl)-2,3,4-trifluorobenzene

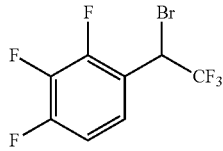

The title molecule was isolated as a colorless oil: ¹H NMR (300 MHz, CDCl₃) δ 7.44 (qd, J=m, 1H), 7.11-7.03 (m, 1H), 5.53-5.45 (m, 1H).

1-(1-Bromo-2,2,2-trifluoroethyl)-2,4,5-trichlorobenzene

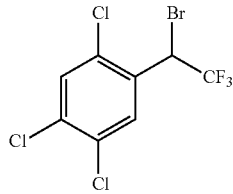 [SMILES: FC(F)(F)C(Br)c1cc(Cl)c(Cl)cc1Cl]

The title molecule was isolated as an off white solid: ¹H NMR (300 MHz, DMSO-d₆) δ 8.06 (d, J=2.1 Hz, 1H), 7.71 (s, 1H), 6.45-6.37 (m, 1H); EIMS m/z 340.0 ([M]⁺); IR (thin film) 1186, 764, 576 cm⁻¹.

4-(1-Bromo-2,2,2-trifluoroethyl)-1-chloro-2-nitrobenzene

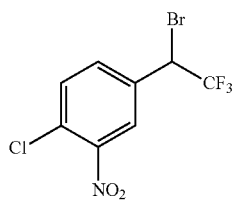 [SMILES: O=[N+]([O-])c1cc(C(Br)C(F)(F)F)ccc1Cl]

The title molecule was isolated as an off white solid: ¹H NMR (300 MHz, DMSO-d₆) δ 8.30 (s, 1H), 7.92 (d, J=9.0

Hz, 1H), 6.43-6.35 (m, 1H); EIMS m/z 317.0 ([M]⁺); IR (thin film) 2927, 1540, 1353, 1177, 766, 530 cm⁻¹.

5-(1-Bromo-2,2,2-trifluoroethyl)-2-fluoro-1,3-dimethylbenzene

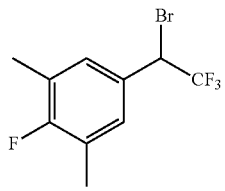

The title molecule was isolated as a colorless liquid: $^1$H NMR (300 MHz, DMSO-d$_6$) δ 7.32 (d, J=7.2 Hz, 2H), 6.15-6.07 (m, 1H), 3.23 (s, 6H); ESIMS m/z 284.1 ([M+H]⁺); IR (thin film) 2962, 1112, 500 cm⁻¹.

4-(1-Bromo-2,2,2-trifluoroethyl)-1-fluoro-2-methylbenzene

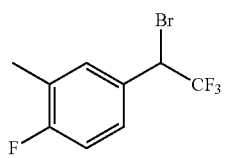

The title molecule was isolated as a colorless liquid: $^1$H NMR (300 MHz, CDCl$_3$) δ 7.34-7.28 (m, 2H), 7.04-6.98 (m, 1H), 5.10-5.03 (m, 1H), 2.29 (s, 3H); EIMS m/z 270.1 ([M]⁺); IR (thin film) 2989, 1163 cm⁻¹.

1-(1-Bromo-2,2,3,3,3-pentafluoropropyl)-3,5-dichlorobenzene

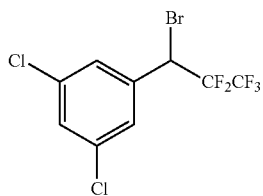

The title molecule was isolated as a colorless liquid: $^1$H NMR (400 MHz, DMSO-d$_6$) δ 7.79 (t, J=2.0 Hz, 1H), 7.63 (S, 2H), 6.37-6.29 (m, 1H); EIMS m/z 356 ([M]⁺); IR (thin film) 1673, 1130, 715, 518 cm⁻¹.

4-(1-Bromo-2,2,2-trifluoroethyl)-2-chloro-1-methylbenzene

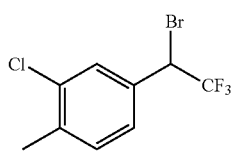

The title molecule was isolated as a colorless liquid: $^1$H NMR (300 MHz, CDCl$_3$) δ 7.55-7.50 (m, 2H), 7.44 (d, J=8.4 Hz, 1H), 6.24-6.16 (m, 1H); IR (thin film) 2983, 1112, 749, 564 cm⁻¹.

1,2-Dibromo-4-(1-bromo-2,2,2-trifluoroethyl)benzene

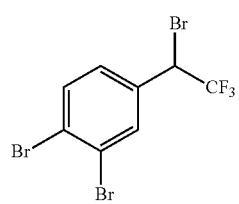 [SMILES: FC(F)(F)C(Br)c1ccc(Br)c(Br)c1]

The title molecule was isolated as a colorless liquid: $^1$H NMR (300 MHz, CDCl$_3$) δ 7.75 (s, 1H), 7.67 (d, J=8.4 Hz, 1H), 7.33-7.30 (m, 1H), 5.07-5.00 (m, 1H); EIMS m/z 393.8 ([M]⁺); IR (thin film) 2981, 1644, 1165 cm⁻¹.

1-(1-Bromo-2,2,2-trifluoroethyl)-3-(trifluoromethoxy)benzene

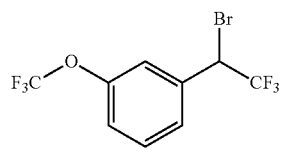 [SMILES: FC(F)(F)Oc1cccc(C(Br)C(F)(F)F)c1]

The title molecule was isolated as a colorless liquid: $^1$H NMR (300 MHz, DMSO-d$_6$) δ 7.65-7.60 (m, 2H), 7.56-7.50 (m, 2H), 6.35-6.27 (m, 1H); EIMS m/z 322 ([M]⁺); IR (thin film) 3413, 1161, 564 cm⁻¹.

5-(1-Bromo-2,2,2-trifluoroethyl)-2-fluorobenzonitrile

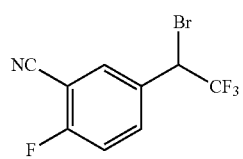 [SMILES: N#Cc1cc(C(Br)C(F)(F)F)ccc1F]

The title molecule was isolated as a pale yellow liquid: $^1$H NMR (300 MHz, CDCl$_3$) δ 8.15-8.12 (m, 1H), 8.00-7.98 (m, 1H), 7.69-7.63 (m, 1H), 6.31-6.26 (m, 1H); EIMS m/z 280.9 ([M]⁺).

1-Bromo-3-(1-bromo-2,2,2-trifluoroethyl-5-chlorobenzene

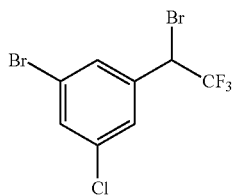

The title molecule was isolated as a pale yellow liquid: $^1$H NMR (400 MHz, DMSO-$d_6$) δ 7.90 (s, 1H), 7.74 (s, 1H), 7.65 (s, 1H), 6.26-6.20 (m, 1H); EIMS m/z 349.9 ([M]$^+$); IR (thin film) 1114, 764 cm$^{-1}$.

1-Bromo-3-(1-bromo-2,2,2-trifluoroethyl)-5-fluorobenzene

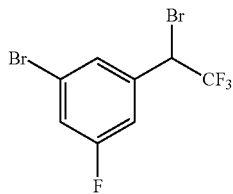 [SMILES: Fc1cc(Br)cc(C(Br)C(F)(F)F)c1]

The title molecule was isolated as a colorless liquid: $^1$H NMR (400 MHz, CDCl$_3$) δ 7.43 (s, 1H), 7.32-7.29 (m, 1H), 7.22 (d, J=8.8 Hz, 1H), 1.06 (q, 1H); EIMS m/z 334.0 ([M]$^+$); IR (thin film) 3087, 1168, 533 cm$^{-1}$.

5-(1-Bromo-2,2,3,3,3-pentafluoropropyl)-1,2,3-trichlorobenzene

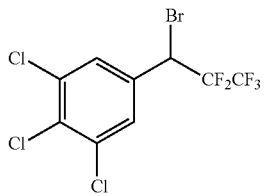

The title molecule was isolated as a colorless liquid: $^1$H NMR (300 MHz, DMSO-$d_6$) δ 7.85 (s, 2H), 6.38-6.29 (m, 1H); EIMS m/z 389.9 ([M]$^+$); IR (thin film) 1208, 798, 560 cm$^{-1}$.

4-(1-Bromo-2,2,2-trifluoroethyl)-2,6-difluorobenzonitrile

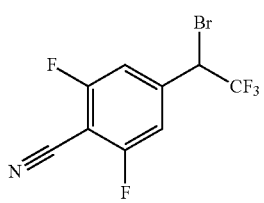 [SMILES: N#Cc1c(F)cc(C(Br)C(F)(F)F)cc1F]

The title molecule was isolated as a purple solid: mp 59-63° C.; $^1$H NMR (400 MHz, CDCl$_3$) δ 7.25 (s, 2H), 5.11-5.07 (m, 1H); ESIMS m/z 299.0 ([M+H]$^+$).

1-(1-Bromo-2,2,2-trifluoroethyl)-3-(trifluoromethyl)benzene

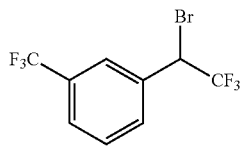 [SMILES: FC(F)(F)c1cccc(C(Br)C(F)(F)F)c1]

The title molecule was isolated as a colorless liquid: mp 59-63° C.; $^1$H NMR (300 MHz, CDCl3) δ 7.75-7.67 (m, 3H), 7.57-7.52 (m, 1H), 5.20-5.13 (m, 1H); ESIMS m/z 306.0 ([M]$^+$); IR (thinfilm) 3436, 2925, 1265, 749 cm$^{-1}$.

5-(1-Bromo-2,2,2-trifluoroethyl)-1,3-difluoro-2-methoxybenzene

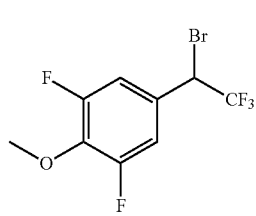 [SMILES: COc1c(F)cc(C(Br)C(F)(F)F)cc1F]

The title molecule was isolated as a pale yellow liquid: $^1$H NMR (400 MHz, CDCl$_3$) δ 7.08 (d, J=8.4 Hz, 2H), 5.03-4.98 (m, 1H), 4.04 (s, 3H); ESIMS m/z 304.1 ([M+H]$^+$); IR (thinfilm) 1114, 613 cm$^{-1}$.

5-(1-Bromo-2,2,2-trifluoroethyl)-1,2-dichloro-3-methylbenzene

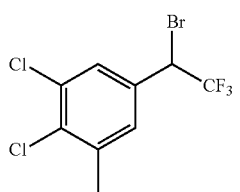

The title molecule was isolated as a colorless liquid: $^1$H NMR (400 MHz, CDCl$_3$) δ 7.46 (s, 1H), 7.27 (s, 1H), 5.04-4.99 (m, 1H), 2.44 (s, 3H); EIMS m/z 320.0 ([M]$^+$); IR (thinfilm) 2925, 1112, 752, 580 cm$^{-1}$.

4-(1-Bromo-2,2-difluoropropyl)-1,2-dichlorobenzene

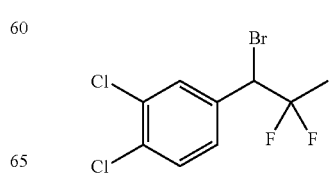

The title molecule was isolated as a colorless liquid: $^1$H NMR (300 MHz, DMSO-$d_6$) δ 7.76-7.70 (m, 2H), 7.54 (dd, J=8.4 1.8 Hz, 1H), 5.81-5.73 (m, 1H), 1.67 (d, J=18.9 Hz, 3H); EIMS m/z 304.0 ([M]$^+$); IR (thinfilm) 1118, 800, 499 cm$^{-1}$.

1-(1-Bromo-2,2,2-trifluoroethyl)-3-chloro-5-ethyl-benzene

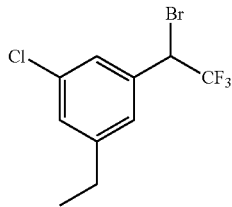

The title molecule was isolated as a colorless liquid: $^1$H NMR (400 MHz, DMSO-$d_6$) δ 7.43 (d, J=5.6 Hz, 2H), 7.39 (s, 1H), 6.20-6.16 (m, 1H), 2.68-2.62 (m, 2H), 1.19 (t, J=7.6 Hz, 3H); EIMS m/z 300.0 ([M]$^+$); IR (thinfilm) 2970, 1167, 716, 539 cm$^{-1}$.

2-Bromo-5-(1-bromo-2,2,2-trifluoroethyl)-1,3-dichlorobenzene

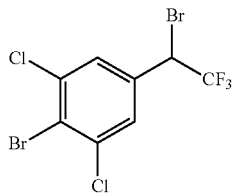

The title molecule was isolated as a colorless liquid: $^1$H NMR (400 MHz, DMSO-$d_6$) δ 7.79 (s, 2H), 6.27-6.21 (m, 1H); EIMS m/z 383.9 ([M]$^+$); IR (thinfilm) 2924, 1114, 749, 534 cm$^{-1}$.

1,3-Dibromo-5-(1-bromo-2,2,2-trifluoroethyl)-2-chlorobenzene

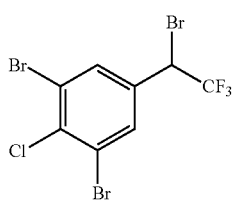 [SMILES: FC(F)(F)C(Br)c1cc(Br)c(Cl)c(Br)c1]

The title molecule was isolated as a pale yellow liquid: $^1$H NMR (300 MHz, DMSO-$d_6$) δ 7.97 (s, 2H), 6.27-6.19 (m, 1H); EIMS m/z 428.0 ([M]$^+$).

Example 2

Preparation of N-Methyl-4-vinylbenzamide (AI9)

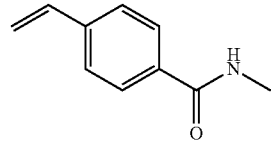

Step 1. 4-Vinylbenzoyl chloride (AI10)

To a stirred solution of 4-vinylbenzoic acid (1 g, 6.75 mmol) in CH$_2$Cl$_2$ (20 mL) at 0° C. were added a catalytic amount of DMF and oxalyl chloride (1.27 g, 10.12 mmol) dropwise over a period of 15 minutes (min) The reaction mixture was stirred at 25° C. for 6 h. After the reaction was deemed complete by TLC, the reaction mixture was concentrated under reduced pressure to give the crude acid chloride.

Step 2. N-Methyl-4-vinylbenzamide (AI9)

To 1 M N-methylamine in THF (13.5 mL, 13.5 mmol) at 0° C. were added TEA (1.34 mL, 10.12 mmol) and the acid chloride from Step 1 above in THF (10 mL), and the reaction mixture was stirred at 25° C. for 3 h. After the reaction was deemed complete by TLC, the reaction mixture was quenched with water and then was extracted with EtOAc (3×). The combined EtOAc layer was washed with brine and dried over Na$_2$SO$_4$ and concentrated under reduced pressure to afford the title compound as an off-white solid (650 mg, 60%): $^1$H NMR (400 MHz, CDCl$_3$) δ 7.76 (d, J=8.0 Hz, 2H), 7.45 (d, J=8.0 Hz, 2H), 6.79 (m, 1H), 6.20 (br s, 1H), 5.82 (d, J=17.6 Hz, 1H), 5.39 (d, J=10.8 Hz, 1H); ESIMS m/z 161.95 ([M+H]$^+$).

The following compounds were made in accordance with the procedures disclosed in accordance with Example 2.

N,N-Dimethyl-4-vinylbenzamide (AI11)

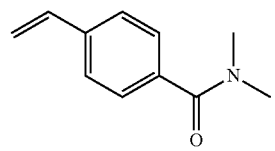

The product was isolated as an off-white solid (650 mg, 60%): $^1$H NMR (400 MHz, CDCl$_3$) δ 7.42 (m, 4H), 6.71 (m, 1H), 5.80 (d, J=17.6 Hz, 1H), 5.31 (d, J=10.8 Hz, 1H), 3.05 (s, 3H), 3.00 (s, 3H); ESIMS m/z 176.01 ([M+H]$^+$).

N-(2,2,3-Trifluoromethyl)-4-vinylbenzamide (AI12)

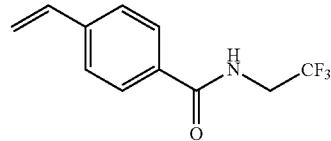 [SMILES: C=Cc1ccc(C(=O)NCC(F)(F)F)cc1]

The product was isolated as an off-white solid (900 mg, 60%): ¹H NMR (400 MHz, CDCl₃) δ 7.76 (d, J=8.0 Hz, 2H), 7.45 (d, J=8.0 Hz, 2H), 6.79 (m, 1H), 6.20 (br s, 1H), 5.82 (d, J=17.6 Hz, 1H), 5.39 (d, J=10.8 Hz, 1H), 4.19 (m, 2H); ESIMS m/z 230.06 ([M+H]⁺).

Morpholino(4-vinylphenyl)methanone (AI13)

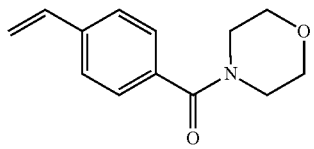 [SMILES: C=Cc1ccc(C(=O)N2CCOCC2)cc1]

The product was isolated as a white solid (850 mg, 60%): ESIMS m/z 218.12 ([M+H]⁺).

Example 3

Preparation of Ethyl 2-methyl-4-vinylbenzoate (AI14)

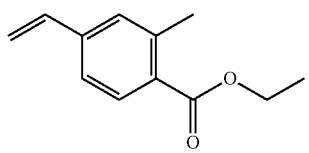

Step 1. 4-Formyl-2-methylbenzoic acid (AI15)

To a stirred solution of 4-bromo-2-methylbenzoic acid (10 g, 46.4 mmol) in dry THF (360 mL) at −78° C. was added n-BuLi (1.6 M solution in hexanes; 58.17 mL, 93.0 mmol) and DMF (8 mL). The reaction mixture was stirred at −78° C. for 1 h then was warmed to 25° C. and stirred for 1 h. The reaction mixture was quenched with 1 N HCl solution and extracted with EtOAc. The combined EtOAc extracts were washed with brine and dried over Na₂SO₄ and concentrated under reduced pressure. The residue was washed with n-hexane to afford the title compound as a solid (3.0 g, 40%): mp 196-198° C.; ¹H NMR (400 MHz, DMSO-d₆) δ 13.32 (br s, 1H), 10.05 (s, 1H), 7.98 (m, 1H), 7.84 (m, 2H), 2.61 (s, 3H); ESIMS m/z 163.00 ([M−H]⁻).

Step 2. Ethyl 4-formyl-2-methylbenzoate (AI16)

To a stirred solution of 4-formyl-2-methylbenzoic acid (3 g, 18.2 mmol) in EtOH (30 mL) was added H₂SO₄ and the reaction mixture was heated at 80° C. for 18 h. The reaction mixture was cooled to 25° C. and concentrated under reduced pressure. The residue was diluted with EtOAc and washed with water. The combined EtOAc extracts were washed with brine, dried over Na₂SO₄ and concentrated under reduced pressure to afford the title compound as a solid (2.8 g, 80%): ¹H NMR (400 MHz, CDCl₃) δ 10.05 (s, 1H), 8.04 (m, 1H), 7.75 (m, 2H), 4.43 (m, 2H), 2.65 (s, 3H), 1.42 (m, 3H).

Step 3. Ethyl 2-methyl-4-vinylbenzoate (AI14)

To a stirred solution of ethyl 4-formyl-2-methylbenzoate (2.8 g, 4 mmol) in 1,4-dioxane (20 mL) were added K₂CO₃ (3.01 g, 21.87 mmol) and methyltriphenyl phosphonium bromide (7.8 g, 21.87 mmol) at 25° C. Then the reaction mixture was heated at 100° C. for 18 h. After the reaction was deemed complete by TLC, the reaction mixture was cooled to 25° C. and filtered, and the filtrate was concentrated under reduced pressure. The crude compound was purified by flash chromatography (SiO₂, 100-200 mesh; eluting with 25-30% EtOAc in n-Hexane) to afford the title compound as a solid (2.0 g, 72%): ¹H NMR (400 MHz, CDCl₃) δ 7.86 (m, 1H), 7.27 (m, 2H), 6.68 (dd, J=17.6, 10.8 Hz, 1H), 5.84 (d, J=17.6 Hz, 1H), 5.39 (d, J=10.8 Hz, 1H), 4.39 (m, 2H), 2.60 (s, 3H), 1.40 (m, 3H); ESIMS m/z 191.10 (M−H⁻); IR (thin film) 2980, 1716, 1257 cm⁻¹.

Example 4

Preparation of tert-Butyl 2-chloro-4-vinylbenzoate (AI17)

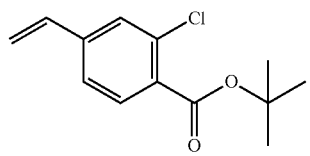 [SMILES: C=Cc1ccc(C(=O)OC(C)(C)C)c(Cl)c1]

Step 1. tert-Butyl 4-bromo-2-chlorobenzoate (AI18)

To a stirred solution of 4-bromo-2-chlorobenzoic acid (5 g, 21.37 mmol) in THF (30 mL) was added di-tert-butyl dicarbonate (25.5 g, 25.58 mmol), TEA (3.2 g, 31.98 mmol) and DMAP (0.78 g, 6.398 mmol), and the reaction mixture was stirred at 25° C. for 18 h. The reaction mixture was diluted with EtOAc and washed with water. The combined organic layer was washed with brine, dried over Na₂SO₄ and concentrated under reduced pressure. The residue was purified by flash chromatography (SiO₂, 100-200 mesh; eluting with 2-3% EtOAc in n-hexane) to afford the title compound as a liquid (3.2 g, 51%): ¹H NMR (400 MHz, CDCl₃) δ 7.62 (m, 2H), 7.44 (d, J=8.4 Hz, 1H), 1.59 (s, 9H); ESIMS m/z 290.10 ([M+H]⁺); IR (thin film) 1728 cm⁻¹.

The following compounds were made in accordance with the procedures disclosed in Step 1 of Example 4.

tert-Butyl 2-bromo-4-iodobenzoate (AI19)

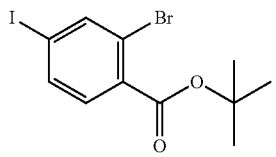

The product was isolated as a colorless oil (1.2 g, 50%): ¹H NMR (400 MHz, CDCl₃) δ 8.01 (s, 1H), 7.68 (d, J=8.4 Hz, 1H), 7.41 (d, J=8.0 Hz, 1H), 1.59 (s, 9H); ESIMS m/z 382.10 ([M+H]⁺); IR (thin film) 1727 cm⁻¹.

tert-Butyl 4-bromo-2-(trifluoromethyl)benzoate
(AI20)

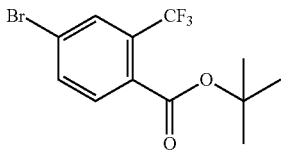 [SMILES: CC(C)(C)OC(=O)c1ccc(Br)cc1C(F)(F)F]

The product was isolated as a colorless oil (1 g, 52%): $^1$H NMR (400 MHz, CDCl$_3$) δ 7.85 (s, 1H), 7.73 (d, J=8.4 Hz, 1H), 7.62 (d, J=8.4 Hz, 1H), 1.57 (s, 9H); ESIMS m/z 324.10 ([M+H]$^+$); IR (thin film) 1725 cm$^{-1}$.

Step 2. tert-Butyl 2-chloro-4-vinylbenzoate (AI17)

To a stirred solution of tert-butyl 4-bromo-2-chlorobenzoate (1.6 g, 5.50 mmol) in toluene (20 mL) was added Pd(PPh$_3$)$_4$ (0.31 mg, 0.27 mmol), K$_2$CO$_3$ (2.27 g, 16.5 mmol) and vinylboronic anhydride pyridine complex (2.0 g, 8.3 mmol) and the reaction mixture was heated to reflux for 16 h. The reaction mixture was filtered, and the filtrate was washed with water and brine, dried over Na$_2$SO$_4$ and concentrated under reduced pressure. Purification by flash column chromatography (SiO$_2$, 100-200 mesh; eluting with 5-6% EtOAc in n-hexane) afforded the title compound as a liquid (0.6 g, 46%): $^1$H NMR (400 MHz, CDCl$_3$) δ 7.72 (d, J=8.1 Hz, 1H), 7.44 (m, 1H), 7.31 (d, J=8.0 Hz, 1H), 6.69 (dd, J=17.6, 10.8 Hz, 1H), 5.85 (d, J=17.6 Hz, 1H), 5.40 (d, J=10.8 Hz, 1H), 1.60 (s, 9H); ESIMS m/z 238.95 ([M+H]$^+$); IR (thin film) 2931, 1725, 1134 cm$^{-1}$.

The following compounds were made in accordance with the procedures disclosed in Step 2 of Example 4.

tert-Butyl 2-bromo-4-vinylbenzoate (AI21)

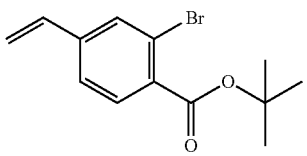 [SMILES: C=Cc1ccc(C(=O)OC(C)(C)C)c(Br)c1]

The product was isolated as a colorless oil (1 g, 52%): $^1$H NMR (400 MHz, CDCl$_3$) δ 7.68 (m, 2H), 7.36 (d, J=8.0 Hz, 1H), 6.68 (dd, J=17.6, 10.8 Hz, 1H), 5.84 (d, J=17.6 Hz, 1H), 5.39 (d, J=10.8 Hz, 1H), 1.60 (s, 9H); ESIMS m/z 282.10 ([M+H]$^+$); IR (thin film) 2978, 1724, 1130 cm$^{-1}$.

tert-Butyl 2-(trifluoromethyl)-4-vinylbenzoate
(AI22)

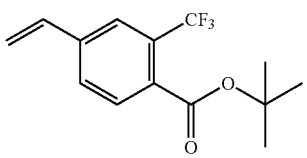 [SMILES: C=Cc1ccc(C(=O)OC(C)(C)C)c(C(F)(F)F)c1]

The product was isolated as a colorless oil (1.2 g, 50%): $^1$H NMR (400 MHz, CDCl$_3$) δ 7.71 (d, J=6.4 Hz, 2H), 7.59 (d, J=7.6 Hz, 1H), 6.77 (dd, J=17.6, 10.8 Hz, 1H), 5.89 (d, J=17.6 Hz, 1H), 5.44 (d, J=10.8 Hz, 1H), 1.58 (s, 9H); ESIMS m/z 272.20 ([M+H]$^+$); IR (thin film) 2982, 1727, 1159 cm$^{-1}$.

Example 5

Preparation of tert-Butyl 2-cyano-4-vinylbenzoate
(AI23)

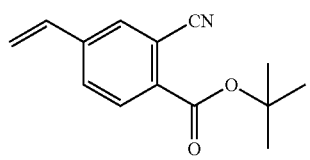 [SMILES: C=Cc1ccc(C(=O)OC(C)(C)C)c(C#N)c1]

To a stirred solution of tert-butyl 2-bromo-4-vinylbenzoate (0.5 g, 1.77 mmol) in DMF (20 mL) was added CuCN (0.23 g, 2.65 mmol), and the reaction mixture was heated at 140° C. for 3 h. The reaction mixture was cooled to 25° C., diluted with water, and extracted with EtOAc. The combined organic layer was washed with brine, dried over Na$_2$SO$_4$, and concentrated under reduced pressure. The residue was purified by flash chromatography (SiO$_2$, 100-200 mesh; eluting with 15% EtOAc in n-hexane) to afford the title compound as a white solid (0.3 g, 72%): mp 51-53° C.; $^1$H NMR (400 MHz, CDCl$_3$) δ 8.03 (s, 1H), 7.77 (s, 1H), 7.64 (d, J=8.4 Hz, 1H), 6.75 (dd, J=17.6, 10.8 Hz, 1H), 5.93 (d, J=17.6 Hz, 1H), 5.51 (d, J=10.8 Hz, 1H), 1.65 (s, 9H); ESIMS m/z 229.84 ([M+H]$^+$); IR (thin film) 2370, 1709, 1142 cm$^{-1}$.

Example 6

Preparation of Ethyl 2-bromo-4-iodobenzoate
(AI46)

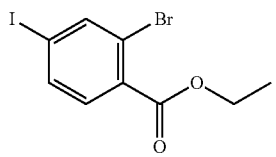

To a stirred solution of 4-iodo-2-bromobenzoic acid (5 g, 15.29 mmol) in EtOH (100 mL) was added H$_2$SO$_4$ (5 mL), and the reaction mixture was heated at 80° C. for 18 h. The reaction mixture was cooled to 25° C. and concentrated under reduced pressure. The residue was diluted with EtOAc (2×100 mL) and washed with water (100 mL). The combined EtOAc extracts were washed with brine, dried over Na$_2$SO$_4$ and concentrated under reduced pressure to afford the compound as a pale yellow solid (5 g, 92%): $^1$H NMR (400 MHz, DMSO-d$_6$) δ 8.04 (d, J=1.2 Hz, 1H), 7.71 (d, J=7.6 Hz, 1H), 7.51 (d, J=8.4 Hz, 1H), 4.41 (q, J=7.2 Hz, 2H), 1.41 (t, J=7.2 Hz, 3H).

The following compounds were made in accordance with the procedures disclosed in Example 6.

Ethyl 4-bromo-2-chlorobenzoate (AI47)

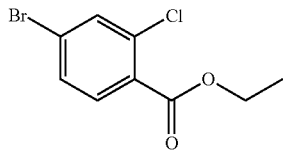

The title compound was isolated as an off-white solid (2.0 g, 80%): ¹H NMR (400 MHz, DMSO-d₆) δ 8.25 (d, J=1.2 Hz, 1H), 7.79 (d, J=7.6 Hz, 1H), 7.65 (d, J=8.4 Hz, 1H), 4.65 (q, J=7.2 Hz, 2H), 1.56 (t, J=7.2 Hz, 3H).

Ethyl 4-bromo-2-methylbenzoate (AI48)

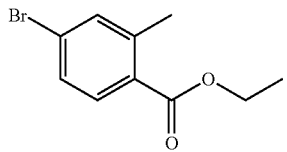

The title compound was isolated as a pale yellow liquid (3.0 g, 83%): ¹H NMR (400 MHz, CDCl₃) δ 7.79 (d, J=8.4 Hz, 1H), 7.41 (s, 1H), 7.39 (d, J=8.4 Hz, 1H), 4.42 (q, J=7.2 Hz, 2H), 2.60 (s, 3H), 1.40 (t, J=7.2 Hz, 3H) ESIMS m/z 229.11 ([M+H]⁺); IR (thin film) 1725 cm⁻¹.

Ethyl 4-bromo-2-fluorobenzoate (AI49)

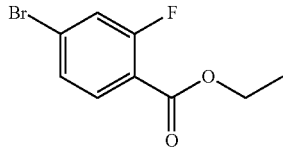

The title compound was isolated as a colorless liquid (9.0 g, 79%): ¹H NMR (400 MHz, DMSO-d₆) δ 7.84 (t, J=8.4 Hz, 1H), 7.76 (d, J=2.0 Hz, 1H), 7.58 (d, J=1.6 Hz, 1H), 4.34 (q, J=7.2 Hz, 2H), 1.32 (t, J=7.2 Hz, 3H); ESIMS m/z 246.99 ([M+H]⁺), IR (thin film) 1734 cm⁻¹.

Example 7

Preparation of Ethyl 4-bromo-2-ethylbenzoate (AI50)

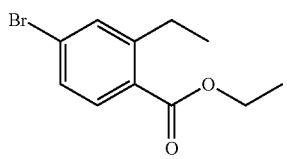

To a stirred solution of 4-bromo-2-fluorobenzoic acid (2.0 g, 9.17 mmol) in THF (16 mL), was added 1.0 M ethyl magnesium bromide in THF (32 mL, 32.0 mmol) dropwise at 0° C. and the resultant reaction mixture was stirred at ambient temperature for 18 h. The reaction mixture was quenched with 2 N HCl and extracted with EtOAc. The combined EtOAc layer was dried over anhydrous Na₂SO₄ and concentrated under reduced pressure to afford crude 4-bromo-2-ethylbenzoic acid as a colorless liquid that was used in the next step without purification (0.4 g): ¹H NMR (400 MHz, CDCl₃) δ 7.64 (d, J=8.4 Hz, 1H), 7.47 (m, 1H), 7.43 (m, 1H), 2.95 (q, J=4.0 Hz, 2H), 1.32 (t, J=4.0 Hz, 3H); ESIMS m/z 228.97 ([M+H]⁺).

The title compound was synthesized from 4-bromo-2-ethylbenzoic acid in accordance to the procedure in Example 6, isolated as a colorless liquid (0.15 g, 68%): ¹H NMR (400 MHz, DMSO-d₆) δ 7.90 (d, J=8.4 Hz, 1H), 7.47 (m, 2H), 4.40 (q, J=7.2 Hz, 2H), 3.06 (q, J=7.6 Hz, 2H), 1.42 (t, J=7.2 Hz, 3H), 1.26 (t, J=7.6 Hz, 3H); ESIMS m/z 226.96 ([M−H]⁻); IR (thin film) 3443, 1686, 568 cm⁻¹.

Example 8

Preparation of Ethyl 2-bromo-4-vinylbenzoate (AI51)

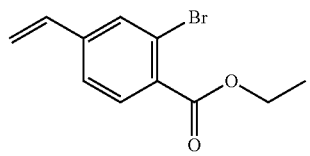

To a stirred solution of ethyl 2-bromo-4-iodobenzoate (5 g, 14.3 mmol) in THF/water (100 mL, 9:1) was added potassium vinyltrifluoroborate (1.89 g, 14.3 mmol), Cs₂CO₃ (18.27 g, 56.07 mmol) and triphenylphosphine (0.22 g, 0.85 mmol) and the reaction mixture was degassed with argon for 20 min, then charged with PdCl₂ (0.05 g, 0.28 mmol). The reaction mixture was heated to reflux for 16 h. The reaction mixture was cooled to ambient temperature and filtered through a Celite® bed and washed with EtOAc. The filtrate was again extracted with EtOAc and the combined organic layers washed with water and brine, dried over Na₂SO₄ and concentrated under reduced pressure to afford crude compound. The crude compound was purified by column chromatography (SiO₂, 100-200 mesh; eluting with 2% EtOAc/petroleum ether) to afford the title compound as a light brown gummy material (2 g, 56%): ¹H NMR (400 MHz, CDCl₃) δ 7.78 (d, J=8.4 Hz, 1H), 7.71 (d, J=1.2 Hz, 1H), 7.51 (d, J=8.4 Hz, 1H), 6.69 (dd, J=17.6, 10.8 Hz, 1H), 5.86 (d, J=17.6 Hz, 1H), 5.42 (d, J=11.2 Hz, 1H), 4.42 (q, J=7.2 Hz, 2H), 1.43 (t, J=3.6 Hz, 3H); ESIMS m/z 255.18 ([M+H]⁺); IR (thin film) 1729 cm⁻¹.

The following compounds were made in accordance with the procedures disclosed in Example 8.

Ethyl 2-methyl-4-vinylbenzoate (AI52)

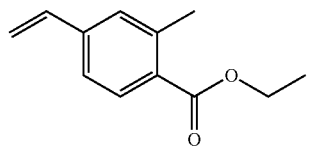

The title compound was isolated as a colorless liquid (0.8 g, 80%): $^1$H NMR (400 MHz, CDCl$_3$) δ 7.89 (d, J=8.4 Hz, 1H), 7.27 (m, 2H), 6.79 (dd, J=17.6, 10.8 Hz, 1H), 5.86 (d, J=17.6 Hz, 1H), 5.42 (d, J=11.2 Hz, 1H), 4.42 (q, J=7.2 Hz, 2H), 2.60 (s, 3H), 1.43 (t, J=7.2 Hz, 3H); ESIMS m/z 191.10 ([M+H]$^+$); IR (thin film) 1717, 1257 cm$^{-1}$.

Ethyl 2-fluoro-4-vinylbenzoate (AI53)

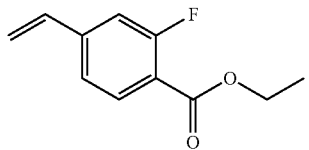

The title compound was isolated as a pale yellow liquid (2.0 g, 50%): $^1$H NMR (400 MHz, DMSO-d$_6$) δ 7.87 (t, J=8.0 Hz, 1H), 7.51 (d, J=16.0 Hz, 1H), 7.48 (d, J=16.0 Hz, 1H), 6.82 (dd, J=17.6, 10.8 Hz, 1H), 6.09 (d, J=17.6 Hz, 1H), 5.50 (d, J=10.8 Hz, 1H), 4.35 (q, J=7.2 Hz, 2H), 1.35 (t, J=7.2 Hz, 3H); ESIMS m/z 195.19 ([M+H]$^+$); IR (thin film) 1728 cm$^{-1}$.

Example 9

Preparation of Ethyl 2-chloro-4-vinylbenzoate (AI54)

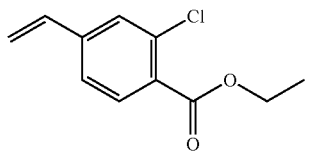

To a stirred solution of ethyl 2-chloro-4-bromobenzoate (2 g, 7.63 mmol) in DMSO (20 mL) was added potassium vinyltrifluoroborate (3.06 g, 22.9 mmol) and K$_2$CO$_3$ (3.16 g, 22.9 mmol). The reaction mixture was degassed with argon for 30 min Bistriphenylphosphine(diphenylphosphinoferrocene)palladium dichloride (0.27 g, 0.38 mmol) was added and the reaction mixture was heated to 80° C. for 1 h. The reaction mixture was diluted with water (100 mL), extracted with EtOAc (2×50 mL), washed with brine, dried over Na$_2$SO$_4$ and concentrated under reduced pressure to obtain the compound as brown gummy material (1.1 g, 69%): $^1$H NMR (400 MHz, CDCl$_3$) δ 7.81 (d, J=8.4 Hz, 1H), 7.46 (s, 1H), 7.33 (d, J=8.4 Hz, 1H), 6.70 (dd, J=17.6, 11.2 Hz, 1H), 5.87 (d, J=17.6 Hz, 1H), 5.42 (d, J=10.8 Hz, 1H), 4.41 (q, J=7.2 Hz, 2H), 1.43 (t, J=7.2 Hz, 3H); ESIMS m/z 211.22 ([M+H]$^+$); IR (thin film) 1729, 886 cm$^{-1}$.

The following compounds were made in accordance with the procedures disclosed in Example 9.

Ethyl 2-ethyl-4-vinylbenzoate (AI55)

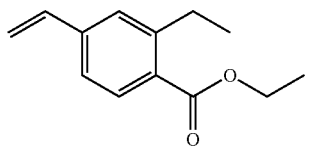

The title compound was isolated as a color less liquid (1.0 g, 66%): $^1$H NMR (300 MHz, CDCl$_3$) δ 7.85 (m, 1H), 7.29 (m, 2H), 6.76 (d, J=10.8 Hz, 1H), 5.86 (d, J=17.6 Hz, 1H), 5.36 (d, J=10.5 Hz, 1H), 4.41 (q, J=7.2 Hz, 2H), 3.10 (q, J=7.2 Hz, 2H), 1.40 (t, J=7.2 Hz, 3H), 1.30 (t, J=7.2 Hz, 3H); ESIMS m/z 205.26 ([M+H]$^+$); IR (thin film) 1720, 1607, 1263 cm$^{-1}$.

Methyl 2-methoxy-4-vinylbenzoate (AI56)

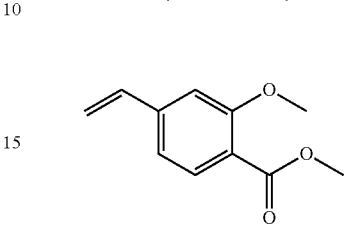

The title compound was isolated as a pale yellow liquid (1.2 g, 75%): $^1$H NMR (400 MHz, CDCl$_3$) δ 7.79 (d, J=8.0 Hz, 1H), 7.04 (d, J=1.2 Hz, 1H), 6.97 (s, 1H), 6.74 (dd, J=11.2, 11.2 Hz, 1H), 5.86 (d, J=17.6 Hz, 1H), 5.39 (d, J=17.6 Hz, 1H) 3.93 (s, 3H), 3.91 (s, 3H); ESIMS m/z 193.18 ([M+H]$^+$); IR (thin film) 1732 cm$^{-1}$.

Ethyl 2-(methylthio)-4-vinylbenzoate

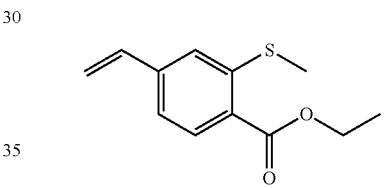

The title compound was isolated as a brown liquid: $^1$H NMR (300 MHz, CDCl$_3$) δ 7.98 (d, J=8.4 Hz, 1H), 7.23-7.18 (m, 2H), 6.78 (dd, J=17.7, 10.8, Hz, 1H), 5.89 (d, J=17.4 Hz, 1H), 5.42 (d, J=10.8 Hz, 1H), 4.39-4.36 (m, 2H), 2.48 (s, 3H), 1.39 (t, J=6.9 Hz, 3H); ESIMS m/z 221.9 ([M+H]$^+$); IR (thin film) 1708 cm$^{-1}$.

Example 10

Preparation of (E)-Ethyl 4-(3-(3,5-dichlorophenyl)-4,4,4-trifluorobut-1-enyl)-2-methylbenzoate (AI24)

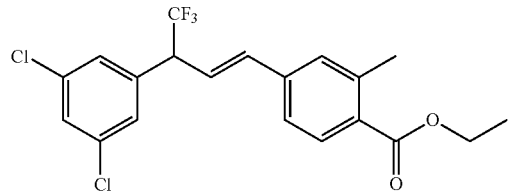 [SMILES: CCOC(=O)c1ccc(/C=C/C(c2cc(Cl)cc(Cl)c2)C(F)(F)F)cc1C]

To a stirred solution of ethyl 2-methyl-4-vinylbenzoate (2.0 g, 10.5 mmol) in 1,2-dichlorobenzene (25 mL) were added 1-(1-bromo-2,2,2-trifluoroethyl)-3,5-dichlorobenzene (6.44 g, 21.0 mmol), CuCl (208 mg, 21 mmol) and 2,2bipyridyl (0.65 g, 4.1 mmol). The reaction mixture was degassed with argon for 30 min and then stirred at 180° C. for 24 h. After the reaction was deemed complete by TLC, the reaction mixture was cooled to 25° C. and filtered, and the filtrate was concentrated under reduced pressure. Purification by flash chromatography (SiO$_2$, 100-200 mesh; eluting with 25-30% EtOAc in petroleum ether) afforded the title compound as a solid (1.7 g, 40%): $^1$H NMR (400 MHz, CDCl$_3$) δ 7.91 (d, J=8.0 Hz, 1H), 7.37 (m, 1H), 7.27-7.24 (m, 4H), 6.59 (d, J=16.0 Hz, 1H), 6.59 (dd, J=16.0, 8.0 Hz, 1H), 4.38 (q, J=7.2 Hz, 2H), 4.08 (m, 1H), 2.62 (s, 3H), 1.42 (t, J=7.2 Hz, 3H); ESIMS m/z 415.06 ([M−H]$^−$); IR (thin film) 1717, 1255, 1114 cm$^{-1}$.

Compounds AI25, AI57-AI68 and AC1-AC5 (Table 1) were made in accordance with the procedures disclosed in Example 10.

(E)-Ethyl 4-(4,4,4-trifluoro-3-(3,4,5-trichlorophenyl)but-1-enyl)-2-(trifluoromethyl)-benzoic acid (AI25)

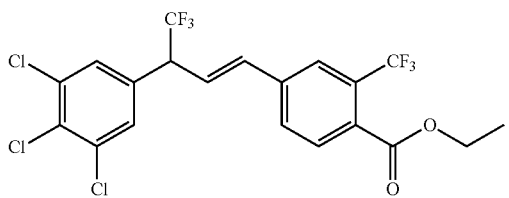 [SMILES: CCOC(=O)c1ccc(/C=C/C(c2cc(Cl)c(Cl)c(Cl)c2)C(F)(F)F)cc1C(F)(F)F]

The product was isolated as a pale brown gummy liquid (500 mg, 40%): $^1$H NMR (400 MHz, CDCl$_3$) δ 7.79 (d, J=8.0 Hz, 1H), 7.71 (m, 1H), 7.61 (d, J=7.6 Hz, 1H), 7.42 (s, 2H), 6.70 (d, J=16.0 Hz, 1H), 6.57 (dd, J=16.0, 8.0 Hz, 1H), 4.42 (q, J=7.2 Hz, 2H), 4.19 (m, 1H), 1.40 (t, J=7.6 Hz, 3H); ESIMS m/z 502.99 ([M−H]$^−$); IR (thin film) 1730, 1201, 1120, 749 cm$^{-1}$.

(E)-Ethyl 4-(3-(3,5-dichlorophenyl)-4,4,4-trifluorobut-1-enyl)-2-fluorobenzoate (AI57)

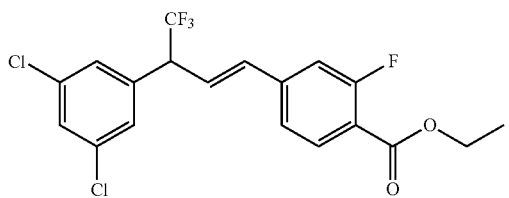 [SMILES: CCOC(=O)c1ccc(/C=C/C(c2cc(Cl)cc(Cl)c2)C(F)(F)F)cc1F]

$^1$H NMR (400 MHz, CDCl$_3$) δ 7.38 (s, 1H), 7.26 (s, 3H), 7.21 (d, J=8.4 Hz, 1H), 7.16 (d, J=11.6 Hz, 1H), 6.59 (d, J=16.0 Hz, 1H), 6.47 (dd, J=, 16.0, 8.0 Hz, 1H), 4.41 (q, J=6.8 Hz, 2H), 4.18 (m, 1H), 1.41 (t, J=6.8 Hz, 3H); ESIMS m/z 419.33 ([M−H]$^−$); IR (thin film) 1723, 1115, 802 cm$^{-1}$.

(E)-Ethyl 4-(3-(3,5-dichlorophenyl)-4,4,4-trifluorobut-1-enyl)-2-bromobenzoate (AI58)

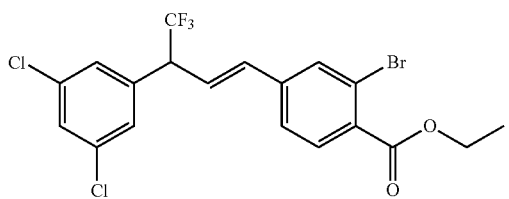 [SMILES: CCOC(=O)c1ccc(/C=C/C(c2cc(Cl)cc(Cl)c2)C(F)(F)F)cc1Br]

$^1$H NMR (400 MHz, CDCl$_3$) δ 7.79 (d, J=8.0 Hz, 1H), 7.67 (s, 1H), 7.38 (m, 2H), 7.26 (m, 2H), 6.56 (d, J=16.0 Hz, 1H), 6.45 (dd, J=16.0, 7.6 Hz, 1H), 4.42 (q, J=7.2 Hz, 2H), 4.39 (m, 1H), 1.42 (t, J=7.2 Hz, 3H); ESIMS m/z 481.22 ([M−H]$^−$); IR (thin film) 1727, 1114, 801, 685 cm$^{-1}$.

(E)-Ethyl 2-bromo-4-(4,4,4-trifluoro-3-(3,4,5-trichlorophenyl)but-1-enyl)benzoate (AI59)

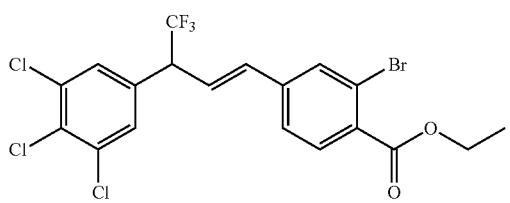 [SMILES: CCOC(=O)c1ccc(/C=C/C(c2cc(Cl)c(Cl)c(Cl)c2)C(F)(F)F)cc1Br]

$^1$H NMR (400 MHz, CDCl$_3$) δ 7.79 (d, J=8.0 Hz, 1H), 7.67 (d, J=1.6 Hz, 1H), 7.40 (s, 2H), 7.36 (d, J=1.6 Hz, 1H), 6.56 (d, J=16.0 Hz, 1H), 6.44 (dd, J=16.0, 7.6 Hz, 1H), 4.42 (q, J=6.8 Hz, 2H), 4.15 (m, 1H), 1.42 (t, J=6.8 Hz, 3H); ESIMS m/z 514.74 ([M−H]$^−$); IR (thin film) 1726, 1115, 808, 620 cm$^{-1}$.

(E)-Ethyl 2-methyl-4-(4,4,4-trifluoro-3-(3,4,5-trichlorophenyl)but-1-enyl)benzoate (AI60)

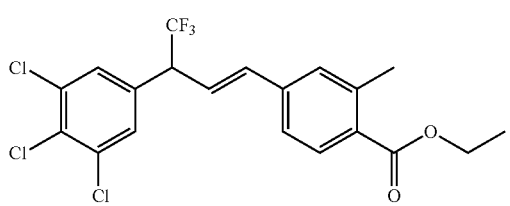 [SMILES: CCOC(=O)c1ccc(/C=C/C(c2cc(Cl)c(Cl)c(Cl)c2)C(F)(F)F)cc1C]

The title compound was isolated as a light brown gummy material: $^1$H NMR (400 MHz, CDCl$_3$) δ 7.90 (d, J=8.8 Hz, 1H), 7.34 (d, J=6.0 Hz, 2H), 7.25 (d, J=7.2 Hz, 2H), 6.59 (d, J=16.0 Hz, 1H), 6.42 (dd, J=16.0, 8.0 Hz, 1H), 4.38 (q, J=7.2 Hz, 2H), 4.19 (m, 1H), 2.63 (s, 3H), 1.41 (t, J=7.2 Hz, 3H).

(E)-Ethyl 2-chloro-4-(4,4,4-trifluoro-3-(3,4,5-trichlorophenyl)but-1-enyl)benzoate (AI61)

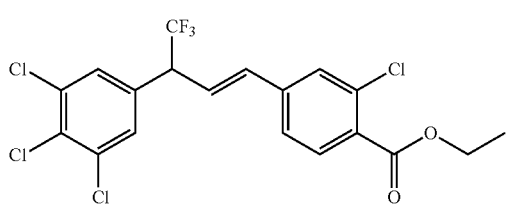 [SMILES: CCOC(=O)c1ccc(/C=C/C(c2cc(Cl)c(Cl)c(Cl)c2)C(F)(F)F)cc1Cl]

$^1$H NMR (400 MHz, CDCl$_3$) δ 7.87 (d, J=8.0 Hz, 1H), 7.46 (d, J=1.6 Hz, 1H), 7.40 (s, 2H), 7.31 (d, J=1.6 Hz, 1H), 6.57 (d, J=16.0 Hz, 1H), 6.44 (dd, J=16.0, 8.0 Hz, 1H), 4.42 (q, J=6.8 Hz, 2H), 4.15 (m, 1H), 1.42 (t, J=6.8 Hz, 3H); ESIMS m/z 470.73 ([M−H]$^−$); IR (thin film) 1726, 1115, 809, 3072 cm$^{-1}$.

(E)-Ethyl 4-(4,4,4-trifluoro-3-(3,4,5-trichlorophenyl)but-1-enyl)-2-(trifluoromethyl)benzoate (AI62)

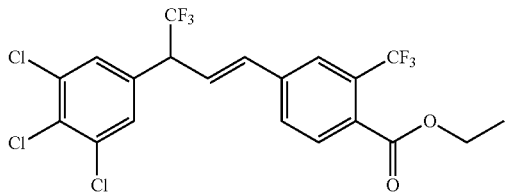 [SMILES: CCOC(=O)c1ccc(/C=C/C(c2cc(Cl)c(Cl)c(Cl)c2)C(F)(F)F)cc1C(F)(F)F]

The title compound was isolated as a pale brown liquid (1.0 g, 46.3%): $^1$H NMR (400 MHz, CDCl$_3$) δ 7.79 (d, J=8.0 Hz, 1H), 7.71 (s, 1H), 7.61 (d, J=7.6 Hz, 1H), 7.41 (s, 2H) 6.65 (d, J=16.0 Hz, 1H), 6.49 (dd, J=16.0, 8.0 Hz, 1H), 4.42 (q, J=7.6 Hz, 2H), 4.15 (m, 1H), 1.42 (t, J=7.6 Hz, 3H); ESIMS m/z 502.99 ([M−H]$^−$); IR (thin film) 1730, 1202, 1120, 750 cm$^{-1}$.

(E)-Ethyl 2-chloro-4-(3-(3,5-dichloro-4-fluorophenyl)-4,4,4-trifluorobut-1-enyl)benzoate (AI63)

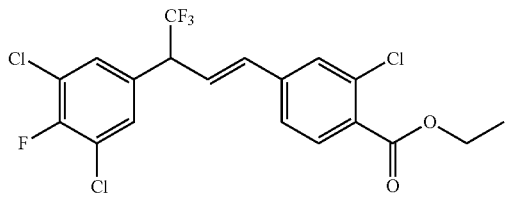 [SMILES: CCOC(=O)c1ccc(/C=C/C(c2cc(Cl)c(F)c(Cl)c2)C(F)(F)F)cc1Cl]

$^1$H NMR (400 MHz, CDCl$_3$) δ 7.85 (d, J=6.0 Hz, 1H), 7.46 (d, J=1.8 Hz, 2H), 7.34 (m, 1H), 7.24 (m, 1H), 6.57 (d, J=16.2 Hz, 1H), 6.45 (dd, J=16.2, 7.2 Hz, 1H), 4.43 (q, J=7.2 Hz, 2H), 4.13 (m, 1H), 1.41 (t, J=7.2 Hz, 3H); ESIMS m/z 455.0 ([M+H]$^+$); IR (thin film) 1728, 1115, 817 cm$^{-1}$.

(E)-Ethyl 2-fluoro-4-(3-(3,5-dichloro-4-fluorophenyl)-4,4,4-trifluorobut-1-enyl)benzoate (AI64)

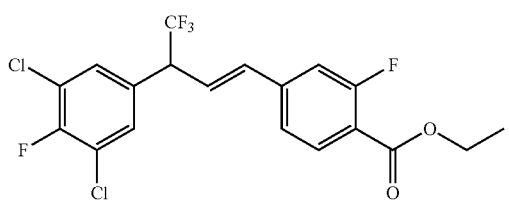 [SMILES: CCOC(=O)c1ccc(/C=C/C(c2cc(Cl)c(F)c(Cl)c2)C(F)(F)F)cc1F]

$^1$H NMR (400 MHz, CDCl$_3$) δ 7.93 (t, J=7.6 Hz, 1H), 7.34 (d, J=5.6 Hz, 2H), 7.21 (d, J=8.0 Hz, 1H), 7.16 (d, J=11.6 Hz, 1H), 6.59 (d, J=16.0 Hz, 1H), 6.49 (dd, J=16.0, 7.6 Hz, 1H), 4.42 (q, J=7.6 Hz, 2H), 4.13 (m, 1H), 1.41 (t, J=7.6 Hz, 3H); ESIMS m/z 436.81 ([M−H]$^−$); IR (thin film) 1725 cm$^{-1}$.

(E)-Ethyl 2-bromo-4-(3-(3,5-dichloro-4-fluorophenyl)-4,4,4-trifluorobut-1-enyl)benzoate (AI65)

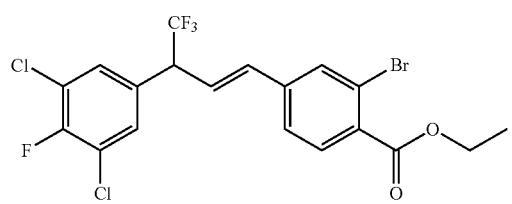

$^1$H NMR (400 MHz, CDCl$_3$) δ 7.94 (d, J=8.0 Hz, 1H), 7.67 (s, 1H), 7.36 (m, 3H), 6.56 (d, J=15.6 Hz, 1H), 6.44 (dd, J=15.6, 8.0 Hz, 1H), 4.42 (q, J=6.8 Hz, 2H), 4.10 (m, 1H), 1.42 (t, J=6.8 Hz, 3H); ESIMS m/z 498.74 ([M−H]$^−$); IR (thin film) 1726, 1114, 820, 623 cm$^{-1}$.

(E)-Ethyl 2-methyl-4-(3-(3,5-dichloro-4-fluorophenyl)-4,4,4-trifluorobut-1-enyl)benzoate (AI66)

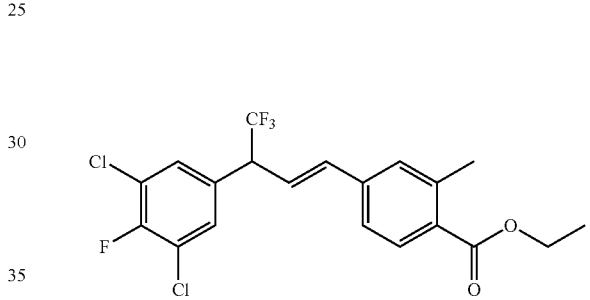

The title compound was isolated as a brown semi-solid: $^1$H NMR (400 MHz, CDCl$_3$) δ 7.90 (d, J=8.8 Hz, 1H), 7.34 (d, J=6.0 Hz, 2H), 7.25 (d, J=7.2 Hz, 2H), 6.59 (d, J=16.0 Hz, 1H), 6.42 (dd, J=16.0, 8.0 Hz, 1H), 4.38 (q, J=7.2 Hz, 2H), 4.19 (m, 1H), 2.63 (s, 3H), 1.41 (t, J=7.2 Hz, 3H); ESIMS m/z 432.90 ([M−H]$^−$); IR (thin film) 1715 cm$^{-1}$.

(E)-Methyl 2-methoxy-4-(3-(3,5-dichloro-4-fluorophenyl)-4,4,4-trifluorobut-1-enyl)benzoate (AI67)

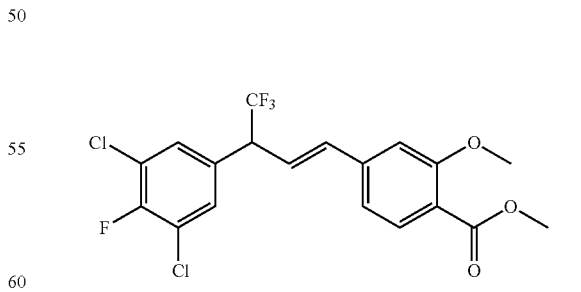

$^1$H NMR (400 MHz, CDCl$_3$) δ 7.80 (d, J=8.4 Hz, 1H), 7.35 (d, J=6.0 Hz, 2H), 7.03 (d, J=1.2 Hz, 1H), 6.92 (s, 1H), 6.59 (d, J=15.6 Hz, 1H), 6.42 (dd, J=15.6, 8.0 Hz, 1H), 4.13 (m, 1H), 3.93 (s, 3H), 3.88 (s, 3H); ESIMS m/z 437.29 ([M+H]$^+$); IR (thin film) 1724 cm$^−$.

(E)-Ethyl 2-ethyl-4-(3-(3,5-dichloro-4-fluorophenyl)-4,4,4-trifluorobut-1-enyl)benzoate (AI68)

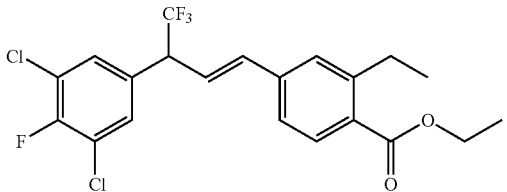 [SMILES: CCOC(=O)c1ccc(/C=C/C(c2cc(Cl)c(F)c(Cl)c2)C(F)(F)F)cc1CC]

¹H NMR (400 MHz, CDCl₃) δ 7.85 (d, J=8.0 Hz, 1H), 7.35 (d, J=9.6 Hz, 2H), 7.26 (m, 1H), 7.24 (m, 1H), 6.60 (d, J=15.6 Hz, 1H), 6.42 (dd, J=15.6, 8.0 Hz, 1H), 4.38 (q, J=7.2 Hz, 2H), 4.14 (m, 1H), 3.01 (q, J=7.6 Hz 2H), 1.41 (t, J=7.2 Hz, 3H), 1.26 (t, J=7.6 Hz, 3H); ESIMS m/z 447.05 ([M−H]⁻); IR (thin film) 1715, 1115, 817 cm⁻¹.

(E)-Ethyl 4-(3-(3,5-dichloro-4-fluorophenyl)-4,4,4-trifluorobut-1-en-1-yl)-2-(methylthio)benzoate

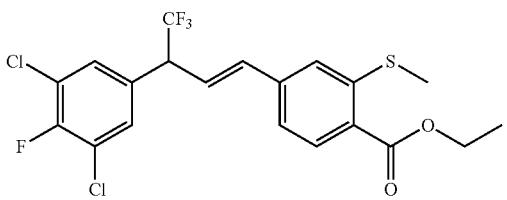 [SMILES: CCOC(=O)c1ccc(/C=C/C(c2cc(Cl)c(F)c(Cl)c2)C(F)(F)F)cc1SC]

Isolated as a brown liquid: ¹H NMR (400 MHz, CDCl₃) δ 7.99 (d, J=8.1 Hz, 2H), 7.35-7.32 (m, 2H), 7.21-7.16 (m, 2H), 6.63 (d, J=15.8 Hz, 1H), 6.45 (dd, J=15.9, 7.8 Hz, 1H), 4.41-4.31 (m, 2H), 4.30-4.10 (m, 1H), 2.47 (s, 3H), 1.40 (t, J=7.5 Hz, 3H); ESIMS m/z 466.88 ([M+H]⁺); IR (thin film) 1705, 1114 cm⁻¹.

(E)-Ethyl 2-bromo-4-(3-(3,5-difluoro-4-methoxyphenyl)-4,4,4-trifluorobut-1-en-1-yl)benzoate

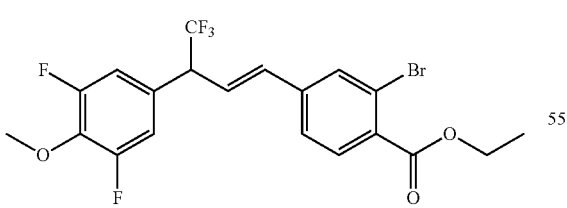

The product was isolated as a pale yellow liquid: ¹H NMR (400 MHz, CDCl₃) δ 7.78 (d, J=8.0 Hz, 1H), 7.66 (d, J=1.6 Hz, 1H), 7.35-7.33 (m, 1H), 6.96-6.90 (m, 2H), 6.54 (d, J=15.6 Hz, 1H), 6.43 (dd, J=15.6, 8.0 Hz, 1H), 4.39 (q, J=6.8 Hz, 2H), 4.09-4.05 (m, 1H), 4.02 (s, 3H), 1.40 (t, J=7.2 Hz, 3H); EIMS m/z 478.2 ([M]⁺); IR (thin film) 1727, 1113 cm⁻¹.

Example 11

Preparation of (E)-4-(3-(3,5-Dichlorophenyl)-4,4,4-trifluorobut-1-enyl)-2-methylbenzoic acid (AI32)

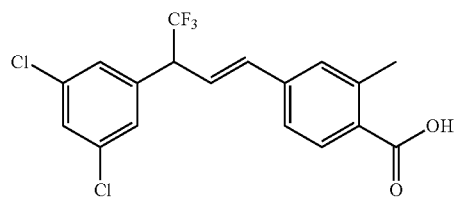

To a stirred solution of (E)-ethyl 4-(3-(3,5-dichlorophenyl)-4,4,4-trifluorobut-1-enyl)-2-methylbenzoate (1.7 g, 4.0 mmol) in 1,4-dioxane (10 mL) was added 11 N HCl (30 mL), and the reaction mixture was heated at 100° C. for 48 h. The reaction mixture was cooled to 25° C. and concentrated under reduced pressure. The residue was diluted with water and extracted with chloroform (CHCl₃). The combined organic layer was dried over Na₂SO₄ and concentrated under reduced pressure, and the crude compound was washed with n-hexane to afford the title compound as a white solid (0.7 g, 50%): mp 142-143° C.; ¹H NMR (400 MHz, DMSO-d₆) δ 12.62 (br s, 1H), 7.81 (d, J=8.0 Hz, 1H), 7.66 (s, 3H), 7.52-7.44 (m, 2H), 6.89 (dd, J=16.0, 8.0 Hz, 1H), 6.78-6.74 (d, J=16.0 Hz, 1H), 4.84 (m, 1H), 2.50 (s, 3H); ESIMS m/z 387.05 ([M−H]⁻); IR (thin film) 3448, 1701, 1109, 777 cm⁻¹.

The following compounds were made in accordance with the procedures disclosed in Example 11.

(E)-2-Methyl-4-(4,4,4-trifluoro-3-(3,4,5-trichlorophenyl)but-1-enyl)benzoic acid (AI26)

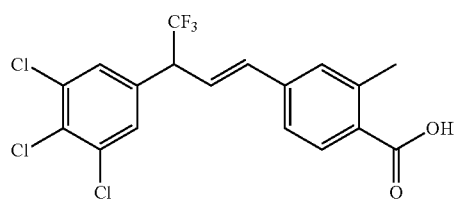 [SMILES: Cc1cc(/C=C/C(c2cc(Cl)c(Cl)c(Cl)c2)C(F)(F)F)ccc1C(=O)O]

The product was isolated as a pale brown gummy liquid (1 g, 46%): ¹H NMR (400 MHz, CDCl₃) δ 7.97 (d, J=8.0 Hz, 1H), 7.77 (s, 1H), 7.65 (m, 1H), 7.41 (s, 2H), 6.68 (d, J=16.0 Hz, 1H), 6.53 (dd, J=16.0, 8.0 Hz, 1H), 4.16 (m, 1H), 2.50 (s, 3H); ESIMS m/z 422.67 ([M−H]⁻).

(E)-2-Chloro-4-(4,4,4-trifluoro-3-(3,4,5-trichlorophenyl)but-1-enyl)benzoic acid (AI27)

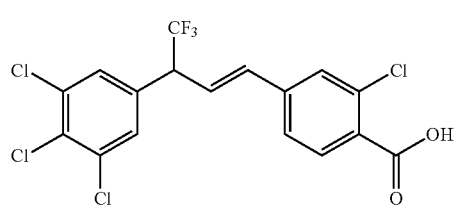 [SMILES: O=C(O)c1ccc(/C=C/C(c2cc(Cl)c(Cl)c(Cl)c2)C(F)(F)F)cc1Cl]

The product was isolated as an off-white semi-solid (1 g, 45%): ¹H NMR (400 MHz, CDCl₃) δ 7.99 (d, J=8.4 Hz, 1H), 7.50 (m, 1H), 7.40 (s, 1H), 7.36 (m, 2H), 6.59 (d, J=15.6 Hz, 1H), 6.48 (dd, J=15.6, 7.6 Hz, 1H), 4.14 (m, 1H); ESIMS m/z 442.72 ([M−H]⁻); IR (thin film) 3472, 1704, 1113, 808 cm⁻¹.

(E)-2-Bromo-4-(4,4,4-trifluoro-3-(3,4,5-trichlorophenyl)but-1-enyl)benzoic acid (AI28)

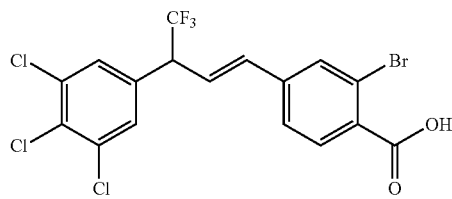 [SMILES: O=C(O)c1ccc(/C=C/C(c2cc(Cl)c(Cl)c(Cl)c2)C(F)(F)F)cc1Br]

The product was isolated as a brown solid (1 g, 45%): mp 70-71° C.; ¹H NMR (400 MHz, CDCl₃) δ 7.99 (d, J=8.0 Hz, 1H), 7.72 (s, 1H), 7.40 (m, 3H), 6.58 (d, J=16.0 Hz, 1H), 6.48 (dd, J=16.0, 8.0 Hz, 1H), 4.14 (m, 1H); ESIMS m/z 484.75 ([M−H]⁻); IR (thin film) 3468, 1700 cm⁻¹.

(E)-2-Cyano-4-(4,4,4-trifluoro-3-(3,4,5-trichlorophenyl)but-1-enyl)benzoic acid (AI29)

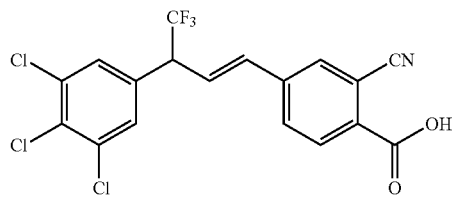 [SMILES: N#Cc1cc(/C=C/C(c2cc(Cl)c(Cl)c(Cl)c2)C(F)(F)F)ccc1C(=O)O]

The product was isolated as an off-white solid (500 mg, 45%): mp 100-101° C.; ¹H NMR (400 MHz, CDCl₃) δ 7.90 (s, 1H), 7.85 (d, J=7.6 Hz, 1H), 7.72 (d, J=8.0 Hz, 1H), 7.65 (br s, 1H), 7.42 (s, 2H), 6.73 (d, J=16.0 Hz, 1H), 6.58 (dd, J=16.0, 8.0 Hz, 1H), 4.19 (m, 1H); ESIMS m/z 431.93 ([M−H]⁻).

(E)-4-(3-(3,4-Dichlorophenyl)-4,4,4-trifluorobut-1-enyl)-2-methylbenzoic acid (AI30)

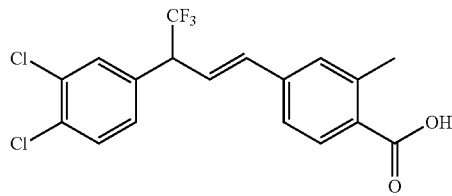 [SMILES: Cc1cc(/C=C/C(c2ccc(Cl)c(Cl)c2)C(F)(F)F)ccc1C(=O)O]

The product was isolated as a pale brown liquid (500 mg, 46%): ¹H NMR (400 MHz, CDCl₃) δ 8.03 (m, 1H), 7.49 (m, 2H), 7.29 (m, 1H), 7.22 (m, 2H), 6.73 (d, J=16.0 Hz, 1H), 6.58 (dd, J=16.0, 7.8 Hz, 1H), 4.16 (m, 1H), 2.64 (s, 3H); ESIMS m/z 386.84 ([M−H]⁻); IR (thin film) 3428, 1690, 1113, 780 cm⁻¹.

(E)-4-(3-(3,5-Dichloro-4-fluorophenyl)-4,4,4-trifluorobut-1-enyl)-2-methylbenzoic acid (AI31)

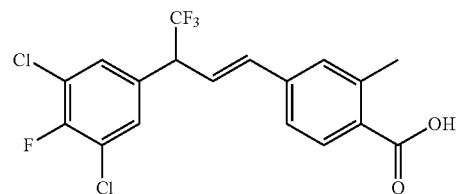 [SMILES: Cc1cc(/C=C/C(c2cc(Cl)c(F)c(Cl)c2)C(F)(F)F)ccc1C(=O)O]

The product was isolated as a white solid (500 mg, 50%): mp 91-93° C.; ¹H NMR (400 MHz, CDCl₃) δ 8.02 (d, J=8.0 Hz, 1H), 7.35 (d, J=5.6 Hz, 1H), 7.30 (m, 3H), 6.61 (d, J=16.0 Hz, 1H), 6.48 (dd, J=16.0, 8.0 Hz, 1H), 4.13 (m, 1H), 2.65 (s, 3H); ESIMS m/z 406.87 ([M−H]⁻).

(E)-4-(4,4,4-Trifluoro-3-(3,4,5-trichlorophenyl)but-1-enyl)-2-(trifluoromethyl)benzoic acid (AI33)

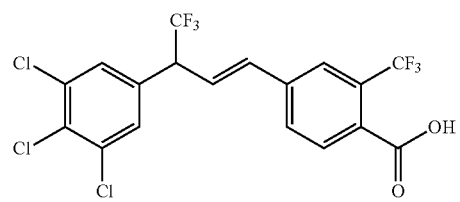

The product was isolated as a white solid (500 mg, 45%): mp 142-143° C.; ¹H NMR (400 MHz, CDCl₃) δ 7.97 (d, J=8.0 Hz, 1H), 7.77 (s, 1H), 7.65 (m, 1H), 7.41 (s, 2H), 6.68 (d, J=16.0 Hz, 1H), 6.53 (dd, J=16.0, 8.0 Hz, 1H), 4.16 (m, 1H); ESIMS m/z 474.87 ([M−H]⁻).

(E)-2-Bromo-4-(4,4,4-trifluoro-3-(3,4,5-trichlorophenyl)but-1-enyl)benzoic acid (AI69)

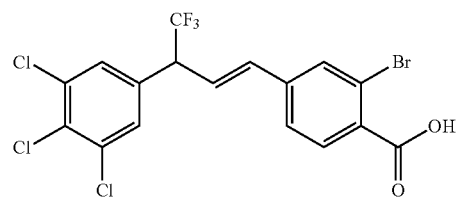 [SMILES: O=C(O)c1ccc(/C=C/C(c2cc(Cl)c(Cl)c(Cl)c2)C(F)(F)F)cc1Br]

The title compound was isolated as a brown solid (0.8 g, 28%): ¹H NMR (400 MHz, CDCl₃) δ 13.42 (br, 1H), 7.98 (d, J=1.5 Hz, 1H), 7.94 (m, 2H), 7.75 (d, J=8.1 Hz, 1H), 7.65 (m, 1H), 7.06 (dd, J=15.9, 9.0 Hz, 1H), 6.80 (d, J=15.9 Hz, 1H), 4.91 (m, 1H); ESIMS m/z 484.75 ([M−H]⁻); IR (thin film) 3469, 1700 cm⁻¹.

(E)-2-Bromo-4-(3-(3,5-dichloro-4-fluorophenyl)-4,4,4-trifluo robut-1-enyl)benzoic acid (AI70)

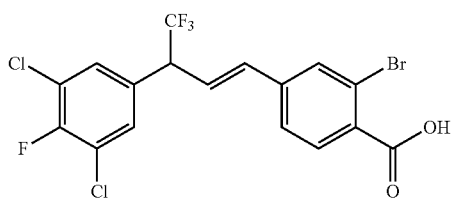 [SMILES: O=C(O)c1ccc(/C=C/C(c2cc(Cl)c(F)c(Cl)c2)C(F)(F)F)cc1Br]

The title compound was isolated as a yellow liquid (0.3 g, crude): $^1$H NMR (300 MHz, CDCl$_3$) δ 7.79 (d, J=8.1 Hz, 1H), 7.67 (s, 1H), 7.34 (m, 3H), 6.56 (d, J=15.9 Hz, 1H), 6.45 (dd, J=15.9, 7.6 Hz, 1H), 4.43 (m, 1H); ESIMS m/z 471.0 ([M−H]$^−$).

(E)-4-(3-(3,5-Dichloro-4-fluorophenyl)-4,4,4-trifluo-robut-1-enyl)-2-ethylbenzoic acid (AI71)

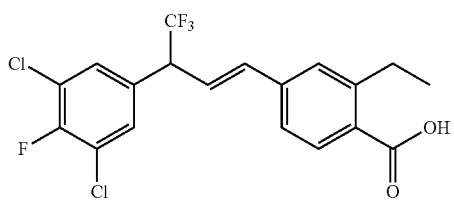

The title compound was isolated as a brown gummy material (0.2 g, crude): $^1$H NMR (300 MHz, DMSO-d$_6$) δ 12.5 (br, 1H), 7.85 (d, J=6.3 Hz, 2H), 7.75 (d, J=8.1 Hz, 1H), 7.52 (m, 2H), 6.96 (dd, J=8.7, 8.7 Hz, 1H), 6.78 (d, J=15.6 Hz, 1H), 6.06 (dd, J=15.6 Hz, 1H), 4.80 (m, 1H), 4.06 (q, J=7.2 Hz, 2H), 1.33 (t, J=7.2 Hz, 3H); ESIMS m/z 419.06 ([M−H]$^−$).

(E)-2-Chloro-4-(3-(3,5-dichloro-4-fluorophenyl)-4,4,4-trifluorobut-1-enyl)benzoic acid (AI72)

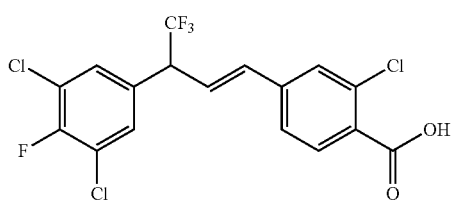 [SMILES: O=C(O)c1ccc(/C=C/C(c2cc(Cl)c(F)c(Cl)c2)C(F)(F)F)cc1Cl]

The title compound was isolated as a yellow liquid (0.7 g, 95%): $^1$H NMR (300 MHz, CDCl$_3$) δ 7.85 (d, J=6.0 Hz, 1H), 7.46 (d, J=1.8 Hz, 1H), 7.41 (s, 3H), 6.57 (d, J=16.0 Hz, 1H), 6.45 (dd, J=16.0, 8.0 Hz, 1H), 4.16 (m, 1H); ESIMS m/z 455.0 ([M+H]$^+$); IR (thin film) 1728, 1115, 817 cm$^{−1}$.

(E)-4-(3-(3,5-Dichloro-4-fluorophenyl)-4,4,4-trifluorobut-1-enyl)-2-methylbenzoic acid (AI73)

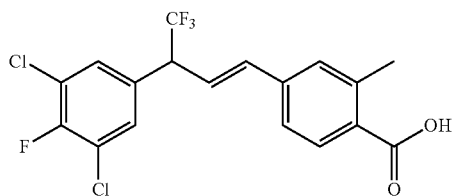 [SMILES: Cc1cc(/C=C/C(c2cc(Cl)c(F)c(Cl)c2)C(F)(F)F)ccc1C(=O)O]

The title compound was isolated as a light brown gummy material (0.7 g, 38%): mp 91-93° C.; $^1$H NMR (400 MHz, CDCl$_3$) δ 8.02 (d, J=8.0 Hz, 1H), 7.35 (d, J=5.6 Hz, 1H), 7.30 (m, 3H), 6.10 (d, J=16.0 Hz, 1H), 6.46 (dd, J=16.0, 8.0 Hz, 1H), 4.03 (m, 1H), 2.65 (s, 3H); ESIMS m/z 406.87 ([M−H]$^−$).

(E)-4-(3-(3,5-Dichlorophenyl)-4,4,4-trifluorobut-1-enyl)-2-fluorobenzoic acid (AI74)

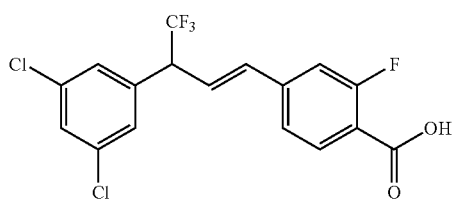 [SMILES: O=C(O)c1ccc(/C=C/C(c2cc(Cl)cc(Cl)c2)C(F)(F)F)cc1F]

The title compound was isolated as a light brown liquid (0.3 g, crude): ESIMS m/z 393.15 ([M−H]$^−$).

(E)-2-Bromo-4-(3-(3,5-dichlorophenyl)-4,4,4-trifluorobut-1-enyl)benzoic acid (AI75)

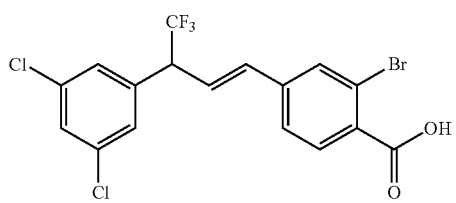 [SMILES: O=C(O)c1ccc(/C=C/C(c2cc(Cl)cc(Cl)c2)C(F)(F)F)cc1Br]

The title compound was isolated as a light brown liquid (0.35 g, crude): ESIMS m/z 451.91 ([M−H]$^−$).

(E)-4-(3-(3,5-Dichloro-4-fluorophenyl)-4,4,4-trifluorobut-1-en-1-yl)-2-(methylthio)benzoic acid

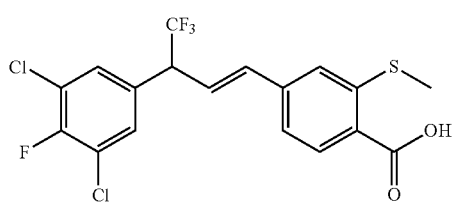

$^1$H NMR (400 MHz, CDCl$_3$) δ 7.88-7.85 (m, 3H), 7.46 (d, J=6.8 Hz, 1H), 7.37 (s, 1H), 6.99 (dd, J=15.6, 8.8 Hz, 1H), 6.85 (d, J=16.0 Hz, 1H), 4.85-4.81 (m, 2H), 2.45 (s, 3H); ESIMS m/z 436.89 ([M−H]$^−$); IR (thinfilm) 3469, 1686, 1259, 714 cm$^{−1}$.

(E)-2-Bromo-4-(3-(3,5-difluoro-4-methoxyphenyl)-4,4,4-trifluorobut-1-en-1-yl)benzoic acid

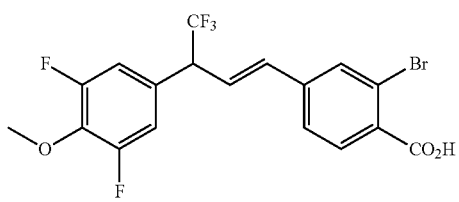 [SMILES: COc1c(F)cc(C(/C=C/c2ccc(C(=O)O)c(Br)c2)C(F)(F)F)cc1F]

The title molecule was isolated as a brown liquid: $^1$H NMR (300 MHz, DMSO-d$_6$) δ 13.48 (bs, 1H), 8.03 (s, 1H), 7.81 (d, J=7.8 Hz, 1H), 7.69 (d, J=8.1 Hz, 1H), 7.48 (d, J=9.3 Hz, 2H), 7.05 (dd, J=15.6, 9.0 Hz, 1H), 6.83 (d, J=15.9 Hz, 1H), 4.86-4.74 (m, 1H), 4.00 (s, 3H); EIMS m/z 451.18 ([M]$^+$); IR (thin film) 3431, 1132 cm$^{−1}$.

Prophetically, compounds AI34, AI36-AI41, AI44-AI45 (Table 1) could be made in accordance with the procedures disclosed in Example 10, or Examples 10 and 11.

Example 12

Preparation of (E)-4-(3-(3,5-Dichlorophenyl)-4,4,4-trifluorobut-1-enyl)-2-methyl-N-(2,2,2-trifluoroethyl)benzamide (AC6)

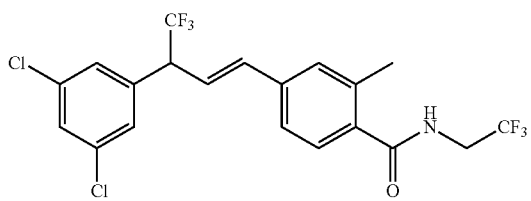 [SMILES: Cc1cc(/C=C/C(c2cc(Cl)cc(Cl)c2)C(F)(F)F)ccc1C(=O)NCC(F)(F)F]

To a stirred solution of (E)-4-(3-(3,5-dichlorophenyl)-4,4,4-trifluorobut-1-enyl)-2-methylbenzoic acid in DMF was added 2,2,2-trifluoroethylamine, HOBt.H$_2$O, EDC.HCl and DIPEA, and the reaction mixture was stirred at 25° C. for 18 h. The reaction mixture was diluted with water and extracted with EtOAc. The combined organic layer was washed with brine, dried over Na$_2$SO$_4$ and concentrated under reduced pressure. Purification by flash column chromatography (SiO$_2$, 100-200 mesh; eluting with hexane:EtOAc afforded a white semi-solid (110 mg, 50%): $^1$H NMR (400 MHz, CDCl$_3$) 7.40 (m, 2H), 7.26 (m, 3H), 6.56 (d, J=16.0 Hz, 1H), 6.48 (dd, J=16.0, 8.0 Hz, 1H), 5.82 (br s, 1H), 4.08 (m, 3H), 2.52 (s, 3H); ESIMS m/z 468.40 ([M−H]$^−$); IR (thin film) 1657, 1113, 804 cm$^{−1}$.

Compounds AC7-AC38, AC40-AC58, AC110-AC112, AC117, and AC118 (Table 1) were made in accordance with the procedures disclosed in Example 12.

Example 13

Preparation of 4-((E)-3-(3,5-Dichlorophenyl)-4,4,4-trifluorobut-1-enyl)-2-methyl-N-((pyrimidin-5-yl)methyl)benzamide (AC39)

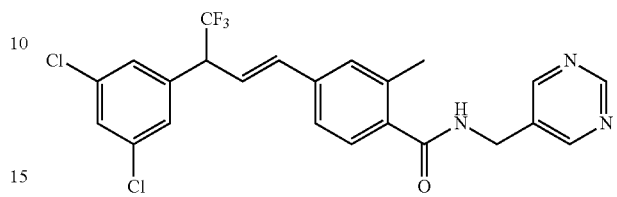

To a stirred solution of (pyrimidin-5-yl)methanamine (0.15 g, 1.43 mmol) in CH$_2$Cl$_2$ (10 mL) was added drop wise trimethylaluminum (2 M solution in toluene; 0.71 mL, 1.43 mmol), and the reaction mixture was stirred at 25° C. for 30 min. A solution of ethyl 4-((E)-3-(3,5-dichlorophenyl)-4,4,4-trifluorobut-1-enyl)-2-methylbenzoate (0.3 g, 0.71 mmol) in CH$_2$Cl$_2$ was added drop wise to the reaction mixture at 25° C. The reaction mixture was stirred at reflux for 18 h, cooled to 25° C., quenched with 0.5 N HCl solution (50 mL) and extracted with EtOAc (2×50 mL). The combined organic extracts were washed with brine, dried over Na$_2$SO$_4$, and concentrated under reduced pressure. The crude compound was purified by flash chromatography (SiO$_2$, 100-200 mesh; eluting with 40% EtOAc in n-hexane) to afford the title compound (0.18 g, 55%): mp 141-144° C.; $^1$H (400 MHz, CDCl$_3$) δ 9.19 (s, 1H), 8.79 (s, 2H), 7.37 (m, 2H), 7.23 (m, 2H), 7.21 (m, 1H), 6.57 (d, J=16.0 Hz, 1H), 6.40 (dd, J=16.0, 7.6 Hz 1H), 6.21 (m, 1H), 4.65 (s, 2H), 4.11 (m, 1H), 2.46 (s, 3H); ESIMS m/z 477.83 ([M−H]$^−$).

Example 14

Preparation of (E)-2-Chloro-N-(2-oxo-2-((2,2,2-trifluoroethyl)amino)ethyl)-4-(4,4,4-trifluoro-3-(3,4,5-trichlorophenyl)but-1-en-1-yl)benzamide (AC64)

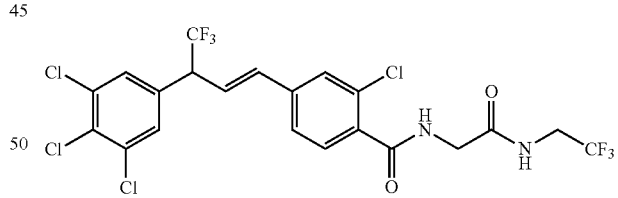

To a stirred solution of glycine amide (0.15 g, 0.58 mmol) in CH$_2$Cl$_2$ (5 mL) was added trimethylaluminum (2 M solution in toluene; 1.45 mL, 2.91 mmol) dropwise, and the reaction mixture was stirred at 28° C. for 30 min. A solution of (E)-ethyl 2-chloro-4-(4,4,4-trifluoro-3-(3,4,5-trichlorophenyl)but-1-enyl)benzoate (0.3 g, 0.58 mmol) in CH$_2$Cl$_2$ (5 mL) was added drop wise to the reaction mixture at 28° C. The reaction mixture was stirred at reflux for 18 h, cooled to 25° C., quenched with 1N HCl solution (50 mL) and extracted with CH$_2$Cl$_2$ (2×50 mL). The combined organic extracts were washed with brine, dried over Na$_2$SO$_4$, and concentrated under reduced pressure. The crude compound was purified by flash chromatography (SiO$_2$, 100-200 mesh; eluting with 40% EtOAc in n-hexane) to afford the title compound as yellow solid (0.15 g, 50%): mp 83-85° C.; $^1$H NMR (400 MHz, CDCl$_3$) δ 7.72 (d, J=8.0 Hz, 1H), 7.44 (s, 1H), 7.40 (s, 2H), 7.36 (d, J=6.8 Hz, 1H), 7.05 (t, J=5.2 Hz, 1H), 6.70 (t, J=5.2 Hz, 1H), 6.57 (d, J=15.6 Hz, 1H), 6.44 (dd, J=15.6, 8.0 Hz, 1H), 4.23 (d, J=5.6 Hz, 2H), 4.15 (m, 1H), 4.01 (m, 2H); ESIMS m/z 580.72 ([M−H]$^−$).

Compounds AC59-AC75 (Table 1) were made in accordance with the procedures disclosed in Example 14.

Example 15

Preparation of (E)-2-Bromo-4-(3-(3,5-dichloro-4-fluorophenyl)-4,4,4-trifluorobut-1-en-1-yl)-N-(2-oxo-2-((2,2,2-trifluoroethyl)amino)ethyl)benzamide (AC79)

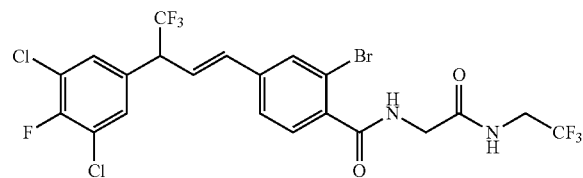 [SMILES: O=C(CNC(=O)c1ccc(/C=C/C(c2cc(Cl)c(F)c(Cl)c2)C(F)(F)F)cc1Br)NCC(F)(F)F]

To a stirred solution of (E)-2-bromo-4-(3-(3,5-dichloro-4-fluorophenyl)-4,4,4-trifluorobut-1-enyl)benzoic acid (300 mg, 0.638 mmol) in CH$_2$Cl$_2$ (5.0 mL) was added 2-amino-N-(2,2,2-trifluoroethyl)acetamide (172. mg, 0.638 mmol) followed by PyBOP (364.5 mg, 0.701 mmol) and DIPEA (0.32 mL, 1.914 mmol), and the resultant reaction mixture was stirred at ambient temperature for 18 h. The reaction mixture was diluted with water and extracted with CH$_2$Cl$_2$. The combined CH$_2$Cl$_2$ layer was washed with brine, dried over Na$_2$SO$_4$ and concentrated under reduced pressure. Purification by flash column chromatography (SiO$_2$, 100-200 mesh; eluting with 40% EtOAc/petroleum ether) afforded the title compound as an off-white solid (121 mg, 31%): $^1$H NMR (400 MHz, CDCl$_3$) δ 8.69 (t, J=6.0 Hz, 1H), 8.58 (t, J=6.0 Hz, 1H), 7.92 (s, 1H), 7.87 (d, J=6.4 Hz, 2H), 7.62 (d, J=8.4 Hz, 1H), 7.45 (d, J=8.4 Hz, 1H), 7.0 (m, 1H), 6.76 (d, J=15.6 Hz, 1H), 4.83 (t, J=8.0 Hz, 1H), 3.98 (m, 4H); ESIMS m/z 610.97 ([M+H]$^+$); IR (thin film) 3303, 1658, 1166, 817 cm$^{-1}$.

Compounds AC76-AC80, AC96-AC102, and AC113 (Table 1) were made in accordance with the procedures disclosed in Example 15.

Example 16

Preparation of (E)-4-(3-(3,5-Dichlorophenyl)-4,4,4-trifluorobut-1-en-1-yl)-N-(1,1-dioxidothietan-3-yl)-2-fluorobenzamide (AC83)

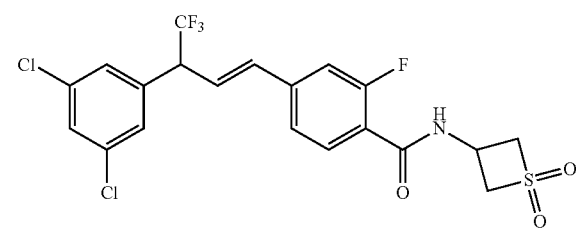 [SMILES: O=C(NC1CS(=O)(=O)C1)c1ccc(/C=C/C(c2cc(Cl)cc(Cl)c2)C(F)(F)F)cc1F]

To a stirred solution of (E)-4-(3-(3,5-dichlorophenyl)-4,4,4-trifluorobut-1-enyl)-2-fluoro-N-(thietan-3-yl)benzamide (100 mg, 0.2159 mmol) in acetone/water (1:1, 5.0 mL) was added oxone (266 mg, 0.4319 mmol) and the resultant reaction mixture was stirred at ambient temperature for 4 h. The reaction mixture was diluted with water and extracted with EtOAc. The combined EtOAc layer was dried over anhydrous Na$_2$SO$_4$ and concentrated under reduced pressure. Purification by flash column chromatography (SiO$_2$, 100-200 mesh; eluting with 30% EtOAc/pet ether) afforded the title compound as an off white solid (70.0 mg, 66%): $^1$H NMR (400 MHz, CDCl$_3$) δ 8.07 (t, J=8.4 Hz, 1H), 7.39 (t, J=1.6 Hz, 1H), 7.31 (d, J=1.2 Hz, 1H), 7.26 (m, 2H), 7.23 (m, 2H), 7.19 (d, J=1.6 Hz, 1H), 6.60 (d, J=16.8 Hz, 1H), 6.49 (dd, J=16.8, 7.6 Hz, 1H), 4.90 (m, 1H), 4.64 (m, 2H), 4.14 (m, 2H); ESIMS m/z 493.83 ([M−H]$^−$); IR (thin film) 1527, 1113, 801, 1167, 1321 cm$^{-1}$.

Compounds AC81-AC87 (Table 1) were made in accordance with the procedures disclosed in Example 16.

Example 17

Preparation of (E)-N-((5-Cyclopropyl-1,3,4-oxadiazol-2-yl)methyl)-4-(3-(3,5-dichlorophenyl)-4,4,4-trifluorobut-1-en-1-yl)-2-methylbenzamide (AC89)

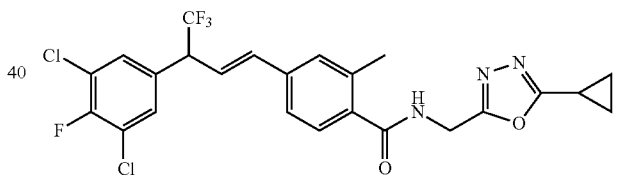

A solution of (E)-N-(2-(2-(cyclopropanecarbonyl)hydrazinyl)-2-oxoethyl)-4-(3-(3,5-dichlorophenyl)-4,4,4-trifluorobut-1-enyl)-2-methylbenzamide (200 mg, 0.379 mmol) in phosphoryl chloride (POCl$_3$, 2.0 mL) was stirred at ambient temperature for 10 min, then the resultant reaction mixture was heated to 50° C. for 1 h. The reaction mixture was quenched with ice water at 0° C. and extracted with EtOAc. The combined EtOAc layer was washed with saturated sodium bicarbonate (NaHCO$_3$) solution and brine solution, dried over anhydrous Na$_2$SO$_4$, and concentrated under reduced pressure. Purification by flash column chromatography (SiO$_2$, 100-200 mesh; eluting with 50% EtOAc/pet ether) afforded the title compound as a light brown gummy material (70.0 mg, 36%): $^1$H NMR (400 MHz, CDCl$_3$) δ 7.43 (m, 2H), 7.27 (m, 2H), 7.23 (m, 2H), 6.58 (d, J=16.0 Hz, 1H), 6.41 (dd, J=16.0, 7.6 Hz, 1H), 4.79 (d, J=5.6 Hz, 2H), 4.14 (m, 1H), 2.48 (s, 3H), 2.18 (m, 1H), 1.16 (m, 4H); ESIMS m/z 509.89 ([M+H]$^+$); IR (thin film) 1666, 1166, 1112, 800 cm$^{-1}$.

Example 18

Preparation of (E)-2-Bromo-N-(2-thioxo-2-((2,2,2-trifluoroethyl)amino)ethyl)-4-(4,4,4-trifluoro-3-(3,4,5-trichlorophenyl)but-1-en-1-yl)benzothioamide (AC90)

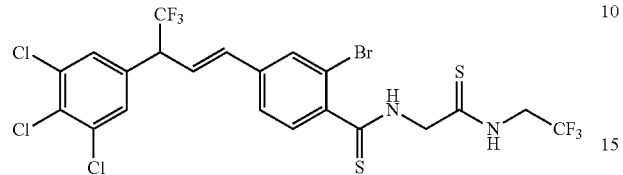

To a stirred solution of (E)-2-bromo-N-(2-oxo-2-((2,2,2-trifluoroethyl)amino)ethyl)-4-(4,4,4-trifluoro-3-(3,4,5-trichlorophenyl)but-1-en-1-yl)benzamide (400 mg, 0.638 mmol) in 5 mL of THF at ambient temperature was added 2,4-bis(4-methoxyphenyl)-1,3,2,4-dithiadiphosphetane-2,4-disulfide (Lawesson's reagent) (336 mg, 0.830 mmol) in one portion. The resulting reaction mixture was stirred for 18 h. TLC showed the reaction was not complete, therefore additional Lawesson's reagent (168 mg, 0.415 mmol) was added and reaction stirred for 48 h. After the reaction was deemed complete by TLC, the reaction mixture was concentrated under reduced pressure. Purification by flash chromatography (SiO$_2$, 230-400 mesh; eluting with 20% EtOAc in hexanes) afforded the title compound as a yellow glassy oil (188 mg, 44.7%): $^1$H NMR (400 MHz, CDCl$_3$) δ 8.34 (m, 1H), 8.27 (m, 1H), 7.60 (d, J=1.6 Hz, 1H), 7.49 (d, J=8.0 Hz, 2H), 7.40 (s, 2H), 7.36 (dd, J=8.2, 1.7 Hz, 1H), 6.53 (d, J=16.0 Hz, 1H), 6.38 (dd, J=15.9, 7.9 Hz, 1H), 4.89 (d, J=8.4, 5.5 Hz, 2H), 4.48 (qd, J=9.0, 6.0 Hz, 2H), 4.11 (m, 1H); ESIMS m/z 656.9 ([M–H]$^-$).

Example 19

Preparation of (E)-2-(2-Bromo-4-(4,4,4-trifluoro-3-(3,4,5-trichlorophenyl)but-1-en-1-yl)phenylthioamido)-N-(2,2,2-trifluoroethyl)acetamide (AC91)

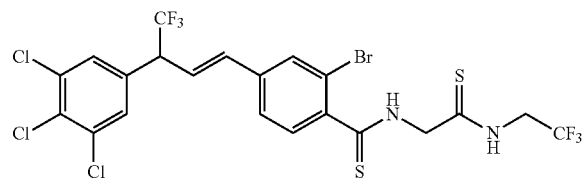

To a stirred solution of (E)-2-bromo-N-(2-oxo-2-((2,2,2-trifluoroethyl)amino)ethyl)-4-(4,4,4-trifluoro-3-(3,4,5-trichlorophenyl)but-1-en-1-yl)benzamide (400 mg, 0.638 mmol) in 5 mL of THF at ambient temperature was added Lawesson's reagent (64.5 mg, 0.160 mmol) in one portion. The resulting reaction mixture was stirred for 18 h, after which time, the reaction mixture was concentrated under reduced pressure. Purification by flash chromatography (SiO$_2$, 230-400 mesh; eluting with 20% EtOAc in hexanes) afforded the title compounds as a yellow oil (18.5 mg, 4.51%): $^1$H NMR (400 MHz, CDCl$_3$) δ 8.18 (t, J=5.0 Hz, 1H), 7.58 (d, J=1.6 Hz, 1H), 7.47 (d, J=8.0 Hz, 1H), 7.40 (s, 2H), 7.34 (dd, J=8.1, 1.6 Hz, 1H), 6.52 (m, 2H), 6.37 (dd, J=15.9, 7.9 Hz, 1H), 4.54 (d, J=4.9 Hz, 2H), 4.12 (m, 1H), 3.99 (qd, J=8.9, 6.5 Hz, 2H); ESIMS m/z 640.9 ([M–H]$^-$).

The following compound was made in accordance with the procedures disclosed in Example 19.

(E)-2-Bromo-N-(2-thioxo-2-((2,2,2-trifluoroethyl)amino)ethyl)-4-(4,4,4-trifluoro-3-(3,4,5-trichlorophenyl)but-1-en-1-yl)benzamide (AC92)

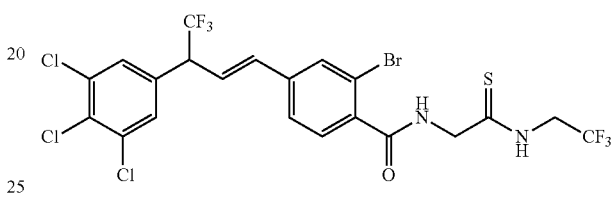

The product was isolated as a colorless oil (17.9 mg, 4.36%): $^1$H NMR (400 MHz, CDCl$_3$) δ 9.16 (d, J=6.1 Hz, 1H), 7.65 (d, J=1.6 Hz, 1H), 7.57 (d, J=8.0 Hz, 1H), 7.41 (m, 3H), 7.21 (t, J=5.6 Hz, 1H), 6.55 (d, J=15.9 Hz, 1H), 6.41 (dd, J=15.9, 7.8 Hz, 1H), 4.59 (d, J=5.6 Hz, 2H), 4.45 (qd, J=9.0, 6.0 Hz, 2H), 4.12 (q, J=7.2 Hz, 1H); ESIMS m/z 640.9 ([M–H]$^-$).

Example 106

Preparation of Ethyl (Z)-2-Bromo-4-(4,4,4-trifluoro-3-(3,4,5-trichlorophenyl)but-1-en-1-yl)benzoate (AI76)

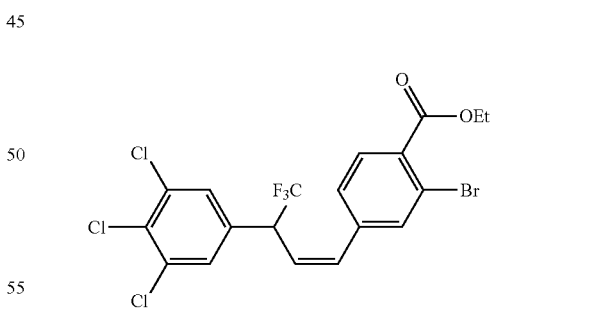

The title compound was made in accordance with the procedure disclosed in Example 88 and was isolated as a yellow viscous oil (416 mg, 23%): $^1$H NMR (400 MHz, CDCl$_3$) δ 7.80 (d, J=8.0 Hz, 1H), 7.40 (d, J=1.7 Hz, 1H), 7.35 (s, 2H), 7.12 (dd, J=8.0, 1.7 Hz, 1H), 6.86 (d, J=11.4 Hz, 1H), 6.23-5.91 (m, 1H), 4.42 (q, J=7.1 Hz, 2H), 4.33-4.10 (m, 1H), 1.42 (t, J=7.2 Hz, 3H); $^{19}$F NMR (376 MHz, CDCl$_3$) δ −69.34 (d, J=8.3 Hz); EIMS m/z 514.10 ([M]$^-$); IR (thin film) 2983, 1727, 1247, 1204, 1116 cm$^{-1}$.

Example 107

Preparation of (Z)-2-Bromo-4-(4,4,4-trifluoro-3-(3,4,5-trichlorophenyl)but-1-en-1-yl)benzoic acid (AI77)

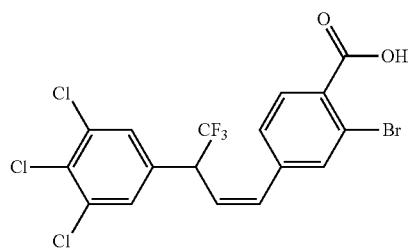 [SMILES: O=C(O)c1ccc(/C=C\C(c2cc(Cl)c(Cl)c(Cl)c2)C(F)(F)F)cc1Br]

To a stirred solution of (Z)-ethyl 2-bromo-4-(4,4,4-trifluoro-3-(3,4,5-trichlorophenyl)but-1-en-1-yl)benzoate (360 mg, 0.70 mmol) in CH₃CN (1.0 mL) was added iodotrimethylsilane (0.28 mL, 2.8 mmol). The reaction mixture was heated to reflux for 20 h, allowed to cool to ambient temperature and partitioned between CH₂Cl₂ and aqueous 10% sodium thiosulfate (Na₂S₂O₃). The organic phase was washed once with aqueous 10% Na₂S₂O₃ and dried over magnesium sulfate (MgSO₄) and concentrated in vacuo. Passing the material through a silica plug with 10% EtOAc in hexanes, followed by 20% MeOH in CH₂Cl₂) as the eluting solvents afforded the title compound as a yellow foam (143 mg, 42%): mp 54-64° C.; $^1$H NMR (400 MHz, CDCl₃) δ 11.36 (s, 1H), 7.99 (d, J=8.0 Hz, 1H), 7.43 (s, 1H), 7.30 (s, 2H), 7.14 (d, J=7.9 Hz, 1H), 6.85 (d, J=11.4 Hz, 1H), 6.15 (t, J=10.9 Hz, 1H), 4.36-4.09 (m, 1H); $^{19}$F NMR (376 MHz, CDCl₃) δ −69.30.

Example 108

Preparation of (Z)-2-Bromo-N-(2-oxo-2-((2,2,2-trifluoroethyl)amino)ethyl)-4-(4,4,4-trifluoro-3-(3,4,5-trichlorophenyl)but-1-en-1-yl)benzamide (AC95)

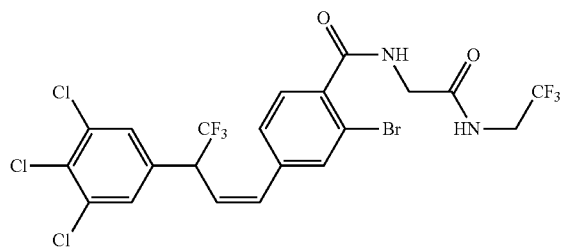 [SMILES: O=C(CNC(=O)c1ccc(/C=C\C(c2cc(Cl)c(Cl)c(Cl)c2)C(F)(F)F)cc1Br)NCC(F)(F)F]

To a stirred solution of (Z)-2-bromo-4-(4,4,4-trifluoro-3-(3,4,5-trichlorophenyl)but-1-en-1-yl)benzoic acid (200 mg, 0.41 mmol) in anhydrous THF (5.0 mL) was added carbonyldiimidazole (82 mg, 0.51 mmol). The mixture was heated in a 50° C. oil bath for 1.5 h, treated with 2-amino-N-(2,2,2-trifluoroethyl)acetamide hydrochloride (109 mg, 0.057 mmol) and the resulting mixture heated to reflux for 8 h. After cooling to ambient temperature, the mixture was taken up in Et₂O and washed twice with aqueous 5% sodium bisulfate (NaHSO₄) (2×) and once with saturated NaCl (1×). After dying over MgSO₄, concentration in vacuo and purification by medium pressure chromatography on silica with EtOAc/Hexanes as the eluents, the title compound was obtained as a white foam (160 mg, 41%) mp 48-61° C.: $^1$H NMR (400 MHz, CDCl₃) δ 7.58 (d, J=7.9 Hz, 1H), 7.44-7.29 (m, 3H), 7.14 (dd, J=7.9, 1.6 Hz, 1H), 6.86 (d, J=11.4 Hz, 1H), 6.76 (t, J=5.9 Hz, 1H), 6.59 (br s, 1H), 6.21-6.04 (m, 1H), 4.23 (d, J=5.5 Hz, 1H), 3.98 (qd, J=9.0, 6.5 Hz, 2H); $^{19}$F NMR (376 MHz, CDCl₃) δ −69.31, −72.3; EIMS m/z 626.9 ([M+H]⁺).

Example 109a

Preparation of (E)-2-Bromo-N-(piperidin-4-yl)-4-(4,4,4-trifluoro-3-(3,4,5-trichlorophenyl)but-1-en-1-yl)benzamide (AC114)

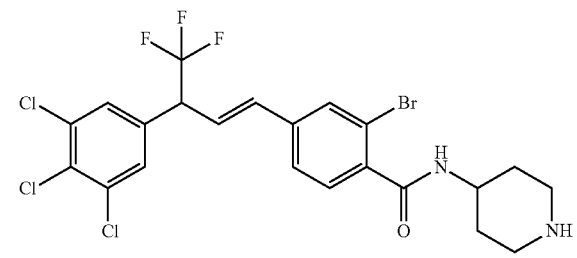 [SMILES: O=C(NC1CCNCC1)c1ccc(/C=C/C(c2cc(Cl)c(Cl)c(Cl)c2)C(F)(F)F)cc1Br]

(E)-tert-Butyl 4-(2-bromo-4-(4,4,4-trifluoro-3-(3,4,5-trichlorophenyl)but-1-enyl)benzamido)piperidine-1-carboxylate (0.75 g, 1.11 mmol) was added to dioxane HCl (10 mL) at 0° C. and was stirred for 18 h. The reaction mixture was concentrated under reduced pressure and triturated with diethylether to afford the compound as a light brown solid (0.6 g, 88%).

Example 109b

Preparation of (E)-N-(1-Acetylpiperidin-4-yl)-2-bromo-4-(4,4,4-trifluoro-3-(3,4,5-trichlorophenyl)but-1-en-1-yl)benzamide (AC103)

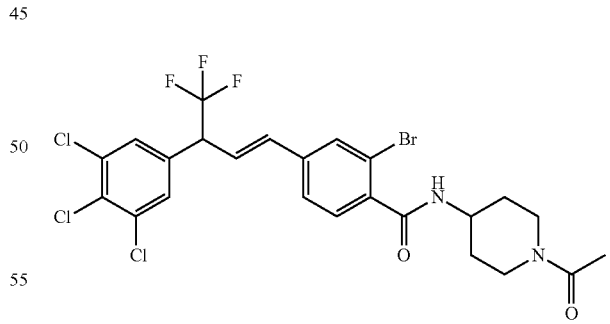

To a stirred solution of (E)-2-bromo-N-(piperidin-4-yl)-4-(4,4,4-trifluoro-3-(3,4,5-trichlorophenyl)but-1-enyl)benzamide (0.1 g, 0.16 mmol) in CH₂Cl₂ (10.0 mL) was added TEA (0.046 mL, 0.35 mmol) and stirred for 10 min. Then acetyl chloride (0.014, 0.18 mmol) was added and stirred for 16 h at ambient temperature. The reaction mixture was diluted with CH₂Cl₂ and washed with saturated NaHCO₃ solution and brine solution. The combined CH₂Cl₂ layer was dried over Na₂SO₄ and concentrated under reduced pressure

Example 110

Preparation of (E)-2-Bromo-4-(4,4,4-trifluoro-3-(3,4,5-trichlorophenyl)but-1-en-1-yl)-N-(1-(3,3,3-trifluoropropanoyl)piperidin-4-yl)benzamide (AC104)

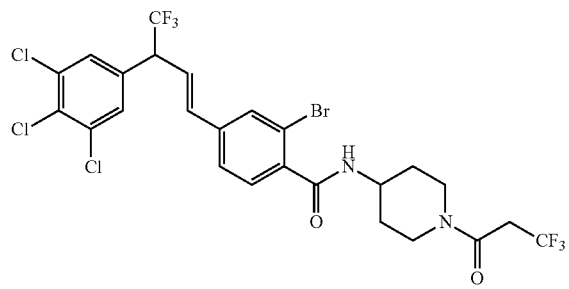 [SMILES: O=C(NC1CCN(C(=O)CC(F)(F)F)CC1)c1ccc(/C=C/C(c2cc(Cl)c(Cl)c(Cl)c2)C(F)(F)F)cc1Br]

To a stirred solution of 3,3,3-trifluoropropanoic acid (0.02 g, 0.16 mmol) in CH$_2$Cl$_2$ (10.0 mL), (E)-2-bromo-N-(piperidin-4-yl)-4-(4,4,4-trifluoro-3-(3,4,5-trichlorophenyl)but-1-enyl)benzamide (0.1 g, 0.16 mmol), PYBOP (0.09 g, 0.17 mmol), and DIPEA (0.06 g, 0.48 mmol) were added at ambient temperature. The reaction mixture was stirred at ambient temperature for 5 h. The reaction mixture was diluted with CH$_2$Cl$_2$. The combined CH$_2$Cl$_2$ layer was washed with 3N HCl and saturated NaHCO$_3$ solution, the separated CH$_2$Cl$_2$ layer was dried over anhydrous Na$_2$SO$_4$ and concentrated under reduced pressure to afford crude compound. The crude compound was purified by column chromatography (SiO$_2$, 100-200 mesh; eluting with 2% MeOH in CH$_2$Cl$_2$) to afford the title compound as an off white gummy material (0.035 g, 29.%).

Example 111

Preparation of (E)-2-Bromo-4-(4,4,4-trifluoro-3-(3,4,5-trichlorophenyl)but-1-en-1-yl)-N-(1-(2,2,2-trifluoroethyl)piperidin-4-yl)benzamide (AC105)

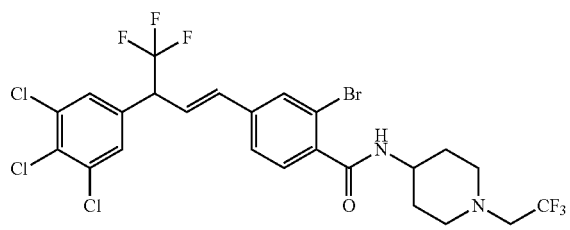 [SMILES: O=C(NC1CCN(CC(F)(F)F)CC1)c1ccc(/C=C/C(c2cc(Cl)c(Cl)c(Cl)c2)C(F)(F)F)cc1Br]

To a stirred solution of (E)-2-bromo-N-(piperidin-4-yl)-4-(4,4,4-trifluoro-3-(3,4,5-trichlorophenyl)but-1-enyl)benzamide (0.1 g, 0.16 mmol) in THF (5.0 mL) was added TEA (0.06 mL, 0.64 mmol) and stirred for 10 min. Then 2,2,2-trifluoroethyl trifluoromethanesulfonate (0.03, 0.16 mmol) was added and stirred for 16 h at ambient temperature. The reaction mixture was diluted with EtOAc and washed with saturated NaHCO$_3$ solution and brine solution. The combined EtOAc layer was dried over Na$_2$SO$_4$ and concentrated under reduced pressure to afford the title compound as a brown solid (0.05 g, 44%).

Example 112

Preparation of (E)-2-Bromo-N-(1-methylpiperidin-4-yl)-4-(4,4,4-trifluoro-3-(3,4,5-trichlorophenyl)but-1-en-1-yl)benzamide (AC106)

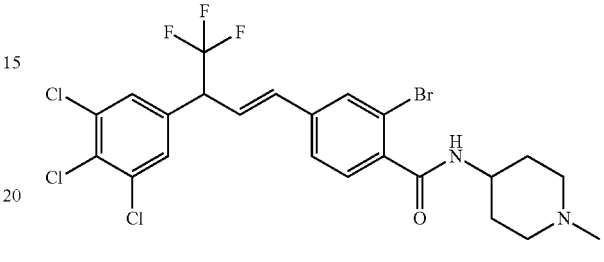

A solution of (E)-2-bromo-N-(piperidin-4-yl)-4-(4,4,4-trifluoro-3-(3,4,5-trichlorophenyl)but-1-enyl)benzamide (0.1 g, 0.16 mmol), formaldehyde (30% in water) (0.1 mL, 0.16 mmol) and AcOH (0.01 mL) in MeOH (5.0 mL) was stirred at ambient temperature for 30 min. After that NaBH$_3$CN (0.01 g, 0.16 mmol) was added at 0° C. and the reaction was stirred for 8 h at ambient temperature. The solvent was removed under reduced pressure to obtain residue which was diluted with EtOAc and washed with saturated aqueous NaHCO$_3$ solution and brine solution. The combined EtOAc layer was dried over Na$_2$SO$_4$ and concentrated under reduced pressure to obtain a residue, which was triturated with Et$_2$O/pentane to afford the title compound as a pale yellow gummy material (0.06 g, 59%).

Example 113

Preparation of ((E)-2-Bromo-N-(1-(cyanomethyl)piperidin-4-yl)-4-(4,4,4-trifluoro-3-(3,4,5-trichlorophenyl)but-1-en-1-yl)benzamide (AC107)

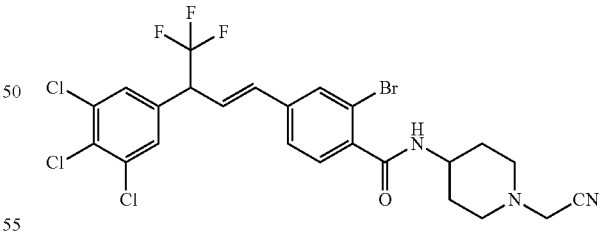

To a stirred solution of (E)-2-bromo-N-(piperidin-4-yl)-4-(4,4,4-trifluoro-3-(3,4,5-trichlorophenyl)but-1-enyl)benzamide (0.25 g, 0.43 mmol) in THF (10.0 mL) was added TEA (0.16 mL, 1.29 mmol) and the reaction was stirred for 10 min. Then 2-bromoacetonitrile (0.07, 0.65 mmol) was added and the reaction was stirred for 8 h at ambient temperature. The reaction mixture was diluted with EtOAc and washed with saturated brine solution. The combined EtOAc layer was dried over Na$_2$SO$_4$ and concentrated under reduced pressure to afford the title compound as an off-white solid (0.125 g, 46.8%).

Example 114

Preparation of (E)-2-Bromo-N-(1-(oxetan-3-yl)piperidin-4-yl)-4-(4,4,4-trifluoro-3-(3,4,5-trichlorophenyl)but-1-en-1-yl)benzamide (AC108)

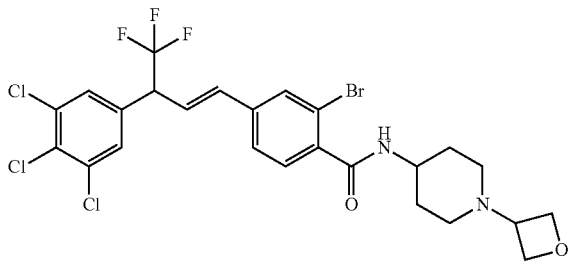 [SMILES: O=C(NC1CCN(C2COC2)CC1)c1ccc(/C=C/C(c2cc(Cl)c(Cl)c(Cl)c2)C(F)(F)F)cc1Br]

A solution of (E)-2-bromo-N-(piperidin-4-yl)-4-(4,4,4-trifluoro-3-(3,4,5-trichlorophenyl)but-1-enyl)benzamide (0.2 g, 0.35 mmol), oxetan-3-one (0.027 g, 0.38 mmol) and AcOH (0.01 mL) in MeOH (5.0 mL) was stirred at ambient temperature for 30 min After that NaBH$_3$CN (0.022 g, 0.35 mmol) was added at 0° C. slowly lot wise over the period of 10 min and the reaction was stirred for 8 h at ambient temperature. The solvent was removed under reduced pressure to obtain a residue which was diluted with EtOAc and washed with saturated NaHCO$_3$ solution and brine solution. The combined EtOAc layer was dried over Na$_2$SO$_4$ and concentrated under reduced pressure to obtain a residue, which was triturated with Et$_2$O/pentane to afford the title compound as an off-white solid (0.05 g, 23%).

Example 115

Preparation of (E)-2-Bromo-N-(1-(2-hydroxyethyl)piperidin-4-yl)-4-(4,4,4-trifluoro-3-(3,4,5-trichlorophenyl)but-1-en-1-yl)benzamide (AC109)

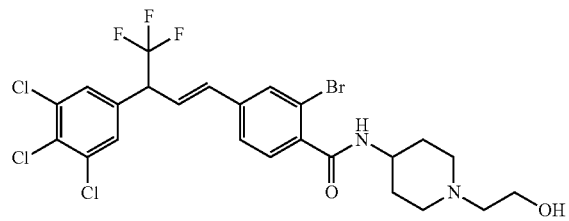 [SMILES: O=C(NC1CCN(CCO)CC1)c1ccc(/C=C/C(c2cc(Cl)c(Cl)c(Cl)c2)C(F)(F)F)cc1Br]

To a stirred solution of (E)-2-bromo-N-(piperidin-4-yl)-4-(4,4,4-trifluoro-3-(3,4,5-trichlorophenyl)but-1-enyl)benzamide (0.25 g, 0.43 mmol) in THF (10.0 mL) was added TEA (0.16 mL, 1.29 mmol) and the reaction was stirred for 10 min. Then 2-chloroethanol (0.05, 0.65 mmol) was added and the reaction was stirred for 8 h at ambient temperature. The reaction mixture was diluted with EtOAc and washed with saturated brine solution. The combined EtOAc layer was dried over Na$_2$SO$_4$ and concentrated under reduced pressure to afford the title compound as an off-white solid (0.09 g, 34%).

Example 116

Preparation of (E)-2-(2-Bromo-4-(4,4,4-trifluoro-3-(3,4,5-trichlorophenyl)but-1-en-1-yl)benzamido)acetic acid (AI78)

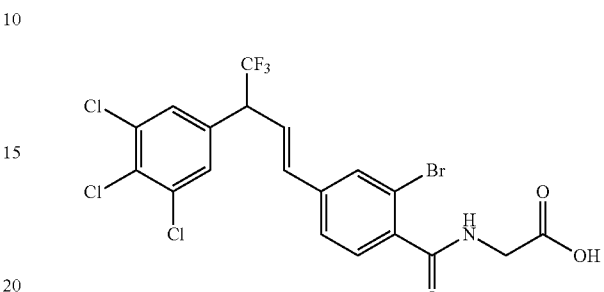

To a stirred solution of (E)-tert-butyl 2-(2-bromo-4-(4,4,4-trifluoro-3-(3,4,5-trichlorophenyl)but-1-enyl)benzamido)acetate (440 mg, 0.734 mmol) in CH$_2$Cl$_2$ (36.0 ml), was added TFA (4.0 mL) and the reaction mixture was stirred at ambient temperature for 1 h. The reaction mixture was concentrated under reduced pressure to obtain residue which was washed with n-pentane to afford the title compound as an off-white solid (310 mg, 78%): $^1$H NMR (400 MHz, CDCl$_3$) δ 13.0 (s, 1H), 8.75 (t, J=5.7 Hz, 1H), 7.93 (m, 2H), 7.62 (d, J=7.5 Hz, 1H), 7.40 (d, J=8.1 Hz, 1H), 6.96 (dd, J=15.3, 9.3 Hz, 1H), 6.78 (d, J=15.3 Hz, 1H), 4.83 (m, 1H), 3.90 (d, J=5.7 Hz, 2H); ESIMS m/z 543.610 ([M+H]$^+$); IR (thin film) 3429, 1635, 1114, 772 cm$^{-1}$.

Example 117

Preparation of (E)-N-((6-Chloropyridin-3-yl)methyl)-4-(3-(3,5-dichlorophenyl)-4,4,4-trifluorobut-1-en-1-yl)-2-methylbenzothioamide (AC115)

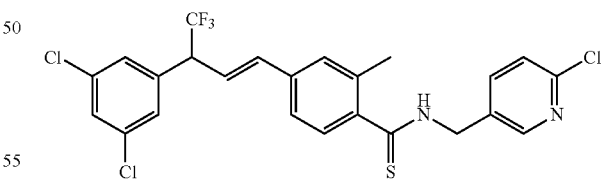

To the stirred solution of (E)-N-((6-chloropyridin-3-yl)methyl)-4-(3-(3,5-dichlorophenyl)-4,4,4-trifluorobut-1-enyl)-2-methylbenzamide (0.06 g, 0.117 mmol) in toluene (3 mL) was added Lawesson's reagent (0.14 g, 0.351 mmol) and the reaction was irradiated at 100° C. for 1 h, then cooled to ambient temperature and concentrated under reduced pressure to provide crude compound. The crude product was purified by preparative HPLC to afford the product as yellow color solid (0.03 g, 49%).

Example 118

Preparation of (E)-4-(3-(3,5-Dichloro-4-fluorophenyl)-4,4,4-trifluorobut-1-en-1-yl)-N-(2-oxo-2-((2,2,2-trifluoroethyl)amino)ethyl)-2-(trifluoromethoxy)benzamide (AC116)

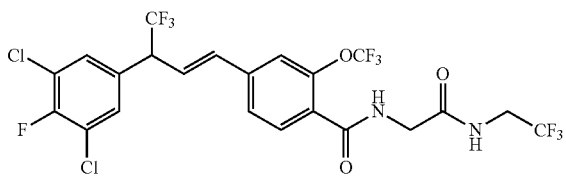 [SMILES: O=C(CNC(=O)c1ccc(/C=C/C(c2cc(Cl)c(F)c(Cl)c2)C(F)(F)F)cc1OC(F)(F)F)NCC(F)(F)F]

Step 1. 2-(Trifluoromethoxy)-4-vinylbenzoic acid (AI79)

To a stirred solution of 4-bromo-2-(trifluoromethoxy)benzoic acid (1 g, 3.67 mmol) in DMSO (20 mL) was added potassium vinyltrifluoroborate (1.47 g, 11.02 mmol) and $K_2CO_3$ (1.52 g, 11.02 mmol). The reaction mixture was degassed with argon for 30 min. Bistriphenylphosphine (diphenylphosphinoferrocene)palladium dichloride (0.13 g, 0.18 mmol) was added and the reaction mixture was heated to 80° C. for 1 h. The reaction mixture was diluted with water (100 mL), extracted with EtOAc (2×50 mL), washed with brine, and dried over $Na_2SO_4$. Concentration under reduced pressure furnished the crude compound which was purified by flash column chromatography to afford the product as pale yellow gummy material (0.4 g, 47%): $^1$H NMR (400 MHz, CDCl$_3$) δ 8.05 (d, J=8.1 Hz, 1H), 7.44 (d, J=1.8 Hz, 1H), 7.35 (s, 1H), 6.78 (dd, J=17.4.1, 11.1 Hz, 1H), 5.92 (d, J=17.4 Hz, 1H), 5.51 (d, J=10.8 Hz, 1H); ESIMS m/z 232.97 ([M+H]$^+$).

Step 2. (E)-4-(3-(3,5-Dichloro-4-fluorophenyl)-4,4,4-trifluorobut-1-enyl)-2-(trifluoromethoxy)benzoic acid (AI80)

To a stirred solution of 2-(trifluoromethoxy)-4-vinylbenzoic acid (0.356 g, 1.53 mmol) in 1N methyl pyrrolidine (5.0 mL) was added 1-(1-bromo-2,2,2-trifluoroethyl)-3,5-dichloro 4-fluorobenzene (1.0 g, 3.07 mmol), CuCl (0.03 g, 0.307 mmol) and 2,2 bipyridyl (0.095 g, 0.614 mmol). The reaction mixture was stirred at 150° C. for 1 h. After the reaction was complete by TLC, the reaction mixture was diluted with water (100 mL) and extracted with EtOAc (2×50 mL). The combined organic layers were washed with brine, dried over $Na_2SO_4$ and concentrated under reduced pressure to obtain the crude compound which was purified by flash column chromatography to afford the product as pale yellow gummy material (0.3 g, 21%): $^1$H NMR (400 MHz, CDCl$_3$) δ 8.08 (d, J=8.0 Hz, 1H), 7.45 (d, J=1.6 Hz, 1H), 7.35 (s, 3H), 6.63 (d, J=16.0 Hz, 1H), 6.50 (dd, J=16.0, 8.0 Hz, 1H), 4.15 (m, 1H); ESIMS m/z 474.81 ([M−H]$^−$).

Step 3. (E)-4-(3-(3,5-Dichloro-4-fluorophenyl)-4,4,4-trifluorobut-1-enyl)-N-(2-oxo-2-(2,2,2-trifluoroethylamino)ethyl)-2-(trifluoromethoxy)benzamide (AC116)

A mixture of (E)-4-(3-(3,5-dichloro-4-fluorophenyl)-4,4,4-trifluorobut-1-enyl)-2-(trifluoromethoxy)benzoic acid (0.25 g, 0.52 mmol), 2-amino-N-(2,2,2-trifluoroethyl)acetamide (0.158 g, 0.62 mmol), PyBOP (0.40 g, 0.78 mmol) and DIPEA (0.134 g, 1.04 mmol) in $CH_2Cl_2$ (10.0 mL) were stirred at ambient temperature for 16 h. The reaction mixture was diluted with water and extracted with $CH_2Cl_2$. The combined $CH_2Cl_2$ layer was washed with brine, dried over $Na_2SO_4$ and concentrated under reduced pressure. Purification by flash column chromatography (SiO$_2$, 100-200 mesh; eluting with 20% EtOAc/pet ether) afforded the title compound as a pale yellow gummy material (0.15 g, 47%).

The following molecules were made in accordance with the procedures disclosed in Example 118, Step 2:

(E)-4-(3-(3,5-Dibromophenyl)-4,4,4-trifluorobut-1-en-1-yl)-2-methylbenzoic acid

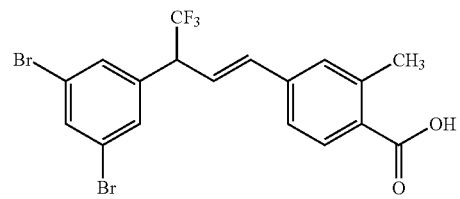

The title molecule was isolated as a brown solid: $^1$H NMR (400 MHz, DMSO-d$_6$) δ 12.90 (bs, 1H), 7.85 (s, 1H), 7.78-7.75 (m, 3H), 7.47-7.41 (m, 2H), 6.89 (dd, J=15.6, 9.2 Hz, 1H), 6.72 (d, J=15.6 Hz, 1H), 4.80-4.75 (m, 1H), 2.33 (s, 3H); ESIMS m/z 474.90 ([M−H]$^−$); IR (thin film) 3437, 1689, 1165, 579 cm$^{-1}$.

(E)-4-(3-(3,5-Dibromophenyl)-4,4,4-trifluorobut-1-en-1-yl)-2-(trifluoromethyl)benzoic acid

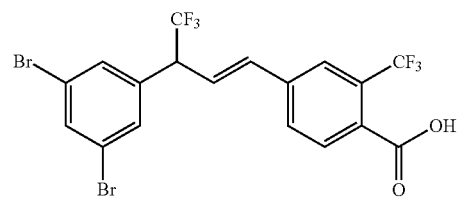

The title molecule was isolated as a brown solid: $^1$H NMR (300 MHz, DMSO-d$_6$) δ 13.5 (bs, 1H), 8.03 (s, 1H), 7.95-7.85 (m, 4H), 7.81 (d, J=7.8 Hz, 1H), 7.14 (dd, J=15.6, 9.6 Hz, 1H), 6.90 (d, J=15.9 Hz, 1H), 4.86-4.79 (m, 1H); ESIMS m/z 528.82 ([M−H]$^+$); IR (thin film) 3437, 1707, 1153, 555 cm$^{-1}$.

(E)-2-Bromo-4-(3-(3,5-dibromophenyl)-4,4,4-trifluorobut-1-en-1-yl)benzoic acid

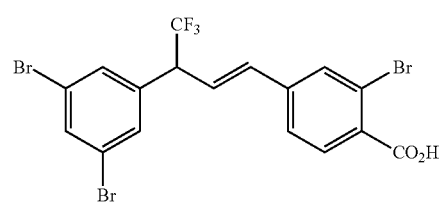

The title molecule was isolated as a brown liquid: ¹H NMR (400 MHz, DMSO-d₆) δ 13.90 (bs, 1H), 7.98 (s, 1H), 7.88 (s, 1H), 7.84 (s, 2H), 7.74 (d, J=7.6 Hz, 1H), 7.64 (d, J=8.8 Hz, 1H), 7.04 (dd, J=15.6, 8.8 Hz, 1H), 6.78 (d, J=15.6 Hz, 1H), 4.80-4.78 (m, 1H); ESIMS m/z 538.74 ([M−H]⁻); IR (thin film) 3424, 1695, 1168, 578 cm⁻¹.

(E)-2-Bromo-4-(4,4,4-trifluoro-3-(3-fluoro-5-(trifluoromethyl)phenyl)but-1-en-1-yl)benzoic acid

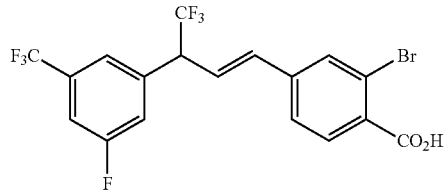 [SMILES: O=C(O)c1ccc(/C=C/C(c2cc(F)cc(C(F)(F)F)c2)C(F)(F)F)cc1Br]

The title molecule was isolated as a brown liquid: ¹H NMR (400 MHz, DMSO-d₆) δ 13.3 (bs, 1H), 7.93 (s, 1H), 7.82-7.77 (m, 2H), 7.72-7.66 (m, 2H), 7.59 (d, J=8.0 Hz, 1H), 7.03 (dd, J=15.6, 9.2 Hz, 1H), 6.76 (d, J=15.6 Hz, 1H), 4.94-4.90 (m, 1H); ESIMS m/z 469.02 ([M−H]⁻); IR (thin film) 3444, 1704, 1172, 513 cm⁻¹.

(E)-4-(3-(3,5-Bis(trifluoromethyl)phenyl)-4,4,4-trifluorobut-1-en-1-yl)-2-bromobenzoic acid

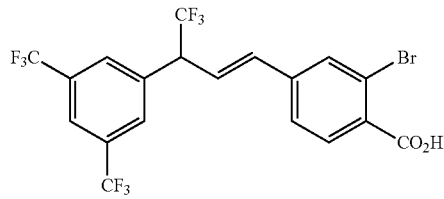 [SMILES: O=C(O)c1ccc(/C=C/C(c2cc(C(F)(F)F)cc(C(F)(F)F)c2)C(F)(F)F)cc1Br]

The title molecule was isolated as a brown solid: ¹H NMR (400 MHz, CDCl₃) δ 7.98 (d, J=7.6 Hz, 1H), 7.92 (s, 1H), 7.83 (s, 2H), 7.73 (d, J=1.6 Hz, 1H), 7.42-7.40 (m, 1H), 6.62 (d, J=16.4 Hz, 1H), 6.55 (dd, J=16.0, 8.0 Hz, 1H), 4.40-4.30 (m, 1H); ESIMS m/z 518.94 ([M−H]⁻); IR (thin film) 3447, 1705, 1171, 526 cm⁻¹.

(E)-2-Bromo-4-(4,4,4-trifluoro-3-(3-(trifluoromethyl)phenyl)but-1-en-1-yl)benzoic acid

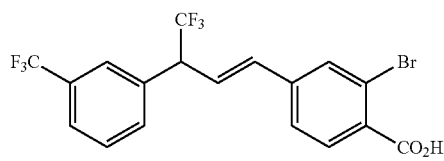 [SMILES: O=C(O)c1ccc(/C=C/C(c2cccc(C(F)(F)F)c2)C(F)(F)F)cc1Br]

The title molecule was isolated as a brown liquid: ¹H NMR (300 MHz, DMSO-d₆) δ 13.50 (bs, 1H), 7.97-7.87 (m, 3H), 7.78-7.61 (m, 4H), 7.08 (dd, J=15.9, 9.3 Hz, 1H), 6.81 (d, J=15.9 Hz, 1H), 4.97-4.84 (m, 1H); ESIMS m/z 518.94 ([M−H]⁻); IR (thin film) 3447, 1705, 1171, 526 cm⁻¹.

(E)-2-Bromo-4-(3-(3-chloro-5-(trifluoromethyl)phenyl)-4,4,4-trifluorobut-1-en-1-yl)benzoic acid

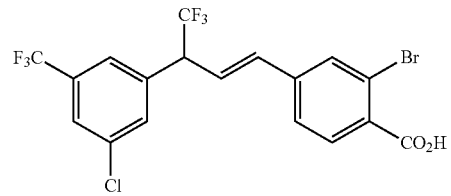 [SMILES: O=C(O)c1ccc(/C=C/C(c2cc(Cl)cc(C(F)(F)F)c2)C(F)(F)F)cc1Br]

The title molecule was isolated as a pale yellow gum: ¹H NMR (300 MHz, DMSO-d₆) δ 13.9 (s, 1H), 8.03 (s, 1H), 7.96-7.91 (m, 3H), 7.72 (d, J=8.1 Hz, 1H), 7.63-7.60 (m, 1H), 7.11 (dd, J=15.9, 9.6 Hz, 1H), 6.79 (d, J=15.9 Hz, 1H), 4.98-4.91 (m, 1H); ESIMS m/z 484.94 ([M−H]⁻); IR (thin film) 3444, 1705, 1171, 764 cm⁻¹.

(E)-2-Bromo-4-(4,4,4-trifluoro-3-(4-fluoro-3-(trifluoromethyl)phenyl)but-1-en-1-yl)benzoic acid

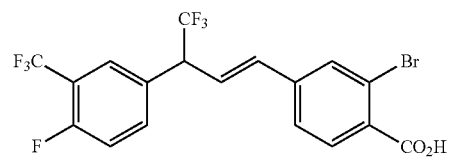 [SMILES: O=C(O)c1ccc(/C=C/C(c2ccc(F)c(C(F)(F)F)c2)C(F)(F)F)cc1Br]

The title molecule was isolated as a brown liquid: ¹H NMR (300 MHz, CDCl₃) δ 8.00 (d, J=8.1 Hz, 1H), 7.71 (s, 1H), 7.61-7.59 (m, 2H), 7.41 (d, J=8.1 Hz, 1H), 7.30-7.24 (m, 1H), 6.59 (dd, J=16.2, 6.0 Hz, 1H), 6.48 (d, J=16.5 Hz, 1H), 4.26-4.21 (m, 1H); ESIMS m/z 469.0 ([M−H]⁻); IR (thin film) 3444, 1699, 1327 cm⁻¹.

(E)-2-Bromo-4-(4,4,4-trifluoro-3-(3,4,5-trifluorophenyl)but-1-en-1-yl)benzoic acid

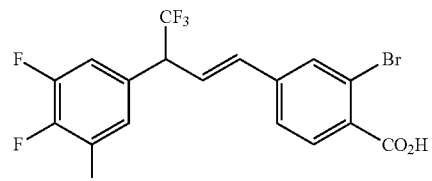

The title molecule was isolated as a brown gum: ¹H NMR (300 MHz, DMSO-d₆) δ 13.60 (bs, 1H), 7.97 (s, 2H), 7.72 (d, J=7.2 Hz, 1H), 7.41-7.31 (m, 2H), 7.04 (dd, J=15.6, 9.0 Hz, 1H), 6.71 (d, J=15.9 Hz, 1H), 4.15-4.11 (m, 1H); ESIMS m/z 438.8 ([M+H]⁺).

(E)-4-(4,4,4-Trifluoro-3-(2,3,4-trifluorophenyl)but-1-en-1-yl)-2-(trifluoromethyl)benzoic acid

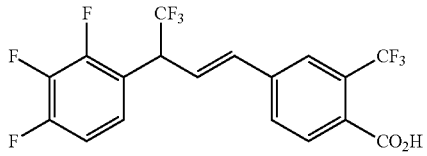 [SMILES: O=C(O)c1ccc(/C=C/C(c2ccc(F)c(F)c2F)C(F)(F)F)cc1C(F)(F)F]

The title molecule was isolated as a brown gum: $^1$H NMR (300 MHz, DMSO-$d_6$) δ 8.00 (s, 1H), 7.93 (d, J=8.4 Hz, 1H), 7.81 (d, J=8.1 Hz, 1H), 7.63-7.60 (m, 1H), 7.47-7.44 (m, 1H), 7.02-7.01 (m, 1H), 5.10-4.90 (m, 1H).

(E)-2-Bromo-4-(4,4,4-trifluoro-3-(2,3,4-trifluorophenyl)but-1-en-1-yl)benzoic acid

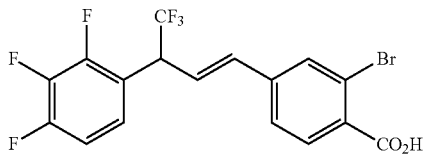 [SMILES: O=C(O)c1ccc(/C=C/C(c2ccc(F)c(F)c2F)C(F)(F)F)cc1Br]

The title molecule was isolated as a brown gum and the crude acid was taken on directly to the next step: $^1$H NMR (300 MHz, DMSO-$d_6$) δ 13.65 (bs, 1H), 7.95 (s, 1H), 7.75 (d, J=7.8 Hz, 1H), 7.62-7.59 (m, 2H), 7.50 (dd, J=15.6, 9.0 Hz, 1H), 6.95 (d, J=15.9 Hz, 1H), 4.86-4.74 (m, 1H); ESIMS m/z 436.92 ([M−H]$^−$); IR (thin film) 3445, 1641, 1116 cm$^{−1}$.

(E)-4-(4,4,4-Trifluoro-3-(2,4,5-trichlorophenyl)but-1-en-1-yl)-2-(trifluoromethyl)benzoic acid

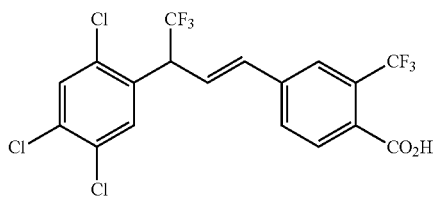 [SMILES: O=C(O)c1ccc(/C=C/C(c2cc(Cl)c(Cl)cc2Cl)C(F)(F)F)cc1C(F)(F)F]

The title molecule was isolated as a brown gum: $^1$H NMR (300 MHz, DMSO-$d_6$) δ 13.6 (s, 1H), 8.04 (s, 1H), 7.96 (d, J=8.4 Hz, 3H), 7.83 (d, J=8.1 Hz, 1H), 7.17-7.03 (m, 2H), 5.16-5.05 (m, 1H); ESIMS m/z 476.9 ([M−H]$^−$); IR (thin film) 3436, 1651, 1116, 661 cm$^{−1}$.

(E)-2-Bromo-4-(4,4,4-trifluoro-3-(2,4,5-trichlorophenyl)but-1-en-1-yl)benzoic acid

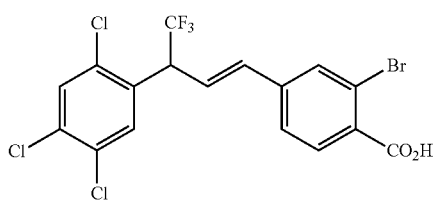 [SMILES: O=C(O)c1ccc(/C=C/C(c2cc(Cl)c(Cl)cc2Cl)C(F)(F)F)cc1Br]

The title molecule was isolated as a brown gum: $^1$H NMR (300 MHz, DMSO-$d_6$) δ (300 MHz, DMSO-$d_6$) δ 13.4 (s, 1H), 7.99 (d, J=10.2 Hz, 3H), 7.76 (d, J=8.1 Hz, 1H), 7.65 (d, J=7.8 Hz, 1H), 7.09-6.91 (m, 2H), 5.11-5.05 (m, 1H); ESIMS m/z 486.8 ([M−H]$^−$); IR (thin film) 3436, 1651, 1115, 737 cm$^{−1}$.

(E)-4-(3-(4-Chloro-3-nitrophenyl)-4,4,4-trifluorobut-1-en-1-yl)-2-(trifluoromethyl)benzoic acid

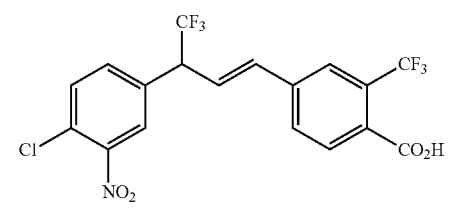 [SMILES: O=C(O)c1ccc(/C=C/C(c2ccc(Cl)c([N+](=O)[O-])c2)C(F)(F)F)cc1Br]

The title molecule was isolated as a brown gum and the crude acid was taken on directly to the next step: $^1$H NMR (300 MHz, DMSO-$d_6$) 13.80 (bs, 1H), 8.33 (s, 1H), 7.94-7.81 (m, 5H), 7.75-7.72 (m, 1H), 7.06 (dd, J=15.9, 8.7 Hz, 1H), 6.90 (d, J=15.9 Hz, 1H), 5.02-4.81 (m, 1H).

(E)-2-Bromo-4-(3-(4-chloro-3-nitrophenyl)-4,4,4-trifluorobut-1-en-1-yl)benzoic acid

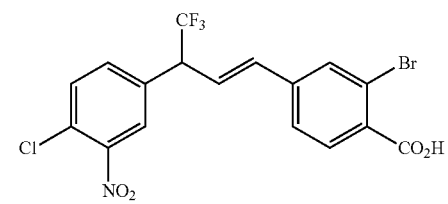

The title molecule was isolated as a brown gum: $^1$H NMR (300 MHz, DMSO-$d_6$) 13.50 (bs, 1H), 8.31 (s, 1H), 8.00-7.77 (m, 3H), 7.75-7.72 (m, 1H), 7.63-7.55 (m, 1H), 7.03 (dd, J=15.9, 9.0 Hz, 1H), 6.81 (d, J=15.9 Hz, 1H), 5.04-4.91 (m, 1H). ESIMS m/z 462.16 ([M−H]$^−$); IR (thin film) 3428, 1697, 1113, 749 cm$^{−1}$.

(E)-4-(4,4,4-Trifluoro-3-(4-fluoro-3,5-dimethylphenyl)but-1-en-1-yl)-2-(trifluoromethyl)benzoic acid

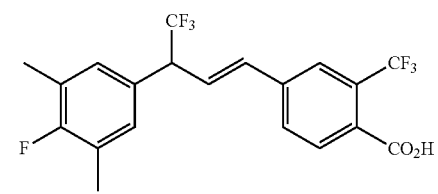 [SMILES: Cc1cc(C(/C=C/c2ccc(C(=O)O)c(C(F)(F)F)c2)C(F)(F)F)cc(C)c1F]

The title molecule was isolated as a brown gum: $^1$H NMR (300 MHz, DMSO-$d_6$) δ 7.96 (s, 1H), 7.92 (d, J=8.4 Hz, 1H), 7.80-7.75 (m, 1H), 7.27 (d, J=6.9 Hz, 2H), 6.96 (dd, J=15.6, 8.7 Hz, 1H), 6.87 (d, J=15.6 Hz, 1H), 4.68-4.56 (m, 1H), 2.23 (s, 6H); ESIMS m/z 419.03 ([M−H]$^−$); IR (thin film) 3445, 2928, 1713, 1146 cm$^{−1}$.

(E)-2-Bromo-4-(4,4,4-trifluoro-3-(4-fluoro-3,5-dimethylphenyl)but-1-en-1-yl)benzoic acid

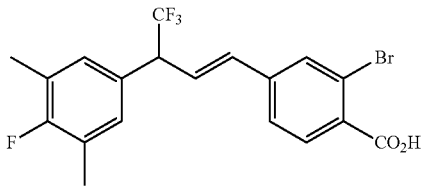 [SMILES: Cc1cc(C(/C=C/c2ccc(C(=O)O)c(Br)c2)C(F)(F)F)cc(C)c1F]

The title molecule was isolated as a brown gum: $^1$H NMR (300 MHz, DMSO-$d_6$) δ 7.91 (s, 1H), 7.74 (d, J=7.8 Hz, 1H), 7.61-7.58 (m, 1H), 7.26 (d, J=6.6 Hz, 2H), 6.93 (dd, J=15.9, 8.7 Hz, 1H), 6.87 (d, J=15.9 Hz, 1H), 4.59-4.53 (m, 1H), 2.23 (s, 6H); ESIMS m/z 428.97 ([M−H]$^−$); IR (thin film) 3473, 1701, 1111, 581 cm$^{-1}$.

(E)-4-(4,4,4-Trifluoro-3-(4-fluoro-3-methylphenyl)but-1-en-1-yl)-2-(trifluoromethyl)benzoic acid

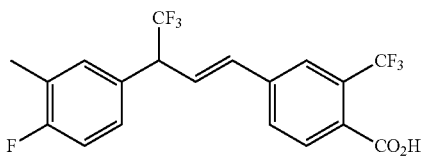 [SMILES: Cc1cc(C(/C=C/c2ccc(C(=O)O)c(C(F)(F)F)c2)C(F)(F)F)ccc1F]

The title molecule was isolated as a brown liquid: $^1$H NMR (300 MHz, DMSO-$d_6$) δ 13.58 (bs, 1H), 7.98 (s, 1H), 7.92-7.90 (m, 1H), 7.80 (d, J=8.1 Hz, 1H), 7.48-7.45 (m, 1H), 7.42-7.37 (m, 1H), 7.22-7.16 (m, 1H), 7.04 (dd, J=15.9, 8.7 Hz, 1H), 6.88 (d, J=15.9 Hz, 1H), 4.70-4.60 (m, 1H), 4.04-3.99 (m, 1H), 2.26 (s, 3H); ESIMS m/z 405.05 ([M−H]$^−$); IR (thin film) 3437, 1710, 1145 cm$^{-1}$.

(E)-2-Bromo-4-(4,4,4-trifluoro-3-(4-fluoro-3-methylphenyl)but-1-en-1-yl)benzoic acid

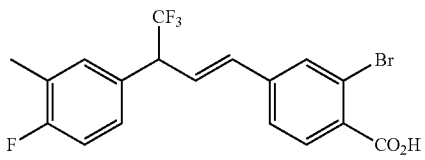 [SMILES: Cc1cc(C(/C=C/c2ccc(C(=O)O)c(Br)c2)C(F)(F)F)ccc1F]

The title molecule was isolated as a brown liquid: $^1$H NMR (300 MHz, DMSO-$d_6$) δ 13.39 (bs, 1H), 7.91 (s, 1H), 7.72 (d, J=8.1 Hz, 1H), 7.61-7.58 (m 1H), 7.47-7.44 (m, 1H), 7.38-7.36 (m, 1H), 7.18 (t, J=9.6 Hz, 1H), 6.95 (dd, J=15.6, 8.7 Hz, 1H), 6.76 (d, J=15.9 Hz, 1H), 4.67-4.61 (m, 1H), 2.25 (s, 3H); ESIMS m/z 415.0 ([M−H]$^−$); IR (thin film) 3435, 2989, 1700, 1260 cm$^{-1}$.

(E)-4-(3-(3,5-Dichlorophenyl)-4,4,5,5,5-pentafluoropent-1-en-1-yl)-2-(trifluoromethyl)benzoic acid

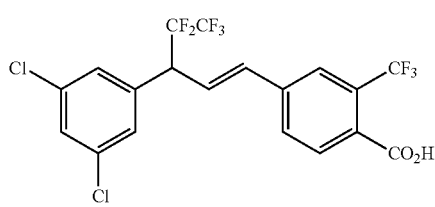

The title molecule was isolated as a brown semi solid: $^1$H NMR (400 MHz, DMSO-$d_6$) δ 13.70 (bs, 1H), 8.01 (s, 1H), 7.91 (s, 1H), 7.80 (d, J=8.4 Hz, 1H), 7.72 (J=1.6 Hz, 2H), 7.66 (t, J=3.2 Hz, 1H), 7.15 (dd, J=15.6, 9.6 Hz, 1H), 6.91 (d, J=15.6 Hz, 1H), 4.86-4.78 (m, 1H); ESIMS m/z 491.0 ([M−H]$^−$); IR (thin film) 3446, 1712, 1141, 749 cm$^{-1}$.

(E)-2-Bromo-4-(3-(3,5-dichlorophenyl)-4,4,5,5,5-pentafluoropent-1-en-1-yl)benzoic acid

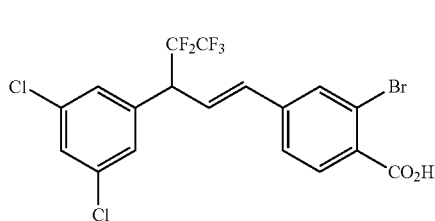

The title molecule was isolated as a brown gum: $^1$H NMR (400 MHz, DMSO-$d_6$) δ 7.85 (s, 1H), 7.70 (s, 2H), 7.65-7.64 (m, 1H), 7.56-7.52 (m, 2H), 6.94 (d, J=9.2 Hz, 1H), 6.76 (d, J=16 Hz, 1H), 4.82-4.80 (m, 1H); ESIMS m/z 500.8 ([M−H]$^−$); IR (thin film) 3422, 1683, 1184, 750, 575 cm$^{-1}$.

(E)-4-(3-(3,4-Dibromophenyl)-4,4,4-trifluorobut-1-en-1-yl)-2-(trifluoromethyl)benzoic acid

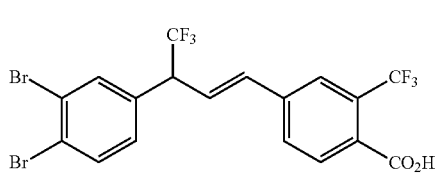

The title molecule was isolated as a brown gum: $^1$H NMR (300 MHz, DMSO-$d_6$) δ 13.5 (bs, 1H), 8.01-7.99 (m, 2H), 7.94-7.91 (m, 1H), 7.85-7.78 (m, 2H), 7.53-7.50 (m, 1H), 7.09 (dd, J=15.6, 8.7 Hz, 1H), 6.89 (d, J=15.9 Hz, 1H), 4.85-4.78 (m, 1H); ESIMS m/z 528.8 ([M−H]$^−$); IR (thin film) 3437, 1722, 1168 cm$^{-1}$.

(E)-2-Bromo-4-(3-(3,4-dibromophenyl)-4,4-trifluorobut-1-en-1-yl)benzoic acid

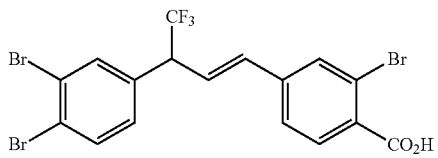

The title molecule was isolated as a brown gum: ¹H NMR (300 MHz, DMSO-d$_6$) δ 13.38 (bs, 1H), 7.98-7.96 (m, 2H), 7.84 (d, J=8.4 Hz, 1H), 7.74 (d, J=8.1 Hz, 1H), 7.63-7.61 (m, 1H), 7.51-7.49 (m, 1H), 7.01 (dd, J=15.9, 9.0 Hz, 1H), 6.78 (d, J=15.6 Hz, 1H), 4.82-4.76 (m, 1H); ESIMS m/z 538.8 ([M−H]⁻); IR (thin film) 3446, 1699, 1166, 581 cm⁻¹.

(E)-4-(4,4,4-Trifluoro-3-(3-(trifluoromethoxy)phenyl)but-1-en-1-yl)-2-(trifluoromethyl)benzoic acid

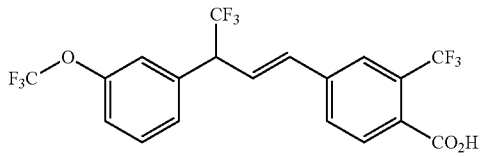 [SMILES: O=C(O)c1ccc(/C=C/C(c2cccc(OC(F)(F)F)c2)C(F)(F)F)cc1C(F)(F)F]

The title molecule was isolated as a brown semi solid: ¹H NMR (300 MHz, DMSO-d$_6$) δ 8.01 (s, 1H), 7.94 (d, J=8.7 Hz, 1H), 7.80 (d, J=8.1 Hz, 1H), 7.63-7.55 (m, 3H), 7.41 (d, J=7.5 Hz, 1H), 7.11 (dd, J=15.6, 9.0 Hz, 1H), 6.92 (d, J=15.9 Hz, 1H), 4.89-4.82 (m, 1H); ESIMS m/z 456.98 ([M−H]⁻); IR (thin film) 3413, 1668, 1161 cm⁻¹.

(E)-2-Bromo-4-(4,4,4-trifluoro-3-(3-(trifluoromethoxy)phenyl)but-1-en-1-yl)benzoic acid

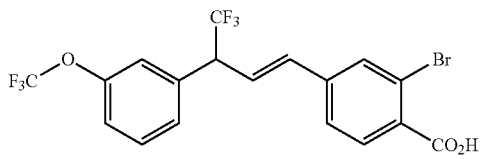 [SMILES: O=C(O)c1ccc(/C=C/C(c2cccc(OC(F)(F)F)c2)C(F)(F)F)cc1Br]

The title molecule was isolated as a brown solid: ¹H NMR (300 MHz, DMSO-d$_6$) δ 7.73 (s, 1H), 7.59 (m, 3H), 7.44 (s, 1H), 7.40 (d, J=7.6 Hz, 2H), 6.88 (dd, J=15.6, 9.0 Hz, 1H), 6.73 (d, J=15.9 Hz, 1H), 4.85-4.82 (m, 1H); ESIMS m/z 466.93 ([M−H]⁻); IR (thin film) 3437, 1703, 1111 cm⁻¹.

(E)-4-(3-(3-Cyano-4-fluorophenyl)-4,4,4-trifluorobut-1-en-1-yl)-2-(trifluoromethyl)benzoic acid

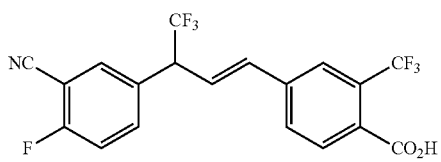 [SMILES: N#Cc1cc(C(/C=C/c2ccc(C(=O)O)c(C(F)(F)F)c2)C(F)(F)F)ccc1F]

The title molecule was isolated as a brown liquid: ¹H NMR (300 MHz, DMSO-d$_6$) δ 13.60 (bs, 1H), 8.21-8.19 (m, 1H), 8.01-7.91 (m, 3H), 7.81 (d, J=8.4 Hz, 1H), 7.12 (dd, J=15.9, 8.1 Hz, 1H), 6.91 (d, J=15.6 Hz, 1H), 4.92-4.86 (m, 1H); ESIMS m/z 416.27 ([M−H]⁻); IR (thin film) 3429, 2238, 1713, 1116 cm⁻¹.

(E)-2-Bromo-4-(3-(3-cyano-4-fluorophenyl)-4,4,4-trifluorobut-1-en-1-yl)benzoic acid

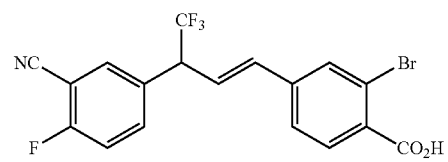 [SMILES: N#Cc1cc(C(/C=C/c2ccc(C(=O)O)c(Br)c2)C(F)(F)F)ccc1F]

The title molecule was isolated as a brown gum: ¹H NMR (300 MHz, DMSO-d$_6$) δ 13.56 (bs, 1H), 8.21-8.18 (m, 1H), 8.00-7.95 (m, 2H), 7.73-7.59 (m, 3H), 7.03 (dd, J=15.9, 9.3 Hz, 1H), 6.79 (d, J=15.3 Hz, 1H), 4.87-4.84 (m, 1H); ESIMS m/z 426.0 ([M−H]⁻).

(E)-2-Bromo-4-(3-(3,4-dichlorophenyl)-4,4,4-trifluorobut-1-en-1-yl)benzoic acid

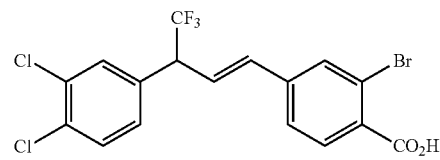 [SMILES: O=C(O)c1ccc(/C=C/C(c2ccc(Cl)c(Cl)c2)C(F)(F)F)cc1Br]

The title molecule was isolated as a brown gum: ¹H NMR (300 MHz, DMSO-d$_6$) δ 13.4 (s, 1H), 7.96 (d, J=1.2 Hz, 1H), 7.88 (d, J=1.8 Hz, 1H), 7.74-7.68 (m, 2H), 7.63 (dd, J=8.1, 1.2 Hz, 1H), 7.57 (dd, J=8.4, 1.8 Hz, 1H), 7.02 (dd, J=15.9, 9.3 Hz, 1H), 6.78 (dd, J=5.9 Hz, 1H), 4.84-4.78 (m, 1H); ESIMS m/z 451.0 ([M−H]⁻); IR (thin film) 3445, 1704, 1113, 740 cm⁻¹.

(E)-4-(3-(3-Bromo-5-chlorophenyl)-4,4,4-trifluorobut-1-en-1-yl)-2-(trifluoromethyl)benzoic acid

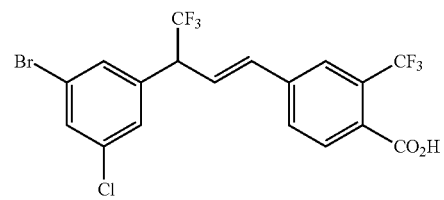

The title molecule was isolated as a brown solid: ¹H NMR (300 MHz, DMSO-d$_6$) δ 13.50 (bs, 1H), 7.91 (s, 1H), 7.86-7.64 (m, 5H), 7.06 (dd, J=15.9, 9.0 Hz, 1H), 6.87 (d, J=15.9 Hz, 1H), 4.85-4.78 (m, 1H); ESIMS m/z 485.17 ([M−H]⁻); IR (thin film) 3438, 1708, 1114, 774, 516 cm⁻¹.

101

(E)-2-Bromo-4-(3-(3-bromo-5-chlorophenyl)-4,4,4-trifluorobut-1-en-1-yl)benzoic acid

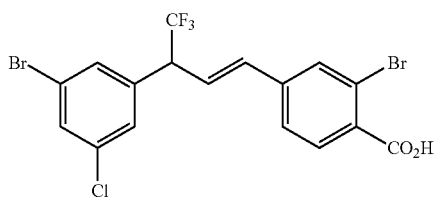 [SMILES: O=C(O)c1ccc(/C=C/C(c2cc(Cl)cc(Br)c2)C(F)(F)F)cc1Br]

The title molecule was isolated as a brown gum: $^1$H NMR (300 MHz, DMSO-$d_6$) δ 13.38 (bs, 1H), 7.98 (s, 1H), 7.80-7.72 (m, 4H), 7.64-7.61 (m, 1H), 7.06 (dd, J=15.9, 9.3 Hz, 1H), 6.79 (d, J=15.6 Hz, 1H), 4.88-4.80 (m, 1H); ESIMS m/z 495.05 ([M−H]$^-$); IR (thin film) 3436, 1699, 1116, 750, 531 cm$^{-1}$.

(E)-4-(3-(3-Bromo-5-fluorophenyl)-4,4,4-trifluorobut-1-en-1-yl)-2-(trifluoromethyl)benzoic acid

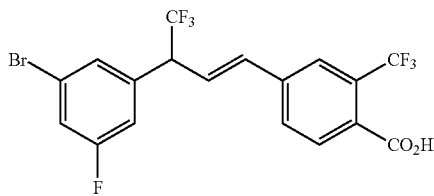 [SMILES: O=C(O)c1ccc(/C=C/C(c2cc(F)cc(Br)c2)C(F)(F)F)cc1C(F)(F)F]

The title molecule was isolated as a brown liquid: $^1$H NMR (300 MHz, DMSO-$d_6$) δ 13.6 (bs, 1H), 8.02 (s, 1H), 7.91-7.89 (m, 1H), 7.81 (d, J=8.0 Hz, 1H), 7.69 (s, 1H), 7.63-7.59 (m, 1H), 7.55 (d, J=9.3 Hz, 1H), 7.11 (dd, J=15.9, 9.0 Hz, 1H), 6.91 (d, J=15.9 Hz, 1H), 4.87-4.80 (m, 1H); ESIMS m/z 469.07 ([M−H]$^-$); IR (thin film) 3428, 1712, 1171, 523 cm$^{-1}$.

(E)-4-(4,4,4-Trifluoro-3-(3,4,5-trichlorophenyl)but-1-en-1-yl)benzoic acid

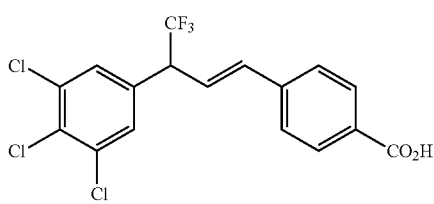 [SMILES: O=C(O)c1ccc(/C=C/C(c2cc(Cl)c(Cl)c(Cl)c2)C(F)(F)F)cc1]

The title molecule was isolated as a yellow solid: $^1$H NMR (400 MHz, CDCl$_3$) δ 8.18-8.03 (m, 2H), 7.49 (d, J=8.3 Hz, 2H), 7.42 (s, 2H), 6.66 (d, J=15.9 Hz, 1H), 6.47 (dd, J=15.9, 8.0 Hz, 1H), 4.13 (p, J=8.6 Hz, 1H); $^{19}$F NMR (376 MHz, CDCl$_3$) δ −68.65; ESIMS m/z 409.1 ([M−H]$^-$).

102

(E)-2-Bromo-4-(3-(3-chloro-4-methylphenyl)-4,4,4-trifluorobut-1-en-1-yl)benzoic acid

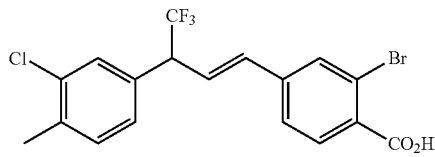 [SMILES: Cc1ccc(C(/C=C/c2ccc(C(=O)O)c(Br)c2)C(F)(F)F)cc1Cl]

The title molecule was isolated as a brown liquid: $^1$H NMR (300 MHz, DMSO-$d_6$) δ 13.30 (bs, 1H), 7.93 (d, J=1.2 Hz, 1H), 7.42 (d, J=8.1 Hz, 1H), 7.62 (dd, J=1.5, 8.1 Hz, 1H), 7.53 (s, 1H), 7.48 (d, J=7.8 Hz, 1H), 7.39 (d, J=7.8 Hz, 1H), 6.96 (dd, J=15.6, 8.7 Hz, 1H), 6.77 (d, J=15.6 Hz, 1H), 4.73-4.61 (m, 1H), 2.35 (s, 3H); ESIMS m/z 431.77 ([M−H]); IR (thin film) 3435, 1701, 1111, 750 cm$^{-1}$.

(E)-4-(3-(3-Chloro-4-methylphenyl)-4,4,4-trifluorobut-1-en-1-yl)-2-(trifluoromethyl)benzoic acid

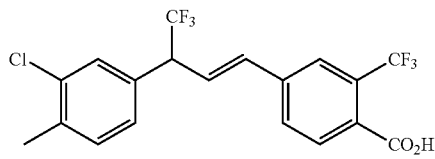 [SMILES: Cc1ccc(C(/C=C/c2ccc(C(=O)O)c(C(F)(F)F)c2)C(F)(F)F)cc1Cl]

The title molecule was isolated as a brown gum: $^1$H NMR (300 MHz, DMSO-$d_6$) δ 13.50 (bs, 1H), 7.98 (s, 1H), 7.92 (d, J=8.1 Hz, 1H), 7.80 (d, J=8.1 Hz, 1H), 7.53 (s, 1H), 7.48 (d, J=8.1 Hz, 1H), 7.40 (d, J=8.4 Hz, 1H), 7.04 (dd, J=15.6, 8.4 Hz, 1H), 6.88 (d, J=15.6 Hz, 1H), 4.72-4.66 (m, 1H), 2.35 (s, 3H); ESIMS m/z 421.82 ([M−H]$^-$); IR (thin film) 3460, 2926, 1712, 1170, 750 cm$^{-1}$.

(E)-4-(4,4,5,5,5-Pentafluoro-3-(3,4,5-trichlorophenyl)pent-1-en-1-yl)-2-(trifluoromethyl)benzoic acid

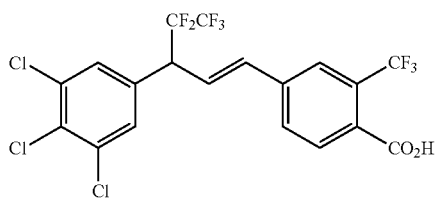

The title molecule was isolated as a dark brown gum: $^1$H NMR (300 MHz, DMSO-$d_6$) δ 13.6 (bs, 1H), 8.03 (s, 1H), 7.95-7.86 (m, 3H), 7.81 (d, J=8.1 Hz, 1H), 7.16 (dd, J=15.3, 9.3 Hz, 1H), 6.92 (d, J=15.6 Hz, 1H), 4.95-4.88 (m, 1H); $^{19}$F NMR (300 MHz, DMSO-$d_6$) δ −80.35, −58.02; ESIMS m/z 526.8 ([M+H]$^+$).

103

(E)-2-Bromo-4-(4,4,5,5,5-pentafluoro-3-(3,4,5-trichlorophenyl)pent-1-en-1-yl)benzoic acid

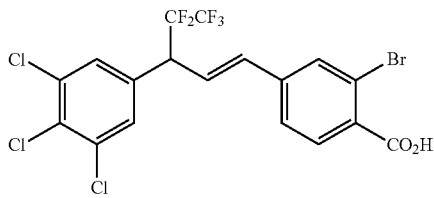

The title molecule was isolated as a dark brown gum: $^1$H NMR (300 MHz, DMSO-$d_6$) δ 13.6 (bs, 1H), 7.94 (s, 2H), 7.78 (d, J=7.8 Hz, 1H), 7.71 (d, J=7.8 Hz, 1H), 7.60 (d, J=7.5 Hz 1H), 7.07 (dd, J=15.0, 8.7 Hz, 1H), 6.79 (d, J=15.6 Hz, 1H), 4.93-4.78 (m, 1H); ESIMS m/z 538.9 ([M+H]$^+$); IR (thinfilm) 3420, 1602, 1123, 746 cm$^{-1}$.

(E)-2-Bromo-4-(3-(4-cyano-3,5-difluorophenyl)-4,4,4-trifluorobut-1-en-1-yl)benzoic acid

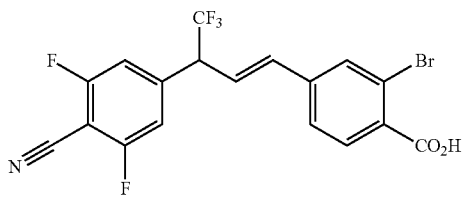 [SMILES: N#Cc1c(F)cc(C(/C=C/c2ccc(C(=O)O)c(Br)c2)C(F)(F)F)cc1F]

The title molecule was isolated as a brown gum: ESIMS m/z 443.91 ([M−H]$^-$); IR (thin film) 3447, 2244, 1703, 1114 cm$^{-1}$.

(E)-2-Chloro-4-(3-(3,5-dibromophenyl)-4,4,4-trifluorobut-1-en-1-yl)benzoic acid

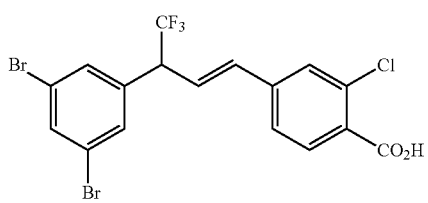 [SMILES: O=C(O)c1ccc(/C=C/C(c2cc(Br)cc(Br)c2)C(F)(F)F)cc1Cl]

The title molecule was isolated as a brown liquid: $^1$H NMR (300 MHz, DMSO-$d_6$) δ 13.39 (bs, 1H), 7.95-7.70 (m, 5H), 7.61 (d, J=8.1 Hz, 1H), 7.07 (dd, J=15.6, 9.3 Hz, 1H), 6.80 (d, J=15.6 Hz, 1H), 4.84-4.78 (m, 1H); ESIMS m/z 496.77 ([M−H]$^-$); IR (thin film) 3439, 2920, 1707, 1165 cm$^{-1}$.

104

(E)-4-(3-(3,5-Dichloro-4-fluorophenyl)-4,4,4-trifluorobut-1-en-1-yl)-2-(trifluoromethyl)benzoic acid

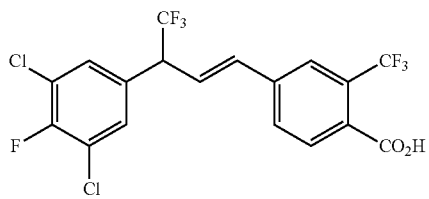 [SMILES: O=C(O)c1ccc(/C=C/C(c2cc(Cl)c(F)c(Cl)c2)C(F)(F)F)cc1C(F)(F)F]

The title molecule was isolated as an off white solid: mp 140-143° C.; $^1$H NMR (400 MHz, DMSO) δ13.60 (bs, 1H), 8.02 (s, 1H), 7.94-7.90 (m, 1H), 7.88-7.86 (m, 2H), 7.81-7.79 (m, 1H), 7.12 (dd, J=15.6, 8.8 Hz, 1H), 6.89 (d, J=15.6 Hz, 1H), 4.86-4.81 (m, 2H); ESIMS m/z 458.88 ([M−H]$^-$).

(E)-4-(3-(3,4-Dichlorophenyl)-4,4,4-trifluorobut-1-en-1-yl)benzoic acid

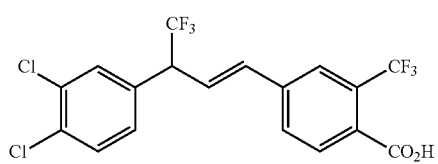 [SMILES: O=C(O)c1ccc(/C=C/C(c2ccc(Cl)c(Cl)c2)C(F)(F)F)cc1C(F)(F)F]

The title molecule was isolated as a light orange crystalline solid (875 mg, 88%): $^1$H NMR (400 MHz, CDCl$_3$) δ 12.35 (s, 1H), 8.08 (d, J=8.4 Hz, 2H), 7.55-7.41 (m, 4H), 7.24 (dd, J=8.3, 2.1 Hz, 1H), 6.64 (d, J=15.8 Hz, 1H), 6.51 (dd, J=15.9, 7.7 Hz, 1H), 4.15 (p, J=8.7 Hz, 1H); $^{19}$F NMR 376 MHz, CDCl$_3$) δ −68.75; ESIMS m/z 375 ([M+H]$^+$).

(E)-4-(3-(3,4-Dichlorophenyl)-4,4,4-trifluorobut-1-en-1-yl)-2-(trifluoromethyl)benzoic acid The title molecule was isolated was isolated as a brown gum: $^1$H NMR (400 MHz, DMSO-$d_6$) δ 13.6 (s, 1H), 8.02 (s, 1H), 7.93-7.89 (m, 2H), 7.80 (d, J=7.6 Hz, 1H), 7.73 (d, J=8.4, Hz, 1H), 7.58 (dd, J=8.4, 2.0 Hz, 1H), 7.09 (dd, J=15.6, 8.8, Hz, 1H), 6.89 (d, J=15.6, Hz, 1H), 4.86-4.81 (m, 1H); ESIMS m/z 441.0 ([M−H]$^-$); IR (thinfilm) 3447, 1710, 1169, 749 cm$^{-1}$.

(E)-4-(3-(3,5-Dichlorophenyl)-4,4,4-trifluorobut-1-en-1-yl)-2-(trifluoromethyl)benzoic acid

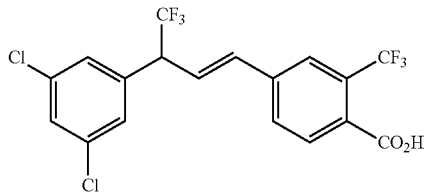 [SMILES: O=C(O)c1ccc(/C=C/C(c2cc(Cl)cc(Cl)c2)C(F)(F)F)cc1C(F)(F)F]

The title molecule was isolated was isolated as a brown gum: $^1$H NMR (300 MHz, DMSO-d$_6$) δ 13.6 (bs, 1H), 7.98 (s, 1H), 7.91 (d, J=7.8 Hz 1H), 7.75-7.66 (m, 1H), 7.10 (dd, J=15.6, 9.0 Hz, 1H), 6.89 (d, J=15.9 Hz 1H), 4.86-4.80 (m, 1H); ESIMS m/z 441.1 ([M−H]$^−$); IR (thinfilm) 3460, 2928, 1721, 1170, 764 cm$^{-1}$.

(E)-4-(3-(3,4-Dichloro-5-methylphenyl)-4,4,4-trifluorobut-1-en-1-yl)-2-(trifluoromethyl)benzoic acid

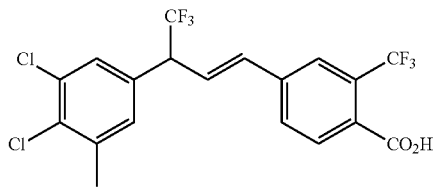 [SMILES: Cc1cc(C(/C=C/c2ccc(C(=O)O)c(C(F)(F)F)c2)C(F)(F)F)cc(Cl)c1Cl]

The title molecule was isolated as a pale yellow semi solid: $^1$H NMR (400 MHz, DMSO-d$_6$) δ 13.58 (bs, 1H), 8.00 (s, 1H), 7.93 (d, J=8.4 Hz, 1H), 7.80 (d, J=8.4 Hz, 1H), 7.72 (s, 1H), 7.55 (s, 1H), 7.07 (dd, J=16.4, 9.6 Hz, 1H), 6.89 (d, J=15.6 Hz, 1H), 4.78-4.73 (m, 1H), 2.42 (s, 3H); ESIMS m/z 455.0 ([M−H]$^−$); IR (thin film) 1713, 1170, 750 cm$^{-1}$.

(E)-2-Bromo-4-(3-(3,4-dichlorophenyl)-4,4-difluoropent-1-en-1-yl)benzoic acid

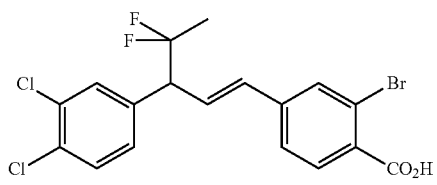 [SMILES: CC(F)(F)C(/C=C/c1ccc(C(=O)O)c(Br)c1)c1ccc(Cl)c(Cl)c1]

The title molecule was isolated as a brown gum: $^1$H NMR (400 MHz, DMSO-d$_6$) δ 13.3 (s, 1H), 7.92 (s, 1H), 7.77-7.71 (m, 2H), 7.68-7.63 (m, 1H), 7.61-7.60 (m, 1H), 7.60-7.58 (m, 1H), 6.98 (dd, J=15.6, 9.2 Hz, 1H), 6.65 (d, J=15.6 Hz, 1H), 4.83-4.80 (m, 1H), 1.59-1.54 (m, 3H); ESIMS m/z 448.8 ([M−H]$^−$).

(E)-2-Bromo-4-(3-(3-chloro-5-ethylphenyl)-4,4,4-trifluorobut-1-en-1-yl)benzoic acid

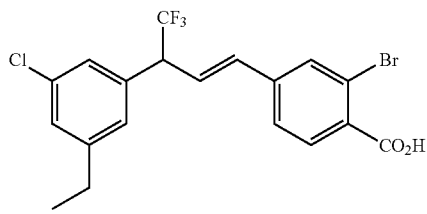 [SMILES: CCc1cc(Cl)cc(C(/C=C/c2ccc(C(=O)O)c(Br)c2)C(F)(F)F)c1]

The title molecule was isolated as a brown liquid: $^1$H NMR (400 MHz, DMSO-d$_6$) δ 13.4 (bs, 1H), 7.97 (s, 2H), 7.91 (s, 1H), 7.74 (d, J=8.4 Hz, 2H), 7.66-7.61 (m, 1H), 7.03 (dd, J=16.0, 8.4 Hz, 1H), 6.8 (d, J=15.6 Hz, 1H), 4.89-4.84 (m, 1H), 2.66-2.65 (m, 2H), 1.25 (t, J=9.2 Hz, 3H); ESIMS m/z 446.8 ([M+H]$^+$).

(E)-2,6-Dimethyl-4-(4,4,4-trifluoro-3-(3,4,5-trichlorophenyl)but-1-enyl)benzoic acid

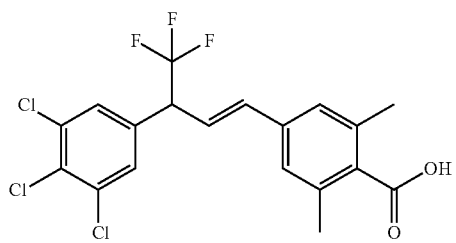 [SMILES: Cc1cc(/C=C/C(c2cc(Cl)c(Cl)c(Cl)c2)C(F)(F)F)cc(C)c1C(=O)O]

The title molecule was isolated as a brown gum: $^1$H NMR (300 MHz, DMSO-d$_6$) δ 13.1 (s, 1H), 7.87 (s, 2H), 7.27 (s, 2H), 6.81 (dd, J=15.6, 8.7 Hz, 1H), 6.69 (d, J=15.3 Hz, 1H), 4.85-4.79 (m, 1H), 2.27 (s, 6H); ESIMS m/z 437.01 ([M−H]$^−$); IR (thin film) 3285, 1621, 1162, 954 cm$^{-1}$.

(E)-2-Bromo-4-(3-(3,5-dibromo-4-chlorophenyl)-4,4,4-trifluorobut-1-en-1-yl)benzoic acid

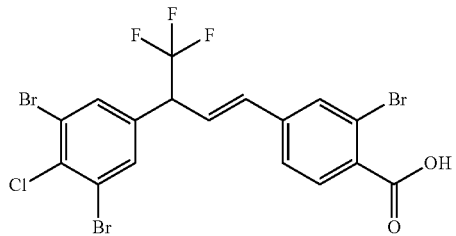 [SMILES: O=C(O)c1ccc(/C=C/C(c2cc(Br)c(Cl)c(Br)c2)C(F)(F)F)cc1Br]

The title molecule was isolated as a brown gum: $^1$H NMR (300 MHz, DMSO-d$_6$) δ 13.40 (bs, 1H), 8.07 (d, J=7.5 Hz, 1H), 7.94-7.89 (m, 2H), 7.66-7.60 (m, 2H), 7.10 (dd, J=8.7, 16.0 Hz, 1H), 6.96 (d, J=15.6 Hz, 1H), 4.82-4.80 (m, 1H); ESIMS m/z 574.7 ([M+H]$^+$).

(E)-4-(3-(3,5-Dibromo-4-chlorophenyl)-4,4,4-trifluorobut-1-en-1-yl)-2-(trifluoromethyl)benzoic acid

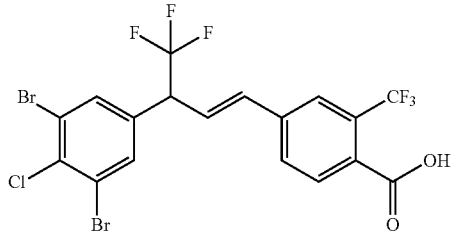 [SMILES: O=C(O)c1ccc(/C=C/C(c2cc(Br)c(Cl)c(Br)c2)C(F)(F)F)cc1C(F)(F)F]

The title molecule was isolated as a brown gum: $^1$H NMR (300 MHz, DMSO-$d_6$) δ 13.36 (bs, 1H) 8.05 (s, 2H), 7.95 (d, J=8.1 Hz, 1H), 7.87-7.67 (m, 2H), 7.14 (dd, J=9.0, 15.6 Hz, 1H), 6.96 (d, J=15.6 Hz, 1H), 4.88-4.82 (m, 1H); ESIMS m/z 564.58 ([M+H]$^+$).

(E)-2-Bromo-4-(3-(4-bromo-3,5-dichlorophenyl)-4,4,4-trifluorobut-1-en-1-yl)benzoic acid

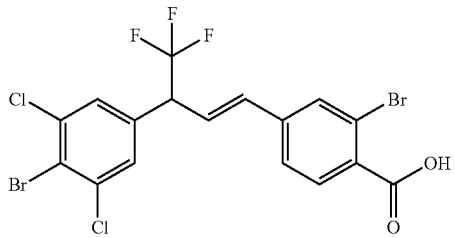

The title molecule was isolated as a brown gum: $^1$H NMR (300 MHz, DMSO-$d_6$) δ 13.40 (bs, 1H), 7.98 (s, 1H), 7.87 (s, 2H), 7.75 (d, J=8.1 Hz, 1H), 7.65-7.62 (m, 1H), 7.06 (dd, J=15.9, 9.3 Hz, 1H), 6.80 (d, J=15.9 Hz, 1H), 4.87-4.80 (m, 1H); ESIMS m/z 518.9 ([M−H]$^−$).

(E)-4-(3-(4-Bromo-3,5-dichlorophenyl)-4,4,4-trifluorobut-1-en-1-yl)-2-(trifluoromethyl)benzoic acid

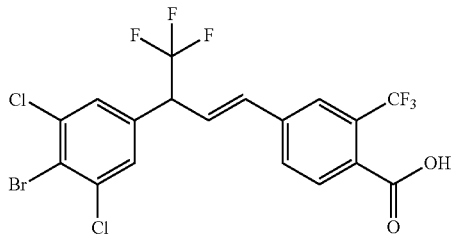

The title molecule was isolated as a brown gum: $^1$H NMR (300 MHz, DMSO-$d_6$) δ 13.6 (bs, 1H) 8.03 (s, 1H), 7.95 (d, J=8.4 Hz, 1H), 7.88 (s, 2H), 7.81 (d, J=8.1 Hz, 1H), 7.13 (dd, J=16.2, 7.5 Hz, 1H), 6.91 (d, J=15.9 Hz, 1H), 4.89-4.83 (m, 1H); ESIMS m/z 532.0 ([M+H]$^+$).

(E)-2-Bromo-4-(3-(3-chloro-4-(trifluoromethoxy)phenyl)-4,4,4-trifluorobut-1-en-1-yl)benzoic acid

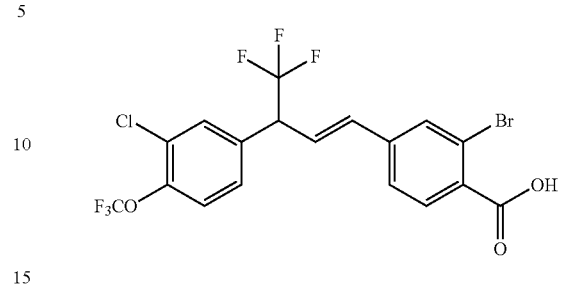

The title molecule was isolated as a brown gum: $^1$H NMR (400 MHz, DMSO-$d_6$) δ 13.36 (bs, 1H) 7.95 (s, 1H), 7.73 (d, J=7.6 Hz, 1H), 7.63 (d, J=8.1 Hz, 1H), 7.46 (s, 1H) 7.35-7.31 (m, 2H), 7.04 (dd, J=16.0, 8.8 Hz, 1H), 6.78 (d, J=16.4 Hz, 1H), 4.71-4.68 (m, 1H); ESIMS m/z 500.8 ([M−H]$^−$).

Example 20

Preparation of 5-vinyl-2,3-dihydro-1H-inden-1-one (BI1)

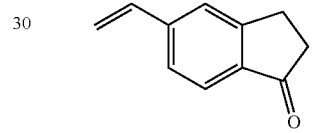

To a stirred solution of 5-bromo-2,3-dihydro-1H-inden-1-one (5 g, 23.7 mmol) in toluene were added vinylboronic anhydride pyridine complex (8.55 g, 35.54 mmol), Pd(PPh$_3$)$_4$ (0.1 g, 0.094 mmol), K$_2$CO$_3$ (22.88 g, 165.83 mmol). The resultant reaction mixture was heated at reflux for 16 h. The reaction mixture was cooled to 25° C. and filtered, and the filtrate was concentrated under reduced pressure. The residue was diluted with EtOAc and washed with water and brine. The combined organic extracts were dried over anhydrous Na$_2$SO$_4$ and concentrated under reduced pressure. The obtained residue was purified by flash column chromatography (SiO$_2$, 5% EtOAc in petroleum ether) afforded the title compound as a solid (1.8 g, 48%): $^1$H NMR (400 MHz, CDCl$_3$) δ 7.74 (d, J=7.2 Hz, 1H), 7.49 (br s, 1H), 7.44 (d, J=7.2 Hz, 1H), 6.82 (m, 1H), 5.90 (d, J=7.4 Hz, 1H), 5.42 (d, J=6.4 Hz, 1H), 3.20 (m, 2H), 2.70 (m, 2H); ESIMS m/z 159.06 ([M+H]$^−$).

The following compound was made in accordance with the procedures disclosed in Example 20.

6-Vinyl-3,4-dihydronaphthalen-1(2H)-one (BI2)

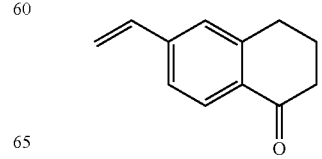

The product was isolated as an off-white solid (5 g, 48%): $^1$H NMR (400 MHz, DMSO-$d_6$) δ 7.85 (d, J=8.4 Hz, 1H), 7.48 (m, 2H), 6.82 (m, 1H), 6.02 (d, J=7.4 Hz, 1H), 5.44 (d, J=6.4 Hz, 1H), 2.95 (m, 2H), 2.60 (m, 2H), 2.00 (m, 2H); ESIMS m/z 173.14 ([M−H]$^−$); IR (thin film) 1681 cm$^{−1}$.

Example 21

Preparation of (E)-5-(4,4,4-Trifluoro-3-(3,4,5-trichlorophenyl)but-1-enyl)-2,3-dihydro-1H-inden-1-one (BI3)

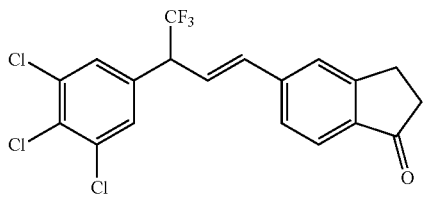 [SMILES: O=C1CCc2cc(/C=C/C(c3cc(Cl)c(Cl)c(Cl)c3)C(F)(F)F)ccc21]

5-(1-Bromo-2,2,2-trifluoroethyl)-1,2,3-trichlorobenzene (4 g, 11.7 mmol), 5-vinyl-2,3-dihydro-1H-inden-1-one (0.92 g, 5.8 mmol), CuCl (0.115 g, 1.171 mmol) and 2,2-bipyridyl (0.053 g, 0.34 mmol) in 1,2-dichlorobenzene (25 mL) were heated at 180° C. for 16 h. The reaction mixture was cooled to 25° C. and concentrated under reduced pressure. The residue was purified by flash column chromatography (SiO$_2$, 5% EtOAc in petroleum ether) to afford the title compound as a liquid (1.28 g, 25%): $^1$H NMR (400 MHz, CDCl$_3$) δ 7.76 (d, J=7.4 Hz, 1H), 7.52 (m, 3H), 6.68 (d, J=7.4 Hz, 1H), 6.52 (m, 1H), 4.18 (m, 1H), 3.18 (m, 2H), 2.75 (m, 2H); ESIMS m/z 419.14 ([M+H]$^−$); IR (thin film) 1708.94, 1113.60, 807.77 cm$^{−1}$.

The following compound was made in accordance with the procedures disclosed in Example 21.

(E)-5-(3-(3,5-Dichloro-4-fluorophenyl)-4,4,4-trifluorobut-1-en-1-yl)-2,3-dihydro-1H-inden-1-one (BI4)

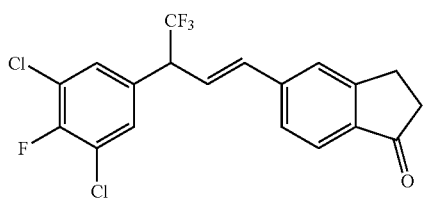 [SMILES: O=C1CCc2cc(/C=C/C(c3cc(Cl)c(F)c(Cl)c3)C(F)(F)F)ccc21]

The product was isolated as a brown semi-solid (1.2 g, 16%): $^1$H NMR (400 MHz, CDCl$_3$) δ 7.76 (d, J=7.4 Hz, 1H), 7.54 (m, 3H), 7.30 (s, 1H), 6.68 (d, J=7.4 Hz, 1H), 6.52 (m, 1H), 4.18 (m, 1H), 3.18 (m, 2H), 2.75 (m, 2H); ESIMS m/z 400.84 ([M−H]$^−$); IR (thin film) 815, 1113, 1709 cm$^{−1}$.

(E)-6-(4,4,4-Trifluoro-3-(3,4,5-trichlorophenyl)but-1-enyl)-3,4-dihydronaphthalen-1(2H)-one (BI5)

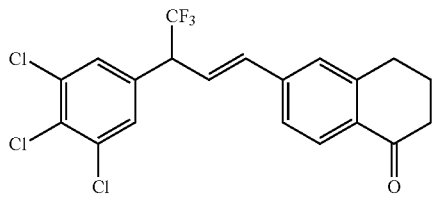 [SMILES: O=C1CCCc2cc(/C=C/C(c3cc(Cl)c(Cl)c(Cl)c3)C(F)(F)F)ccc21]

The product was isolated as a pale yellow semi solid (1.2 g, 30%): $^1$H NMR (400 MHz, CDCl$_3$) δ 8.20 (d, J=8.0 Hz, 1H), 7.42 (s, 2H), 7.35 (m, 1H), 7.24 (m, 2H), 6.62 (d, J=16 Hz, 1H), 6.46 (m, 1H), 4.18 (m, 1H), 2.95 (m, 2H), 2.65 (m, 2H), 2.19 (m, 2H); ESIMS m/z 432.94 ([M−H]$^−$); IR (thin film) 1680, 1113, 808 cm$^{−1}$.

Example 22

Preparation of (E)-5-(3-(3,5-Dichloro-4-fluorophenyl)-4,4,4-trifluorobut-1-en-1-yl)-2-fluoro-2,3-dihydro-1H-inden-1-one (BI6)

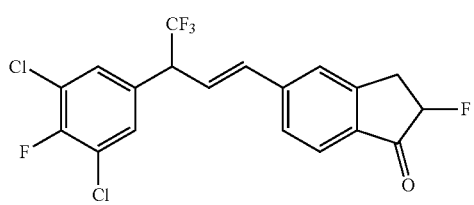 [SMILES: O=C1c2ccc(/C=C/C(c3cc(Cl)c(F)c(Cl)c3)C(F)(F)F)cc2CC1F]

To a stirred solution of (E)-5-(3-(3,5-dichloro-4-fluorophenyl)-4,4,4-trifluorobut-1-enyl)-2,3-dihydro-1H-inden-1-one (0.5 g, 1.24 mmol) in MeCN (20 mL), was added Selectfluor® (0.52 g, 1.48 mmol) and the reaction was heated to reflux temperature for 16 h. The reaction mixture was cooled to room temperature, concentrated under reduced pressure and diluted with CH$_2$Cl$_2$. The solution was washed with water and brine, dried over anhydrous Na$_2$SO$_4$ and concentrated under reduced pressure to give the crude product which was purified by flash column chromatography (SiO$_2$, 100-200 mesh; 15% EtOAc in petroleum ether) to afford the title compound as a pale yellow semi solid (0.1 g, 24%): $^1$H NMR (400 MHz, CDCl$_3$) δ 7.80 (m, 1H), 7.48 (m, 2H), 7.32 (m, 2H), 6.65 (d, J=16.0 Hz, 1H), 6.54 (dd, J=16.0, 8.0 Hz, 1H), 5.38 (m, 1H), 4.18 (m, 1H), 3.62 (m, 1H), 3.32 (m, 1H); ESIMS m/z 419.06 ([M−H]$^−$); IR (thin film) 1728, 1114, 817 cm$^{−1}$.

Example 23

Preparation of (E)-5-(3-(3,5-Dichloro-4-fluorophenyl)-4,4,4-trifluorobut-1-en-1-yl)-N-(3,3,3-trifluoropropyl)-2,3-dihydro-1H-inden-1-amine (BC10)

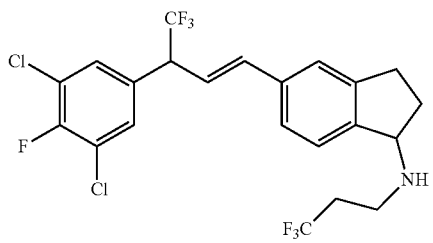 [SMILES: Fc1c(Cl)cc(C(/C=C/c2ccc3c(c2)CCC3NCCC(F)(F)F)C(F)(F)F)cc1Cl]

To a stirred solution of (E)-5-(3-(3,5-dichloro-4-fluorophenyl)-4,4,4-trifluorobut-1-enyl)-2,3-dihydro-1H-inden-1-one (0.15 g, 0.35 mmol) in DCE (10 mL), was added trifluoropropyl amine (0.048 g, 0.42 mmol) and NaBH$_3$CN (0.055 g, 0.875 mmol) in cooling and the reaction mixture was stirred at room temperature for 16 h. The reaction mixture was diluted with DCE, was washed with water and brine and dried over anhydrous Na$_2$SO$_4$. Concentration under reduced pressure gave the crude compound, which was purified by flash column chromatography (SiO$_2$, 100-200 mesh; 10-15% EtOAc in petroleum ether) to afford the title compound as a colorless gummy material (0.042 g, 24%): $^1$H NMR (400 MHz, CDCl$_3$) δ 7.38-7.20 (m, 5H), 6.62 (d, J=16.0 Hz, 1H), 6.34 (dd, J=16.0, 8.0 Hz, 1H), 5.83 (br, 1H), 5.52 (m, 1H), 4.12 (m, 1H), 3.02 (m, 3H), 2.82 (m, 1H), 2.50 (m, 2H), 1.82 (m, 1H), 1.42 (m, 1H); ESIMS m/z 497.98 ([M−H]$^−$); IR (thin film) 3027, 1654, 815 cm$^{−1}$.

Example 24

Preparation of 6-((E)-4,4,4-Trifluoro-3-(3,4,5-trichlorophenyl)but-1-enyl)-3,4-dihydronaphthalen-1(2H)-one oxime (BI5a)

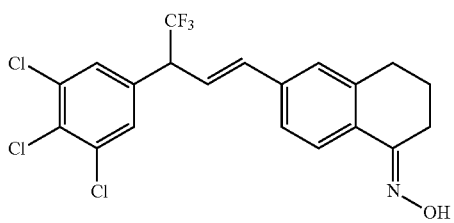 [SMILES: O/N=C1\CCCc2cc(/C=C/C(c3cc(Cl)c(Cl)c(Cl)c3)C(F)(F)F)ccc21]

To a stirred solution of ((E)-6-(4,4,4-trifluoro-3-(3,4,5-trichlorophenyl)but-1-enyl)-3,4-dihydronaphthalen-1(2H)-one (0.4 g, 0.92 mmol) in EtOH (50 mL) were added hydroxylamine hydrochloride (0.128 g, 1.85 mmol) and sodium acetate (NaOAc, 0.23 g, 2.77 mmol), and the reaction mixture was heated at reflux for 3 h. The reaction mixture was concentrated under reduced pressure, and the residue was diluted with water and extracted with EtOAc. The combined organic extracts were washed with brine, dried over anhydrous Na$_2$SO$_4$ and concentrated under reduced pressure to give the crude compound, which was purified by flash column chromatography (SiO$_2$, 100-200 mesh; 10-15% EtOAc in petroleum ether). The title compound was isolated as a solid (0.3 g, 73%): mp 155-158° C.; $^1$H NMR (400 MHz, CDCl$_3$) δ 7.89 (d, J=8.4 Hz, 1H), 7.41 (s, 2H), 7.24 (m, 1H), 7.17 (m, 1H), 6.57 (d, J=16 Hz, 1H), 6.46 (dd, J=16.0, 8.0 Hz, 1H), 4.13 (m, 1H), 2.82 (m, 4H), 2.04 (m, 2H); ESIMS m/z 445.95 ([M−H]$^−$).

Example 25

Preparation of (E)-5-(4,4,4-Trifluoro-3-(3,4,5-trichlorophenyl)but-1-enyl)-2,3-dihydro-1H-inden-1-amine (BI5b)

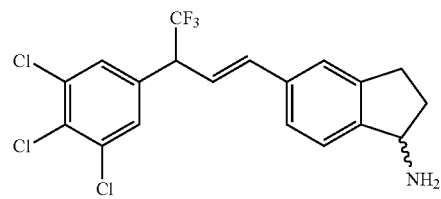 [SMILES: NC1CCc2cc(/C=C/C(c3cc(Cl)c(Cl)c(Cl)c3)C(F)(F)F)ccc21]

To a stirred solution of (E)-5-(4,4,4-trifluoro-3-(3,4,5-trichlorophenyl)but-1-enyl)-2,3-dihydro-1H-inden-1-one (1 g, 2.39 mmol) in MeOH (10 mL) were added ammonium acetate (NH$_4$OAc, 1.84 g, 23.9 mmol) and NaBH$_3$CN (0.44 g, 7.17 mmol,) and the reaction mixture was heated at reflux for 16 h. The reaction mixture was concentrated under reduced pressure, and the residue was diluted with water and extracted with EtOAc. The combined organic extracts were washed with water and saturated aqueous NaHCO$_3$ solution, dried over anhydrous Na$_2$SO$_4$, and concentrated under reduced pressure to afford the title compound as a liquid (500 mg, crude): $^1$H NMR (400 MHz, DMSO-d$_6$) δ 7.85 (s, 2H), 7.40 (s, 1H), 7.30 (s, 2H), 6.71 (s, 2H), 4.78 (m, 1H), 4.2 (m, 1H), 2.80 (m, 1H), 2.73 (m, 1H), 1.60 (m, 2H); ESIMS m/z 419.02 ([M+H]$^+$); IR (thin film) 2924, 1552, 1112, 807 cm$^{−1}$.

The following compound was made in accordance with the procedures disclosed in Example 25.

(E)-5-(3-(3,5-Dichloro-4-fluorophenyl)-4,4,4-trifluorobut-1-en-1-yl)-2,3-dihydro-1H-inden-1-amine (BI7)

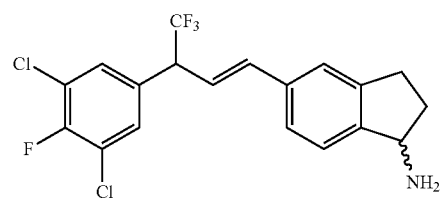 [SMILES: NC1CCc2cc(/C=C/C(c3cc(Cl)c(F)c(Cl)c3)C(F)(F)F)ccc21]

The product was isolated as a light brown gummy material, taken as such to the next step (0.15 g, crude compound): ESIMS m/z 401.97 ([M−H]$^−$).

(E)-5-(3-(3,5-Dichloro-4-fluorophenyl)-4,4,4-trifluo-robut-1-en-1-yl)-2-fluoro-2,3-dihydro-1H-inden-1-amine (BI8)

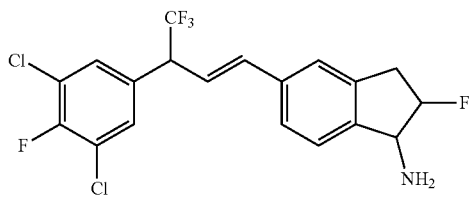 [SMILES: NC1c2ccc(/C=C/C(c3cc(Cl)c(F)c(Cl)c3)C(F)(F)F)cc2CC1F]

The product was isolated as a light brown gummy material, taken as such to the next step (0.15 g, crude compound): ESIMS m/z 420.15 ([M−H]⁻).

(E)-6-(4,4,4-Trifluoro-3-(3,4,5-trichlorophenyl)but-1-enyl)-1,2,3,4-tetrahydronaphthalen-1-amine (BI9)

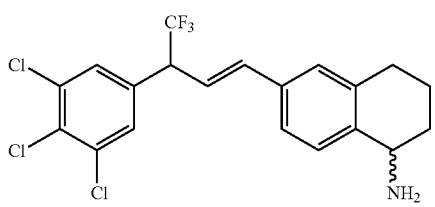

The product was isolated as a pale yellow liquid (500 mg crude).

Example 26

Preparation of (E)-1-Methyl-3-(5-(4,4,4-trifluoro-3-(3,4,5-trichlorophenyl)-but-1-enyl)-2,3-dihydro-1H-inden-1-yl)thiourea (BC1)

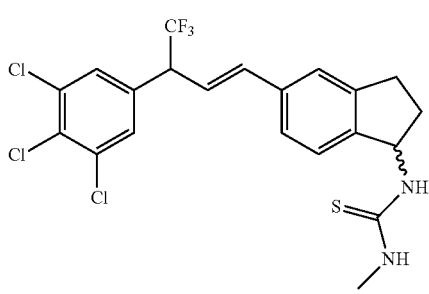 [SMILES: CNC(=S)NC1CCc2cc(/C=C/C(c3cc(Cl)c(Cl)c(Cl)c3)C(F)(F)F)ccc21]

To a stirred solution of (E)-5-(4,4,4-trifluoro-3-(3,4,5-trichlorophenyl)but-1-enyl)-2,3-dihydro-1H-inden-1-amine (0.1 g, 0.23 mmol) in Et₂O (5 mL) was added methylisothiocyanate (0.026 g, 0.35 mmol), and the mixture was stirred for 2 h at 25° C. The reaction mixture was concentrated under reduced pressure, and the residue was purified by flash column chromatography (SiO₂, 20% EtOAc in petroleum ether). The title compound was isolated as a liquid (65 mg, 50%): ¹H NMR (400 MHz, CDCl₃) δ 7.39 (s, 2H), 7.25-7.18 (m, 3H), 6.58 (d, J=16.0 Hz, 1H), 6.30 (dd, J=16.0, 8.4 Hz, 1H), 5.91-5.70 (br, 2H), 4.05 (m, 1H), 3.05-2.80 (m, 6H), 2.70 (m, 1H), 1.81 (m, 1H); ESIMS m/z 492.17 ([M+H]⁺); IR (thin film) 3211, 1569, 1113, 806 cm⁻¹.

Compounds BC2-BC3 in Table 1 were made in accordance with the procedures disclosed in Example 26.

Example 27

Preparation of (E)-3,3,3-Trifluoro-N-(5-(4,4,4-trifluoro-3-(3,4,5-trichlorophenyl)but-1-enyl)-2,3-dihydro-1H-inden-1-yl)propanamide (BC4)

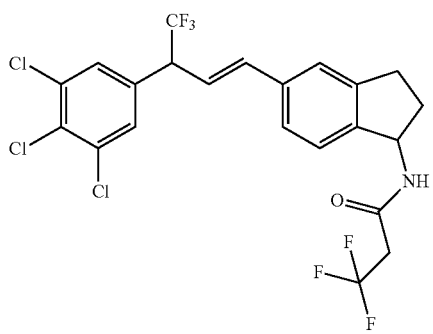 [SMILES: O=C(CC(F)(F)F)NC1CCc2cc(/C=C/C(c3cc(Cl)c(Cl)c(Cl)c3)C(F)(F)F)ccc21]

To a stirred solution of (E)-5-(4,4,4-trifluoro-3-(3,4,5-trichlorophenyl)but-1-enyl)-2,3-dihydro-1H-inden-1-amine (0.1 g, 0.23 mmol) in CH₂Cl₂ (10 mL) were added trifluoropropionic acid (0.044 g, 0.34 mmol), EDC.HCl (0.038 g, 0.35 mmol), HOBt.H₂O (0.07 g, 0.46 mmol) and DIPEA (0.074 g, 0.57 mmol), and the reaction mixture was stirred for 16 h at 25° C. The reaction mixture was diluted with CH₂Cl₂ and washed with water. The combined organic layer was washed with brine, dried over anhydrous Na₂SO₄, and concentrated under reduced pressure. The crude material was purified by flash column chromatography (SiO₂, 15% EtOAc in petroleum ether) to afford the title compound as a liquid (65 mg, 65%): ¹H NMR (400 MHz, CDCl₃) δ 7.39 (s, 2H), 7.25-7.20 (m, 3H), 6.34 (d, J=16.0 Hz, 1H), 6.30 (dd, J=16.0, 8.0 Hz, 1H), 5.81 (br, 1H), 5.48 (m, 1H), 4.10 (m, 1H), 3.10 (m, 2H), 2.86-3.07 (m, 2H), 2.86 (m, 1H), 1.81 (m, 1H); ESIMS m/z 529.02 ([M+H]⁺); IR (thin film) 3283, 1652, 1241, 811 cm⁻¹.

Compounds BC5-BC9, BC11 in Table 1 were made in accordance with the procedures disclosed in Example 27.

Example 28

Preparation of tert-Butyl 5-vinylindoline-1-carboxylate (BI10)

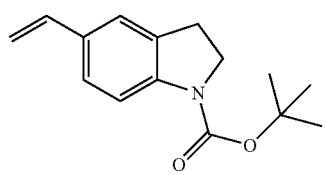 [SMILES: C=Cc1ccc2c(c1)CCN2C(=O)OC(C)(C)C]

Step 1. 5-Bromo-indoline (BI11)

To 5-Bromo-1H-indole (2.5 g, 12.82 mmol) in AcOH (10.0 mL), NaBH₃CN (2.38 g, 38.46 mmol) was added portion wise at 10° C. over the period of 20 min. After that the reaction mixture was stirred at ambient temperature for 3 h. The reaction mixture was diluted with water and extracted with Et$_2$O. The organic layer was washed with saturated NaHCO$_3$, water and brine solution. The combined ether layer was dried over anhydrous Na$_2$SO$_4$ and concentrated under reduced pressure to afford title compound as a pale yellow semi-solid (1.8 g, 71%).

Step 2. tert-Butyl-5-bromoindoline-1-carboxylate (BI12)

To a stirred solution of 5-bromo-indoline (3.0 g, 15 mmol) in MeCN (100 ml), was added DMAP (0.185 g, 1.522 mmol) and di-tert-butyl dicarbonate (3.98 g, 18.3 mmol) and the reaction was stirred at ambient temperature for 16 h. The reaction mixture was concentrated on reduced pressure to obtain a residue which was diluted with Et$_2$O and washed with water and brine solution (2×). The combined ether layer was dried over anhydrous Na$_2$SO$_4$ and concentrated under reduced pressure to afford the crude product as an off-white solid, which was used in the next step without further purification (3.0 g).

Step 3. tert-Butyl-5-vinylindoline-1-carboxylate (BI10)

A stirred solution of tert-butyl-5-bromoindoline-1-carboxylate (2.0 g, 6.73 mmol), potassium vinyl trifluoroborate (2.6 g, 20.20 mmol) and K$_2$CO$_3$ (2.78 g, 20.2 mmol) in DMSO (50.0 mL) was degassed with argon for 20 min at ambient temperature. PdCl$_2$(dppf) (0.49 g, 0.67 mmol) was added at ambient temperature, then the reaction mixture was heated to 100° C. for 3 h. The reaction mixture was cooled to ambient temperature and filtered through a Celite® bed under vacuum and washed with Et$_2$O. The reaction mixture was extracted with Et$_2$O. The combined Et$_2$O layer was dried over Na$_2$SO$_4$ and concentrated under reduced pressure to afford crude product. The crude compound was purified by column chromatography (SiO$_2$, 100-200 mesh; eluting with 2% EtOAc/petroleum ether) to afford the title compound as an off-white solid (1.2 g, 73%): mp 85.5-88.6° C.; $^1$H NMR (400 MHz, CDCl$_3$) δ 7.23 (m, 3H), 6.69 (dd, J=17.4, 10.8 Hz, 1H), 5.64 (d, J=10.5 Hz, 1H), 5.13 (d, J=10.5 Hz, 1H), 4.00 (t, J=9.0 Hz, 2H), 3.10 (t, J=9.0 Hz, 2H), 1.55 (bs, 9H).

Example 29

Preparation of (E)-tert-Butyl 5-(3-(3,5-dichloro-4-fluorophenyl)-4,4,4-trifluorobut-1-en-1-yl)indoline-1-carboxylate (BI13)

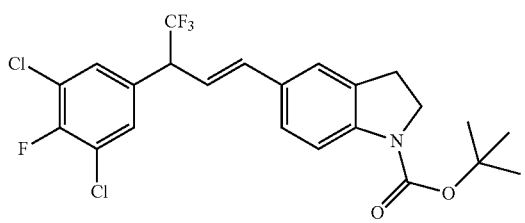 [SMILES: CC(C)(C)OC(=O)N1CCc2cc(/C=C/C(c3cc(Cl)c(F)c(Cl)c3)C(F)(F)F)ccc21]

To a stirred solution of tert-butyl-5-vinylindoline-1-carboxylate (1.28 g, 5.23 mmol) in 1,2-dichlorobenzene (10.0 mL), was added 5-(1-bromo-2,2,2-trifluoroethyl)-1,3-dichloro-2-fluorobenzene (3.4 g, 10 mmol), CuCl (103 mg, 1.05 mmol) and 2,2-bipyridyl (0.326 g, 2.092 mmol) and the resultant reaction mixture was degassed with argon for 30 min and heated to 150° C. for 1 h. The reaction mixture was cooled to ambient temperature and filtered and the filtrate was concentrated under reduced pressure. The crude compound was purified by column chromatography (SiO$_2$, 100-200 mesh; 2% EtOAc/petroleum ether) to afford the title compound as a pale yellow gummy solid (0.3 g, 61%): $^1$H NMR (400 MHz, CDCl$_3$) δ 7.34 (d, J=6.0 Hz, 2H), 7.22 (s, 2H), 7.16 (d, J=8.4 Hz, 1H), 6.52 (d, J=16.0 Hz, 1H), 6.21 (dd, J=16.0, 7.6 Hz, 1H), 4.07 (m, 3H), 3.10 (t, J=8.4 Hz, 2H), 1.55 (s, 9H); ESIMS m/z 433.79 ([M–H]$^-$); IR (thin film) 1168, 858 cm$^{-1}$.

Example 30

Preparation of (E)-5-(3-(3,5-Dichloro-4-fluorophenyl)-4,4,4-trifluorobut-1-en-1-yl)indolin-1-amine (BI14)

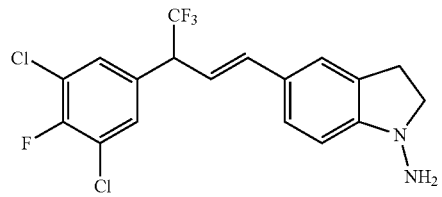 [SMILES: NN1CCc2cc(/C=C/C(c3cc(Cl)c(F)c(Cl)c3)C(F)(F)F)ccc21]

Step 1. (E)-5-(3-(3,5-Dichloro-4-fluorophenyl)-4,4,4-trifluorobut-1-enyl)indoline (BI15)

To a stirred solution of (E)-tert-butyl-5-(3-(3,5-dichloro-4-fluorophenyl)-4,4,4-trifluorobut-1-enyl)indoline-1-carboxylate (0.2 g, 0.4 mmol) in CH$_2$Cl$_2$ (10.0 mL) was added TFA (0.6 mL) and the reaction was stirred at ambient temperature for 2 h. The reaction mixture was diluted with CH$_2$Cl$_2$, washed with saturated aq NaHCO$_3$, water and brine solution. The separated CH$_2$Cl$_2$ layer was dried over anhydrous Na$_2$SO$_4$ and concentrated under reduced pressure to afford the crude product as a light brown gummy material which was used in the next step without further purification (0.12 g): $^1$H NMR (400 MHz, CDCl$_3$) δ 7.33 (d, J=6.4 Hz, 2H), 7.21 (s, 1H), 7.02 (d, J=8.0 Hz, 1H), 6.57 (d, J=8.4 Hz, 1H), 6.49 (d, J=15.6 Hz, 1H), 6.21 (dd, J=15.6, 8.4 Hz, 1H), 4.07 (m, 1H), 3.61 (t, J=8.4 Hz, 2H), 3.05 (t, J=8.4 Hz, 2H); ESIMS m/z 389.89 ([M+H]$^+$); IR (thin film) 3385, 1112, 816 cm$^{-1}$.

Step 2. 5-(3-(3,5-Dichloro-4-fluorophenyl)-4,4,4-trifluorobut-1-enyl)-1-nitrosoindoline (BI16)

To (E)-5-(3-(3,5-dichloro-4-fluorophenyl)-4,4,4-trifluorobut-1-enyl)indoline (0.2 g, 0.5 mmol) in concentrated HCl (5.0 ml) at 5° C., was added slowly NaNO$_2$ in water and the reaction was allowed to stir at ambient temperature for 2 h. The reaction mixture was diluted with CH$_2$Cl$_2$, and the CH$_2$Cl$_2$ layer washed with water and brine solution. The separated CH$_2$Cl$_2$ layer was dried over anhydrous Na$_2$SO$_4$ and concentrated under reduced pressure to afford the crude product as a pale yellow solid that was used in the next step without further purification (0.2 g): $^1$H NMR (400 MHz, CDCl$_3$) δ 7.33 (d, J=8.4 Hz, 1H), 7.39 (m, 4H), 6.61 (d, J=16.0 Hz, 1H), 6.35 (dd, J=16.0, 8.4 Hz, 1H), 4.07 (m, 3H), 3.23 (t, J=8.4 Hz, 2H); ESIMS m/z 418.82 ([M+H]$^+$); IR (thin film) 1488, 1112, 860 cm$^{-1}$.

Step 3. (E)-5-(3-(3,5-Dichloro-4-fluorophenyl)-4,4,4-trifluorobut-1-en-1-yl)indolin-1-amine (BI14)

To (E)-5-(3-(3,5-dichloro-4-fluorophenyl)-4,4,4-trifluorobut-1-enyl)-1-nitrosoindoline (0.1 g, 0.2 mmol) in MeOH (10.0 mL) was added zinc powder (77.5 mg) and NH$_4$Cl (36.9 mg, 0.69 mmol) in water (2.0 mL). The reaction mixture was stirred at ambient temperature for 3 h. The reaction mixture was diluted with CH$_2$Cl$_2$ and the CH$_2$Cl$_2$ layer was washed with water and brine solution. The separated CH$_2$Cl$_2$ layer was dried over anhydrous Na$_2$SO$_4$ and concentrated under reduced pressure to afford the crude compound, which was purified by column chromatography (SiO$_2$, 100-200 mesh; eluting with 2% EtOAc/petroleum ether) to afford the title compound as a light brown gummy material (0.08 g): ESIMS m/z 404.86 ([M+H]$^+$).

Example 31

Preparation of (E)-N-(5-(3-(3,5-Dichloro-4-fluorophenyl)-4,4,4-trifluorobut-1-en-1-yl)indolin-1-yl)-3,3,3-trifluoropropanamide (BC12)

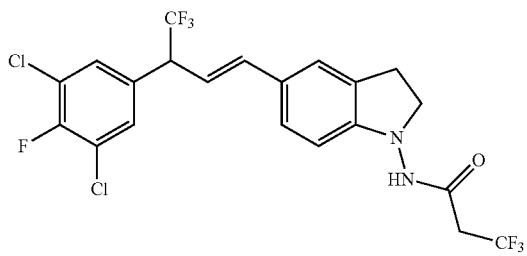

To a stirred solution of (E)-5-(3-(3,5-dichloro-4-fluorophenyl)-4,4,4-trifluorobut-1-enyl)indoline-1-amine (0.1 g, 0.247 mmol) in CH$_2$Cl$_2$ (10.0 ml) was added 3,3,3-trifluoropropanoic acid (0.038 g, 0.297 mmol), PyBOP (0.192 g, 0.370 mmol) and DIPEA (0.047 g, 0.370 mmol) and the reaction was stirred at ambient temperature for 18 h. The reaction mixture was diluted with CH$_2$Cl$_2$, and the separated CH$_2$Cl$_2$ layer dried over anhydrous Na$_2$SO$_4$ and concentrated under reduced pressure to afford the crude compound. The crude compound was purified by column chromatography (SiO$_2$, 100-200 mesh; 20-25% EtOAc/petroleum ether) to afford the title compound as a light brown gummy material (0.12 g, 33%): $^1$H NMR (400 MHz, CDCl$_3$) δ 7.32, (d, J=6.0 Hz, 2H) 7.28 (m, 1H), 7.20 (d, J=8.0, 1H), 7.14 (d, J=8.8, 1H), 6.70 (d, J=8.0 Hz, 1H), 6.60 (m, 2H), 4.15 (m, 1H), 3.85 (m, 1H), 3.65 (m, 1H), 3.46 (m, 2H), 3.19 (m, 2H); ESIMS m/z 514.86 ([M+H]$^+$); IR (thin film) 3428, 1112, 857 cm$^{-1}$.

Example 32

Preparation of tert-Butyl-5-vinyl-1H-indole-1-carboxylate (BI17)

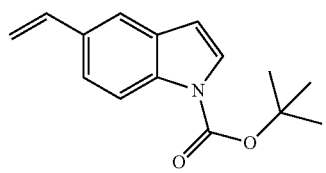 [SMILES: C=Cc1ccc2c(ccn2C(=O)OC(C)(C)C)c1]

Step 1. 5-Vinyl-1H-indole (BI18)

A mixture of 5-bromo-1H-indole (2.5 g, 12.82 mmol), potassium vinyltrifluoroborate (2.57 g, 19.2 mmol), Cs$_2$CO$_3$ (12.53 g, 38.46 mmol) and triphenylphosphine (201 mg, 0.769 mmol) in THF/water (9:1, 75 ml) was degassed with argon for 20 min, then charged with PdCl$_2$ (45.3 mg, 0.256 mmol). The reaction mixture was heated to reflux for 16 h, then cooled to ambient temperature, filtered through Celite® bed and washed with EtOAc. The filtrate was again extracted with EtOAc, and the combined organic layer washed with water and brine, dried over Na$_2$SO$_4$ and concentrated under reduced pressure to afford the crude compound. The crude compound was purified by column chromatography (SiO$_2$, 100-200 mesh; 2% EtOAc/petroleum ether) to afford the title compound as a light brown gummy material (1.5 g, 83%): $^1$H NMR (400 MHz, CDCl$_3$) δ 8.20 (br, 1H), 7.68 (s, 1H), 7.45 (s, 2H), 7.21 (m, 1H), 6.90 (dd, J=16.0, 10.8 Hz, 1H), 6.55 (m, 1H), 5.75 (d, J=10.5 Hz, 1H), 5.21 (d, J=10.5 Hz, 1H); ESIMS m/z 142.05 ([M−H]$^-$).

Step 2. tert-Butyl-5-vinyl-1H-indole-1-carboxylate (BI17)

To a stirred solution of 5-vinyl-1H-indole (0.7 g, 4.89 mmol) in MeCN (20 ml) was added DMAP (59.65 mg, 0.489 mmol) and di-tert-butyl dicarbonate (1.38 g, 6.36 mmol), and the reaction was stirred at ambient temperature for 3 h. The reaction mixture was concentrated under reduced pressure to obtain a residue which was diluted with CH$_2$Cl$_2$ and washed with water and brine solution. The combined CH$_2$Cl$_2$ layer was dried over anhydrous Na$_2$SO$_4$ and concentrated under reduced pressure to afford the crude compound. The crude compound was purified by column chromatography (SiO$_2$, 100-200 mesh; 2% EtOAc/petroleum ether) to afford the title compound as an off-white semi-solid (0.7 g, 59%): $^1$H NMR (400 MHz, CDCl$_3$) δ 8.15 (d, J=8.0 Hz, 1H), 7.60 (s, 2H), 7.30 (d, J=8.4 Hz, 1H), 7.21 (m, 1H), 6.90 (dd, J=16.0, 10.8 Hz, 1H), 6.59 (s, 1H), 5.75 (d, J=10.5 Hz, 1H), 5.21 (d, J=10.5 Hz, 1H), 1.65 (s, 9H); ESIMS m/z 242.10 ([M−H]$^-$); IR (thin film) 1630 cm$^{-1}$.

Example 33

Preparation of (E)-tert-Butyl 5-(3-(3,5-dichloro-4-fluorophenyl)-4,4,4-trifluorobut-1-en-1-yl)-1H-indole-1-carboxylate (BI19)

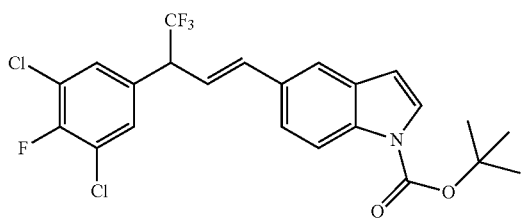 [SMILES: CC(C)(C)OC(=O)n1ccc2cc(/C=C/C(c3cc(Cl)c(F)c(Cl)c3)C(F)(F)F)ccc21]

To a stirred solution of tert-butyl 5-vinyl-1H-indole-1-carboxylate (0.65 g, 2.67 mmol), in 1,2-dichlorobenzene (10.0 mL) was added 5-(1-bromo-2,2,2-trifluoroethyl)-1,3-dichloro-2-fluorobenzene (1.74 g, 5.37 mmol), CuCl (53 mg, 0.537 mmol) and 2,2-bipyridyl (167 mg, 1.07 mmol). The resultant reaction mixture was degassed with argon for 30 min and heated to 150° C. for 2 h. The reaction mixture was cooled to ambient temperature and filtered, and the filtrate concentrated under reduced pressure. The crude compound was purified by column chromatography (SiO$_2$, 100-200 mesh; 2% EtOAc/petroleum ether) to afford the title compound as a light brown gummy material (0.25 g, 10%): $^1$H NMR (400 MHz, CDCl$_3$) δ 8.20 (d, J=8.0 Hz, 1H), 7.60 (m, 2H), 7.39 (m, 3H), 6.69 (d, J=16.0 Hz, 1H), 6.55 (d, J=10.5 Hz, 1H), 6.36 (dd, J=16.0, 8.0 Hz, 1H), 4.10 (m, 1H), 1.65 (s, 9H); ESIMS m/z 485.91 ([M−H]$^-$); IR (thin film) 1165, 854 cm$^{-1}$.

Example 34

Preparation of (E)-5-(3-(3,5-Dichloro-4-fluorophenyl)-4,4,4-trifluorobut-1-en-1-yl)-1H-indole (BI20)

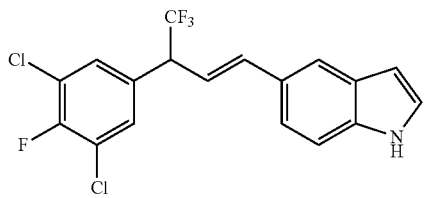 [SMILES: Fc1c(Cl)cc(C(/C=C/c2ccc3[nH]ccc3c2)C(F)(F)F)cc1Cl]

To a stirred solution of (E)-tert-butyl 5-(3-(3,5-dichloro-4-fluorophenyl)-4,4,4-trifluorobut-1-enyl)-1H-indole-1-carboxylate (0.2 g, 0.40 mmol) in CH$_2$Cl$_2$ (10.0 mL) was added TFA (70 mg, 0.61 mmol) and the reaction was stirred at ambient temperature for 2 h. The reaction mixture was diluted with CH$_2$Cl$_2$ and washed with saturated NaHCO$_3$ solution, water and brine solution. The separated CH$_2$Cl$_2$ layer was dried over anhydrous Na$_2$SO$_4$ and concentrated under reduced pressure to afford the title compound as a light brown solid (0.2 g, 97%): mp 132.9-138.8° C.; $^1$H NMR (400 MHz, CDCl$_3$) δ 11.19 (br, 1H), 8.20 (d, J=8.0 Hz, 1H), 7.60 (m, 2H), 7.39 (m, 3H), 6.69 (d, J=16.0 Hz, 1H), 6.55 (d, J=10.5 Hz, 1H), 6.36 (dd, J=16.0, 8.0 Hz, 1H), 4.82 (m, 1H); ESIMS m/z 387.98 ([M+H]$^+$).

Example 35

Preparation of 4-Nitrophenyl 2-((tert-butoxycarbonyl)amino)acetate (BI21)

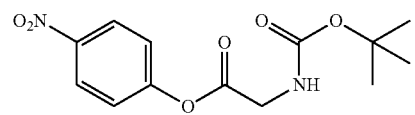 [SMILES: CC(C)(C)OC(=O)NCC(=O)Oc1ccc([N+](=O)[O-])cc1]

To a stirred solution of 4-nitrophenol (1.0 g, 7.19 mmol) in CH$_2$Cl$_2$ (20.0 mL) was added N-Boc glycine (1.38 g, 7.91 mmol) and EDC HCl (2.05 g, 10.785 mmol) and the reaction was stirred at ambient temperature for 24 h. The reaction mixture was diluted with CH$_2$Cl$_2$ and washed with water and saturated brine solution. The separated CH$_2$Cl$_2$ layer was dried over anhydrous Na$_2$SO$_4$ and concentrated under reduced pressure to afford the title compound as a light brown gummy material that was used in the next step without further purification (1.1 g): $^1$H NMR (400 MHz, CDCl$_3$) δ 8.29 (d, J=9.2 Hz, 2H), 7.33 (d, J=8.8 Hz, 2H), 5.07 (br, 1H), 4.20 (s, 2H), 1.47 (s, 9H); ESIMS m/z 296.27 ([M+H]$^+$).

Example 36

Preparation of (E)-tert-Butyl (2-(5-(3-(3,5-dichloro-4-fluorophenyl)-4,4,4-trifluorobut-1-en-1-yl)-1H-indol-1-yl)-2-oxoethyl)carbamate (BI22)

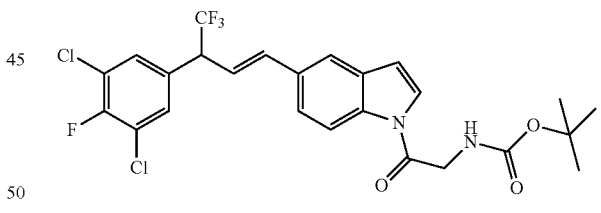

To a stirred solution of (E)-5-(3-(3,5-dichloro-4-fluorophenyl)-4,4,4-trifluorobut-1-enyl)-1H-indole (0.1 g, 0.258 mmol) in MeCN (5.0 mL) was added 4-nitrophenyl 2-(tert-butoxycarbonylamino) acetate (0.114 g, 0.387 mmol), KF (0.03 g, 0.516 mmol), 18-crown-6-ether (0.075 g, 0.283 mmol) and DIPEA (0.0332 g, 0.258 mmol) and the reaction was stirred at ambient temperature for 16 h. The reaction mixture was concentrated to obtain a residue which was diluted with CH$_2$Cl$_2$ and washed with water and brine solution. The separated CH$_2$Cl$_2$ layer was dried over anhydrous Na$_2$SO$_4$ and concentrated under reduced pressure to afford the crude title compound as a light brown gummy material which was used in the next step without further purification (0.1 g): ESIMS m/z 545.23 ([M+H]$^+$).

Example 37

Preparation of (E)-N-(2-(5-(3-(3,5-Dichloro-4-fluorophenyl)-4,4,4-trifluorobut-1-en-1-yl)-1H-indol-1-yl)-2-oxoethyl)-3,3,3-trifluoropropanamide (BC13)

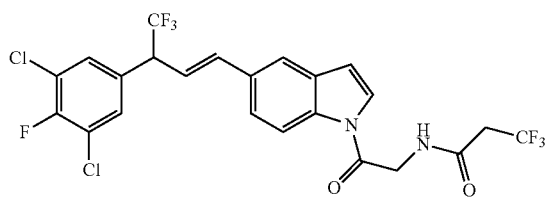 [SMILES: O=C(CC(F)(F)F)NCC(=O)n1ccc2cc(/C=C/C(c3cc(Cl)c(F)c(Cl)c3)C(F)(F)F)ccc21]

Step 1. (E)-2-Amino-1-(5-(3-(3,5-dichloro-4-fluorophenyl)-4,4,4-trifluorobut-1-enyl)-1H-indol-1-yl) ethanone (BI23)

To a stirred solution of (E)-tert-butyl 2(5-(3-(3,5-dichloro-4-fluorophenyl)-4,4,4-trifluorobut-1-enyl)-1H-indol-1-yl)-2-oxoethylcarbamate (0.05 g, 0.09 mmol) in $CH_2Cl_2$ (5.0 mL) was added TFA (0.01 mL) and the reaction was stirred at ambient temperature for 16 h. The reaction mixture was diluted with $CH_2Cl_2$ and washed with saturated $NaHCO_3$ solution, water and brine solution. The separated $CH_2Cl_2$ layer was dried over anhydrous $Na_2SO_4$ and concentrated under reduced pressure to afford the crude title compound which was used in the next step without further purification (50 mg).

Step 2. (E)-N-(2-(5-(3-(3,5-Dichloro-4-fluorophenyl)-4,4,4-trifluorobut-1-en-1-yl)-1H-indol-1-yl)-2-oxoethyl)-3,3,3-trifluoropropanamide (BC13)

To a stirred solution of (E)-2-amino-1-(5-(3-(3,5-dichloro-4-fluorophenyl)-4,4,4-trifluorobut-1-enyl)-1H-indol-1-yl) ethanone (0.04 g, 0.09 mmol) in $CH_2Cl_2$ (5.0 ml) was added 3,3,3-trifluoropropanoic acid (17.5 mg, 0.136 mmol), PyBOP (70 mg, 0.135 mmol) and DIPEA (29 mg, 0.225 mmol) and the reaction was stirred at ambient temperature for 16 h. The reaction mixture was diluted with $CH_2Cl_2$, and the $CH_2Cl_2$ layer was washed with water and saturated brine solution. The separated $CH_2Cl_2$ layer was dried over anhydrous $Na_2SO_4$ and concentrated under reduced pressure to afford the crude compound, which was purified by column chromatography ($SiO_2$, 100-200 mesh; 10% EtOAc/petroleum ether) to afford the title compound as an off-white solid (30 mg, 60%): mp 121-126° C.; $^1$H NMR (400 MHz, $CDCl_3$) δ 8.33 (br, 1H), 7.59 (s, 1H), 7.45 (m, 4H), 6.72 (d, J=3.6 Hz, 3H), 6.39 (m, 1H), 4.71 (t, J=7.2 Hz, 2H), 4.15 (m, 1H), 3.51 (m, 1H), 3.28 (m, 1H); ESIMS m/z 553.06 ([M−H]$^-$).

Example 38

Preparation of Ethyl 2-(1-oxo-6-vinylphthalazin-2 (1H)-yl)acetate (BI24)

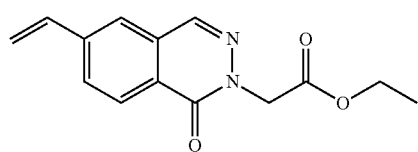 [SMILES: C=Cc1ccc2c(=O)n(CC(=O)OCC)ncc2c1]

Step 1. 5-Bromo-3-hydroxyisoindoline-1-one (BI25)

A mixture of Zn powder (1.73 g, 26.154 mmol), copper (II) sulfate pentahydrate (0.02 g, 0.08 mmol) and 2M aq NaOH (27 mL) were cooled to 0° C. 5-Bromoisoindoline-1,3-dione (5 g, 22 mmol) was added at the same temperature over the period of 30 min. The reaction mixture was stirred at 0° C. for 30 min and 3 h at ambient temperature. The reaction mixture was filtered and the filtrate was neutralized with concentrated HCl. The reaction mixture was diluted with ethanol and extracted with EtOAc. The combined EtOAc layer was dried over $Na_2SO_4$ and concentrated under reduced pressure to afford the crude title compound as a brown solid, which was used in the next step without further purification (1.3 g): mp 258-261° C.; $^1$H NMR (400 MHz, DMSO-$d_6$) δ 9.03 (br, 1H), 7.81 (m, 2H), 7.69 (m, 1H), 6.44 (m, 1H), 5.88 (d, J=9.3 Hz, 1H); ESIMS m/z 225.83 ([M−H]$^-$); IR (thin film) 1684, 3246, 606 cm$^{-1}$.

Step 2. 6-Bromophthalazine-1(2H)-one (BI26)

To a stirred solution of 5-bromo-3-hydroxyisoindoline-1-one (1.0 g, 4.40 mmol) in water, was added hydrazine hydrate (0.45 g, 8.80 mmol) and heated to 95° C. for 5 h. The reaction mixture was cooled to ambient temperature, filtered and washed with $Et_2O$ and pentane (1:1) to afford the title compound as a white solid that was used in the next step without further purification (0.5 g): ESIMS m/z 225.15 ([M+H]$^+$).

Step 3. 6-Vinylphthalazine-1(2H)-one (BI27)

A solution of 6-bromophthalazine-1(2H)-one (0.25 g, 1.11 mmol), potassium vinyl trifluoroborate (0.446 g, 3.33 mmol) and $K_2CO_3$ (0.46 g, 3.33 mmol) in DMSO (2 mL) was degassed with argon for 20 min at ambient temperature. $PdCl_2$(dppf) (0.04 g, 0.055 mmol) was added at ambient temperature, and the reaction mixture was heated to 80° C. for 2 h. The reaction mixture was cooled to ambient temperature and filtered through Celite® bed under vacuum and washed with EtOAc. The reaction mixture was extracted with EtOAc and the combined EtOAc layer dried over $Na_2SO_4$ and concentrated under reduced pressure to afford the crude product. The crude compound was purified by column chromatography ($SiO_2$, 100-200 mesh; 50% EtOAc/petroleum ether) to afford the title compound as a brown solid (0.12 g, 63%): $^1$H NMR (400 MHz, DMSO-$d_6$) δ 13.61 (br, 1H), 8.33 (m, 1H), 8.19 (m, 1H), 8.01 (m, 2H), 6.97 (m, 1H), 6.15 (m, 1H), 5.56 (d, J=10.8 Hz, 1H); ESIMS m/z 172.93 ([M+H]$^+$); IR (thin film) 1748, 1655, 3241 cm$^{-1}$.

Step 4. Ethyl-2-(1-oxo-6-vinylphthalazine-2(1H)-yl acetate (BI24)

To a stirred solution of 6-vinylphthalazine-1(2H)-one (0.5 g, 2.90 mmol) in DMF (5.0 mL) was added $Cs_2CO_3$ (0.94 g, 2.90 mmol) and the reaction was stirred for 10 min Ethyl bromoacetate (0.48 g, 2.90 mmol) was added to the reaction mixture at ambient temperature and the reaction was stirred for 8 h at ambient temperature. The reaction mixture was diluted and extracted with EtOAc, and the EtOAc layer was washed with water and brine solution (2×). The separated EtOAc layer was dried over anhydrous $Na_2SO_4$ and concentrated under reduced pressure to afford crude product. The crude compound was purified by column chromatography ($SiO_2$, 100-200 mesh; 25% EtOAc/petroleum ether) to afford the title compound as a brown solid (0.34 g, 45%): $^1$H NMR (400 MHz, DMSO-$d_6$) δ 8.45 (m, 1H), 8.24 (m, 1H), 8.04 (m, 2H), 7.01 (m, 1H), 6.17 (d, J=2.1 Hz, 1H), 5.56 (d, J=10.8 Hz, 1H), 4.92 (s, 2H), 4.19 (m, 2H), 1.23 (m, 3H). ESIMS m/z 259.10 ([M+H]$^+$); IR (thin film) 1750, 1660 cm$^{-1}$.

Example 39

Preparation of (E)-Ethyl 2-(6-(3-(3,5-dichloro-4-fluorophenyl)-4,4,4-trifluorobut-1-en-1-yl)-1-oxophthalazin-2(1H)-yl)acetate (BI28)

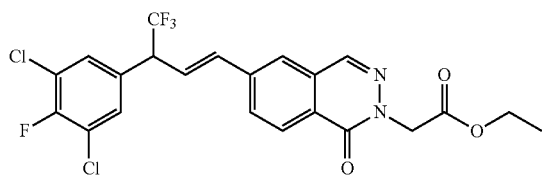 [SMILES: CCOC(=O)Cn1ncc2cc(/C=C/C(c3cc(Cl)c(F)c(Cl)c3)C(F)(F)F)ccc2c1=O]

To a stirred solution of ethyl-2-(1-oxo-6-vinylphthalazine-2(1H)-yl acetate (0.07 g, 0.27 mmol) in 1,2-dichlorobenzene (1.0 mL) was added 5-(1-bromo-2,2,2-trifluoroethyl)-1,3-dichloro-2fluorobenzene (0.17 g, 0.54 mmol), CuCl (0.005 g, 0.05 mmol) and 2,2-bipyridyl (0.016 g, 0.10 mmol) and the resultant reaction mixture was degassed with argon for 30 min and heated to 180° C. for 12 h. The reaction mixture was cooled to ambient temperature and filtered and the filtrated was concentrated under reduced pressure. The crude compound was purified by column chromatography (SiO$_2$, 100-200 mesh; 10-15% EtOAc/petroleum ether) to afford the title compound as a brown solid (40 mg, 29%): $^1$H NMR (400 MHz, DMSO-$d_6$) δ 8.40 (d, J=8.4 Hz, 1H), 7.84 (d, J=1.5 Hz, 1H), 7.65 (s, 1H), 7.37 (d, J=6.3 Hz, 2H), 6.76 (d, J=16.0 Hz, 1H), 6.59 (dd, J=16.0, 8.0 Hz, 1H), 4.96 (s, 2H), 4.29 (m, 3H), 1.31 (t, J=7.2 Hz, 3H); ESIMS m/z 503.0 ([M+H]$^+$); IR (thin film) 1660, 1114, 817 cm$^{-1}$.

Example 40

Preparation of (E)-2-(6-(3-(3,5-Dichloro-4-fluorophenyl)-4,4,4-trifluorobut-1-en-1-yl)-1-oxophthalazin-2(1H)-yl)acetic acid (BI29)

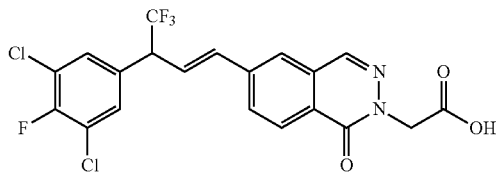 [SMILES: O=C(O)Cn1ncc2cc(/C=C/C(c3cc(Cl)c(F)c(Cl)c3)C(F)(F)F)ccc2c1=O]

A solution of (E)-ethyl-2-(6-(3-(3,5-dichloro-4-fluorophenyl)-4,4,4-trifluorobut-1-enyl)-1-oxophthalazin-2(1H)-yl) acetate (0.04 g, 0.07 mmol) in HCl (0.5 mL) and AcOH (0.5 mL) was heated to 100° C. for 3 h. The solvent was removed under reduced pressure and the residue diluted with water. The aqueous layer was extracted with EtOAc and the separated EtOAc layer dried over anhydrous Na$_2$SO$_4$ and concentrated under reduced pressure to afford the crude compound. The crude compound was triturated with Et$_2$O-pentane mixture to afford the title compound as a brown solid (0.03 g): $^1$H NMR (400 MHz, DMSO-$d_6$) δ 13.0 (br s, 1H), 8.43 (m, 1H), 8.23 (d, J=8.1 Hz, 1H), 8.14 (m, 2H), 7.91 (m, 2H), 7.16 (dd, J=16.0, 8.0 Hz, 1H), 6.99 (d, J=16.0 Hz, 1H), 4.96 (m, 3H); ESIMS m/z 473.0 ([M−H]$^-$); IR (thin film) 1629, 1168, 817 cm$^{-1}$.

Example 41

Preparation of (E)-2-(6-(3-(3,5-Dichloro-4-fluorophenyl)-4,4,4-trifluorobut-1-en-1-yl)-1-oxophthalazin-2(1H)-yl)-N-(2,2,2-trifluoroethyl)acetamide (BC14)

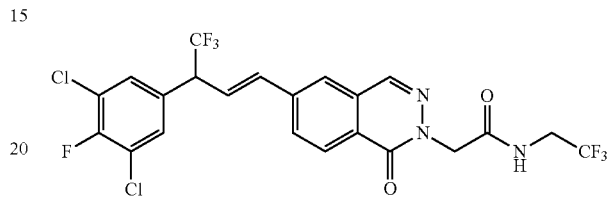

To a stirred solution of (E)-2-(6-(3-(3,5-dichloro-4-fluorophenyl)-4,4,4-trifluorobut-1-enyl)-1-oxophthalazin-2 (1H)-yl)acetic acid (0.15 g, 0.31 mmol) in CH$_2$Cl$_2$ (20.0 ml) was added 2,2,2,-trifluoroethanamine (0.03 g, 0.31 mmol), PyBOP (0.17 g, 0.34 mmol) and DIPEA (0.15 ml, 0.93 mmol) at ambient temperature, and the reaction was stirred for 18 h. The reaction mixture was diluted with CH$_2$Cl$_2$ and washed with 3N HCl (2×20 mL), NaHCO$_3$ (2×20 mL) and brine solution (2×). The separated CH$_2$Cl$_2$ layer was dried over anhydrous Na$_2$SO$_4$ and concentrated under reduced pressure to afford the crude compound. The crude compound was purified by column chromatography (SiO$_2$, 100-200 mesh; 20-25% EtOAc/petroleum ether) to afford the title compound as a brown solid (0.11 g): mp 172-175° C.; $^1$H NMR (400 MHz, CDCl$_3$) δ 8.83 (t, J=6.6 Hz, 1H), 8.42 (t, J=14.7 Hz, 1H), 8.22 (d, J=8.1 Hz, 1H), 8.13 (t, J=6.3 Hz, 1H), 7.98-7.86 (m, 2H), 7.16-7.07 (m, 1H), 7.01-6.93 (m, 1H), 4.96-4.81 (m, 3H), 4.00-3.88 (m, 2H); ESIMS m/z 554.0 ([M−H]$^-$).

Example 42

Preparation of 2-(4-Vinylbenzyl)isoindoline-1,3-dione (CI1)

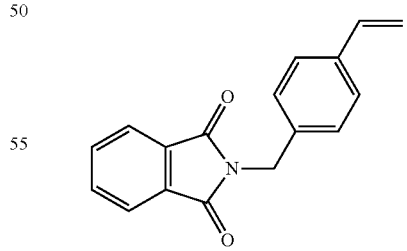

To a stirred solution of 1-(chloromethyl)-4-vinylbenzene (10 g, 66 mmol) in DMF (100 mL) was added potassium phthalimide (13.3 g, 72.1 mmol), and the resultant reaction mixture was heated at 70° C. for 16 h. The reaction mixture was diluted with water and extracted with CHCl$_3$. The combined CHCl$_3$ layer was washed with brine, dried over Na$_2$SO$_4$ and concentrated under reduced pressure. Recrystallization from MeOH afforded the title compound as an off-white solid (8 g, 46%): $^1$H NMR (400 MHz, CDCl$_3$) δ 7.83 (m, 2H), 7.71 (m, 2H), 7.39 (m, 4H), 6.65 (dd, J=17.6, 10.8 Hz, 1H), 5.72 (d, J=17.6 Hz, 1H), 5.21 (d, J=10.8 Hz, 1H), 4.82 (s, 2H); GCMS m/z 263.2 ([M]$^+$); IR (thin film) 3420, 1133, 718 cm$^{-1}$.

Example 43

Preparation of (E)-2-(4-(3-(3,5-Dichlorophenyl)-4,4,4-trifluorobut-1-en-1-yl)benzyl)isoindoline-1,3-dione (CI2)

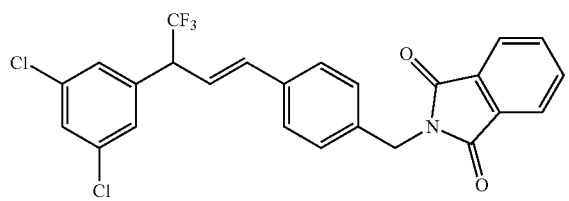 [SMILES: O=C1c2ccccc2C(=O)N1Cc1ccc(/C=C/C(c2cc(Cl)cc(Cl)c2)C(F)(F)F)cc1]

Using the procedure of Example 10 with 2-(4-vinylbenzyl)isoindoline-1,3-dione and 1-(1-bromoethyl)-3,5-dichlorobenzene as the starting materials, the title compound was isolated as an off-white solid (0.3 g, 40-50%): mp 142-145° C.; $^1$H NMR (400 MHz, CDCl$_3$) δ 7.86 (m, 2H), 7.74 (m, 2H), 7.42 (m, 2H), 7.36 (m, 3H), 7.27 (m, 2H), 6.58 (d, J=16.0 Hz, 1H), 6.32 (dd, J=16.0, 8.0 Hz, 1H), 4.82 (s, 2H), 4.05 (m, 1H); ESIMS m/z 488.17 ([M−H]$^−$).

The following compound was made in accordance with the procedures disclosed in Example 43.

(E)-2-(4-(4,4,4-Trifluoro-3-(3,4,5-trichlorophenyl)but-1-en-1-yl)benzyl)isoindoline-1,3-dione (CI3)

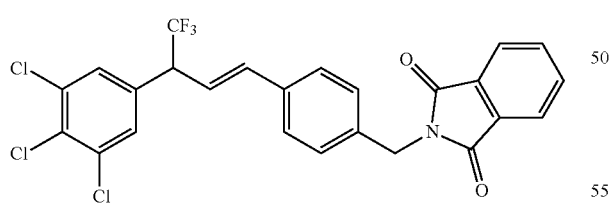

The title compound was isolated as an off white solid (0.3 g, 56%): mp 145-146° C.; $^1$H NMR (400 MHz, CDCl$_3$) δ 7.86 (m, 2H), 7.74 (m, 2H), 7.42-7.31 (m, 6H), 6.58 (d, J=16.0 Hz, 1H), 6.53 (dd, J=16.0, 8.0 Hz, 1H), 4.82 (s, 2H), 4.05 (m, 1H); ESIMS m/z 522.2 ([M−H]$^−$); IR (thin film) 1716, 1110, 712 cm$^{-1}$.

Prophetically, compounds CI4-CI5 (Table 1) could be made in accordance with the procedures disclosed in Example 43.

Example 44

Preparation of (E)-(4-(3-(3,5-Dichlorophenyl)-4,4,4-trifluorobut-1-en-1-yl)phenyl)methanamine (CI6)

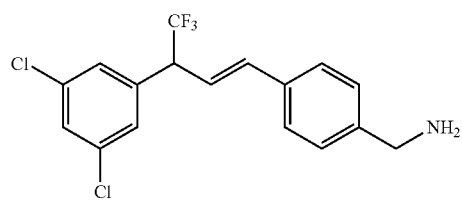 [SMILES: NCc1ccc(/C=C/C(c2cc(Cl)cc(Cl)c2)C(F)(F)F)cc1]

To a stirred solution of (E)-2-(4-(3-(3,5-dichlorophenyl)but-1-en-1-yl)benzyl)-isoindoline-1,3-dione (1.2 g, 2.45 mmol) in EtOH was added hydrazine hydrate (0.61 g, 12 mmol), and the resultant reaction mixture was heated at 90° C. for 1 h. The reaction mixture was filtered, and the filtrate was concentrated. The residue was dissolved in CH$_2$Cl$_2$, washed with brine, dried over Na$_2$SO$_4$, and concentrated under reduced pressure to afford the crude title compound as a gummy liquid (0.9 g) which was used without further purification.

The following compounds were made in accordance with the procedures disclosed in Example 44.

(E)-(4-(4,4,4-Trifluoro-3-(3,4,5-trichlorophenyl)but-1-en-1-yl)phenyl)methanamine (CI7)

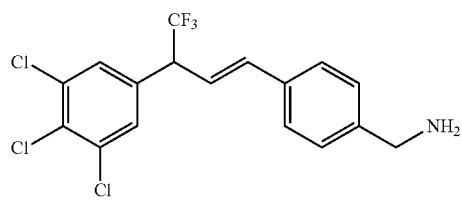 [SMILES: NCc1ccc(/C=C/C(c2cc(Cl)c(Cl)c(Cl)c2)C(F)(F)F)cc1]

The title compound was isolated and used without further purification.

Prophetically, compounds CI8-CI9 (Table 1) could be made in accordance with the procedures disclosed in Example 44.

Example 45

Preparation of 4-(Bromomethyl)-3-chlorobenzonitrile (CI10)

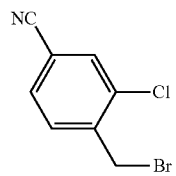

To a stirred solution of 3-chloro-4-methylbenzonitrile (5 g, 25.4 mmol) in CCl$_4$ (50 mL) under an argon atmosphere was added NBS (5.16 g, 29 mmol), and the mixture was degassed for 30 min. To this was added AIBN (0.3 g, 1.8 mmol), and the resultant reaction mixture was heated at reflux for 4 h. The reaction mixture was cooled to ambient temperature, washed with water, and extracted with CH$_2$Cl$_2$. The combined CH$_2$Cl$_2$ layer was washed with brine, dried over Na$_2$SO$_4$, and concentrated under reduced pressure. The crude compound was purified by flash column chromatography (SiO$_2$, 100-200 mesh; 5% EtOAc in n-Hexane) to afford the title compound as a white solid (4.8 g, 68%): mp 87-88° C.; $^1$H NMR (400 MHz, CDCl$_3$) δ 7.71 (s, 1H), 7.59 (s, 2H), 4.60 (s, 2H); ESIMS m/z 229.77 ([M+H]$^+$); IR (thin film) 2235, 752, 621 cm$^{-1}$.

The following compounds were made in accordance with the procedures disclosed in Example 45.

4-(Bromomethyl)-3-(trifluoromethyl)benzonitrile (CI11)

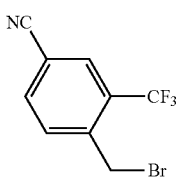 [SMILES: N#Cc1ccc(CBr)c(C(F)(F)F)c1]

The title compound was isolated as an off-white gummy material (5 g, 66%): $^1$H NMR (400 MHz, CDCl$_3$) δ 7.96 (s, 1H), 7.86 (d, J=8.0 Hz, 1H), 7.76 (d, J=8.0 Hz, 1H), 4.62 (s, 2H); ESIMS m/z 262.11 ([M−H]$^−$); IR (thin film) 2236, 1132, 617 cm$^{-1}$.

3-Bromo-4-(bromomethyl)benzonitrile (CI12)

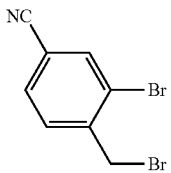

The title compound was isolated as an off-white solid (5 g, 67%): mp 82-83° C.; $^1$H NMR (400 MHz, CDCl$_3$) δ 7.90 (s, 1H), 7.61 (m, 2H), 4.62 (s, 2H); EIMS m/z 272.90; IR (thin film) 2229, 618 cm$^{-1}$.

4-(Bromomethyl)-3-fluorobenzonitrile (CI13)

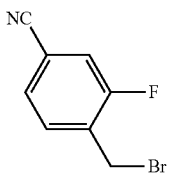 [SMILES: N#Cc1ccc(CBr)c(F)c1]

The title compound was isolated as an off-white solid (2 g, 60%): mp 79-81° C.; $^1$H NMR (400 MHz, CDCl$_3$) δ 7.54 (t, J=8.0 Hz, 1H), 7.48 (dd, J=8.0 Hz, 8.0, 1H), 7.38 (dd, J=5 Hz, 1H), 4.5 (s, 2H); EIMS m/z 215.

Example 46

Preparation of 4-(Bromomethyl)-3-chlorobenzaldehyde (CI14)

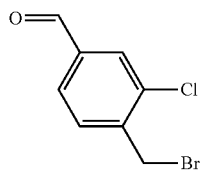 [SMILES: O=Cc1ccc(CBr)c(Cl)c1]

To a stirred solution of 4-(bromomethyl)-3-chlorobenzonitrile (4.8 g, 17 mmol) in toluene (50 mL) at 0° C. was added dropwise DIBAl-H (1.0 M solution in toluene; 23.9 mL), and the reaction mixture was stirred at 0° C. for 1 h. 10 M HCl in water (5 mL) was added until the reaction mixture turned to a white slurry and then additional 1 N HCl (20 mL) was added. The organic layer was collected and the aqueous layer was extracted with CHCl$_3$. The combined organic layer was dried over Na$_2$SO$_4$ and concentrated under reduced pressure. The crude compound was purified by flash column chromatography (SiO$_2$, 100-200 mesh; 5% EtOAc in n-Hexane) to afford the title compound as a white solid (3.8 g, 80%): mp 64-66° C.; $^1$H NMR (400 MHz, CDCl$_3$) δ 10.00 (s, 1H), 7.92 (s, 1H), 7.78 (d, J=8.0 Hz, 1H), 7.64 (d, J=8.0 Hz, 1H), 4.60 (s, 2H); ESIMS m/z 232.78 ([M+H]$^+$).

The following compounds were made in accordance with the procedures disclosed in Example 46.

4-(Bromomethyl)-3-(trifluoromethyl)benzaldehyde (CI15)

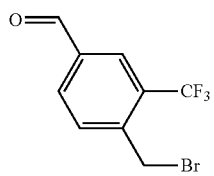 [SMILES: O=Cc1ccc(CBr)c(C(F)(F)F)c1]

The title compound was isolated as a pale yellow low-melting solid (5 g, 60%): $^1$H NMR (400 MHz, CDCl$_3$) δ 10.09 (s, 1H), 8.19 (s, 1H), 8.09 (m, 1H), 7.81 (m, 1H), 4.61 (s, 2H); ESIMS m/z 265.04 ([M−H]$^−$); IR (thin film) 1709, 1126, 649 cm$^{-1}$.

3-Bromo-4-(bromomethyl)benzaldehyde (CI16)

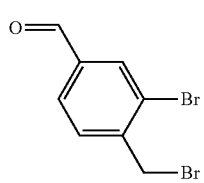 [SMILES: O=Cc1ccc(CBr)c(Br)c1]

The title compound was isolated as a pale yellow solid (5 g, 62%): mp 94-95° C.; $^1$H NMR (400 MHz, CDCl$_3$) δ 9.96 (s, 1H), 8.05 (s, 1H), 7.81 (d, J=8.0 Hz, 1H), 7.62 (d, J=8.0 Hz, 1H), 4.60 (s, 2H); EIMS m/z 275.90 ([M]$^+$).

4-(Bromomethyl)-3-fluorobenzaldehyde (CI17)

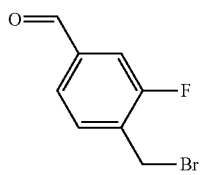 [SMILES: O=Cc1ccc(CBr)c(F)c1]

The title compound was isolated as an off-white solid (5 g, 61%): mp 43-45° C.; $^1$H NMR (400 MHz, CDCl$_3$) δ 9.1 (s, 1H), 7.54 (t, J=8 Hz, 1H), 7.48 (d, J=8 Hz, 1H), 7.38 (d, J=5 Hz, 1H), 4.5 (s, 2H); EIMS m/z 216 ([M]$^+$).

Example 47

Preparation of 3-Chloro-4-((1,3-dioxoisoindolin-2-yl)methyl)benzaldehyde (CI18)

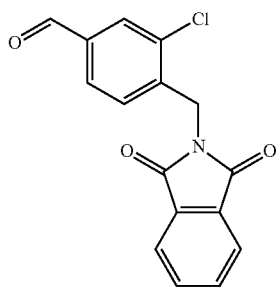 [SMILES: O=Cc1ccc(CN2C(=O)c3ccccc3C2=O)c(Cl)c1]

To a stirred solution of 4-(bromomethyl)-3-chlorobenzaldehyde (3.8 g, 14 mmol) in DMF (40 mL) was added potassium pthalimide (3.54 g, 19.14 mmol), and the mixture was heated at 60° C. for 6 h. The reaction mixture was cooled to ambient temperature and diluted with water (100 mL). The solid obtained was separated by filtration and dried under vacuum to afford the title compound as a white solid (2.8 g, 60%): mp 123-126° C.; $^1$H NMR (400 MHz, CDCl$_3$) δ 9.95 (s, 1H), 8.21 (s, 1H), 7.91 (m, 3H), 7.80 (m, 2H), 7.20 (m, 1H), 5.05 (s, 2H); ESIMS m/z 298.03 ([M−H]$^-$).

The following compounds were made in accordance with the procedures disclosed in Example 47.

4-((1,3-Dioxoisoindolin-2-yl)-3-(trifluoromethyl)benzaldehyde (CI19)

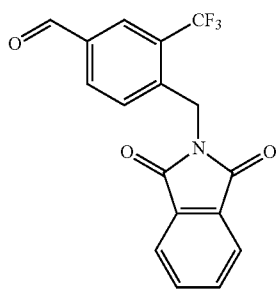 [SMILES: O=Cc1ccc(CN2C(=O)c3ccccc3C2=O)c(C(F)(F)F)c1]

The title compound was isolated as an off white solid (1 g, 62%): mp 142-143° C.; $^1$H NMR (400 MHz, CDCl$_3$) δ 10.05 (s, 1H), 8.15 (s, 1H), 7.91 (m, 2H), 7.80 (m, 3H), 7.27 (m, 1H), 5.19 (s, 2H); ESIMS m/z 332.03 ([M−H]$^-$).

3-Bromo-4-((1,3-dioxoisoindolin-2-yl)methyl)benzaldehyde (CI20)

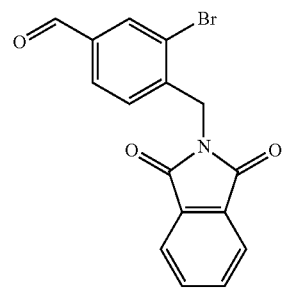 [SMILES: O=Cc1ccc(CN2C(=O)c3ccccc3C2=O)c(Br)c1]

The title compound was isolated as an off-white solid (0.5 g, 64%): mp 159-161° C.; $^1$H NMR (400 MHz, CDCl$_3$) δ 9.95 (s, 1H), 8.21 (s, 1H), 7.91 (m, 3H), 7.80 (m, 2H), 7.20 (m, 1H), 5.05 (s, 2H); ESIMS m/z 314.00 ([M−CHO]$^-$).

4-((1,3-Dioxoisoindolin-2-yl)-3-fluorobenzaldehyde (CI21)

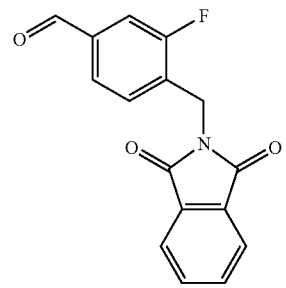 [SMILES: O=Cc1ccc(CN2C(=O)c3ccccc3C2=O)c(F)c1]

The title compound was isolated as a white solid (2 g, 60%): mp 154-156° C.; $^1$H NMR (400 MHz, CDCl$_3$) δ 9.95 (s, 1H), 7.9 (m, 2H), 7.75 (m, 2H), 7.6 (m, 2H), 7.5 (t, J=7.6 Hz, 1H), 5.05 (s, 2H); EIMS m/z 283.1 ([M]$^+$).

Example 48

Preparation of 2-(2-Chloro-4-vinylbenzyl)isoindoline-1,3-dione (CI22)

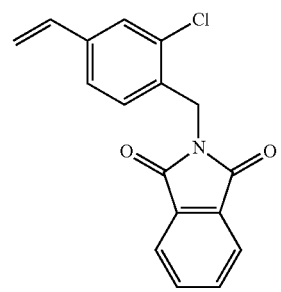

To a stirred solution of 3-chloro-4-((1,3-dioxoisoindolin-2-yl)methyl)benzaldehyde (2.8 g, 8.2 mmol) in 1,4-dioxane (30 mL) were added K$_2$CO$_3$ (1.68 g, 12.24 mmol) and methyl triphenyl phosphonium bromide (4.37 g, 12.24 mmol) at ambient temperature. Then the resultant reaction mixture was heated at 100° C. for 18 h. After the reaction was deemed complete by TLC, the reaction mixture was cooled to ambient temperature and filtered, and the obtained filtrate was concentrated under reduced pressure. The residue was purified by flash chromatography (SiO$_2$, 100-200 mesh; 20% EtOAc in n-Hexane) to afford the title compound as a white solid (1.94 g, 70%): mp 141-143° C.; $^1$H NMR (400 MHz, CDCl$_3$) δ 7.85 (m, 2H), 7.70 (m, 2H), 7.41 (m, 1H), 7.21 (m, 2H), 6.71 (dd, J=17.6, 10.8 Hz, 1H), 5.72 (d, J=17.6 Hz, 1H), 5.23 (d, J=10.8 Hz, 1H), 4.92 (s, 2H); ESIMS m/z 298.10 ([M–H]$^-$).

The following compounds were made in accordance with the procedures disclosed in Example 48.

2-(2-(Trifluoromethyl)-4-vinylbenzyl)isoindoline-1,3-dione (CI23)

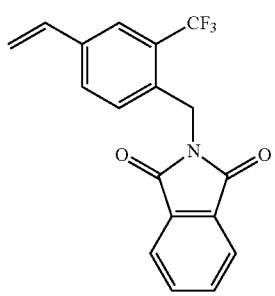

The title compound was isolated as a light brown solid (0.5 g, 60%): mp 134-135° C.; $^1$H NMR (400 MHz, CDCl$_3$) δ 7.92 (m, 2H), 7.80 (m, 2H), 7.71 (s, 1H), 7.46 (d, J=8.0 Hz, 1H), 7.16 (d, J=8.0 Hz, 1H), 6.65 (m, 1H), 5.80 (d, J=17.8 Hz, 1H), 5.19 (d, J=10.8 Hz, 1H), 5.09 (s, 2H); ESIMS m/z 332.10 ([M]$^+$).

2-(2-Bromo-4-vinylbenzyl)isoindoline-1,3-dione (CI24)

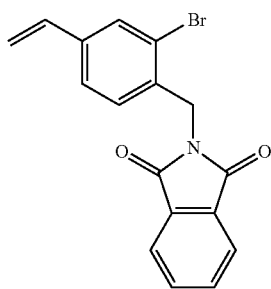 [SMILES: C=Cc1ccc(CN2C(=O)c3ccccc3C2=O)c(Cl)c1]

The title compound was isolated as an off white solid (0.5 g, 62%): mp 126-128° C.; $^1$H NMR (400 MHz, CDCl$_3$) δ 7.92 (m, 2H), 7.79 (m, 2H), 7.62 (s, 1H), 7.21 (m, 1H), 7.16 (d, J=8.0 Hz, 1H), 6.62 (m, 1H), 5.72 (d, J=17.8 Hz, 1H), 5.15 (d, J=10.8 Hz, 1H), 4.95 (s, 2H); EIMS m/z 341.10 ([M]$^+$).

2-(2-Fluoro-4-vinylbenzyl)isoindoline-1,3-dione (CI25)

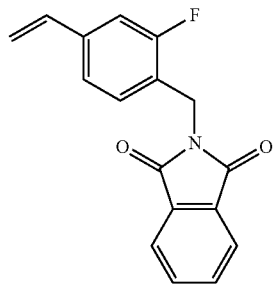 [SMILES: C=Cc1ccc(CN2C(=O)c3ccccc3C2=O)c(F)c1]

The title compound was isolated as a white solid (0.5 g, 61%): mp 140-142° C.; $^1$H NMR (400 MHz, CDCl$_3$) δ 7.85 (m, 2H), 7.72 (m, 2H), 7.25 (m, 1H), 7.11 (m, 2H), 6.63 (m, 1H), 5.80 (d, J=17.6 Hz, 1H), 5.28 (d, J=10.8 Hz, 1H), 4.92 (s, 2H); EIMS m/z 282.08.

Example 49

Preparation of (E)-2-(2-Chloro-4-(3-(3,5-dichlorophenyl)-4,4,4-trifluorobut-1-en-1-yl)benzyl)isoindoline-1,3-dione (CI26)

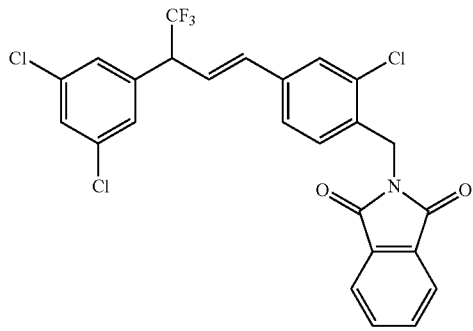 [SMILES: O=C1c2ccccc2C(=O)N1Cc1ccc(/C=C/C(c2cc(Cl)cc(Cl)c2)C(F)(F)F)cc1Cl]

To a stirred solution of 2-(2-chloro-4-vinylbenzyl)isoindoline-1,3-dione (2.0 g, 6.51 mmol) in 1,2-dichlorobenzene (25 mL) were added 1-(1-bromo-2,2,2-trifluoroethyl)-3,5-dichlorobenzene (3.48 g, 11.36 mmol), CuCl (112 mg, 1.13 mmol) and 2,2-bipyridyl (0.35 g). The resultant reaction mixture was degassed with argon for 30 min and then was stirred at 180° C. for 24 h. After the reaction was deemed complete by TLC, the reaction mixture was cooled to ambient temperature and filtered, and the filtrate was concentrated under reduced pressure. The residue was purified by flash chromatography (SiO$_2$, 100-200 mesh; 25-30% EtOAc in n-hexane) to afford the title compound as solid (1.3 g, 50%): mp 141-143° C.; $^1$H NMR (400 MHz, CDCl$_3$) δ 7.92 (m, 2H), 7.79 (m, 2H), 7.42 (m, 2H), 7.24 (m, 2H), 7.20 (m, 2H), 6.54 (d, J=16.0 Hz, 1H), 6.34 (dd, J=16.0, 8.0 Hz, 1H), 5.00 (s, 2H), 4.10 (m, 1H); ESIMS m/z 524.07 ([M+H]$^+$).

The following compounds were made in accordance with the procedures disclosed in Example 49.

(E)-2-(2-Chloro-4-(4,4-trifluoro-3-(3,4,5-trichloro-phenyl)but-1-en-1-yl)benzyl)isoindoline-1,3-dione (CI27)

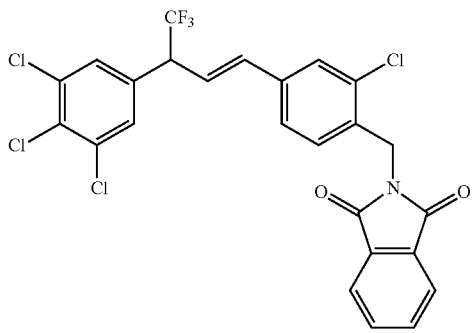

The title compound was isolated as a pale white solid (0.2 g, 55%): mp 128-129° C.; $^1$H NMR (400 MHz, CDCl$_3$) δ 7.92 (m, 2H), 7.79 (m, 2H), 7.42 (m, 3H), 7.22 (m, 2H), 6.52 (d, J=16.0 Hz, 1H), 6.32 (dd, J=16.0, 8.0 Hz, 1H), 5.00 (s, 2H), 4.05 (m, 1H); ESIMS m/z 557.99 ([M+H]$^+$).

(E)-2-(2-Chloro-4-(3-(3,5-dichloro-4-fluorophenyl)-4,4,4-trifluorobut-1-en-1-yl)benzyl)isoindoline-1,3-dione (CI28)

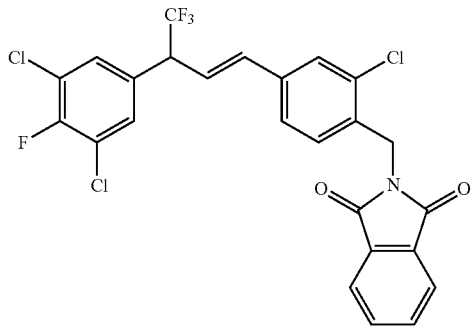

The title compound was isolated as an off white solid (0.2 g, 54%): mp 177-180° C.; $^1$H NMR (400 MHz, CDCl$_3$) δ 7.90 (m, 2H), 7.77 (m, 2H), 7.42 (s, 1H), 7.32 (d, J=8.0 Hz, 2H), 7.21 (m, 2H), 6.52 (d, J=16.0 Hz, 1H), 6.32 (dd, J=16.0, 8.0 Hz, 1H), 5.00 (s, 2H), 4.05 (m, 1H); ESIMS m/z 540.08 ([M−H]$^−$); IR (thin film) 1716 cm$^{−1}$.

(E)-2-(2-Chloro-4-(3-(3,4-dichlorophenyl)-4,4,4-trifluorobut-1-en-1-yl)benzyl)isoindoline-1,3-dione (CI29)

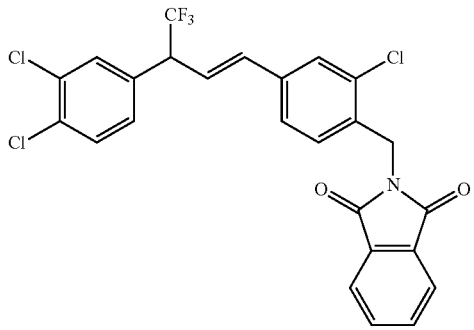 [SMILES: O=C1c2ccccc2C(=O)N1Cc1ccc(/C=C/C(c2ccc(Cl)c(Cl)c2)C(F)(F)F)cc1Cl]

The title compound was isolated as an off-white solid (0.2 g, 59%): $^1$H NMR (400 MHz, CDCl$_3$) δ 7.89 (m, 2H), 7.76 (m, 2H), 7.47 (m, 3H), 7.21 (m, 3H), 6.50 (d, J=16.0 Hz, 1H), 6.32 (dd, J=16.0, 7.6 Hz, 1H), 4.97 (s, 2H), 4.11 (m, 1H); ESIMS m/z 522.27 ([M−H]$^−$); IR (thin film) 3064, 1717, 1111, 715 cm$^{−1}$.

(E)-2-(4-(3-(3,5-Dichlorophenyl)-4,4,4-trifluorobut-1-en-1-yl)-2-(trifluoromethyl)-benzyl)isoindoline-1,3-dione (CI30)

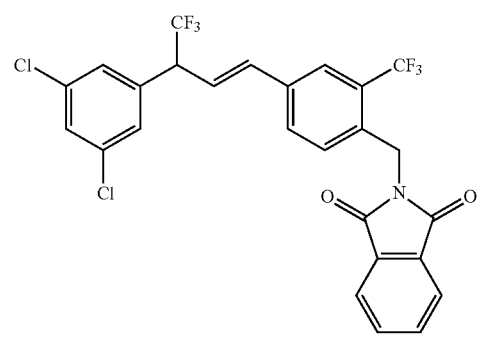 [SMILES: O=C1c2ccccc2C(=O)N1Cc1ccc(/C=C/C(c2cc(Cl)cc(Cl)c2)C(F)(F)F)cc1C(F)(F)F]

The title compound was isolated as an off-white solid (0.2 g, 54%): mp 141-142° C.; $^1$H NMR (400 MHz, CDCl$_3$) 7.94 (m, 2H), 7.80 (m, 2H), 7.69 (s, 1H), 7.44 (m, 1H), 7.38 (m, 1H), 7.24 (m, 2H), 7.19 (m, 1H), 6.60 (d, J=16.0 Hz, 1H), 6.39 (dd, J=16.0, 7.6 Hz, 1H), 5.10 (s, 2H), 4.11 (m, 1H); ESIMS m/z 556.00 ([M−H]$^−$).

(E)-2-(4-(4,4,4-Trifluoro-3-(3,4,5-trichlorophenyl)but-1-en-1-yl)-2-(trifluoromethyl)-benzyl)isoindoline-1,3-dione (CI31)

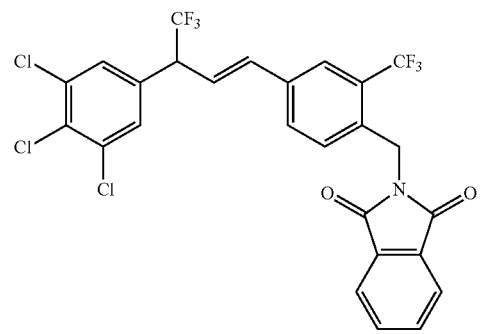

The title compound was isolated as an off-white solid (0.2 g, 56%): mp 130-132° C.; $^1$H NMR (400 MHz, CDCl$_3$) δ 7.94 (m, 2H), 7.80 (m, 2H), 7.69 (s, 1H), 7.44 (m, 3H), 7.19 (m, 1H), 6.61 (d, J=16.0 Hz, 1H), 6.38 (dd, J=16.0, 7.6 Hz, 1H), 5.10 (s, 2H), 4.12 (m, 1H); ESIMS m/z 589.57 ([M−2H]$^−$).

(E)-2-(2-Bromo-4-(4,4,4-trifluoro-3-(3,4,5-trichlorophenyl)but-1-en-1-yl)benzyl)-isoindoline-1,3-dione (CI32)

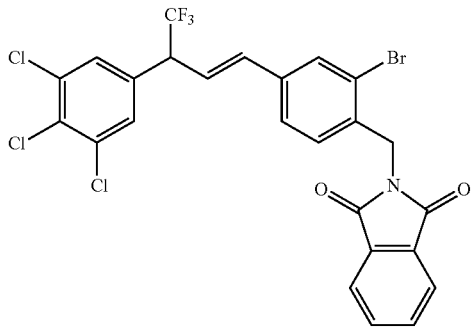 [SMILES: O=C1c2ccccc2C(=O)N1Cc1ccc(/C=C/C(c2cc(Cl)c(Cl)c(Cl)c2)C(F)(F)F)cc1Br]

The title compound was isolated as a pale yellow solid (0.2 g, 55%): mp 160-162° C.; ¹H NMR (400 MHz, CDCl₃) δ 7.92 (m, 2H), 7.80 (m, 2H), 7.62 (s, 1H), 7.39 (s, 2H), 7.24 (m, 1H), 7.16 (m, 1H), 6.52 (d, J=16.0 Hz, 1H), 6.32 (dd, J=16.0, 8.0 Hz, 1H), 4.98 (s, 2H), 4.12 (m, 1H); ESIMS m/z 599.78 ([M−H]⁻).

(E)-2-(2-Fluoro-4-(4,4,4-trifluoro-3-(3,4,5-trichlorophenyl)but-1-en-1-yl)benzyl)-isoindoline-1,3-dione (CI33)

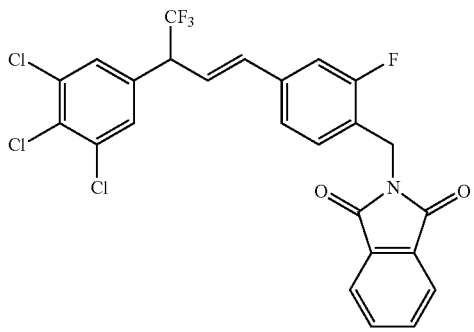 [SMILES: O=C1c2ccccc2C(=O)N1Cc1ccc(/C=C/C(c2cc(Cl)c(Cl)c(Cl)c2)C(F)(F)F)cc1F]

The title compound was isolated as an off-white solid (0.2 g, 55%): mp 72-74° C.; ¹H NMR (400 MHz, CDCl₃) δ 7.88 (m, 2H), 7.74 (m, 2H), 7.38 (s, 2H), 7.34 (m, 1H), 7.18 (m, 2H), 6.54 (d, J=16.0 Hz, 1H), 6.32 (dd, J=16.0, 8.0 Hz, 1H), 4.91 (s, 2H), 4.08 (m, 1H); ESIMS m/z 539.89 ([M−H]⁻); IR (thin film) 1773 cm⁻¹.

Prophetically, compounds CI34-CI41 (Table 1) could be made in accordance with the procedures disclosed in Example 49.

Example 50

Preparation of (E)-(2-Chloro-4-(3-(3,5-dichlorophenyl)-4,4,4-trifluorobut-1-en-1-yl)phenyl)methanamine (CI42)

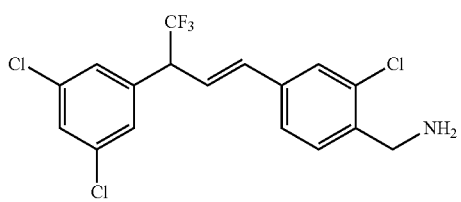

To a stirred solution of (E)-2-(2-chloro-4-(3-(3,5-dichlorophenyl)-4,4,4-trifluorobut-1-en-1-yl)benzyl)isoindoline-1,3-dione (0.4 g, 0.76 mmol) in EtOH was added hydrazine hydrate (0.38 g, 7.6 mmol), and the resultant reaction mixture was heated at 80° C. for 2 h. The reaction mixture was filtered, and the filtrate was concentrated. The residue was dissolved in CH₂Cl₂, washed with brine, dried over Na₂SO₄, and concentrated under reduced pressure to afford the title compound as a gummy liquid (0.3 g), which was carried on to the next step without further purification.

The following compounds were made in accordance with the procedures disclosed in Example 50.

(E)-(2-Chloro-4-(4,4,4-trifluoro-3-(3,4,5-trichlorophenyl)but-1-en-1-yl)phenyl)-methanamine (CI43)

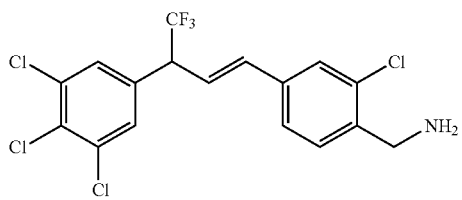 [SMILES: NCc1ccc(/C=C/C(c2cc(Cl)c(Cl)c(Cl)c2)C(F)(F)F)cc1Cl]

The product obtained in this reaction was carried on to the next step without further purification.

(E)-(2-Chloro-4-(3-(3,4-dichlorophenyl)-4,4,4-trifluorobut-1-en-1-yl)phenyl)-methanamine (CI44)

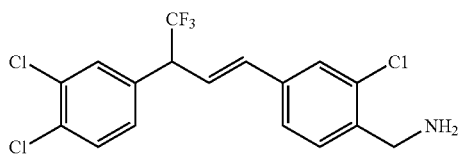

The product obtained in this reaction was carried on to the next step without further purification: ¹H NMR (400 MHz, CDCl₃) δ 7.48 (d, J=8.4 Hz, 2H), 7.39 (m, 2H), 7.23 (m, 2H), 6.52 (d, J=16.0 Hz, 1H), 6.38 (dd, J=16.0, 7.6 Hz, 1H), 4.12 (m, 1H), 3.90 (s, 2H); ESIMS m/z 391.90 ([M−H]⁻); IR (thin film) 3370, 3280, 1111, 817 cm⁻¹.

(E)-(4-(4,4,4-Trifluoro-3-(3,4,5-trichlorophenyl)but-1-en-1-yl)-2-(trifluoromethyl)-phenyl)methanamine (CI45)

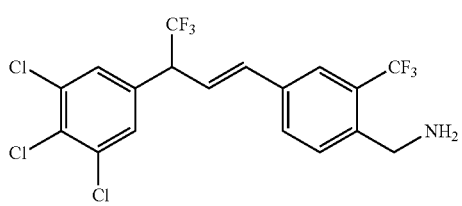 [SMILES: NCc1ccc(/C=C/C(c2cc(Cl)c(Cl)c(Cl)c2)C(F)(F)F)cc1C(F)(F)F]

The title compound was isolated as a gummy material. The product obtained in this reaction was carried on to the next step without further purification.

(E)-(2-Bromo-4-(3-(3,5-dichlorophenyl)-4,4,4-trifluorobut-1-en-1-yl)phenyl)-methanamine (CI46)

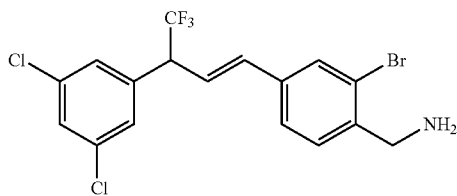 [SMILES: NCc1ccc(/C=C/C(c2cc(Cl)cc(Cl)c2)C(F)(F)F)cc1Br]

The title compound was isolated as a gummy material: The product obtained in this reaction was carried on to the next step without further purification.

(E)-(2-Bromo-4-(4,4,4-trifluoro-3-(3,4,5-trichlorophenyl)but-1-en-1-yl)phenyl)-methanamine (CI47)

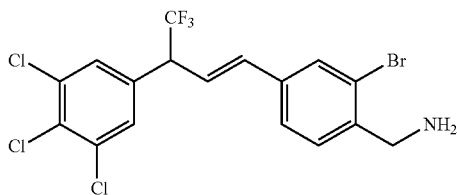 [SMILES: NCc1ccc(/C=C/C(c2cc(Cl)c(Cl)c(Cl)c2)C(F)(F)F)cc1Br]

The title compound was isolated as a gummy material. The product obtained in this reaction was carried on to the next step without further purification.

(E)-(2-Fluoro-4-(4,4,4-trifluoro-3-(3,4,5-trichlorophenyl)but-1-en-1-yl)phenyl)-methanamine (CI48)

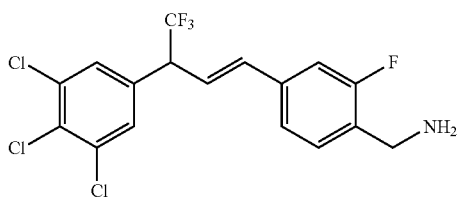 [SMILES: NCc1ccc(/C=C/C(c2cc(Cl)c(Cl)c(Cl)c2)C(F)(F)F)cc1F]

The title compound was isolated as a gummy material: $^1$H NMR (400 MHz, CDCl$_3$) δ 7.40 (s, 2H), 7.33 (t, J=7.6 Hz, 1H), 7.13 (m, 2H), 6.56 (d, J=16.0 Hz, 1H), 6.33 (dd, J=16.0, 7.6 Hz, 1H), 4.08 (m, 1H), 3.90 (s, 2H); ESIMS m/z 413.84 ([M+H]$^+$); IR (thin film) 3368, 3274, 1114, 808 cm$^{-1}$.

Prophetically, compounds CI49-CI57 (Table 1) could be made in accordance with the procedures disclosed in Example 50.

Example 51

Preparation of 3-Chloro-4-((pyridin-2-ylamino)methyl)benzaldehyde (CI58)

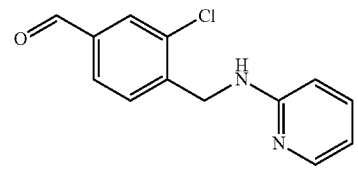 [SMILES: O=Cc1ccc(CNc2ccccn2)c(Cl)c1]

To a stirred solution of 4-(bromomethyl)-3-chlorobenzaldehyde (2 g, 9 mmol) in N,N-dimethylacetamide (DMA; 20 mL) was added K$_2$CO$_3$ (2.36 g, 17.16 mmol) and 2-aminopyridine (0.84 g, 8.58 mmol), and the reaction mixture was stirred at ambient temperature for 4 h. The reaction mixture was diluted with water and extracted with EtOAc. The combined organic layer was washed with brine, dried over Na$_2$SO$_4$, and concentrated under reduced pressure. The residue was purified by flash column chromatography (SiO$_2$, 100-200 mesh; 20% EtOAc in n-Hexane) to afford the title compound as off-white solid (1.05 g, 50%): mp 122-123° C.; $^1$H NMR (400 MHz, CDCl$_3$) δ 9.94 (s, 1H), 8.11 (s, 1H), 7.88 (s, 1H), 7.72 (d, J=4.8 Hz, 1H), 7.62 (d, J=5.7 Hz, 1H), 7.4 (m, 1H), 6.64 (d, J=3.9 Hz, 1H), 6.38 (d, J=6.3 Hz, 1H), 5.04 (br s, 1H), 4.71 (s, 2H); ESIMS m/z 246.97 ([M+H]$^+$).

Example 52

Preparation of N-(2-Chloro-4-vinylbenzyl)pyridin-2-amine (CI59)

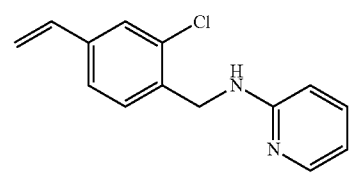 [SMILES: C=Cc1ccc(CNc2ccccn2)c(Cl)c1]

To a stirred solution of 3-chloro-4-((pyridin-2-ylamino)methyl)benzaldehyde (1 g, 4. mmol) in 1,4-dioxane (20 mL) were added K$_2$CO$_3$ (0.84 g, 6.09 mmol) and methyl triphenyl phosphonium bromide (2.17 g, 6.09 mmol) at ambient temperature. Then the resultant reaction mixture was heated at 100° C. for 18 h. After the reaction was deemed complete by TLC, the reaction mixture was cooled to ambient temperature and filtered, and the obtained filtrate was concentrated under reduced pressure. The residue was purified by flash chromatography (SiO$_2$, 100-200 mesh; 10% EtOAc in n-Hexane) to afford the title compound as a white solid (0.5 g, 50%): mp 119-121° C.; $^1$H NMR (400 MHz, CDCl$_3$) δ 8.12 (s, 1H), 7.42-7.40 (m, 3H), 7.26 (s, 1H), 6.66 (m, 2H), 6.36 (d, J=6.3 Hz, 1H), 5.75 (d, J=13.2 Hz, 1H), 4.92 (br s, 1H), 4.60 (s, 2H); ESIMS m/z 245.05 ([M+H]$^+$).

Example 53

Preparation of Ethyl 2-amino-2-(5-bromo-3-chloro-pyridin-2-yl)acetate (CI60)

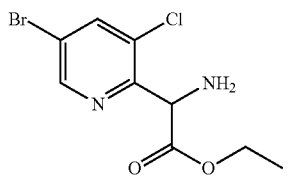

Ethyl 2-(diphenylmethyleneamino)acetate (10.2 g, 38.2 mmol) was added to sodium hydride (NaH; 3.18 g, 133.52 mmol) in DMF (50 mL) at 0° C., and the mixture was stirred for 30 min. To this was added 5-bromo-2,3-dichloropyridine (12.9 g, 57.23 mmol), and the reaction mixture was stirred for 3 h at ambient temperature. The reaction mixture was quenched with 2 N HCl solution and then stirred for 4 h at ambient temperature. The mixture was extracted with EtOAc. The combined EtOAc layer was washed with brine, dried over anhydrous $Na_2SO_4$, and concentrated under reduced pressure. Purification by flash column chromatography (20-30% EtOAc in hexane) afforded the title compound as a liquid (1.3 g, 20%): $^1$H NMR (400 MHz, $CDCl_3$) δ 8.52 (s, 1H), 7.89 (s, 1H), 5.09 (s1H), 4.23 (m, 2H), 2.27 (br s, 2H), 1.26 (m, 3H); ESIMS m/z 293.05 ([M+H]$^+$); IR (thin film) 3381, 3306, 1742, 759, 523 cm$^{-1}$.

Example 54

Preparation of (5-Bromo-3-chloropyridin-2-yl)methanamine hydrochloride (CI61)

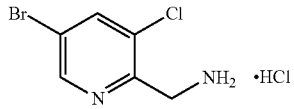

A stirred solution of ethyl 2-amino-2-(5-bromo-3-chloropyridin-2-yl)acetate (0.5 g, 1.7 mmol) in 3 N HCl (25 mL) was heated at reflux for 4 h. The reaction mixture was washed with $Et_2O$ and water. The combined ether layer was concentrated under reduced pressure to afford the title compound as an off-white solid (400 mg, 65%): $^1$H NMR (400 MHz, $CDCl_3$) δ 8.78 (s, 1H), 8.70 (br s, 2H), 8.45 (s, 1H), 4.56 (m, 2H); ESIMS m/z 221.15 ([M+H]$^+$).

Example 55

Preparation of 2-((5-Bromo-3-chloropyridin-2-yl)methyl)isoindoline-1,3-dione (CI62)

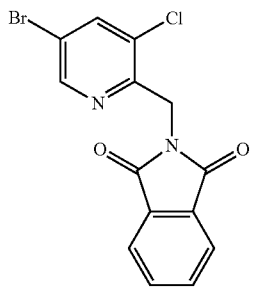 [SMILES: O=C1c2ccccc2C(=O)N1Cc1ncc(Br)cc1Cl]

To a stirred solution of (5-bromo-3-chloropyridin-2-yl)methanamine hydrochloride (0.3 g, 1.4 mmol) in toluene (40 mL) was added TEA (0.41 g, 4.08 mmol) and phthalic anhydride (0.24 g, 1.63 mmol), and the reaction mixture was heated at reflux for 2 h. The reaction mixture was concentrated under reduced pressure, and the residue was diluted with water and extracted with EtOAc. The combined EtOAc layer was washed with brine, dried over anhydrous $Na_2SO_4$, and concentrated under reduced pressure. The residue was purified by column chromatography (20-30% EtOAc in hexane) to afford the title compound as a white solid (0.25 g, 65%): $^1$H NMR (400 MHz, $CDCl_3$) δ 8.78 (s, 1H), 8.45 (s, 1H), 7.88 (m, 2H), 7.74 (m, 2H), 4.56 (m, 2H); ESIMS m/z 349 ([M−H]$^−$); IR (thin film) 3307, 1665, 1114, 813 cm$^{-1}$.

Example 56

Preparation of 2-((3-Chloro-5-vinylpyridin-2-yl)methyl)isoindoline-1,3-dione (CI63)

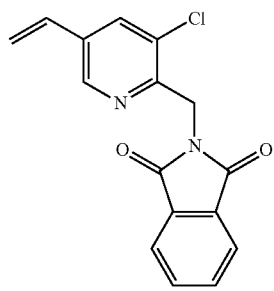 [SMILES: C=Cc1cnc(CN2C(=O)c3ccccc3C2=O)c(Cl)c1]

To a stirred solution of 2-((5-bromo-3-chloropyridin-2-yl)methyl)isoindoline-1,3-dione (0.23 g, 0.65 mmol) in toluene (10 mL) were added $Pd(PPh_3)_4$ (3.7 mg, 0.003 mmol), $K_2CO_3$ (0.269 g, 1.95 mmol) and vinyl boronic anhydride pyridine complex (0.78 g, 3.28 mmol), and the reaction mixture was heated at reflux for 16 h. The reaction mixture was filtered, and the filtrate was washed with water and brine, dried over anhydrous $Na_2SO_4$, and concentrated under reduced pressure. Purification by flash column chromatography (20-30% EtOAc in hexane) afforded the title compound as an off-white solid (0.2 g, 65%): $^1$H NMR (400 MHz, $CDCl_3$) δ 8.30 (s, 1H), 7.91 (m, 2H), 7.77 (m, 3H), 7.72 (m, 1H), 6.63 (m, 1H), 5.79 (d, J=16.0 Hz, 1H), 5.39 (d, J=16.0 Hz, 1H), 5.12 (s, 2H); ESIMS m/z 299.20 ([M+H]$^+$).

Example 57

Preparation of (E)-2-((3-Chloro-5-(4,4,4-trifluoro-3-(3,4,5-trichloro-phenyl)but-1-en-1-yl)pyridin-2-yl)methyl)isoindoline-1,3-dione (CI64)

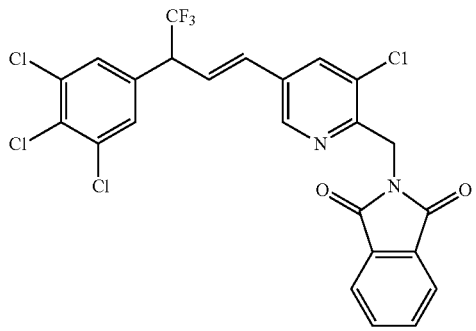

To a stirred solution of 2-((3-chloro-5-vinylpyridin-2-yl)methyl)isoindoline-1,3-dione (0.35 g, 1.17 mmol) in 1,2-dichlorobenzene (10 mL) were added 5-(1-bromo-2,2,2-trifluoroethyl)-1,2,3-trichlorobenzene (0.8 g, 2.3 mmol), CuCl (23 mg, 0.12 mmol), 2,2-bipyridyl (0.073 g, 0.234 mmol), and the reaction mixture was heated at 180° C. for 16 h. The reaction mixture was concentrated under reduced pressure and purified by column chromatography (20-30% EtOAc in hexane) to afford the title compound as a liquid (0.4 g, 50%): mp 79-82° C.; $^1$H NMR (400 MHz, CDCl$_3$) δ 8.27 (s, 1H), 7.91 (m, 2H), 7.77 (m, 3H), 7.36 (s, 2H), 6.51 (d, J=15.6 Hz, 1H), 6.32 (dd, J=15.6, 8.0 Hz, 1H), 5.30 (s, 2H), 4.13 (m, 1H); ESIMS m/z 559 ([M+H]$^+$).

Example 58

Preparation of (E)-(3-Chloro-5-(4,4,4-trifluoro-3-(3,4,5-trichlorophenyl)but-1-en-1-yl)pyridin-2-yl)methanamine (CI65)

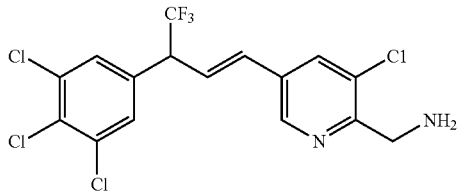

To a stirred solution of (E)-2-((3-chloro-5-(4,4,4-trifluoro-3-(3,4,5-trichlorophenyl)but-1-en-1-yl)pyridin-2-yl)methyl)isoindoline-1,3-dione (200 mg, 0.358 mmol) in EtOH (5 mL) was added hydrazine hydrate (89.6 mg, 1.79 mmol), and the reaction mixture was heated at reflux for 2 h. The reaction mixture was concentrated under reduced pressure, and the residue was dissolved in CH$_2$Cl$_2$. The organic layer was washed with water and brine, dried over anhydrous Na$_2$SO$_4$, and concentrated under reduced pressure to afford the title compound as a solid (100 mg). The product obtained in this reaction was carried on to the next step without further purification.

Example 59

Preparation of 4-(Bromomethyl)-1-naphthonitrile (CI66)

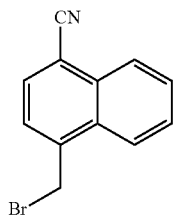

To a stirred solution of 4-methyl-1-naphthonitrile (5 g, 30 mmol) in CCl$_4$ (50 mL) under argon atmosphere was added NBS (6.06 g, 34.09 mmol), and the reaction mixture was degassed for 30 min. AIBN (0.3 g, 2.1 mmol) was added, and the resultant reaction mixture was heated at reflux for 4 h. The reaction mixture was cooled to ambient temperature, diluted with water and extracted with CH$_2$Cl$_2$ (3×100 mL). The combined CH$_2$Cl$_2$ layer was washed with brine, dried over Na$_2$SO$_4$, and concentrated under reduced pressure. The residue was purified by flash column chromatography (SiO$_2$, 100-200 mesh; 5% EtOAc in n-Hexane) to afford the title compound as a white solid (3.8 g, 52%): mp 131-133° C.; $^1$H NMR (400 MHz, CDCl$_3$) δ 8.33 (m, 1H), 8.24 (m, 1H), 7.88 (d, J=8.0 Hz, 1H), 7.78 (m, 2H), 7.62 (d, J=8.0 Hz, 1H), 4.95 (s, 2H); ESIMS m/z 245.92 ([M+H]$^+$); IR (thin film) 2217 cm$^{-1}$.

Example 60

Preparation of 4-(Bromomethyl)-1-naphthaldehyde (CI67)

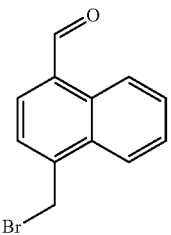 [SMILES: O=Cc1ccc(CBr)c2ccccc12]

To a stirred solution of 4-(bromomethyl)-1-naphthonitrile (8 g, 33 mmol) in toluene (100 mL) at 0° C. was added dropwise DIBAL-H (1.0 M solution in toluene; 43 mL), and the reaction mixture was stirred at 0° C. for 1 h. 3 N HCl in water (50 mL) was added to the mixture until it became a white slurry and then additional 1 N HCl (20 mL) was added. The organic layer was collected and the aqueous layer was extracted with EtOAc (3×100 mL). The combined organic layer was dried over Na$_2$SO$_4$ and concentrated under reduced pressure. Purification by flash column chromatography (SiO$_2$, 100-200 mesh; 5% EtOAc in petroleum ether) afforded the title compound as a white solid (7 g, 88%): mp 115-116° C.; $^1$H NMR (400 MHz, CDCl$_3$) δ 10.41 (s, 1H), 9.35 (m, 1H), 8.22 (m, 1H), 7.90 (d, J=8.0 Hz, 1H), 7.75 (m, 3H), 4.95 (s, 2H); ESIMS m/z 248.88 ([M+H]$^+$).

Example 61

Preparation of 4-((1,3-Dioxoisoindolin-2-yl)methyl)-1-naphthaldehyde (CI68)

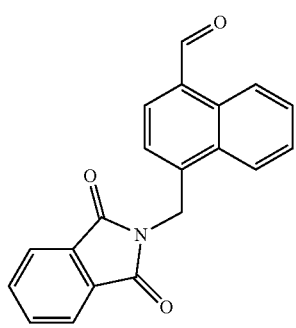 [SMILES: O=Cc1ccc(CN2C(=O)c3ccccc3C2=O)c2ccccc12]

To a stirred solution of 4-(bromomethyl)-1-naphthaldehyde (7 g, 28 mmol) in DMF (100 mL) was added potassium phthalimide (7.3 g, 39.5 mmol), and the mixture was heated at 85° C. for 2 h. The reaction mixture was cooled to ambient temperature and diluted with water (100 mL). The obtained solid was separated by filtration and dried under vacuum to afford the title compound as a white solid (8.8 g, 98%): mp 190-192° C.; $^1$H NMR (400 MHz, CDCl$_3$) δ 10.39 (s, 1H), 9.25 (m, 1H), 8.41 (m, 1H), 8.10 (d, J=8.0 Hz, 1H), 7.95 (m, 4H), 7.80 (m, 4H), 7.61 (m, 4H), 5.39 (s, 2H); ESIMS m/z 316.09 ([M+H]$^+$); IR (thin film) 1708 cm$^{-1}$.

Example 62

Preparation of 2-((4-Vinylnaphthalen-1-yl)methyl) isoindoline-1,3-dione (CI69)

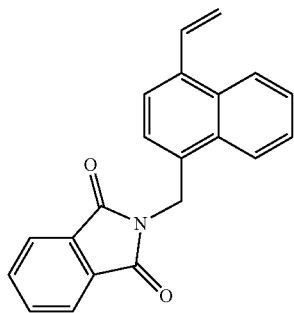 [SMILES: C=Cc1ccc(CN2C(=O)c3ccccc3C2=O)c2ccccc12]

To a stirred solution of 4-((1,3-dioxoisoindolin-2-yl) methyl)-1-naphthaldehyde (9 g, 28.5 mmol) in 1,4-dioxane (100 mL) were added K$_2$CO$_3$ (6 g, 42.8 mmol) and methyl triphenyl phosphonium bromide (15.3 g, 35.7 mmol) at ambient temperature. The reaction mixture was heated at 100° C. for 14 h and then was cooled to ambient temperature. The reaction mixture was filtered, and the obtained filtrate was concentrated under reduced pressure. Purification by flash chromatography (SiO$_2$, 100-200 mesh; 20% EtOAc in petroleum ether) afforded the title compound as a white solid (6 g, 67%): mp 146-147° C.; $^1$H NMR (400 MHz, CDCl$_3$) δ 8.35 (m, 2H), 7.95 (m, 4H), 7.65 (m, 4H), 7.39 (m, 1H), 5.81 (m, 1H), 5.45 (m, 1H), 5.21 (s, 2H); ESIMS m/z 314.13 ([M+H]$^+$).

Example 63

Preparation of (E)-2-((4-(4,4,4-Trifluoro-3-(3,4,5-trichlorophenyl)but-1-en-1-yl)naphthalen-1-yl) methyl)isoindoline-1,3-dione (CI70)

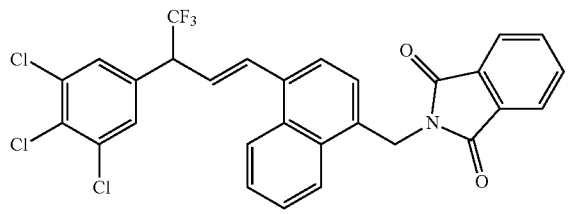 [SMILES: O=C1c2ccccc2C(=O)N1Cc1ccc(/C=C/C(c2cc(Cl)c(Cl)c(Cl)c2)C(F)(F)F)c2ccccc12]

To a stirred solution of 2-((4-vinylnaphthalen-1-yl) methyl)isoindoline-1,3-dione (1.5 g, 4.79 mmol) in 1,2-dichlorobenzene (15 mL) were added 1-(1-bromo-2,2,2-trifluoroethyl)-3,4,5-trichlorobenzene (3.2 g, 9.5 mmol), CuCl (24 mg, 0.24 mmol) and 2,2-bipyridyl (0.149 g, 0.95 mmol), and the resultant reaction mixture was degassed with argon for 30 min and then stirred at 180° C. for 14 h. After the reaction was deemed complete by TLC, the reaction mixture was cooled to ambient temperature and filtered, and the filtrate was concentrated under reduced pressure. Purification by flash chromatography (SiO$_2$, 100-200 mesh; 25-30% EtOAc in petroleum ether) afforded the title compound as an off-white solid (1.5 g, 56%): mp 158-160° C.; $^1$H NMR (400 MHz, CDCl$_3$) δ 8.40 (m, 1H), 7.89 (m, 2H), 7.74 (m, 2H), 7.64 (m, 2H), 7.58 (m, 2H), 7.46 (s, 2H), 7.36 (m, 2H), 6.31 (m, 1H), 5.30 (s, 2H), 4.21 (m, 1H); ESIMS m/z 572.08 ([M−H]$^-$).

Example 64

Preparation of (E)-(4-(4,4,4-Trifluoro-3-(3,4,5-trichlorophenyl)but-1-en-1-yl)naphthalen-1-yl)methanamine (CI71)

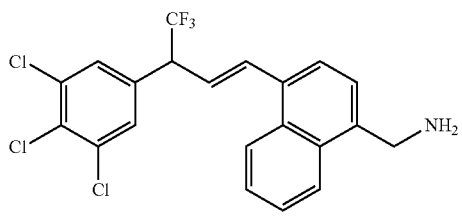 [SMILES: NCc1ccc(/C=C/C(c2cc(Cl)c(Cl)c(Cl)c2)C(F)(F)F)c2ccccc12]

To a stirred solution of (E)-2-((4-(4,4,4-trifluoro-3-(3,4,5-trichlorophenyl)but-1-en-1-yl)naphthalen-1-yl)methyl) isoindoline-1,3-dione (0.4 g, 0.7 mmol) in EtOH was added hydrazine hydrate (0.18 g, 3.5 mmol), and the resultant reaction mixture was heated at 80° C. for 2 h. The reaction mixture was filtered, and the filtrate was concentrated. The residue was dissolved in CH$_2$Cl$_2$, and the solution was washed with brine, dried over Na$_2$SO$_4$, and concentrated under reduced pressure. The title compound was isolated as a gummy liquid (150 mg, 50%). The product obtained in this reaction was carried on to the next step without further purification.

Example 65

Preparation of 2-((4-Bromophenyl)amino)isoindoline-1,3-dione (CI72)

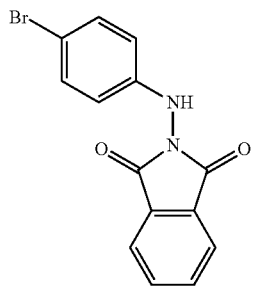 [SMILES: O=C1c2ccccc2C(=O)N1Nc1ccc(Br)cc1]

To a stirred solution of (4-bromophenyl)hydrazine hydrochloride (0.5 g, 2.2 mmol) in AcOH (8 mL) was added phthalic anhydride (0.398 g, 2.690 mmol), and the reaction mixture was stirred at 130° C. for 1 h under a nitrogen atmosphere. The reaction mixture was quenched with satd aqueous NaHCO₃ solution and filtered to give a solid. Purification by column chromatography (SiO₂, 0-10% EtOAc in petroleum ether) afforded the title compound as a solid (60 mg, 84%): mp 205-206° C.; ¹H NMR (400 MHz, CDCl₃) δ 8.71 (s, 1H), 7.99 (m, 4H), 7.32 (d, J=8.8 Hz, 2H), 6.79 (d, J=8.8 Hz, 2H); ESIMS m/z 314.95 ([M−H]⁻).

Example 66

Preparation of 2-((4-Vinylphenyl)amino)isoindoline-1,3-dione (CI73)

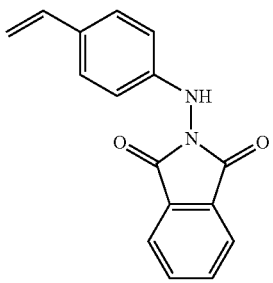 [SMILES: C=Cc1ccc(NN2C(=O)c3ccccc3C2=O)cc1]

To a solution of 2-(4-bromophenylamino)isoindoline-1,3-dione (2 g, 6 mmol) in 1,2-dimethoxyethane (20 mL) and water (4 mL) were added vinyl boronic anhydride pyridine complex (4.57 g, 18.98 mmol) and K₂CO₃ (1.3 g, 9.5 mmol) followed by Pd(PPh₃)₄ (0.219 g, 0.189 mmol). The resultant reaction mixture was heated at 150° C. in a microwave for 30 min and then was concentrated under reduced pressure. Purification by column chromatography (SiO₂, 15% EtOAc in petroleum ether) afforded the title compound as a solid (200 mg, 13%): mp 174-176° C.; ¹H NMR (400 MHz, CDCl₃) δ 8.65 (s, 1H), 7.94 (m, 4H), 7.29 (d, J=8.4 Hz, 2H), 6.72 (d, J=8.4 Hz, 2H), 6.61 (m, 1H), 5.61 (d, J=17.6 Hz, 1H), 5.05 (d, J=11.2 Hz, 1H); ESIMS m/z 263.18 ([M−H]⁻).

Example 67

Preparation of (E)-2-((4-(4,4,4-Trifluoro-3-(3,4,5-trichlorophenyl)but-1-en-1-yl)phenyl)amino)isoindoline-1,3-dione (CI74)

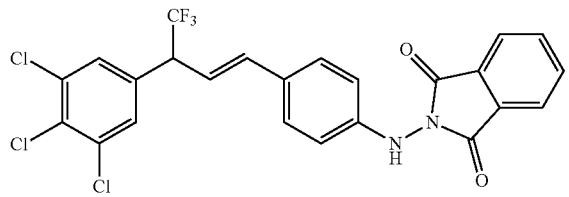 [SMILES: O=C1c2ccccc2C(=O)N1Nc1ccc(/C=C/C(c2cc(Cl)c(Cl)c(Cl)c2)C(F)(F)F)cc1]

To a stirred solution of 2-(4-vinylphenylamino)isoindoline-1,3-dione (0.3 g, 1.1 mmol) in 1,2-dichlorobenzene (5 mL) were added CuCl (0.022 g, 0.273 mmol), 2,2-bipyridyl (0.07 g, 0.46 mmol) and 5-(1-bromo-2,2,2-trifluoroethyl)-1,2,3-trichlorobenzene (0.77 g, 2.27 mmol). The reaction mixture was degassed with argon for 30 min and was heated at 180° C. for 2 h. The reaction mixture was then concentrated under reduced pressure, and the residue was purified by column chromatography (SiO₂, 0-30% EtOAc in petroleum ether) to afford the title compound as a solid (450 mg, 75%): mp 187-189° C.; ¹H NMR (400 MHz, CDCl₃) δ 8.75 (s, 1H), 7.96 (m, 4H), 7.82 (s, 2H), 7.37 (d, J=8.8 Hz, 1H), 6.73 (d, J=8.4 Hz, 2H), 6.61 (m, 2H), 6.58 (m, 1H), 4.59 (m, 1H); ESIMS m/z 523.05 ([M−H]⁻).

Example 68

Preparation of (E)-(4-(4,4,4-Trifluoro-3-(3,4,5-trichlorophenyl)but-1-en-1-yl)phenyl)hydrazine (CI75)

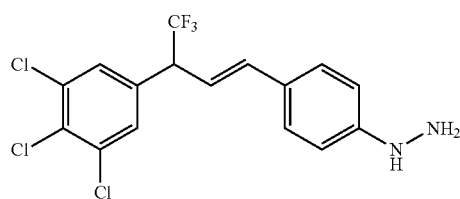

To a stirred solution of (E)-2-(4-(4,4,4-trifluoro-3-(3,4,5-trichlorophenyl)but-1-enyl)phenylamino)isoindoline-1,3-dione (0.16 g, 0.31 mmol) in EtOH (5 mL), was added hydrazine hydrate (0.076 g, 1.52 mmol), and the reaction mixture was heated at 85° C. for 1 h. The reaction mixture was cooled to ambient temperature and filtered, and the filtrate was concentrated under reduced pressure to afford the title compound as a solid (0.08 g, 66%) which was carried on to the next step without further purification.

Example 69

Preparation of 2-(4-Vinylphenoxy)isoindoline-1,3-dione (CI76)

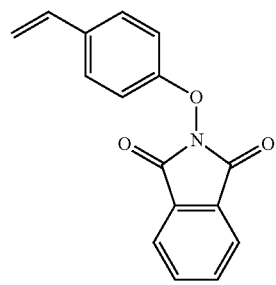 [SMILES: C=Cc1ccc(ON2C(=O)c3ccccc3C2=O)cc1]

To a stirred solution of 4-vinylphenylboronic acid (2 g, 13 mmol), 2-hydroxyisoindoline-1,3-dione (3.63 g, 24.53 mmol), and CuCl (1.214 g 12.26 mmol) in 1,2-dichloroethane (50 mL) was added pyridine (1.065 g, 13.48 mmol), and the resultant reaction mixture was stirred at ambient temperature for 48 h. The reaction mixture was diluted with water and extracted with CHCl₃. The combined CHCl₃ layer was washed with brine, dried over Na₂SO₄ and concentrated under reduced pressure. Purification by flash column chromatography (SiO₂; 20% EtOAc in petroleum ether) afforded the title compound as a white solid (2 g, 63%): mp 129-131° C.; ¹H NMR (400 MHz, CDCl₃) δ 7.93 (d, J=2.0 Hz, 2H), 7.82 (d, J=3.2 Hz, 2H), 7.38 (d, J=2.0 Hz, 2H), 7.14 (d, J=2.0

Hz, 2H), 6.70 (m, 1H), 5.83 (d, J=16.0 Hz, 1H), 5.22 (d, J=10.8 Hz, 1H); ESIMS m/z 266.12 ([M+H]+).

Example 70

Preparation of (E)-2-(4-(4,4,4-Trifluoro-3-(3,4,5-trichlorophenyl)but-1-en-1-yl)phenoxy)isoindoline-1,3-dione (CI771

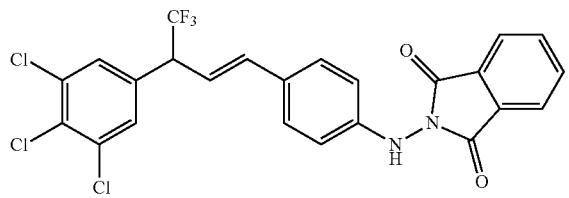 [SMILES: O=C1c2ccccc2C(=O)N1Nc1ccc(/C=C/C(c2cc(Cl)c(Cl)c(Cl)c2)C(F)(F)F)cc1]

To a stirred solution of 2-(4-vinylphenoxy)isoindoline-1,3-dione (0.3 g, 1.1 mmol) in 1,2-dichlorobenzene (10 mL) was added 1-(1-bromoethyl)-3,4,5-trichlorobenzene (769 mg, 2.26 mmol), CuCl (22 mg, 0.22 mmol) and 2,2-bipyridyl (35 mg, 0.44 mmol), and the resultant reaction mixture was degassed with argon for 30 min and heated to 180° C. for 24 h. The reaction mixture was cooled to ambient temperature and filtered, and the filtrate was concentrated under reduced pressure. The crude material was purified by column chromatography (SiO$_2$, 100-200 mesh; 20% EtOAc in petroleum ether) to afford the title compound as a solid (0.29 g, 50%): $^1$H NMR (400 MHz, CDCl$_3$) δ 7.90 (m, 1H), 7.62 (m, 2H), 7.50 (m, 1H), 7.40 (s, 2H), 7.12 (s, 1H), 6.90 (m, 2H), 6.60 (m, 2H), 6.20 (m, 1H), 4.08 (m, 1H); ESIMS m/z 524.09 ([M−H]−).

Example 71

Preparation of (E)-O-(4-(4,4,4-Trifluoro-3-(3,4,5-trichlorophenyl)but-1-en-1-yl)phenyl)hydroxylamine (CI78)

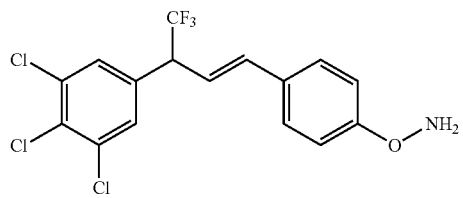 [SMILES: NOc1ccc(/C=C/C(c2cc(Cl)c(Cl)c(Cl)c2)C(F)(F)F)cc1]

To a stirred solution of (E)-2-(4-(4,4,4-trifluoro-3-(3,4,5-trichlorophenyl)but-1-enyl)phenoxy)isoindoline-1,3-dione (0.2 g, 0.4 mmol) in EtOH was added hydrazine hydrate (0.1 g, 1.9 mmol), and the resultant reaction mixture was heated at 90° C. for 1 h. The reaction mixture was filtered, and the filtrate was concentrated. The residue was dissolved in CH$_2$Cl$_2$, washed with brine, dried over Na$_2$SO$_4$ and concentrated under reduced pressure to afford the crude title compound as a gummy liquid (0.08 g, 53%): $^1$H NMR (400 MHz, CDCl$_3$) δ 7.40 (s, 2H), 6.98 (s, 1H), 6.82 (s, 2H), 6.48 (m, 1H), 6.20 (m, 1H), 5.02 (s, 1H), 4.08 (m, 1H); ESIMS m/z 394.94 ([M−H]−).

Example 72

Preparation of (E)-N-(4-(3-(3,5-Dichlorophenyl)-4,4,4-trifluorobut-1-enyl)benzyl)acetamide (CC1)

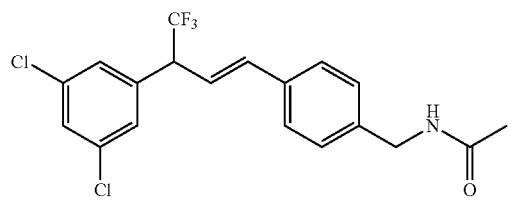 [SMILES: CC(=O)NCc1ccc(/C=C/C(c2cc(Cl)cc(Cl)c2)C(F)(F)F)cc1]

To a stirred solution of (E)-(2-chloro-4-(3-(3,5-dichlorophenyl)-4,4,4-trifluorobut-1-en-1-yl)phenyl)methanamine (0.3 g, 0.8 mmol) in CH$_2$Cl$_2$ (10 mL) was added acetic anhydride (0.12 mL, 1.14 mmol), and TEA (0.217 mL, 1.52 mmol), and the resultant reaction mixture was stirred at ambient temperature for 6 h. The reaction mixture was diluted with water and extracted with CH$_2$Cl$_2$. The combined CH$_2$Cl$_2$ layer was washed with brine, dried over Na$_2$SO$_4$, and concentrated under reduced pressure. Purification by flash column chromatography (SiO$_2$, 100-200 mesh; 30-50% EtOAc in hexane) afforded the title compound as an off-white solid (0.2 g, 60%) mp 107-109° C.; $^1$H NMR (400 MHz, CDCl$_3$) δ 7.37 (m, 3H), 7.28 (m, 4H), 6.60 (d, J=16.0 Hz, 1H), 6.36 (dd, J=16.0, 8.0 Hz, 1H), 5.75 (br s, 1H), 4.46 (d, J=6 Hz, 2H), 4.01 (m, 1H), 2.11 (s, 3H); ESIMS m/z 402.00 ([M+H]+).

Compounds CC2-CC6 in Table 1 were made in accordance with the procedures disclosed in Example 72. In addition, compound DC56 in Table 1 was made from compound DC55 in accordance with the procedures disclosed in Example 72.

Example 73

Preparation of (E)-N-(2-Chloro-4-(3-(3,5-dichlorophenyl)-4,4,4-trifluorobut-1-en-1-yl)benzyl)acetamide (CC7)

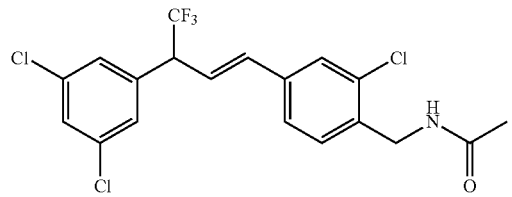 [SMILES: CC(=O)NCc1ccc(/C=C/C(c2cc(Cl)cc(Cl)c2)C(F)(F)F)cc1Cl]

To a stirred solution of (E)-(2-chloro-4-(3-(3,5-dichlorophenyl)-4,4,4-trifluorobut-1-en-1-yl)phenyl)methanamine (0.3 g, 0.8 mmol) in DMF (5 mL) was added 2,2,2-trifluoropropanoic acid (97 mg, 0.76 mmol), HOBt.H$_2$O (174 mg, 1.14 mmol) and EDC.HCl (217 mg, 1.14 mmol) and DIPEA (196 mg, 1.52 mmol), and the resultant reaction mixture was stirred at ambient temperature for 18 h. The reaction mixture was diluted with water and extracted with EtOAc. The combined EtOAc layer was washed with brine, dried over Na$_2$SO$_4$, and concentrated under reduced pressure. Purification by flash column chromatography (SiO$_2$, 100-200 mesh; EtOAc in hexane (30-50% afforded the title compound as an off-white solid (0.2 g, 60%): mp 127-128° C.; $^1$H NMR (400 MHz, CDCl$_3$) δ 7.42 (m, 4H), 7.24 (m, 2H), 6.53 (d, J=16.0 Hz, 1H), 6.36 (dd, J=16.0, 8.0 Hz, 1H), 5.86 (br s, 1H), 4.51 (d, J=6.0 Hz, 2H), 4.05 (m, 1H), 2.02 (s, 3H); ESIMS m/z 436.03 ([M+H]$^+$).

Compounds CC8-CC28 in Table 1 were made in accordance with the procedures disclosed in Example 73.

Example 74

Preparation of (E)-N-(Pyridin-2-ylmethyl)-N-(4-(4,4,4-trifluoro-3-(3,4,5-trichlorophenyl)but-1-enyl)-2-(trifluoromethyl)benzyl)cyclopropanecarboxamide (CC29)

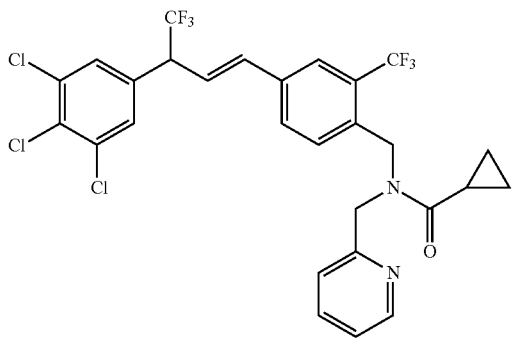 [SMILES: O=C(C1CC1)N(Cc1ccccn1)Cc1ccc(/C=C/C(c2cc(Cl)c(Cl)c(Cl)c2)C(F)(F)F)cc1C(F)(F)F]

Step 1: (E)-1-(Pyridin-2-yl)-N-(4-(4,4,4-trifluoro-3-(3,4,5-trichlorophenyl)but-1-enyl)-2-(trifluoromethyl)benzyl)methanamine (E)-(4-(4,4,4-Trifluoro-3-(3,4,5-trichlorophenyl)but-1-en-1-yl)-2-(trifluoromethyl)phenyl)methanamine (0.46 g, 1 mmol) was dissolved in MeOH (3 mL). To this was added pyridine-2-carbaldehyde (0.107 g, 1 mmol). The reaction mixture was stirred for 1 h. After 1 h, NaBH$_4$ (0.076 g, 2 mmol) was added and left at ambient temperature for 3 h. The reaction mixture was concentrated to give an oily residue. Purification by flash column chromatography (SiO$_2$, 100-200 mesh; 30-50% EtOAc in hexane) afforded the title compound as a pale yellow liquid (0.22 g, 40%): $^1$H NMR (400 MHz, CDCl$_3$) δ 8.58 (d, J=4.8 Hz, 1H), 7.74 (m, 1H), 7.62 (m, 2H), 7.52 (m, 1H), 7.4 (s, 2H), 7.3 (m, 1H), 7.2 (m, 2H), 6.60 (d, J=16.0 Hz, 1H), 6.38 (dd, J=16.0, 8.0 Hz, 1H), 4.10 (m, 1H), 4.02 (s, 2H), 3.96 (s, 2H); ESIMS m/z 552.95 ([M+H]$^+$); IR (thin film) 3338, 1114, 808 cm$^{-1}$.

Step 2: (E)-N-(Pyridin-2-ylmethyl)-N-(4-(4,4,4-trifluoro-3-(3,4,5-trichlorophenyl)but-1-enyl)-2-(trifluoromethyl)benzyl)cyclopropanecarboxamide (E)-1-(Pyridin-2-yl)-N-(4-(4,4,4-trifluoro-3-(3,4,5-trichlorophenyl)but-1-en-1-yl)-2-(trifluoromethyl)benzyl)methanamine (0.27 g, 0.05 mmol) was taken up in CH$_2$Cl$_2$ (3 mL). To this was added TEA (0.14 mL, 0.1 mmol). The reaction mixture was stirred for 10 min After 10 min, the reaction mixture was cooled to 0° C., and cyclopropylcarbonyl chloride (0.08 mL, 0.075 mmol) was added. The reaction mixture was stirred at ambient temperature for 1 h and then was washed with water and satd aq NaHCO$_3$ solution. The organic layer was dried over anhydrous Na$_2$SO$_4$ and evaporated to obtain pale yellow gummy material (0.15 g, 50%): $^1$H NMR (400 MHz, CDCl$_3$) δ 8.58 (d, J=4.6 Hz, 1H), 7.74 (m, 1H), 7.62 (m, 2H), 7.52 (m, 1H), 7.4 (s, 2H), 7.3 (m, 1H), 7.2 (m, 2H), 6.60 (d, J=16.0 Hz, 1H), 6.38 (dd, J=16.0, 8.0 Hz, 1H), 5.02 (s, 1H), 4.8 (s, 1H), 4.8 (d, J=10 Hz, 2H), 4.10 (m, 1H), 1.8 (m, 1H), 1.2 (m, 2H), 0.6 (m, 2H); ESIMS m/z 620.86 ([M-H]$^-$); IR (thin film) 1645, 1115, 808 cm$^{-1}$.

Example 75

Preparation of (E)-N-(2-Chloro-4-(4,4,4-trifluoro-3-(3,4,5-trichlorophenyl)but-1-en-1-yl)benzyl)-3-(methylsulfonyl)propanamide (CC30)

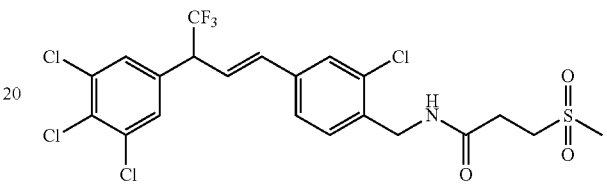

(E)-N-(2-Chloro-4-(4,4,4-trifluoro-3-(3,4,5-trichlorophenyl)but-1-en-1-yl)benzyl)-3-(methylthio)propanamide (0.15 g, 0.28 mmol) was treated with oxone (0.175 g, 0.569 mmol) in 1:1 acetone:water (20 mL) for 4 h at ambient temperature. The acetone was evaporated to obtain a white solid (0.095 g, 60%): mp 101-104° C.; $^1$H NMR (400 MHz, CDCl$_3$) δ 7.41 (m, 4H), 7.24 (m, 1H), 6.53 (d, J=16.0 Hz, 1H), 6.35 (dd, J=16.0, 8.0 Hz, 1H), 6.12 (br s, 1H), 4.53 (m, 2H), 4.10 (m, 1H), 3.42 (m, 2H), 2.91 (s, 3H), 2.78 (m, 2H); ESIMS m/z 559.75 ([M-H]$^-$).

Example 76

Preparation of (E)-1-(2-Chloro-4-(3-(3,5-dichlorophenyl)-4,4,4-trifluorobut-1-en-1-yl)benzyl)-3-ethylurea (CC31)

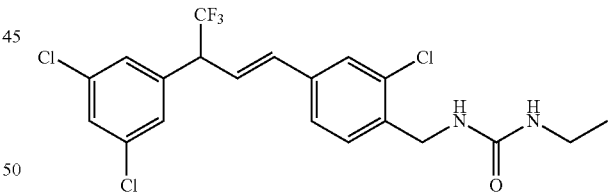

To a stirred solution of (E)-(2-chloro-4-(3-(3,5-dichlorophenyl)-4,4,4-trifluorobut-1-en-1-yl)phenyl)methanamine (0.2 g, 0.5 mmol) in CH$_2$Cl$_2$ (5 mL) at 0° C. were added TEA (0.141 mL, 1 mmol) and ethylisocyanate (0.053 g, 0.75 mmol), and the reaction mixture was stirred for 1 h at 0° C. The reaction mixture was diluted with CH$_2$Cl$_2$. The organic layer was washed with water and brine, dried over Na$_2$SO$_4$, and concentrated under reduced pressure. Purification by column chromatography (SiO$_2$, 100-200 mesh; 30-50% EtOAc in hexane) afforded the title compound as a solid (0.141 g, 60%): mp 177-178° C.; $^1$H NMR (400 MHz, CDCl$_3$) δ 7.58 (m, 2H), 7.41 (m, 3H), 7.24 (m, 1H), 6.53 (d, J=16.0 Hz, 1H), 6.35 (dd, J=16.0, 8.0 Hz, 1H), 4.70 (br s, 1H), 4.43 (s, 2H), 4.08 (m, 1H), 3.21 (m, 2H), 1.25 (m, 3H); ESIMS m/z 463 ([M-H]$^-$).

Compounds CC32-CC35 in Table 1 were made in accordance with the procedures disclosed in Example 76.

Example 77

Preparation of (E)-3-(2-Chloro-4-(4,4,4-trifluoro-3-(3,4,5-trichlorophenyl)but-1-en-1-yl)benzyl)-1,1-dimethylurea (CC36)

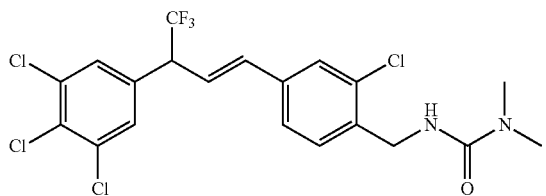 [SMILES: CN(C)C(=O)NCc1ccc(/C=C/C(c2cc(Cl)c(Cl)c(Cl)c2)C(F)(F)F)cc1Cl]

To a stirred solution of (E)-(2-chloro-4-(3-(3,4,5-trichlorophenyl)-4,4,4-trifluorobut-1-en-1-yl)phenyl)methanamine (0.2 g, 0.5 mmol) in $CH_2Cl_2$ (5 mL) at 0° C. were added TEA (0.141 mL, 1 mmol) and N,N-dimethylcarbamoyl chloride (0.08 g, 0.075 mmol), and the reaction mixture was stirred for 1 h at 0° C. The reaction mixture was diluted with $CH_2Cl_2$. The organic layer was washed with water and brine, dried over $Na_2SO_4$, and concentrated under reduced pressure. Purification by column chromatography ($SiO_2$, 100-200 mesh; 30-50% EtOAc in hexane) afforded the title compound as a solid (0.15 g, 60%): $^1H$ NMR (400 MHz, $CDCl_3$) δ 7.39 (m, 4H), 7.28 (m, 1H), 6.54 (d, J=16.0 Hz, 1H), 6.34 (dd, J=16.0, 8.0 Hz, 1H), 4.97 (br s, 1H), 4.38 (d, J=6.0 Hz, 2H), 4.10 (m, 1H), 2.9 (s, 3H), 2.7 (s, 3H); ESIMS m/z 497 ([M−H]$^-$); IR (thin film) 3350, 1705, 1114, 808 cm$^{-1}$.

Example 78

Preparation of (E)-1-(2-Chloro-4-(4,4,4-trifluoro-3-(3,4,5-trichlorophenyl)but-1-en-1-yl)benzyl)-3-ethyl-thiourea (CC37)

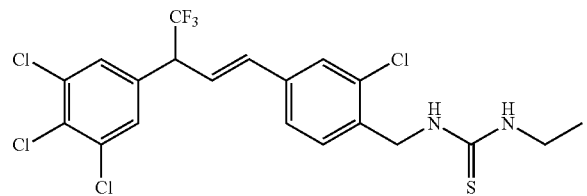 [SMILES: CCNC(=S)NCc1ccc(/C=C/C(c2cc(Cl)c(Cl)c(Cl)c2)C(F)(F)F)cc1Cl]

To a stirred solution of (E)-(2-chloro-4-(3-(3,4,5-trichlorophenyl)-4,4,4-trifluorobut-1-en-1-yl)phenyl)methanamine (0.2 g, 0.5 mmol) in $CH_2Cl_2$ (5 mL) at 0° C. were added TEA (0.141 mL, 1 mmol) and ethyl isothicyanate (0.053 g, 0.75 mmol), and the reaction mixture was stirred for 1 h at 0° C. The reaction mixture was diluted with $CH_2Cl_2$. The organic layer was washed with water and brine, dried over $Na_2SO_4$, and concentrated under reduced pressure. Purification by column chromatography ($SiO_2$, 100-200 mesh; 30-50% EtOAc in hexane) afforded the title compound as a solid (0.14 g, 60%): mp 88-91° C.; $^1H$ NMR (400 MHz, $CDCl_3$) δ 7.49 (d, J=8 Hz, 1H), 7.41 (d, J=7.2 Hz, 2H), 7.26 (m, 2H), 6.50 (d, J=16 Hz, 1H), 6.35 (dd, J=16.0, 8.0 Hz, 1H), 6.0 (br s, 1H), 5.73 (br s, 1H), 4.80 (br s, 2H), 4.09 (m, 1H), 1.23 (m, 3H); ESIMS m/z 515.01 ([M+H]$^+$).

Compound CC38 in Table 1 was made in accordance with the procedures disclosed in Example 78.

Example 79

Preparation of (E)-tert-Butyl (2-chloro-4-(3-(3,5-dichlorophenyl)-4,4,4-trifluorobut-1-en-1-yl)benzyl)-3-ethylurea (CC39)

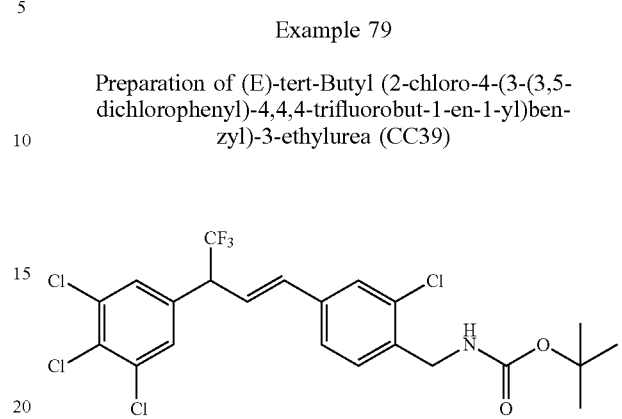

To a stirred solution of (E)-(2-chloro-4-(3-(3,4,5-trichlorophenyl)-4,4,4-trifluorobut-1-en-1-yl)phenyl)methanamine (0.2 g, 0.5 mmol in $CH_2Cl_2$ (5 mL) at 0° C. were added TEA (0.141 mL, 1 mmol) and di-tert-butyl dicarbonate (0.163 mL, 0.75 mmol), and the reaction mixture was stirred for 4 h at ambient temperature. The reaction mixture was diluted with $CH_2Cl_2$. The organic layer was washed with water and brine, dried over $Na_2SO_4$, and concentrated under reduced pressure. Purification by column chromatography ($SiO_2$, 100-200 mesh; 10-20% EtOAc in hexane) afforded the title compound as a white solid (0.147 g, 60%): $^1H$ NMR (400 MHz, $CDCl_3$) δ 7.39 (m, 4H), 7.28 (m, 1H), 6.54 (d, J=16.0 Hz, 1H), 6.34 (dd, J=16.0, 8.0 Hz, 1H), 4.97 (br s, 1H), 4.38 (d, J=6.0 Hz, 2H), 4.10 (m, 1H), 1.53 (s, 9H); ESIMS m/z 526.09 ([M−H]$^-$); IR (thin film) 3350, 1705, 1114, 808 cm$^{-1}$.

Compound CC40 in Table 1 was made in accordance with the procedures disclosed in Example 79.

Example 80

Preparation of (E)-Methyl 2-((2-chloro-4-(4,4,4-trifluoro-3-(3,4,5-trichlorophenyl)but-1-en-1-yl)benzyl)amino)-2-oxoacetate (CC41)

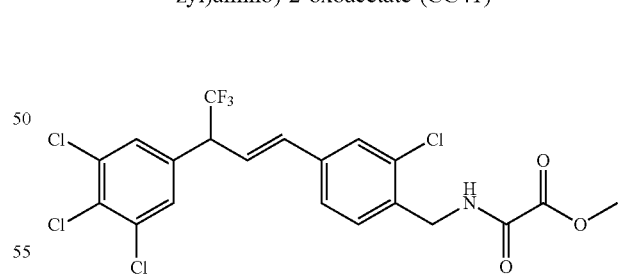

To a stirred solution of (E)-(2-chloro-4-(3-(3,4,5-trichlorophenyl)-4,4,4-trifluorobut-1-en-1-yl)phenyl)methanamine (0.2 g, 0.5 mmol) in $CH_2Cl_2$ (5 mL) at 0° C. were added TEA (0.141 mL, 1 mmol) and methyl 2-chloro-2-oxoacetate (0.09 g, 0.75 mmol), and the reaction mixture was stirred for 1 h at 0° C. The reaction mixture was diluted with $CH_2Cl_2$. The organic layer was washed with water and brine, dried over $Na_2SO_4$, and concentrated under reduced pressure. Purification by column chromatography ($SiO_2$, 100-200 mesh; 20% EtOAc in hexane) afforded the title compound as a solid (0.12 g, 50%): $^1$H NMR (400 MHz, CDCl$_3$) δ 7.48 (m, 1H), 7.43 (m, 3H), 7.38 (m, 1H), 7.23 (s, 1H), 6.55 (d, J=16.0 Hz, 1H), 6.36 (dd, J=16.0, 8.0 Hz, 1H), 4.60 (d, J=4.4 Hz, 2H), 4.18 (m, 1H), 3.85 (s, 3H); ESIMS m/z 512.22 ([M−H]$^−$); IR (thin film) 1740, 1701, 1114, 808 cm$^{-1}$.

Example 81

Preparation of (E)-N$^1$-(2-Chloro-4-(4,4,4-trifluoro-3-(3,4,5-trichlorophenyl)but-1-en-1-yl)benzyl)-N$^2$-(2,2,2-trifluoroethyl)oxalamide (CC42)

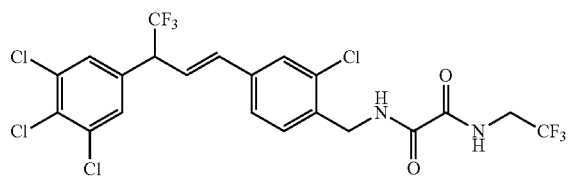 [SMILES: O=C(NCc1ccc(/C=C/C(c2cc(Cl)c(Cl)c(Cl)c2)C(F)(F)F)cc1Cl)C(=O)NCC(F)(F)F]

To a stirred solution of 2,2,2-trifluoroethylamine hydrochloride (0.1 g, 0.77 mmol) in CH$_2$Cl$_2$ (10 mL) was added dropwise trimethylaluminum (2 M solution in toluene; 0.39 mL, 0.77 mmol), and the reaction mixture was stirred at 25° C. for 30 min. A solution of (E)-methyl 2-((2-chloro-4-(4,4,4-trifluoro-3-(3,4,5-trichlorophenyl)but-1-en-1-yl)benzyl)-2-oxoacetate (0.2 g, 0.38 mmol) in CH$_2$Cl$_2$ (5 mL) was added dropwise to the reaction mixture at 25° C. The reaction mixture was stirred at reflux for 18 h, cooled to 25° C., quenched with 0.5 N HCl solution (50 mL) and extracted with EtOAc (2×50 mL). The combined organic extracts were washed with brine, dried over Na$_2$SO$_4$, and concentrated under reduced pressure. The crude compound was purified by flash chromatography (SiO$_2$, 100-200 mesh; 20%-40% EtOAc in n-hexane) to afford the title compound (0.13 g, 60%): mp 161-163° C.; $^1$H NMR (400 MHz, DMSO-d$_6$) δ 9.45 (br s, 2H), 7.90 (s, 2H), 7.75 (s, 1H), 7.46 (s, 1H), 7.28 (s, 1H), 6.93 (m, 1H), 6.75 (m, 1H), 4.80 (m, 1H), 4.40 (s, 2H), 3.90 (s, 2H); ESIMS m/z 578.96 ([M−H]$^−$).

Example 82

Preparation of (E)-N-(2-Chloro-4-(4,4,4-trifluoro-3-(3,4,5-trichlorophenyl)but-1-en-1-yl)benzyl)pyridin-2-amine (CC43)

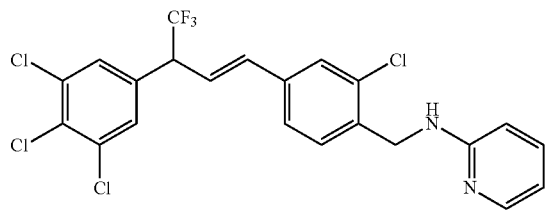 [SMILES: FC(F)(F)C(/C=C/c1ccc(CNc2ccccn2)c(Cl)c1)c1cc(Cl)c(Cl)c(Cl)c1]

To a stirred solution of N-(2-chloro-4-vinylbenzyl)pyridin-2-amine (0.3 g, 1.22 mmol) in 1,2-dichlorobenzene (5 mL) were added 5-(1-bromo-2,2,2-trifluoroethyl)-1,2,3-trichlorobenzene (0.83 g, 2.44 mmol), CuCl (24 mg, 0.24 mmol) and 2,2-bipyridyl (76 mg, 0.48 mmol). The resultant reaction mixture was degassed with argon for 30 min and then stirred at 180° C. for 24 h. After the reaction was deemed complete by TLC, the reaction mixture was cooled to ambient temperature and filtered, and the filtrate was concentrated under reduced pressure. Purification by flash chromatography (SiO$_2$, 100-200 mesh; 15% EtOAc in n-hexane) afforded the title compound as an off-white solid (0.2 g, 35%): mp 140-142° C.; $^1$H NMR (400 MHz, CDCl$_3$) δ 8.11 (d, J=4.0 Hz, 1H), 7.40 (m, 5H), 7.22 (m, 1H), 6.61 (m, 2H), 6.35 (m, 2H), 4.94 (br s, 1H), 4.61 (d, J=6.4 Hz, 2H), 4.11 (m, 1H); ESIMS m/z 505.39 ([M+H]$^+$).

Example 83

Preparation of (E)-N-((3-Chloro-5-(4,4,4-trifluoro-3-(3,4,5-trichlorophenyl)-but-1-en-1-yl)pyridin-2-yl)methyl)-3,3,3-trifluoropropanamide (CC44)

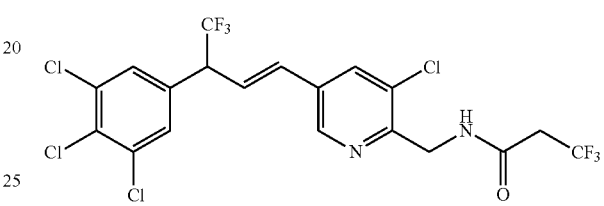

To a stirred solution of (E)-(3-chloro-5-(4,4,4-trifluoro-3-(3,4,5-trichlorophenyl)but-1-en-1-yl)pyridin-2-yl)methanamine (0.1 g, 0.2 mmol) in CH$_2$Cl$_2$ (5 mL) were added 3,3,3-trifluoropropanoic acid (45 mg, 0.350 mmol), EDC.HCl (67 mg, 0.350 mmol), HOBt.H$_2$O (71 mg, 0.467 mmol) and DIPEA (60.2 mg, 0.467 mmol), and the reaction mixture was stirred at ambient temperature for 18 h. The reaction mixture was diluted with CH$_2$Cl$_2$ and washed with water. The combined CH$_2$Cl$_2$ layer was washed with brine, dried over anhydrous Na$_2$SO$_4$, and concentrated under reduced pressure. Purification by flash column chromatography (SiO$_2$, 100-200 mesh; 15% EtOAc in petroleum ether) afforded the title compound as a pale yellow liquid (30 mg, 35%): $^1$H NMR (400 MHz, CDCl$_3$) δ 8.41 (s, 1H), 7.77 (s, 1H), 7.47 (br s, 1H), 7.40 (s, 2H), 6.58 (d, J=16.0 Hz, 1H), 6.45 (dd, J=16.0, 8.0 Hz, 1H), 4.68 (d, J=4.0 Hz, 2H), 4.14 (m, 1H), 3.24 (q, J=10.8 Hz, 2H); ESIMS m/z 536.88 ([M−H]$^−$); IR (thin film) 3320, 1674, 1114, 808.

Compound CC45 in Table 1 was made in accordance with the procedures disclosed in Example 83.

Example 84

Preparation of (E)-3,3,3-Trifluoro-N-((4-(4,4,4-trifluoro-3-(3,4,5-trichlorophenyl)but-1-en-1-yl)naphthalen-1-yl)methyl)propanamide (CC46)

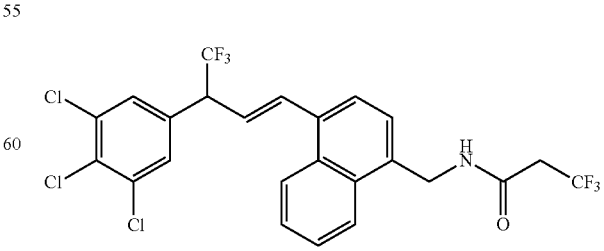

To a stirred solution of (E)-(4-(4,4,4-trifluoro-3-(3,4,5-trichlorophenyl)but-1-en-1-yl)naphthalen-1-yl)methanamine (0.1 g, 0.22 mmol) in CH$_2$Cl$_2$ (8 mL) were added 3,3,3-trifluoropanoic acid (0.032 g, 0.24 mmol), HOBt.H$_2$O (52 mg, 0.33 mmol), EDC.HCl (0.065 g, 0.33 mmol) and DIPEA (0.044 g, 0.45 mmol), and the resultant reaction mixture was stirred at ambient temperature for 18 h. The reaction mixture was diluted with water and extracted with EtOAc (3×30 mL). The combined EtOAc layer was washed with brine, dried over Na$_2$SO$_4$, and concentrated under reduced pressure. Purification by flash column chromatography (SiO$_2$, 100-200 mesh; 15% EtOAc in n-hexane) afforded the title compound as a gummy material (60 mg, 50%): mp 151-153° C.; $^1$H NMR (400 MHz, CDCl$_3$) δ 8.06 (m, 1H), 7.61 (m, 4H), 7.48 (s, 2H), 7.44 (d, J=8.0 Hz, 1H), 7.38 (m, 1H), 6.42 (m, 1H), 5.92 (br s, 1H), 4.92 (m, 2H), 4.24 (m, 1H), 3.12 (m, 2H); ESIMS m/z 554.04 ([M−H]$^−$).

Compounds CC47-CC48 in Table 1 were made in accordance with the procedures disclosed in Example 84.

Example 85

Preparation of (E)-1-Ethyl-3-((4-(4,4,4-trifluoro-3-(3,4,5-trichlorophenyl)but-1-en-1-yl)naphthalen-1-yl)methyl)urea (CC49)

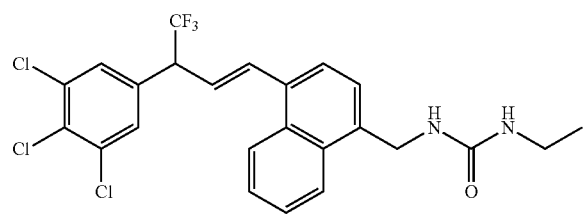 [SMILES: CCNC(=O)NCc1ccc(/C=C/C(c2cc(Cl)c(Cl)c(Cl)c2)C(F)(F)F)c2ccccc12]

To a stirred solution of (E)-(4-(4,4,4-trifluoro-3-(3,4,5-trichlorophenyl)but-1-en-1-yl)naphthalen-1-yl)methanamine (0.1 g, 0.22 mmol) in CH$_2$Cl$_2$ at 0° C. were added TEA (0.064 mL, 0.44 mmol) and ethylisocyanate (0.023 mL, 0.33 mmol), and the reaction mixture was stirred for 1 h at 0° C. The reaction mixture was diluted with CH$_2$Cl$_2$. The organic layer was washed with water and brine, dried over Na$_2$SO$_4$, and concentrated under reduced pressure. Purification by column chromatography (SiO$_2$, 100-200 mesh; 30% EtOAc in hexane) afforded the title compound as a solid (0.07 g, 60%): mp 84-87° C.; $^1$H NMR (400 MHz, CDCl$_3$) δ 8.06 (m, 1H), 7.98 (m, 1H), 7.61 (m, 3H), 7.48 (s, 2H), 7.44 (d, J=8.0 Hz, 1H), 7.38 (m, 2H), 6.42 (m, 1H), 4.92 (s, 2H), 4.6 (br s, 1H), 4.24 (m, 1H), 3.21 (m, 2H), 1.2 (t, J=4.6 Hz, 3H); ESIMS m/z 515.33 ([M+H]$^+$).

Example 86

Preparation of (E)-N'-(4-(4,4,4-Trifluoro-3-(3,4,5-trichlorophenyl)but-1-en-1-yl)phenyl)cyclopropanecarbohydrazide (CC50)

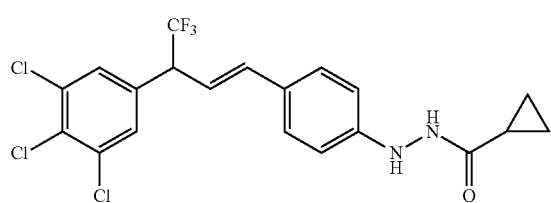 [SMILES: O=C(NNc1ccc(/C=C/C(c2cc(Cl)c(Cl)c(Cl)c2)C(F)(F)F)cc1)C1CC1]

To a stirred solution of (E)-(4-(4,4,4-trifluoro-3-(3,4,5-trichlorophenyl)but-1-en-1-yl)phenyl)hydrazine (0.1 g, 0.3 mmol) in CH$_2$Cl$_2$ (10 mL) was added DIPEA (65 mg, 0.51 mmol), HOBt.H$_2$O (59 mg, 0.38 mmol), EDC.HCl (73 mg, 0.38 mmol) and cyclopropanecarbonyl chloride (0.024 g, 0.28 mmol), and the reaction mixture was stirred at ambient temperature for 1 h. The reaction mixture was diluted with satd aq NaHCO$_3$ solution and extracted with CH$_2$Cl$_2$. The combined CH$_2$Cl$_2$ layer was washed with brine, dried over anhydrous Na$_2$SO$_4$, and concentrated under reduced pressure. Purification by flash column chromatography (SiO$_2$; 5-25% EtOAc in petroleum ether) afforded the title compound as a solid (65 mg, 55%): mp 138-140° C.; $^1$H NMR (400 MHz, CDCl$_3$) δ 9.81 (s, 1H), 7.90 (s, 1H), 7.84 (s, 2H), 7.34 (d, J=8.4 Hz, 2H), 6.65 (d, J=15.6 Hz, 1H), 6.61 (m, 1H), 6.57 (s, 1H), 6.48 (dd, J=15.6, 8.8 Hz, 1H), 4.74 (m, 1H), 1.64 (m, 1H), 0.75 (m, 4H); ESIMS m/z 461.32 ([M−H]$^−$).

Compound CC51 in Table 1 was made in accordance with the procedures disclosed in Example 86.

Example 87

Preparation of (E)-N-(4-(4,4,4-Trifluoro-3-(3,4,5-trichlorophenyl)but-1-en-1-yl)phenoxy)cyclopropanecarboxamide (CC52)

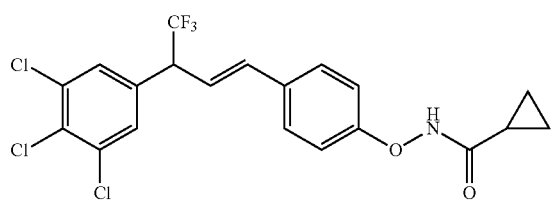 [SMILES: O=C(NOc1ccc(/C=C/C(c2cc(Cl)c(Cl)c(Cl)c2)C(F)(F)F)cc1)C1CC1]

To a stirred solution of (E)-O-(4-(4,4,4-trifluoro-3-(3,4,5-trichlorophenyl)but-1-en-1-yl)phenyl)hydroxylamine (0.15 g, 0.38 mmol) in CH$_2$Cl$_2$ (5 mL) was added EDC.HCl (0.109 g, 0.569 mmol), HOBt.H$_2$O (0.087 g, 0.569 mmol), DIPEA (0.097 g, 0.758 mmol) and cyclopropanecarboxylic acid (0.049 g, 0.569 mmol). The resultant reaction mixture was stirred at ambient temperature for 18 h. The reaction mixture was diluted with water and extracted with CHCl$_3$ (35 mL) The combined CHCl$_3$ layer was washed with brine, dried over Na$_2$SO$_4$ and concentrated under reduced pressure. Purification by flash column chromatography (SiO$_2$; 20% EtOAc in hexane) afforded the title compound as a brown liquid (0.06 g, 34%): $^1$H NMR (400 MHz, CDCl$_3$) δ 7.40 (s, 2H), 7.18 (s, 1H), 7.08 (s, 1H), 6.85 (m, 1H), 6.45 (m, 1H), 6.65 (m, 1H), 6.20 (m, 1H), 5.55 (s, 1H), 4.08 (m, 1H), 1.90 (m, 1H), 1.30-1.10 (m, 4H); ESIMS m/z 464.87 ([M−H]$^−$).

Compound CC53 in Table 1 was made in accordance with the procedures disclosed in Example 87.

Example 88

Preparation of (Z)-3,3,3-Trifluoro-N-(4-(4,4,4-trifluoro-3-(3,4,5-trichlorophenyl)but-1-en-1-yl)benzyl)propanamide (CC54)

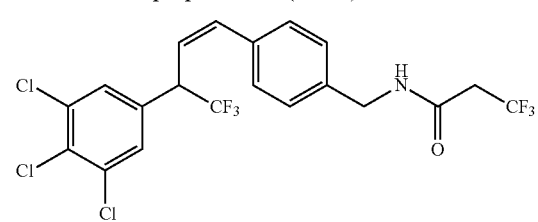

A silicon borate vial was charged with (E)-3,3,3-trifluoro-N-(4-(4,4,4-trifluoro-3-(3,4,5-trichlorophenyl)but-1-en-1-yl)benzyl)propanamide (133 mg, 0.269 mmol) and dimethyl sulfoxide (DMSO; 10 mL). The mixture was placed within 0.6 to 1 meter (m) of a bank of eight 115 watt Sylvania FR48T12/350BL/VHO/180 Fluorescent Tube Black Lights and four 115 watt Sylvania (daylight) F48T12/D/VHO Straight T12 Fluorescent Tube Lights for 72 h. The mixture was concentrated in vacuo and purified by reverse phase chromatography to give the title compound as a colorless oil (11 mg, 8%): $^1$H NMR (300 MHz, CDCl$_3$) δ 7.28 (s, 2H), 7.25 (m, 2H), 7.10 (d, J=8.0 Hz, 2H), 6.89 (d, J=11.4 Hz, 1H), 6.07 (br s, 1H), 6.01 (m, 1H), 4.51 (d, J=5.8 Hz, 2H), 4.34 (m, 1H), 3.12 (q, J=7.5 Hz, 2H); $^{13}$C NMR (101 MHz, CDCl$_3$) δ 162.44, 137.20, 135.38, 135.23, 134.82, 134.68, 131.71, 129.00, 128.80, 128.69, 128.10, 127.96, 122.63, 76.70, 47.33 (q, J=28 Hz), 43.59, 42.12 (q, J=30 Hz); ESIMS m/z 504 ([M+H]$^+$).

Compounds DC46, AC93. AC94 in Table 1 were made in accordance with the procedures disclosed in Example 88.

Example 89

Preparation of 1-(1-Bromo-2,2,2-trifluoroethyl)-3-chlorobenzene (DI2)

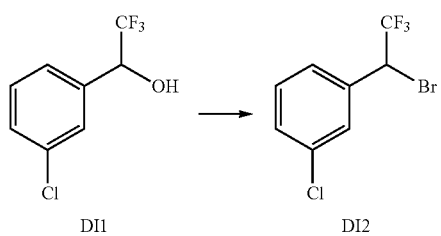

The title compound was synthesized in two steps via 1-(3-chlorophenyl)-2,2,2-trifluoroethanol (DI1, prepared as in Step 1, Method B in Example 1); isolated as a colorless viscous oil (1.5 g, 75%): $^1$H NMR (400 MHz, CDCl$_3$) δ 7.50 (s, 1H), 7.42-7.35 (m, 3H), 5.02 (m, 1H), 2.65 (br s, 1H)) and Step 2 in Example 1 and isolated (0.14 g, 22%): $^1$H NMR (400 MHz, CDCl$_3$) δ 7.50 (br s, 1H), 7.42-7.35 (m, 3H), 5.07 (m, 1H).

The following compounds were made in accordance with the procedures disclosed in Example 89.

(1-Bromo-2,2,2-trifluoroethyl)benzene (DI4)

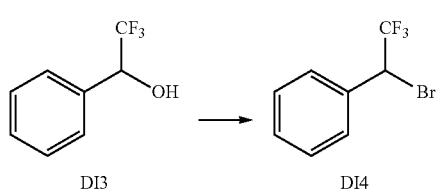

2,2,2-Trifluoro-1-phenylethanol (DI3) was isolated (10 g, 80%): $^1$H NMR (300 MHz, CDCl$_3$) δ 7.48 (m, 2H), 7.40 (m, 3H), 5.02 (m, 1H), 2.65 (d, J=7.1 Hz, 1H). The title compound (DI4) was isolated as a liquid (8.0 g, 60%): $^1$H NMR (400 MHz, CDCl$_3$) δ 7.50 (m, 2H), 7.40 (m, 3H), 5.00 (q, J=7.5 Hz, 1H).

1-(1-Bromo-2,2,2-trifluoroethyl)-3,5-dimethylbenzene (DI20)

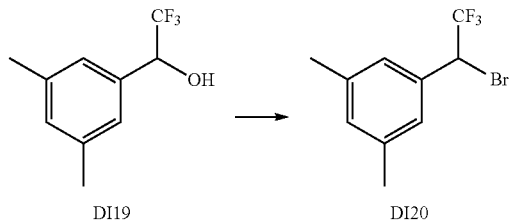

1-(3,5-Dimethylphenyl)-2,2,2-trifluoroethanol (DI19) was isolated an off white solid: $^1$H NMR (400 MHz, CDCl$_3$) δ 7.05 (s, 2H), 7.02 (s, 1H), 4.95 (m, 1H), 2.32 (s, 6H); ESIMS m/z 204 ([M]$^-$). The title compound (DI20) was isolated (3.0 g, 51%).

1-(1-Bromo-2,2,2-trifluoroethyl)-2,4-dichlorobenzene (DI22)

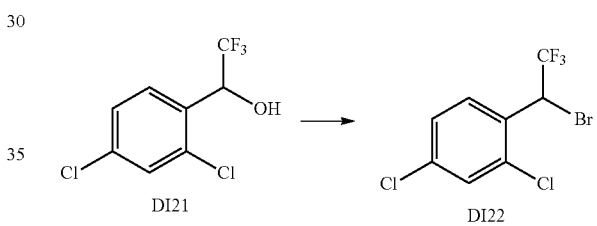

1-(2,4-Dichlorophenyl)-2,2,2-trifluoroethanol (DI21) was isolated as an off white powder (5.3 g, 61%): mp 49-51° C.; $^1$H NMR (400 MHz, CDCl$_3$) δ 7.62-7.66 (d, 1H), 7.42-7.44 (d, 1H), 7.32-7.36 (d, 1H), 5.6 (m, 1H), 2.7 (s, 1H); ESIMS m/z 244 ([M]$^+$). The title compound (DI22) was isolated (3.2 g, 50%): $^1$H NMR (400 MHz, CDCl$_3$) δ 7.62-7.72 (m, 1H), 7.4-7.42 (m, 1H), 7.3-7.38 (m, 1H), 5.7-5.8 (m, 1H).

1-(1-Bromo-2,2,2-trifluoroethyl)-2,3-dichlorobenzene (DI24)

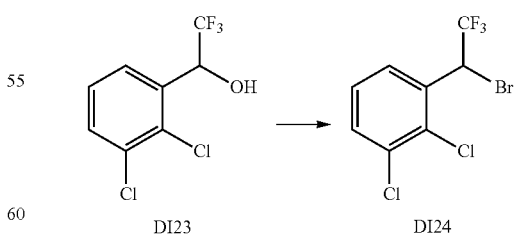

1-(2,3-Dichlorophenyl)-2,2,2-trifluoroethanol (DI23) was isolated as a pale yellow oil (5.2 g, 60%): $^1$H NMR (400 MHz, CDCl$_3$) δ 7.62-7.64 (d, 1H), 7.52-7.54 (m, 1H), 7.29-7.33 (t, 1H), 5.6-5.76 (m, 1H), 2.7 (s, 1H); ESIMS m/z 243.9 ([M]$^+$). The title compound (DI24) was isolated an oil (8.7 g, 60%): ¹H NMR (400 MHz, CDCl₃) δ 7.62-7.71 (m, 1H), 7.44-7.52 (m, 1H), 7.27-7.3 (s, 1H), 5.81-5.91 (m, 1H).

2-(1-Bromo-2,2,2-trifluoroethyl)-1,4-dichlorobenzene (DI26)

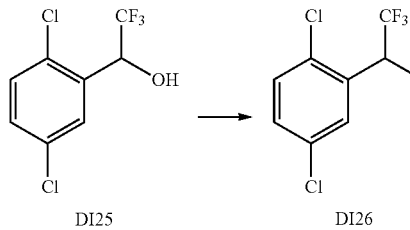

1-(2,5-Dichlorophenyl)-2,2,2-trifluoroethanol (DI25) was isolated as a yellow oil (4.1 g, 60%): ¹H NMR (400 MHz, CDCl₃) δ 7.68-7.7 (s, 1H), 7.3-7.37 (m, 2H), 5.51-5.6 (m, 1H), 2.7 (s, 1H); ESIMS m/z 244 ([M]⁺). The title compound (DI26) was isolated (3.0 g, 60%): ¹H NMR (400 MHz, CDCl₃) δ 7.7-7.78 (m, 1H), 7.3-7.4 (m, 2H), 5.7-5.8 (m, 1H).

1-(1-Bromo-2,2,2-trifluoroethyl-3,5-bis(trifluoromethyl)benzene (DI28)

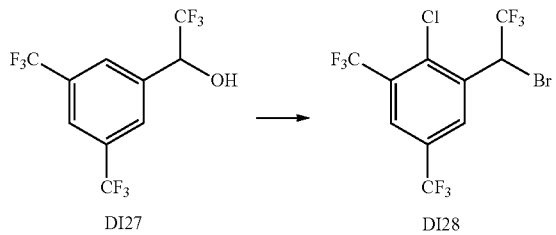

1-(3,5-Bis(trifluoromethyl)phenyl)-2,2,2-trifluoroethanol (DI27) was isolated (3.8 g, 60%): ¹H NMR (400 MHz, CDCl₃) δ 7.98 (m, 3H), 5.25 (m, 1H), 3.2 (br, 1H); ESIMS m/z 312.2 ([M]⁺). The title compound (DI28) was prepared and carried on crude.

1-(1-Bromo-2,2,2-trifluoroethyl)-2,3,5-trichlorobenzene (DI30)

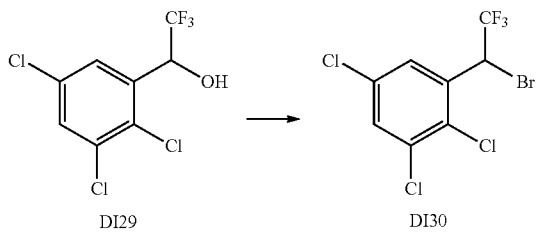

2,2,2-Trifluoro-1-(2,3,5-trichlorophenyl)ethanol (DI29) was isolated as a white solid (4.0 g, 60%): mp 113-115° C.; ¹H NMR (400 MHz, CDCl₃) δ 7.62 (d, 1H), 7.50 (d, 1H), 5.60-5.70 (m, 1H), 2.75 (s, 1H); ESIMS m/z 278.0 ([M⁺]).

The title compound (DI30) was isolated (2.9 g, 60%): ¹H NMR (400 MHz, CDCl₃) δ 7.70 (d, 1H), 7.50 (d, 1H), 5.72-5.82 (m, 1H).

1-(1-Bromo-2,2,2-trifluoroethyl)-3-chloro-5-(trifluoromethyl)benzene (DI32)

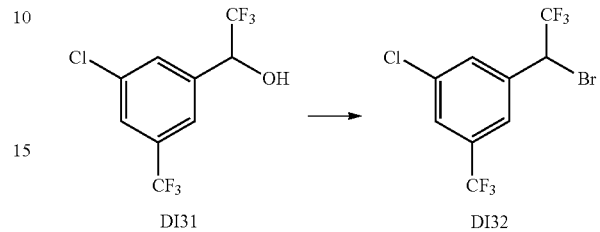

1-(3-Chloro-5-(trifluoromethyl)phenyl)-2,2,2-trifluoroethanol (DI31) was isolated as a pale yellow oil (2.0 g, 50%): ¹H NMR (400 MHz, CDCl₃) δ 7.51 (m, 3H), 5.08 (m, 1H), 2.81 (s, 1H); ESIMS m/z 278.1 ([M]⁺). The title compound (DI32) was isolated oil (2.0 g, 40%): ESIMS m/z 342 ([M]⁺).

5-(1-Bromo-2,2,2-trifluoroethyl)-1,3-dichloro-2-methoxybenzene (DI34)

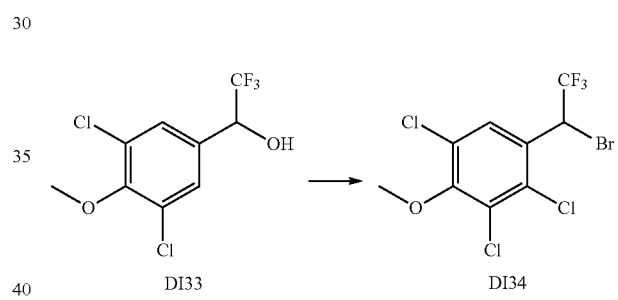

1-(3,5-Dichloro-4-methoxyphenyl)-2,2,2-trifluoroethanol (DI33) was isolated as an off white solid (0.8 g, 60%); mp 92-95° C.: ¹H NMR (400 MHz, CDCl₃) δ 7.41 (s, 2H), 5.00 (m, 1H), 3.89 (s, 3H), 2.64 (m, 1H); ESIMS m/z 274 ([M]⁺). The title compound (DI34) was isolated as a colorless liquid (0.6 g, 57%).

Example 90

Preparation of 1-(1-Bromo-2,2,2-trifluoroethyl)-3,5-difluorobenzene (DI36)

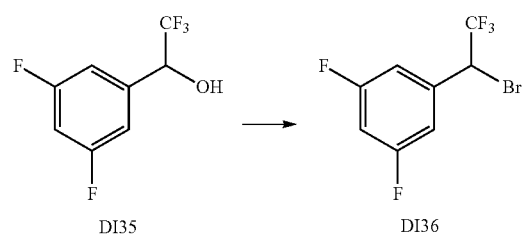

The title compound was synthesized in two steps via 1-(3,5-difluorophenyl)-2,2,2-trifluoroethanol (DI35, prepared as in Step 1, Method A in Example 1; isolated as a colorless oil (0.2 g, 75%): $^1$H NMR (400 MHz, CDCl$_3$) δ 7.05 (m, 2H), 6.88 (m, 1H), 5.06 (m, 1H), 2.66 (s, 1H); ESIMS m/z 212 ([M]$^+$) and Step 2 in Example 1 and isolated (3.2 g, 50%); $^1$H NMR (400 MHz, CDCl$_3$) δ 7.05 (m, 2H), 6.86 (m, 1H), 5.03 (q, J=7.4 Hz, 1H).

The following compounds were made in accordance with the procedures disclosed in Example 90.

1-(1-Bromo-2,2,2-trifluoroethyl)-4-chlorobenzene (DI38)

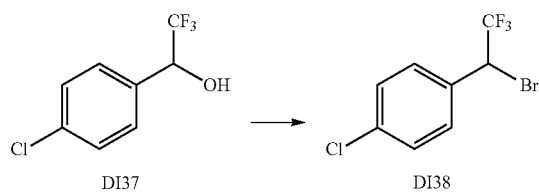

1-(4-Chlorophenyl)-2,2,2-trifluoroethanol (DI37) was isolated as a colorless oil (5.0 g, 99%): $^1$H NMR (400 MHz, CDCl$_3$) δ 7.44-7.38 (m, 4H), 5.05 (m, 1H), 2.55 (s, 1H); ESIMS m/z 210 ([M]$^+$). The title compound (DI38) was isolated (3.0 g, 46%): $^1$H NMR (400 MHz, CDCl$_3$) δ 7.45 (d, J=8.2 Hz, 2H), 7.37 (d, J=8.2 Hz, 2H), 5.10 (q, J=7.2 Hz, 1H).

1-(1-Bromo-2,2,2-trifluoroethyl)-4-methoxybenzene (DI40)

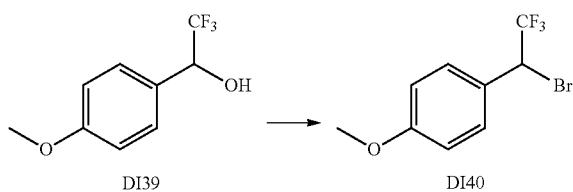

2,2,2-Trifluoro-1-(4-methoxyphenyl)ethanol (DI39) was isolated as a pale yellow liquid: $^1$H NMR (400 MHz, CDCl$_3$) δ 7.41 (d, J=8.8 Hz, 2H), 6.95 (m, J=8.8 Hz, 2H), 5.00 (m, 1H), 3.82 (s, 3H), 2.44 (s, 1H); ESIMS m/z 206.1 ([M]$^+$). The title compound (DI40) was isolated (3.8 g, 62%).

1-(1-Bromo-2,2,2-trifluoroethyl)-4-fluorobenzene (DI42)

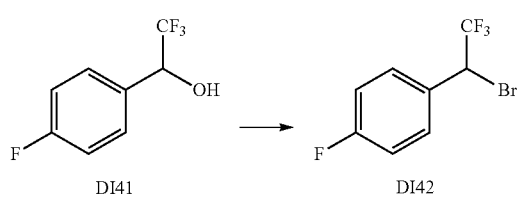

2,2,2-Trifluoro-1-(4-fluorophenyl)ethanol (DI41) was isolated as a colorless oil (5 g, 99%): $^1$H NMR (400 MHz, CDCl$_3$) δ 7.48-7.45 (m, 2H), 7.13-7.07 (m, 2H), 5.06 (m, 1H), 2.53 (s, 1H); ESIMS m/z 194 ([M]$^+$). The title compound (DI42) was prepared and carried on as crude intermediate.

1-(1-Bromo-2,2,2-trifluoroethyl)-4-methylbenzene (DI44)

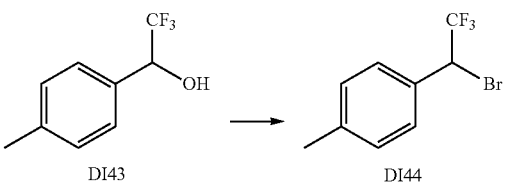

2,2,2-Trifluoro-1-(p-tolyl)ethanol (DI43) was isolated as colorless oil (5.0 g, 99%): $^1$H NMR (400 MHz, CDCl$_3$) δ 7.37 (d, J=8.0 Hz, 2H), 7.23 (d, J=8.0 Hz, 2H), 5.02 (m, 1H), 2.46 (m, 1H), 2.37 (s, 3H); ESIMS m/z 190 ([M]$^+$). The title compound (DI44) was isolated (3.0 g, 45%).

1-(1-Bromo-2,2,2-trifluoroethyl)-3-fluorobenzene (DI46)

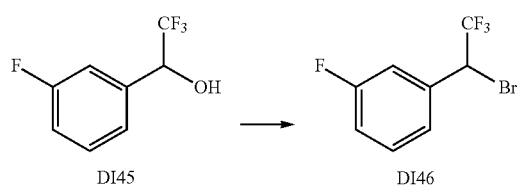

2,2,2-Trifluoro-1-(3-fluorophenyl)ethanol (DI45) was isolated as a colorless viscous oil (2.8 g, 93%): $^1$H NMR (400 MHz, CDCl$_3$) δ 7.41 (m, 1H), 7.25 (m, 2H), 7.14 (m, 1H), 5.06 (m, 1H), 2.60 (s, 1H); ESIMS m/z 194 ([M]$^+$). The title compound (DI46) was isolated (2.0 g, 61%).

1-(1-Bromo-2,2,2-trifluoroethyl)-2-fluorobenzene (DI48)

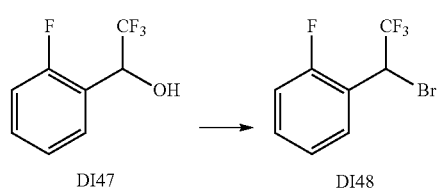

2,2,2-Trifluoro-1-(2-fluorophenyl)ethanol (DI47) was isolated as a colorless oil (2.5 g, 99%): $^1$H NMR (400 MHz, CDCl$_3$) δ 7.40 (m, 1H), 7.43 (m, 1H), 7.24 (m, 1H), 7.13 (m, 1H), 5.42 (m, 1H), 2.65 (s, 1H); ESIMS m/z 194 ([M]$^+$). The title compound (DI48) was isolated (2.0 g, 61%): $^1$H NMR (400 MHz, CDCl$_3$) δ 7.61 (m, 1H), 7.40 (m, 1H), 7.23 (m, 1H), 7.10 (m, 1H), 5.40 (m, 1H); GCMS m/z 255 ([M–H]$^−$).

Example 91

Preparation of 4-(1H-1,2,4-triazol-1-yl)benzaldehyde (DI5)

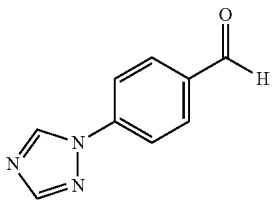 [SMILES: O=Cc1ccc(-n2cncn2)cc1]

To a stirring solution of 4-fluorobenzaldehyde (10.0 g, 80.6 mmol) in DMF (150 mL) were added $K_2CO_3$ (13.3 g, 96.7 mmol) and 1,2,4-triazole (6.67 g, 96.7 mmol) and the resultant reaction mixture was stirred at 120° C. for 6 h. After completion of reaction (by TLC), the reaction mixture was diluted with water and extracted with EtOAc (3×100 mL). The combined EtOAc layer was washed with water and brine, dried over $Na_2SO_4$, and concentrated under reduced pressure to afford the title compound as a solid (9.0 g, 65%): mp 145-149° C.; $^1$H NMR (400 MHz, $CDCl_3$) δ 10.08 (s, 1H), 8.70 (s, 1H), 8.16 (s, 1H), 8.06 (d, J=8.0 Hz, 2H), 7.92 (d, J=8.0 Hz, 2H); ESIMS m/z 173.9 ([M+H]$^+$).

The following compound was made in accordance with the procedures disclosed in Example 91.

5-Formyl-2-(1H-1,2,4-triazol-1-yl)benzonitrile (DI49)

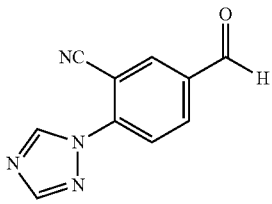 [SMILES: N#Cc1cc(C=O)ccc1-n1cncn1]

The title compound was isolated (2.8 g, 60%); $^1$H NMR (400 MHz, $CDCl_3$) δ 10.10 (s, 1H), 8.98 (s, 1H), 8.35 (s, 1H), 8.30 (d, 1H), 8.22 (s, 1H), 8.07 (d, 1H); IR (thin film) 3433, 3120, 1702, 1599, 1510 cm$^{-1}$.

2-Chloro-4-(1H-1,2,4-triazol-1-yl)benzaldehyde (DI50)

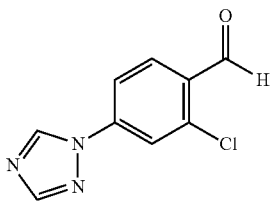 [SMILES: O=Cc1ccc(-n2cncn2)cc1Cl]

The title compound was isolated as an off white solid (3.0 g, 40%): mp 149-151° C.; $^1$H NMR (400 MHz, $CDCl_3$) δ 10.05 (s, 1H), 8.74 (s, 1H), 8.17 (s, 1H), 8.10 (s, 1H), 7.90 (m, 2H); ESIMS m/z 208.10 ([M+H]$^+$).

5-Methyl-4-(1H-1,2,4-triazol-1-yl)benzaldehyde (DI51)

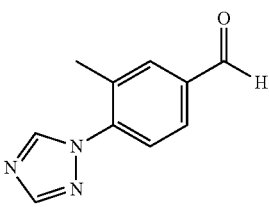

The title compound was isolated as a white solid (0.5 g, 74%): mp 109-111° C.; $^1$H NMR (400 MHz, $D_6$-DMSO) δ 10.06 (s, 1H), 9.00 (s, 1H), 8.30 (s, 1H), 7.99 (s, 1H), 7.92 (d, J=9.2 Hz, 1H), 7.69 (d, J=9.2 Hz, 1H), 2.30 (s, 3H); ESIMS m/z 188.13 ([M+H]$^+$).

Example 92

Preparation of 5-Formyl-2-(3-nitro-1H-1,2,4-triazol-1-yl)benzonitrile (DI52)

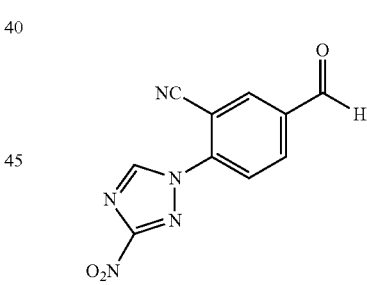

To a stirring solution of 2-fluoro-5-formylbenzonitrile (0.5 g, 3.3 mmol) in DMF (25 mL) were added $K_2CO_3$ (0.68 g, 4.95 mmol) and 3-nitro-1,2,4 triazole (0.45 g, 4.2 mmol) and the resultant reaction mixture was stirred at ambient temperature for 14 h. After completion of reaction (TLC), the reaction mixture was diluted with water and extracted with EtOAc. The combined EtOAc layer was washed with water and brine then dried over $Na_2SO_4$ and concentrated under reduced pressure to afforded the title compound as a pale yellow solid (0.36 g, 45%): mp 170-172° C.; $^1$H NMR (300 MHz, DMSO-$d_6$) δ 10.12 (s, 1H), 9.61 (s, 1H), 8.69 (s, 1H), 8.45 (d, J=9.3 Hz, 1H), 8.23 (d, J=9.3 Hz, 1H); ESIMS m/z 242.3 ([M−H]$^−$); IR (thin film) 2238, 1705, 1551, 1314 cm$^{-1}$.

Example 93

Preparation of 4-(3-Methyl-1H-1,2,4-triazol-1-yl)benzaldehyde (DI53)

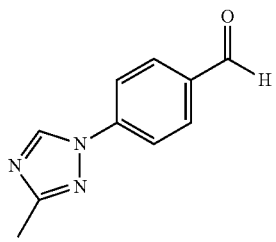

To a stirring solution of 4-fluorobenzaldehyde (5.0 g, 40.32 mmol) in DMF (50 mL), were added $K_2CO_3$ (3.34 g, 40.32 mmol) and 3-methyl-1,2,4-trizole (3.34 g, 40.32 mmol) and the resultant reaction mixture was stirred at ambient temperature for 4 h. After completion of the reaction (TLC), the reaction mixture was diluted with water and extracted with EtOAc (3×). The combined EtOAc layer was washed with water and brine then dried over $Na_2SO_4$ and concentrated under reduced pressure to afforded the title compound as a white solid (4.1 g, 60%): mp 125-128° C.; $^1$H NMR (400 MHz, CDCl$_3$) δ 10.05 (s, 1H), 8.76 (s, 1H), 8.02 (d, 2H), 7.85 (d, 2H), 2.50 (s, 3H); ESIMS m/z 188.04 ([M+H]$^+$).

The following compound was made in accordance with the procedures disclosed in Example 93.

4-(1H-1,2,4-triazol-1-yl)-3-(trifluoromethyl)benzaldehyde (DI54)

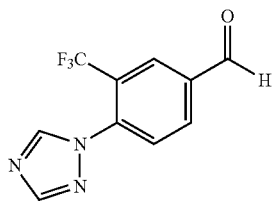 [SMILES: O=Cc1ccc(-n2cncn2)c(C(F)(F)F)c1]

The title compound was isolated as white solid (1.05 g, 60%): mp 81-83° C.; $^1$H NMR (400 MHz, CDCl$_3$) δ 10.15 (s, 1H), 8.43 (s, 1H), 8.37 (s, 1H), 8.25 (d, J=7.2 Hz, 1H), 8.18 (s, 1H), 7.79 (d, J=7.2 Hz, 1H); ESIMS m/z 241.0 ([M]$^+$).

4-(3-Nitro-1H-1,2,4-triazol-1-yl)benzaldehyde (DI55)

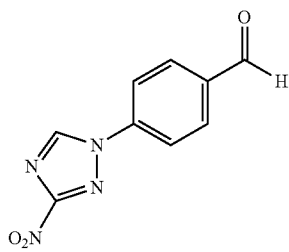 [SMILES: O=Cc1ccc(-n2cnc([N+](=O)[O-])n2)cc1]

The title compound was isolated as pale yellow solid (0.10 g, 23%): mp 159-161° C.; $^1$H NMR (400 MHz, CDCl$_3$) δ 10.10 (s, 1H), 8.89 (s, 1H), 8.15 (m, 2H), 8.00 (m, 2H); ESIMS m/z 217.11 ([M–H]$^-$).

3-Bromo-4-(1H-1,2,4-triazol-1-yl)benzaldehyde (DI56)

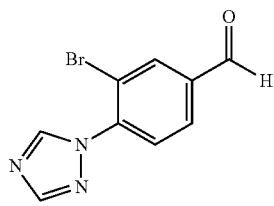 [SMILES: O=Cc1ccc(-n2cncn2)c(Br)c1]

The title compound was isolated as white solid (3.2 g, 51%): mp 126-128° C.; $^1$H NMR (400 MHz, CDCl$_3$) δ 10.04 (s, 1H), 8.69 (s, 1H), 8.27 (M, 1H, 8.18 (s, 1H) 7.99 (d, J=9.2 Hz, 1H), 7.76 (d, J=9.2 Hz, 1H); ESIMS m/z 250.9 ([M]$^+$).

5-Formyl-2-(3-methyl-1H-1,2,4-triazol-1-yl)benzonitrile (DI57)

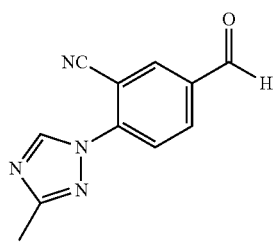 [SMILES: Cc1ncn(-c2ccc(C=O)cc2C#N)n1]

The title compound was isolated as white solid (0.13 g, 30%): mp 147-149° C.; $^1$H NMR (400 MHz, CDCl$_3$) δ 10.07 (s, 1H), 8.89 (s, 1H), 8.32 (d, J=1.8 Hz, 1H), 8.24 (dd, J=8.6, 1.3 Hz, 1H), 8.06 (d, J=8.6 Hz, 1H), 2.54 (s, 3H); ESIMS m/z 213.09 ([M+H]$^+$); IR (thin film) 2239, 1697 cm$^{-1}$.

3-Nitro-4-(1H-1,2,4-triazol-1-yl)benzaldehyde (DI58)

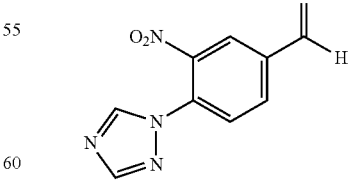

The title compound was isolated as pale yellow solid (3.0 g, 60%): mp 116-118° C.; $^1$H NMR (400 MHz, CDCl$_3$) δ 10.15 (s, 1H), 8.48 (s, 1H), 8.46 (s, 1H), 8.26 (d, J=6.9 Hz, 1H), 8.16 (s, 1H), 7.83 (d, J=6.9 Hz, 1H); ESIMS m/z 219.00 ([M+H]$^+$).

Example 94

Preparation of 1-(4-Vinylphenyl)-1H-1,2,4-triazole (DI59)

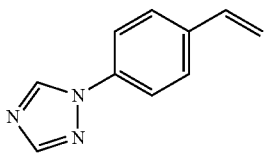

To a stirred solution of 4-[1,2,4]triazol-1-yl-benzaldehyde (9.0 g, 52 mmol) in 1,4-dioxane (100 mL), were added $K_2CO_3$ (10.76 g, 78 mmol) and methyl triphenyl phosphonium bromide (22.2 g, 62.4 mmol) at room temperature. The resultant reaction mixture was heated to 70° C. for 18 h. After completion of the reaction (TLC), the reaction mixture was cooled to room temperature and filtered and the obtained filtrate was concentrated under reduced pressure. Purification by flash chromatography ($SiO_2$, 100-200 mesh; 25-30% EtOAc in petroleum ether) to afforded the title compound as a white solid (5.6 g, 63%): ESIMS m/z 172.09 ([M+H]$^+$).

The following compound was made in accordance with the procedures disclosed in Example 94.

1-(2-Methyl-4-vinylphenyl)-1H-1,2,4-triazole (DI60)

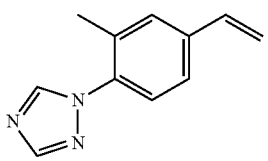

The title compound was isolated as an off white solid (1.5 g, 76%): $^1$H NMR (400 MHz, CDCl$_3$) δ 8.25 (s, 1H), 8.11 (s, 1H), 7.35 (m, 2H), 7.27 (d, J=8.7 Hz, 1H), 6.74 (m, 1H), 5.82 (d, J=17.3 Hz, 1H), 5.36 (d, J=10.0 Hz, 1H), 2.25 (s, 3H); ESIMS m/z 186.14 ([M+H]$^+$).

2-(1H-1,2,4-Triazol-1-yl)-5-vinylbenzonitrile (DI61)

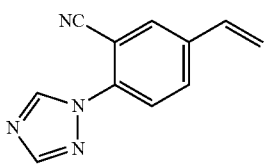

The title compound was isolated as an off-white solid (1.40 g, 71%): mp 126-129° C.; $^1$H NMR (400 MHz, CDCl$_3$) δ 8.76 (s, 1H), 8.18 (s, 1H), 7.82-7.84 (m, 1H), 7.72-7.80 (m, 2H), 6.70-6.80 (dd, J=17.6, 10.8 Hz, 1H), 5.90-5.95 (d, J=17.6 Hz, 1H), 5.50-5.70 (d, J=10.8 Hz, 1H); ESIMS m/z 197.03 ([M+H]$^+$).

Example 95

Preparation of 2-(3-Nitro-1H-1,2,4-triazol-1-yl)-5-vinylbenzonitrile (DI62)

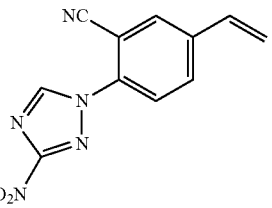

To a stirred solution of 5-formyl-2-(3-nitro-1H-1,2,4-triazol-1-yl)benzonitrile (0.36 g, 1.49 mmol) in 1,4-dioxane (25 mL), were added $K_2CO_3$ (0.3 g, 2.2 mmol) and methyl triphenyl phosphonium bromide (0.63 g, 1.79 mmol). The resultant reaction mixture was heated to 100° C. for 18 h. After completion of the reaction (TLC), the reaction mixture was cooled to room temperature and filtered and the obtained filtrate was concentrated under reduced pressure. Purification by flash chromatography ($SiO_2$, 100-200 mesh; 25-30% EtOAc in petroleum ether) to afford the title compound as a solid (0.25 g, 70%): mp 103-105° C.; $^1$H NMR (400 MHz, DMSO-d$_6$) δ 9.50 (s, 1H), 8.34 (m, 1H), 7.98 (d, J=7.8 Hz, 1H), 7.68 (d, J=7.8 Hz, 1H), 6.87 (m, 1H), 6.20 (d, J=15.7 Hz, 1H), 5.56 (d, J=11.8 Hz, 1H); ESIMS m/z 240.27 ([M−H]$^−$); IR (thin film) 2240, 1514, 1312 cm$^{-1}$.

The following compound was made in accordance with the procedures disclosed in Example 95.

1-(3-Chloro-4-vinylphenyl)-1H-1,2,4-triazole (DI63)

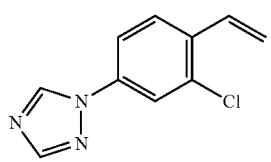

The title compound was isolated as an off-white solid (2.3 g, 80%): mp 134-137° C.; $^1$H NMR (400 MHz, CDCl$_3$) δ 8.56 (s, 1H), 8.11 (s, 1H), 7.76 (s, 1H), 7.70 (d, J=9.0 Hz, 1H), 7.57 (d, J=9.0 Hz, 1H), 7.10 (m, 1H), 5.80 (d, J=17.2 Hz, 1H), 5.47 (d, J=12.4 Hz, 1H); ESIMS m/z 206.04 ([M+H]$^+$.

3-Methyl-1-(4-vinylphenyl)-1H-1,2,4-triazole (DI64)

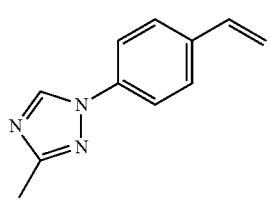

The title compound was isolated as a white solid (0.6 g, 60%): mp 109-111° C.; $^1$H NMR (400 MHz, CDCl$_3$) δ 8.42 (s, 1H), 7.40-7.60 (m, 4H), 6.70-7.00 (dd, J=17.6, 10.8 Hz, 1H), 5.80 (d, J=17.6 Hz, 1H), 5.30 (d, J=17.6 Hz, 1H), 2.50 (s, 3H); ESIMS m/z 186.20 ([M+H]$^+$).

1-(2-(Trifluoromethyl)-4-vinylphenyl)-1H-1,2,4-triazole (DI65)

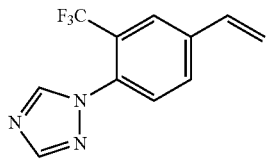 [SMILES: C=Cc1ccc(-n2cncn2)c(C(F)(F)F)c1]

The title compound was isolated as a colorless oil (0.6 g, 60%): $^1$H NMR (400 MHz, CDCl$_3$) δ 8.32 (s, 1H), 8.14 (s, 1H), 7.84 (s, 1H), 7.72 (d, J=8.0 Hz, 1H), 7.50 (d, J=7.6 Hz, 1H), 6.70-6.90 (dd, J=17.6, 10.8 Hz, 1H), 5.90-6.00 (d, J=17.6 Hz, 1H), 5.50-5.80 (d, J=10.8 Hz 1H); ESIMS m/z 240.16 ([M+H]$^+$).

3-Nitro-1-(4-vinylphenyl)-1H-1,2,4-triazole (DI66)

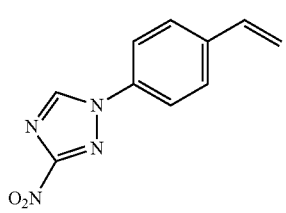 [SMILES: C=Cc1ccc(-n2cnc([N+](=O)[O-])n2)cc1]

The title compound was isolated as a pale yellow solid (61 mg, 20%): mp 137-139° C.; $^1$H NMR (400 MHz, CDCl$_3$) δ 8.60 (s, 1H), 7.68 (d, J=7.7 Hz, 2H), 7.60 (d, J=8.3 Hz, 2H), 6.77 (dd, J=17.7, 10.8, 1H), 5.87 (d, J=17.7 Hz, 1H), 5.42 (d, J=10.8 Hz, 1H); ESIMS m/z 217.28 ([M+H]$^+$).

1-(2-Bromo-4-vinylphenyl)-1H-1,2,4-triazole (DI67)

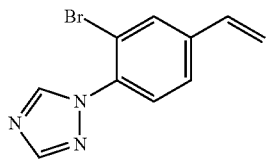

The title compound was isolated as a white solid (1.2 g, 40%): mp 75-77° C.; $^1$H NMR (400 MHz, CDCl$_3$) δ 8.48 (s, 1H), 8.12 (s, 1H), 7.75 (s, 1H) 7.42 (s, 2H), 6.70 (m, 1H), 5.83 (d, J=18 Hz, 1H), 5.42 (d, J=12 Hz, 1H); ESIMS m/z 249.1 ([M]$^+$).

2-(3-Methyl-1H-1,2,4-triazol-1-yl)-5-vinylbenzonitrile (DI68)

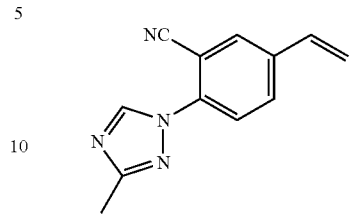

The title compound was isolated as an off-white solid (0.6 g, 60%): mp 96-97° C.; $^1$H NMR (400 MHz, CDCl$_3$) δ 8.66 (s, 1H), 7.80 (s, 1H), 7.74 (m, 2H), 6.73 (dd, J=17.6 Hz, 10.8 Hz, 1H), 5.88 (d, J=17.6 Hz, 1H), 5.49 (d, J=10.8 Hz, 1H), 2.52 (s, 3H); ESIMS m/z 211.10 ([M+H]$^+$); IR (thin film) 2229 cm$^{-1}$.

1-(2-Nitro-4-vinylphenyl)-1H-1,2,4-triazole (DI69)

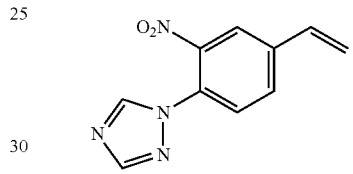

The title compound was isolated as a yellow solid (1.78 g, 60%): mp 102-104° C.; $^1$H NMR (400 MHz, CDCl$_3$) δ 8.40 (s, 1H), 8.12 (s, 1H), 8.02 (s, 1H), 7.72-7.76 (d, J=8.0 Hz, 1H), 7.52-7.56 (d, J=17.6 Hz, 1H), 6.70-6.82 (dd, J=17.6, 10.8 Hz, 1H), 5.85-6.00 (d, J=17.6 Hz, 1H), 5.50-5.60 (d, J=10.8, Hz 1H); ESIMS m/z 217.0 ([M+H]$^+$).

Example 96

Preparation of 3-Methyl-2-(1H-1,2,4-triazol-1-yl)-5-vinylbenzonitrile (DI70)

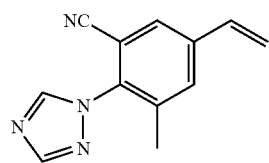 [SMILES: C=Cc1cc(C)c(-n2cncn2)c(C#N)c1]

Step 1. 5-Bromo-2-fluoro-3-methylbenzaldehyde

To a stirred solution of di-isopropyl amine (4.01 g, 39.88 mmol) in THF (20 mL) was added n-BuLi (1.6 M in hexane) (19.9 mL, 31.91 mmol) at −78° C. slowly dropwise over the period of 10 min, the reaction mixture was stirred at −78° C. for 30 min. A solution of 4-bromo-1-fluoro-2-methylbenzene (5.0 g, 26.6 mmol) in THF (30.0 mL) was added at −78° C., and the reaction mixture was stirred for 1 h at the same temperature. DMF (5.0 mL) was added and stirred at −78° C. for another 30 min. The reaction was monitored by TLC; then the reaction mixture was quenched with 1N HCl solution (aq) at 0° C. The aqueous layer was extracted with Et₂O, washed with water and saturated brine solution. The combined organic layer was dried over anhydrous Na₂SO₄ and concentrated under reduced pressure to obtain the crude compound purified by flash column chromatography (SiO₂, 100-200 mesh; eluting with 5% EtOAc/pet ether) to afford the title compound as a white solid (3.6 g, 64%); mp 48-50° C.: ¹H NMR (400 MHz, CDCl₃) δ 8.33 (s, 1H), 8.22 (s, 1H), 7.67 (s, 1H), 7.60 (s, 1H), 6.75 (dd, J=17.6, 10.8 Hz, 1H), 5.92 (dd, J=17.6, 10.8 Hz, 1H), 5.52 (d, J=17.6 Hz, 1H), 2.21 (s, 3H); ESIMS m/z 211.35 ([M−H]⁻).

Step 2.
((E)-5-Bromo-2-fluoro-3-methylbenzaldehyde oxime

To a stirred solution of 5-bromo-2-fluoro-3-methylbenzaldehyde (3.5 g, 16.2 mmol) in ethanol (50.0 mL) were added NaOAc (2.0 g, 24.3 mmol) and hydroxylamine hydrochloride (1.69 g, 24.3 mmol) at ambient temperature. The reaction mixture was stirred at ambient temperature for 3 h. The reaction mixture was concentrated on rotavapour to obtain crude compound, which was washed with water filtered and dried under vacuum to afford the title compound as a white solid: mp 126-127° C.; ¹H NMR (400 MHz, CDCl₃) δ 8.32 (s, 1H), 7.73 (d, J=2.4 Hz, 1H), 7.51 (s, 1H), 7.34 (d, J=2.4 Hz, 1H), 2.25 (s, 3H); ESIMS m/z 232.10 ([M+H]⁺).

Step 3. 5-Bromo-2-fluoro-3-methylbenzonitrile

A stirred solution of (E)-5-bromo-2-fluoro-3-methylbenzaldehyde oxime (0.5 g, 2.2 mmol) in acetic anhydride (5.0 mL) was heated to reflux for 18 h. The reaction mixture was diluted with water and extracted with EtOAc. The combined EtOAc layer was washed with brine and dried over Na₂SO₄ and concentrated under reduced pressure to afford the crude compound as a light brown gummy material (0.4 g, crude): ESIMS m/z 213.82 ([M+H]⁺).

Step 4. 5-Bromo-3-methyl-2-(1H-1,2,4-triazol-1-yl) benzonitrile (DI71)

To a stirred solution of 5-bromo-2-fluoro-3-methylbenzonitrile (1.0 g, 47.716 mmol), in DMF (10.0 mL) was added K₂CO₃ (1.95 g, 14.14 mmol) followed by 1H-1,2,4-triazole (0.811 g, 9.433 mmol) at ambient temperature. The reaction mixture was heated to 140° C. for 18 h. The reaction mixture was cooled to ambient temperature, diluted with water and extracted with EtOAc (2×100 mL). The combined EtOAc layer was washed with brine and dried over Na₂SO₄ and concentrated under reduced pressure to afford the crude compound purified by flash column chromatography (SiO₂, 100-200 mesh; eluting with 30% EtOAc/pet ether) to afford the title compound as a pink solid (0.6 g, 49%): ¹H NMR (400 MHz, CDCl₃) δ 8.39 (s, 1H), 8.23 (s, 1H), 7.91 (d, J=2.4 Hz, 2H), 2.21 (s, 3H), ESIMS m/z 262.57 ([M+H]⁺); IR (thin film) 2231, 554 cm⁻¹.

Step 5. 3-Methyl-2-(1H-1,2,4-triazol-1-yl)-5-vinyl-benzonitrile (DI70)

A mixture of 5-bromo-3-methyl-2-(1H-1,2,4-triazol-1-yl) benzonitrile (0.6 g, 2.3 mmol), K₂CO₃ (0.95 g, 6.87 mmol), vinyl boronic anhydride (0.82 g, 3.43 mmol) and triphenylphosphine (0.13 g, 0.114 mmol) in toluene (20.0 mL) were stirred and degassed with argon for 30 min. The reaction mixture was heated to reflux for 18 h. The reaction mixture was cooled to ambient temperature, diluted with water and extracted with EtOAc (2×100 mL). The combined EtOAc layer was washed with brine, dried over Na₂SO₄ and concentrated under reduced pressure to afford the crude compound that was purified by flash column chromatography (SiO₂, 100-200 mesh; eluting with 30% EtOAc/pet ether) to afford the title compound as a pink solid (0.25 g, 52%): ¹H NMR (400 MHz, CDCl₃) δ 8.33 (s, 1H), 8.22 (s, 1H), 7.67 (s, 1H), 7.60 (s, 1H), 6.75 (dd, J=17.6, 10.8 Hz, 1H), 5.92 (d, J=17.6, 1H), 5.52 (d, J=10.8 Hz, 1H), 2.21 (s, 3H), ESIMS m/z 211.35 ([M+H]⁺); IR (thin film) 2236, 1511 cm⁻¹.

The following compound was made in accordance with the procedures disclosed in Steps 4 and 5 of Example 96.

1-(2-Fluoro-4-vinylphenyl)-1H-1,2,4-triazole (DI72)

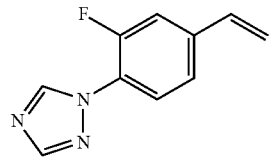

1-(4-Bromo-2-fluorophenyl)-1H-1,2,4-triazole (DI73) was isolated as a pale yellow solid (3.0 g, 75%): mp 113-116° C.; ¹H NMR (400 MHz, CDCl₃) δ 8.69 (s, 1H), 8.13 (m, 2H), 7.50 (m, 1H), 7.21 (m, 1H); ESIMS m/z 241.93 ([M]⁺). The title compound (DI72) was isolated as a yellow solid (1.0 g, 71%): mp 67-70° C.; ¹H NMR (400 MHz, CDCl₃) δ 8.67 (s, 1H), 8.13 (s, 1H), 7.94 (m, 1H), 7.41 (m, 1H), 7.24 (s, 1H), 6.75 (dd, J=17.6, 10.8 Hz, 1H), 5.81 (d, J=17.6 Hz, 1H), 5.37 (d, J=10.8 Hz, 1H); ESIMS m/z 190.00 ([M+H]⁺).

Example 119

Preparation of 1-(1-(4-Vinylphenyl)-1H-1,2,4-triazol-5-yl)ethanone (DI78)

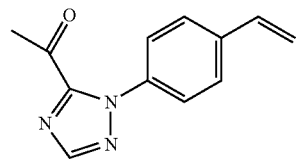 [SMILES: C=Cc1ccc(-n2ncnc2C(C)=O)cc1]

To a stirred solution of 1-(4-vinyl-phenyl)-1H-[1,2,4]triazole (1 g, 5.8 mmol) in 25 mL of THF, was added n-BuLi (0.37 g, 5.8 mmol) at −78° C. and stirred for 30 min. To this N-methoxy-N-methyl acetamide in THF (0.66 g, 6.4 mmol) was added and the resultant reaction mixture was stirred at ambient temperature for 16 h. The reaction mixture was quenched with a saturated aqueous NH₄Cl solution and extracted with EtOAc (3×50 mL). The combined EtOAc layer was washed with brine and dried over sodium sulphate and concentrated under reduced pressure. The crude compound was purified by flash chromatography (SiO₂, 100-200 mesh, 40% EtOAc in Pet ether) to afford the title compound as an off white solid (280 mg, 23%): mp 97-98° C.; ¹H NMR (400 MHz, CDCl₃) δ 8.10 (s, 1H), 7.50 (d, 2H), 7.38 (d, 2H), 6.68 (dd, 1H), 5.85 (d, 1H), 5.38 (d, 1H), 2.75 (s, 3H); ESIMS m/z 214.14 ([M+H]⁺).

Example 120

Preparation of Cyclopropyl(1-(4-vinylphenyl)-1H-1,2,4-triazol-5-yl)methanone (DI79)

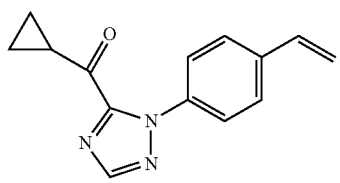 [SMILES: C=Cc1ccc(-n2ncnc2C(=O)C2CC2)cc1]

To a stirred solution of 1-(4-vinyl-phenyl)-1H-[1,2,4]triazole (1 g, 5.8 mmol) in 25 mL of THF, was added n-BuLi (0.37 g, 5.8 mmol) at −78° C. and stirred for 30 min. To this N-methoxy N-methylcyclopropoxide in THF (0.82 g, 6.4 mmol) was added and the resultant reaction mixture was stirred at ambient temperature for 16 h. The reaction mixture was quenched with a saturated aqueous NH$_4$Cl solution and extracted with EtOAc (3×25 mL). The combined EtOAc layer was washed with brine and dried over sodium sulphate and concentrated under reduced pressure. The crude compound was purified by flash chromatography (SiO$_2$, 100-200 mesh, 40% EtOAc in Pet ether) to afford the title compound as an off white solid (420 mg, 30%): mp 90-91° C.; $^1$H NMR (400 MHz, CDCl$_3$) δ 8.12 (s, 1H), 7.50 (d, J=7.8 Hz, 2H), 7.38 (d, J=7.8 Hz, 2H), 6.75 (dd, J=16.3, 10.7 Hz, 1H), 5.81 (d, J=16.3 Hz, 1H), 5.35 (d, J=10.7 Hz, 1H), 3.22 (m, 1H), 1.27 (m, 2H), 1.18 (m, 2H); ESIMS m/z 240.18 ([M+H]$^+$); IR (thin film) 2922, 1630 cm$^{-1}$.

Example 121

Preparation of 5-(Methylthio)-1-(4-vinylphenyl)-1H-1,2,4-triazole (DI80)

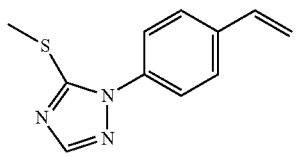

To a stirred solution of 1-(4-vinyl-phenyl)-1H-[1,2,4]triazole (1 g, 5.8 mmol) in 50 mL of THF, was added n-BuLi (0.41 g, 6.4 mmol) at −78° C. and stirred for 30 min. To this dimethyldisulfide in THF (0.6 g, 6.43 mmol) was added and the resultant reaction mixture was stirred at ambient temperature for 16 h. The reaction mixture was quenched with a saturated aqueous NH$_4$Cl solution and extracted with EtOAc (3×25 mL). The combined EtOAc layer was washed with brine and dried over sodium sulphate and concentrated under reduced pressure. The crude compound was purified by flash chromatography (SiO$_2$, 100-200 mesh, 40% EtOAc in Pet ether) to afford the title compound as an off white solid (0.6 g, 48%): mp 68-70° C.; $^1$H NMR (400 MHz, CDCl$_3$) δ 7.96 (s, 1H), 7.05 (m, 4H), 6.75 (dd, J=16.4, 10.7 Hz, 1H), 5.81 (d, J=16.4 Hz, 1H), 5.35 (d, J=10.7 Hz, 1H), 2.73 (s, 3H); ESIMS m/z 218.09 ([M+H]$^+$).

Example 122

Preparation of 5-Methyl-1-(4-vinylphenyl)-1H-1,2,4-triazole (DI81)

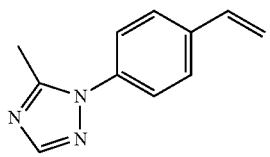

To a stirred solution of 1-(4-vinyl-phenyl)-1H-[1,2,4]triazole (0.5 g, 2.9 mmol) in 10 mL of THF, was added n-BuLi (0.22 g, 3.5 mmol) at −78° C. and stirred for 30 min. To this methyl iodide in THF (0.50 g, 3.5 mmol) was added and the resultant reaction mixture was stirred at ambient temperature for 16 h. The reaction mixture was quenched with a saturated aqueous NH$_4$Cl solution and extracted with EtOAc (3×25 mL). The combined EtOAc layer was washed with brine and dried over sodium sulphate and concentrated under reduced pressure The crude compound was purified by flash chromatography (SiO$_2$, 100-200 mesh, 40% EtOAc in Pet ether) afford the title compound as a pale brown liquid (250 mg, 46%): $^1$H NMR (400 MHz, CDCl$_3$) δ 7.93 (s, 1H), 7.55 (d, J=9 Hz, 2H), 7.42 (d, J=9 Hz, 2H), 6.76 (dd, J=18, 11 Hz, 1H), 5.83 (d, J=18 Hz, 1H), 5.38 (d, J=11 Hz, 1H), 2.55 (s, 3H); ESIMS m/z 186.13 ([M+H]$^+$); IR (thin film) 1517, 1386, 1182, 847 cm$^{-1}$.

Example 97

Preparation of (E)-1-(4-(3-(3,5-Dichlorophenyl)-4,4,4-trifluorobut-1-en-1-yl)phenyl)-1H-1,2,4-triazole (DC1)

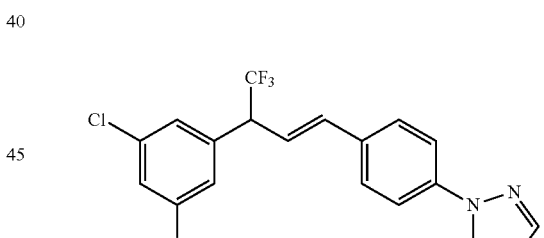

To a stirred solution of 1-(1-bromo-2,2,2-trifluoro-ethyl)-3,5-dichloro-benzene (2.0 g, 6.51 mmol) in 1,2-dichlorobenzene (25 mL), were added 1-(4-vinyl-phenyl)-1H-[1,2,4]triazole (2.22 g, 13.0 mmol), CuCl (64 mg, 0.65 mmol) and 2,2-bipyridyl (0.2 g, 1.3 mmol). The resultant reaction mixture was degassed with argon for 30 min, then stirred at 180° C. for 24 h. After completion of reaction (TLC), the reaction mixture was cooled to ambient temperature and filtered and the filtrate concentrated under reduced pressure. Purification by flash chromatography (SiO$_2$, 100-200 mesh; 25-30% EtOAc in petroleum ether) afforded the title compound as an off-white solid (0.8 g, 32%): mp 93-97° C.; $^1$H NMR (300 MHz, CDCl$_3$) δ 8.56 (s, 1H), 8.11 (s, 1H), 7.68 (d, J=8.4 Hz, 2H), 7.54 (d, J=8.4 Hz, 2H), 7.38 (t, J=1.8 Hz, 1H), 7.29 (s, 2H), 6.62 (d, J=15.6 Hz, 1H), 6.42 (dd, J=15.6, 8.2 Hz, 1H), 4.15 (m, 1H); ESIMS m/z 398.05 ([M+H]$^+$).

Compounds DC2-DC37, DC44, DC45, DC47-49, DC50, DC51, DC54, DC58, DC60, DC62, and DC63-DC67 in Table 1 were made in accordance with the procedures disclosed in Example 97.

Example 98

Preparation of (E)-2-(3-Nitro-1H-1,2,4-triazol-1-yl)-5-(4,4,4-trifluoro-3-(3,4,5-trichlorophenyl)but-1-en-1-yl)benzonitrile (DC40)

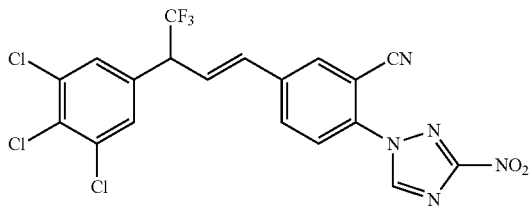

To a stirred solution of 2-(3-nitro-1H-1,2,4-triazol-1-yl)-5-vinylbenzonitrile (0.9 g, 3.7 mmol) in 1,2-dichlorobenzene (10 mL), were added 5-(1-bromo-2,2,2-trifluoroethyl)-1,2,3-trichlorobenzene (2.5 g, 7.5 mmol), CuCl (73 mg, 0.74 mmol) and 2,2-bipyridyl (0.23 g, 1.49 mmol) and the resultant reaction mixture was degassed with argon for 30 min and then stirred at 180° C. for 14 h. After completion of the reaction (TLC), the reaction mixture was cooled to ambient temperature and filtered and the filtrate was concentrated under reduced pressure. Purification by flash chromatography (SiO$_2$, 100-200 mesh, 25-30% EtOAc in Pet ether) afforded the title compound as an off white solid (0.9 g, 50%): mp 70-73° C.; $^1$H NMR (300 MHz, CDCl$_3$) δ 8.86 (s, 1H), 7.88 (m, 3H), 7.44 (s, 2H), 6.67 (d, J=16.0 Hz, 1H), 6.56 (dd, J=16.0, 7.6 Hz, 1H), 4.19 (m, 1H); ESIMS m/z 436.11 ([M−2H]$^−$).

Example 99

Preparation of (E)-2-(3-Amino-1H-1,2,4-triazol-1-yl)-5-(4,4,4-trifluoro-3-(3,4,5-trichlorophenyl)but-1-en-1-yl)benzonitrile (DC41)

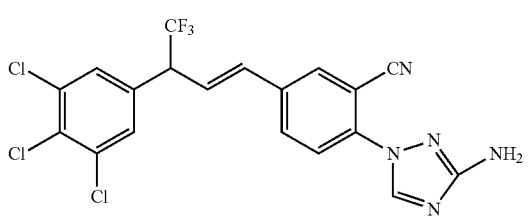 [SMILES: N#Cc1cc(/C=C/C(c2cc(Cl)c(Cl)c(Cl)c2)C(F)(F)F)ccc1-n1cnc(N)n1]

To a stirred solution of (E)-2-(3-nitro-1H-1,2,4-triazol-1-yl)-5-(4,4,4-trifluoro-3-(3,4,5-trichlorophenyl)but-1-enyl)benzonitrile (0.6 g, 1.2 mmol) in MeOH (10 mL), were added Zn dust (0.39 g, 5.98 mmol) and saturated aqueous NH$_4$Cl solution (5 mL) and the resultant reaction mixture was stirred at ambient temperature for 2 h. After completion of the reaction (TLC), the reaction mass was concentrated under reduced pressure. The reaction mass was diluted with CH$_2$Cl$_2$, filtered through a Celite® bed, and the obtained filtrate concentrated under reduced pressure to afford the title compound as a solid (0.5 g, 89%): mp 72-75° C.; $^1$H NMR (300 MHz, DMSO-d$_6$) δ 8.72 (s, 1H), 8.26 (s, 1H), 8.01 (d, J=8.4 Hz, 1H), 7.91 (s, 2H), 7.77 (d, J=8.4 Hz, 1H), 6.42 (dd, J=15.6, 9.2 Hz, 1H), 6.83 (d, J=15.6 Hz, 1H), 5.87 (s, 2H), 4.89 (m, 1H); ESIMS m/z 469.95 ([M−H]$^−$).

Compound DC38 in Table 1 was made in accordance with the procedures disclosed in Example 99. Also, compound DC55 in Table 1 was made from compound DC54 in accordance with the procedures disclosed in Example 99, with the exception of using ammonium formate in place of NH$_4$Cl.

Example 100

Preparation of (E)-N-(1-(2-Cyano-4-(4,4,4-trifluoro-3-(3,4,5-trichlorophenyl)but-1-en-1-yl)phenyl)-1H-1,2,4-triazol-3-yl)-N-(cyclopropanecarbonyl)cyclopropanecarboxamide (DC42)

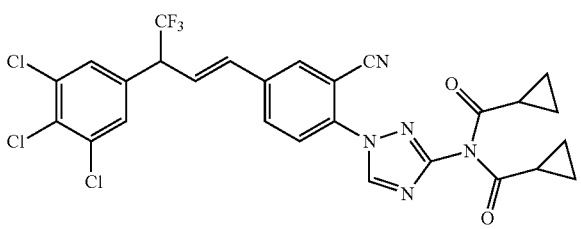 [SMILES: N#Cc1cc(/C=C/C(c2cc(Cl)c(Cl)c(Cl)c2)C(F)(F)F)ccc1-n1cnc(N(C(=O)C2CC2)C(=O)C2CC2)n1]

To a stirred solution of (E)-2-(3-amino-1H-1,2,4-triazol-1-yl)-5-(4,4,4-trifluoro-3-(3,4,5-trichlorophenyl)but-1-enyl)benzonitrile (0.1 g, 0.21 mmol) in CH$_2$Cl$_2$ at ambient temperature, was added cyclopropylcarbonyl chloride (0.045 g, 0.42 mmol) and the reaction mixture was stirred for 2 h at ambient temperature. The reaction mixture was diluted with CH$_2$Cl$_2$ and washed with water and brine and dried over Na$_2$SO$_4$. Concentration under reduced pressure and purification by preparative HPLC afforded the title compound as a solid (0.09 g, 79%): mp 104-107° C.; $^1$H NMR (300 MHz, CDCl$_3$) δ 8.78 (s, 2H), 7.83 (s, 1H), 7.80 (m, 2H), 7.42 (s, 2H), 6.65 (d, J=16.4 Hz, 1H), 6.51 (dd, J=7.6, 8.0 Hz, 1H), 4.17 (m, 1H), 2.16 (m, 2H), 1.25 (m, 4H), 1.00 (m, 4H); ESIMS m/z 609.98 ([M+H]$^+$); IR (thin film) 2234, 1714, 1114, 807 cm$^{−1}$.

Example 101

Preparation of (E)-N-(1-(2-Cyano-4-(4,4,4-trifluoro-3-(3,4,5-trichlorophenyl)but-1-en-1-yl)phenyl)-1H-1,2,4-triazol-3-yl)cyclopropanecarboxamide (DC43)

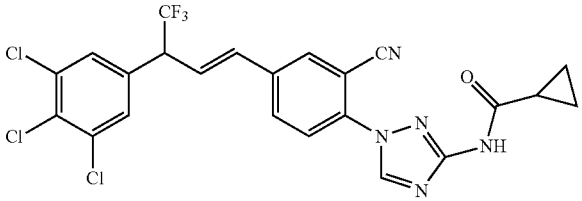 [SMILES: N#Cc1cc(/C=C/C(c2cc(Cl)c(Cl)c(Cl)c2)C(F)(F)F)ccc1-n1cnc(NC(=O)C2CC2)n1]

To a stirred solution of (E)-2-(3-amino-1H-1,2,4-triazol-1-yl)-5-(4,4,4-trifluoro-3-(3,4,5-trichlorophenyl)but-1-enyl)benzonitrile (0.15 g, 0.31 mmol) in CH$_2$Cl$_2$ at 0° C., were added TEA (0.1 g, 1 mmol) and cyclopropylcarbonyl chloride (0.04 g, 0.38 mmol) and the reaction mixture was stirred for 1 h at 0° C. The reaction mixture was diluted with CH$_2$Cl$_2$ and washed with water and brine and dried over Na$_2$SO$_4$. Concentration under reduced pressure and purification by column chromatography (SiO$_2$, 100-200 mesh) afforded the title compound as a solid (66 mg, 34%): mp 109-112° C.; $^1$H NMR (300 MHz, DMSO-d$_6$) δ 10.94 (br s, 1H), 8.36 (s, 1H), 8.08 (m, J=8.4 Hz, 1H), 7.91 (s, 2H), 7.84 (d, J=8.4 Hz, 1H), 7.13 (dd, J=15.6, 9.2 Hz, 1H), 6.87 (d, J=15.6 Hz, 1H), 4.92 (m, 1H), 1.99 (br s, 1H), 0.82 (s, 4H); ESIMS m/z 540.04 ([M+H]$^+$); IR (thin film) 3233, 2233, 1699, 1114, 807 cm$^{-1}$.

Compound DC39 in Table 1 was made in accordance with the procedures disclosed in Example 101.

Example 102

Preparation of 1-(4-(1H-1,2,4-triazol-1-yl)phenyl) ethanone (DI74)

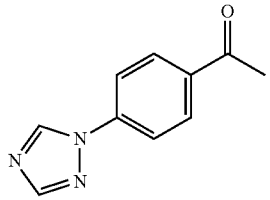

To a stirred solution of 4-bromoacetophenone (10 g, 50 mmol) in DMF (100 mL), were added 1,2,4-triazole (5 g, 75 mmol), Cs$_2$CO$_3$ (32.6 g, 100.5 mmol) and CuI (1.4 g, 10.1 mmol) and the resultant reaction mixture was refluxed for 48 h. After completion of the reaction (by TLC), the reaction mixture was cooled to ambient temperature and diluted with water (200 mL) and extracted with EtOAc. The combined organic layer was washed with brine and dried over Na$_2$SO$_4$ and concentrated under reduced pressure. Purification by washing with Et$_2$O afforded the title compound as a solid (5 g, 96%): $^1$H NMR (400 MHz, CDCl$_3$) δ 8.71 (s, 1H), 8.16, (s, 1H), 8.13 (d, J=8.6 Hz, 2H), 7.83 (d, J=8.6 Hz, 2H), 2.66 (s, 3H); ESIMS m/z 186.02 ([M−H]$^-$).

Example 103

Preparation of 1-(4-(1H-1,2,4-triazol-1-yl)phenyl)- 3-(3,5-dichlorophenyl)-4,4,4-trifluorobutan-1-one (DI75)

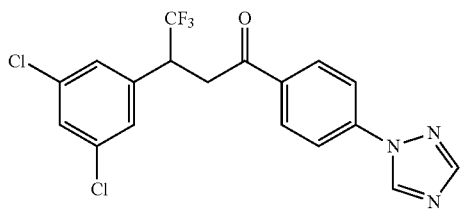 [SMILES: O=C(CC(c1cc(Cl)cc(Cl)c1)C(F)(F)F)c1ccc(-n2cncn2)cc1]

Step 1. 1-(4-(1-(Trimethylsilyloxy)vinyl)phenyl)- 1H-1,2,4-triazole (DI76)

To a stirred solution of 1-(4-(1H-1,2,4-triazol-1-yl)phenyl)ethanone (4.5 g, 24.0 mmol) in CH$_2$Cl$_2$ at 0° C., were added TEA (3.7 g, 36.1 mmol) and trimethylsilyl trifluoromethanesulfonate (8 g, 36 mmol) and the resultant reaction mixture was stirred for 1 h. The reaction mixture was quenched with a mixture of sat aqueous NaHCO$_3$ solution and ether. The ether layer and was separated, washed with brine, dried over Na$_2$SO$_4$ and concentrated under reduced pressure to afford the title compound (5.5 g) which was taken directly to next step.

Step 2. 1-(4-(1H-1,2,4-Triazol-1-yl)phenyl)-3-(3,5-dichlorophenyl)-4,4,4-trifluorobutan-1-one (DI75)

To a stirred solution of 1-(4-(1-(trimethylsilyloxy)vinyl) phenyl)-1H-1,2,4-triazole (6 g, 23 mmol) and 1-(1-bromo-2,2,2-trifluoro-ethyl)-3,5-dichlorobenzene (7.1 g, 34.7 mmol) in 1,2-dichlorobenzene (30 mL) was degassed with argon. To this CuCl (0.23 g, 2.31 mmol) and 2,2-bipyridyl (0.73 g, 4.63 mmol) was added to the above reaction mixture and the resultant reaction mixture was heated to 180° C. for 18 h. After completion of the reaction (by TLC), the reaction mixture was absorbed onto silica gel and purified by column chromatography (SiO2; 10% EtOAc in petroleum ether) to afford title compound as a solid (3 g, 31%): $^1$H NMR (400 MHz, CDCl$_3$) δ 8.67 (s, 1H), 8.15 (s, 1H), 8.10 (d, J=8.3 Hz, 2H), 7.82 (d, J=8.3 Hz, 2H), 7.33 (m, 1H), 7.30 (m, 2H), 4.20 (m, 1H), 3.63 (m, 2H); ESIMS m/z 412.14 ([M−H]$^-$).

Example 104

Preparation of 2-(4-(1H-1,2,4-triazol-1-yl)phenyl)- 4-(3,5-dichlorophenyl)-5,5,5-trifluoropentan-2-ol (DI77)

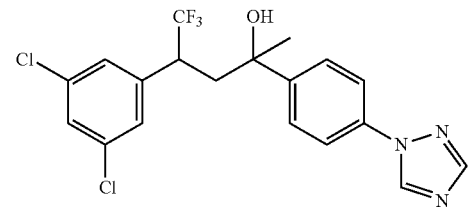 [SMILES: CC(O)(CC(c1cc(Cl)cc(Cl)c1)C(F)(F)F)c1ccc(-n2cncn2)cc1]

To a solution of 1-(4-(1H-1,2,4-triazol-1-yl)phenyl)-3-(3, 5-dichlorophenyl)-4,4,4-trifluorobutan-1-one (300 mg, 0.726 mmol) in THF cooled to 0° C. was added methylmagnesium bromide (450 mg, 5 mmol) drop wise. The reaction was stirred for 3 h at 0° C., then the reaction mixture was quenched with sat aqueous NH$_4$Cl solution and extracted with EtOAc. The combined EtOAc layer was washed with water and brine, dried over Na$_2$SO$_4$ and concentrated under reduced pressure. Purification by column chromatography (SiO$_2$, 100-200 mesh; 20%-25% EtOAc in petroleum ether) afforded the title compound as a solid (100 mg, 32%): $^1$H NMR (400 MHz, CDCl$_3$) δ two diastereoisomers 8.58 (s, 1H, minor), 8.48 (s, 1H, major), 8.13 (s, 1H, minor), 8.09 (s, 1H, major), 7.70 (d, J=9.0 Hz, 2H, minor), 7.53 (d, J=9.0 Hz, 2H, minor), 7.40 (d, J=9.0 Hz, 2H, major), 7.31 (m, 1H, minor), 7.27 (d, J=9.0 Hz, 2H, major), 7.20 (m, 2H, minor), 7.01 (m, 1H, major), 6.75 (m, 2H, major), 350 (m, 1H), 2.50 (m, 2H), 1.56 (s, 3H, major), 1.54 (s, 3H, minor); ESIMS m/z 430.05 ([M+H]$^+$).

Example 105

Preparation of (E)-1-(4-(4-(3,5-Dichlorophenyl)-5,5,5-trifluoropent-2-en-2-yl)phenyl)-1H-1,2,4-triazole (DC68)

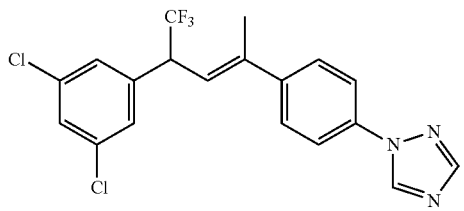 [SMILES: C/C(=C\C(c1cc(Cl)cc(Cl)c1)C(F)(F)F)c1ccc(-n2cncn2)cc1]

To a solution of 2-(4-(1H-1,2,4-triazol-1-yl)phenyl)-4-(3,5-dichlorophenyl)-5,5,5-trifluoropentan-2-ol (100 mg, 0.233 mmol) in toluene was added a catalytic amount of p-toluenesulfonic acid and the water was removed by azeotropic distillation over the course of 12 h. The reaction mixture was cooled to room temperature and dissolved in EtOAc. The solution was washed with sat aqueous $NaHCO_3$ solution and brine, dried over $Na_2SO_4$ and concentrated under reduced pressure. Purification by column chromatography ($SiO_2$, 100-200 mesh; 20%-25% EtOAc in petroleum ether) afforded the title compound as a solid (30 mg, 31%).

Example 123

Preparation of (E)-5-(3-(3,5-Dichlorophenyl)-4,4,4-trifluorobut-1-en-1-yl)-2-(1H-1,2,4-triazol-1-yl)benzaldehyde (DC52)

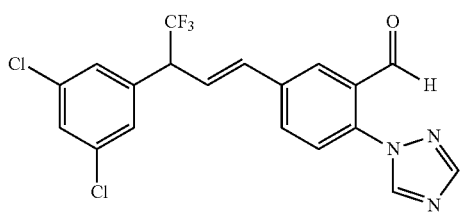 [SMILES: O=Cc1cc(/C=C/C(c2cc(Cl)cc(Cl)c2)C(F)(F)F)ccc1-n1cncn1]

To a stirred solution of (E)-5-(3-(3,5-dichlorophenyl)-4,4,4-trifluorobut-1-en-1-yl)-2-(1H-1,2,4-triazol-1-yl)benzonitrile (0.3 g, 0.71 mmol) in toluene (10 mL) at −78° C. was added dropwise diisobutylaluminum hydride (DIBAL-H, 1.0 M solution in toluene; 0.85 mL), and the reaction mixture was stirred at −78° C. for 20 min. The reaction mixture was quenched with the addition of 1 N HCl solution, then the aqueous layer was extracted with EtOAc (2×). The combined organic layers were washed with brine, dried over $Na_2SO_4$ and concentrated under reduced pressure. The crude compound was purified by flash column chromatography ($SiO_2$; 50% EtOAc/Pet ether) to afford the title compound as a yellow oil.

Compound DC53 in Table 1 was made in accordance with the procedures disclosed in Example 123.

Example 124

Preparation of (E)-5-(3-(3,5-Dichlorophenyl)-4,4,4-trifluorobut-1-en-1-yl)-N-methyl-2-(1H-1,2,4-triazol-1-yl)aniline (DC57)

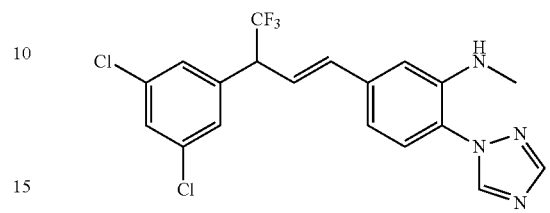

To a stirred solution of (E)-5-(3-(3,5-dichlorophenyl)-4,4,4-trifluorobut-1-en-1-yl)-2-(1H-1,2,4-triazol-1-yl)aniline (0.3 g, 0.7 mmol) in $CH_2Cl_2$ (10 mL) was added TEA (0.155 mL, 1.09 mmol) and methyl iodide (0.124 g, 0.873 mmol). The reaction was stirred at ambient temperature for 18 h. The $CH_2Cl_2$ layer was washed with water and brine, dried over $Na_2SO_4$ and concentrated under reduced pressure. The crude compound was purified by flash column chromatography ($SiO_2$; 50% EtOAc/Pet ether) to afford the title compound as a yellow semi-solid (0.07 g, 70%).

Example 125

Preparation of (E)-5-(3-(3,5-Dichlorophenyl)-4,4,4-trifluorobut-1-en-1-yl)-2-(1H-1,2,4-triazol-1-yl)benzoic acid (DC61)

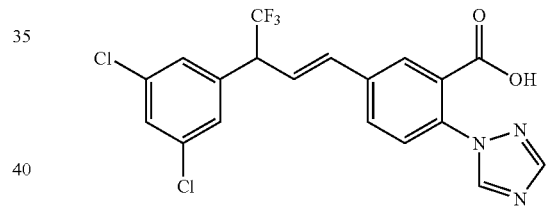

A solution of (E)-ethyl 5-(3-(3,5-dichlorophenyl)-4,4,4-trifluorobut-1-en-1-yl)-2-(1H-1,2,4-triazol-1-yl)benzoate (0.2 g, 0.4 mmol) in 6 N HCl (10 mL) was stirred at 100° C. for 18 h. The reaction was cooled to ambient temperature, resulting in a white solid precipitate. The precipitate was filtered to afford the title compound as a white solid (0.12 g, 60%).

Example 126

Preparation of (Z)-5-((E)-3-(3,5-Dichlorophenyl)-4,4,4-trifluorobut-1-en-1-yl)-N'-hydroxy-2-(1H-1,2,4-triazol-1-yl)benzimidamide (DC59)

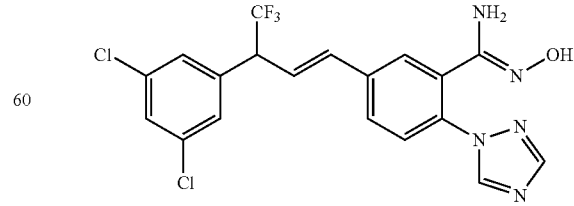

A solution of (E)-5-(3-(3,5-dichlorophenyl)-4,4,4-trifluorobut-1-en-1-yl)-2-(1H-1,2,4-triazol-1-yl)benzonitrile (0.3 g, 0.71 mmol), NaOAc (0.087 g, 1.065 mmol) and hydroxylammonium chloride (0.072 g, 1.065 mmol) in 9:1 ethanol/water mixture (10 mL) was stirred at 70° C. for 8 h. The reaction was cooled to ambient temperature, and the ethanol was evaporated. The residue was dissolved in water and extracted with EtOAc (2×). The combined organic layers were washed with brine, dried over $Na_2SO_4$ and concentrated under reduced pressure to afford the title compound as an off white solid.

Example 127

Preparation of (E)-1-(4-(3-(3,5-Dichlorophenyl)-4,4,4-trifluoro-3-methoxybut-1-en-1-yl)phenyl)-1H-1,2,4-triazole (DC70)

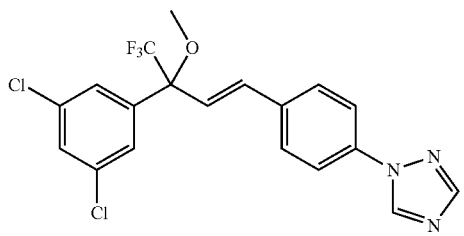 [SMILES: COC(/C=C/c1ccc(-n2cncn2)cc1)(c1cc(Cl)cc(Cl)c1)C(F)(F)F]

Step 1. (E)-3-(4-(1H-1,2,4-triazol-1-yl)phenyl)-1-(3,5-dichlorophenyl)prop-2-en-1-one To a solution of 1-(3,5-dichlorophenyl)ethanone (0.5 g, 2.6 mmol) in ethanol (20 mL) was added 4-(1H-1,2,4-triazol-1-yl)benzaldehyde (0.46 g, 2.65 mmol) and the reaction was cooled to 0° C. NaOH (0.22 g, 5.29 mmol) in water (10 mL) was then added and the reaction was allowed to stir for 2 h at 0° C. The reaction was extracted with EtOAc and the combined organic layers were dried over $Na_2SO_4$ and concentrated under reduced pressure to afford the title compound (0.149 g, 17%):); ESIMS m/z 430.05 ([M+H]$^+$) 344.08

Step 2. (E)-4-(4-(1H-1,2,4-triazol-1-yl)phenyl)-2-(3,5-dichlorophenyl)-1,1,1-trifluorobut-3-en-2-ol (DC69)

To a solution of (E)-3-(4-(1H-1,2,4-triazol-1-yl)phenyl)-1-(3,5-dichlorophenyl)prop-2-en-1-one (1 g, 3 mmol) in THF (150 mL) was added trifluoromethyltrimethylsilane (0.517 g, 3.644 mmol) and tetra-n-butylammonium fluoride (TBAF) (1.0 M, 1 mL) at 0° C. The reaction was slowly warmed to ambient temperature and allowed to stir for 2 h. The reaction was then cooled to 0° C. and 5 M HCl solution was added and the reaction was stirred for an additional 4 h at ambient temperature. The reaction was extracted with $CH_2Cl_2$ and the combined organic layers were dried over $Na_2SO_4$ and concentrated under reduced pressure. The crude compound was purified by flash column chromatography ($SiO_2$; 25% EtOAc/hexanes) to afford the title compound as an off-white solid (0.3 g, 25%).

Step 3. (E)-1-(4-(3-(3,5-Dichlorophenyl)-4,4,4-trifluoro-3-methoxybut-1-en-1-yl)phenyl)-1H-1,2,4-triazole (DC70)

To a solution of (E)-4-(4-(1H-1,2,4-triazol-1-yl)phenyl)-2-(3,5-dichlorophenyl)-1,1,1-trifluorobut-3-en-2-ol (0.15 g, 0.36 mmol) in THF (5 mL) was added NaH (60%, 10 mg, 0.44 mmol) at 0° C. The reaction was allowed to stir at 0° C. for 30 min, then methyl iodide (61 mg, 0.44 mmol) was added slowly and the reaction was warmed to ambient temperature and allowed to stir for 4 h. The reaction was quenched with aqueous $NH_4Cl$ solution and extracted with $CH_2Cl_2$. The combined organic layers were dried over $Na_2SO_4$ and concentrated under reduced pressure to afford the title compound as an off-white solid (55 mg, 35%).

Example 128

Preparation of tert-Butyl (2-methyl-1-oxo-1-((2,2,2-trifluoroethyl)amino)propan-2-yl)carbamate

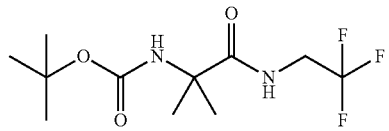 [SMILES: CC(C)(C)OC(=O)NC(C)(C)C(=O)NCC(F)(F)F]

To a stirred solution of 2-((tert-butoxycarbonyl)amino)-2-methylpropanoic acid (4.58 g, 22.6 mmol) in methylene chloride (50 mL) was added EDC HCl (4.75 g, 24.8 mmol) followed by 2,2,2-trifluoroethylamine (2.67 g, 27.0 mmol) and DMAP (3.03 g, 24.8 mmol). The reaction mixture was stirred at ambient temperature for 18 h, then washed with aqueous 5% $NaHSO_4$ (2×), aqueous 10% HCl (1×) and aqueous saturated $NaHCO_3$ (2×). The organic phase was dried ($MgSO_4$) and concentrated in vacuo to afford the title compound as a white solid (2.97 g, 46%).

The following molecules were made in accordance with the procedures disclosed in Example 128:

(S)-tert-Butyl (1-oxo-1-((2,2,2-trifluoroethyl)amino)butan-2-yl)carbamate

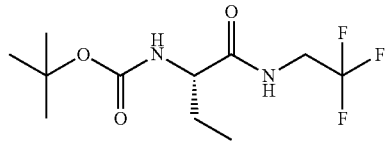 [SMILES: CC[C@H](NC(=O)OC(C)(C)C)C(=O)NCC(F)(F)F]

The title molecule was isolated as a white solid: mp 108-111° C.; $^1$H NMR (400 MHz, CDCl$_3$) δ 6.90 (s, 1H), 5.04 (m, 1H), 4.07 (m, 1H), 3.92 (m, 3H), 1.87 (m, 1H), 1.66 (m, 1H), 1.44 (s, 9H), 0.96 (t, J=7.4 Hz, 3H); $^{19}$F NMR (376 MHz, CDCl$_3$) δ −72.54; $^{13}$C NMR (101 MHz, CDCl$_3$) δ 173.05, 156.04, 124.03 (q, J=278.5 Hz), 80.30, 55.56, 40.43 (q, J=34.7 Hz), 28.19, 25.63, 9.80; [α]$_D$=−33.3 (c, 10.1 mg/mL in $CH_2Cl_2$).

tert-Butyl (1-oxo-1-((2,2,2-trifluoroethyl)amino)butan-2-yl)carbamate

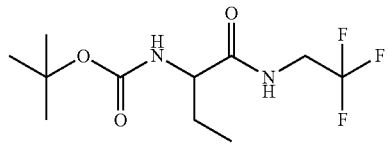 [SMILES: CCC(NC(=O)OC(C)(C)C)C(=O)NCC(F)(F)F]

The title molecule was isolated as a white solid: mp 113-116° C.; $^1$H NMR (400 MHz, CDCl$_3$) δ 7.36 (d, J=8.4 Hz, 1H), 5.43-5.25 (m, 1H), 4.16 (m, 1H), 3.98 (m, 1H), 3.82 (m, 1H), 1.84 (dt, J=14.0, 7.0 Hz, 1H), 1.66 (dt, J=14.2, 7.3 Hz, 1H), 1.44 (s, 9H), 0.95 (t, J=7.3 Hz, 3H); $^{19}$F NMR (376 MHz, CDCl$_3$) δ -72.51; $^{13}$C NMR (101 MHz, CDCl$_3$) δ 172.94, 156.02, 124.47 (q, J=380.8 Hz), 80.33, 55.54, 40.46 (q, J=34.8 Hz), 28.19, 25.61, 9.79.

tert-Butyl (2-oxo-2-((1,1,1-trifluoropropan-2-yl) amino)ethyl)carbamate

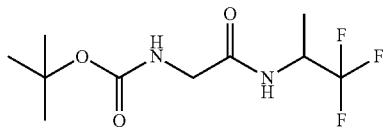 [SMILES: CC(NC(=O)CNC(=O)OC(C)(C)C)C(F)(F)F]

The title molecule was isolated as a white solid: mp 84-88° C.; $^1$H NMR (400 MHz, CDCl$_3$) δ 6.89 (s, 1H), 5.44 (t, J=5.8 Hz, 1H), 4.77-4.48 (m, 1H), 3.83 (d, J=5.9 Hz, 2H), 1.45 (s, 9H), 1.33 (d, J=7.0 Hz, 3H); $^{19}$F NMR (376 MHz, CDCl$_3$) δ -77.63; $^{13}$C NMR (101 MHz, CDCl$_3$) δ 169.84, 156.33, 125.19 (q, J=280.9 Hz), 80.29, 46.20 (q, J=31.7 Hz), 44.15, 28.11, 13.88; EIMS m/z 270 ([M]$^+$).

(R)-tert-Butyl (1-((2-fluoroethyl)amino)-1-oxopropan-2-yl)carbamate

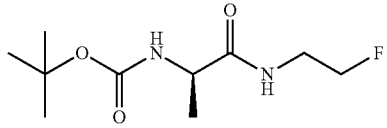 [SMILES: C[C@@H](NC(=O)OC(C)(C)C)C(=O)NCCF]

The title molecule was isolated as a white solid: mp 91-94° C.; $^1$H NMR (300 MHz, DMSO-d$_6$) δ 7.98 (bs, 1H), 6.87 (t, J=7.2 Hz, 1H), 4.47 (t, J=4.8 Hz, 1H), 4.32 (t, J=5.1 Hz, 1H), 3.97-3.92 (m, 1H), 3.41-3.37 (m, 1H), 3.33-3.28 (m, 1H), 1.37 (s, 9H), 1.16 (d, J=7.3 Hz, 3H); ESIMS m/z 235.0 ([M+H]$^+$).

tert-Butyl (3-oxo-3-((2,2,2-trifluoroethyl)amino) propyl)carbamate

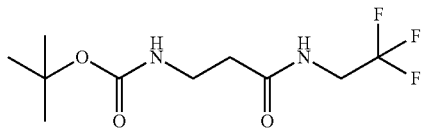 [SMILES: CC(C)(C)OC(=O)NCCC(=O)NCC(F)(F)F]

The title molecule was isolated as a white solid: mp 123-125° C.; $^1$H NMR (400 MHz, CDCl$_3$) δ 6.42-6.22 (m, 1H), 5.07 (s, 1H), 3.92 (qd, J=9.1, 6.4 Hz, 2H), 3.43 (q, J=6.2 Hz, 2H), 2.50 (t, J=6.0 Hz, 2H), 1.43 (s, 9H); $^{19}$F NMR (376 MHz, CDCl$_3$) δ -72.50; $^{13}$C NMR (101 MHz, CDCl$_3$) δ 171.76, 156.30, 124.02 (q, J=278.5 Hz), 79.67, 40.53 (q, J=34.8 Hz), 36.41, 36.27, 28.31.

(R)-tert-Butyl (1-(ethylamino)-1-oxopropan-2-yl) carbamate

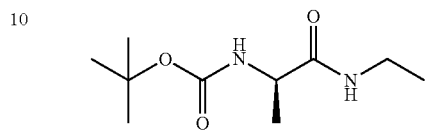

The title molecule was isolated as a white solid: mp 88-93° C.; $^1$H NMR (400 MHz, CDCl$_3$) δ 6.35 (s, 1H), 5.25-5.04 (m, 1H), 4.21-3.99 (m, 1H), 3.29 (dd, J=7.5, 5.9 Hz, 2H), 1.45 (s, 8H), 1.35 (d, J=7.0 Hz, 3H), 1.13 (t, J=7.3 Hz, 3H); $^{13}$C NMR (101 MHz, CDCl$_3$) δ 172.79, 155.51, 79.59, 49.97, 34.16, 28.25, 18.77, 14.60.

(R)-tert-Butyl (1-oxo-1-((3,3,3-trifluoropropyl) amino)propan-2-yl)carbamate

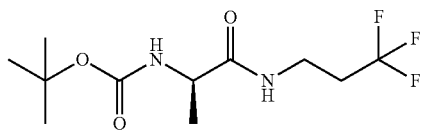 [SMILES: C[C@@H](NC(=O)OC(C)(C)C)C(=O)NCCC(F)(F)F]

The title molecule was isolated as an off white solid: mp 101-105° C.; $^1$H NMR (300 MHz, DMSO-d$_6$) δ 7.96 (bs, 1H), 6.90 (d, J=6.9 Hz, 1H), 3.91-3.86 (m, 1H), 3.34-3.19 (m, 2H), 2.50-2.32 (m, 2H), 1.37 (s, 9H), 1.15 (d, J=7.2 Hz, 3H).

(R)-tert-Butyl (1-oxo-1-((2,2,2-trifluoroethyl)amino) pentan-2-yl)carbamate

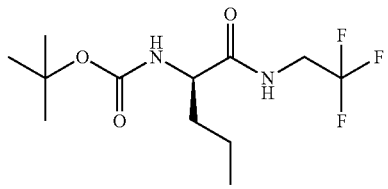 [SMILES: CCC[C@@H](NC(=O)OC(C)(C)C)C(=O)NCC(F)(F)F]

The title molecule was isolated as a white solid: mp 107-122° C.; $^1$H NMR (400 MHz, CDCl3) δ 6.90 (s, 1H), 5.00 (d, J=8.0 Hz, 1H), 4.12 (d, J=7.3 Hz, 1H), 3.99-3.76 (m, 2H), 1.87-1.73 (m, 1H), 1.65-1.52 (m, 1H), 1.44 (s, 9H), 1.38 (m, 2H), 0.94 (t, J=7.3 Hz, 3H); $^{19}$F NMR (376 MHz, CDCl$_3$) δ rotomer -72.55, -73.27; $^{13}$C NMR (101 MHz, CD$_3$OD) δ rotomers 176.08, 157.86, minor 126.13 (q, J=279.8 Hz), major 125.83 (q, J=278.8 Hz), 80.65, 55.90, minor 42.27 (q, J=35.4 Hz), major 41.24 (q, J=35.4 Hz), 35.50, 28.73, 20.04, 14.03.

(R)-Benzyl (3-methyl-1-oxo-1-((2,2,2-trifluoroethyl)amino)butan-2-yl)carbamate

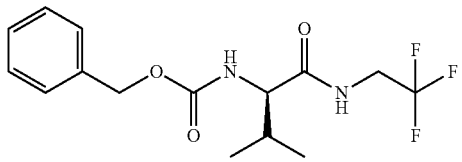 [SMILES: CC(C)[C@@H](NC(=O)OCc1ccccc1)C(=O)NCC(F)(F)F]

The title molecule was isolated as a white solid: mp 157-161° C.; ¹H NMR (400 MHz, CDCl₃) δ 7.46-7.31 (m, 5H), 6.57 (d, J=8.3 Hz, 1H), 5.34 (d, J=8.9 Hz, 1H), 5.11 (s, 2H), 4.02 (dq, J=16.1, 8.8, 7.7 Hz, 2H), 3.78 (td, J=9.0, 4.7 Hz, 1H), 2.15 (q, J=6.7 Hz, 1H), 0.97 (d, J=6.8 Hz, 3H), 0.94 (d, J=6.8 Hz, 3H); ¹⁹F NMR (376 MHz, CDCl₃) δ −72.44.

Example 129

Preparation of N-(2,2,2-Trifluoroethyl) 1-amino-2-methylpropanecarboxamide hydrochloride

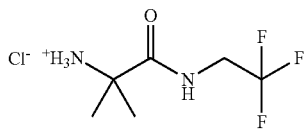

To tert-butyl (2-methyl-1-oxo-1-((2,2,2-trifluoroethyl)amino)propan-2-yl)carbamate (2.61 g, 9.18 mmol) in methylene chloride (20 mL) was added 4 M HCl in dioxane (20 mL). The solution was stirred for 6 h at ambient temperature. The reaction mixture was concentrated in vacuo to afford the title compound as a white solid (2.18 g).

The following molecules were made in accordance with the procedures disclosed in Example 129:

(R)-1-Oxo-1-((2,2,2-trifluoroethyl)amino)propan-2-aminium chloride

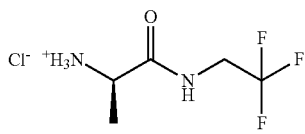

The title molecule was isolated as a white solid: mp 210-213° C.; ¹H NMR (400 MHz, DMSO-d₆) δ 9.22 (t, J=6.3 Hz, 1H), 8.37-8.27 (m, 3H), 4.07-3.95 (m, 2H), 3.95-3.84 (m, 1H), 1.38 (d, J=7.0 Hz, 3H); ¹⁹F NMR (376 MHz, DMSO-d₆) δ −0.75; [α]=−6.6 (c, 5.0 mg/mL in MeOH).

1-Oxo-1-((2,2,2-trifluoroethyl)amino)butan-2-aminium chloride

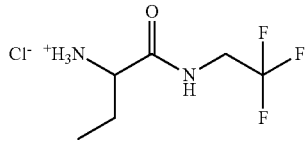

The title molecule was isolated as a white solid: ¹H NMR (300 MHz, DMSO-d₆) δ 9.12 (t, J=5.7 Hz, 1H), 8.19 (s, 3H), 4.14-3.93 (m, 2H), 3.78 (t, J=6.0 Hz, 1H), 1.81-1.71 (m, 2H), 0.88 (t, J=7.2 Hz, 3H); ESIMS m/z 184.90 ([M−TFA)+H]⁺); IR (thinfilm) 3269, 1681, 1158 cm⁻¹.

2-Oxo-2-((1,1,1-trifluoropropan-2-yl)amino)ethan-aminium chloride

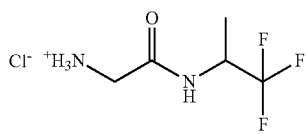

The title molecule was isolated as a white solid: ¹H NMR (300 MHz, DMSO-d₆) δ 8.96 (d, J=8.7 Hz, 1H), 8.09 (bs, 3H), 4.71-4.59 (m, 1H), 3.64-3.62 (m, 2H), 1.27 (d, J=6.9 Hz, 3H); EIMS m/z 170.1 ([M]⁺).

(R)-1-((2-Fluoroethyl)amino)-1-oxopropan-2-aminium chloride

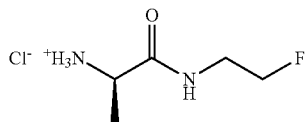

The title molecule was isolated as a white solid: ¹H NMR (300 MHz, DMSO-d₆) δ 8.76 (t, J=5.1 Hz, 1H), 8.21 (bs, 3H), 4.54 (t, J=5.1 Hz, 1H), 4.38 (t, J=4.8 Hz, 1H), 3.85-3.79 (m, 1H), 3.50-3.45 (m, 1H), 3.41-3.36 (m, 1H), 1.36 (d, J=7.2 Hz, 3H); ESIMS m/z 135.1 ([M+H]⁺); IR (thinfilm) 3331, 2983-1660, 1161, 597 cm⁻¹.

3-Oxo-3-((2,2,2-trifluoroethyl)amino)propan-1-aminium chloride

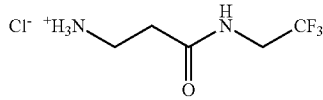 [SMILES: [Cl-] ; [NH3+]CCC(=O)NCC(F)(F)F]

The title molecule was isolated as a white solid: mp 193-197° C.; ¹H NMR (400 MHz, DMSO-d₆) δ 8.94 (t, J=6.4 Hz, 1H), 8.16 (s, 3H), 3.99-3.79 (m, 2H), 2.98 (t, J=7.3 Hz, 2H), 2.64 (t, J=7.3 Hz, 2H); ¹⁹F NMR (376 MHz, DMSO-d₆) δ −70.74.

(R)-1-(Ethylamino)-1-oxopropan-2-aminium chloride

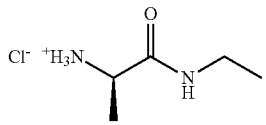

The title molecule was isolated as a white solid: mp 223-236° C.; ¹H NMR (400 MHz, DMSO-d₆) δ 8.65 (t, J=5.4 Hz, 1H), 8.32 (s, 3H), 3.89-3.66 (m, 1H), 3.12 (p, J=7.0 Hz, 2H), 1.35 (d, J=6.9 Hz, 3H), 1.05 (t, J=7.2 Hz, 3H); ¹³C NMR (101 MHz, DMSO-d₆) δ 168.98, 48.08, 33.54, 17.16, 14.43.

(R)-1-Oxo-1-((3,3,3-trifluoropropyl)amino)propan-2-aminium chloride

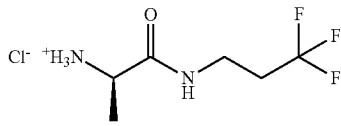

The title molecule was isolated as an off white solid: mp 128-131° C.; ¹H NMR (300 MHz, DMSO-d₆) δ 8.62 (bs, 1H), 8.10 (bs, 3H), 3.82-3.79 (m, 1H), 3.50-3.38 (m, 2H), 2.50-2.37 (m, 2H), 1.34 (d, J=6.9 Hz, 3H).

(R)-1-Oxo-1-((2,2,2-trifluoroethyl)amino)pentan-2-aminium chloride

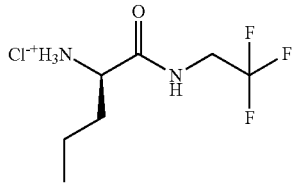

The title molecule was isolated as a white solid: mp 204-210° C.; ¹H NMR (400 MHz, CD₃OD) δ 4.17-4.00 (m, 1H), 3.98-3.69 (m, 2H), 1.83 (dt, J=15.0, 7.5 Hz, 2H), 1.50-1.35 (m, 2H), 0.99 (t, J=7.3 Hz, 3H); ¹⁹F NMR (376 MHz, CD₃OD) δ −73.90; ¹³C NMR (101 MHz, CD₃OD) δ 170.97, 125.72 (q, J=277.9 Hz), 54.37, 41.30 (q, J=34.7 Hz), 34.65, 19.00, 13.94.

Example 130

Preparation of (R)-tert-Butyl 1-thioxo-1-(2,2,2-trifluoroethylamino)propan-2-ylcarbamate

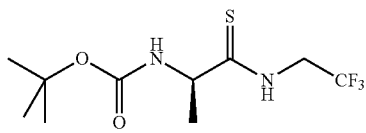 [SMILES: C[C@@H](NC(=O)OC(C)(C)C)C(=S)NCC(F)(F)F]

To a stirred solution of (R)-tert-butyl 1-oxo-1-(2,2,2-trifluoroethylamino)propan-2-ylcarbamate (100 mg, 0.37 mmol) in CH₂Cl₂ (10 mL) was added P₂S₅ (24 mg, 0.11 mmol) and hexamethyldisiloxane (HMDO) (0.13 mL, 0.59 mmol) at room temperature and the mixture was refluxed for 3 h. The reaction mixture was cooled to room temperature and another portion of P₂S₅ (24 mg, 0.11 mmol) was added and the resulting mixture was refluxed for 18 h. The volatiles were evaporated, pentane (25 mL) was added to the residue and stirred for 10-15 min. The pentane layer was decanted, concentrated in vacuo and the residue was passed through a short silica pad eluting with pentane followed by CH₂Cl₂ to give the title compound as colorless liquid (30 mg, 30%): ¹H NMR (400 MHz, DMSO-d₆) δ 10.27 (t, J=5.4 Hz, 1H), 7.00 (d, J=6.8 Hz, 1H), 4.57-4.35 (m, 3H), 1.32 (s, 9H), 1.25 (d, J=7.6 Hz, 3H); ESIMS m/z 286.2 ([M+H]⁺); IR (thin film) 3233, 1683, 1257 cm⁻¹.

Example 131

Preparation of (R)-1-Thioxo-1-((2,2,2-trifluoroethyl)amino)propan-2-aminium 2,2,2-trifluoroacetate

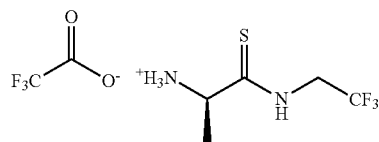

To a stirred solution of (R)-tert-butyl 1-thioxo-1-(2,2,2-trifluoroethylamino)propan-2-ylcarbamate (200 mg, 0.69 mmol) in CH₂Cl₂ (5 mL) was added TFA (0.5 mL) dropwise and the reaction mixture was stirred for 18 h. The volatiles were evaporated and the residue was triturated with pentane to give the title compound as colorless gum, which was taken to next step without further purification (200 mg): ¹H NMR (300 MHz, DMSO-d₆) δ 10.99 (bs, 1H), 8.23 (bs, 2H), 4.62-4.55 (m, 2H), 4.23-4.19 (m, 1H), 1.43 (d, J=8.4 Hz, 3H); ESIMS m/z 186.2 ([M+H]⁺); IR (thin film) 3445, 2967, 1168 cm⁻¹.

The following molecule was made in accordance with the procedures disclosed in Example 131:

(S)-1-Oxo-1-((2,2,2-trifluoroethyl)amino)butan-2-aminium 2,2,2-trifluoroacetate

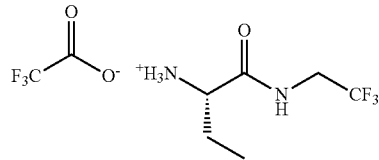

The title molecule was isolated as a colorless gum: ¹H NMR (300 MHz, DMSO-d₆) δ 9.12 (t, J=5.7 Hz, 1H), 8.19 (bs, 2H), 4.14-3.93 (m, 2H), 3.80 (t, J=6.0 Hz, 1H), 1.81-1.71 (m, 2H), 0.88 (t, J=7.2 Hz, 3H); ESIMS m/z 185.00 ([M+H]⁺); IR (thin film) 3459, 1674, 1169 cm⁻¹.

Example 132

Preparation of 2-Bromo-N—((S)-1-oxo-1-((2,2,2-trifluoroethyl)amino)propan-2-yl)-4-((E)-4,4,4-trifluoro-3-(3,4,5-trichlorophenyl)but-1-en-1-yl)benzamide (F10 and F11)

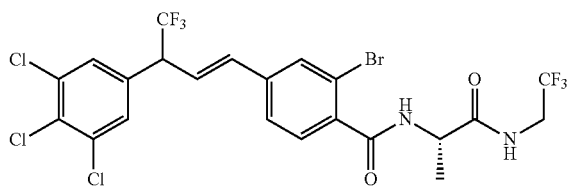 [SMILES: C[C@H](NC(=O)c1ccc(/C=C/C(c2cc(Cl)c(Cl)c(Cl)c2)C(F)(F)F)cc1Br)C(=O)NCC(F)(F)F]

The title molecule was prepared as described in Example 15. The diastereomeric pairs were separated by chiral HPLC using Chiralpak® IA (4.6×250 mm) 5 μm column using 0.1% TFA in hexane and isopropanol as the mobile phase (isocratic 70:30) with a flow rate 1.0 mL/min at ambient temperature. Diastereomer F10 was collected at a retention time of 4.55 min and possessed an optical rotation of $[\alpha]_D^{30}=+35.6$ (c, 0.5% in $CH_2Cl_2$). Diastereomer F11 was collected at 8.71 min and possessed an optical rotation of $[\alpha]_D^{30}=-82.0$ (c, 0.5% in $CH_2Cl_2$). Characterization data for these molecules are listed in Table 2.

Example 133

Preparation of 2-Bromo-N—((R)-1-oxo-1-((2,2,2-trifluoroethyl)amino)propan-2-yl)-4-((E)-4,4,4-trifluoro-3-(3,4,5-trichlorophenyl)but-1-en-1-yl)benzamide (F12 and F13)

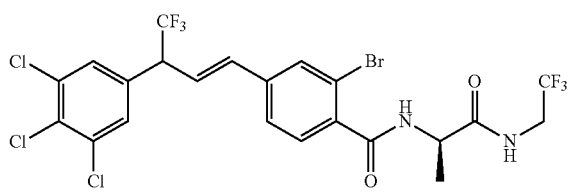 [SMILES: C[C@@H](NC(=O)c1ccc(/C=C/C(c2cc(Cl)c(Cl)c(Cl)c2)C(F)(F)F)cc1Br)C(=O)NCC(F)(F)F]

The title molecule was prepared as described in Example 15. The diastereomeric pairs were separated by chiral HPLC using Chiralpak® IA (4.6×250 mm) 5 μm column using 0.1% TFA in hexane and isopropanol as the mobile phase (isocratic 70:30) with a flow rate 1.0 mL/min at ambient temperature. Diastereomer F12 was collected at a retention time of 5.62 min and possessed an optical rotation of $[\alpha]_D^{30}=+59.4$ (c, 1% in $CH_2Cl_2$). Diastereomer F13 was collected at 8.85 min and possessed an optical rotation of $[\alpha]_D^{30}=-44.0$ (c, 1% in $CH_2Cl_2$). Characterization data for these molecules are listed in Table 2.

The following molecules was prepared in accordance with the procedures disclosed in Example 133:

N—((R)-1-Oxo-1-((2,2,2-trifluoroethyl)amino)propan-2-yl)-4-((E)-4,4,4-trifluoro-3-(3,4,5-trichlorophenyl)but-1-en-1-yl)-2-(trifluoromethyl)benzamide (F20A and F20B)

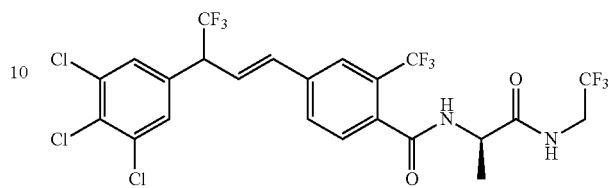

Diastereomer F20A (isomer 1) was collected at a retention time of 4.13 min and possessed an optical rotation of $[\alpha]_D^{25}=+49.2$ (c, 1.0% in $CH_2Cl_2$). Diastereomer F20B was collected at 4.88 min and possessed an optical rotation of $[\alpha]_D^{25}=-38.8$ (c, 1.0% in $CH_2Cl_2$). Characterization data for these molecules are listed in Table 2.

F20A and F20B Stereochemical Assignment

F20A and F20B were dissolved in $CDCl_3$ and placed in a 100 μm path length cell with $BaF_2$ windows. IR and vibrational circular dichroism (VCD) spectra were recorded on a IR-2XTM VCD spectrometer (BioTools, Inc.) equipped with dual PEM accessory, with 4 $cm^{-1}$ resolution. The sample and $CDCl_3$ spectra were acquired for 21 h on an instrument optimized at 1400 $cm^{-1}$. The solvent-subtracted IR and VCD spectra were collected.

Theoretical Calculations:

F20 with R,R- and S,R-configurations were built with Maestro (Schrodinger, LLC. New York, N.Y.). The conformational search was carried out with MacroModel (Schrodinger, LLC. New York, N.Y.) with MMFF94x force field to generate low-energy conformers. Single point calculation (SPE), geometry, frequency, and IR and VCD calculations were performed at the DFT level (B3LYP/lacvp**) in Jaguar (Schrodinger, LLC. New York, N.Y.). A scaling factor of 0.96 was applied to the frequency calculation. Analysis: for F20 with R,R- and S,R-configurations, the top 100 low-energy conformers generated with MacroModel were selected for DFT SPE calculations. These calculations resulted in the 8 and 4 conformers that have energies within 1 kcal/mol higher than the lowest energy conformer for R,R- and S,R-configurations, respectively. The frequency calculations were performed on these conformers to determine the IR and VCD spectra. The Boltzmann-weighted IR and VCD spectra of these conformers were compared with the observed IR and VCD spectra. Based on the overall agreement in VCD pattern between the observed and calculated spectra, the absolute configuration of F20A is assigned as R,R-configuration. The assignment was evaluated by CompareVOA program (BioTools). The confidence level of the assignment is 88% based on a database that includes 105 previous correct assignments for different chiral structures. However, the observed spectrum for F20B does not agree well with the calculated spectrum for S,R-configuration with a confidence level of 65%. But considering that the compound has only one chiral center, two possible configurations and F20A is of R,R-configuration, F20B can be with high confidence assigned as the S,R-configuration.

Example 134

Preparation of (E)-2-Methyl-N-(2-methyl-1-thioxo-1-(2,2,2-trifluoroethylamino)propan-2-yl)-4-(4,4,4-trifluoro-3-(3,4,5-trichlorophenyl)but-1-enyl)benzothioamide (F31)

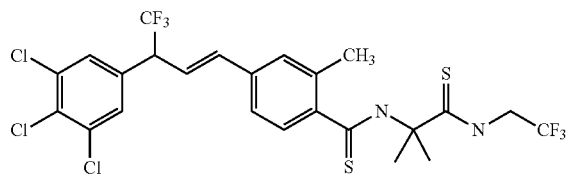 [SMILES: Cc1cc(/C=C/C(c2cc(Cl)c(Cl)c(Cl)c2)C(F)(F)F)ccc1C(=S)NC(C)(C)C(=S)NCC(F)(F)F]

To a stirred solution of (E)-2-methyl-N-(2-methyl-1-oxo-1-(2,2,2-trifluoroethylamino)propan-2-yl)-4-(4,4,4-trifluoro-3-(3,4,5-trichlorophenyl)but-1-enyl)benzamide (400 mg, 0.68 mmol) in CH$_2$Cl$_2$ (50 mL) was added P$_2$S$_5$ (75 mg, 0.34 mmol) and HMDO (0.25 mL, 1.12 mmol) at room temperature and the mixture was refluxed for 3 h. The reaction mixture was cooled to room temperature and another portion of P$_2$S$_5$ (75 mg, 0.34 mmol) was added and the resulting mixture was refluxed for 18 h. The volatiles were evaporated and the residue was purified by prep TLC to give the title compound as pale yellow gum (47 mg, 11%). Characterization data for this molecule is listed in Table 2.

Example 135

Preparation of (E)-2-Bromo-N-(2-methyl-1-oxo-1-((2,2,2-trifluoroethyl)amino)propan-2-yl)-4-(4,4,4-trifluoro-3-(3,4,5-trichlorophenyl)but-1-en-1-yl)benzamide (F1)

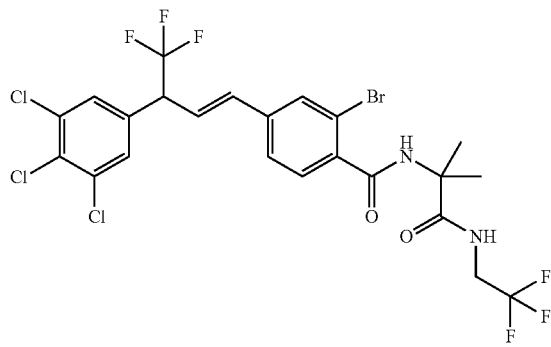 [SMILES: CC(C)(NC(=O)c1ccc(/C=C/C(c2cc(Cl)c(Cl)c(Cl)c2)C(F)(F)F)cc1Br)C(=O)NCC(F)(F)F]

To (E)-2-bromo-4-(4,4,4-trifluoro-3-(3,4,5-trichlorophenyl)but-1-enyl)benzoic acid (200 mg, 0.409 mmol) in MeCN (5 mL) was added 1H-benzo[d][1,2,3]triazol-1-ol hydrate (63 mg, 0.411 mmol), HBTU (155 mg, 0.409 mmol), N-(2,2,2-trifluoroethyl) 1-amino-2-methyl-propanecarboxamide hydrochloride (180 mg, 0.816 mmol) and diisopropylethylamine (0.24 mL, 1.38 mmol). After 24 h the material was concentrated in vacuo. The crude product was purified by passing the crude reaction mixture through a silica frit and eluting with EtOAc/hexane (1:2). The recovered material was further purified by medium pressure chromatography on silica with EtOAc/hexane as the eluent to afford the title as a white foam (147 mg, 55%). Characterization data for this molecule is listed in Table 2.

Example 136

Preparation of 1-(3,5-Difluoro-4-methoxyphenyl)-2,2,2-trifluoroethanone

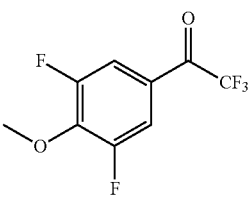 [SMILES: COc1c(F)cc(C(=O)C(F)(F)F)cc1F]

Isopropyl magnesium chloride lithium chloride complex (22.0 mL, 28.02 mmol) was added dropwise to a stirred solution of 5-bromo-1,3-difluoro-2-methoxybenzene (5.0 g, 22.42 mmol) at −5° C. in THF (100 mL) and the reaction mixture was stirred at same temperature for 30 min. Methyl trifluoroacetate (3.67 g, 28.69 mmol) was added dropwise and the reaction mixture was stirred at ambient temperature for 2 h. A 2 N HCl solution (200 mL) was added to quench the reaction and then it was extracted with diethylether. The combined organic layers were washed with brine, dried (Na$_2$SO$_4$) filtered and concentrated to afford the title compound (5.4 g, crude) as a yellow liquid. The material was taken to next step without further purification. $^1$H NMR (400 MHz, CDCl$_3$) δ 7.68-7.60 (m, 2H) 4.19 (s, 3H); ESIMS m/z 240.1 ([M]$^+$).

The following molecule was prepared in accordance with the procedures disclosed in Example 136:

2,6-Difluoro-4-(2,2,2-trifluoroacetyl)benzonitrile

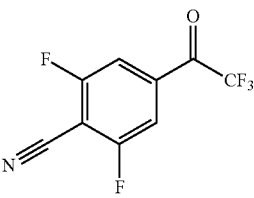 [SMILES: N#Cc1c(F)cc(C(=O)C(F)(F)F)cc1F]

$^1$H NMR (400 MHz, CDCl3) δ 7.45 (d, J=8.4 Hz, 1H), 7.37 (d, J=8.4 Hz, 1H). EIMS m/z 235.1 ([M]$^+$).

Example 137

Preparation of (E)-N-(1-((2-Fluoroethyl)amino)-1-oxopropan-2-yl)-4-(4,4,4-trifluoro-3-(3,4,5-trichlorophenyl)but-1-en-1-yl)-2-(trifluoromethyl)benzamide (P1618A)

Step 1: (2R)-tert-Butyl 2-(4-((E)-4,4,4-trifluoro-3-(3,4,5-trichlorophenyl)but-1-enyl)-2-(trifluoromethyl)benzamido)propanoate The title compound was prepared according to procedures outlined in Example 15: $^1$HNMR (400 MHz, DMSO d$_6$) δ 8.73 (d, J=6.8 Hz, 1H), 7.92-7.90 (m, 3H), 7.61 (d, J=7.2 Hz, 1H), 7.36 (d, J=7.6 Hz, 1H), 6.99 (dd, J=15.2, 9.2 Hz, 1H), 6.77 (d, J=15.2 Hz, 1H), 4.85-4.80 (m, 1H), 4.30-4.26 (m, 1H), 1.43 (s, 9H), 1.33 (d, J=6.8 Hz, 3H); ESIMS m/z 601.9 ([M−H]$^−$); IR (KBr) 3414, 1732, 1661, 1170, 748 cm$^{-1}$.

Step 2: (2R)-(4-((E)-4,4,4-Trifluoro-3-(3,4,5-trichlorophenyl)but-1-enyl)-2-(trifluoromethyl)benzamido)propanoic acid TFA (1 mL) was added to a stirred solution of tert-butyl 2-(2-bromo-4-((E)-4,4,4-trifluoro-3-(3,4,5-trichlorophenyl)but-1-enyl)benzamido)propanoate (1.0 g, 1.63 mmol) in CH$_2$Cl$_2$ (20 mL) at 0° C. and the reaction mixture was stirred at ambient temperature for 18 h. The volatiles were evaporated under vacuum and the residue was triturated with pentane to afford the title compound as brown solid (0.65 g, 67%): $^1$HNMR (400 MHz, DMSO-d$_6$) δ 12.60 (bs, 1H), 8.82 (d, J=8.0 Hz, 1H), 7.99 (s, 1H), 7.92-7.89 (m, 3H), 7.51 (d, J=8.0 Hz, 1H), 7.08 (dd, J=15.6, 8.8 Hz, 1H), 6.88 (d, J=15.6 Hz, 1H), 4.88-4.83 (m, 1H), 4.41-4.34 (m, 1H), 1.34 (d, J=7.2 Hz, 3H); ESIMS: m/z 545.7 ([M+H]$^+$); IR (KBr) 3410, 3281, 2928, 1728, 1172, 744 cm$^{-1}$.

Step 3. (E)-N-(1-((2-Fluoroethyl)amino)-1-oxopropan-2-yl)-4-(4,4,4-trifluoro-3-(3,4,5-trichlorophenyl)but-1-en-1-yl)-2-(trifluoromethyl)benzamide (P1618)

DIPEA (0.60 mL, 1.08 mmol), PyBOP (180 mg, 0.36 mmol) 2-(4-((E)-4,4,4-trifluoro-3-(3,4,5-trichlorophenyl)but-1-enyl)-2-(trifluoromethyl)benzamido)propanoic acid (35 mg, 0.36 mmol) were added to a stirred solution of compound 1 (200 mg, 0.36 mmol) in CH$_2$Cl$_2$ (10 mL) at ambient temperature and the reaction mixture was stirred for 18 h. The reaction mixture was diluted CH$_2$Cl$_2$, washed with 1N HCl, followed by a saturated NaHCO$_3$ solution, water and brine. The organic phase was dried (Na$_2$SO$_4$), filtered, concentrated and the residue was purified by column chromatography on silica (100-200 mesh) eluting with 10% EtOAc in petroleum ether to afford the title compound as a brown solid (85 mg, 39%).

The following molecule was prepared in accordance with the procedures disclosed in Example 137, Step 1:

tert-Butyl 2-(2-bromo-4-((E)-4,4,4-trifluoro-3-(3,4,5-trichlorophenyl)but-1-enyl)benzamido)propanoate

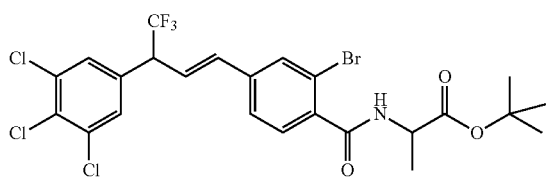 [SMILES: CC(NC(=O)c1ccc(/C=C/C(c2cc(Cl)c(Cl)c(Cl)c2)C(F)(F)F)cc1Br)C(=O)OC(C)(C)C]

$^1$H NMR (400 MHz, DMSO-d$_6$): δ 8.82 (d, J=7.6 Hz, 1H), 7.99 (s, 1H), 7.91-7.90 (m, 3H), 7.50 (d, J=7.6 Hz, 1H), 7.07 (dd, J=16.0, 8.8 Hz, 1H), 6.88 (d, J=15.2 Hz, 1H), 4.88-4.83 (m, 1H), 4.31-4.27 (m, 1H), 1.42 (s, 9H), 1.32 (d, J=7.6 Hz, 3H); ESIMS m/z 611.7 ([M−H]$^−$); IR (KBr) 3296, 2932, 1732, 1162, 743, 556 cm$^{-1}$.

(E)-tert-Butyl 2-(2-bromo-4-(4,4,4-trifluoro-3-(3,4,5-trichlorophenyl)but-1-enyl)benzamido)acetate

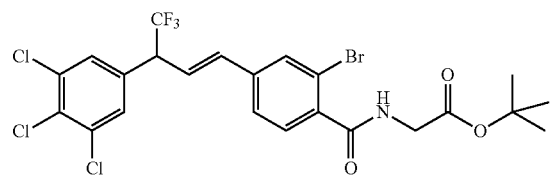 [SMILES: CC(C)(C)OC(=O)CNC(=O)c1ccc(/C=C/C(c2cc(Cl)c(Cl)c(Cl)c2)C(F)(F)F)cc1Br]

Isolated as a (620 mg, 72%) pale yellow solid. $^1$H NMR (400 MHz, DMSO-d$_6$) δ 8.77 (t, J=6.0 Hz, 1H), 7.93-7.91 (m, 3H), 7.62 (d, J=6.8 Hz, 1H), 7.39 (d, J=8.0 Hz, 1H), 7.00 (dd, J=15.6, 9.2 Hz, 1H), 6.77 (d, J=16.0 Hz, 1H), 4.86-4.81 (m, 1H), 3.86-3.85 (m, 2H), 1.33 (s, 9H). ESIMS m/z 599.87 ([M+H]$^+$).

The following molecule was prepared in accordance with the procedures disclosed in Example 137, Step 2:

2-(2-Bromo-4-((E)-4,4,4-trifluoro-3-(3,4,5-trichlorophenyl)but-1-enyl)benzamido)propanoic acid

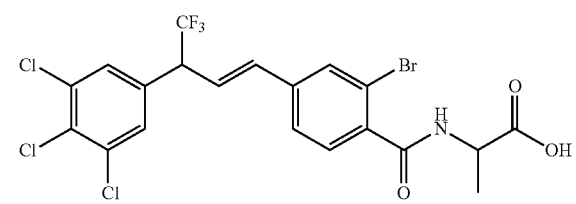 [SMILES: CC(NC(=O)c1ccc(/C=C/C(c2cc(Cl)c(Cl)c(Cl)c2)C(F)(F)F)cc1Br)C(=O)O]

$^1$HNMR (400 MHz, DMSO-d$_6$): δ 12.62 (bs, 1H), 8.73 (d, J=9.6 Hz, 1H), 7.93-7.91 (m, 3H), 7.61 (d, J=8.1 Hz, 1H), 7.37 (d, J=7.8 Hz, 1H), 7.01 (dd, J=15.6, 9.0 Hz, 1H), 6.78 (d, J=15.9 Hz, 1H), 4.89-4.79 (m, 1H), 4.42-4.32 (m, 1H), 1.36 (d, J=7.2 Hz, 3H); ESIMS: m/z 558.0 ([M+H]$^+$); IR (KBr) 3418, 1650, 1115, 747, 560 cm$^{-1}$.

(E)-2-(2-Bromo-4-(4,4,4-trifluoro-3-(3,4,5-trichlorophenyl)but-1-enyl)benzamido)acetic acid

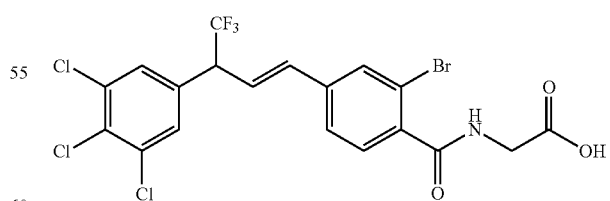

Isolated as an (550 mg, 97%) off white solid. $^1$H NMR (300 MHz, DMSO-d6) δ 12.56 (bs, 1H), 8.73 (t, J=5.4 Hz, 1H), 7.93-7.91 (m, 3H), 7.62 (d, J=9.3 Hz, 1H), 7.40 (d, J=8.1 Hz, 1H), 7.01 (dd, J=15.9, 9.0 Hz, 1H), 6.78 (d, J=15.9 Hz, 1H), 4.89-4.80 (m, 1H), 3.90-3.88 (m, 2H). ESIMS m/z 541.82 ([M−H]$^−$).

Example 138

Preparation of (E)-2-Chloro-5-hydroxy-N-(2-oxo-2-((2,2,2-trifluoroethyl)amino)ethyl)-4-(4,4,4-trifluoro-3-(3,4,5-trichlorophenyl)but-1-en-1-yl)benzamide

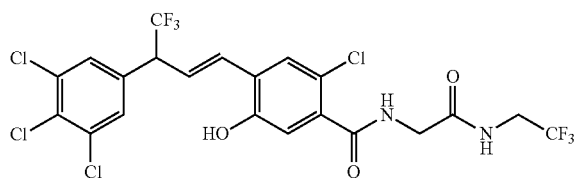 [SMILES: O=C(CNC(=O)c1cc(O)c(/C=C/C(c2cc(Cl)c(Cl)c(Cl)c2)C(F)(F)F)cc1Cl)NCC(F)(F)F]

Step 1. Methyl 4-bromo-2-chloro-5-methoxybenzoate

A 25 mL round bottomed flask equipped with a magnetic stir bar was charged with 4-bromo-2-chloro-5-methoxybenzoic acid (*JACS*, 1963, 730-2; 1.25 g, 4.72 mmol), 20% MeOH/EtOAc (25 mL) and cooled in an ice-water bath. Trimethylsilyldiazomethane (TMSCHN$_2$ 2 M in hexanes, 2.6 mL, 5.20 mmol) was added dropwise via an addition funnel. The reaction continued to stir for 1 h then it was concentrated to afford the title compound as a white solid (1.31 g, 100%): mp 78-79° C.; $^1$H NMR (400 MHz, CDCl$_3$) δ 7.65 (s, 1H), 7.36 (s, 1H), 3.94 (s, 3H), 3.93 (s, 3H); EIMS m/z 280 ([M]$^+$).

Step 2. 2-Chloro-5-methoxy-4-vinylbenzoic acid

A 25 mL round bottomed flask was charged with methyl 4-bromo-2-chloro-5-methoxybenzoate (640 mg, 2.29 mmol), K$_2$CO$_3$ (665 mg, 4.81 mmol), potassium trifluoro(vinyl)borate (920 mg, 6.87 mmol), PdCl$_2$(dppf) (84 mg, 0.11 mmol) and anhydrous DMSO (15 mL) and stirred at 80° C. for 2 h. The reaction was allowed to cool, water (150 mL) was added and then extracted several times with Et$_2$O. The organic layer was washed with brine, dried over MgSO$_4$, filtered and concentrated to give a brown residue. The crude product was purified via flash chromatography eluting with 15% Et$_2$O/hexanes to give methyl 2-chloro-5-methoxy-4-vinylbenzoate as a yellow oil (440 mg, 85%). To a 25 mL round bottomed flask containing methyl 2-chloro-5-methoxy-4-vinylbenzoate (440 mg, 1.94 mmol) and MeOH (10 mL) was added 1N NaOH (2 mL, 2.04 mmol) and reaction stirred at ambient temperature for 18 h. The reaction mixture was concentrated to give a solid residue. The residue was dissolved in water and extracted 1× with 50% Et$_2$O/hexanes. The aqueous layer was made acidic with 2N HCl and extracted 2× with CH$_2$Cl$_2$, dried over MgSO$_4$, filtered and concentrated to afford the title compound as a white solid (0.39 g, 94%): $^1$H NMR (400 MHz, CDCl$_3$) δ 7.54 (d, J=0.5 Hz, 1H), 7.52 (s, 1H), 6.98 (ddd, J=17.7, 11.2, 0.6 Hz, 1H), 5.87 (dd, J=17.7, 1.1 Hz, 1H), 5.45 (dd, J=11.2, 1.1 Hz, 1H), 3.90 (s, 3H).

Step 3. (E)-2-Chloro-5-methoxy-4-(4,4,4-trifluoro-3-(3,4,5-trichlorophenyl)but-1-en-1-yl)benzoic acid A 50 mL 3 neck round bottomed flask was charged with 2-chloro-5-methoxy-4-vinylbenzoic acid (390 mg, 1.84 mmol)), 5-(1-bromo-2,2,2-trifluoroethyl)-1,2,3-trichlorobenzene (754 mg, 2.20 mmol) and anhydrous N-methyl pyrrolidinone (10 mL). Nitrogen was bubbled into the reaction mixture for 15 min. After which time, 2,2'-dipyridyl (57.3 mg, 0.37 mmol) and CuBr (11.7 mg, 0.18 mmol) were added and reaction mixture stirred at 150° C. for 1 h. Reaction mixture was allowed to cool, water (300 mL) was added and extracted several times with Et$_2$O. Organic layer was washed repeatedly with water, dried over MgSO$_4$, filtered and concentrated to afford—the title compound as a light brown foam (870 mg, 100%). This material was 95% pure by LC/MS; ESIMS m/z 473 ([M−H]$^-$). This material was used without further purification.

Step 4. (E)-2-Chloro-5-methoxy-N-(2-oxo-2-((2,2,2-trifluoroethyl)amino)ethyl)-4-(4,4,4-trifluoro-3-(3,4,5-trichlorophenyl)but-1-en-1-yl)benzamide A 50 mL round bottomed flask was charged with (E)-2-chloro-5-methoxy-4-(4,4,4-trifluoro-3-(3,4,5-trichlorophenyl)but-1-en-1-yl)benzoic acid (780 mg, 1.65 mmol)), di(1H-imidazol-1-yl)methanone (267 mg, 1.65 mmol) and anhydrous THF (30 mL). The resulting mixture was heated at reflux until it ceased giving off gas. 2-Amino-N-(2,2,2-trifluoroethyl)acetamide HCl (257 mg, 1.65 mmol) was added in one portion and the reaction mixture continued to stir at reflux for 18 h. The reaction mixture was concentrated to dryness and the residue was taken up in Et$_2$O (50 mL) and 0.1N HCl (10 mL). The layers were separated. The aqueous layer was extracted 2× with Et$_2$O. The Et$_2$O layers were combined and washed 1× with aqueous NaHCO$_3$, 1× with brine, dried over MgSO$_4$, filtered and concentrated to give a brown oil. The crude product was purified via flash chromatography eluting with 30-40% EtOAc/hexanes to afford the title compound—as an off white foam (280 mg, 28%): $^1$H NMR (400 MHz, CDCl$_3$) δ 7.45 (s, 1H), 7.41 (s, 2H), 7.29 (s, 1H), 7.28 (s, 1H), 6.84 (m, 2H), 6.43 (dd, J=16.0, 8.3 Hz, 1H), 4.25 (d, J=5.4 Hz, 2H), 4.10 (m, 1H), 3.97 (qd, J=9.0, 6.4 Hz, 2H), 3.87 (s, 3H); ESIMS m/z 613.1 ([M+H]$^+$).

Step 5. (E)-2-Chloro-5-hydroxy-N-(2-oxo-2-((2,2,2-trifluoroethyl)amino)ethyl)-4-(4,4,4-trifluoro-3-(3,4,5-trichlorophenyl)but-1-en-1-yl)benzamide A 25 mL round bottomed flask was charged with (E)-2-chloro-5-methoxy-N-(2-oxo-2-((2,2,2-trifluoroethyl)amino)ethyl)-4-(4,4,4-trifluoro-3-(3,4,5-trichlorophenyl)but-1-en-1-yl)benzamide (57 mg, 0.093 mmol) and CH$_2$Cl$_2$ (3 mL). The reaction mixture was cooled to −78° C. and boron tribromide (BBr$_3$, 1.0M solution in CH$_2$Cl$_2$, 0.33 mL, 0.326 mmol) was added slowly via syringe. The reaction allowed to warm to ambient temperature and stirred for 18 h. An additional 0.3-0.4 mL of BBr$_3$ was added at ambient temperature and continued to stir for 3 h. The reaction mixture was added to aqueous NaHCO$_3$ and extracted 3× with CH$_2$Cl$_2$. The CH$_2$Cl$_2$ layers were combined and dried over MgSO$_4$, filtered and concentrated to give an oil. The crude material was purified via flash chromatography eluting with 50% EtOAc/hexanes to afford the title compound as a white solid (18 mg, 33%): mp 190° C. (dec.); $^1$H NMR (400 MHz, CDCl$_3$) δ 9.81 (s, 1H), 8.06 (d, J=7.0 Hz, 1H), 7.71 (m, 1H), 7.44 (d, J=2.8 Hz, 2H), 7.37 (s, 1H), 7.20 (s, 1H), 6.82 (d, J=15.9 Hz, 1H), 6.50 (m, 1H), 4.14 (m, 3H), 3.89 (m, 2H); ESIMS m/z 599 ([M+H]$^+$).

Example 139

Preparation of 1-(3,4-Dichlorophenyl)-2,2-difluoropropan-1-one

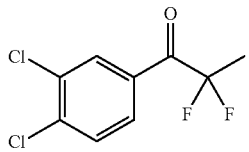

To a magnetically stirred solution of 4-bromo-1,2-dichlorobenzene (5.64 g, 24.98 mmol) in dry Et$_2$O (109 mL) was added n-BuLi (10.86 mL, 24.98 mmol) via an addition funnel under a nitrogen atmosphere. The reaction mixture was stirred at −78° C. for 30 min, A solution of ethyl 2,2-difluoropropanoate (3.0 g, 21.7 mmol) in Et$_2$O (10 mL) was added dropwise over 15 min and allowed to stir for 1 h. The reaction was then carefully quenched with 1 N HCl (4 mL) and allowed to warm to 23° C. The solution was dilute with Et$_2$O and washed with water. The combined organic layers were dried over Na$_2$SO$_4$, concentrated under reduced pressure and the resulting material was purified via flash column chromatography using 100% hexanes to 5% acetone/95% hexanes as eluent. The relevant fractions were concentrated under reduced pressure to afford the title compound as a colorless oil (3.89 g, 71%): $^1$H NMR (400 MHz, CDCl$_3$) δ 8.21-8.18 (m, 1H), 7.99-7.93 (m, 1H), 7.59 (dd, J=8.4, 4.2 Hz, 1H), 1.89 (t, J=19.6 Hz, 3H); $^{19}$F NMR (376 MHz, CDCl$_3$) δ −92.08-−93.21 (m); EISMS m/z 240 ([M−H]$^+$).

Example 140

(E)-4-(4,4,4-Trifluoro-3-(3,4,5-trichlorophenyl)but-1-enyl)-2-vinylbenzoic acid

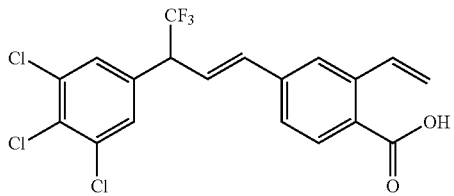 [SMILES: C=Cc1cc(/C=C/C(c2cc(Cl)c(Cl)c(Cl)c2)C(F)(F)F)ccc1C(=O)O]

To a stirred solution of (E)-2-bromo-4-(4,4,4-trifluoro-3-(3,4,5-trichlorophenyl)but-1-enyl)benzoic acid (600 mg, 1.23 mmol) in dry toluene (10 mL) was added tributyl(vinyl)stannane (470 mg, 1.48 mmol) and the mixture was degassed with argon for 15 min Pd(PPh$_3$)$_4$ (72 mg, 0.06 mmol) was added and the reaction mixture was refluxed for 2 h. The reaction mixture was brought to ambient temperature, water was added and the mixture extracted with EtOAc. The organic layer was washed with 2N HCl and brine, dried (Na$_2$SO$_4$), filtered, and concentrated. The residue was purified by column chromatography on silica eluting with 30% EtOAc in petroleum ether to afford the title compound as brown solid (295 mg, 55%): $^1$H NMR (300 MHz, DMSO-d$_6$) δ 13.05 (bs, 1H), 7.91 (s, 2H), 7.81-7.75 (m, 2H), 7.59 (d, J=8.1 Hz, 1H), 7.48 (dd, J=17.4, 10.8 Hz, 1H), 7.03 (dd, J=15.9, 8.7 Hz, 1H), 6.84 (d, J=15.6 Hz, 1H), 5.88 (d, J=16.5 Hz, 1H), 5.39 (d, J=12.3 Hz, 1H), 4.89-4.82 (m, 1H); ESIMS m/z 432.18 ([M−H]$^-$); IR (thinfilm) 3418, 1689, 1114, 747 cm$^{-1}$.

Example 141

(E)-2-Iodo-4-(4,4,4-trifluoro-3-(3,4,5-trichlorophenyl)but-1-enyl)benzoic acid

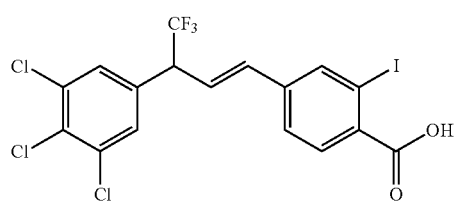

Per Buchwald, et al.; *JACS*, 2002, 124, 14844-14845, potassium iodide (KI, 273 mg, 1.64 mmol), CuI (31 mg, 0.16 mmol) and trans-N,N'-dimethylcyclohexane-1,2-diamine (catalytic amount) were added to a solution of (E)-2-bromo-4-(4,4,4-trifluoro-3-(3,4,5-trichlorophenyl)but-1-enyl)benzoic acid (400 mg, 0.82 mmol) in 1,4-dioxane (8 mL). The mixture in an Ace pressure tube was heated at 100° C. for 3 h. The reaction mixture was brought to ambient temperature and filtered through a Celite® pad. The filtrate was concentrated and residue was diluted with EtOAc and washed with 1N HCl followed by brine. The organic layer was dried (Na$_2$SO$_4$), filtered, and concentrated. The residue was purified by column chromatography on silica eluting with 25% EtOAc in petroleum ether to afford the title compound as brown semi solid (240 mg, 55%): $^1$H NMR (400 MHz, DMSO-d$_6$) δ 13.3 (bs, 1H), 8.21 (s, 1H), 7.91 (s, 2H), 7.71-7.64 (m, 2H), 7.01 (dd, J=15.6, 9.2 Hz, 1H), 6.75 (d, J=15.6 Hz, 1H), 4.85-4.81 (m, 1H); ESIMS m/z 532.8 ([M−H]$^-$); IR (thinfilm) 3436, 1699, 1113, 750 cm$^{-1}$.

Example 142

Preparation of (E)-2-Bromo-N-(2-methyl-1-(neopentylamino)-1-oxopropan-2-yl)-4-(4,4,4-trifluoro-3-(3,4,5-trichlorophenyl)but-1-en-1-yl)benzamide

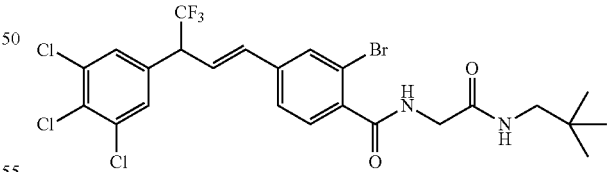

Step 1. (E)-2-(2-Bromo-4-(4,4,4-trifluoro-3-(3,4,5-trichlorophenyl)but-1-en-1-yl)benzamido)-2-methyl-propanoic acid A 25 mL round bottomed flask equipped with a magnetic stir bar and reflux condenser was charged with (E)-2-bromo-4-(4,4,4-trifluoro-3-(3,4,5-trichlorophenyl)but-1-en-1-yl)benzoic acid (400 mg, 0.82 mmol) and 1,2-dichloroethane (DCE) (5 mL). Thionyl chloride (0.12 mL, 1.64 mmol) was added neat in one portion and the resulting reaction mixture was heated at reflux for 2 h. After which time, reaction mixture was allowed to cool and concentrated to give the crude acid chloride which was used without further purification. To a solution containing NaHCO$_3$ (68.8 mg, 0.82 mmol), 2-amino-2-methylpropanoic acid (84 mg, 0.82 mmol) and dodecyltrimethylammonium bromide (2.52 mg, 8.19 μmol) in 10 mL of THF was added to the acid chloride in THF (1 mL). The resulting mixture was heated at reflux for 18 h. Reaction mixture was allowed to cool and added to water, made acidic with 0.1N HCl, extracted (3×) with Et$_2$O, washed (1×) with brine, dried over MgSO$_4$, filtered and evaporated to afford the title compound as a light brown foam (400 mg, 85%): $^1$H NMR (400 MHz, CDCl$_3$) δ 7.60 (d, J=1.6 Hz, 1H), 7.59 (d, J=8.0 Hz, 1H), 7.40 (s, 2H), 7.37 (dd, J=8.1, 1.6 Hz, 1H), 6.63 (s, 1H), 6.53 (d, J=15.9 Hz, 1H), 6.38 (dd, J=15.9, 7.9 Hz, 1H), 4.10 (p, J=8.3 Hz, 1H), 1.73 (s, 6H). This material is used without further purification.

Step 2. (E)-2-(2-Bromo-4-(4,4,4-trifluoro-3-(3,4,5-trichlorophenyl)but-1-en-1-yl)phenyl)-4,4-dimethyloxazol-5(4H)-one A 25 mL round bottomed flask was charged with (E)-2-(2-bromo-4-(4,4,4-trifluoro-3-(3,4,5-trichlorophenyl)but-1-en-1-yl)benzamido)-2-methylpropanoic acid (400 mg, 0.70 mmol), CH$_2$Cl$_2$ (10 mL) and stirred at 0° C. EDC.HCl (134 mg, 0.70 mmol) was added in one portion as a solid and the reaction mixture was allowed to warm toward ambient temperature and continued to stir for 1 h. The reaction was diluted with CH$_2$Cl$_2$, washed with brine, dried over MgSO$_4$, filtered and evaporated to give a dark oil. The crude product was purified via flash chromatography eluting with 50% hexanes/CH$_2$Cl$_2$ to afford the title compound as an off white foam (220 mg, 57): $^1$H NMR (400 MHz, CDCl$_3$) δ 7.76 (d, J=8.1 Hz, 1H), 7.73 (d, J=1.6 Hz, 1H), 7.42 (d, J=7.8 Hz, 3H), 6.56 (d, J=15.9 Hz, 1H), 6.45 (dd, J=15.9, 7.7 Hz, 1H), 4.12 (p, J=8.5 Hz, 1H), 1.57 (s, 6H); $^{19}$F NMR (376 MHz, CDCl$_3$) δ −68.55; ESIMS m/z 554 ([M−H]$^-$).

Step 3. (E)-2-Bromo-N-(2-methyl-1-(neopentylamino)-1-oxopropan-2-yl)-4-(4,4,4-trifluoro-3-(3,4,5-trichlorophenyl)but-1-en-1-yl)benzamide A 10 mL round bottomed flask was charged with (E)-2-(2-bromo-4-(4,4,4-trifluoro-3-(3,4,5-trichlorophenyl)but-1-en-1-yl)phenyl)-4,4-dimethyloxazol-5(4H)-one (90 mg, 0.16 mmol) and CH$_2$Cl$_2$ (2 mL). 2,2-Dimethylpropan-1-amine (28.2 mg, 0.324 mmol) was added neat via pipette and the reaction stirred at ambient temperature for 18 h. The reaction mixture was evaporated to give an oil. The crude product was purified via flash chromatography eluting with 20% EtOAc/hexanes to afford the title compound as a white foam (90 mg, 86%): $^1$H NMR (400 MHz, CDCl$_3$) δ 7.60 (d, J=1.6 Hz, 1H), 7.51 (d, J=8.0 Hz, 1H), 7.40 (s, 2H), 7.36 (dd, J=8.1, 1.6 Hz, 1H), 6.66 (d, J=10.0 Hz, 2H), 6.53 (d, J=15.9 Hz, 1H), 6.38 (dd, J=15.9, 7.8 Hz, 1H), 4.11 (m, 1H), 3.12 (d, J=6.2 Hz, 2H), 1.72 (s, 6H), 0.93 (s, 9H); 19F NMR (376 MHz, CDCl$_3$) δ −68.62; ESIMS m/z 643.19 ([M+H]$^+$).

Example 143

Preparation of 3,5-Dibromo-4-chlorobenzaldehyde

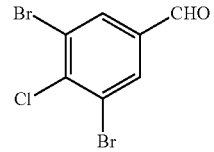

Step 1. Methyl 4-amino-3,5-dibromobenzoate conc. H$_2$SO$_4$ (1.35 mL, 25.48 mmol) was added dropwise to a stirred solution of 4-amino-3,5-dibromobenzoic acid (5.0 g, 16.99 mmol) in MeOH (50 mL) at ambient temperature and the reaction mixture was then stirred at 80° C. for 8 h. The reaction mixture was brought to ambient temperature, volatiles were evaporated and ice cold water was added to the residue and which was then extracted with EtOAc. The organic layer was washed with an aqueous NaHCO$_3$ solution followed by brine and water. The solution was then dried (Na$_2$SO$_4$), filtered and concentrated to afford the title compound as an off white solid (5.0 g, 95%): $^1$H NMR (300 MHz, DMSO-d$_6$) δ 7.91 (s, 2H), 6.20 (bs, 2H), 3.78 (s, 3H); ESIMS m/z 307.0 ([M]$^+$); IR (thin film) 3312, 2953, 1726, 595 cm$^{-1}$.

Step 2. Methyl 3,5-dibromo-4-chlorobenzoate

CuCl$_2$ (2.82 g, 21.0 mmol) in MeCN (30 mL) was stirred at 80° C. for 30 min. To this mixture tert-butylnitrite (2.7 mL, 23 mmol) was then added dropwise at same temperature and the mixture was stirred for another 10 min. Methyl 4-amino-3,5-dibromobenzoate (5.0 g, 16 mmol) in MeCN (30 mL) was added dropwise to the reaction mixture and then stirred at 80° C. for 30 min. The reaction mixture was brought to ambient temperature and an aqueous ammonia solution (20 mL) was added to the reaction mixture and extracted with petroleum ether. The organic layer was washed with brine followed by water, dried (Na$_2$SO$_4$), filtered and concentrated to afford the title compound as an off white solid (4.5 g, 84%). $^1$H NMR (300 MHz, DMSO-d$_6$) δ 8.21 (s, 2H), 3.94 (s, 3H); ESIMS m/z 326 ([M]$^+$); IR (thin film) 1732, 746 cm$^{-1}$.

Step 3. (3,5-Dibromo-4-chlorophenyl)methanol

NaBH$_4$ (1.53 g, 40.65 mmol) was added portionwise to a stirred solution of methyl 3,5-dibromo-4-chlorobenzoate (4.45 g, 13.6 mmol) in MeOH (50 mL) at 0° C. The reaction mixture was then stirred at ambient temperature for 8 h. The volatiles were evaporated and the residue was diluted with CH$_2$Cl$_2$ and washed with brine followed by water. The organic layer was dried (Na$_2$SO$_4$), filtered and concentrated to afford the title compound as an off white solid (3.3 g, 80%): $^1$H NMR (300 MHz, DMSO-d$_6$) δ 7.71 (s, 2H), 5.49 (bs, 1H), 4.48 (d, J=4.5 Hz, 2H); ESIMS m/z 297.9 ([M]$^+$); IR (thin film) 3460, 747, 534 cm$^{-1}$.

Step 4. 3,5-Dibromo-4-chlorobenzaldehyde

Pyridinium chlorochormate (PCC, 3.44 g, 15.9 mmol) was added in one portion to a stirred solution of (3,5- dibromo-4-chlorophenyl)methanol (3.2 g, 11.0 mmol) in CHCl₃ (40 mL) at ambient temperature and the reaction mixture was stirred overnight. The reaction mixture was filtered through Celite®, the Celite® pad was washed with CHCl₃ and the filtrate was concentrated to afford the title compound as an off white solid (2.0 g, 62%): mp 110-113° C.; ¹H NMR (300 MHz, DMSO-d₆) δ 9.93 (s, 1H), 8.27 (s, 2H); ESIMS m/z 297.0 ([M]⁺).

Example 144

Preparation of 4-Bromo-3,5-dichlorobenzaldehyde

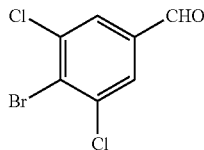

Step 1. Methyl 4-amino-3,5-dichlorobenzoate conc. H₂SO₄ (2.5 mL, 97.04 mmol) was added drop wise to a stirred solution of 4-amino-3,5-dichlorobenzoic acid (10.0 g, 48.54 mmol) in MeOH (150 mL) at 0° C. and the reaction mixture was then stirred at 80° C. for 8 h. The volatiles were evaporated; ice cold water was added to the residue and which was then extracted with EtOAc. The combined organic layers were washed with brine, dried (Na₂SO₄), filtered and concentrated under reduced pressure to afford the title compound as a white solid (7.5 g, 70%): ¹H NMR (300 MHz, DMSO-d₆) δ 8.05 (s, 2H), 3.96 (s, 3H); ESIMS m/z 282 ([M]⁺); IR (KBr): 1733, 762, 514 cm⁻¹.

Step 2. Methyl 4-bromo-3,5-dichlorobenzoate

CuBr₂ (7.5 g, 34.08 mmol) in MeCN (50 mL) was stirred at 80° C. for 30 min. To this solution tert-butylnitrite (6.5 mL, 54.55 mmol) was added dropwise at the same temperature and the mixture was stirred for another 10 min. Methyl 4-amino-3,5-dichlorobenzoate in MeCN (30 mL) was added dropwise to the reaction mixture which was then stirred at 80° C. for 30 min. The reaction mixture was brought to ambient temperature. Aqueous ammonia solution (20 mL) was added and extracted with petroleum ether. The organic layer was washed with brine followed by water. The organic solution was dried (Na₂SO₄), filtered and concentrated to afford the title compound as an off white solid (7.5 g, 77%): ¹H NMR (300 MHz, DMSO-d₆) δ 8.02 (s, 2H), 3.94 (s, 3H); ESIMS m/z 282 ([M]⁺); IR (thin film) 1733, 762, 514 cm⁻¹.

Step 3. (4-Bromo-3,5-dichlorophenyl)methanol

DIBAL-H (1M in toluene, 66 mL, and 66.0 mmol) was added dropwise to a stirred solution of methyl 4-bromo-3,5-dichlorobenzoate (7.5 g, 26.0 mmol) in THF (50 mL) at −78° C. The reaction mixture was brought to ambient temperature and stirred for 6 h. The reaction mixture was poured into ice-water and extracted with CH₂Cl₂. The organic layer was washed with brine followed by water, dried (Na₂SO₄), filtered and concentrated to afford a mixture of (4-bromo-3,5-dichlorophenyl)methanol and 4-bromo-3, 5-dichlorobenzaldehyde (6.0 g) as an off white solid which was taken to next step without purification.

Step 4. 4-Bromo-3,5-dichlorobenzaldehyde

PCC (7.5 g, 35.16 mmol) was added in one portion to a stirred solution containing a mixture of (4-bromo-3,5-dichlorophenyl)methanol and 4-bromo-3,5-dichlorobenzaldehyde (6.0 g) in CHCl₃ (40 mL) at ambient temperature and the reaction mixture was stirred overnight. The reaction mixture was filtered through celite. The celite pad was washed with CHCl₃. The filtrate was concentrated to afford the title compound as an off white solid (3.5 g, 67%): mp 125-128° C.; ¹H NMR (300 MHz, DMSO-d₆) δ 9.96 (s, 1H), 8.10 (s, 2H); ESIMS m/z 252 ([M]⁺).

Example 145

3-Chloro-5-ethylbenzaldehyde

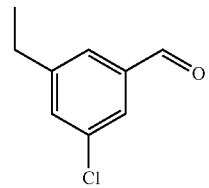

PdCl₂(dppf) (37 mg, 0.046 mmol), potassium phosphate (1.93 g, 9.11 mmol) and triethylborane (1M in hexane, 0.45 g, 4.56 mmol) were added to a solution of 3-bromo-5-chloro-benzaldehyde (1.0 g, 4.56 mmol) in THF (20 mL) at ambient temperature and the mixture was refluxed for 12 h. The reaction mixture was brought to ambient temperature, diluted with EtOAc and washed with water. The organic layer was dried (Na₂SO₄), filtered, concentrated and the residue was purified by column chromatography on silica (100-200 mesh) eluting with 2% EtOAc in petroleum ether to afford the title compound (330 mg, 41%) as a pale yellow liquid: ¹H NMR (400 MHz, DMSO-d₆) δ 9.97 (s, 1H), 7.75 (d, J=1.6 Hz 1H), 7.73 (s, 1H), 7.65 (s, 1H), 2.74-2.68 (m, 2H), 1.23 (t, J=7.6 Hz, 3H); ESIMS m/z 168.0 ([M]⁺); IR (thin film) 3071, 1699, 692 cm⁻¹.

Example 146

(E)-2-Amino-4-(3-(3,5-dichloro-4-fluorophenyl)-4,4,4-trifluorobut-1-enyl)-N-(2-oxo-2-(2,2,2-trifluoroethylamino)ethyl)benzamide

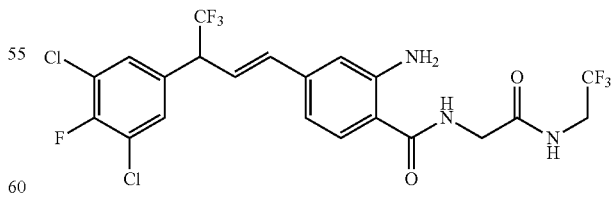

Step 1. (E)-Ethyl 4-(3-(3,5-dichloro-4-fluorophenyl)-4,4,4-trifluorobut-1-enyl)-2-nitrobenzoate 5-(1-Bromo-2,2,2-trifluoroethyl)-1,3-dichloro-2-fluorobenzene (3.5 g, 10.8 mmol), CuCl (54 mg, 0.54 mmol) and 2,2-bipyridyl (169 mg, 1.08 mmol) were added to a stirred solution of ethyl 2-nitro-4-vinylbenzoate (1.2 g, 5.42 mmol) in 1,2-dichlorobenzene (12 mL) at ambient temperature and the mixture was then stirred at 180° C. for 18 h. The reaction mixture was then cooled to ambient temperature, adsorbed on silica gel and purified by column chromatography eluting with 10% EtOAc in petroleum ether to afford the title compound (1.3 g, 53%) as a brown liquid: $^1$H NMR (DMSO-$d_6$, 300 MHz) δ 8.31 (s, 1H), 8.02-7.95 (m, 1H), 7.88-7.85 (m, 3H), 7.20 (dd, J=15.9, 9.3 Hz, 1H), 6.91 (d, J=15.6 Hz, 1H), 4.91-4.85 (m, 1H), 4.34-4.27 (m, 2H), 1.27 (t, J=6.6 Hz, 3H); ESIMS m/z 463.8 ([M−H]$^−$); IR (KBr) 3439, 2985, 1731, 1251 cm$^{-1}$.

Step 2. (E)-4-(3-(3,5-Dichloro-4-fluorophenyl)-4,4,4-trifluorobut-1-enyl)-2-nitrobenzoic acid Concentrated HCl (16.0 mL) was added dropwise to a stirred solution of (E)-ethyl 4-(3-(3,5-dichloro-4-fluorophenyl)-4,4,4-trifluorobut-1-enyl)-2-nitrobenzoate (800 mg, 1.72 mmol) in 1,4-dioxane (8.0 mL) at 0° C. and the reaction mixture was refluxed for 36 h. The volatiles were evaporated; the residue was diluted with EtOAc and washed with brine and water. The organic layer was dried (Na$_2$SO$_4$), filtered, concentrated and the residue was purified by column chromatography on silica (100-200 mesh) eluting with 30% EtOAc in petroleum ether to afford the title compound as a yellow solid (390 mg, 52%): $^1$H NMR (400 MHz, DMSO-$d_6$) δ 13.9 (bs, 1H), 8.22 (s, 1H), 7.93-7.91 (m, 1H), 7.86-7.84 (m, 3H), 7.16 (dd, J=15.6, 9.2 Hz, 1H), 6.89 (d, J=15.6 Hz, 1H), 4.89-4.85 (m, 1H). ESIMS m/z 435.9 ([M−H]$^−$); IR (KBr) 3445, 2924, 1708, 1541, 817 cm$^{-1}$.

Step 3. (E)-4-(3-(3,5-Dichloro-4-fluorophenyl)-4,4,4-trifluorobut-1-enyl)-2-nitro-N-(2-oxo-2-(2,2,2-trifluoroethylamino)ethyl)benzamide 2-Amino-N-(2,2,2-trifluoroethyl)acetamide hydrochloride (96 mg, 0.35 mmol), PyBOP (165 mg, 0.32 mmol) and DIPEA (0.1 mL, 0.57 mmol) were added to a stirred solution of (E)-4-(3-(3,5-dichloro-4-fluorophenyl)-4,4,4-trifluorobut-1-enyl)-2-nitrobenzoic acid (130 mg, 0.29 mmol) in CH$_2$Cl$_2$ (3 mL) and the reaction mixture was stirred at ambient temperature for 8 h. Water was added to reaction mixture and extracted with CH$_2$Cl$_2$. The organic layer was washed with brine, dried (Na$_2$SO$_4$), filtered, concentrated and the residue was purified by column chromatography on silica (100-200 mesh) eluting with 30% EtOAc in petroleum ether to afford the title compound as a yellow solid (120 mg, 74%): $^1$H NMR (300 MHz, DMSO-$d_6$) δ 9.04 (t, J=5.7 Hz, 1H), 8.60 (t, J=6.0 Hz, 1H), 8.25 (s, 1H), 7.97-7.94 (m, 1H), 7.87 (d, J=6.3 Hz, 2H), 7.69 (d, J=7.5 Hz, 1H), 7.15 (dd, J=15.9, 9.3 Hz, 1H), 6.89 (d, J=15.9 Hz, 1H), 4.88-4.83 (m, 1H), 3.98-3.89 (m, 4H); ESIMS m/z 575.87 ([M+H]$^+$); IR (KBr) 3430, 2925, 1663, 1168, 832 cm$^{-1}$.

Step 4. (E)-2-Amino-4-(3-(3,5-dichloro-4-fluorophenyl)-4,4,4-trifluorobut-1-enyl)-N-(2-oxo-2-(2,2,2-trifluoroethylamino)ethyl)benzamide Iron powder (81.8 mg, 1.46 mmol) and NH$_4$Cl (104 mg, 1.94 mmol) was added to a stirred solution of (E)-4-(3-(3,5-dichloro-4-fluorophenyl)-4,4,4-trifluorobut-1-enyl)-2-nitro-N-(2-oxo-2-(2,2,2-trifluoroethylamino)ethyl)benzamide (280 mg, 0.486 mmol) in EtOH: water (6 mL, 1:1) at ambient temperature and the mixture was stirred at reflux for 90 min. The reaction mixture was cooled to ambient temperature and filtered through celite. The filtrate was concentrated and the residue was dissolved in EtOAc and washed with saturated NaHCO$_3$ solution, brine and water. The organic layer was dried (Na$_2$SO$_4$), filtered, concentrated and the residue was purified by column chromatography on silica (10-200 mesh) eluting with 35% EtOAc in petroleum ether to afford the titled compound as a yellow solid (215 mg, 81%).

Example 147

(E)-2-Bromo-4-(3-(3,5-dichloro-4-hydroxyphenyl)-4,4,4-trifluorobut-1-enyl)-N-(2-oxo-2-(2,2,2-trifluoroethylamino)ethyl)benzamide

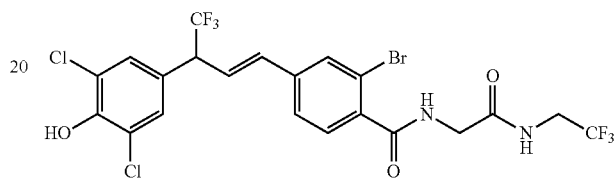

DIPEA (0.20 mL, 1.26 mmol), PyBOP (245 mg, 0.47 mmol) and 2-amino-N-(2,2,2-trifluoroethyl)acetamide (90 mg, 0.47 mmol) were added to a stirred solution of (E)-2-bromo-4-(3-(3,5-dichloro-4-hydroxyphenyl)-4,4,4-trifluorobut-1-enyl)benzoic acid (200 mg, 0.42 mmol, 66% purity) in CH$_2$Cl$_2$ (5 mL) at ambient temperature. The resulting mixture was then stirred for 12 h. The reaction mixture was diluted with CH$_2$Cl$_2$, washed with 1N HCl, followed by saturated sodium bicarbonate solution, brine solution and water. The organic layer was dried (Na$_2$SO$_4$), filtered, concentrated under vacuum. The residue was purified by column chromatography on silica (100-200 mesh) eluting with 30% EtOAc in petroleum ether to give the title compound as light green solid (130 mg, 52%).

Example 148

Preparation of (R)-2-Amino-3-methyl-N-(2,2,2-trifluoroethyl)butanamide

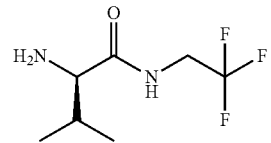

A Parr shaker flask charged with (R)-benzyl (3-methyl-1-oxo-1-((2,2,2-trifluoroethyl)amino)-butan-2-yl)carbamate (4.95 g, 14.9 mmol) in 100 mL of EtOAc and 25 mL of EtOH was treated with 175 mg of 10% Pd/C. The mixture was placed under 40 psi of hydrogen and shaken for 6 h. An additional 65 mg of 10% Pd/C was added to the reaction mixture which was then placed under 40 psi of hydrogen and shaken for 3.5 h. The reaction solution was then filtered through a pad of celite, concentrated in vacuo and purified by sublimation (75 to 85° C., 200-230 millibar) to afford the title compound as a white solid (1.92 g, 65%): mp 43-47° C.; $^1$H NMR (400 MHz, CDCl$_3$) δ 8.04-7.74 (m, 1H), 3.92 (ddd, J=16.0, 9.3, 6.8 Hz, 1H), 3.84-3.60 (m, 1H), 3.23 (d, J=3.8

Hz, 1H), 2.23 (ddd, J=10.7, 7.0, 3.5 Hz, 1H), 0.92 (d, J=7.0 Hz, 3H), 0.75 (d, J=6.9 Hz, 3H); $^{19}$F NMR (376 MHz, CDCl$_3$) δ −72.70.

Example 149

Preparation of (E)-4-(3-(3,5-Dichloro-4-fluorophenyl)-4,4,4-trifluorobut-1-enyl)-2-(methylsulfonyl)-N-(2-oxo-2-(2,2,2-trifluoroethylamino)ethyl)benzamide

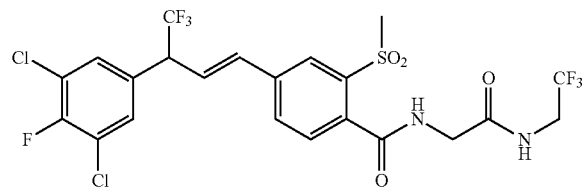 [SMILES: Nc1cc(/C=C/C(c2cc(Cl)c(F)c(Cl)c2)C(F)(F)F)ccc1C(=O)NCC(=O)NCC(F)(F)F]

Oxone (320 mg, 0.50 mmol) was added to a stirred solution of (E)-4-(3-(3,5-dichloro-4-fluorophenyl)-4,4,4-trifluorobut-1-enyl)-2-(methylthio)-N-(2-oxo-2-(2,2,2-trifluoroethylamino)ethyl)benzamide (150 mg, 0.25 mmol) in acetone-water (10 mL, 1:1) at ambient temperature and the reaction mixture was stirred for 18 h. The reaction mixture was then extracted with CH$_2$Cl$_2$. The organic layer was washed with brine and water, dried (Na$_2$SO$_4$), filtered, concentrated and the residue was triturated with pentane-Et$_2$O (1:1) to afford the title compound as an off white solid (85 mg, 56%): $^1$H NMR (300 MHz, DMSO-d$_6$) δ 9.01 (t, J=6.0, 1H), 8.37 (t, J=6.4 Hz, 1H), 8.08 (s, 1H), 8.01-7.96 (m, 1H), 7.88-7.86 (m, 2H), 7.64 (d, J=7.6 Hz, 1H), 7.05 (dd, J=16.4, 8.8 Hz, 1H), 6.91 (d, J=15.6 Hz, 1H), 4.87-4.80 (m, 1H), 3.98-3.91 (m, 4H), 3.38 (s, 3H); ESIMS m/z 608.85 ([M+H]$^+$); IR (thin film) 337, 416, 721, 164, 768 cm$^{-1}$.

The following prophetic molecules could be made in accordance with the procedures disclosed in this application:

| Compound Number | Structure |
|---|---|
| P1 | 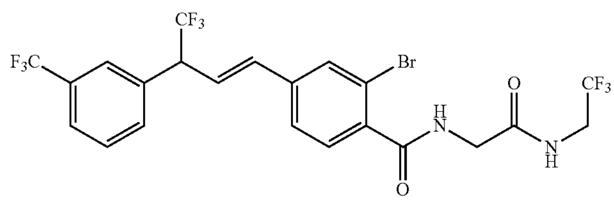 [SMILES: O=C(CNC(=O)c1ccc(/C=C/C(c2cccc(C(F)(F)F)c2)C(F)(F)F)cc1Br)NCC(F)(F)F] |
| P2 | 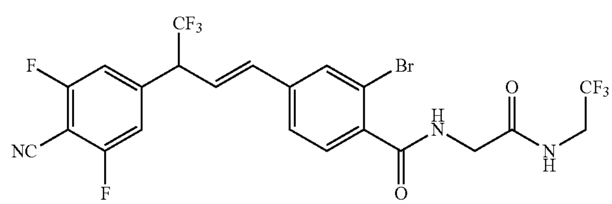 [SMILES: N#Cc1c(F)cc(C(/C=C/c2ccc(C(=O)NCC(=O)NCC(F)(F)F)c(Br)c2)C(F)(F)F)cc1F] |
| P3 | 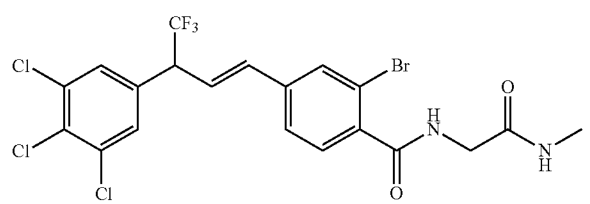 [SMILES: CNC(=O)CNC(=O)c1ccc(/C=C/C(c2cc(Cl)c(Cl)c(Cl)c2)C(F)(F)F)cc1Br] |
| P4 | 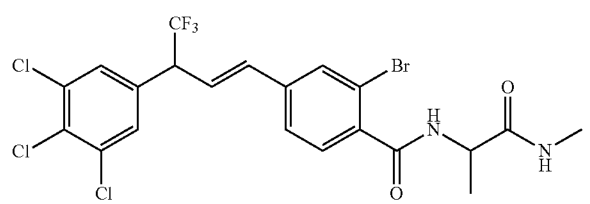 [SMILES: CNC(=O)C(C)NC(=O)c1ccc(/C=C/C(c2cc(Cl)c(Cl)c(Cl)c2)C(F)(F)F)cc1Br] |
| P5 | 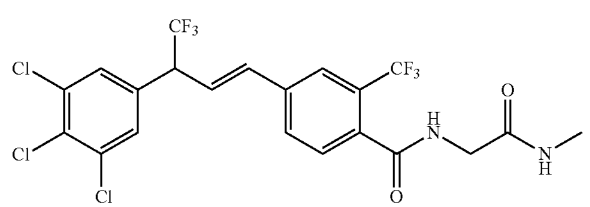 [SMILES: CNC(=O)CNC(=O)c1ccc(/C=C/C(c2cc(Cl)c(Cl)c(Cl)c2)C(F)(F)F)cc1C(F)(F)F] |

| Compound Number | Structure |
|---|---|
| P6 | 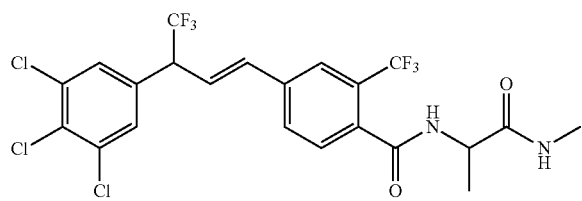 [SMILES: CNC(=O)C(C)NC(=O)c1ccc(/C=C/C(c2cc(Cl)c(Cl)c(Cl)c2)C(F)(F)F)cc1C(F)(F)F] |
| P7 | 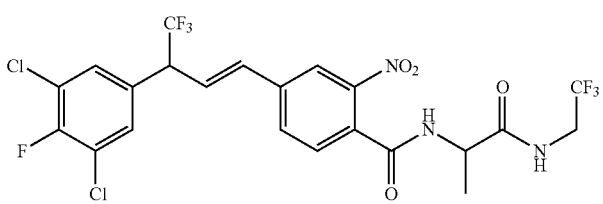 [SMILES: CC(NC(=O)c1ccc(/C=C/C(c2cc(Cl)c(F)c(Cl)c2)C(F)(F)F)cc1[N+](=O)[O-])C(=O)NCC(F)(F)F] |
| P8 | 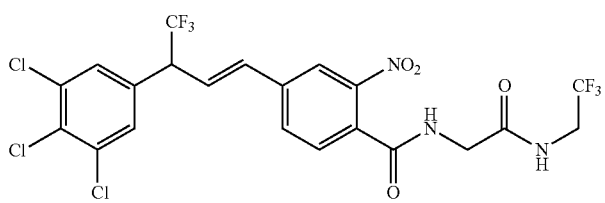 [SMILES: O=C(CNC(=O)c1ccc(/C=C/C(c2cc(Cl)c(Cl)c(Cl)c2)C(F)(F)F)cc1[N+](=O)[O-])NCC(F)(F)F] |
| P9 | 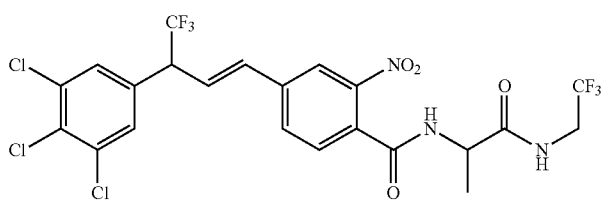 [SMILES: CC(NC(=O)c1ccc(/C=C/C(c2cc(Cl)c(Cl)c(Cl)c2)C(F)(F)F)cc1[N+](=O)[O-])C(=O)NCC(F)(F)F] |
| P10 | 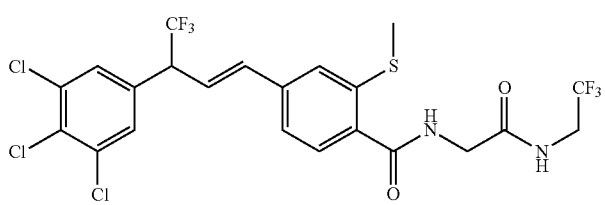 |
| P11 | 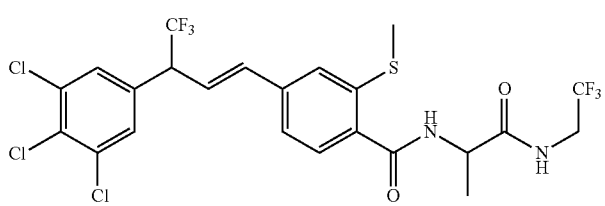 [SMILES: CSc1cc(/C=C/C(c2cc(Cl)c(Cl)c(Cl)c2)C(F)(F)F)ccc1C(=O)NC(C)C(=O)NCC(F)(F)F] |
| P12 | 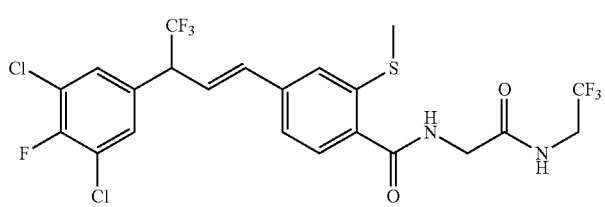 [SMILES: CSc1cc(/C=C/C(c2cc(Cl)c(F)c(Cl)c2)C(F)(F)F)ccc1C(=O)NCC(=O)NCC(F)(F)F] |

-continued

| Compound Number | Structure |
|---|---|
| P13 | 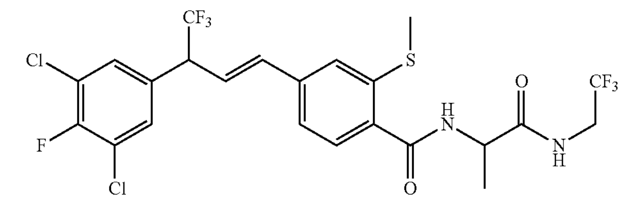 [SMILES: CSc1cc(/C=C/C(c2cc(Cl)c(F)c(Cl)c2)C(F)(F)F)ccc1C(=O)NC(C)C(=O)NCC(F)(F)F] |
| P14 | 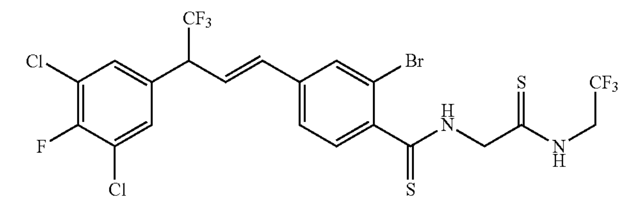 |
| P15 | 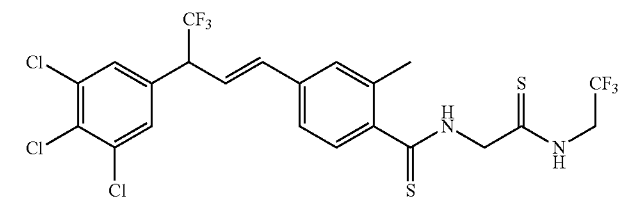 [SMILES: Cc1cc(/C=C/C(c2cc(Cl)c(Cl)c(Cl)c2)C(F)(F)F)ccc1C(=S)NCC(=S)NCC(F)(F)F] |
| P16 | 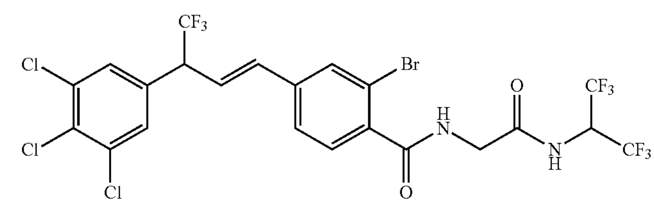 [SMILES: O=C(CNC(=O)c1ccc(/C=C/C(c2cc(Cl)c(Cl)c(Cl)c2)C(F)(F)F)cc1Br)NC(C(F)(F)F)C(F)(F)F] |
| P17 | 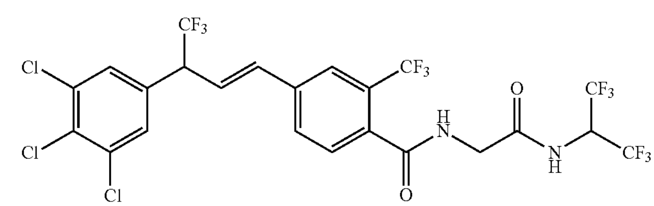 [SMILES: O=C(CNC(=O)c1ccc(/C=C/C(c2cc(Cl)c(Cl)c(Cl)c2)C(F)(F)F)cc1C(F)(F)F)NC(C(F)(F)F)C(F)(F)F] |
| P18 | 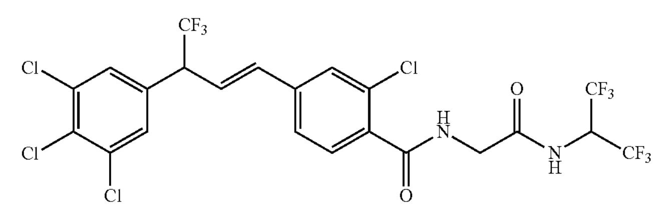 [SMILES: O=C(CNC(=O)c1ccc(/C=C/C(c2cc(Cl)c(Cl)c(Cl)c2)C(F)(F)F)cc1Cl)NC(C(F)(F)F)C(F)(F)F] |
| P19 | 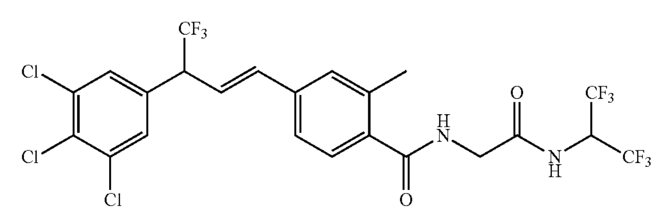 [SMILES: Cc1cc(/C=C/C(c2cc(Cl)c(Cl)c(Cl)c2)C(F)(F)F)ccc1C(=O)NCC(=O)NC(C(F)(F)F)C(F)(F)F] |

-continued
| Compound Number | Structure |
|---|---|
| P20 | 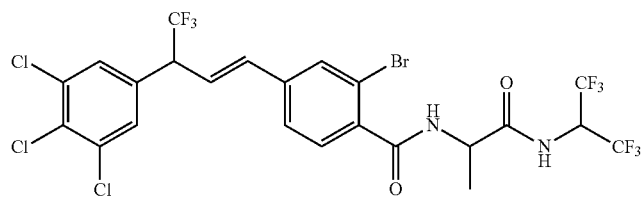 [SMILES: CC(NC(=O)c1ccc(/C=C/C(c2cc(Cl)c(Cl)c(Cl)c2)C(F)(F)F)cc1Br)C(=O)NC(C(F)(F)F)C(F)(F)F] |
| P21 | 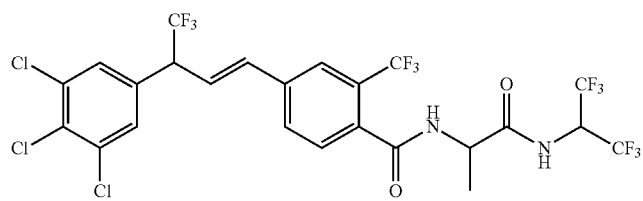 [SMILES: CC(NC(=O)c1ccc(/C=C/C(c2cc(Cl)c(Cl)c(Cl)c2)C(F)(F)F)cc1C(F)(F)F)C(=O)NC(C(F)(F)F)C(F)(F)F] |
| P22 | 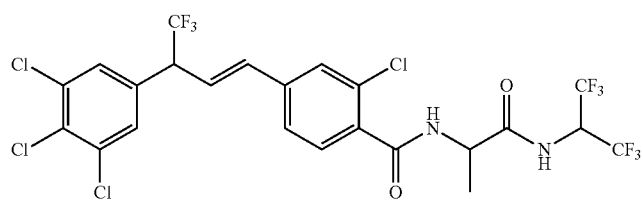 [SMILES: CC(NC(=O)c1ccc(/C=C/C(c2cc(Cl)c(Cl)c(Cl)c2)C(F)(F)F)cc1Cl)C(=O)NC(C(F)(F)F)C(F)(F)F] |
| P23 | 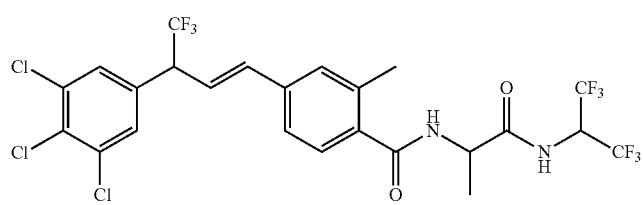 [SMILES: Cc1cc(/C=C/C(c2cc(Cl)c(Cl)c(Cl)c2)C(F)(F)F)ccc1C(=O)NC(C)C(=O)NC(C(F)(F)F)C(F)(F)F] |
| P24 | 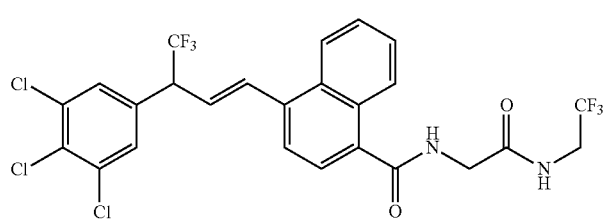 [SMILES: O=C(CNC(=O)c1ccc(/C=C/C(c2cc(Cl)c(Cl)c(Cl)c2)C(F)(F)F)c2ccccc12)NCC(F)(F)F] |
| P25 | 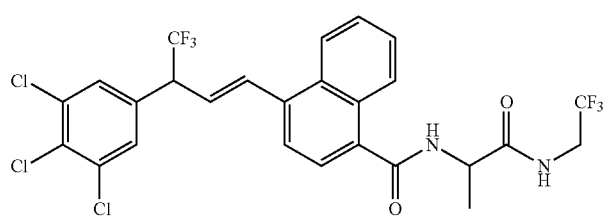 [SMILES: CC(NC(=O)c1ccc(/C=C/C(c2cc(Cl)c(Cl)c(Cl)c2)C(F)(F)F)c2ccccc12)C(=O)NCC(F)(F)F] |
| P26 | 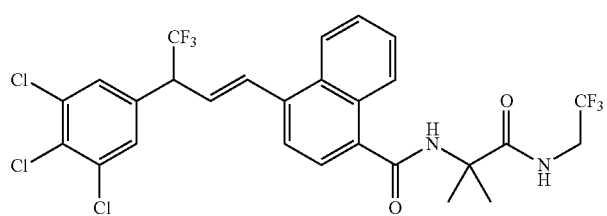 [SMILES: CC(C)(NC(=O)c1ccc(/C=C/C(c2cc(Cl)c(Cl)c(Cl)c2)C(F)(F)F)c2ccccc12)C(=O)NCC(F)(F)F] |

213
-continued
| Compound Number | Structure |
|---|---|
| P27 | 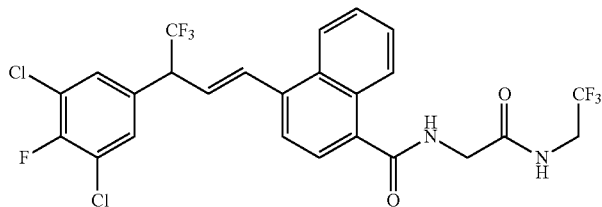 [SMILES: O=C(CNC(=O)c1ccc(/C=C/C(c2cc(Cl)c(F)c(Cl)c2)C(F)(F)F)c2ccccc12)NCC(F)(F)F] |
| P28 | 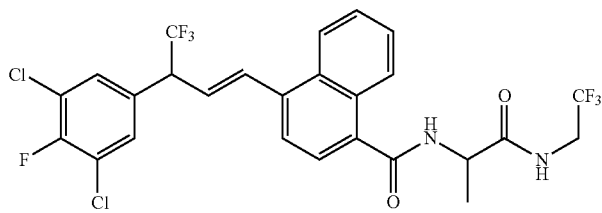 [SMILES: CC(NC(=O)c1ccc(/C=C/C(c2cc(Cl)c(F)c(Cl)c2)C(F)(F)F)c2ccccc12)C(=O)NCC(F)(F)F] |
| P29 | 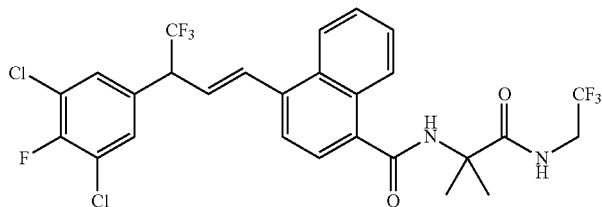 [SMILES: CC(C)(NC(=O)c1ccc(/C=C/C(c2cc(Cl)c(F)c(Cl)c2)C(F)(F)F)c2ccccc12)C(=O)NCC(F)(F)F] |
| P30 | 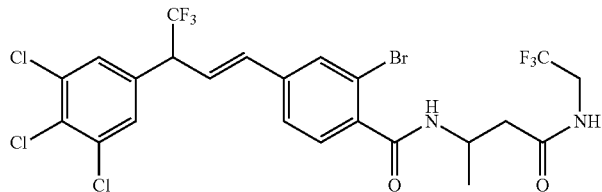 [SMILES: CC(CC(=O)NCC(F)(F)F)NC(=O)c1ccc(/C=C/C(c2cc(Cl)c(Cl)c(Cl)c2)C(F)(F)F)cc1Br] |
| P31 | 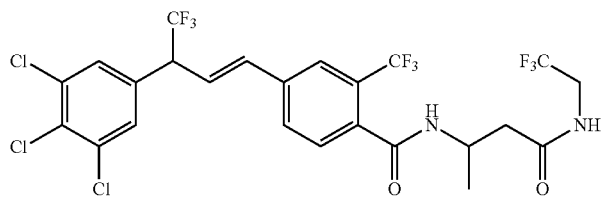 |
| P32 | 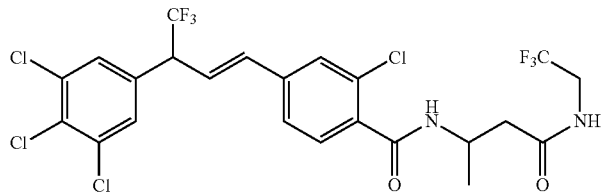 [SMILES: CC(CC(=O)NCC(F)(F)F)NC(=O)c1ccc(/C=C/C(c2cc(Cl)c(Cl)c(Cl)c2)C(F)(F)F)cc1Cl] |
| P33 | 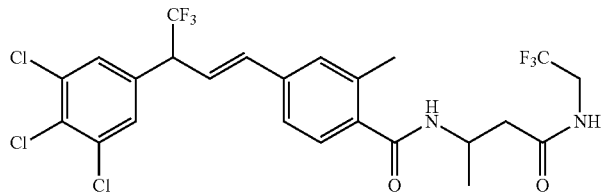 [SMILES: Cc1cc(/C=C/C(c2cc(Cl)c(Cl)c(Cl)c2)C(F)(F)F)ccc1C(=O)NC(C)CC(=O)NCC(F)(F)F] |

| Compound Number | Structure |
|---|---|
| P34 | 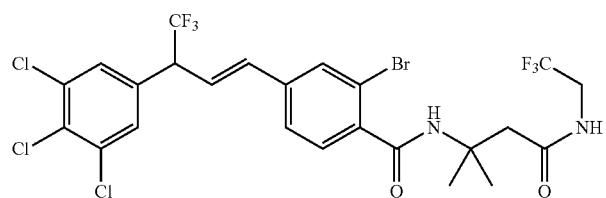 [SMILES: CC(C)(CC(=O)NCC(F)(F)F)NC(=O)c1ccc(/C=C/C(c2cc(Cl)c(Cl)c(Cl)c2)C(F)(F)F)cc1Br] |
| P35 | 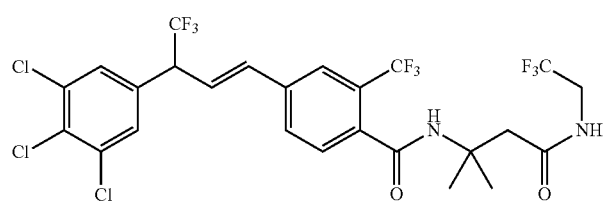 |
| P36 | 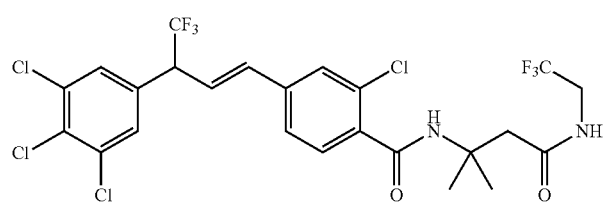 [SMILES: CC(C)(CC(=O)NCC(F)(F)F)NC(=O)c1ccc(/C=C/C(c2cc(Cl)c(Cl)c(Cl)c2)C(F)(F)F)cc1Cl] |
| P37 | 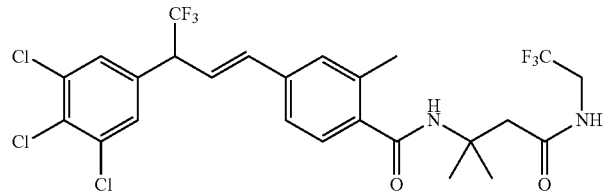 [SMILES: Cc1cc(/C=C/C(c2cc(Cl)c(Cl)c(Cl)c2)C(F)(F)F)ccc1C(=O)NC(C)(C)CC(=O)NCC(F)(F)F] |
| P38 | 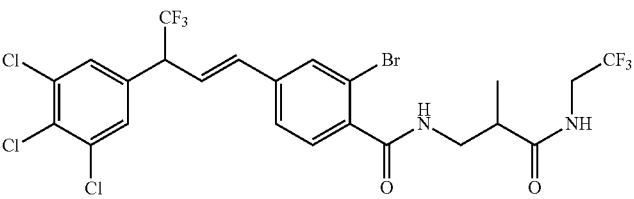 [SMILES: CC(CNC(=O)c1ccc(/C=C/C(c2cc(Cl)c(Cl)c(Cl)c2)C(F)(F)F)cc1Br)C(=O)NCC(F)(F)F] |
| P39 | 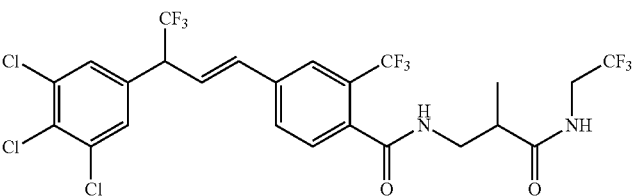 |
| P40 | 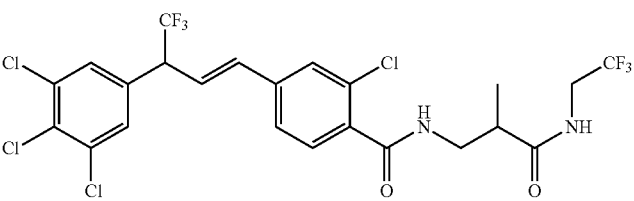 [SMILES: CC(CNC(=O)c1ccc(/C=C/C(c2cc(Cl)c(Cl)c(Cl)c2)C(F)(F)F)cc1Cl)C(=O)NCC(F)(F)F] |

| Compound Number | Structure |
|---|---|
| P41 | ![P41 structure] |
| P42 | ![P42 structure] |
| P43 | ![P43 structure] |
| P44 | ![P44 structure] |
| P45 | ![P45 structure] |

The following prophetic molecules could be made in accordance with the procedures disclosed in this application:

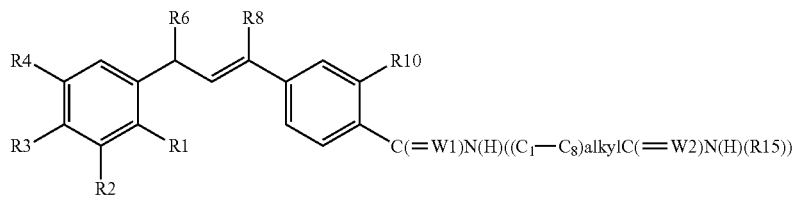

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P46 | F | F | F | H | $CF_3$ | H | Br | O | $CH_2$ | O | $CH_2CF_3$ |
| P47 | F | F | F | H | $CF_3$ | H | Cl | O | $CH_2$ | O | $CH_2CF_3$ |
| P48 | F | F | F | H | $CF_3$ | H | $CF_3$ | O | $CH_2$ | O | $CH_2CF_3$ |
| P49 | F | F | F | H | $CF_3$ | H | $CH_3$ | O | $CH_2$ | O | $CH_2CF_3$ |
| P50 | F | F | F | H | $CF_3$ | H | Br | O | $CH_2$ | S | $CH_2CF_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P51 | F | F | F | H | CF$_3$ | H | Cl | O | CH$_2$ | S | CH$_2$CF$_3$ |
| P52 | F | F | F | H | CF$_3$ | H | CF$_3$ | O | CH$_2$ | S | CH$_2$CF$_3$ |
| P53 | F | F | F | H | CF$_3$ | H | CH$_3$ | O | CH$_2$ | S | CH$_2$CF$_3$ |
| P54 | F | F | F | H | CF$_3$ | H | Br | S | CH$_2$ | O | CH$_2$CF$_3$ |
| P55 | F | F | F | H | CF$_3$ | H | Cl | S | CH$_2$ | O | CH$_2$CF$_3$ |
| P56 | F | F | F | H | CF$_3$ | H | CF$_3$ | S | CH$_2$ | O | CH$_2$CF$_3$ |
| P57 | F | F | F | H | CF$_3$ | H | CH$_3$ | S | CH$_2$ | O | CH$_2$CF$_3$ |
| P58 | F | F | F | H | CF$_3$ | H | Br | O | CH$_2$ | O | CH$_2$CHF$_2$ |
| P59 | F | F | F | H | CF$_3$ | H | Cl | O | CH$_2$ | O | CH$_2$CHF$_2$ |
| P60 | F | F | F | H | CF$_3$ | H | CF$_3$ | O | CH$_2$ | O | CH$_2$CHF$_2$ |
| P61 | F | F | F | H | CF$_3$ | H | CH$_3$ | O | CH$_2$ | O | CH$_2$CHF$_2$ |
| P62 | F | F | F | H | CF$_3$ | CF$_3$ | Br | O | CH$_2$ | O | CH$_2$CF$_3$ |
| P63 | F | F | F | H | CF$_3$ | CF$_3$ | Cl | O | CH$_2$ | O | CH$_2$CF$_3$ |
| P64 | F | F | F | H | CF$_3$ | CF$_3$ | CF$_3$ | O | CH$_2$ | O | CH$_2$CF$_3$ |
| P65 | F | F | F | H | CF$_3$ | CF$_3$ | CH$_3$ | O | CH$_2$ | O | CH$_2$CF$_3$ |
| P66 | F | F | F | H | CF$_2$CF$_3$ | H | Br | O | CH$_2$ | O | CH$_2$CF$_3$ |
| P67 | F | F | F | H | CF$_2$CF$_3$ | H | Cl | O | CH$_2$ | O | CH$_2$CF$_3$ |
| P68 | F | F | F | H | CF$_2$CF$_3$ | H | CF$_3$ | O | CH$_2$ | O | CH$_2$CF$_3$ |
| P69 | F | F | F | H | CF$_2$CF$_3$ | H | CH$_3$ | O | CH$_2$ | O | CH$_2$CF$_3$ |
| P70 | F | F | F | H | CF$_3$ | H | Br | O | CH$_2$ | O | CH(CH$_3$)CF$_3$ |
| P71 | F | F | F | H | CF$_3$ | H | Cl | O | CH$_2$ | O | CH(CH$_3$)CF$_3$ |
| P72 | F | F | F | H | CF$_3$ | H | CF$_3$ | O | CH$_2$ | O | CH(CH$_3$)CF$_3$ |
| P73 | F | F | F | H | CF$_3$ | H | CH$_3$ | O | CH$_2$ | O | CH(CH$_3$)CF$_3$ |
| P74 | F | F | F | H | CF$_3$ | CF$_3$ | Br | O | CH(CH$_3$) | O | CH$_2$CF$_3$ |
| P75 | F | F | F | H | CF$_3$ | CF$_3$ | Cl | O | CH(CH$_3$) | O | CH$_2$CF$_3$ |
| P76 | F | F | F | H | CF$_3$ | CF$_3$ | CF$_3$ | O | CH(CH$_3$) | O | CH$_2$CF$_3$ |
| P77 | F | F | F | H | CF$_3$ | CF$_3$ | CH$_3$ | O | CH(CH$_3$) | O | CH$_2$CF$_3$ |
| P78 | F | F | F | H | CF$_2$CF$_3$ | H | Br | O | CH(CH$_3$) | O | CH$_2$CF$_3$ |
| P79 | F | F | F | H | CF$_2$CF$_3$ | H | Cl | O | CH(CH$_3$) | O | CH$_2$CF$_3$ |
| P80 | F | F | F | H | CF$_2$CF$_3$ | H | CF$_3$ | O | CH(CH$_3$) | O | CH$_2$CF$_3$ |
| P81 | F | F | F | H | CF$_2$CF$_3$ | H | CH$_3$ | O | CH(CH$_3$) | O | CH$_2$CF$_3$ |
| P82 | F | F | F | H | CF$_3$ | H | Br | O | CH(CH$_3$) | O | CH$_2$CF$_3$ |
| P83 | F | F | F | H | CF$_3$ | H | Cl | O | CH(CH$_3$) | O | CH$_2$CF$_3$ |
| P84 | F | F | F | H | CF$_3$ | H | CF$_3$ | O | CH(CH$_3$) | O | CH$_2$CF$_3$ |
| P85 | F | F | F | H | CF$_3$ | H | CH$_3$ | O | CH(CH$_3$) | O | CH$_2$CF$_3$ |
| P86 | F | F | F | H | CF$_3$ | H | Br | O | CH(CH$_3$) | S | CH$_2$CF$_3$ |
| P87 | F | F | F | H | CF$_3$ | H | Cl | O | CH(CH$_3$) | S | CH$_2$CF$_3$ |
| P88 | F | F | F | H | CF$_3$ | H | CF$_3$ | O | CH(CH$_3$) | S | CH$_2$CF$_3$ |
| P89 | F | F | F | H | CF$_3$ | H | CH$_3$ | O | CH(CH$_3$) | S | CH$_2$CF$_3$ |
| P90 | F | F | F | H | CF$_3$ | H | Br | S | CH(CH$_3$) | O | CH$_2$CF$_3$ |
| P91 | F | F | F | H | CF$_3$ | H | Cl | S | CH(CH$_3$) | O | CH$_2$CF$_3$ |
| P92 | F | F | F | H | CF$_3$ | H | CF$_3$ | S | CH(CH$_3$) | O | CH$_2$CF$_3$ |
| P93 | F | F | F | H | CF$_3$ | H | CH$_3$ | S | CH(CH$_3$) | O | CH$_2$CF$_3$ |
| P94 | F | F | F | H | CF$_3$ | H | Br | O | CH(CH$_3$) | O | CH$_2$CHF$_2$ |
| P95 | F | F | F | H | CF$_3$ | H | Cl | O | CH(CH$_3$) | O | CH$_2$CHF$_2$ |
| P96 | F | F | F | H | CF$_3$ | H | CF$_3$ | O | CH(CH$_3$) | O | CH$_2$CHF$_2$ |
| P97 | F | F | F | H | CF$_3$ | H | CH$_3$ | O | CH(CH$_3$) | O | CH$_2$CHF$_2$ |
| P98 | F | F | F | H | CF$_3$ | H | Br | O | CH(CH$_3$) | O | CH(CH$_3$)CF$_3$ |
| P99 | F | F | F | H | CF$_3$ | H | Cl | O | CH(CH$_3$) | O | CH(CH$_3$)CF$_3$ |
| P100 | F | F | F | H | CF$_3$ | H | CF$_3$ | O | CH(CH$_3$) | O | CH(CH$_3$)CF$_3$ |
| P101 | F | F | F | H | CF$_3$ | H | CH$_3$ | O | CH(CH$_3$) | O | CH(CH$_3$)CF$_3$ |
| P102 | F | F | F | H | CF$_3$ | H | Br | O | CH(CH$_3$) | O | CH$_2$CH$_2$CF$_3$ |
| P103 | F | F | F | H | CF$_3$ | H | Cl | O | CH(CH$_3$) | O | CH$_2$CH$_2$CF$_3$ |
| P104 | F | F | F | H | CF$_3$ | H | CF$_3$ | O | CH(CH$_3$) | O | CH$_2$CH$_2$CF$_3$ |
| P105 | F | F | F | H | CF$_3$ | H | CH$_3$ | O | CH(CH$_3$) | O | CH$_2$CH$_2$CF$_3$ |
| P106 | F | F | F | H | CF$_3$ | H | Br | O | CH(CH$_2$CH$_3$) | O | CH$_2$CF$_3$ |
| P107 | F | F | F | H | CF$_3$ | H | Cl | O | CH(CH$_2$CH$_3$) | O | CH$_2$CF$_3$ |
| P108 | F | F | F | H | CF$_3$ | H | CF$_3$ | O | CH(CH$_2$CH$_3$) | O | CH$_2$CF$_3$ |
| P109 | F | F | F | H | CF$_3$ | H | CH$_3$ | O | CH(CH$_2$CH$_3$) | O | CH$_2$CF$_3$ |
| P110 | F | F | F | H | CF$_3$ | H | Br | O | C(CH$_3$)$_2$ | O | CH$_2$CF$_3$ |
| P111 | F | F | F | H | CF$_3$ | H | Cl | O | C(CH$_3$)$_2$ | O | CH$_2$CF$_3$ |
| P112 | F | F | F | H | CF$_3$ | H | CF$_3$ | O | C(CH$_3$)$_2$ | O | CH$_2$CF$_3$ |
| P113 | F | F | F | H | CF$_3$ | H | CH$_3$ | O | C(CH$_3$)$_2$ | O | CH$_2$CF$_3$ |
| P114 | F | F | F | H | CF$_3$ | H | Br | O | CH$_2$CH$_2$ | O | CH$_2$CF$_3$ |
| P115 | F | F | F | H | CF$_3$ | H | Cl | O | CH$_2$CH$_2$ | O | CH$_2$CF$_3$ |
| P116 | F | F | F | H | CF$_3$ | H | CF$_3$ | O | CH$_2$CH$_2$ | O | CH$_2$CF$_3$ |
| P117 | F | F | F | H | CF$_3$ | H | CH$_3$ | O | CH$_2$CH$_2$ | O | CH$_2$CF$_3$ |
| P118 | Cl | Cl | H | Cl | CF$_3$ | H | Br | O | CH$_2$ | O | CH$_2$CF$_3$ |
| P119 | Cl | Cl | H | Cl | CF$_3$ | H | Cl | O | CH$_2$ | O | CH$_2$CF$_3$ |
| P120 | Cl | Cl | H | Cl | CF$_3$ | H | CF$_3$ | O | CH$_2$ | O | CH$_2$CF$_3$ |
| P121 | Cl | Cl | H | Cl | CF$_3$ | H | CH$_3$ | O | CH$_2$ | O | CH$_2$CF$_3$ |
| P122 | Cl | Cl | H | Cl | CF$_3$ | H | Br | O | CH$_2$ | S | CH$_2$CF$_3$ |
| P123 | Cl | Cl | H | Cl | CF$_3$ | H | Cl | O | CH$_2$ | S | CH$_2$CF$_3$ |
| P124 | Cl | Cl | H | Cl | CF$_3$ | H | CF$_3$ | O | CH$_2$ | S | CH$_2$CF$_3$ |
| P125 | Cl | Cl | H | Cl | CF$_3$ | H | CH$_3$ | O | CH$_2$ | S | CH$_2$CF$_3$ |
| P126 | Cl | Cl | H | Cl | CF$_3$ | H | Br | S | CH$_2$ | O | CH$_2$CF$_3$ |
| P127 | Cl | Cl | H | Cl | CF$_3$ | H | Cl | S | CH$_2$ | O | CH$_2$CF$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P128 | Cl | Cl | H | Cl | CF$_3$ | H | CF$_3$ | S | CH$_2$ | O | CH$_2$CF$_3$ |
| P129 | Cl | Cl | H | Cl | CF$_3$ | H | CH$_3$ | S | CH$_2$ | O | CH$_2$CF$_3$ |
| P130 | Cl | Cl | H | Cl | CF$_3$ | H | Br | O | CH$_2$ | O | CH$_2$CHF$_2$ |
| P131 | Cl | Cl | H | Cl | CF$_3$ | H | Cl | O | CH$_2$ | O | CH$_2$CHF$_2$ |
| P132 | Cl | Cl | H | Cl | CF$_3$ | H | CF$_3$ | O | CH$_2$ | O | CH$_2$CHF$_2$ |
| P133 | Cl | Cl | H | Cl | CF$_3$ | H | CH$_3$ | O | CH$_2$ | O | CH$_2$CHF$_2$ |
| P134 | Cl | Cl | H | Cl | CF$_3$ | CF$_3$ | Br | O | CH$_2$ | O | CH$_2$CF$_3$ |
| P135 | Cl | Cl | H | Cl | CF$_3$ | CF$_3$ | Cl | O | CH$_2$ | O | CH$_2$CF$_3$ |
| P136 | Cl | Cl | H | Cl | CF$_3$ | CF$_3$ | CF$_3$ | O | CH$_2$ | O | CH$_2$CF$_3$ |
| P137 | Cl | Cl | H | Cl | CF$_3$ | CF$_3$ | CH$_3$ | O | CH$_2$ | O | CH$_2$CF$_3$ |
| P138 | Cl | Cl | H | Cl | CF$_2$CF$_3$ | H | Br | O | CH$_2$ | O | CH$_2$CF$_3$ |
| P139 | Cl | Cl | H | Cl | CF$_2$CF$_3$ | H | Cl | O | CH$_2$ | O | CH$_2$CF$_3$ |
| P140 | Cl | Cl | H | Cl | CF$_2$CF$_3$ | H | CF$_3$ | O | CH$_2$ | O | CH$_2$CF$_3$ |
| P141 | Cl | Cl | H | Cl | CF$_2$CF$_3$ | H | CH$_3$ | O | CH$_2$ | O | CH$_2$CF$_3$ |
| P142 | Cl | Cl | H | Cl | CF$_3$ | H | Br | O | CH$_2$ | O | CH(CH$_3$)CF$_3$ |
| P143 | Cl | Cl | H | Cl | CF$_3$ | H | Cl | O | CH$_2$ | O | CH(CH$_3$)CF$_3$ |
| P144 | Cl | Cl | H | Cl | CF$_3$ | H | CF$_3$ | O | CH$_2$ | O | CH(CH$_3$)CF$_3$ |
| P145 | Cl | Cl | H | Cl | CF$_3$ | H | CH$_3$ | O | CH$_2$ | O | CH(CH$_3$)CF$_3$ |
| P146 | Cl | Cl | H | Cl | CF$_3$ | CF$_3$ | Br | O | CH(CH$_3$) | O | CH$_2$CF$_3$ |
| P147 | Cl | Cl | H | Cl | CF$_3$ | CF$_3$ | Cl | O | CH(CH$_3$) | O | CH$_2$CF$_3$ |
| P148 | Cl | Cl | H | Cl | CF$_3$ | CF$_3$ | CF$_3$ | O | CH(CH$_3$) | O | CH$_2$CF$_3$ |
| P149 | Cl | Cl | H | Cl | CF$_3$ | CF$_3$ | CH$_3$ | O | CH(CH$_3$) | O | CH$_2$CF$_3$ |
| P150 | Cl | Cl | H | Cl | CF$_2$CF$_3$ | H | Br | O | CH(CH$_3$) | O | CH$_2$CF$_3$ |
| P151 | Cl | Cl | H | Cl | CF$_2$CF$_3$ | H | Cl | O | CH(CH$_3$) | O | CH$_2$CF$_3$ |
| P152 | Cl | Cl | H | Cl | CF$_2$CF$_3$ | H | CF$_3$ | O | CH(CH$_3$) | O | CH$_2$CF$_3$ |
| P153 | Cl | Cl | H | Cl | CF$_2$CF$_3$ | H | CH$_3$ | O | CH(CH$_3$) | O | CH$_2$CF$_3$ |
| P154 | Cl | Cl | H | Cl | CF$_3$ | H | Br | O | CH(CH$_3$) | O | CH$_2$CF$_3$ |
| P155 | Cl | Cl | H | Cl | CF$_3$ | H | Cl | O | CH(CH$_3$) | O | CH$_2$CF$_3$ |
| P156 | Cl | Cl | H | Cl | CF$_3$ | H | CF$_3$ | O | CH(CH$_3$) | O | CH$_2$CF$_3$ |
| P157 | Cl | Cl | H | Cl | CF$_3$ | H | CH$_3$ | O | CH(CH$_3$) | O | CH$_2$CF$_3$ |
| P158 | Cl | Cl | H | Cl | CF$_3$ | H | Br | O | CH(CH$_3$) | S | CH$_2$CF$_3$ |
| P159 | Cl | Cl | H | Cl | CF$_3$ | H | Cl | O | CH(CH$_3$) | S | CH$_2$CF$_3$ |
| P160 | Cl | Cl | H | Cl | CF$_3$ | H | CF$_3$ | O | CH(CH$_3$) | S | CH$_2$CF$_3$ |
| P161 | Cl | Cl | H | Cl | CF$_3$ | H | CH$_3$ | O | CH(CH$_3$) | S | CH$_2$CF$_3$ |
| P162 | Cl | Cl | H | Cl | CF$_3$ | H | Br | S | CH(CH$_3$) | O | CH$_2$CF$_3$ |
| P163 | Cl | Cl | H | Cl | CF$_3$ | H | Cl | S | CH(CH$_3$) | O | CH$_2$CF$_3$ |
| P164 | Cl | Cl | H | Cl | CF$_3$ | H | CF$_3$ | S | CH(CH$_3$) | O | CH$_2$CF$_3$ |
| P165 | Cl | Cl | H | Cl | CF$_3$ | H | CH$_3$ | S | CH(CH$_3$) | O | CH$_2$CF$_3$ |
| P166 | Cl | Cl | H | Cl | CF$_3$ | H | Br | O | CH(CH$_3$) | O | CH$_2$CHF$_2$ |
| P167 | Cl | Cl | H | Cl | CF$_3$ | H | Cl | O | CH(CH$_3$) | O | CH$_2$CHF$_2$ |
| P168 | Cl | Cl | H | Cl | CF$_3$ | H | CF$_3$ | O | CH(CH$_3$) | O | CH$_2$CHF$_2$ |
| P169 | Cl | Cl | H | Cl | CF$_3$ | H | CH$_3$ | O | CH(CH$_3$) | O | CH$_2$CHF$_2$ |
| P170 | Cl | Cl | H | Cl | CF$_3$ | H | Br | O | CH(CH$_3$) | O | CH(CH$_3$)CF$_3$ |
| P171 | Cl | Cl | H | Cl | CF$_3$ | H | Cl | O | CH(CH$_3$) | O | CH(CH$_3$)CF$_3$ |
| P172 | Cl | Cl | H | Cl | CF$_3$ | H | CF$_3$ | O | CH(CH$_3$) | O | CH(CH$_3$)CF$_3$ |
| P173 | Cl | Cl | H | Cl | CF$_3$ | H | CH$_3$ | O | CH(CH$_3$) | O | CH(CH$_3$)CF$_3$ |
| P174 | Cl | Cl | H | Cl | CF$_3$ | H | Br | O | CH(CH$_3$) | O | CH$_2$CH$_2$CF$_3$ |
| P175 | Cl | Cl | H | Cl | CF$_3$ | H | Cl | O | CH(CH$_3$) | O | CH$_2$CH$_2$CF$_3$ |
| P176 | Cl | Cl | H | Cl | CF$_3$ | H | CF$_3$ | O | CH(CH$_3$) | O | CH$_2$CH$_2$CF$_3$ |
| P177 | Cl | Cl | H | Cl | CF$_3$ | H | CH$_3$ | O | CH(CH$_3$) | O | CH$_2$CH$_2$CF$_3$ |
| P178 | Cl | Cl | H | Cl | CF$_3$ | H | Br | O | CH(CH$_2$CH$_3$) | O | CH$_2$CF$_3$ |
| P179 | Cl | Cl | H | Cl | CF$_3$ | H | Cl | O | CH(CH$_2$CH$_3$) | O | CH$_2$CF$_3$ |
| P180 | Cl | Cl | H | Cl | CF$_3$ | H | CF$_3$ | O | CH(CH$_2$CH$_3$) | O | CH$_2$CF$_3$ |
| P181 | Cl | Cl | H | Cl | CF$_3$ | H | CH$_3$ | O | CH(CH$_2$CH$_3$) | O | CH$_2$CF$_3$ |
| P182 | Cl | Cl | H | Cl | CF$_3$ | H | Br | O | C(CH$_3$)$_2$ | O | CH$_2$CF$_3$ |
| P183 | Cl | Cl | H | Cl | CF$_3$ | H | Cl | O | C(CH$_3$)$_2$ | O | CH$_2$CF$_3$ |
| P184 | Cl | Cl | H | Cl | CF$_3$ | H | CF$_3$ | O | C(CH$_3$)$_2$ | O | CH$_2$CF$_3$ |
| P185 | Cl | Cl | H | Cl | CF$_3$ | H | CH$_3$ | O | C(CH$_3$)$_2$ | O | CH$_2$CF$_3$ |
| P186 | Cl | Cl | H | Cl | CF$_3$ | H | Br | O | CH$_2$CH$_2$ | O | CH$_2$CF$_3$ |
| P187 | Cl | Cl | H | Cl | CF$_3$ | H | Cl | O | CH$_2$CH$_2$ | O | CH$_2$CF$_3$ |
| P188 | Cl | Cl | H | Cl | CF$_3$ | H | CF$_3$ | O | CH$_2$CH$_2$ | O | CH$_2$CF$_3$ |
| P189 | Cl | Cl | H | Cl | CF$_3$ | H | CH$_3$ | O | CH$_2$CH$_2$ | O | CH$_2$CF$_3$ |
| P190 | H | H | H | OCF$_3$ | CF$_3$ | H | Br | O | CH$_2$ | O | CH$_2$CF$_3$ |
| P191 | H | H | H | OCF$_3$ | CF$_3$ | H | Cl | O | CH$_2$ | O | CH$_2$CF$_3$ |
| P192 | H | H | H | OCF$_3$ | CF$_3$ | H | CF$_3$ | O | CH$_2$ | O | CH$_2$CF$_3$ |
| P193 | H | H | H | OCF$_3$ | CF$_3$ | H | CH$_3$ | O | CH$_2$ | O | CH$_2$CF$_3$ |
| P194 | H | H | H | OCF$_3$ | CF$_3$ | H | Br | O | CH$_2$ | S | CH$_2$CF$_3$ |
| P195 | H | H | H | OCF$_3$ | CF$_3$ | H | Cl | O | CH$_2$ | S | CH$_2$CF$_3$ |
| P196 | H | H | H | OCF$_3$ | CF$_3$ | H | CF$_3$ | O | CH$_2$ | S | CH$_2$CF$_3$ |
| P197 | H | H | H | OCF$_3$ | CF$_3$ | H | CH$_3$ | O | CH$_2$ | S | CH$_2$CF$_3$ |
| P198 | H | H | H | OCF$_3$ | CF$_3$ | H | Br | S | CH$_2$ | O | CH$_2$CF$_3$ |
| P199 | H | H | H | OCF$_3$ | CF$_3$ | H | Cl | S | CH$_2$ | O | CH$_2$CF$_3$ |
| P200 | H | H | H | OCF$_3$ | CF$_3$ | H | CF$_3$ | S | CH$_2$ | O | CH$_2$CF$_3$ |
| P201 | H | H | H | OCF$_3$ | CF$_3$ | H | CH$_3$ | S | CH$_2$ | O | CH$_2$CF$_3$ |
| P202 | H | H | H | OCF$_3$ | CF$_3$ | H | Br | O | CH$_2$ | O | CH$_2$CHF$_2$ |
| P203 | H | H | H | OCF$_3$ | CF$_3$ | H | Cl | O | CH$_2$ | O | CH$_2$CHF$_2$ |
| P204 | H | H | H | OCF$_3$ | CF$_3$ | H | CF$_3$ | O | CH$_2$ | O | CH$_2$CHF$_2$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P205 | H | H | H | $OCF_3$ | $CF_3$ | H | $CH_3$ | O | $CH_2$ | O | $CH_2CHF_2$ |
| P206 | H | H | H | $OCF_3$ | $CF_3$ | $CF_3$ | Br | O | $CH_2$ | O | $CH_2CF_3$ |
| P207 | H | H | H | $OCF_3$ | $CF_3$ | $CF_3$ | Cl | O | $CH_2$ | O | $CH_2CF_3$ |
| P208 | H | H | H | $OCF_3$ | $CF_3$ | $CF_3$ | $CF_3$ | O | $CH_2$ | O | $CH_2CF_3$ |
| P209 | H | H | H | $OCF_3$ | $CF_3$ | $CF_3$ | $CH_3$ | O | $CH_2$ | O | $CH_2CF_3$ |
| P210 | H | H | H | $OCF_3$ | $CF_2CF_3$ | H | Br | O | $CH_2$ | O | $CH_2CF_3$ |
| P211 | H | H | H | $OCF_3$ | $CF_2CF_3$ | H | Cl | O | $CH_2$ | O | $CH_2CF_3$ |
| P212 | H | H | H | $OCF_3$ | $CF_2CF_3$ | H | $CF_3$ | O | $CH_2$ | O | $CH_2CF_3$ |
| P213 | H | H | H | $OCF_3$ | $CF_2CF_3$ | H | $CH_3$ | O | $CH_2$ | O | $CH_2CF_3$ |
| P214 | H | H | H | $OCF_3$ | $CF_3$ | H | Br | O | $CH_2$ | O | $CH(CH_3)CF_3$ |
| P215 | H | H | H | $OCF_3$ | $CF_3$ | H | Cl | O | $CH_2$ | O | $CH(CH_3)CF_3$ |
| P216 | H | H | H | $OCF_3$ | $CF_3$ | H | $CF_3$ | O | $CH_2$ | O | $CH(CH_3)CF_3$ |
| P217 | H | H | H | $OCF_3$ | $CF_3$ | H | $CH_3$ | O | $CH_2$ | O | $CH(CH_3)CF_3$ |
| P218 | H | H | H | $OCF_3$ | $CF_3$ | $CF_3$ | Br | O | $CH(CH_3)$ | O | $CH_2CF_3$ |
| P219 | H | H | H | $OCF_3$ | $CF_3$ | $CF_3$ | Cl | O | $CH(CH_3)$ | O | $CH_2CF_3$ |
| P220 | H | H | H | $OCF_3$ | $CF_3$ | $CF_3$ | $CF_3$ | O | $CH(CH_3)$ | O | $CH_2CF_3$ |
| P221 | H | H | H | $OCF_3$ | $CF_3$ | $CF_3$ | $CH_3$ | O | $CH(CH_3)$ | O | $CH_2CF_3$ |
| P222 | H | H | H | $OCF_3$ | $CF_2CF_3$ | H | Br | O | $CH(CH_3)$ | O | $CH_2CF_3$ |
| P223 | H | H | H | $OCF_3$ | $CF_2CF_3$ | H | Cl | O | $CH(CH_3)$ | O | $CH_2CF_3$ |
| P224 | H | H | H | $OCF_3$ | $CF_2CF_3$ | H | $CF_3$ | O | $CH(CH_3)$ | O | $CH_2CF_3$ |
| P225 | H | H | H | $OCF_3$ | $CF_2CF_3$ | H | $CH_3$ | O | $CH(CH_3)$ | O | $CH_2CF_3$ |
| P226 | H | H | H | $OCF_3$ | $CF_3$ | H | Br | O | $CH(CH_3)$ | O | $CH_2CF_3$ |
| P227 | H | H | H | $OCF_3$ | $CF_3$ | H | Cl | O | $CH(CH_3)$ | O | $CH_2CF_3$ |
| P228 | H | H | H | $OCF_3$ | $CF_3$ | H | $CF_3$ | O | $CH(CH_3)$ | O | $CH_2CF_3$ |
| P229 | H | H | H | $OCF_3$ | $CF_3$ | H | $CH_3$ | O | $CH(CH_3)$ | O | $CH_2CF_3$ |
| P230 | H | H | H | $OCF_3$ | $CF_3$ | H | Br | O | $CH(CH_3)$ | S | $CH_2CF_3$ |
| P231 | H | H | H | $OCF_3$ | $CF_3$ | H | Cl | O | $CH(CH_3)$ | S | $CH_2CF_3$ |
| P232 | H | H | H | $OCF_3$ | $CF_3$ | H | $CF_3$ | O | $CH(CH_3)$ | S | $CH_2CF_3$ |
| P233 | H | H | H | $OCF_3$ | $CF_3$ | H | $CH_3$ | O | $CH(CH_3)$ | S | $CH_2CF_3$ |
| P234 | H | H | H | $OCF_3$ | $CF_3$ | H | Br | S | $CH(CH_3)$ | O | $CH_2CF_3$ |
| P235 | H | H | H | $OCF_3$ | $CF_3$ | H | Cl | S | $CH(CH_3)$ | O | $CH_2CF_3$ |
| P236 | H | H | H | $OCF_3$ | $CF_3$ | H | $CF_3$ | S | $CH(CH_3)$ | O | $CH_2CF_3$ |
| P237 | H | H | H | $OCF_3$ | $CF_3$ | H | $CH_3$ | S | $CH(CH_3)$ | O | $CH_2CF_3$ |
| P238 | H | H | H | $OCF_3$ | $CF_3$ | H | Br | O | $CH(CH_3)$ | O | $CH_2CHF_2$ |
| P239 | H | H | H | $OCF_3$ | $CF_3$ | H | Cl | O | $CH(CH_3)$ | O | $CH_2CHF_2$ |
| P240 | H | H | H | $OCF_3$ | $CF_3$ | H | $CF_3$ | O | $CH(CH_3)$ | O | $CH_2CHF_2$ |
| P241 | H | H | H | $OCF_3$ | $CF_3$ | H | $CH_3$ | O | $CH(CH_3)$ | O | $CH_2CHF_2$ |
| P242 | H | H | H | $OCF_3$ | $CF_3$ | H | Br | O | $CH(CH_3)$ | O | $CH(CH_3)CF_3$ |
| P243 | H | H | H | $OCF_3$ | $CF_3$ | H | Cl | O | $CH(CH_3)$ | O | $CH(CH_3)CF_3$ |
| P244 | H | H | H | $OCF_3$ | $CF_3$ | H | $CF_3$ | O | $CH(CH_3)$ | O | $CH(CH_3)CF_3$ |
| P245 | H | H | H | $OCF_3$ | $CF_3$ | H | $CH_3$ | O | $CH(CH_3)$ | O | $CH(CH_3)CF_3$ |
| P246 | H | H | H | $OCF_3$ | $CF_3$ | H | Br | O | $CH(CH_3)$ | O | $CH_2CH_2CF_3$ |
| P247 | H | H | H | $OCF_3$ | $CF_3$ | H | Cl | O | $CH(CH_3)$ | O | $CH_2CH_2CF_3$ |
| P248 | H | H | H | $OCF_3$ | $CF_3$ | H | $CF_3$ | O | $CH(CH_3)$ | O | $CH_2CH_2CF_3$ |
| P249 | H | H | H | $OCF_3$ | $CF_3$ | H | $CH_3$ | O | $CH(CH_3)$ | O | $CH_2CH_2CF_3$ |
| P250 | H | H | H | $OCF_3$ | $CF_3$ | H | Br | O | $CH(CH_2CH_3)$ | O | $CH_2CF_3$ |
| P251 | H | H | H | $OCF_3$ | $CF_3$ | H | Cl | O | $CH(CH_2CH_3)$ | O | $CH_2CF_3$ |
| P252 | H | H | H | $OCF_3$ | $CF_3$ | H | $CF_3$ | O | $CH(CH_2CH_3)$ | O | $CH_2CF_3$ |
| P253 | H | H | H | $OCF_3$ | $CF_3$ | H | $CH_3$ | O | $CH(CH_2CH_3)$ | O | $CH_2CF_3$ |
| P254 | H | H | H | $OCF_3$ | $CF_3$ | H | Br | O | $C(CH_3)_2$ | O | $CH_2CF_3$ |
| P255 | H | H | H | $OCF_3$ | $CF_3$ | H | Cl | O | $C(CH_3)_2$ | O | $CH_2CF_3$ |
| P256 | H | H | H | $OCF_3$ | $CF_3$ | H | $CF_3$ | O | $C(CH_3)_2$ | O | $CH_2CF_3$ |
| P257 | H | H | H | $OCF_3$ | $CF_3$ | H | $CH_3$ | O | $C(CH_3)_2$ | O | $CH_2CF_3$ |
| P258 | H | H | H | $OCF_3$ | $CF_3$ | H | Br | O | $CH_2CH_2$ | O | $CH_2CF_3$ |
| P259 | H | H | H | $OCF_3$ | $CF_3$ | H | Cl | O | $CH_2CH_2$ | O | $CH_2CF_3$ |
| P260 | H | H | H | $OCF_3$ | $CF_3$ | H | $CF_3$ | O | $CH_2CH_2$ | O | $CH_2CF_3$ |
| P261 | H | H | H | $OCF_3$ | $CF_3$ | H | $CH_3$ | O | $CH_2CH_2$ | O | $CH_2CF_3$ |
| P262 | H | F | H | Br | $CF_3$ | H | Br | O | $CH_2$ | O | $CH_2CF_3$ |
| P263 | H | F | H | Br | $CF_3$ | H | Cl | O | $CH_2$ | O | $CH_2CF_3$ |
| P264 | H | F | H | Br | $CF_3$ | H | $CF_3$ | O | $CH_2$ | O | $CH_2CF_3$ |
| P265 | H | F | H | Br | $CF_3$ | H | $CH_3$ | O | $CH_2$ | O | $CH_2CF_3$ |
| P266 | H | F | H | Br | $CF_3$ | H | Br | O | $CH_2$ | S | $CH_2CF_3$ |
| P267 | H | F | H | Br | $CF_3$ | H | Cl | O | $CH_2$ | S | $CH_2CF_3$ |
| P268 | H | F | H | Br | $CF_3$ | H | $CF_3$ | O | $CH_2$ | S | $CH_2CF_3$ |
| P269 | H | F | H | Br | $CF_3$ | H | $CH_3$ | O | $CH_2$ | S | $CH_2CF_3$ |
| P270 | H | F | H | Br | $CF_3$ | H | Br | S | $CH_2$ | O | $CH_2CF_3$ |
| P271 | H | F | H | Br | $CF_3$ | H | Cl | S | $CH_2$ | O | $CH_2CF_3$ |
| P272 | H | F | H | Br | $CF_3$ | H | $CF_3$ | S | $CH_2$ | O | $CH_2CF_3$ |
| P273 | H | F | H | Br | $CF_3$ | H | $CH_3$ | S | $CH_2$ | O | $CH_2CF_3$ |
| P274 | H | F | H | Br | $CF_3$ | H | Br | O | $CH_2$ | O | $CH_2CHF_2$ |
| P275 | H | F | H | Br | $CF_3$ | H | Cl | O | $CH_2$ | O | $CH_2CHF_2$ |
| P276 | H | F | H | Br | $CF_3$ | H | $CF_3$ | O | $CH_2$ | O | $CH_2CHF_2$ |
| P277 | H | F | H | Br | $CF_3$ | H | $CH_3$ | O | $CH_2$ | O | $CH_2CHF_2$ |
| P278 | H | F | H | Br | $CF_3$ | $CF_3$ | Br | O | $CH_2$ | O | $CH_2CF_3$ |
| P279 | H | F | H | Br | $CF_3$ | $CF_3$ | Cl | O | $CH_2$ | O | $CH_2CF_3$ |
| P280 | H | F | H | Br | $CF_3$ | $CF_3$ | $CF_3$ | O | $CH_2$ | O | $CH_2CF_3$ |
| P281 | H | F | H | Br | $CF_3$ | $CF_3$ | $CH_3$ | O | $CH_2$ | O | $CH_2CF_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P282 | H | F | H | Br | $CF_2CF_3$ | H | Br | O | $CH_2$ | O | $CH_2CF_3$ |
| P283 | H | F | H | Br | $CF_2CF_3$ | H | Cl | O | $CH_2$ | O | $CH_2CF_3$ |
| P284 | H | F | H | Br | $CF_2CF_3$ | H | $CF_3$ | O | $CH_2$ | O | $CH_2CF_3$ |
| P285 | H | F | H | Br | $CF_2CF_3$ | H | $CH_3$ | O | $CH_2$ | O | $CH_2CF_3$ |
| P286 | H | F | H | Br | $CF_3$ | H | Br | O | $CH_2$ | O | $CH(CH_3)CF_3$ |
| P287 | H | F | H | Br | $CF_3$ | H | Cl | O | $CH_2$ | O | $CH(CH_3)CF_3$ |
| P288 | H | F | H | Br | $CF_3$ | H | $CF_3$ | O | $CH_2$ | O | $CH(CH_3)CF_3$ |
| P289 | H | F | H | Br | $CF_3$ | H | $CH_3$ | O | $CH_2$ | O | $CH(CH_3)CF_3$ |
| P290 | H | F | H | Br | $CF_3$ | $CF_3$ | Br | O | $CH(CH_3)$ | O | $CH_2CF_3$ |
| P291 | H | F | H | Br | $CF_3$ | $CF_3$ | Cl | O | $CH(CH_3)$ | O | $CH_2CF_3$ |
| P292 | H | F | H | Br | $CF_3$ | $CF_3$ | $CF_3$ | O | $CH(CH_3)$ | O | $CH_2CF_3$ |
| P293 | H | F | H | Br | $CF_3$ | $CF_3$ | $CH_3$ | O | $CH(CH_3)$ | O | $CH_2CF_3$ |
| P294 | H | F | H | Br | $CF_2CF_3$ | H | Br | O | $CH(CH_3)$ | O | $CH_2CF_3$ |
| P295 | H | F | H | Br | $CF_2CF_3$ | H | Cl | O | $CH(CH_3)$ | O | $CH_2CF_3$ |
| P296 | H | F | H | Br | $CF_2CF_3$ | H | $CF_3$ | O | $CH(CH_3)$ | O | $CH_2CF_3$ |
| P297 | H | F | H | Br | $CF_2CF_3$ | H | $CH_3$ | O | $CH(CH_3)$ | O | $CH_2CF_3$ |
| P298 | H | F | H | Br | $CF_3$ | H | Br | O | $CH(CH_3)$ | O | $CH_2CF_3$ |
| P299 | H | F | H | Br | $CF_3$ | H | Cl | O | $CH(CH_3)$ | O | $CH_2CF_3$ |
| P300 | H | F | H | Br | $CF_3$ | H | $CF_3$ | O | $CH(CH_3)$ | O | $CH_2CF_3$ |
| P301 | H | F | H | Br | $CF_3$ | H | $CH_3$ | O | $CH(CH_3)$ | O | $CH_2CF_3$ |
| P302 | H | F | H | Br | $CF_3$ | H | Br | O | $CH(CH_3)$ | S | $CH_2CF_3$ |
| P303 | H | F | H | Br | $CF_3$ | H | Cl | O | $CH(CH_3)$ | S | $CH_2CF_3$ |
| P304 | H | F | H | Br | $CF_3$ | H | $CF_3$ | O | $CH(CH_3)$ | S | $CH_2CF_3$ |
| P305 | H | F | H | Br | $CF_3$ | H | $CH_3$ | O | $CH(CH_3)$ | S | $CH_2CF_3$ |
| P306 | H | F | H | Br | $CF_3$ | H | Br | S | $CH(CH_3)$ | O | $CH_2CF_3$ |
| P307 | H | F | H | Br | $CF_3$ | H | Cl | S | $CH(CH_3)$ | O | $CH_2CF_3$ |
| P308 | H | F | H | Br | $CF_3$ | H | $CF_3$ | S | $CH(CH_3)$ | O | $CH_2CF_3$ |
| P309 | H | F | H | Br | $CF_3$ | H | $CH_3$ | S | $CH(CH_3)$ | O | $CH_2CF_3$ |
| P310 | H | F | H | Br | $CF_3$ | H | Br | O | $CH(CH_3)$ | O | $CH_2CHF_2$ |
| P311 | H | F | H | Br | $CF_3$ | H | Cl | O | $CH(CH_3)$ | O | $CH_2CHF_2$ |
| P312 | H | F | H | Br | $CF_3$ | H | $CF_3$ | O | $CH(CH_3)$ | O | $CH_2CHF_2$ |
| P313 | H | F | H | Br | $CF_3$ | H | $CH_3$ | O | $CH(CH_3)$ | O | $CH_2CHF_2$ |
| P314 | H | F | H | Br | $CF_3$ | H | Br | O | $CH(CH_3)$ | O | $CH(CH_3)CF_3$ |
| P315 | H | F | H | Br | $CF_3$ | H | Cl | O | $CH(CH_3)$ | O | $CH(CH_3)CF_3$ |
| P316 | H | F | H | Br | $CF_3$ | H | $CF_3$ | O | $CH(CH_3)$ | O | $CH(CH_3)CF_3$ |
| P317 | H | F | H | Br | $CF_3$ | H | $CH_3$ | O | $CH(CH_3)$ | O | $CH(CH_3)CF_3$ |
| P318 | H | F | H | Br | $CF_3$ | H | Br | O | $CH(CH_3)$ | O | $CH_2CH_2CF_3$ |
| P319 | H | F | H | Br | $CF_3$ | H | Cl | O | $CH(CH_3)$ | O | $CH_2CH_2CF_3$ |
| P320 | H | F | H | Br | $CF_3$ | H | $CF_3$ | O | $CH(CH_3)$ | O | $CH_2CH_2CF_3$ |
| P321 | H | F | H | Br | $CF_3$ | H | $CH_3$ | O | $CH(CH_3)$ | O | $CH_2CH_2CF_3$ |
| P322 | H | F | H | Br | $CF_3$ | H | Br | O | $CH(CH_2CH_3)$ | O | $CH_2CF_3$ |
| P323 | H | F | H | Br | $CF_3$ | H | Cl | O | $CH(CH_2CH_3)$ | O | $CH_2CF_3$ |
| P324 | H | F | H | Br | $CF_3$ | H | $CF_3$ | O | $CH(CH_2CH_3)$ | O | $CH_2CF_3$ |
| P325 | H | F | H | Br | $CF_3$ | H | $CH_3$ | O | $CH(CH_2CH_3)$ | O | $CH_2CF_3$ |
| P326 | H | F | H | Br | $CF_3$ | H | Br | O | $C(CH_3)_2$ | O | $CH_2CF_3$ |
| P327 | H | F | H | Br | $CF_3$ | H | Cl | O | $C(CH_3)_2$ | O | $CH_2CF_3$ |
| P328 | H | F | H | Br | $CF_3$ | H | $CF_3$ | O | $C(CH_3)_2$ | O | $CH_2CF_3$ |
| P329 | H | F | H | Br | $CF_3$ | H | $CH_3$ | O | $C(CH_3)_2$ | O | $CH_2CF_3$ |
| P330 | H | F | H | Br | $CF_3$ | H | Br | O | $CH_2CH_2$ | O | $CH_2CF_3$ |
| P331 | H | F | H | Br | $CF_3$ | H | Cl | O | $CH_2CH_2$ | O | $CH_2CF_3$ |
| P332 | H | F | H | Br | $CF_3$ | H | $CF_3$ | O | $CH_2CH_2$ | O | $CH_2CF_3$ |
| P333 | H | F | H | Br | $CF_3$ | H | $CH_3$ | O | $CH_2CH_2$ | O | $CH_2CF_3$ |
| P334 | H | $CH_3$ | Cl | H | $CF_3$ | H | Br | O | $CH_2$ | O | $CH_2CF_3$ |
| P335 | H | $CH_3$ | Cl | H | $CF_3$ | H | Cl | O | $CH_2$ | O | $CH_2CF_3$ |
| P336 | H | $CH_3$ | Cl | H | $CF_3$ | H | $CF_3$ | O | $CH_2$ | O | $CH_2CF_3$ |
| P337 | H | $CH_3$ | Cl | H | $CF_3$ | H | $CH_3$ | O | $CH_2$ | O | $CH_2CF_3$ |
| P338 | H | $CH_3$ | Cl | H | $CF_3$ | H | Br | O | $CH_2$ | S | $CH_2CF_3$ |
| P339 | H | $CH_3$ | Cl | H | $CF_3$ | H | Cl | O | $CH_2$ | S | $CH_2CF_3$ |
| P340 | H | $CH_3$ | Cl | H | $CF_3$ | H | $CF_3$ | O | $CH_2$ | S | $CH_2CF_3$ |
| P341 | H | $CH_3$ | Cl | H | $CF_3$ | H | $CH_3$ | O | $CH_2$ | S | $CH_2CF_3$ |
| P342 | H | $CH_3$ | Cl | H | $CF_3$ | H | Br | S | $CH_2$ | O | $CH_2CF_3$ |
| P343 | H | $CH_3$ | Cl | H | $CF_3$ | H | Cl | S | $CH_2$ | O | $CH_2CF_3$ |
| P344 | H | $CH_3$ | Cl | H | $CF_3$ | H | $CF_3$ | S | $CH_2$ | O | $CH_2CF_3$ |
| P345 | H | $CH_3$ | Cl | H | $CF_3$ | H | $CH_3$ | S | $CH_2$ | O | $CH_2CF_3$ |
| P346 | H | $CH_3$ | Cl | H | $CF_3$ | H | Br | O | $CH_2$ | O | $CH_2CHF_2$ |
| P347 | H | $CH_3$ | Cl | H | $CF_3$ | H | Cl | O | $CH_2$ | O | $CH_2CHF_2$ |
| P348 | H | $CH_3$ | Cl | H | $CF_3$ | H | $CF_3$ | O | $CH_2$ | O | $CH_2CHF_2$ |
| P349 | H | $CH_3$ | Cl | H | $CF_3$ | H | $CH_3$ | O | $CH_2$ | O | $CH_2CHF_2$ |
| P350 | H | $CH_3$ | Cl | H | $CF_3$ | $CF_3$ | Br | O | $CH_2$ | O | $CH_2CF_3$ |
| P351 | H | $CH_3$ | Cl | H | $CF_3$ | $CF_3$ | Cl | O | $CH_2$ | O | $CH_2CF_3$ |
| P352 | H | $CH_3$ | Cl | H | $CF_3$ | $CF_3$ | $CF_3$ | O | $CH_2$ | O | $CH_2CF_3$ |
| P353 | H | $CH_3$ | Cl | H | $CF_3$ | $CF_3$ | $CH_3$ | O | $CH_2$ | O | $CH_2CF_3$ |
| P354 | H | $CH_3$ | Cl | H | $CF_2CF_3$ | H | Br | O | $CH_2$ | O | $CH_2CF_3$ |
| P355 | H | $CH_3$ | Cl | H | $CF_2CF_3$ | H | Cl | O | $CH_2$ | O | $CH_2CF_3$ |
| P356 | H | $CH_3$ | Cl | H | $CF_2CF_3$ | H | $CF_3$ | O | $CH_2$ | O | $CH_2CF_3$ |
| P357 | H | $CH_3$ | Cl | H | $CF_2CF_3$ | H | $CH_3$ | O | $CH_2$ | O | $CH_2CF_3$ |
| P358 | H | $CH_3$ | Cl | H | $CF_3$ | H | Br | O | $CH_2$ | O | $CH(CH_3)CF_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P359 | H | CH$_3$ | Cl | H | CF$_3$ | H | Cl | O | CH$_2$ | O | CH(CH$_3$)CF$_3$ |
| P360 | H | CH$_3$ | Cl | H | CF$_3$ | H | CF$_3$ | O | CH$_2$ | O | CH(CH$_3$)CF$_3$ |
| P361 | H | CH$_3$ | Cl | H | CF$_3$ | H | CH$_3$ | O | CH$_2$ | O | CH(CH$_3$)CF$_3$ |
| P362 | H | CH$_3$ | Cl | H | CF$_3$ | CF$_3$ | Br | O | CH(CH$_3$) | O | CH$_2$CF$_3$ |
| P363 | H | CH$_3$ | Cl | H | CF$_3$ | CF$_3$ | Cl | O | CH(CH$_3$) | O | CH$_2$CF$_3$ |
| P364 | H | CH$_3$ | Cl | H | CF$_3$ | CF$_3$ | CF$_3$ | O | CH(CH$_3$) | O | CH$_2$CF$_3$ |
| P365 | H | CH$_3$ | Cl | H | CF$_3$ | CF$_3$ | CH$_3$ | O | CH(CH$_3$) | O | CH$_2$CF$_3$ |
| P366 | H | CH$_3$ | Cl | H | CF$_2$CF$_3$ | H | Br | O | CH(CH$_3$) | O | CH$_2$CF$_3$ |
| P367 | H | CH$_3$ | Cl | H | CF$_2$CF$_3$ | H | Cl | O | CH(CH$_3$) | O | CH$_2$CF$_3$ |
| P368 | H | CH$_3$ | Cl | H | CF$_2$CF$_3$ | H | CF$_3$ | O | CH(CH$_3$) | O | CH$_2$CF$_3$ |
| P369 | H | CH$_3$ | Cl | H | CF$_2$CF$_3$ | H | CH$_3$ | O | CH(CH$_3$) | O | CH$_2$CF$_3$ |
| P370 | H | CH$_3$ | Cl | H | CF$_3$ | H | Br | O | CH(CH$_3$) | O | CH$_2$CF$_3$ |
| P371 | H | CH$_3$ | Cl | H | CF$_3$ | H | Cl | O | CH(CH$_3$) | O | CH$_2$CF$_3$ |
| P372 | H | CH$_3$ | Cl | H | CF$_3$ | H | CF$_3$ | O | CH(CH$_3$) | O | CH$_2$CF$_3$ |
| P373 | H | CH$_3$ | Cl | H | CF$_3$ | H | CH$_3$ | O | CH(CH$_3$) | O | CH$_2$CF$_3$ |
| P374 | H | CH$_3$ | Cl | H | CF$_3$ | H | Br | O | CH(CH$_3$) | S | CH$_2$CF$_3$ |
| P375 | H | CH$_3$ | Cl | H | CF$_3$ | H | Cl | O | CH(CH$_3$) | S | CH$_2$CF$_3$ |
| P376 | H | CH$_3$ | Cl | H | CF$_3$ | H | CF$_3$ | O | CH(CH$_3$) | S | CH$_2$CF$_3$ |
| P377 | H | CH$_3$ | Cl | H | CF$_3$ | H | CH$_3$ | O | CH(CH$_3$) | S | CH$_2$CF$_3$ |
| P378 | H | CH$_3$ | Cl | H | CF$_3$ | H | Br | S | CH(CH$_3$) | O | CH$_2$CF$_3$ |
| P379 | H | CH$_3$ | Cl | H | CF$_3$ | H | Cl | S | CH(CH$_3$) | O | CH$_2$CF$_3$ |
| P380 | H | CH$_3$ | Cl | H | CF$_3$ | H | CF$_3$ | S | CH(CH$_3$) | O | CH$_2$CF$_3$ |
| P381 | H | CH$_3$ | Cl | H | CF$_3$ | H | CH$_3$ | S | CH(CH$_3$) | O | CH$_2$CF$_3$ |
| P382 | H | CH$_3$ | Cl | H | CF$_3$ | H | Br | O | CH(CH$_3$) | O | CH$_2$CHF$_2$ |
| P383 | H | CH$_3$ | Cl | H | CF$_3$ | H | Cl | O | CH(CH$_3$) | O | CH$_2$CHF$_2$ |
| P384 | H | CH$_3$ | Cl | H | CF$_3$ | H | CF$_3$ | O | CH(CH$_3$) | O | CH$_2$CHF$_2$ |
| P385 | H | CH$_3$ | Cl | H | CF$_3$ | H | CH$_3$ | O | CH(CH$_3$) | O | CH$_2$CHF$_2$ |
| P386 | H | CH$_3$ | Cl | H | CF$_3$ | H | Br | O | CH(CH$_3$) | O | CH(CH$_3$)CF$_3$ |
| P387 | H | CH$_3$ | Cl | H | CF$_3$ | H | Cl | O | CH(CH$_3$) | O | CH(CH$_3$)CF$_3$ |
| P388 | H | CH$_3$ | Cl | H | CF$_3$ | H | CF$_3$ | O | CH(CH$_3$) | O | CH(CH$_3$)CF$_3$ |
| P389 | H | CH$_3$ | Cl | H | CF$_3$ | H | CH$_3$ | O | CH(CH$_3$) | O | CH(CH$_3$)CF$_3$ |
| P390 | H | CH$_3$ | Cl | H | CF$_3$ | H | Br | O | CH(CH$_3$) | O | CH$_2$CH$_2$CF$_3$ |
| P391 | H | CH$_3$ | Cl | H | CF$_3$ | H | Cl | O | CH(CH$_3$) | O | CH$_2$CH$_2$CF$_3$ |
| P392 | H | CH$_3$ | Cl | H | CF$_3$ | H | CF$_3$ | O | CH(CH$_3$) | O | CH$_2$CH$_2$CF$_3$ |
| P393 | H | CH$_3$ | Cl | H | CF$_3$ | H | CH$_3$ | O | CH(CH$_3$) | O | CH$_2$CH$_2$CF$_3$ |
| P394 | H | CH$_3$ | Cl | H | CF$_3$ | H | Br | O | CH(CH$_2$CH$_3$) | O | CH$_2$CF$_3$ |
| P395 | H | CH$_3$ | Cl | H | CF$_3$ | H | Cl | O | CH(CH$_2$CH$_3$) | O | CH$_2$CF$_3$ |
| P396 | H | CH$_3$ | Cl | H | CF$_3$ | H | CF$_3$ | O | CH(CH$_2$CH$_3$) | O | CH$_2$CF$_3$ |
| P397 | H | CH$_3$ | Cl | H | CF$_3$ | H | CH$_3$ | O | CH(CH$_2$CH$_3$) | O | CH$_2$CF$_3$ |
| P398 | H | CH$_3$ | Cl | H | CF$_3$ | H | Br | O | C(CH$_3$)$_2$ | O | CH$_2$CF$_3$ |
| P399 | H | CH$_3$ | Cl | H | CF$_3$ | H | Cl | O | C(CH$_3$)$_2$ | O | CH$_2$CF$_3$ |
| P400 | H | CH$_3$ | Cl | H | CF$_3$ | H | CF$_3$ | O | C(CH$_3$)$_2$ | O | CH$_2$CF$_3$ |
| P401 | H | CH$_3$ | Cl | H | CF$_3$ | H | CH$_3$ | O | C(CH$_3$)$_2$ | O | CH$_2$CF$_3$ |
| P402 | H | CH$_3$ | Cl | H | CF$_3$ | H | Br | O | CH$_2$CH$_2$ | O | CH$_2$CF$_3$ |
| P403 | H | CH$_3$ | Cl | H | CF$_3$ | H | Cl | O | CH$_2$CH$_2$ | O | CH$_2$CF$_3$ |
| P404 | H | CH$_3$ | Cl | H | CF$_3$ | H | CF$_3$ | O | CH$_2$CH$_2$ | O | CH$_2$CF$_3$ |
| P405 | H | CH$_3$ | Cl | H | CF$_3$ | H | CH$_3$ | O | CH$_2$CH$_2$ | O | CH$_2$CF$_3$ |
| P406 | H | Cl | CH$_3$ | H | CF$_3$ | H | Br | O | CH$_2$ | O | CH$_2$CF$_3$ |
| P407 | H | Cl | CH$_3$ | H | CF$_3$ | H | Cl | O | CH$_2$ | O | CH$_2$CF$_3$ |
| P408 | H | Cl | CH$_3$ | H | CF$_3$ | H | CF$_3$ | O | CH$_2$ | O | CH$_2$CF$_3$ |
| P409 | H | Cl | CH$_3$ | H | CF$_3$ | H | CH$_3$ | O | CH$_2$ | O | CH$_2$CF$_3$ |
| P410 | H | Cl | CH$_3$ | H | CF$_3$ | H | Br | O | CH$_2$ | S | CH$_2$CF$_3$ |
| P411 | H | Cl | CH$_3$ | H | CF$_3$ | H | Cl | O | CH$_2$ | S | CH$_2$CF$_3$ |
| P412 | H | Cl | CH$_3$ | H | CF$_3$ | H | CF$_3$ | O | CH$_2$ | S | CH$_2$CF$_3$ |
| P413 | H | Cl | CH$_3$ | H | CF$_3$ | H | CH$_3$ | O | CH$_2$ | S | CH$_2$CF$_3$ |
| P414 | H | Cl | CH$_3$ | H | CF$_3$ | H | Br | S | CH$_2$ | O | CH$_2$CF$_3$ |
| P415 | H | Cl | CH$_3$ | H | CF$_3$ | H | Cl | S | CH$_2$ | O | CH$_2$CF$_3$ |
| P416 | H | Cl | CH$_3$ | H | CF$_3$ | H | CF$_3$ | S | CH$_2$ | O | CH$_2$CF$_3$ |
| P417 | H | Cl | CH$_3$ | H | CF$_3$ | H | CH$_3$ | S | CH$_2$ | O | CH$_2$CF$_3$ |
| P418 | H | Cl | CH$_3$ | H | CF$_3$ | H | Br | O | CH$_2$ | O | CH$_2$CHF$_2$ |
| P419 | H | Cl | CH$_3$ | H | CF$_3$ | H | Cl | O | CH$_2$ | O | CH$_2$CHF$_2$ |
| P420 | H | Cl | CH$_3$ | H | CF$_3$ | H | CF$_3$ | O | CH$_2$ | O | CH$_2$CHF$_2$ |
| P421 | H | Cl | CH$_3$ | H | CF$_3$ | H | CH$_3$ | O | CH$_2$ | O | CH$_2$CHF$_2$ |
| P422 | H | Cl | CH$_3$ | H | CF$_3$ | CF$_3$ | Br | O | CH$_2$ | O | CH$_2$CF$_3$ |
| P423 | H | Cl | CH$_3$ | H | CF$_3$ | CF$_3$ | Cl | O | CH$_2$ | O | CH$_2$CF$_3$ |
| P424 | H | Cl | CH$_3$ | H | CF$_3$ | CF$_3$ | CF$_3$ | O | CH$_2$ | O | CH$_2$CF$_3$ |
| P425 | H | Cl | CH$_3$ | H | CF$_3$ | CF$_3$ | CH$_3$ | O | CH$_2$ | O | CH$_2$CF$_3$ |
| P426 | H | Cl | CH$_3$ | H | CF$_2$CF$_3$ | H | Br | O | CH$_2$ | O | CH$_2$CF$_3$ |
| P427 | H | Cl | CH$_3$ | H | CF$_2$CF$_3$ | H | Cl | O | CH$_2$ | O | CH$_2$CF$_3$ |
| P428 | H | Cl | CH$_3$ | H | CF$_2$CF$_3$ | H | CF$_3$ | O | CH$_2$ | O | CH$_2$CF$_3$ |
| P429 | H | Cl | CH$_3$ | H | CF$_2$CF$_3$ | H | CH$_3$ | O | CH$_2$ | O | CH$_2$CF$_3$ |
| P430 | H | Cl | CH$_3$ | H | CF$_3$ | H | Br | O | CH$_2$ | O | CH(CH$_3$)CF$_3$ |
| P431 | H | Cl | CH$_3$ | H | CF$_3$ | H | Cl | O | CH$_2$ | O | CH(CH$_3$)CF$_3$ |
| P432 | H | Cl | CH$_3$ | H | CF$_3$ | H | CF$_3$ | O | CH$_2$ | O | CH(CH$_3$)CF$_3$ |
| P433 | H | Cl | CH$_3$ | H | CF$_3$ | H | CH$_3$ | O | CH$_2$ | O | CH(CH$_3$)CF$_3$ |
| P434 | H | Cl | CH$_3$ | H | CF$_3$ | CF$_3$ | Br | O | CH(CH$_3$) | O | CH$_2$CF$_3$ |
| P435 | H | Cl | CH$_3$ | H | CF$_3$ | CF$_3$ | Cl | O | CH(CH$_3$) | O | CH$_2$CF$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P436 | H | Cl | CH$_3$ | H | CF$_3$ | CF$_3$ | CF$_3$ | O | CH(CH$_3$) | O | CH$_2$CF$_3$ |
| P437 | H | Cl | CH$_3$ | H | CF$_3$ | CF$_3$ | CH$_3$ | O | CH(CH$_3$) | O | CH$_2$CF$_3$ |
| P438 | H | Cl | CH$_3$ | H | CF$_2$CF$_3$ | H | Br | O | CH(CH$_3$) | O | CH$_2$CF$_3$ |
| P439 | H | Cl | CH$_3$ | H | CF$_2$CF$_3$ | H | Cl | O | CH(CH$_3$) | O | CH$_2$CF$_3$ |
| P440 | H | Cl | CH$_3$ | H | CF$_2$CF$_3$ | H | CF$_3$ | O | CH(CH$_3$) | O | CH$_2$CF$_3$ |
| P441 | H | Cl | CH$_3$ | H | CF$_2$CF$_3$ | H | CH$_3$ | O | CH(CH$_3$) | O | CH$_2$CF$_3$ |
| P442 | H | Cl | CH$_3$ | H | CF$_3$ | H | Br | O | CH(CH$_3$) | O | CH$_2$CF$_3$ |
| P443 | H | Cl | CH$_3$ | H | CF$_3$ | H | Cl | O | CH(CH$_3$) | O | CH$_2$CF$_3$ |
| P444 | H | Cl | CH$_3$ | H | CF$_3$ | H | CF$_3$ | O | CH(CH$_3$) | O | CH$_2$CF$_3$ |
| P445 | H | Cl | CH$_3$ | H | CF$_3$ | H | CH$_3$ | O | CH(CH$_3$) | O | CH$_2$CF$_3$ |
| P446 | H | Cl | CH$_3$ | H | CF$_3$ | H | Br | O | CH(CH$_3$) | S | CH$_2$CF$_3$ |
| P447 | H | Cl | CH$_3$ | H | CF$_3$ | H | Cl | O | CH(CH$_3$) | S | CH$_2$CF$_3$ |
| P448 | H | Cl | CH$_3$ | H | CF$_3$ | H | CF$_3$ | O | CH(CH$_3$) | S | CH$_2$CF$_3$ |
| P449 | H | Cl | CH$_3$ | H | CF$_3$ | H | CH$_3$ | O | CH(CH$_3$) | S | CH$_2$CF$_3$ |
| P450 | H | Cl | CH$_3$ | H | CF$_3$ | H | Br | S | CH(CH$_3$) | O | CH$_2$CF$_3$ |
| P451 | H | Cl | CH$_3$ | H | CF$_3$ | H | Cl | S | CH(CH$_3$) | O | CH$_2$CF$_3$ |
| P452 | H | Cl | CH$_3$ | H | CF$_3$ | H | CF$_3$ | S | CH(CH$_3$) | O | CH$_2$CF$_3$ |
| P453 | H | Cl | CH$_3$ | H | CF$_3$ | H | CH$_3$ | S | CH(CH$_3$) | O | CH$_2$CF$_3$ |
| P454 | H | Cl | CH$_3$ | H | CF$_3$ | H | Br | O | CH(CH$_3$) | O | CH$_2$CHF$_2$ |
| P455 | H | Cl | CH$_3$ | H | CF$_3$ | H | Cl | O | CH(CH$_3$) | O | CH$_2$CHF$_2$ |
| P456 | H | Cl | CH$_3$ | H | CF$_3$ | H | CF$_3$ | O | CH(CH$_3$) | O | CH$_2$CHF$_2$ |
| P457 | H | Cl | CH$_3$ | H | CF$_3$ | H | CH$_3$ | O | CH(CH$_3$) | O | CH$_2$CHF$_2$ |
| P458 | H | Cl | CH$_3$ | H | CF$_3$ | H | Br | O | CH(CH$_3$) | O | CH(CH$_3$)CF$_3$ |
| P459 | H | Cl | CH$_3$ | H | CF$_3$ | H | Cl | O | CH(CH$_3$) | O | CH(CH$_3$)CF$_3$ |
| P460 | H | Cl | CH$_3$ | H | CF$_3$ | H | CF$_3$ | O | CH(CH$_3$) | O | CH(CH$_3$)CF$_3$ |
| P461 | H | Cl | CH$_3$ | H | CF$_3$ | H | CH$_3$ | O | CH(CH$_3$) | O | CH(CH$_3$)CF$_3$ |
| P462 | H | Cl | CH$_3$ | H | CF$_3$ | H | Br | O | CH(CH$_3$) | O | CH$_2$CH$_2$CF$_3$ |
| P463 | H | Cl | CH$_3$ | H | CF$_3$ | H | Cl | O | CH(CH$_3$) | O | CH$_2$CH$_2$CF$_3$ |
| P464 | H | Cl | CH$_3$ | H | CF$_3$ | H | CF$_3$ | O | CH(CH$_3$) | O | CH$_2$CH$_2$CF$_3$ |
| P465 | H | Cl | CH$_3$ | H | CF$_3$ | H | CH$_3$ | O | CH(CH$_3$) | O | CH$_2$CH$_2$CF$_3$ |
| P466 | H | Cl | CH$_3$ | H | CF$_3$ | H | Br | O | CH(CH$_2$CH$_3$) | O | CH$_2$CF$_3$ |
| P467 | H | Cl | CH$_3$ | H | CF$_3$ | H | Cl | O | CH(CH$_2$CH$_3$) | O | CH$_2$CF$_3$ |
| P468 | H | Cl | CH$_3$ | H | CF$_3$ | H | CF$_3$ | O | CH(CH$_2$CH$_3$) | O | CH$_2$CF$_3$ |
| P469 | H | Cl | CH$_3$ | H | CF$_3$ | H | CH$_3$ | O | CH(CH$_2$CH$_3$) | O | CH$_2$CF$_3$ |
| P470 | H | Cl | CH$_3$ | H | CF$_3$ | H | Br | O | C(CH$_3$)$_2$ | O | CH$_2$CF$_3$ |
| P471 | H | Cl | CH$_3$ | H | CF$_3$ | H | Cl | O | C(CH$_3$)$_2$ | O | CH$_2$CF$_3$ |
| P472 | H | Cl | CH$_3$ | H | CF$_3$ | H | CF$_3$ | O | C(CH$_3$)$_2$ | O | CH$_2$CF$_3$ |
| P473 | H | Cl | CH$_3$ | H | CF$_3$ | H | CH$_3$ | O | C(CH$_3$)$_2$ | O | CH$_2$CF$_3$ |
| P474 | H | Cl | CH$_3$ | H | CF$_3$ | H | Br | O | CH$_2$CH$_2$ | O | CH$_2$CF$_3$ |
| P475 | H | Cl | CH$_3$ | H | CF$_3$ | H | Cl | O | CH$_2$CH$_2$ | O | CH$_2$CF$_3$ |
| P476 | H | Cl | CH$_3$ | H | CF$_3$ | H | CF$_3$ | O | CH$_2$CH$_2$ | O | CH$_2$CF$_3$ |
| P477 | H | Cl | CH$_3$ | H | CF$_3$ | H | CH$_3$ | O | CH$_2$CH$_2$ | O | CH$_2$CF$_3$ |
| P478 | H | CH$_3$ | F | CH$_3$ | CF$_3$ | H | Br | O | CH$_2$ | O | CH$_2$CF$_3$ |
| P479 | H | CH$_3$ | F | CH$_3$ | CF$_3$ | H | Cl | O | CH$_2$ | O | CH$_2$CF$_3$ |
| P480 | H | CH$_3$ | F | CH$_3$ | CF$_3$ | H | CF$_3$ | O | CH$_2$ | O | CH$_2$CF$_3$ |
| P481 | H | CH$_3$ | F | CH$_3$ | CF$_3$ | H | CH$_3$ | O | CH$_2$ | O | CH$_2$CF$_3$ |
| P482 | H | CH$_3$ | F | CH$_3$ | CF$_3$ | H | Br | O | CH$_2$ | S | CH$_2$CF$_3$ |
| P483 | H | CH$_3$ | F | CH$_3$ | CF$_3$ | H | Cl | O | CH$_2$ | S | CH$_2$CF$_3$ |
| P484 | H | CH$_3$ | F | CH$_3$ | CF$_3$ | H | CF$_3$ | O | CH$_2$ | S | CH$_2$CF$_3$ |
| P485 | H | CH$_3$ | F | CH$_3$ | CF$_3$ | H | CH$_3$ | O | CH$_2$ | S | CH$_2$CF$_3$ |
| P486 | H | CH$_3$ | F | CH$_3$ | CF$_3$ | H | Br | S | CH$_2$ | O | CH$_2$CF$_3$ |
| P487 | H | CH$_3$ | F | CH$_3$ | CF$_3$ | H | Cl | S | CH$_2$ | O | CH$_2$CF$_3$ |
| P488 | H | CH$_3$ | F | CH$_3$ | CF$_3$ | H | CF$_3$ | S | CH$_2$ | O | CH$_2$CF$_3$ |
| P489 | H | CH$_3$ | F | CH$_3$ | CF$_3$ | H | CH$_3$ | S | CH$_2$ | O | CH$_2$CF$_3$ |
| P490 | H | CH$_3$ | F | CH$_3$ | CF$_3$ | H | Br | O | CH$_2$ | O | CH$_2$CHF$_2$ |
| P491 | H | CH$_3$ | F | CH$_3$ | CF$_3$ | H | Cl | O | CH$_2$ | O | CH$_2$CHF$_2$ |
| P492 | H | CH$_3$ | F | CH$_3$ | CF$_3$ | H | CF$_3$ | O | CH$_2$ | O | CH$_2$CHF$_2$ |
| P493 | H | CH$_3$ | F | CH$_3$ | CF$_3$ | H | CH$_3$ | O | CH$_2$ | O | CH$_2$CHF$_2$ |
| P494 | H | CH$_3$ | F | CH$_3$ | CF$_3$ | CF$_3$ | Br | O | CH$_2$ | O | CH$_2$CF$_3$ |
| P495 | H | CH$_3$ | F | CH$_3$ | CF$_3$ | CF$_3$ | Cl | O | CH$_2$ | O | CH$_2$CF$_3$ |
| P496 | H | CH$_3$ | F | CH$_3$ | CF$_3$ | CF$_3$ | CF$_3$ | O | CH$_2$ | O | CH$_2$CF$_3$ |
| P497 | H | CH$_3$ | F | CH$_3$ | CF$_3$ | CF$_3$ | CH$_3$ | O | CH$_2$ | O | CH$_2$CF$_3$ |
| P498 | H | CH$_3$ | F | CH$_3$ | CF$_2$CF$_3$ | H | Br | O | CH$_2$ | O | CH$_2$CF$_3$ |
| P499 | H | CH$_3$ | F | CH$_3$ | CF$_2$CF$_3$ | H | Cl | O | CH$_2$ | O | CH$_2$CF$_3$ |
| P500 | H | CH$_3$ | F | CH$_3$ | CF$_2$CF$_3$ | H | CF$_3$ | O | CH$_2$ | O | CH$_2$CF$_3$ |
| P501 | H | CH$_3$ | F | CH$_3$ | CF$_2$CF$_3$ | H | CH$_3$ | O | CH$_2$ | O | CH$_2$CF$_3$ |
| P502 | H | CH$_3$ | F | CH$_3$ | CF$_3$ | H | Br | O | CH$_2$ | O | CH(CH$_3$)CF$_3$ |
| P503 | H | CH$_3$ | F | CH$_3$ | CF$_3$ | H | Cl | O | CH$_2$ | O | CH(CH$_3$)CF$_3$ |
| P504 | H | CH$_3$ | F | CH$_3$ | CF$_3$ | H | CF$_3$ | O | CH$_2$ | O | CH(CH$_3$)CF$_3$ |
| P505 | H | CH$_3$ | F | CH$_3$ | CF$_3$ | H | CH$_3$ | O | CH$_2$ | O | CH(CH$_3$)CF$_3$ |
| P506 | H | CH$_3$ | F | CH$_3$ | CF$_3$ | CF$_3$ | Br | O | CH(CH$_3$) | O | CH$_2$CF$_3$ |
| P507 | H | CH$_3$ | F | CH$_3$ | CF$_3$ | CF$_3$ | Cl | O | CH(CH$_3$) | O | CH$_2$CF$_3$ |
| P508 | H | CH$_3$ | F | CH$_3$ | CF$_3$ | CF$_3$ | CF$_3$ | O | CH(CH$_3$) | O | CH$_2$CF$_3$ |
| P509 | H | CH$_3$ | F | CH$_3$ | CF$_3$ | CF$_3$ | CH$_3$ | O | CH(CH$_3$) | O | CH$_2$CF$_3$ |
| P510 | H | CH$_3$ | F | CH$_3$ | CF$_2$CF$_3$ | H | Br | O | CH(CH$_3$) | O | CH$_2$CF$_3$ |
| P511 | H | CH$_3$ | F | CH$_3$ | CF$_2$CF$_3$ | H | Cl | O | CH(CH$_3$) | O | CH$_2$CF$_3$ |
| P512 | H | CH$_3$ | F | CH$_3$ | CF$_2$CF$_3$ | H | CF$_3$ | O | CH(CH$_3$) | O | CH$_2$CF$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P513 | H | CH$_3$ | F | CH$_3$ | CF$_2$CF$_3$ | H | CH$_3$ | O | CH(CH$_3$) | O | CH$_2$CF$_3$ |
| P514 | H | CH$_3$ | F | CH$_3$ | CF$_3$ | H | Br | O | CH(CH$_3$) | O | CH$_2$CF$_3$ |
| P515 | H | CH$_3$ | F | CH$_3$ | CF$_3$ | H | Cl | O | CH(CH$_3$) | O | CH$_2$CF$_3$ |
| P516 | H | CH$_3$ | F | CH$_3$ | CF$_3$ | H | CF$_3$ | O | CH(CH$_3$) | O | CH$_2$CF$_3$ |
| P517 | H | CH$_3$ | F | CH$_3$ | CF$_3$ | H | CH$_3$ | O | CH(CH$_3$) | O | CH$_2$CF$_3$ |
| P518 | H | CH$_3$ | F | CH$_3$ | CF$_3$ | H | Br | O | CH(CH$_3$) | S | CH$_2$CF$_3$ |
| P519 | H | CH$_3$ | F | CH$_3$ | CF$_3$ | H | Cl | O | CH(CH$_3$) | S | CH$_2$CF$_3$ |
| P520 | H | CH$_3$ | F | CH$_3$ | CF$_3$ | H | CF$_3$ | O | CH(CH$_3$) | S | CH$_2$CF$_3$ |
| P521 | H | CH$_3$ | F | CH$_3$ | CF$_3$ | H | CH$_3$ | O | CH(CH$_3$) | S | CH$_2$CF$_3$ |
| P522 | H | CH$_3$ | F | CH$_3$ | CF$_3$ | H | Br | S | CH(CH$_3$) | O | CH$_2$CF$_3$ |
| P523 | H | CH$_3$ | F | CH$_3$ | CF$_3$ | H | Cl | S | CH(CH$_3$) | O | CH$_2$CF$_3$ |
| P524 | H | CH$_3$ | F | CH$_3$ | CF$_3$ | H | CF$_3$ | S | CH(CH$_3$) | O | CH$_2$CF$_3$ |
| P525 | H | CH$_3$ | F | CH$_3$ | CF$_3$ | H | CH$_3$ | S | CH(CH$_3$) | O | CH$_2$CF$_3$ |
| P526 | H | CH$_3$ | F | CH$_3$ | CF$_3$ | H | Br | O | CH(CH$_3$) | O | CH$_2$CHF$_2$ |
| P527 | H | CH$_3$ | F | CH$_3$ | CF$_3$ | H | Cl | O | CH(CH$_3$) | O | CH$_2$CHF$_2$ |
| P528 | H | CH$_3$ | F | CH$_3$ | CF$_3$ | H | CF$_3$ | O | CH(CH$_3$) | O | CH$_2$CHF$_2$ |
| P529 | H | CH$_3$ | F | CH$_3$ | CF$_3$ | H | CH$_3$ | O | CH(CH$_3$) | O | CH$_2$CHF$_2$ |
| P530 | H | CH$_3$ | F | CH$_3$ | CF$_3$ | H | Br | O | CH(CH$_3$) | O | CH(CH$_3$)CF$_3$ |
| P531 | H | CH$_3$ | F | CH$_3$ | CF$_3$ | H | Cl | O | CH(CH$_3$) | O | CH(CH$_3$)CF$_3$ |
| P532 | H | CH$_3$ | F | CH$_3$ | CF$_3$ | H | CF$_3$ | O | CH(CH$_3$) | O | CH(CH$_3$)CF$_3$ |
| P533 | H | CH$_3$ | F | CH$_3$ | CF$_3$ | H | CH$_3$ | O | CH(CH$_3$) | O | CH(CH$_3$)CF$_3$ |
| P534 | H | CH$_3$ | F | CH$_3$ | CF$_3$ | H | Br | O | CH(CH$_3$) | O | CH$_2$CH$_2$CF$_3$ |
| P535 | H | CH$_3$ | F | CH$_3$ | CF$_3$ | H | Cl | O | CH(CH$_3$) | O | CH$_2$CH$_2$CF$_3$ |
| P536 | H | CH$_3$ | F | CH$_3$ | CF$_3$ | H | CF$_3$ | O | CH(CH$_3$) | O | CH$_2$CH$_2$CF$_3$ |
| P537 | H | CH$_3$ | F | CH$_3$ | CF$_3$ | H | CH$_3$ | O | CH(CH$_3$) | O | CH$_2$CH$_2$CF$_3$ |
| P538 | H | CH$_3$ | F | CH$_3$ | CF$_3$ | H | Br | O | CH(CH$_2$CH$_3$) | O | CH$_2$CF$_3$ |
| P539 | H | CH$_3$ | F | CH$_3$ | CF$_3$ | H | Cl | O | CH(CH$_2$CH$_3$) | O | CH$_2$CF$_3$ |
| P540 | H | CH$_3$ | F | CH$_3$ | CF$_3$ | H | CF$_3$ | O | CH(CH$_2$CH$_3$) | O | CH$_2$CF$_3$ |
| P541 | H | CH$_3$ | F | CH$_3$ | CF$_3$ | H | CH$_3$ | O | CH(CH$_2$CH$_3$) | O | CH$_2$CF$_3$ |
| P542 | H | CH$_3$ | F | CH$_3$ | CF$_3$ | H | Br | O | C(CH$_3$)$_2$ | O | CH$_2$CF$_3$ |
| P543 | H | CH$_3$ | F | CH$_3$ | CF$_3$ | H | Cl | O | C(CH$_3$)$_2$ | O | CH$_2$CF$_3$ |
| P544 | H | CH$_3$ | F | CH$_3$ | CF$_3$ | H | CF$_3$ | O | C(CH$_3$)$_2$ | O | CH$_2$CF$_3$ |
| P545 | H | CH$_3$ | F | CH$_3$ | CF$_3$ | H | CH$_3$ | O | C(CH$_3$)$_2$ | O | CH$_2$CF$_3$ |
| P546 | H | CH$_3$ | F | CH$_3$ | CF$_3$ | H | Br | O | CH$_2$CH$_2$ | O | CH$_2$CF$_3$ |
| P547 | H | CH$_3$ | F | CH$_3$ | CF$_3$ | H | Cl | O | CH$_2$CH$_2$ | O | CH$_2$CF$_3$ |
| P548 | H | CH$_3$ | F | CH$_3$ | CF$_3$ | H | CF$_3$ | O | CH$_2$CH$_2$ | O | CH$_2$CF$_3$ |
| P549 | H | CH$_3$ | F | CH$_3$ | CF$_3$ | H | CH$_3$ | O | CH$_2$CH$_2$ | O | CH$_2$CF$_3$ |
| P550 | H | Cl | H | Br | CF$_3$ | H | Br | O | CH$_2$ | O | CH$_2$CF$_3$ |
| P551 | H | Cl | H | Br | CF$_3$ | H | Cl | O | CH$_2$ | O | CH$_2$CF$_3$ |
| P552 | H | Cl | H | Br | CF$_3$ | H | CF$_3$ | O | CH$_2$ | O | CH$_2$CF$_3$ |
| P553 | H | Cl | H | Br | CF$_3$ | H | CH$_3$ | O | CH$_2$ | O | CH$_2$CF$_3$ |
| P554 | H | Cl | H | Br | CF$_3$ | H | Br | O | CH$_2$ | S | CH$_2$CF$_3$ |
| P555 | H | Cl | H | Br | CF$_3$ | H | Cl | O | CH$_2$ | S | CH$_2$CF$_3$ |
| P556 | H | Cl | H | Br | CF$_3$ | H | CF$_3$ | O | CH$_2$ | S | CH$_2$CF$_3$ |
| P557 | H | Cl | H | Br | CF$_3$ | H | CH$_3$ | O | CH$_2$ | S | CH$_2$CF$_3$ |
| P558 | H | Cl | H | Br | CF$_3$ | H | Br | S | CH$_2$ | O | CH$_2$CF$_3$ |
| P559 | H | Cl | H | Br | CF$_3$ | H | Cl | S | CH$_2$ | O | CH$_2$CF$_3$ |
| P560 | H | Cl | H | Br | CF$_3$ | H | CF$_3$ | S | CH$_2$ | O | CH$_2$CF$_3$ |
| P561 | H | Cl | H | Br | CF$_3$ | H | CH$_3$ | S | CH$_2$ | O | CH$_2$CF$_3$ |
| P562 | H | Cl | H | Br | CF$_3$ | H | Br | O | CH$_2$ | O | CH$_2$CHF$_2$ |
| P563 | H | Cl | H | Br | CF$_3$ | H | Cl | O | CH$_2$ | O | CH$_2$CHF$_2$ |
| P564 | H | Cl | H | Br | CF$_3$ | H | CF$_3$ | O | CH$_2$ | O | CH$_2$CHF$_2$ |
| P565 | H | Cl | H | Br | CF$_3$ | H | CH$_3$ | O | CH$_2$ | O | CH$_2$CHF$_2$ |
| P566 | H | Cl | H | Br | CF$_3$ | CF$_3$ | Br | O | CH$_2$ | O | CH$_2$CF$_3$ |
| P567 | H | Cl | H | Br | CF$_3$ | CF$_3$ | Cl | O | CH$_2$ | O | CH$_2$CF$_3$ |
| P568 | H | Cl | H | Br | CF$_3$ | CF$_3$ | CF$_3$ | O | CH$_2$ | O | CH$_2$CF$_3$ |
| P569 | H | Cl | H | Br | CF$_3$ | CF$_3$ | CH$_3$ | O | CH$_2$ | O | CH$_2$CF$_3$ |
| P570 | H | Cl | H | Br | CF$_2$CF$_3$ | H | Br | O | CH$_2$ | O | CH$_2$CF$_3$ |
| P571 | H | Cl | H | Br | CF$_2$CF$_3$ | H | Cl | O | CH$_2$ | O | CH$_2$CF$_3$ |
| P572 | H | Cl | H | Br | CF$_2$CF$_3$ | H | CF$_3$ | O | CH$_2$ | O | CH$_2$CF$_3$ |
| P573 | H | Cl | H | Br | CF$_2$CF$_3$ | H | CH$_3$ | O | CH$_2$ | O | CH$_2$CF$_3$ |
| P574 | H | Cl | H | Br | CF$_3$ | H | Br | O | CH$_2$ | O | CH(CH$_3$)CF$_3$ |
| P575 | H | Cl | H | Br | CF$_3$ | H | Cl | O | CH$_2$ | O | CH(CH$_3$)CF$_3$ |
| P576 | H | Cl | H | Br | CF$_3$ | H | CF$_3$ | O | CH$_2$ | O | CH(CH$_3$)CF$_3$ |
| P577 | H | Cl | H | Br | CF$_3$ | H | CH$_3$ | O | CH$_2$ | O | CH(CH$_3$)CF$_3$ |
| P578 | H | Cl | H | Br | CF$_3$ | CF$_3$ | Br | O | CH(CH$_3$) | O | CH$_2$CF$_3$ |
| P579 | H | Cl | H | Br | CF$_3$ | CF$_3$ | Cl | O | CH(CH$_3$) | O | CH$_2$CF$_3$ |
| P580 | H | Cl | H | Br | CF$_3$ | CF$_3$ | CF$_3$ | O | CH(CH$_3$) | O | CH$_2$CF$_3$ |
| P581 | H | Cl | H | Br | CF$_3$ | CF$_3$ | CH$_3$ | O | CH(CH$_3$) | O | CH$_2$CF$_3$ |
| P582 | H | Cl | H | Br | CF$_2$CF$_3$ | H | Br | O | CH(CH$_3$) | O | CH$_2$CF$_3$ |
| P583 | H | Cl | H | Br | CF$_2$CF$_3$ | H | Cl | O | CH(CH$_3$) | O | CH$_2$CF$_3$ |
| P584 | H | Cl | H | Br | CF$_2$CF$_3$ | H | CF$_3$ | O | CH(CH$_3$) | O | CH$_2$CF$_3$ |
| P585 | H | Cl | H | Br | CF$_2$CF$_3$ | H | CH$_3$ | O | CH(CH$_3$) | O | CH$_2$CF$_3$ |
| P586 | H | Cl | H | Br | CF$_3$ | H | Br | O | CH(CH$_3$) | O | CH$_2$CF$_3$ |
| P587 | H | Cl | H | Br | CF$_3$ | H | Cl | O | CH(CH$_3$) | O | CH$_2$CF$_3$ |
| P588 | H | Cl | H | Br | CF$_3$ | H | CF$_3$ | O | CH(CH$_3$) | O | CH$_2$CF$_3$ |
| P589 | H | Cl | H | Br | CF$_3$ | H | CH$_3$ | O | CH(CH$_3$) | O | CH$_2$CF$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P590 | H | Cl | H | Br | CF$_3$ | H | Br | O | CH(CH$_3$) | S | CH$_2$CF$_3$ |
| P591 | H | Cl | H | Br | CF$_3$ | H | Cl | O | CH(CH$_3$) | S | CH$_2$CF$_3$ |
| P592 | H | Cl | H | Br | CF$_3$ | H | CF$_3$ | O | CH(CH$_3$) | S | CH$_2$CF$_3$ |
| P593 | H | Cl | H | Br | CF$_3$ | H | CH$_3$ | O | CH(CH$_3$) | S | CH$_2$CF$_3$ |
| P594 | H | Cl | H | Br | CF$_3$ | H | Br | S | CH(CH$_3$) | O | CH$_2$CF$_3$ |
| P595 | H | Cl | H | Br | CF$_3$ | H | Cl | S | CH(CH$_3$) | O | CH$_2$CF$_3$ |
| P596 | H | Cl | H | Br | CF$_3$ | H | CF$_3$ | S | CH(CH$_3$) | O | CH$_2$CF$_3$ |
| P597 | H | Cl | H | Br | CF$_3$ | H | CH$_3$ | S | CH(CH$_3$) | O | CH$_2$CF$_3$ |
| P598 | H | Cl | H | Br | CF$_3$ | H | Br | O | CH(CH$_3$) | O | CH$_2$CHF$_2$ |
| P599 | H | Cl | H | Br | CF$_3$ | H | Cl | O | CH(CH$_3$) | O | CH$_2$CHF$_2$ |
| P600 | H | Cl | H | Br | CF$_3$ | H | CF$_3$ | O | CH(CH$_3$) | O | CH$_2$CHF$_2$ |
| P601 | H | Cl | H | Br | CF$_3$ | H | CH$_3$ | O | CH(CH$_3$) | O | CH$_2$CHF$_2$ |
| P602 | H | Cl | H | Br | CF$_3$ | H | Br | O | CH(CH$_3$) | O | CH(CH$_3$)CF$_3$ |
| P603 | H | Cl | H | Br | CF$_3$ | H | Cl | O | CH(CH$_3$) | O | CH(CH$_3$)CF$_3$ |
| P604 | H | Cl | H | Br | CF$_3$ | H | CF$_3$ | O | CH(CH$_3$) | O | CH(CH$_3$)CF$_3$ |
| P605 | H | Cl | H | Br | CF$_3$ | H | CH$_3$ | O | CH(CH$_3$) | O | CH(CH$_3$)CF$_3$ |
| P606 | H | Cl | H | Br | CF$_3$ | H | Br | O | CH(CH$_3$) | O | CH$_2$CH$_2$CF$_3$ |
| P607 | H | Cl | H | Br | CF$_3$ | H | Cl | O | CH(CH$_3$) | O | CH$_2$CH$_2$CF$_3$ |
| P608 | H | Cl | H | Br | CF$_3$ | H | CF$_3$ | O | CH(CH$_3$) | O | CH$_2$CH$_2$CF$_3$ |
| P609 | H | Cl | H | Br | CF$_3$ | H | CH$_3$ | O | CH(CH$_3$) | O | CH$_2$CH$_2$CF$_3$ |
| P610 | H | Cl | H | Br | CF$_3$ | H | Br | O | CH(CH$_2$CH$_3$) | O | CH$_2$CF$_3$ |
| P611 | H | Cl | H | Br | CF$_3$ | H | Cl | O | CH(CH$_2$CH$_3$) | O | CH$_2$CF$_3$ |
| P612 | H | Cl | H | Br | CF$_3$ | H | CF$_3$ | O | CH(CH$_2$CH$_3$) | O | CH$_2$CF$_3$ |
| P613 | H | Cl | H | Br | CF$_3$ | H | CH$_3$ | O | CH(CH$_2$CH$_3$) | O | CH$_2$CF$_3$ |
| P614 | H | Cl | H | Br | CF$_3$ | H | Br | O | C(CH$_3$)$_2$ | O | CH$_2$CF$_3$ |
| P615 | H | Cl | H | Br | CF$_3$ | H | Cl | O | C(CH$_3$)$_2$ | O | CH$_2$CF$_3$ |
| P616 | H | Cl | H | Br | CF$_3$ | H | CF$_3$ | O | C(CH$_3$)$_2$ | O | CH$_2$CF$_3$ |
| P617 | H | Cl | H | Br | CF$_3$ | H | CH$_3$ | O | C(CH$_3$)$_2$ | O | CH$_2$CF$_3$ |
| P618 | H | Cl | H | Br | CF$_3$ | H | Br | O | CH$_2$CH$_2$ | O | CH$_2$CF$_3$ |
| P619 | H | Cl | H | Br | CF$_3$ | H | Cl | O | CH$_2$CH$_2$ | O | CH$_2$CF$_3$ |
| P620 | H | Cl | H | Br | CF$_3$ | H | CF$_3$ | O | CH$_2$CH$_2$ | O | CH$_2$CF$_3$ |
| P621 | H | Cl | H | Br | CF$_3$ | H | CH$_3$ | O | CH$_2$CH$_2$ | O | CH$_2$CF$_3$ |
| P622 | H | H | Br | Br | CF$_3$ | H | Br | O | CH$_2$ | O | CH$_2$CF$_3$ |
| P623 | H | H | Br | Br | CF$_3$ | H | Cl | O | CH$_2$ | O | CH$_2$CF$_3$ |
| P624 | H | H | Br | Br | CF$_3$ | H | CF$_3$ | O | CH$_2$ | O | CH$_2$CF$_3$ |
| P625 | H | H | Br | Br | CF$_3$ | H | CH$_3$ | O | CH$_2$ | O | CH$_2$CF$_3$ |
| P626 | H | H | Br | Br | CF$_3$ | H | Br | O | CH$_2$ | S | CH$_2$CF$_3$ |
| P627 | H | H | Br | Br | CF$_3$ | H | Cl | O | CH$_2$ | S | CH$_2$CF$_3$ |
| P628 | H | H | Br | Br | CF$_3$ | H | CF$_3$ | O | CH$_2$ | S | CH$_2$CF$_3$ |
| P629 | H | H | Br | Br | CF$_3$ | H | CH$_3$ | O | CH$_2$ | S | CH$_2$CF$_3$ |
| P630 | H | H | Br | Br | CF$_3$ | H | Br | S | CH$_2$ | O | CH$_2$CF$_3$ |
| P631 | H | H | Br | Br | CF$_3$ | H | Cl | S | CH$_2$ | O | CH$_2$CF$_3$ |
| P632 | H | H | Br | Br | CF$_3$ | H | CF$_3$ | S | CH$_2$ | O | CH$_2$CF$_3$ |
| P633 | H | H | Br | Br | CF$_3$ | H | CH$_3$ | S | CH$_2$ | O | CH$_2$CF$_3$ |
| P634 | H | H | Br | Br | CF$_3$ | H | Br | O | CH$_2$ | O | CH$_2$CHF$_2$ |
| P635 | H | H | Br | Br | CF$_3$ | H | Cl | O | CH$_2$ | O | CH$_2$CHF$_2$ |
| P636 | H | H | Br | Br | CF$_3$ | H | CF$_3$ | O | CH$_2$ | O | CH$_2$CHF$_2$ |
| P637 | H | H | Br | Br | CF$_3$ | H | CH$_3$ | O | CH$_2$ | O | CH$_2$CHF$_2$ |
| P638 | H | H | Br | Br | CF$_3$ | CF$_3$ | Br | O | CH$_2$ | O | CH$_2$CF$_3$ |
| P639 | H | H | Br | Br | CF$_3$ | CF$_3$ | Cl | O | CH$_2$ | O | CH$_2$CF$_3$ |
| P640 | H | H | Br | Br | CF$_3$ | CF$_3$ | CF$_3$ | O | CH$_2$ | O | CH$_2$CF$_3$ |
| P641 | H | H | Br | Br | CF$_3$ | CF$_3$ | CH$_3$ | O | CH$_2$ | O | CH$_2$CF$_3$ |
| P642 | H | H | Br | Br | CF$_2$CF$_3$ | H | Br | O | CH$_2$ | O | CH$_2$CF$_3$ |
| P643 | H | H | Br | Br | CF$_2$CF$_3$ | H | Cl | O | CH$_2$ | O | CH$_2$CF$_3$ |
| P644 | H | H | Br | Br | CF$_2$CF$_3$ | H | CF$_3$ | O | CH$_2$ | O | CH$_2$CF$_3$ |
| P645 | H | H | Br | Br | CF$_2$CF$_3$ | H | CH$_3$ | O | CH$_2$ | O | CH$_2$CF$_3$ |
| P646 | H | H | Br | Br | CF$_3$ | H | Br | O | CH$_2$ | O | CH(CH$_3$)CF$_3$ |
| P647 | H | H | Br | Br | CF$_3$ | H | Cl | O | CH$_2$ | O | CH(CH$_3$)CF$_3$ |
| P648 | H | H | Br | Br | CF$_3$ | H | CF$_3$ | O | CH$_2$ | O | CH(CH$_3$)CF$_3$ |
| P649 | H | H | Br | Br | CF$_3$ | H | CH$_3$ | O | CH$_2$ | O | CH(CH$_3$)CF$_3$ |
| P650 | H | H | Br | Br | CF$_3$ | CF$_3$ | Br | O | CH(CH$_3$) | O | CH$_2$CF$_3$ |
| P651 | H | H | Br | Br | CF$_3$ | CF$_3$ | Cl | O | CH(CH$_3$) | O | CH$_2$CF$_3$ |
| P652 | H | H | Br | Br | CF$_3$ | CF$_3$ | CF$_3$ | O | CH(CH$_3$) | O | CH$_2$CF$_3$ |
| P653 | H | H | Br | Br | CF$_3$ | CF$_3$ | CH$_3$ | O | CH(CH$_3$) | O | CH$_2$CF$_3$ |
| P654 | H | H | Br | Br | CF$_2$CF$_3$ | H | Br | O | CH(CH$_3$) | O | CH$_2$CF$_3$ |
| P655 | H | H | Br | Br | CF$_2$CF$_3$ | H | Cl | O | CH(CH$_3$) | O | CH$_2$CF$_3$ |
| P656 | H | H | Br | Br | CF$_2$CF$_3$ | H | CF$_3$ | O | CH(CH$_3$) | O | CH$_2$CF$_3$ |
| P657 | H | H | Br | Br | CF$_2$CF$_3$ | H | CH$_3$ | O | CH(CH$_3$) | O | CH$_2$CF$_3$ |
| P658 | H | H | Br | Br | CF$_3$ | H | Br | O | CH(CH$_3$) | O | CH$_2$CF$_3$ |
| P659 | H | H | Br | Br | CF$_3$ | H | Cl | O | CH(CH$_3$) | O | CH$_2$CF$_3$ |
| P660 | H | H | Br | Br | CF$_3$ | H | CF$_3$ | O | CH(CH$_3$) | O | CH$_2$CF$_3$ |
| P661 | H | H | Br | Br | CF$_3$ | H | CH$_3$ | O | CH(CH$_3$) | O | CH$_2$CF$_3$ |
| P662 | H | H | Br | Br | CF$_3$ | H | Br | O | CH(CH$_3$) | S | CH$_2$CF$_3$ |
| P663 | H | H | Br | Br | CF$_3$ | H | Cl | O | CH(CH$_3$) | S | CH$_2$CF$_3$ |
| P664 | H | H | Br | Br | CF$_3$ | H | CF$_3$ | O | CH(CH$_3$) | S | CH$_2$CF$_3$ |
| P665 | H | H | Br | Br | CF$_3$ | H | CH$_3$ | O | CH(CH$_3$) | S | CH$_2$CF$_3$ |
| P666 | H | H | Br | Br | CF$_3$ | H | Br | S | CH(CH$_3$) | O | CH$_2$CF$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P667 | H | H | Br | Br | $CF_3$ | H | Cl | S | $CH(CH_3)$ | O | $CH_2CF_3$ |
| P668 | H | H | Br | Br | $CF_3$ | H | $CF_3$ | S | $CH(CH_3)$ | O | $CH_2CF_3$ |
| P669 | H | H | Br | Br | $CF_3$ | H | $CH_3$ | S | $CH(CH_3)$ | O | $CH_2CF_3$ |
| P670 | H | H | Br | Br | $CF_3$ | H | Br | O | $CH(CH_3)$ | O | $CH_2CHF_2$ |
| P671 | H | H | Br | Br | $CF_3$ | H | Cl | O | $CH(CH_3)$ | O | $CH_2CHF_2$ |
| P672 | H | H | Br | Br | $CF_3$ | H | $CF_3$ | O | $CH(CH_3)$ | O | $CH_2CHF_2$ |
| P673 | H | H | Br | Br | $CF_3$ | H | $CH_3$ | O | $CH(CH_3)$ | O | $CH_2CHF_2$ |
| P674 | H | H | Br | Br | $CF_3$ | H | Br | O | $CH(CH_3)$ | O | $CH(CH_3)CF_3$ |
| P675 | H | H | Br | Br | $CF_3$ | H | Cl | O | $CH(CH_3)$ | O | $CH(CH_3)CF_3$ |
| P676 | H | H | Br | Br | $CF_3$ | H | $CF_3$ | O | $CH(CH_3)$ | O | $CH(CH_3)CF_3$ |
| P677 | H | H | Br | Br | $CF_3$ | H | $CH_3$ | O | $CH(CH_3)$ | O | $CH(CH_3)CF_3$ |
| P678 | H | H | Br | Br | $CF_3$ | H | Br | O | $CH(CH_3)$ | O | $CH_2CH_2CF_3$ |
| P679 | H | H | Br | Br | $CF_3$ | H | Cl | O | $CH(CH_3)$ | O | $CH_2CH_2CF_3$ |
| P680 | H | H | Br | Br | $CF_3$ | H | $CF_3$ | O | $CH(CH_3)$ | O | $CH_2CH_2CF_3$ |
| P681 | H | H | Br | Br | $CF_3$ | H | $CH_3$ | O | $CH(CH_3)$ | O | $CH_2CH_2CF_3$ |
| P682 | H | H | Br | Br | $CF_3$ | H | Br | O | $CH(CH_2CH_3)$ | O | $CH_2CF_3$ |
| P683 | H | H | Br | Br | $CF_3$ | H | Cl | O | $CH(CH_2CH_3)$ | O | $CH_2CF_3$ |
| P684 | H | H | Br | Br | $CF_3$ | H | $CF_3$ | O | $CH(CH_2CH_3)$ | O | $CH_2CF_3$ |
| P685 | H | H | Br | Br | $CF_3$ | H | $CH_3$ | O | $CH(CH_2CH_3)$ | O | $CH_2CF_3$ |
| P686 | H | H | Br | Br | $CF_3$ | H | Br | O | $C(CH_3)_2$ | O | $CH_2CF_3$ |
| P687 | H | H | Br | Br | $CF_3$ | H | Cl | O | $C(CH_3)_2$ | O | $CH_2CF_3$ |
| P688 | H | H | Br | Br | $CF_3$ | H | $CF_3$ | O | $C(CH_3)_2$ | O | $CH_2CF_3$ |
| P689 | H | H | Br | Br | $CF_3$ | H | $CH_3$ | O | $C(CH_3)_2$ | O | $CH_2CF_3$ |
| P690 | H | H | Br | Br | $CF_3$ | H | Br | O | $CH_2CH_2$ | O | $CH_2CF_3$ |
| P691 | H | H | Br | Br | $CF_3$ | H | Cl | O | $CH_2CH_2$ | O | $CH_2CF_3$ |
| P692 | H | H | Br | Br | $CF_3$ | H | $CF_3$ | O | $CH_2CH_2$ | O | $CH_2CF_3$ |
| P693 | H | H | Br | Br | $CF_3$ | H | $CH_3$ | O | $CH_2CH_2$ | O | $CH_2CF_3$ |
| P694 | H | H | Cl | $NO_2$ | $CF_3$ | H | Br | O | $CH_2$ | O | $CH_2CF_3$ |
| P695 | H | H | Cl | $NO_2$ | $CF_3$ | H | Cl | O | $CH_2$ | O | $CH_2CF_3$ |
| P696 | H | H | Cl | $NO_2$ | $CF_3$ | H | $CF_3$ | O | $CH_2$ | O | $CH_2CF_3$ |
| P697 | H | H | Cl | $NO_2$ | $CF_3$ | H | $CH_3$ | O | $CH_2$ | O | $CH_2CF_3$ |
| P698 | H | H | Cl | $NO_2$ | $CF_3$ | H | Br | O | $CH_2$ | S | $CH_2CF_3$ |
| P699 | H | H | Cl | $NO_2$ | $CF_3$ | H | Cl | O | $CH_2$ | S | $CH_2CF_3$ |
| P700 | H | H | Cl | $NO_2$ | $CF_3$ | H | $CF_3$ | O | $CH_2$ | S | $CH_2CF_3$ |
| P701 | H | H | Cl | $NO_2$ | $CF_3$ | H | $CH_3$ | O | $CH_2$ | S | $CH_2CF_3$ |
| P702 | H | H | Cl | $NO_2$ | $CF_3$ | H | Br | S | $CH_2$ | O | $CH_2CF_3$ |
| P703 | H | H | Cl | $NO_2$ | $CF_3$ | H | Cl | S | $CH_2$ | O | $CH_2CF_3$ |
| P704 | H | H | Cl | $NO_2$ | $CF_3$ | H | $CF_3$ | S | $CH_2$ | O | $CH_2CF_3$ |
| P705 | H | H | Cl | $NO_2$ | $CF_3$ | H | $CH_3$ | S | $CH_2$ | O | $CH_2CF_3$ |
| P706 | H | H | Cl | $NO_2$ | $CF_3$ | H | Br | O | $CH_2$ | O | $CH_2CHF_2$ |
| P707 | H | H | Cl | $NO_2$ | $CF_3$ | H | Cl | O | $CH_2$ | O | $CH_2CHF_2$ |
| P708 | H | H | Cl | $NO_2$ | $CF_3$ | H | $CF_3$ | O | $CH_2$ | O | $CH_2CHF_2$ |
| P709 | H | H | Cl | $NO_2$ | $CF_3$ | H | $CH_3$ | O | $CH_2$ | O | $CH_2CHF_2$ |
| P710 | H | H | Cl | $NO_2$ | $CF_3$ | $CF_3$ | Br | O | $CH_2$ | O | $CH_2CF_3$ |
| P711 | H | H | Cl | $NO_2$ | $CF_3$ | $CF_3$ | Cl | O | $CH_2$ | O | $CH_2CF_3$ |
| P712 | H | H | Cl | $NO_2$ | $CF_3$ | $CF_3$ | $CF_3$ | O | $CH_2$ | O | $CH_2CF_3$ |
| P713 | H | H | Cl | $NO_2$ | $CF_3$ | $CF_3$ | $CH_3$ | O | $CH_2$ | O | $CH_2CF_3$ |
| P714 | H | H | Cl | $NO_2$ | $CF_2CF_3$ | H | Br | O | $CH_2$ | O | $CH_2CF_3$ |
| P715 | H | H | Cl | $NO_2$ | $CF_2CF_3$ | H | Cl | O | $CH_2$ | O | $CH_2CF_3$ |
| P716 | H | H | Cl | $NO_2$ | $CF_2CF_3$ | H | $CF_3$ | O | $CH_2$ | O | $CH_2CF_3$ |
| P717 | H | H | Cl | $NO_2$ | $CF_2CF_3$ | H | $CH_3$ | O | $CH_2$ | O | $CH_2CF_3$ |
| P718 | H | H | Cl | $NO_2$ | $CF_3$ | H | Br | O | $CH_2$ | O | $CH(CH_3)CF_3$ |
| P719 | H | H | Cl | $NO_2$ | $CF_3$ | H | Cl | O | $CH_2$ | O | $CH(CH_3)CF_3$ |
| P720 | H | H | Cl | $NO_2$ | $CF_3$ | H | $CF_3$ | O | $CH_2$ | O | $CH(CH_3)CF_3$ |
| P721 | H | H | Cl | $NO_2$ | $CF_3$ | H | $CH_3$ | O | $CH_2$ | O | $CH(CH_3)CF_3$ |
| P722 | H | H | Cl | $NO_2$ | $CF_3$ | $CF_3$ | Br | O | $CH(CH_3)$ | O | $CH_2CF_3$ |
| P723 | H | H | Cl | $NO_2$ | $CF_3$ | $CF_3$ | Cl | O | $CH(CH_3)$ | O | $CH_2CF_3$ |
| P724 | H | H | Cl | $NO_2$ | $CF_3$ | $CF_3$ | $CF_3$ | O | $CH(CH_3)$ | O | $CH_2CF_3$ |
| P725 | H | H | Cl | $NO_2$ | $CF_3$ | $CF_3$ | $CH_3$ | O | $CH(CH_3)$ | O | $CH_2CF_3$ |
| P726 | H | H | Cl | $NO_2$ | $CF_2CF_3$ | H | Br | O | $CH(CH_3)$ | O | $CH_2CF_3$ |
| P727 | H | H | Cl | $NO_2$ | $CF_2CF_3$ | H | Cl | O | $CH(CH_3)$ | O | $CH_2CF_3$ |
| P728 | H | H | Cl | $NO_2$ | $CF_2CF_3$ | H | $CF_3$ | O | $CH(CH_3)$ | O | $CH_2CF_3$ |
| P729 | H | H | Cl | $NO_2$ | $CF_2CF_3$ | H | $CH_3$ | O | $CH(CH_3)$ | O | $CH_2CF_3$ |
| P730 | H | H | Cl | $NO_2$ | $CF_3$ | H | Br | O | $CH(CH_3)$ | O | $CH_2CF_3$ |
| P731 | H | H | Cl | $NO_2$ | $CF_3$ | H | Cl | O | $CH(CH_3)$ | O | $CH_2CF_3$ |
| P732 | H | H | Cl | $NO_2$ | $CF_3$ | H | $CF_3$ | O | $CH(CH_3)$ | O | $CH_2CF_3$ |
| P733 | H | H | Cl | $NO_2$ | $CF_3$ | H | $CH_3$ | O | $CH(CH_3)$ | O | $CH_2CF_3$ |
| P734 | H | H | Cl | $NO_2$ | $CF_3$ | H | Br | O | $CH(CH_3)$ | S | $CH_2CF_3$ |
| P735 | H | H | Cl | $NO_2$ | $CF_3$ | H | Cl | O | $CH(CH_3)$ | S | $CH_2CF_3$ |
| P736 | H | H | Cl | $NO_2$ | $CF_3$ | H | $CF_3$ | O | $CH(CH_3)$ | S | $CH_2CF_3$ |
| P737 | H | H | Cl | $NO_2$ | $CF_3$ | H | $CH_3$ | O | $CH(CH_3)$ | S | $CH_2CF_3$ |
| P738 | H | H | Cl | $NO_2$ | $CF_3$ | H | Br | S | $CH(CH_3)$ | O | $CH_2CF_3$ |
| P739 | H | H | Cl | $NO_2$ | $CF_3$ | H | Cl | S | $CH(CH_3)$ | O | $CH_2CF_3$ |
| P740 | H | H | Cl | $NO_2$ | $CF_3$ | H | $CF_3$ | S | $CH(CH_3)$ | O | $CH_2CF_3$ |
| P741 | H | H | Cl | $NO_2$ | $CF_3$ | H | $CH_3$ | S | $CH(CH_3)$ | O | $CH_2CF_3$ |
| P742 | H | H | Cl | $NO_2$ | $CF_3$ | H | Br | O | $CH(CH_3)$ | O | $CH_2CHF_2$ |
| P743 | H | H | Cl | $NO_2$ | $CF_3$ | H | Cl | O | $CH(CH_3)$ | O | $CH_2CHF_2$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P744 | H | H | Cl | NO$_2$ | CF$_3$ | H | CF$_3$ | O | CH(CH$_3$) | O | CH$_2$CHF$_2$ |
| P745 | H | H | Cl | NO$_2$ | CF$_3$ | H | CH$_3$ | O | CH(CH$_3$) | O | CH$_2$CHF$_2$ |
| P746 | H | H | Cl | NO$_2$ | CF$_3$ | H | Br | O | CH(CH$_3$) | O | CH(CH$_3$)CF$_3$ |
| P747 | H | H | Cl | NO$_2$ | CF$_3$ | H | Cl | O | CH(CH$_3$) | O | CH(CH$_3$)CF$_3$ |
| P748 | H | H | Cl | NO$_2$ | CF$_3$ | H | CF$_3$ | O | CH(CH$_3$) | O | CH(CH$_3$)CF$_3$ |
| P749 | H | H | Cl | NO$_2$ | CF$_3$ | H | CH$_3$ | O | CH(CH$_3$) | O | CH(CH$_3$)CF$_3$ |
| P750 | H | H | Cl | NO$_2$ | CF$_3$ | H | Br | O | CH(CH$_3$) | O | CH$_2$CH$_2$CF$_3$ |
| P751 | H | H | Cl | NO$_2$ | CF$_3$ | H | Cl | O | CH(CH$_3$) | O | CH$_2$CH$_2$CF$_3$ |
| P752 | H | H | Cl | NO$_2$ | CF$_3$ | H | CF$_3$ | O | CH(CH$_3$) | O | CH$_2$CH$_2$CF$_3$ |
| P753 | H | H | Cl | NO$_2$ | CF$_3$ | H | CH$_3$ | O | CH(CH$_3$) | O | CH$_2$CH$_2$CF$_3$ |
| P754 | H | H | Cl | NO$_2$ | CF$_3$ | H | Br | O | CH(CH$_2$CH$_3$) | O | CH$_2$CF$_3$ |
| P755 | H | H | Cl | NO$_2$ | CF$_3$ | H | Cl | O | CH(CH$_2$CH$_3$) | O | CH$_2$CF$_3$ |
| P756 | H | H | Cl | NO$_2$ | CF$_3$ | H | CF$_3$ | O | CH(CH$_2$CH$_3$) | O | CH$_2$CF$_3$ |
| P757 | H | H | Cl | NO$_2$ | CF$_3$ | H | CH$_3$ | O | CH(CH$_2$CH$_3$) | O | CH$_2$CF$_3$ |
| P758 | H | H | Cl | NO$_2$ | CF$_3$ | H | Br | O | C(CH$_3$)$_2$ | O | CH$_2$CF$_3$ |
| P759 | H | H | Cl | NO$_2$ | CF$_3$ | H | Cl | O | C(CH$_3$)$_2$ | O | CH$_2$CF$_3$ |
| P760 | H | H | Cl | NO$_2$ | CF$_3$ | H | CF$_3$ | O | C(CH$_3$)$_2$ | O | CH$_2$CF$_3$ |
| P761 | H | H | Cl | NO$_2$ | CF$_3$ | H | CH$_3$ | O | C(CH$_3$)$_2$ | O | CH$_2$CF$_3$ |
| P762 | H | H | Cl | NO$_2$ | CF$_3$ | H | Br | O | CH$_2$CH$_2$ | O | CH$_2$CF$_3$ |
| P763 | H | H | Cl | NO$_2$ | CF$_3$ | H | Cl | O | CH$_2$CH$_2$ | O | CH$_2$CF$_3$ |
| P764 | H | H | Cl | NO$_2$ | CF$_3$ | H | CF$_3$ | O | CH$_2$CH$_2$ | O | CH$_2$CF$_3$ |
| P765 | H | H | Cl | NO$_2$ | CF$_3$ | H | CH$_3$ | O | CH$_2$CH$_2$ | O | CH$_2$CF$_3$ |
| P766 | H | H | F | CN | CF$_3$ | H | Br | O | CH$_2$ | O | CH$_2$CF$_3$ |
| P767 | H | H | F | CN | CF$_3$ | H | Cl | O | CH$_2$ | O | CH$_2$CF$_3$ |
| P768 | H | H | F | CN | CF$_3$ | H | CF$_3$ | O | CH$_2$ | O | CH$_2$CF$_3$ |
| P769 | H | H | F | CN | CF$_3$ | H | CH$_3$ | O | CH$_2$ | O | CH$_2$CF$_3$ |
| P770 | H | H | F | CN | CF$_3$ | H | Br | O | CH$_2$ | S | CH$_2$CF$_3$ |
| P771 | H | H | F | CN | CF$_3$ | H | Cl | O | CH$_2$ | S | CH$_2$CF$_3$ |
| P772 | H | H | F | CN | CF$_3$ | H | CF$_3$ | O | CH$_2$ | S | CH$_2$CF$_3$ |
| P773 | H | H | F | CN | CF$_3$ | H | CH$_3$ | O | CH$_2$ | S | CH$_2$CF$_3$ |
| P774 | H | H | F | CN | CF$_3$ | H | Br | S | CH$_2$ | O | CH$_2$CF$_3$ |
| P775 | H | H | F | CN | CF$_3$ | H | Cl | S | CH$_2$ | O | CH$_2$CF$_3$ |
| P776 | H | H | F | CN | CF$_3$ | H | CF$_3$ | S | CH$_2$ | O | CH$_2$CF$_3$ |
| P777 | H | H | F | CN | CF$_3$ | H | CH$_3$ | S | CH$_2$ | O | CH$_2$CF$_3$ |
| P778 | H | H | F | CN | CF$_3$ | H | Br | O | CH$_2$ | O | CH$_2$CHF$_2$ |
| P779 | H | H | F | CN | CF$_3$ | H | Cl | O | CH$_2$ | O | CH$_2$CHF$_2$ |
| P780 | H | H | F | CN | CF$_3$ | H | CF$_3$ | O | CH$_2$ | O | CH$_2$CHF$_2$ |
| P781 | H | H | F | CN | CF$_3$ | H | CH$_3$ | O | CH$_2$ | O | CH$_2$CHF$_2$ |
| P782 | H | H | F | CN | CF$_3$ | CF$_3$ | Br | O | CH$_2$ | O | CH$_2$CF$_3$ |
| P783 | H | H | F | CN | CF$_3$ | CF$_3$ | Cl | O | CH$_2$ | O | CH$_2$CF$_3$ |
| P784 | H | H | F | CN | CF$_3$ | CF$_3$ | CF$_3$ | O | CH$_2$ | O | CH$_2$CF$_3$ |
| P785 | H | H | F | CN | CF$_3$ | CF$_3$ | CH$_3$ | O | CH$_2$ | O | CH$_2$CF$_3$ |
| P786 | H | H | F | CN | CF$_2$CF$_3$ | H | Br | O | CH$_2$ | O | CH$_2$CF$_3$ |
| P787 | H | H | F | CN | CF$_2$CF$_3$ | H | Cl | O | CH$_2$ | O | CH$_2$CF$_3$ |
| P788 | H | H | F | CN | CF$_2$CF$_3$ | H | CF$_3$ | O | CH$_2$ | O | CH$_2$CF$_3$ |
| P789 | H | H | F | CN | CF$_2$CF$_3$ | H | CH$_3$ | O | CH$_2$ | O | CH$_2$CF$_3$ |
| P790 | H | H | F | CN | CF$_3$ | H | Br | O | CH$_2$ | O | CH(CH$_3$)CF$_3$ |
| P791 | H | H | F | CN | CF$_3$ | H | Cl | O | CH$_2$ | O | CH(CH$_3$)CF$_3$ |
| P792 | H | H | F | CN | CF$_3$ | H | CF$_3$ | O | CH$_2$ | O | CH(CH$_3$)CF$_3$ |
| P793 | H | H | F | CN | CF$_3$ | H | CH$_3$ | O | CH$_2$ | O | CH(CH$_3$)CF$_3$ |
| P794 | H | H | F | CN | CF$_3$ | CF$_3$ | Br | O | CH(CH$_3$) | O | CH$_2$CF$_3$ |
| P795 | H | H | F | CN | CF$_3$ | CF$_3$ | Cl | O | CH(CH$_3$) | O | CH$_2$CF$_3$ |
| P796 | H | H | F | CN | CF$_3$ | CF$_3$ | CF$_3$ | O | CH(CH$_3$) | O | CH$_2$CF$_3$ |
| P797 | H | H | F | CN | CF$_3$ | CF$_3$ | CH$_3$ | O | CH(CH$_3$) | O | CH$_2$CF$_3$ |
| P798 | H | H | F | CN | CF$_2$CF$_3$ | H | Br | O | CH(CH$_3$) | O | CH$_2$CF$_3$ |
| P799 | H | H | F | CN | CF$_2$CF$_3$ | H | Cl | O | CH(CH$_3$) | O | CH$_2$CF$_3$ |
| P800 | H | H | F | CN | CF$_2$CF$_3$ | H | CF$_3$ | O | CH(CH$_3$) | O | CH$_2$CF$_3$ |
| P801 | H | H | F | CN | CF$_2$CF$_3$ | H | CH$_3$ | O | CH(CH$_3$) | O | CH$_2$CF$_3$ |
| P802 | H | H | F | CN | CF$_3$ | H | Br | O | CH(CH$_3$) | O | CH$_2$CF$_3$ |
| P803 | H | H | F | CN | CF$_3$ | H | Cl | O | CH(CH$_3$) | O | CH$_2$CF$_3$ |
| P804 | H | H | F | CN | CF$_3$ | H | CF$_3$ | O | CH(CH$_3$) | O | CH$_2$CF$_3$ |
| P805 | H | H | F | CN | CF$_3$ | H | CH$_3$ | O | CH(CH$_3$) | O | CH$_2$CF$_3$ |
| P806 | H | H | F | CN | CF$_3$ | H | Br | O | CH(CH$_3$) | S | CH$_2$CF$_3$ |
| P807 | H | H | F | CN | CF$_3$ | H | Cl | O | CH(CH$_3$) | S | CH$_2$CF$_3$ |
| P808 | H | H | F | CN | CF$_3$ | H | CF$_3$ | O | CH(CH$_3$) | S | CH$_2$CF$_3$ |
| P809 | H | H | F | CN | CF$_3$ | H | CH$_3$ | O | CH(CH$_3$) | S | CH$_2$CF$_3$ |
| P810 | H | H | F | CN | CF$_3$ | H | Br | S | CH(CH$_3$) | O | CH$_2$CF$_3$ |
| P811 | H | H | F | CN | CF$_3$ | H | Cl | S | CH(CH$_3$) | O | CH$_2$CF$_3$ |
| P812 | H | H | F | CN | CF$_3$ | H | CF$_3$ | S | CH(CH$_3$) | O | CH$_2$CF$_3$ |
| P813 | H | H | F | CN | CF$_3$ | H | CH$_3$ | S | CH(CH$_3$) | O | CH$_2$CF$_3$ |
| P814 | H | H | F | CN | CF$_3$ | H | Br | O | CH(CH$_3$) | O | CH$_2$CHF$_2$ |
| P815 | H | H | F | CN | CF$_3$ | H | Cl | O | CH(CH$_3$) | O | CH$_2$CHF$_2$ |
| P816 | H | H | F | CN | CF$_3$ | H | CF$_3$ | O | CH(CH$_3$) | O | CH$_2$CHF$_2$ |
| P817 | H | H | F | CN | CF$_3$ | H | CH$_3$ | O | CH(CH$_3$) | O | CH$_2$CHF$_2$ |
| P818 | H | H | F | CN | CF$_3$ | H | Br | O | CH(CH$_3$) | O | CH(CH$_3$)CF$_3$ |
| P819 | H | H | F | CN | CF$_3$ | H | Cl | O | CH(CH$_3$) | O | CH(CH$_3$)CF$_3$ |
| P820 | H | H | F | CN | CF$_3$ | H | CF$_3$ | O | CH(CH$_3$) | O | CH(CH$_3$)CF$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P821 | H | H | F | CN | $CF_3$ | H | $CH_3$ | O | $CH(CH_3)$ | O | $CH(CH_3)CF_3$ |
| P822 | H | H | F | CN | $CF_3$ | H | Br | O | $CH(CH_3)$ | O | $CH_2CH_2CF_3$ |
| P823 | H | H | F | CN | $CF_3$ | H | Cl | O | $CH(CH_3)$ | O | $CH_2CH_2CF_3$ |
| P824 | H | H | F | CN | $CF_3$ | H | $CF_3$ | O | $CH(CH_3)$ | O | $CH_2CH_2CF_3$ |
| P825 | H | H | F | CN | $CF_3$ | H | $CH_3$ | O | $CH(CH_3)$ | O | $CH_2CH_2CF_3$ |
| P826 | H | H | F | CN | $CF_3$ | H | Br | O | $CH(CH_2CH_3)$ | O | $CH_2CF_3$ |
| P827 | H | H | F | CN | $CF_3$ | H | Cl | O | $CH(CH_2CH_3)$ | O | $CH_2CF_3$ |
| P828 | H | H | F | CN | $CF_3$ | H | $CF_3$ | O | $CH(CH_2CH_3)$ | O | $CH_2CF_3$ |
| P829 | H | H | F | CN | $CF_3$ | H | $CH_3$ | O | $CH(CH_2CH_3)$ | O | $CH_2CF_3$ |
| P830 | H | H | F | CN | $CF_3$ | H | Br | O | $C(CH_3)_2$ | O | $CH_2CF_3$ |
| P831 | H | H | F | CN | $CF_3$ | H | Cl | O | $C(CH_3)_2$ | O | $CH_2CF_3$ |
| P832 | H | H | F | CN | $CF_3$ | H | $CF_3$ | O | $C(CH_3)_2$ | O | $CH_2CF_3$ |
| P833 | H | H | F | CN | $CF_3$ | H | $CH_3$ | O | $C(CH_3)_2$ | O | $CH_2CF_3$ |
| P834 | H | H | F | CN | $CF_3$ | H | Br | O | $CH_2CH_2$ | O | $CH_2CF_3$ |
| P835 | H | H | F | CN | $CF_3$ | H | Cl | O | $CH_2CH_2$ | O | $CH_2CF_3$ |
| P836 | H | H | F | CN | $CF_3$ | H | $CF_3$ | O | $CH_2CH_2$ | O | $CH_2CF_3$ |
| P837 | H | H | F | CN | $CF_3$ | H | $CH_3$ | O | $CH_2CH_2$ | O | $CH_2CF_3$ |
| P838 | H | Cl | $OCF_3$ | Cl | $CF_3$ | H | Br | O | $CH_2$ | O | $CH_2CF_3$ |
| P839 | H | Cl | $OCF_3$ | Cl | $CF_3$ | H | Cl | O | $CH_2$ | O | $CH_2CF_3$ |
| P840 | H | Cl | $OCF_3$ | Cl | $CF_3$ | H | $CF_3$ | O | $CH_2$ | O | $CH_2CF_3$ |
| P841 | H | Cl | $OCF_3$ | Cl | $CF_3$ | H | $CH_3$ | O | $CH_2$ | O | $CH_2CF_3$ |
| P842 | H | Cl | $OCF_3$ | Cl | $CF_3$ | H | Br | O | $CH_2$ | S | $CH_2CF_3$ |
| P843 | H | Cl | $OCF_3$ | Cl | $CF_3$ | H | Cl | O | $CH_2$ | S | $CH_2CF_3$ |
| P844 | H | Cl | $OCF_3$ | Cl | $CF_3$ | H | $CF_3$ | O | $CH_2$ | S | $CH_2CF_3$ |
| P845 | H | Cl | $OCF_3$ | Cl | $CF_3$ | H | $CH_3$ | O | $CH_2$ | S | $CH_2CF_3$ |
| P846 | H | Cl | $OCF_3$ | Cl | $CF_3$ | H | Br | S | $CH_2$ | O | $CH_2CF_3$ |
| P847 | H | Cl | $OCF_3$ | Cl | $CF_3$ | H | Cl | S | $CH_2$ | O | $CH_2CF_3$ |
| P848 | H | Cl | $OCF_3$ | Cl | $CF_3$ | H | $CF_3$ | S | $CH_2$ | O | $CH_2CF_3$ |
| P849 | H | Cl | $OCF_3$ | Cl | $CF_3$ | H | $CH_3$ | S | $CH_2$ | O | $CH_2CF_3$ |
| P850 | H | Cl | $OCF_3$ | Cl | $CF_3$ | H | Br | O | $CH_2$ | O | $CH_2CHF_2$ |
| P851 | H | Cl | $OCF_3$ | Cl | $CF_3$ | H | Cl | O | $CH_2$ | O | $CH_2CHF_2$ |
| P852 | H | Cl | $OCF_3$ | Cl | $CF_3$ | H | $CF_3$ | O | $CH_2$ | O | $CH_2CHF_2$ |
| P853 | H | Cl | $OCF_3$ | Cl | $CF_3$ | H | $CH_3$ | O | $CH_2$ | O | $CH_2CHF_2$ |
| P854 | H | Cl | $OCF_3$ | Cl | $CF_3$ | $CF_3$ | Br | O | $CH_2$ | O | $CH_2CF_3$ |
| P855 | H | Cl | $OCF_3$ | Cl | $CF_3$ | $CF_3$ | Cl | O | $CH_2$ | O | $CH_2CF_3$ |
| P856 | H | Cl | $OCF_3$ | Cl | $CF_3$ | $CF_3$ | $CF_3$ | O | $CH_2$ | O | $CH_2CF_3$ |
| P857 | H | Cl | $OCF_3$ | Cl | $CF_3$ | $CF_3$ | $CH_3$ | O | $CH_2$ | O | $CH_2CF_3$ |
| P858 | H | Cl | $OCF_3$ | Cl | $CF_2CF_3$ | H | Br | O | $CH_2$ | O | $CH_2CF_3$ |
| P859 | H | Cl | $OCF_3$ | Cl | $CF_2CF_3$ | H | Cl | O | $CH_2$ | O | $CH_2CF_3$ |
| P860 | H | Cl | $OCF_3$ | Cl | $CF_2CF_3$ | H | $CF_3$ | O | $CH_2$ | O | $CH_2CF_3$ |
| P861 | H | Cl | $OCF_3$ | Cl | $CF_2CF_3$ | H | $CH_3$ | O | $CH_2$ | O | $CH_2CF_3$ |
| P862 | H | Cl | $OCF_3$ | Cl | $CF_3$ | H | Br | O | $CH_2$ | O | $CH(CH_3)CF_3$ |
| P863 | H | Cl | $OCF_3$ | Cl | $CF_3$ | H | Cl | O | $CH_2$ | O | $CH(CH_3)CF_3$ |
| P864 | H | Cl | $OCF_3$ | Cl | $CF_3$ | H | $CF_3$ | O | $CH_2$ | O | $CH(CH_3)CF_3$ |
| P865 | H | Cl | $OCF_3$ | Cl | $CF_3$ | H | $CH_3$ | O | $CH_2$ | O | $CH(CH_3)CF_3$ |
| P866 | H | Cl | $OCF_3$ | Cl | $CF_3$ | $CF_3$ | Br | O | $CH(CH_3)$ | O | $CH_2CF_3$ |
| P867 | H | Cl | $OCF_3$ | Cl | $CF_3$ | $CF_3$ | Cl | O | $CH(CH_3)$ | O | $CH_2CF_3$ |
| P868 | H | Cl | $OCF_3$ | Cl | $CF_3$ | $CF_3$ | $CF_3$ | O | $CH(CH_3)$ | O | $CH_2CF_3$ |
| P869 | H | Cl | $OCF_3$ | Cl | $CF_3$ | $CF_3$ | $CH_3$ | O | $CH(CH_3)$ | O | $CH_2CF_3$ |
| P870 | H | Cl | $OCF_3$ | Cl | $CF_2CF_3$ | H | Br | O | $CH(CH_3)$ | O | $CH_2CF_3$ |
| P871 | H | Cl | $OCF_3$ | Cl | $CF_2CF_3$ | H | Cl | O | $CH(CH_3)$ | O | $CH_2CF_3$ |
| P872 | H | Cl | $OCF_3$ | Cl | $CF_2CF_3$ | H | $CF_3$ | O | $CH(CH_3)$ | O | $CH_2CF_3$ |
| P873 | H | Cl | $OCF_3$ | Cl | $CF_2CF_3$ | H | $CH_3$ | O | $CH(CH_3)$ | O | $CH_2CF_3$ |
| P874 | H | Cl | $OCF_3$ | Cl | $CF_3$ | H | Br | O | $CH(CH_3)$ | O | $CH_2CF_3$ |
| P875 | H | Cl | $OCF_3$ | Cl | $CF_3$ | H | Cl | O | $CH(CH_3)$ | O | $CH_2CF_3$ |
| P876 | H | Cl | $OCF_3$ | Cl | $CF_3$ | H | $CF_3$ | O | $CH(CH_3)$ | O | $CH_2CF_3$ |
| P877 | H | Cl | $OCF_3$ | Cl | $CF_3$ | H | $CH_3$ | O | $CH(CH_3)$ | O | $CH_2CF_3$ |
| P878 | H | Cl | $OCF_3$ | Cl | $CF_3$ | H | Br | O | $CH(CH_3)$ | S | $CH_2CF_3$ |
| P879 | H | Cl | $OCF_3$ | Cl | $CF_3$ | H | Cl | O | $CH(CH_3)$ | S | $CH_2CF_3$ |
| P880 | H | Cl | $OCF_3$ | Cl | $CF_3$ | H | $CF_3$ | O | $CH(CH_3)$ | S | $CH_2CF_3$ |
| P881 | H | Cl | $OCF_3$ | Cl | $CF_3$ | H | $CH_3$ | O | $CH(CH_3)$ | S | $CH_2CF_3$ |
| P882 | H | Cl | $OCF_3$ | Cl | $CF_3$ | H | Br | S | $CH(CH_3)$ | O | $CH_2CF_3$ |
| P883 | H | Cl | $OCF_3$ | Cl | $CF_3$ | H | Cl | S | $CH(CH_3)$ | O | $CH_2CF_3$ |
| P884 | H | Cl | $OCF_3$ | Cl | $CF_3$ | H | $CF_3$ | S | $CH(CH_3)$ | O | $CH_2CF_3$ |
| P885 | H | Cl | $OCF_3$ | Cl | $CF_3$ | H | $CH_3$ | S | $CH(CH_3)$ | O | $CH_2CF_3$ |
| P886 | H | Cl | $OCF_3$ | Cl | $CF_3$ | H | Br | O | $CH(CH_3)$ | O | $CH_2CHF_2$ |
| P887 | H | Cl | $OCF_3$ | Cl | $CF_3$ | H | Cl | O | $CH(CH_3)$ | O | $CH_2CHF_2$ |
| P888 | H | Cl | $OCF_3$ | Cl | $CF_3$ | H | $CF_3$ | O | $CH(CH_3)$ | O | $CH_2CHF_2$ |
| P889 | H | Cl | $OCF_3$ | Cl | $CF_3$ | H | $CH_3$ | O | $CH(CH_3)$ | O | $CH_2CHF_2$ |
| P890 | H | Cl | $OCF_3$ | Cl | $CF_3$ | H | Br | O | $CH(CH_3)$ | O | $CH(CH_3)CF_3$ |
| P891 | H | Cl | $OCF_3$ | Cl | $CF_3$ | H | Cl | O | $CH(CH_3)$ | O | $CH(CH_3)CF_3$ |
| P892 | H | Cl | $OCF_3$ | Cl | $CF_3$ | H | $CF_3$ | O | $CH(CH_3)$ | O | $CH(CH_3)CF_3$ |
| P893 | H | Cl | $OCF_3$ | Cl | $CF_3$ | H | $CH_3$ | O | $CH(CH_3)$ | O | $CH(CH_3)CF_3$ |
| P894 | H | Cl | $OCF_3$ | Cl | $CF_3$ | H | Br | O | $CH(CH_3)$ | O | $CH_2CH_2CF_3$ |
| P895 | H | Cl | $OCF_3$ | Cl | $CF_3$ | H | Cl | O | $CH(CH_3)$ | O | $CH_2CH_2CF_3$ |
| P896 | H | Cl | $OCF_3$ | Cl | $CF_3$ | H | $CF_3$ | O | $CH(CH_3)$ | O | $CH_2CH_2CF_3$ |
| P897 | H | Cl | $OCF_3$ | Cl | $CF_3$ | H | $CH_3$ | O | $CH(CH_3)$ | O | $CH_2CH_2CF_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P898 | H | Cl | OCF$_3$ | Cl | CF$_3$ | H | Br | O | CH(CH$_2$CH$_3$) | O | CH$_2$CF$_3$ |
| P899 | H | Cl | OCF$_3$ | Cl | CF$_3$ | H | Cl | O | CH(CH$_2$CH$_3$) | O | CH$_2$CF$_3$ |
| P900 | H | Cl | OCF$_3$ | Cl | CF$_3$ | H | CF$_3$ | O | CH(CH$_2$CH$_3$) | O | CH$_2$CF$_3$ |
| P901 | H | Cl | OCF$_3$ | Cl | CF$_3$ | H | CH$_3$ | O | CH(CH$_2$CH$_3$) | O | CH$_2$CF$_3$ |
| P902 | H | Cl | OCF$_3$ | Cl | CF$_3$ | H | Br | O | C(CH$_3$)$_2$ | O | CH$_2$CF$_3$ |
| P903 | H | Cl | OCF$_3$ | Cl | CF$_3$ | H | Cl | O | C(CH$_3$)$_2$ | O | CH$_2$CF$_3$ |
| P904 | H | Cl | OCF$_3$ | Cl | CF$_3$ | H | CF$_3$ | O | C(CH$_3$)$_2$ | O | CH$_2$CF$_3$ |
| P905 | H | Cl | OCF$_3$ | Cl | CF$_3$ | H | CH$_3$ | O | C(CH$_3$)$_2$ | O | CH$_2$CF$_3$ |
| P906 | H | Cl | OCF$_3$ | Cl | CF$_3$ | H | Br | O | CH$_2$CH$_2$ | O | CH$_2$CF$_3$ |
| P907 | H | Cl | OCF$_3$ | Cl | CF$_3$ | H | Cl | O | CH$_2$CH$_2$ | O | CH$_2$CF$_3$ |
| P908 | H | Cl | OCF$_3$ | Cl | CF$_3$ | H | CF$_3$ | O | CH$_2$CH$_2$ | O | CH$_2$CF$_3$ |
| P909 | H | Cl | OCF$_3$ | Cl | CF$_3$ | H | CH$_3$ | O | CH$_2$CH$_2$ | O | CH$_2$CF$_3$ |
| P910 | H | Cl | CN | Cl | CF$_3$ | H | Br | O | CH$_2$ | O | CH$_2$CF$_3$ |
| P911 | H | Cl | CN | Cl | CF$_3$ | H | Cl | O | CH$_2$ | O | CH$_2$CF$_3$ |
| P912 | H | Cl | CN | Cl | CF$_3$ | H | CF$_3$ | O | CH$_2$ | O | CH$_2$CF$_3$ |
| P913 | H | Cl | CN | Cl | CF$_3$ | H | CH$_3$ | O | CH$_2$ | O | CH$_2$CF$_3$ |
| P914 | H | Cl | CN | Cl | CF$_3$ | H | Br | O | CH$_2$ | S | CH$_2$CF$_3$ |
| P915 | H | Cl | CN | Cl | CF$_3$ | H | Cl | O | CH$_2$ | S | CH$_2$CF$_3$ |
| P916 | H | Cl | CN | Cl | CF$_3$ | H | CF$_3$ | O | CH$_2$ | S | CH$_2$CF$_3$ |
| P917 | H | Cl | CN | Cl | CF$_3$ | H | CH$_3$ | O | CH$_2$ | S | CH$_2$CF$_3$ |
| P918 | H | Cl | CN | Cl | CF$_3$ | H | Br | S | CH$_2$ | O | CH$_2$CF$_3$ |
| P919 | H | Cl | CN | Cl | CF$_3$ | H | Cl | S | CH$_2$ | O | CH$_2$CF$_3$ |
| P920 | H | Cl | CN | Cl | CF$_3$ | H | CF$_3$ | S | CH$_2$ | O | CH$_2$CF$_3$ |
| P921 | H | Cl | CN | Cl | CF$_3$ | H | CH$_3$ | S | CH$_2$ | O | CH$_2$CF$_3$ |
| P922 | H | Cl | CN | Cl | CF$_3$ | H | Br | O | CH$_2$ | O | CH$_2$CHF$_2$ |
| P923 | H | Cl | CN | Cl | CF$_3$ | H | Cl | O | CH$_2$ | O | CH$_2$CHF$_2$ |
| P924 | H | Cl | CN | Cl | CF$_3$ | H | CF$_3$ | O | CH$_2$ | O | CH$_2$CHF$_2$ |
| P925 | H | Cl | CN | Cl | CF$_3$ | H | CH$_3$ | O | CH$_2$ | O | CH$_2$CHF$_2$ |
| P926 | H | Cl | CN | Cl | CF$_3$ | CF$_3$ | Br | O | CH$_2$ | O | CH$_2$CF$_3$ |
| P927 | H | Cl | CN | Cl | CF$_3$ | CF$_3$ | Cl | O | CH$_2$ | O | CH$_2$CF$_3$ |
| P928 | H | Cl | CN | Cl | CF$_3$ | CF$_3$ | CF$_3$ | O | CH$_2$ | O | CH$_2$CF$_3$ |
| P929 | H | Cl | CN | Cl | CF$_3$ | CF$_3$ | CH$_3$ | O | CH$_2$ | O | CH$_2$CF$_3$ |
| P930 | H | Cl | CN | Cl | CF$_2$CF$_3$ | H | Br | O | CH$_2$ | O | CH$_2$CF$_3$ |
| P931 | H | Cl | CN | Cl | CF$_2$CF$_3$ | H | Cl | O | CH$_2$ | O | CH$_2$CF$_3$ |
| P932 | H | Cl | CN | Cl | CF$_2$CF$_3$ | H | CF$_3$ | O | CH$_2$ | O | CH$_2$CF$_3$ |
| P933 | H | Cl | CN | Cl | CF$_2$CF$_3$ | H | CH$_3$ | O | CH$_2$ | O | CH$_2$CF$_3$ |
| P934 | H | Cl | CN | Cl | CF$_3$ | H | Br | O | CH$_2$ | O | CH(CH$_3$)CF$_3$ |
| P935 | H | Cl | CN | Cl | CF$_3$ | H | Cl | O | CH$_2$ | O | CH(CH$_3$)CF$_3$ |
| P936 | H | Cl | CN | Cl | CF$_3$ | H | CF$_3$ | O | CH$_2$ | O | CH(CH$_3$)CF$_3$ |
| P937 | H | Cl | CN | Cl | CF$_3$ | H | CH$_3$ | O | CH$_2$ | O | CH(CH$_3$)CF$_3$ |
| P938 | H | Cl | CN | Cl | CF$_3$ | CF$_3$ | Br | O | CH(CH$_3$) | O | CH$_2$CF$_3$ |
| P939 | H | Cl | CN | Cl | CF$_3$ | CF$_3$ | Cl | O | CH(CH$_3$) | O | CH$_2$CF$_3$ |
| P940 | H | Cl | CN | Cl | CF$_3$ | CF$_3$ | CF$_3$ | O | CH(CH$_3$) | O | CH$_2$CF$_3$ |
| P941 | H | Cl | CN | Cl | CF$_3$ | CF$_3$ | CH$_3$ | O | CH(CH$_3$) | O | CH$_2$CF$_3$ |
| P942 | H | Cl | CN | Cl | CF$_2$CF$_3$ | H | Br | O | CH(CH$_3$) | O | CH$_2$CF$_3$ |
| P943 | H | Cl | CN | Cl | CF$_2$CF$_3$ | H | Cl | O | CH(CH$_3$) | O | CH$_2$CF$_3$ |
| P944 | H | Cl | CN | Cl | CF$_2$CF$_3$ | H | CF$_3$ | O | CH(CH$_3$) | O | CH$_2$CF$_3$ |
| P945 | H | Cl | CN | Cl | CF$_2$CF$_3$ | H | CH$_3$ | O | CH(CH$_3$) | O | CH$_2$CF$_3$ |
| P946 | H | Cl | CN | Cl | CF$_3$ | H | Br | O | CH(CH$_3$) | O | CH$_2$CF$_3$ |
| P947 | H | Cl | CN | Cl | CF$_3$ | H | Cl | O | CH(CH$_3$) | O | CH$_2$CF$_3$ |
| P948 | H | Cl | CN | Cl | CF$_3$ | H | CF$_3$ | O | CH(CH$_3$) | O | CH$_2$CF$_3$ |
| P949 | H | Cl | CN | Cl | CF$_3$ | H | CH$_3$ | O | CH(CH$_3$) | O | CH$_2$CF$_3$ |
| P950 | H | Cl | CN | Cl | CF$_3$ | H | Br | O | CH(CH$_3$) | S | CH$_2$CF$_3$ |
| P951 | H | Cl | CN | Cl | CF$_3$ | H | Cl | O | CH(CH$_3$) | S | CH$_2$CF$_3$ |
| P952 | H | Cl | CN | Cl | CF$_3$ | H | CF$_3$ | O | CH(CH$_3$) | S | CH$_2$CF$_3$ |
| P953 | H | Cl | CN | Cl | CF$_3$ | H | CH$_3$ | O | CH(CH$_3$) | S | CH$_2$CF$_3$ |
| P954 | H | Cl | CN | Cl | CF$_3$ | H | Br | S | CH(CH$_3$) | O | CH$_2$CF$_3$ |
| P955 | H | Cl | CN | Cl | CF$_3$ | H | Cl | S | CH(CH$_3$) | O | CH$_2$CF$_3$ |
| P956 | H | Cl | CN | Cl | CF$_3$ | H | CF$_3$ | S | CH(CH$_3$) | O | CH$_2$CF$_3$ |
| P957 | H | Cl | CN | Cl | CF$_3$ | H | CH$_3$ | S | CH(CH$_3$) | O | CH$_2$CF$_3$ |
| P958 | H | Cl | CN | Cl | CF$_3$ | H | Br | O | CH(CH$_3$) | O | CH$_2$CHF$_2$ |
| P959 | H | Cl | CN | Cl | CF$_3$ | H | Cl | O | CH(CH$_3$) | O | CH$_2$CHF$_2$ |
| P960 | H | Cl | CN | Cl | CF$_3$ | H | CF$_3$ | O | CH(CH$_3$) | O | CH$_2$CHF$_2$ |
| P961 | H | Cl | CN | Cl | CF$_3$ | H | CH$_3$ | O | CH(CH$_3$) | O | CH$_2$CHF$_2$ |
| P962 | H | Cl | CN | Cl | CF$_3$ | H | Br | O | CH(CH$_3$) | O | CH(CH$_3$)CF$_3$ |
| P963 | H | Cl | CN | Cl | CF$_3$ | H | Cl | O | CH(CH$_3$) | O | CH(CH$_3$)CF$_3$ |
| P964 | H | Cl | CN | Cl | CF$_3$ | H | CF$_3$ | O | CH(CH$_3$) | O | CH(CH$_3$)CF$_3$ |
| P965 | H | Cl | CN | Cl | CF$_3$ | H | CH$_3$ | O | CH(CH$_3$) | O | CH(CH$_3$)CF$_3$ |
| P966 | H | Cl | CN | Cl | CF$_3$ | H | Br | O | CH(CH$_3$) | O | CH$_2$CH$_2$CF$_3$ |
| P967 | H | Cl | CN | Cl | CF$_3$ | H | Cl | O | CH(CH$_3$) | O | CH$_2$CH$_2$CF$_3$ |
| P968 | H | Cl | CN | Cl | CF$_3$ | H | CF$_3$ | O | CH(CH$_3$) | O | CH$_2$CH$_2$CF$_3$ |
| P969 | H | Cl | CN | Cl | CF$_3$ | H | CH$_3$ | O | CH(CH$_3$) | O | CH$_2$CH$_2$CF$_3$ |
| P970 | H | Cl | CN | Cl | CF$_3$ | H | Br | O | CH(CH$_2$CH$_3$) | O | CH$_2$CF$_3$ |
| P971 | H | Cl | CN | Cl | CF$_3$ | H | Cl | O | CH(CH$_2$CH$_3$) | O | CH$_2$CF$_3$ |
| P972 | H | Cl | CN | Cl | CF$_3$ | H | CF$_3$ | O | CH(CH$_2$CH$_3$) | O | CH$_2$CF$_3$ |
| P973 | H | Cl | CN | Cl | CF$_3$ | H | CH$_3$ | O | CH(CH$_2$CH$_3$) | O | CH$_2$CF$_3$ |
| P974 | H | Cl | CN | Cl | CF$_3$ | H | Br | O | C(CH$_3$)$_2$ | O | CH$_2$CF$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P975 | H | Cl | CN | Cl | $CF_3$ | H | Cl | O | $C(CH_3)_2$ | O | $CH_2CF_3$ |
| P976 | H | Cl | CN | Cl | $CF_3$ | H | $CF_3$ | O | $C(CH_3)_2$ | O | $CH_2CF_3$ |
| P977 | H | Cl | CN | Cl | $CF_3$ | H | $CH_3$ | O | $C(CH_3)_2$ | O | $CH_2CF_3$ |
| P978 | H | Cl | CN | Cl | $CF_3$ | H | Br | O | $CH_2CH_2$ | O | $CH_2CF_3$ |
| P979 | H | Cl | CN | Cl | $CF_3$ | H | Cl | O | $CH_2CH_2$ | O | $CH_2CF_3$ |
| P980 | H | Cl | CN | Cl | $CF_3$ | H | $CF_3$ | O | $CH_2CH_2$ | O | $CH_2CF_3$ |
| P981 | H | Cl | CN | Cl | $CF_3$ | H | $CH_3$ | O | $CH_2CH_2$ | O | $CH_2CF_3$ |
| P982 | H | $CH_3$ | H | Br | $CF_3$ | H | Br | O | $CH_2$ | O | $CH_2CF_3$ |
| P983 | H | $CH_3$ | H | Br | $CF_3$ | H | Cl | O | $CH_2$ | O | $CH_2CF_3$ |
| P984 | H | $CH_3$ | H | Br | $CF_3$ | H | $CF_3$ | O | $CH_2$ | O | $CH_2CF_3$ |
| P985 | H | $CH_3$ | H | Br | $CF_3$ | H | $CH_3$ | O | $CH_2$ | O | $CH_2CF_3$ |
| P986 | H | $CH_3$ | H | Br | $CF_3$ | H | Br | O | $CH_2$ | S | $CH_2CF_3$ |
| P987 | H | $CH_3$ | H | Br | $CF_3$ | H | Cl | O | $CH_2$ | S | $CH_2CF_3$ |
| P988 | H | $CH_3$ | H | Br | $CF_3$ | H | $CF_3$ | O | $CH_2$ | S | $CH_2CF_3$ |
| P989 | H | $CH_3$ | H | Br | $CF_3$ | H | $CH_3$ | O | $CH_2$ | S | $CH_2CF_3$ |
| P990 | H | $CH_3$ | H | Br | $CF_3$ | H | Br | S | $CH_2$ | O | $CH_2CF_3$ |
| P991 | H | $CH_3$ | H | Br | $CF_3$ | H | Cl | S | $CH_2$ | O | $CH_2CF_3$ |
| P992 | H | $CH_3$ | H | Br | $CF_3$ | H | $CF_3$ | S | $CH_2$ | O | $CH_2CF_3$ |
| P993 | H | $CH_3$ | H | Br | $CF_3$ | H | $CH_3$ | S | $CH_2$ | O | $CH_2CF_3$ |
| P994 | H | $CH_3$ | H | Br | $CF_3$ | H | Br | O | $CH_2$ | O | $CH_2CHF_2$ |
| P995 | H | $CH_3$ | H | Br | $CF_3$ | H | Cl | O | $CH_2$ | O | $CH_2CHF_2$ |
| P996 | H | $CH_3$ | H | Br | $CF_3$ | H | $CF_3$ | O | $CH_2$ | O | $CH_2CHF_2$ |
| P997 | H | $CH_3$ | H | Br | $CF_3$ | H | $CH_3$ | O | $CH_2$ | O | $CH_2CHF_2$ |
| P998 | H | $CH_3$ | H | Br | $CF_3$ | $CF_3$ | Br | O | $CH_2$ | O | $CH_2CF_3$ |
| P999 | H | $CH_3$ | H | Br | $CF_3$ | $CF_3$ | Cl | O | $CH_2$ | O | $CH_2CF_3$ |
| P1000 | H | $CH_3$ | H | Br | $CF_3$ | $CF_3$ | $CF_3$ | O | $CH_2$ | O | $CH_2CF_3$ |
| P1001 | H | $CH_3$ | H | Br | $CF_3$ | $CF_3$ | $CH_3$ | O | $CH_2$ | O | $CH_2CF_3$ |
| P1002 | H | $CH_3$ | H | Br | $CF_2CF_3$ | H | Br | O | $CH_2$ | O | $CH_2CF_3$ |
| P1003 | H | $CH_3$ | H | Br | $CF_2CF_3$ | H | Cl | O | $CH_2$ | O | $CH_2CF_3$ |
| P1004 | H | $CH_3$ | H | Br | $CF_2CF_3$ | H | $CF_3$ | O | $CH_2$ | O | $CH_2CF_3$ |
| P1005 | H | $CH_3$ | H | Br | $CF_2CF_3$ | H | $CH_3$ | O | $CH_2$ | O | $CH_2CF_3$ |
| P1006 | H | $CH_3$ | H | Br | $CF_3$ | H | Br | O | $CH_2$ | O | $CH(CH_3)CF_3$ |
| P1007 | H | $CH_3$ | H | Br | $CF_3$ | H | Cl | O | $CH_2$ | O | $CH(CH_3)CF_3$ |
| P1008 | H | $CH_3$ | H | Br | $CF_3$ | H | $CF_3$ | O | $CH_2$ | O | $CH(CH_3)CF_3$ |
| P1009 | H | $CH_3$ | H | Br | $CF_3$ | H | $CH_3$ | O | $CH_2$ | O | $CH(CH_3)CF_3$ |
| P1010 | H | $CH_3$ | H | Br | $CF_3$ | $CF_3$ | Br | O | $CH(CH_3)$ | O | $CH_2CF_3$ |
| P1011 | H | $CH_3$ | H | Br | $CF_3$ | $CF_3$ | Cl | O | $CH(CH_3)$ | O | $CH_2CF_3$ |
| P1012 | H | $CH_3$ | H | Br | $CF_3$ | $CF_3$ | $CF_3$ | O | $CH(CH_3)$ | O | $CH_2CF_3$ |
| P1013 | H | $CH_3$ | H | Br | $CF_3$ | $CF_3$ | $CH_3$ | O | $CH(CH_3)$ | O | $CH_2CF_3$ |
| P1014 | H | $CH_3$ | H | Br | $CF_2CF_3$ | H | Br | O | $CH(CH_3)$ | O | $CH_2CF_3$ |
| P1015 | H | $CH_3$ | H | Br | $CF_2CF_3$ | H | Cl | O | $CH(CH_3)$ | O | $CH_2CF_3$ |
| P1016 | H | $CH_3$ | H | Br | $CF_2CF_3$ | H | $CF_3$ | O | $CH(CH_3)$ | O | $CH_2CF_3$ |
| P1017 | H | $CH_3$ | H | Br | $CF_2CF_3$ | H | $CH_3$ | O | $CH(CH_3)$ | O | $CH_2CF_3$ |
| P1018 | H | $CH_3$ | H | Br | $CF_3$ | H | Br | O | $CH(CH_3)$ | O | $CH_2CF_3$ |
| P1019 | H | $CH_3$ | H | Br | $CF_3$ | H | Cl | O | $CH(CH_3)$ | O | $CH_2CF_3$ |
| P1020 | H | $CH_3$ | H | Br | $CF_3$ | H | $CF_3$ | O | $CH(CH_3)$ | O | $CH_2CF_3$ |
| P1021 | H | $CH_3$ | H | Br | $CF_3$ | H | $CH_3$ | O | $CH(CH_3)$ | O | $CH_2CF_3$ |
| P1022 | H | $CH_3$ | H | Br | $CF_3$ | H | Br | O | $CH(CH_3)$ | S | $CH_2CF_3$ |
| P1023 | H | $CH_3$ | H | Br | $CF_3$ | H | Cl | O | $CH(CH_3)$ | S | $CH_2CF_3$ |
| P1024 | H | $CH_3$ | H | Br | $CF_3$ | H | $CF_3$ | O | $CH(CH_3)$ | S | $CH_2CF_3$ |
| P1025 | H | $CH_3$ | H | Br | $CF_3$ | H | $CH_3$ | O | $CH(CH_3)$ | S | $CH_2CF_3$ |
| P1026 | H | $CH_3$ | H | Br | $CF_3$ | H | Br | S | $CH(CH_3)$ | O | $CH_2CF_3$ |
| P1027 | H | $CH_3$ | H | Br | $CF_3$ | H | Cl | S | $CH(CH_3)$ | O | $CH_2CF_3$ |
| P1028 | H | $CH_3$ | H | Br | $CF_3$ | H | $CF_3$ | S | $CH(CH_3)$ | O | $CH_2CF_3$ |
| P1029 | H | $CH_3$ | H | Br | $CF_3$ | H | $CH_3$ | S | $CH(CH_3)$ | O | $CH_2CF_3$ |
| P1030 | H | $CH_3$ | H | Br | $CF_3$ | H | Br | O | $CH(CH_3)$ | O | $CH_2CHF_2$ |
| P1031 | H | $CH_3$ | H | Br | $CF_3$ | H | Cl | O | $CH(CH_3)$ | O | $CH_2CHF_2$ |
| P1032 | H | $CH_3$ | H | Br | $CF_3$ | H | $CF_3$ | O | $CH(CH_3)$ | O | $CH_2CHF_2$ |
| P1033 | H | $CH_3$ | H | Br | $CF_3$ | H | $CH_3$ | O | $CH(CH_3)$ | O | $CH_2CHF_2$ |
| P1034 | H | $CH_3$ | H | Br | $CF_3$ | H | Br | O | $CH(CH_3)$ | O | $CH(CH_3)CF_3$ |
| P1035 | H | $CH_3$ | H | Br | $CF_3$ | H | Cl | O | $CH(CH_3)$ | O | $CH(CH_3)CF_3$ |
| P1036 | H | $CH_3$ | H | Br | $CF_3$ | H | $CF_3$ | O | $CH(CH_3)$ | O | $CH(CH_3)CF_3$ |
| P1037 | H | $CH_3$ | H | Br | $CF_3$ | H | $CH_3$ | O | $CH(CH_3)$ | O | $CH(CH_3)CF_3$ |
| P1038 | H | $CH_3$ | H | Br | $CF_3$ | H | Br | O | $CH(CH_3)$ | O | $CH_2CH_2CF_3$ |
| P1039 | H | $CH_3$ | H | Br | $CF_3$ | H | Cl | O | $CH(CH_3)$ | O | $CH_2CH_2CF_3$ |
| P1040 | H | $CH_3$ | H | Br | $CF_3$ | H | $CF_3$ | O | $CH(CH_3)$ | O | $CH_2CH_2CF_3$ |
| P1041 | H | $CH_3$ | H | Br | $CF_3$ | H | $CH_3$ | O | $CH(CH_3)$ | O | $CH_2CH_2CF_3$ |
| P1042 | H | $CH_3$ | H | Br | $CF_3$ | H | Br | O | $CH(CH_2CH_3)$ | O | $CH_2CF_3$ |
| P1043 | H | $CH_3$ | H | Br | $CF_3$ | H | Cl | O | $CH(CH_2CH_3)$ | O | $CH_2CF_3$ |
| P1044 | H | $CH_3$ | H | Br | $CF_3$ | H | $CF_3$ | O | $CH(CH_2CH_3)$ | O | $CH_2CF_3$ |
| P1045 | H | $CH_3$ | H | Br | $CF_3$ | H | $CH_3$ | O | $CH(CH_2CH_3)$ | O | $CH_2CF_3$ |
| P1046 | H | $CH_3$ | H | Br | $CF_3$ | H | Br | O | $C(CH_3)_2$ | O | $CH_2CF_3$ |
| P1047 | H | $CH_3$ | H | Br | $CF_3$ | H | Cl | O | $C(CH_3)_2$ | O | $CH_2CF_3$ |
| P1048 | H | $CH_3$ | H | Br | $CF_3$ | H | $CF_3$ | O | $C(CH_3)_2$ | O | $CH_2CF_3$ |
| P1049 | H | $CH_3$ | H | Br | $CF_3$ | H | $CH_3$ | O | $C(CH_3)_2$ | O | $CH_2CF_3$ |
| P1050 | H | $CH_3$ | H | Br | $CF_3$ | H | Br | O | $CH_2CH_2$ | O | $CH_2CF_3$ |
| P1051 | H | $CH_3$ | H | Br | $CF_3$ | H | Cl | O | $CH_2CH_2$ | O | $CH_2CF_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1052 | H | CH$_3$ | H | Br | CF$_3$ | H | CF$_3$ | O | CH$_2$CH$_2$ | O | CH$_2$CF$_3$ |
| P1053 | H | CH$_3$ | H | Br | CF$_3$ | H | CH$_3$ | O | CH$_2$CH$_2$ | O | CH$_2$CF$_3$ |
| P1054 | H | H | F | CH$_3$ | CF$_3$ | H | Br | O | CH$_2$ | O | CH$_2$CF$_3$ |
| P1055 | H | H | F | CH$_3$ | CF$_3$ | H | Cl | O | CH$_2$ | O | CH$_2$CF$_3$ |
| P1056 | H | H | F | CH$_3$ | CF$_3$ | H | CF$_3$ | O | CH$_2$ | O | CH$_2$CF$_3$ |
| P1057 | H | H | F | CH$_3$ | CF$_3$ | H | CH$_3$ | O | CH$_2$ | O | CH$_2$CF$_3$ |
| P1058 | H | H | F | CH$_3$ | CF$_3$ | H | Br | O | CH$_2$ | S | CH$_2$CF$_3$ |
| P1059 | H | H | F | CH$_3$ | CF$_3$ | H | Cl | O | CH$_2$ | S | CH$_2$CF$_3$ |
| P1060 | H | H | F | CH$_3$ | CF$_3$ | H | CF$_3$ | O | CH$_2$ | S | CH$_2$CF$_3$ |
| P1061 | H | H | F | CH$_3$ | CF$_3$ | H | CH$_3$ | O | CH$_2$ | S | CH$_2$CF$_3$ |
| P1062 | H | H | F | CH$_3$ | CF$_3$ | H | Br | S | CH$_2$ | O | CH$_2$CF$_3$ |
| P1063 | H | H | F | CH$_3$ | CF$_3$ | H | Cl | S | CH$_2$ | O | CH$_2$CF$_3$ |
| P1064 | H | H | F | CH$_3$ | CF$_3$ | H | CF$_3$ | S | CH$_2$ | O | CH$_2$CF$_3$ |
| P1065 | H | H | F | CH$_3$ | CF$_3$ | H | CH$_3$ | S | CH$_2$ | O | CH$_2$CF$_3$ |
| P1066 | H | H | F | CH$_3$ | CF$_3$ | H | Br | O | CH$_2$ | O | CH$_2$CHF$_2$ |
| P1067 | H | H | F | CH$_3$ | CF$_3$ | H | Cl | O | CH$_2$ | O | CH$_2$CHF$_2$ |
| P1068 | H | H | F | CH$_3$ | CF$_3$ | H | CF$_3$ | O | CH$_2$ | O | CH$_2$CHF$_2$ |
| P1069 | H | H | F | CH$_3$ | CF$_3$ | H | CH$_3$ | O | CH$_2$ | O | CH$_2$CHF$_2$ |
| P1070 | H | H | F | CH$_3$ | CF$_3$ | CF$_3$ | Br | O | CH$_2$ | O | CH$_2$CF$_3$ |
| P1071 | H | H | F | CH$_3$ | CF$_3$ | CF$_3$ | Cl | O | CH$_2$ | O | CH$_2$CF$_3$ |
| P1072 | H | H | F | CH$_3$ | CF$_3$ | CF$_3$ | CF$_3$ | O | CH$_2$ | O | CH$_2$CF$_3$ |
| P1073 | H | H | F | CH$_3$ | CF$_3$ | CF$_3$ | CH$_3$ | O | CH$_2$ | O | CH$_2$CF$_3$ |
| P1074 | H | H | F | CH$_3$ | CF$_2$CF$_3$ | H | Br | O | CH$_2$ | O | CH$_2$CF$_3$ |
| P1075 | H | H | F | CH$_3$ | CF$_2$CF$_3$ | H | Cl | O | CH$_2$ | O | CH$_2$CF$_3$ |
| P1076 | H | H | F | CH$_3$ | CF$_2$CF$_3$ | H | CF$_3$ | O | CH$_2$ | O | CH$_2$CF$_3$ |
| P1077 | H | H | F | CH$_3$ | CF$_2$CF$_3$ | H | CH$_3$ | O | CH$_2$ | O | CH$_2$CF$_3$ |
| P1078 | H | H | F | CH$_3$ | CF$_3$ | H | Br | O | CH$_2$ | O | CH(CH$_3$)CF$_3$ |
| P1079 | H | H | F | CH$_3$ | CF$_3$ | H | Cl | O | CH$_2$ | O | CH(CH$_3$)CF$_3$ |
| P1080 | H | H | F | CH$_3$ | CF$_3$ | H | CF$_3$ | O | CH$_2$ | O | CH(CH$_3$)CF$_3$ |
| P1081 | H | H | F | CH$_3$ | CF$_3$ | H | CH$_3$ | O | CH$_2$ | O | CH(CH$_3$)CF$_3$ |
| P1082 | H | H | F | CH$_3$ | CF$_3$ | CF$_3$ | Br | O | CH(CH$_3$) | O | CH$_2$CF$_3$ |
| P1083 | H | H | F | CH$_3$ | CF$_3$ | CF$_3$ | Cl | O | CH(CH$_3$) | O | CH$_2$CF$_3$ |
| P1084 | H | H | F | CH$_3$ | CF$_3$ | CF$_3$ | CF$_3$ | O | CH(CH$_3$) | O | CH$_2$CF$_3$ |
| P1085 | H | H | F | CH$_3$ | CF$_3$ | CF$_3$ | CH$_3$ | O | CH(CH$_3$) | O | CH$_2$CF$_3$ |
| P1086 | H | H | F | CH$_3$ | CF$_2$CF$_3$ | H | Br | O | CH(CH$_3$) | O | CH$_2$CF$_3$ |
| P1087 | H | H | F | CH$_3$ | CF$_2$CF$_3$ | H | Cl | O | CH(CH$_3$) | O | CH$_2$CF$_3$ |
| P1088 | H | H | F | CH$_3$ | CF$_2$CF$_3$ | H | CF$_3$ | O | CH(CH$_3$) | O | CH$_2$CF$_3$ |
| P1089 | H | H | F | CH$_3$ | CF$_2$CF$_3$ | H | CH$_3$ | O | CH(CH$_3$) | O | CH$_2$CF$_3$ |
| P1090 | H | H | F | CH$_3$ | CF$_3$ | H | Br | O | CH(CH$_3$) | O | CH$_2$CF$_3$ |
| P1091 | H | H | F | CH$_3$ | CF$_3$ | H | Cl | O | CH(CH$_3$) | O | CH$_2$CF$_3$ |
| P1092 | H | H | F | CH$_3$ | CF$_3$ | H | CF$_3$ | O | CH(CH$_3$) | O | CH$_2$CF$_3$ |
| P1093 | H | H | F | CH$_3$ | CF$_3$ | H | CH$_3$ | O | CH(CH$_3$) | O | CH$_2$CF$_3$ |
| P1094 | H | H | F | CH$_3$ | CF$_3$ | H | Br | O | CH(CH$_3$) | S | CH$_2$CF$_3$ |
| P1095 | H | H | F | CH$_3$ | CF$_3$ | H | Cl | O | CH(CH$_3$) | S | CH$_2$CF$_3$ |
| P1096 | H | H | F | CH$_3$ | CF$_3$ | H | CF$_3$ | O | CH(CH$_3$) | S | CH$_2$CF$_3$ |
| P1097 | H | H | F | CH$_3$ | CF$_3$ | H | CH$_3$ | O | CH(CH$_3$) | S | CH$_2$CF$_3$ |
| P1098 | H | H | F | CH$_3$ | CF$_3$ | H | Br | S | CH(CH$_3$) | O | CH$_2$CF$_3$ |
| P1099 | H | H | F | CH$_3$ | CF$_3$ | H | Cl | S | CH(CH$_3$) | O | CH$_2$CF$_3$ |
| P1100 | H | H | F | CH$_3$ | CF$_3$ | H | CF$_3$ | S | CH(CH$_3$) | O | CH$_2$CF$_3$ |
| P1101 | H | H | F | CH$_3$ | CF$_3$ | H | CH$_3$ | S | CH(CH$_3$) | O | CH$_2$CF$_3$ |
| P1102 | H | H | F | CH$_3$ | CF$_3$ | H | Br | O | CH(CH$_3$) | O | CH$_2$CHF$_2$ |
| P1103 | H | H | F | CH$_3$ | CF$_3$ | H | Cl | O | CH(CH$_3$) | O | CH$_2$CHF$_2$ |
| P1104 | H | H | F | CH$_3$ | CF$_3$ | H | CF$_3$ | O | CH(CH$_3$) | O | CH$_2$CHF$_2$ |
| P1105 | H | H | F | CH$_3$ | CF$_3$ | H | CH$_3$ | O | CH(CH$_3$) | O | CH$_2$CHF$_2$ |
| P1106 | H | H | F | CH$_3$ | CF$_3$ | H | Br | O | CH(CH$_3$) | O | CH(CH$_3$)CF$_3$ |
| P1107 | H | H | F | CH$_3$ | CF$_3$ | H | Cl | O | CH(CH$_3$) | O | CH(CH$_3$)CF$_3$ |
| P1108 | H | H | F | CH$_3$ | CF$_3$ | H | CF$_3$ | O | CH(CH$_3$) | O | CH(CH$_3$)CF$_3$ |
| P1109 | H | H | F | CH$_3$ | CF$_3$ | H | CH$_3$ | O | CH(CH$_3$) | O | CH(CH$_3$)CF$_3$ |
| P1110 | H | H | F | CH$_3$ | CF$_3$ | H | Br | O | CH(CH$_3$) | O | CH$_2$CH$_2$CF$_3$ |
| P1111 | H | H | F | CH$_3$ | CF$_3$ | H | Cl | O | CH(CH$_3$) | O | CH$_2$CH$_2$CF$_3$ |
| P1112 | H | H | F | CH$_3$ | CF$_3$ | H | CF$_3$ | O | CH(CH$_3$) | O | CH$_2$CH$_2$CF$_3$ |
| P1113 | H | H | F | CH$_3$ | CF$_3$ | H | CH$_3$ | O | CH(CH$_3$) | O | CH$_2$CH$_2$CF$_3$ |
| P1114 | H | H | F | CH$_3$ | CF$_3$ | H | Br | O | CH(CH$_2$CH$_3$) | O | CH$_2$CF$_3$ |
| P1115 | H | H | F | CH$_3$ | CF$_3$ | H | Cl | O | CH(CH$_2$CH$_3$) | O | CH$_2$CF$_3$ |
| P1116 | H | H | F | CH$_3$ | CF$_3$ | H | CF$_3$ | O | CH(CH$_2$CH$_3$) | O | CH$_2$CF$_3$ |
| P1117 | H | H | F | CH$_3$ | CF$_3$ | H | CH$_3$ | O | CH(CH$_2$CH$_3$) | O | CH$_2$CF$_3$ |
| P1118 | H | H | F | CH$_3$ | CF$_3$ | H | Br | O | C(CH$_3$)$_2$ | O | CH$_2$CF$_3$ |
| P1119 | H | H | F | CH$_3$ | CF$_3$ | H | Cl | O | C(CH$_3$)$_2$ | O | CH$_2$CF$_3$ |
| P1120 | H | H | F | CH$_3$ | CF$_3$ | H | CF$_3$ | O | C(CH$_3$)$_2$ | O | CH$_2$CF$_3$ |
| P1121 | H | H | F | CH$_3$ | CF$_3$ | H | CH$_3$ | O | C(CH$_3$)$_2$ | O | CH$_2$CF$_3$ |
| P1122 | H | H | F | CH$_3$ | CF$_3$ | H | Br | O | CH$_2$CH$_2$ | O | CH$_2$CF$_3$ |
| P1123 | H | H | F | CH$_3$ | CF$_3$ | H | Cl | O | CH$_2$CH$_2$ | O | CH$_2$CF$_3$ |
| P1124 | H | H | F | CH$_3$ | CF$_3$ | H | CF$_3$ | O | CH$_2$CH$_2$ | O | CH$_2$CF$_3$ |
| P1125 | H | H | F | CH$_3$ | CF$_3$ | H | CH$_3$ | O | CH$_2$CH$_2$ | O | CH$_2$CF$_3$ |
| P1126 | H | H | F | Cl | CF$_3$ | H | Cl | O | CH$_2$ | O | CH$_2$CF$_3$ |
| P1127 | H | H | F | Cl | CF$_3$ | H | CF$_3$ | O | CH$_2$ | O | CH$_2$CF$_3$ |
| P1128 | H | H | F | Cl | CF$_3$ | H | CH$_3$ | O | CH$_2$ | O | CH$_2$CF$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1129 | H | H | F | Cl | CF$_3$ | H | Br | O | CH$_2$ | S | CH$_2$CF$_3$ |
| P1130 | H | H | F | Cl | CF$_3$ | H | Cl | O | CH$_2$ | S | CH$_2$CF$_3$ |
| P1131 | H | H | F | Cl | CF$_3$ | H | CF$_3$ | O | CH$_2$ | S | CH$_2$CF$_3$ |
| P1132 | H | H | F | Cl | CF$_3$ | H | CH$_3$ | O | CH$_2$ | S | CH$_2$CF$_3$ |
| P1133 | H | H | F | Cl | CF$_3$ | H | Br | S | CH$_2$ | O | CH$_2$CF$_3$ |
| P1134 | H | H | F | Cl | CF$_3$ | H | Cl | S | CH$_2$ | O | CH$_2$CF$_3$ |
| P1135 | H | H | F | Cl | CF$_3$ | H | CF$_3$ | S | CH$_2$ | O | CH$_2$CF$_3$ |
| P1136 | H | H | F | Cl | CF$_3$ | H | CH$_3$ | S | CH$_2$ | O | CH$_2$CF$_3$ |
| P1137 | H | H | F | Cl | CF$_3$ | H | Br | O | CH$_2$ | O | CH$_2$CHF$_2$ |
| P1138 | H | H | F | Cl | CF$_3$ | H | Cl | O | CH$_2$ | O | CH$_2$CHF$_2$ |
| P1139 | H | H | F | Cl | CF$_3$ | H | CF$_3$ | O | CH$_2$ | O | CH$_2$CHF$_2$ |
| P1140 | H | H | F | Cl | CF$_3$ | H | CH$_3$ | O | CH$_2$ | O | CH$_2$CHF$_2$ |
| P1141 | H | H | F | Cl | CF$_3$ | CF$_3$ | Br | O | CH$_2$ | O | CH$_2$CF$_3$ |
| P1142 | H | H | F | Cl | CF$_3$ | CF$_3$ | Cl | O | CH$_2$ | O | CH$_2$CF$_3$ |
| P1143 | H | H | F | Cl | CF$_3$ | CF$_3$ | CF$_3$ | O | CH$_2$ | O | CH$_2$CF$_3$ |
| P1144 | H | H | F | Cl | CF$_3$ | CF$_3$ | CH$_3$ | O | CH$_2$ | O | CH$_2$CF$_3$ |
| P1145 | H | H | F | Cl | CF$_2$CF$_3$ | H | Br | O | CH$_2$ | O | CH$_2$CF$_3$ |
| P1146 | H | H | F | Cl | CF$_2$CF$_3$ | H | Cl | O | CH$_2$ | O | CH$_2$CF$_3$ |
| P1147 | H | H | F | Cl | CF$_2$CF$_3$ | H | CF$_3$ | O | CH$_2$ | O | CH$_2$CF$_3$ |
| P1148 | H | H | F | Cl | CF$_2$CF$_3$ | H | CH$_3$ | O | CH$_2$ | O | CH$_2$CF$_3$ |
| P1149 | H | H | F | Cl | CF$_3$ | H | Br | O | CH$_2$ | O | CH(CH$_3$)CF$_3$ |
| P1150 | H | H | F | Cl | CF$_3$ | H | Cl | O | CH$_2$ | O | CH(CH$_3$)CF$_3$ |
| P1151 | H | H | F | Cl | CF$_3$ | H | CF$_3$ | O | CH$_2$ | O | CH(CH$_3$)CF$_3$ |
| P1152 | H | H | F | Cl | CF$_3$ | H | CH$_3$ | O | CH$_2$ | O | CH(CH$_3$)CF$_3$ |
| P1153 | H | H | F | Cl | CF$_3$ | CF$_3$ | Br | O | CH(CH$_3$) | O | CH$_2$CF$_3$ |
| P1154 | H | H | F | Cl | CF$_3$ | CF$_3$ | Cl | O | CH(CH$_3$) | O | CH$_2$CF$_3$ |
| P1155 | H | H | F | Cl | CF$_3$ | CF$_3$ | CF$_3$ | O | CH(CH$_3$) | O | CH$_2$CF$_3$ |
| P1156 | H | H | F | Cl | CF$_3$ | CF$_3$ | CH$_3$ | O | CH(CH$_3$) | O | CH$_2$CF$_3$ |
| P1157 | H | H | F | Cl | CF$_2$CF$_3$ | H | Br | O | CH(CH$_3$) | O | CH$_2$CF$_3$ |
| P1158 | H | H | F | Cl | CF$_2$CF$_3$ | H | Cl | O | CH(CH$_3$) | O | CH$_2$CF$_3$ |
| P1159 | H | H | F | Cl | CF$_2$CF$_3$ | H | CF$_3$ | O | CH(CH$_3$) | O | CH$_2$CF$_3$ |
| P1160 | H | H | F | Cl | CF$_2$CF$_3$ | H | CH$_3$ | O | CH(CH$_3$) | O | CH$_2$CF$_3$ |
| P1161 | H | H | F | Cl | CF$_3$ | H | Br | O | CH(CH$_3$) | O | CH$_2$CF$_3$ |
| P1162 | H | H | F | Cl | CF$_3$ | H | Cl | O | CH(CH$_3$) | O | CH$_2$CF$_3$ |
| P1163 | H | H | F | Cl | CF$_3$ | H | CF$_3$ | O | CH(CH$_3$) | O | CH$_2$CF$_3$ |
| P1164 | H | H | F | Cl | CF$_3$ | H | CH$_3$ | O | CH(CH$_3$) | O | CH$_2$CF$_3$ |
| P1165 | H | H | F | Cl | CF$_3$ | H | Br | O | CH(CH$_3$) | S | CH$_2$CF$_3$ |
| P1166 | H | H | F | Cl | CF$_3$ | H | Cl | O | CH(CH$_3$) | S | CH$_2$CF$_3$ |
| P1167 | H | H | F | Cl | CF$_3$ | H | CF$_3$ | O | CH(CH$_3$) | S | CH$_2$CF$_3$ |
| P1168 | H | H | F | Cl | CF$_3$ | H | CH$_3$ | O | CH(CH$_3$) | S | CH$_2$CF$_3$ |
| P1169 | H | H | F | Cl | CF$_3$ | H | Br | S | CH(CH$_3$) | O | CH$_2$CF$_3$ |
| P1170 | H | H | F | Cl | CF$_3$ | H | Cl | S | CH(CH$_3$) | O | CH$_2$CF$_3$ |
| P1171 | H | H | F | Cl | CF$_3$ | H | CF$_3$ | S | CH(CH$_3$) | O | CH$_2$CF$_3$ |
| P1172 | H | H | F | Cl | CF$_3$ | H | CH$_3$ | S | CH(CH$_3$) | O | CH$_2$CF$_3$ |
| P1173 | H | H | F | Cl | CF$_3$ | H | Br | O | CH(CH$_3$) | O | CH$_2$CHF$_2$ |
| P1174 | H | H | F | Cl | CF$_3$ | H | Cl | O | CH(CH$_3$) | O | CH$_2$CHF$_2$ |
| P1175 | H | H | F | Cl | CF$_3$ | H | CF$_3$ | O | CH(CH$_3$) | O | CH$_2$CHF$_2$ |
| P1176 | H | H | F | Cl | CF$_3$ | H | CH$_3$ | O | CH(CH$_3$) | O | CH$_2$CHF$_2$ |
| P1177 | H | H | F | Cl | CF$_3$ | H | Br | O | CH(CH$_3$) | O | CH(CH$_3$)CF$_3$ |
| P1178 | H | H | F | Cl | CF$_3$ | H | Cl | O | CH(CH$_3$) | O | CH(CH$_3$)CF$_3$ |
| P1179 | H | H | F | Cl | CF$_3$ | H | CF$_3$ | O | CH(CH$_3$) | O | CH(CH$_3$)CF$_3$ |
| P1180 | H | H | F | Cl | CF$_3$ | H | CH$_3$ | O | CH(CH$_3$) | O | CH(CH$_3$)CF$_3$ |
| P1181 | H | H | F | Cl | CF$_3$ | H | Br | O | CH(CH$_3$) | O | CH$_2$CH$_2$CF$_3$ |
| P1182 | H | H | F | Cl | CF$_3$ | H | Cl | O | CH(CH$_3$) | O | CH$_2$CH$_2$CF$_3$ |
| P1183 | H | H | F | Cl | CF$_3$ | H | CF$_3$ | O | CH(CH$_3$) | O | CH$_2$CH$_2$CF$_3$ |
| P1184 | H | H | F | Cl | CF$_3$ | H | CH$_3$ | O | CH(CH$_3$) | O | CH$_2$CH$_2$CF$_3$ |
| P1185 | H | H | F | Cl | CF$_3$ | H | Br | O | CH(CH$_2$CH$_3$) | O | CH$_2$CF$_3$ |
| P1186 | H | H | F | Cl | CF$_3$ | H | Cl | O | CH(CH$_2$CH$_3$) | O | CH$_2$CF$_3$ |
| P1187 | H | H | F | Cl | CF$_3$ | H | CF$_3$ | O | CH(CH$_2$CH$_3$) | O | CH$_2$CF$_3$ |
| P1188 | H | H | F | Cl | CF$_3$ | H | CH$_3$ | O | CH(CH$_2$CH$_3$) | O | CH$_2$CF$_3$ |
| P1189 | H | H | F | Cl | CF$_3$ | H | Br | O | C(CH$_3$)$_2$ | O | CH$_2$CF$_3$ |
| P1190 | H | H | F | Cl | CF$_3$ | H | Cl | O | C(CH$_3$)$_2$ | O | CH$_2$CF$_3$ |
| P1191 | H | H | F | Cl | CF$_3$ | H | CF$_3$ | O | C(CH$_3$)$_2$ | O | CH$_2$CF$_3$ |
| P1192 | H | H | F | Cl | CF$_3$ | H | CH$_3$ | O | C(CH$_3$)$_2$ | O | CH$_2$CF$_3$ |
| P1193 | H | H | F | Cl | CF$_3$ | H | Br | O | CH$_2$CH$_2$ | O | CH$_2$CF$_3$ |
| P1194 | H | H | F | Cl | CF$_3$ | H | Cl | O | CH$_2$CH$_2$ | O | CH$_2$CF$_3$ |
| P1195 | H | H | F | Cl | CF$_3$ | H | CF$_3$ | O | CH$_2$CH$_2$ | O | CH$_2$CF$_3$ |
| P1196 | H | H | F | Cl | CF$_3$ | H | CH$_3$ | O | CH$_2$CH$_2$ | O | CH$_2$CF$_3$ |
| P1197 | H | F | F | F | CF$_3$ | H | Br | O | CH$_2$ | O | CH$_2$CF$_3$ |
| P1198 | H | F | F | F | CF$_3$ | H | Cl | O | CH$_2$ | O | CH$_2$CF$_3$ |
| P1199 | H | F | F | F | CF$_3$ | H | CF$_3$ | O | CH$_2$ | O | CH$_2$CF$_3$ |
| P1200 | H | F | F | F | CF$_3$ | H | CH$_3$ | O | CH$_2$ | O | CH$_2$CF$_3$ |
| P1201 | H | F | F | F | CF$_3$ | H | Br | O | CH$_2$ | S | CH$_2$CF$_3$ |
| P1202 | H | F | F | F | CF$_3$ | H | Cl | O | CH$_2$ | S | CH$_2$CF$_3$ |
| P1203 | H | F | F | F | CF$_3$ | H | CF$_3$ | O | CH$_2$ | S | CH$_2$CF$_3$ |
| P1204 | H | F | F | F | CF$_3$ | H | CH$_3$ | O | CH$_2$ | S | CH$_2$CF$_3$ |
| P1205 | H | F | F | F | CF$_3$ | H | Br | S | CH$_2$ | O | CH$_2$CF$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1206 | H | F | F | F | CF$_3$ | H | Cl | S | CH$_2$ | O | CH$_2$CF$_3$ |
| P1207 | H | F | F | F | CF$_3$ | H | CF$_3$ | S | CH$_2$ | O | CH$_2$CF$_3$ |
| P1208 | H | F | F | F | CF$_3$ | H | CH$_3$ | S | CH$_2$ | O | CH$_2$CF$_3$ |
| P1209 | H | F | F | F | CF$_3$ | H | Br | O | CH$_2$ | O | CH$_2$CHF$_2$ |
| P1210 | H | F | F | F | CF$_3$ | H | Cl | O | CH$_2$ | O | CH$_2$CHF$_2$ |
| P1211 | H | F | F | F | CF$_3$ | H | CF$_3$ | O | CH$_2$ | O | CH$_2$CHF$_2$ |
| P1212 | H | F | F | F | CF$_3$ | H | CH$_3$ | O | CH$_2$ | O | CH$_2$CHF$_2$ |
| P1213 | H | F | F | F | CF$_3$ | CF$_3$ | Br | O | CH$_2$ | O | CH$_2$CF$_3$ |
| P1214 | H | F | F | F | CF$_3$ | CF$_3$ | Cl | O | CH$_2$ | O | CH$_2$CF$_3$ |
| P1215 | H | F | F | F | CF$_3$ | CF$_3$ | CF$_3$ | O | CH$_2$ | O | CH$_2$CF$_3$ |
| P1216 | H | F | F | F | CF$_3$ | CF$_3$ | CH$_3$ | O | CH$_2$ | O | CH$_2$CF$_3$ |
| P1217 | H | F | F | F | CF$_2$CF$_3$ | H | Br | O | CH$_2$ | O | CH$_2$CF$_3$ |
| P1218 | H | F | F | F | CF$_2$CF$_3$ | H | Cl | O | CH$_2$ | O | CH$_2$CF$_3$ |
| P1219 | H | F | F | F | CF$_2$CF$_3$ | H | CF$_3$ | O | CH$_2$ | O | CH$_2$CF$_3$ |
| P1220 | H | F | F | F | CF$_2$CF$_3$ | H | CH$_3$ | O | CH$_2$ | O | CH$_2$CF$_3$ |
| P1221 | H | F | F | F | CF$_3$ | H | Br | O | CH$_2$ | O | CH(CH$_3$)CF$_3$ |
| P1222 | H | F | F | F | CF$_3$ | H | Cl | O | CH$_2$ | O | CH(CH$_3$)CF$_3$ |
| P1223 | H | F | F | F | CF$_3$ | H | CF$_3$ | O | CH$_2$ | O | CH(CH$_3$)CF$_3$ |
| P1224 | H | F | F | F | CF$_3$ | H | CH$_3$ | O | CH$_2$ | O | CH(CH$_3$)CF$_3$ |
| P1225 | H | F | F | F | CF$_3$ | CF$_3$ | Br | O | CH(CH$_3$) | O | CH$_2$CF$_3$ |
| P1226 | H | F | F | F | CF$_3$ | CF$_3$ | Cl | O | CH(CH$_3$) | O | CH$_2$CF$_3$ |
| P1227 | H | F | F | F | CF$_3$ | CF$_3$ | CF$_3$ | O | CH(CH$_3$) | O | CH$_2$CF$_3$ |
| P1228 | H | F | F | F | CF$_3$ | CF$_3$ | CH$_3$ | O | CH(CH$_3$) | O | CH$_2$CF$_3$ |
| P1229 | H | F | F | F | CF$_2$CF$_3$ | H | Br | O | CH(CH$_3$) | O | CH$_2$CF$_3$ |
| P1230 | H | F | F | F | CF$_2$CF$_3$ | H | Cl | O | CH(CH$_3$) | O | CH$_2$CF$_3$ |
| P1231 | H | F | F | F | CF$_2$CF$_3$ | H | CF$_3$ | O | CH(CH$_3$) | O | CH$_2$CF$_3$ |
| P1232 | H | F | F | F | CF$_2$CF$_3$ | H | CH$_3$ | O | CH(CH$_3$) | O | CH$_2$CF$_3$ |
| P1233 | H | F | F | F | CF$_3$ | H | Br | O | CH(CH$_3$) | O | CH$_2$CF$_3$ |
| P1234 | H | F | F | F | CF$_3$ | H | Cl | O | CH(CH$_3$) | O | CH$_2$CF$_3$ |
| P1235 | H | F | F | F | CF$_3$ | H | CF$_3$ | O | CH(CH$_3$) | O | CH$_2$CF$_3$ |
| P1236 | H | F | F | F | CF$_3$ | H | CH$_3$ | O | CH(CH$_3$) | O | CH$_2$CF$_3$ |
| P1237 | H | F | F | F | CF$_3$ | H | Br | O | CH(CH$_3$) | S | CH$_2$CF$_3$ |
| P1238 | H | F | F | F | CF$_3$ | H | Cl | O | CH(CH$_3$) | S | CH$_2$CF$_3$ |
| P1239 | H | F | F | F | CF$_3$ | H | CF$_3$ | O | CH(CH$_3$) | S | CH$_2$CF$_3$ |
| P1240 | H | F | F | F | CF$_3$ | H | CH$_3$ | O | CH(CH$_3$) | S | CH$_2$CF$_3$ |
| P1241 | H | F | F | F | CF$_3$ | H | Br | S | CH(CH$_3$) | O | CH$_2$CF$_3$ |
| P1242 | H | F | F | F | CF$_3$ | H | Cl | S | CH(CH$_3$) | O | CH$_2$CF$_3$ |
| P1243 | H | F | F | F | CF$_3$ | H | CF$_3$ | S | CH(CH$_3$) | O | CH$_2$CF$_3$ |
| P1244 | H | F | F | F | CF$_3$ | H | CH$_3$ | S | CH(CH$_3$) | O | CH$_2$CF$_3$ |
| P1245 | H | F | F | F | CF$_3$ | H | Br | O | CH(CH$_3$) | O | CH$_2$CHF$_2$ |
| P1246 | H | F | F | F | CF$_3$ | H | Cl | O | CH(CH$_3$) | O | CH$_2$CHF$_2$ |
| P1247 | H | F | F | F | CF$_3$ | H | CF$_3$ | O | CH(CH$_3$) | O | CH$_2$CHF$_2$ |
| P1248 | H | F | F | F | CF$_3$ | H | CH$_3$ | O | CH(CH$_3$) | O | CH$_2$CHF$_2$ |
| P1249 | H | F | F | F | CF$_3$ | H | Br | O | CH(CH$_3$) | O | CH(CH$_3$)CF$_3$ |
| P1250 | H | F | F | F | CF$_3$ | H | Cl | O | CH(CH$_3$) | O | CH(CH$_3$)CF$_3$ |
| P1251 | H | F | F | F | CF$_3$ | H | CF$_3$ | O | CH(CH$_3$) | O | CH(CH$_3$)CF$_3$ |
| P1252 | H | F | F | F | CF$_3$ | H | CH$_3$ | O | CH(CH$_3$) | O | CH(CH$_3$)CF$_3$ |
| P1253 | H | F | F | F | CF$_3$ | H | Br | O | CH(CH$_3$) | O | CH$_2$CH$_2$CF$_3$ |
| P1254 | H | F | F | F | CF$_3$ | H | Cl | O | CH(CH$_3$) | O | CH$_2$CH$_2$CF$_3$ |
| P1255 | H | F | F | F | CF$_3$ | H | CF$_3$ | O | CH(CH$_3$) | O | CH$_2$CH$_2$CF$_3$ |
| P1256 | H | F | F | F | CF$_3$ | H | CH$_3$ | O | CH(CH$_3$) | O | CH$_2$CH$_2$CF$_3$ |
| P1257 | H | F | F | F | CF$_3$ | H | Br | O | CH(CH$_2$CH$_3$) | O | CH$_2$CF$_3$ |
| P1258 | H | F | F | F | CF$_3$ | H | Cl | O | CH(CH$_2$CH$_3$) | O | CH$_2$CF$_3$ |
| P1259 | H | F | F | F | CF$_3$ | H | CF$_3$ | O | CH(CH$_2$CH$_3$) | O | CH$_2$CF$_3$ |
| P1260 | H | F | F | F | CF$_3$ | H | CH$_3$ | O | CH(CH$_2$CH$_3$) | O | CH$_2$CF$_3$ |
| P1261 | H | F | F | F | CF$_3$ | H | Br | O | C(CH$_3$)$_2$ | O | CH$_2$CF$_3$ |
| P1262 | H | F | F | F | CF$_3$ | H | Cl | O | C(CH$_3$)$_2$ | O | CH$_2$CF$_3$ |
| P1263 | H | F | F | F | CF$_3$ | H | CF$_3$ | O | C(CH$_3$)$_2$ | O | CH$_2$CF$_3$ |
| P1264 | H | F | F | F | CF$_3$ | H | CH$_3$ | O | C(CH$_3$)$_2$ | O | CH$_2$CF$_3$ |
| P1265 | H | F | F | F | CF$_3$ | H | Br | O | CH$_2$CH$_2$ | O | CH$_2$CF$_3$ |
| P1266 | H | F | F | F | CF$_3$ | H | Cl | O | CH$_2$CH$_2$ | O | CH$_2$CF$_3$ |
| P1267 | H | F | F | F | CF$_3$ | H | CF$_3$ | O | CH$_2$CH$_2$ | O | CH$_2$CF$_3$ |
| P1268 | H | F | F | F | CF$_3$ | H | CH$_3$ | O | CH$_2$CH$_2$ | O | CH$_2$CF$_3$ |
| P1269 | H | CF$_3$ | H | CF$_3$ | CF$_3$ | H | Br | O | CH$_2$ | O | CH$_2$CF$_3$ |
| P1270 | H | CF$_3$ | H | CF$_3$ | CF$_3$ | H | Cl | O | CH$_2$ | O | CH$_2$CF$_3$ |
| P1271 | H | CF$_3$ | H | CF$_3$ | CF$_3$ | H | CF$_3$ | O | CH$_2$ | O | CH$_2$CF$_3$ |
| P1272 | H | CF$_3$ | H | CF$_3$ | CF$_3$ | H | CH$_3$ | O | CH$_2$ | O | CH$_2$CF$_3$ |
| P1273 | H | CF$_3$ | H | CF$_3$ | CF$_3$ | H | Br | O | CH$_2$ | S | CH$_2$CF$_3$ |
| P1274 | H | CF$_3$ | H | CF$_3$ | CF$_3$ | H | Cl | O | CH$_2$ | S | CH$_2$CF$_3$ |
| P1275 | H | CF$_3$ | H | CF$_3$ | CF$_3$ | H | CF$_3$ | O | CH$_2$ | S | CH$_2$CF$_3$ |
| P1276 | H | CF$_3$ | H | CF$_3$ | CF$_3$ | H | CH$_3$ | O | CH$_2$ | S | CH$_2$CF$_3$ |
| P1277 | H | CF$_3$ | H | CF$_3$ | CF$_3$ | H | Br | S | CH$_2$ | O | CH$_2$CF$_3$ |
| P1278 | H | CF$_3$ | H | CF$_3$ | CF$_3$ | H | Cl | S | CH$_2$ | O | CH$_2$CF$_3$ |
| P1279 | H | CF$_3$ | H | CF$_3$ | CF$_3$ | H | CF$_3$ | S | CH$_2$ | O | CH$_2$CF$_3$ |
| P1280 | H | CF$_3$ | H | CF$_3$ | CF$_3$ | H | CH$_3$ | S | CH$_2$ | O | CH$_2$CF$_3$ |
| P1281 | H | CF$_3$ | H | CF$_3$ | CF$_3$ | H | Br | O | CH$_2$ | O | CH$_2$CHF$_2$ |
| P1282 | H | CF$_3$ | H | CF$_3$ | CF$_3$ | H | Cl | O | CH$_2$ | O | CH$_2$CHF$_2$ |

| Cmpd No. | R1 | R2 | R3 | R4 | R6 | R8 | R10 | W1 | (C1-C8) alkyl | W2 | R15 |
| --- | --- | --- | --- | --- | --- | --- | --- | --- | --- | --- | --- |
| P1283 | H | $CF_3$ | H | $CF_3$ | $CF_3$ | H | $CF_3$ | O | $CH_2$ | O | $CH_2CHF_2$ |
| P1284 | H | $CF_3$ | H | $CF_3$ | $CF_3$ | H | $CH_3$ | O | $CH_2$ | O | $CH_2CHF_2$ |
| P1285 | H | $CF_3$ | H | $CF_3$ | $CF_3$ | $CF_3$ | Br | O | $CH_2$ | O | $CH_2CF_3$ |
| P1286 | H | $CF_3$ | H | $CF_3$ | $CF_3$ | $CF_3$ | Cl | O | $CH_2$ | O | $CH_2CF_3$ |
| P1287 | H | $CF_3$ | H | $CF_3$ | $CF_3$ | $CF_3$ | $CF_3$ | O | $CH_2$ | O | $CH_2CF_3$ |
| P1288 | H | $CF_3$ | H | $CF_3$ | $CF_3$ | $CF_3$ | $CH_3$ | O | $CH_2$ | O | $CH_2CF_3$ |
| P1289 | H | $CF_3$ | H | $CF_3$ | $CF_2CF_3$ | H | Br | O | $CH_2$ | O | $CH_2CF_3$ |
| P1290 | H | $CF_3$ | H | $CF_3$ | $CF_2CF_3$ | H | Cl | O | $CH_2$ | O | $CH_2CF_3$ |
| P1291 | H | $CF_3$ | H | $CF_3$ | $CF_2CF_3$ | H | $CF_3$ | O | $CH_2$ | O | $CH_2CF_3$ |
| P1292 | H | $CF_3$ | H | $CF_3$ | $CF_2CF_3$ | H | $CH_3$ | O | $CH_2$ | O | $CH_2CF_3$ |
| P1293 | H | $CF_3$ | H | $CF_3$ | $CF_3$ | H | Br | O | $CH_2$ | O | $CH(CH_3)CF_3$ |
| P1294 | H | $CF_3$ | H | $CF_3$ | $CF_3$ | H | Cl | O | $CH_2$ | O | $CH(CH_3)CF_3$ |
| P1295 | H | $CF_3$ | H | $CF_3$ | $CF_3$ | H | $CF_3$ | O | $CH_2$ | O | $CH(CH_3)CF_3$ |
| P1296 | H | $CF_3$ | H | $CF_3$ | $CF_3$ | H | $CH_3$ | O | $CH_2$ | O | $CH(CH_3)CF_3$ |
| P1297 | H | $CF_3$ | H | $CF_3$ | $CF_3$ | $CF_3$ | Br | O | $CH(CH_3)$ | O | $CH_2CF_3$ |
| P1298 | H | $CF_3$ | H | $CF_3$ | $CF_3$ | $CF_3$ | Cl | O | $CH(CH_3)$ | O | $CH_2CF_3$ |
| P1299 | H | $CF_3$ | H | $CF_3$ | $CF_3$ | $CF_3$ | $CF_3$ | O | $CH(CH_3)$ | O | $CH_2CF_3$ |
| P1300 | H | $CF_3$ | H | $CF_3$ | $CF_3$ | $CF_3$ | $CH_3$ | O | $CH(CH_3)$ | O | $CH_2CF_3$ |
| P1301 | H | $CF_3$ | H | $CF_3$ | $CF_2CF_3$ | H | Br | O | $CH(CH_3)$ | O | $CH_2CF_3$ |
| P1302 | H | $CF_3$ | H | $CF_3$ | $CF_2CF_3$ | H | Cl | O | $CH(CH_3)$ | O | $CH_2CF_3$ |
| P1303 | H | $CF_3$ | H | $CF_3$ | $CF_2CF_3$ | H | $CF_3$ | O | $CH(CH_3)$ | O | $CH_2CF_3$ |
| P1304 | H | $CF_3$ | H | $CF_3$ | $CF_2CF_3$ | H | $CH_3$ | O | $CH(CH_3)$ | O | $CH_2CF_3$ |
| P1305 | H | $CF_3$ | H | $CF_3$ | $CF_3$ | H | Cl | O | $CH(CH_3)$ | O | $CH_2CF_3$ |
| P1306 | H | $CF_3$ | H | $CF_3$ | $CF_3$ | H | $CF_3$ | O | $CH(CH_3)$ | O | $CH_2CF_3$ |
| P1307 | H | $CF_3$ | H | $CF_3$ | $CF_3$ | H | $CH_3$ | O | $CH(CH_3)$ | O | $CH_2CF_3$ |
| P1308 | H | $CF_3$ | H | $CF_3$ | $CF_3$ | H | Br | O | $CH(CH_3)$ | S | $CH_2CF_3$ |
| P1309 | H | $CF_3$ | H | $CF_3$ | $CF_3$ | H | Cl | O | $CH(CH_3)$ | S | $CH_2CF_3$ |
| P1310 | H | $CF_3$ | H | $CF_3$ | $CF_3$ | H | $CF_3$ | O | $CH(CH_3)$ | S | $CH_2CF_3$ |
| P1311 | H | $CF_3$ | H | $CF_3$ | $CF_3$ | H | $CH_3$ | O | $CH(CH_3)$ | S | $CH_2CF_3$ |
| P1312 | H | $CF_3$ | H | $CF_3$ | $CF_3$ | H | Br | S | $CH(CH_3)$ | O | $CH_2CF_3$ |
| P1313 | H | $CF_3$ | H | $CF_3$ | $CF_3$ | H | Cl | S | $CH(CH_3)$ | O | $CH_2CF_3$ |
| P1314 | H | $CF_3$ | H | $CF_3$ | $CF_3$ | H | $CF_3$ | S | $CH(CH_3)$ | O | $CH_2CF_3$ |
| P1315 | H | $CF_3$ | H | $CF_3$ | $CF_3$ | H | $CH_3$ | S | $CH(CH_3)$ | O | $CH_2CF_3$ |
| P1316 | H | $CF_3$ | H | $CF_3$ | $CF_3$ | H | Br | O | $CH(CH_3)$ | O | $CH_2CHF_2$ |
| P1317 | H | $CF_3$ | H | $CF_3$ | $CF_3$ | H | Cl | O | $CH(CH_3)$ | O | $CH_2CHF_2$ |
| P1318 | H | $CF_3$ | H | $CF_3$ | $CF_3$ | H | $CF_3$ | O | $CH(CH_3)$ | O | $CH_2CHF_2$ |
| P1319 | H | $CF_3$ | H | $CF_3$ | $CF_3$ | H | $CH_3$ | O | $CH(CH_3)$ | O | $CH_2CHF_2$ |
| P1320 | H | $CF_3$ | H | $CF_3$ | $CF_3$ | H | Br | O | $CH(CH_3)$ | O | $CH(CH_3)CF_3$ |
| P1321 | H | $CF_3$ | H | $CF_3$ | $CF_3$ | H | Cl | O | $CH(CH_3)$ | O | $CH(CH_3)CF_3$ |
| P1322 | H | $CF_3$ | H | $CF_3$ | $CF_3$ | H | $CF_3$ | O | $CH(CH_3)$ | O | $CH(CH_3)CF_3$ |
| P1323 | H | $CF_3$ | H | $CF_3$ | $CF_3$ | H | $CH_3$ | O | $CH(CH_3)$ | O | $CH(CH_3)CF_3$ |
| P1324 | H | $CF_3$ | H | $CF_3$ | $CF_3$ | H | Br | O | $CH(CH_3)$ | O | $CH_2CH_2CF_3$ |
| P1325 | H | $CF_3$ | H | $CF_3$ | $CF_3$ | H | Cl | O | $CH(CH_3)$ | O | $CH_2CH_2CF_3$ |
| P1326 | H | $CF_3$ | H | $CF_3$ | $CF_3$ | H | $CF_3$ | O | $CH(CH_3)$ | O | $CH_2CH_2CF_3$ |
| P1327 | H | $CF_3$ | H | $CF_3$ | $CF_3$ | H | $CH_3$ | O | $CH(CH_3)$ | O | $CH_2CH_2CF_3$ |
| P1328 | H | $CF_3$ | H | $CF_3$ | $CF_3$ | H | Br | O | $CH(CH_2CH_3)$ | O | $CH_2CF_3$ |
| P1329 | H | $CF_3$ | H | $CF_3$ | $CF_3$ | H | Cl | O | $CH(CH_2CH_3)$ | O | $CH_2CF_3$ |
| P1330 | H | $CF_3$ | H | $CF_3$ | $CF_3$ | H | $CF_3$ | O | $CH(CH_2CH_3)$ | O | $CH_2CF_3$ |
| P1331 | H | $CF_3$ | H | $CF_3$ | $CF_3$ | H | $CH_3$ | O | $CH(CH_2CH_3)$ | O | $CH_2CF_3$ |
| P1332 | H | $CF_3$ | H | $CF_3$ | $CF_3$ | H | Br | O | $C(CH_3)_2$ | O | $CH_2CF_3$ |
| P1333 | H | $CF_3$ | H | $CF_3$ | $CF_3$ | H | Cl | O | $C(CH_3)_2$ | O | $CH_2CF_3$ |
| P1334 | H | $CF_3$ | H | $CF_3$ | $CF_3$ | H | $CF_3$ | O | $C(CH_3)_2$ | O | $CH_2CF_3$ |
| P1335 | H | $CF_3$ | H | $CF_3$ | $CF_3$ | H | $CH_3$ | O | $C(CH_3)_2$ | O | $CH_2CF_3$ |
| P1336 | H | $CF_3$ | H | $CF_3$ | $CF_3$ | H | Br | O | $CH_2CH_2$ | O | $CH_2CF_3$ |
| P1337 | H | $CF_3$ | H | $CF_3$ | $CF_3$ | H | Cl | O | $CH_2CH_2$ | O | $CH_2CF_3$ |
| P1338 | H | $CF_3$ | H | $CF_3$ | $CF_3$ | H | $CF_3$ | O | $CH_2CH_2$ | O | $CH_2CF_3$ |
| P1339 | H | $CF_3$ | H | $CF_3$ | $CF_3$ | H | $CH_3$ | O | $CH_2CH_2$ | O | $CH_2CF_3$ |
| P1340 | H | F | H | $CF_3$ | $CF_3$ | H | Br | O | $CH_2$ | O | $CH_2CF_3$ |
| P1341 | H | F | H | $CF_3$ | $CF_3$ | H | Cl | O | $CH_2$ | O | $CH_2CF_3$ |
| P1342 | H | F | H | $CF_3$ | $CF_3$ | H | $CF_3$ | O | $CH_2$ | O | $CH_2CF_3$ |
| P1343 | H | F | H | $CF_3$ | $CF_3$ | H | $CH_3$ | O | $CH_2$ | O | $CH_2CF_3$ |
| P1344 | H | F | H | $CF_3$ | $CF_3$ | H | Br | O | $CH_2$ | S | $CH_2CF_3$ |
| P1345 | H | F | H | $CF_3$ | $CF_3$ | H | Cl | O | $CH_2$ | S | $CH_2CF_3$ |
| P1346 | H | F | H | $CF_3$ | $CF_3$ | H | $CF_3$ | O | $CH_2$ | S | $CH_2CF_3$ |
| P1347 | H | F | H | $CF_3$ | $CF_3$ | H | $CH_3$ | O | $CH_2$ | S | $CH_2CF_3$ |
| P1348 | H | F | H | $CF_3$ | $CF_3$ | H | Br | S | $CH_2$ | O | $CH_2CF_3$ |
| P1349 | H | F | H | $CF_3$ | $CF_3$ | H | Cl | S | $CH_2$ | O | $CH_2CF_3$ |
| P1350 | H | F | H | $CF_3$ | $CF_3$ | H | $CF_3$ | S | $CH_2$ | O | $CH_2CF_3$ |
| P1351 | H | F | H | $CF_3$ | $CF_3$ | H | $CH_3$ | S | $CH_2$ | O | $CH_2CF_3$ |
| P1352 | H | F | H | $CF_3$ | $CF_3$ | H | Br | O | $CH_2$ | O | $CH_2CHF_2$ |
| P1353 | H | F | H | $CF_3$ | $CF_3$ | H | Cl | O | $CH_2$ | O | $CH_2CHF_2$ |
| P1354 | H | F | H | $CF_3$ | $CF_3$ | H | $CF_3$ | O | $CH_2$ | O | $CH_2CHF_2$ |
| P1355 | H | F | H | $CF_3$ | $CF_3$ | H | $CH_3$ | O | $CH_2$ | O | $CH_2CHF_2$ |
| P1356 | H | F | H | $CF_3$ | $CF_3$ | $CF_3$ | Br | O | $CH_2$ | O | $CH_2CF_3$ |
| P1357 | H | F | H | $CF_3$ | $CF_3$ | $CF_3$ | Cl | O | $CH_2$ | O | $CH_2CF_3$ |
| P1358 | H | F | H | $CF_3$ | $CF_3$ | $CF_3$ | $CF_3$ | O | $CH_2$ | O | $CH_2CF_3$ |
| P1359 | H | F | H | $CF_3$ | $CF_3$ | $CF_3$ | $CH_3$ | O | $CH_2$ | O | $CH_2CF_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1360 | H | F | H | $CF_3$ | $CF_2CF_3$ | H | Br | O | $CH_2$ | O | $CH_2CF_3$ |
| P1361 | H | F | H | $CF_3$ | $CF_2CF_3$ | H | Cl | O | $CH_2$ | O | $CH_2CF_3$ |
| P1362 | H | F | H | $CF_3$ | $CF_2CF_3$ | H | $CF_3$ | O | $CH_2$ | O | $CH_2CF_3$ |
| P1363 | H | F | H | $CF_3$ | $CF_2CF_3$ | H | $CH_3$ | O | $CH_2$ | O | $CH_2CF_3$ |
| P1364 | H | F | H | $CF_3$ | $CF_3$ | H | Br | O | $CH_2$ | O | $CH(CH_3)CF_3$ |
| P1365 | H | F | H | $CF_3$ | $CF_3$ | H | Cl | O | $CH_2$ | O | $CH(CH_3)CF_3$ |
| P1366 | H | F | H | $CF_3$ | $CF_3$ | H | $CF_3$ | O | $CH_2$ | O | $CH(CH_3)CF_3$ |
| P1367 | H | F | H | $CF_3$ | $CF_3$ | H | $CH_3$ | O | $CH_2$ | O | $CH(CH_3)CF_3$ |
| P1368 | H | F | H | $CF_3$ | $CF_3$ | $CF_3$ | Br | O | $CH(CH_3)$ | O | $CH_2CF_3$ |
| P1369 | H | F | H | $CF_3$ | $CF_3$ | $CF_3$ | Cl | O | $CH(CH_3)$ | O | $CH_2CF_3$ |
| P1370 | H | F | H | $CF_3$ | $CF_3$ | $CF_3$ | $CF_3$ | O | $CH(CH_3)$ | O | $CH_2CF_3$ |
| P1371 | H | F | H | $CF_3$ | $CF_3$ | $CF_3$ | $CH_3$ | O | $CH(CH_3)$ | O | $CH_2CF_3$ |
| P1372 | H | F | H | $CF_3$ | $CF_2CF_3$ | H | Br | O | $CH(CH_3)$ | O | $CH_2CF_3$ |
| P1373 | H | F | H | $CF_3$ | $CF_2CF_3$ | H | Cl | O | $CH(CH_3)$ | O | $CH_2CF_3$ |
| P1374 | H | F | H | $CF_3$ | $CF_2CF_3$ | H | $CF_3$ | O | $CH(CH_3)$ | O | $CH_2CF_3$ |
| P1375 | H | F | H | $CF_3$ | $CF_2CF_3$ | H | $CH_3$ | O | $CH(CH_3)$ | O | $CH_2CF_3$ |
| P1376 | H | F | H | $CF_3$ | $CF_3$ | H | Cl | O | $CH(CH_3)$ | O | $CH_2CF_3$ |
| P1377 | H | F | H | $CF_3$ | $CF_3$ | H | $CF_3$ | O | $CH(CH_3)$ | O | $CH_2CF_3$ |
| P1378 | H | F | H | $CF_3$ | $CF_3$ | H | $CH_3$ | O | $CH(CH_3)$ | O | $CH_2CF_3$ |
| P1379 | H | F | H | $CF_3$ | $CF_3$ | H | Br | O | $CH(CH_3)$ | S | $CH_2CF_3$ |
| P1380 | H | F | H | $CF_3$ | $CF_3$ | H | Cl | O | $CH(CH_3)$ | S | $CH_2CF_3$ |
| P1381 | H | F | H | $CF_3$ | $CF_3$ | H | $CF_3$ | O | $CH(CH_3)$ | S | $CH_2CF_3$ |
| P1382 | H | F | H | $CF_3$ | $CF_3$ | H | $CH_3$ | O | $CH(CH_3)$ | S | $CH_2CF_3$ |
| P1383 | H | F | H | $CF_3$ | $CF_3$ | H | Br | S | $CH(CH_3)$ | O | $CH_2CF_3$ |
| P1384 | H | F | H | $CF_3$ | $CF_3$ | H | Cl | S | $CH(CH_3)$ | O | $CH_2CF_3$ |
| P1385 | H | F | H | $CF_3$ | $CF_3$ | H | $CF_3$ | S | $CH(CH_3)$ | O | $CH_2CF_3$ |
| P1386 | H | F | H | $CF_3$ | $CF_3$ | H | $CH_3$ | S | $CH(CH_3)$ | O | $CH_2CF_3$ |
| P1387 | H | F | H | $CF_3$ | $CF_3$ | H | Br | O | $CH(CH_3)$ | O | $CH_2CHF_2$ |
| P1388 | H | F | H | $CF_3$ | $CF_3$ | H | Cl | O | $CH(CH_3)$ | O | $CH_2CHF_2$ |
| P1389 | H | F | H | $CF_3$ | $CF_3$ | H | $CF_3$ | O | $CH(CH_3)$ | O | $CH_2CHF_2$ |
| P1390 | H | F | H | $CF_3$ | $CF_3$ | H | $CH_3$ | O | $CH(CH_3)$ | O | $CH_2CHF_2$ |
| P1391 | H | F | H | $CF_3$ | $CF_3$ | H | Br | O | $CH(CH_3)$ | O | $CH(CH_3)CF_3$ |
| P1392 | H | F | H | $CF_3$ | $CF_3$ | H | Cl | O | $CH(CH_3)$ | O | $CH(CH_3)CF_3$ |
| P1393 | H | F | H | $CF_3$ | $CF_3$ | H | $CF_3$ | O | $CH(CH_3)$ | O | $CH(CH_3)CF_3$ |
| P1394 | H | F | H | $CF_3$ | $CF_3$ | H | $CH_3$ | O | $CH(CH_3)$ | O | $CH(CH_3)CF_3$ |
| P1395 | H | F | H | $CF_3$ | $CF_3$ | H | Br | O | $CH(CH_3)$ | O | $CH_2CH_2CF_3$ |
| P1396 | H | F | H | $CF_3$ | $CF_3$ | H | Cl | O | $CH(CH_3)$ | O | $CH_2CH_2CF_3$ |
| P1397 | H | F | H | $CF_3$ | $CF_3$ | H | $CF_3$ | O | $CH(CH_3)$ | O | $CH_2CH_2CF_3$ |
| P1398 | H | F | H | $CF_3$ | $CF_3$ | H | $CH_3$ | O | $CH(CH_3)$ | O | $CH_2CH_2CF_3$ |
| P1399 | H | F | H | $CF_3$ | $CF_3$ | H | Br | O | $CH(CH_2CH_3)$ | O | $CH_2CF_3$ |
| P1400 | H | F | H | $CF_3$ | $CF_3$ | H | Cl | O | $CH(CH_2CH_3)$ | O | $CH_2CF_3$ |
| P1401 | H | F | H | $CF_3$ | $CF_3$ | H | $CF_3$ | O | $CH(CH_2CH_3)$ | O | $CH_2CF_3$ |
| P1402 | H | F | H | $CF_3$ | $CF_3$ | H | $CH_3$ | O | $CH(CH_2CH_3)$ | O | $CH_2CF_3$ |
| P1403 | H | F | H | $CF_3$ | $CF_3$ | H | Br | O | $C(CH_3)_2$ | O | $CH_2CF_3$ |
| P1404 | H | F | H | $CF_3$ | $CF_3$ | H | Cl | O | $C(CH_3)_2$ | O | $CH_2CF_3$ |
| P1405 | H | F | H | $CF_3$ | $CF_3$ | H | $CF_3$ | O | $C(CH_3)_2$ | O | $CH_2CF_3$ |
| P1406 | H | F | H | $CF_3$ | $CF_3$ | H | $CH_3$ | O | $C(CH_3)_2$ | O | $CH_2CF_3$ |
| P1407 | H | F | H | $CF_3$ | $CF_3$ | H | Br | O | $CH_2CH_2$ | O | $CH_2CF_3$ |
| P1408 | H | F | H | $CF_3$ | $CF_3$ | H | Cl | O | $CH_2CH_2$ | O | $CH_2CF_3$ |
| P1409 | H | F | H | $CF_3$ | $CF_3$ | H | $CF_3$ | O | $CH_2CH_2$ | O | $CH_2CF_3$ |
| P1410 | H | F | H | $CF_3$ | $CF_3$ | H | $CH_3$ | O | $CH_2CH_2$ | O | $CH_2CF_3$ |
| P1411 | H | Cl | H | $CF_3$ | $CF_3$ | H | Br | O | $CH_2$ | O | $CH_2CF_3$ |
| P1412 | H | Cl | H | $CF_3$ | $CF_3$ | H | Cl | O | $CH_2$ | O | $CH_2CF_3$ |
| P1413 | H | Cl | H | $CF_3$ | $CF_3$ | H | $CF_3$ | O | $CH_2$ | O | $CH_2CF_3$ |
| P1414 | H | Cl | H | $CF_3$ | $CF_3$ | H | $CH_3$ | O | $CH_2$ | O | $CH_2CF_3$ |
| P1415 | H | Cl | H | $CF_3$ | $CF_3$ | H | Br | O | $CH_2$ | S | $CH_2CF_3$ |
| P1416 | H | Cl | H | $CF_3$ | $CF_3$ | H | Cl | O | $CH_2$ | S | $CH_2CF_3$ |
| P1417 | H | Cl | H | $CF_3$ | $CF_3$ | H | $CF_3$ | O | $CH_2$ | S | $CH_2CF_3$ |
| P1418 | H | Cl | H | $CF_3$ | $CF_3$ | H | $CH_3$ | O | $CH_2$ | S | $CH_2CF_3$ |
| P1419 | H | Cl | H | $CF_3$ | $CF_3$ | H | Br | S | $CH_2$ | O | $CH_2CF_3$ |
| P1420 | H | Cl | H | $CF_3$ | $CF_3$ | H | Cl | S | $CH_2$ | O | $CH_2CF_3$ |
| P1421 | H | Cl | H | $CF_3$ | $CF_3$ | H | $CF_3$ | S | $CH_2$ | O | $CH_2CF_3$ |
| P1422 | H | Cl | H | $CF_3$ | $CF_3$ | H | $CH_3$ | S | $CH_2$ | O | $CH_2CF_3$ |
| P1423 | H | Cl | H | $CF_3$ | $CF_3$ | H | Br | O | $CH_2$ | O | $CH_2CHF_2$ |
| P1424 | H | Cl | H | $CF_3$ | $CF_3$ | H | Cl | O | $CH_2$ | O | $CH_2CHF_2$ |
| P1425 | H | Cl | H | $CF_3$ | $CF_3$ | H | $CF_3$ | O | $CH_2$ | O | $CH_2CHF_2$ |
| P1426 | H | Cl | H | $CF_3$ | $CF_3$ | H | $CH_3$ | O | $CH_2$ | O | $CH_2CHF_2$ |
| P1427 | H | Cl | H | $CF_3$ | $CF_3$ | $CF_3$ | Br | O | $CH_2$ | O | $CH_2CF_3$ |
| P1428 | H | Cl | H | $CF_3$ | $CF_3$ | $CF_3$ | Cl | O | $CH_2$ | O | $CH_2CF_3$ |
| P1429 | H | Cl | H | $CF_3$ | $CF_3$ | $CF_3$ | $CF_3$ | O | $CH_2$ | O | $CH_2CF_3$ |
| P1430 | H | Cl | H | $CF_3$ | $CF_3$ | $CF_3$ | $CH_3$ | O | $CH_2$ | O | $CH_2CF_3$ |
| P1431 | H | Cl | H | $CF_3$ | $CF_2CF_3$ | H | Br | O | $CH_2$ | O | $CH_2CF_3$ |
| P1432 | H | Cl | H | $CF_3$ | $CF_2CF_3$ | H | Cl | O | $CH_2$ | O | $CH_2CF_3$ |
| P1433 | H | Cl | H | $CF_3$ | $CF_2CF_3$ | H | $CF_3$ | O | $CH_2$ | O | $CH_2CF_3$ |
| P1434 | H | Cl | H | $CF_3$ | $CF_2CF_3$ | H | $CH_3$ | O | $CH_2$ | O | $CH_2CF_3$ |
| P1435 | H | Cl | H | $CF_3$ | $CF_3$ | H | Br | O | $CH_2$ | O | $CH(CH_3)CF_3$ |
| P1436 | H | Cl | H | $CF_3$ | $CF_3$ | H | Cl | O | $CH_2$ | O | $CH(CH_3)CF_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1437 | H | Cl | H | $CF_3$ | $CF_3$ | H | $CF_3$ | O | $CH_2$ | O | $CH(CH_3)CF_3$ |
| P1438 | H | Cl | H | $CF_3$ | $CF_3$ | H | $CH_3$ | O | $CH_2$ | O | $CH(CH_3)CF_3$ |
| P1439 | H | Cl | H | $CF_3$ | $CF_3$ | $CF_3$ | Br | O | $CH(CH_3)$ | O | $CH_2CF_3$ |
| P1440 | H | Cl | H | $CF_3$ | $CF_3$ | $CF_3$ | Cl | O | $CH(CH_3)$ | O | $CH_2CF_3$ |
| P1441 | H | Cl | H | $CF_3$ | $CF_3$ | $CF_3$ | $CF_3$ | O | $CH(CH_3)$ | O | $CH_2CF_3$ |
| P1442 | H | Cl | H | $CF_3$ | $CF_3$ | $CF_3$ | $CH_3$ | O | $CH(CH_3)$ | O | $CH_2CF_3$ |
| P1443 | H | Cl | H | $CF_3$ | $CF_2CF_3$ | H | Br | O | $CH(CH_3)$ | O | $CH_2CF_3$ |
| P1444 | H | Cl | H | $CF_3$ | $CF_2CF_3$ | H | Cl | O | $CH(CH_3)$ | O | $CH_2CF_3$ |
| P1445 | H | Cl | H | $CF_3$ | $CF_2CF_3$ | H | $CF_3$ | O | $CH(CH_3)$ | O | $CH_2CF_3$ |
| P1446 | H | Cl | H | $CF_3$ | $CF_2CF_3$ | H | $CH_3$ | O | $CH(CH_3)$ | O | $CH_2CF_3$ |
| P1447 | H | Cl | H | $CF_3$ | $CF_3$ | H | Br | O | $CH(CH_3)$ | O | $CH_2CF_3$ |
| P1448 | H | Cl | H | $CF_3$ | $CF_3$ | H | Cl | O | $CH(CH_3)$ | O | $CH_2CF_3$ |
| P1449 | H | Cl | H | $CF_3$ | $CF_3$ | H | $CF_3$ | O | $CH(CH_3)$ | O | $CH_2CF_3$ |
| P1450 | H | Cl | H | $CF_3$ | $CF_3$ | H | $CH_3$ | O | $CH(CH_3)$ | O | $CH_2CF_3$ |
| P1451 | H | Cl | H | $CF_3$ | $CF_3$ | H | Br | O | $CH(CH_3)$ | S | $CH_2CF_3$ |
| P1452 | H | Cl | H | $CF_3$ | $CF_3$ | H | Cl | O | $CH(CH_3)$ | S | $CH_2CF_3$ |
| P1453 | H | Cl | H | $CF_3$ | $CF_3$ | H | $CF_3$ | O | $CH(CH_3)$ | S | $CH_2CF_3$ |
| P1454 | H | Cl | H | $CF_3$ | $CF_3$ | H | $CH_3$ | O | $CH(CH_3)$ | S | $CH_2CF_3$ |
| P1455 | H | Cl | H | $CF_3$ | $CF_3$ | H | Br | S | $CH(CH_3)$ | O | $CH_2CF_3$ |
| P1456 | H | Cl | H | $CF_3$ | $CF_3$ | H | Cl | S | $CH(CH_3)$ | O | $CH_2CF_3$ |
| P1457 | H | Cl | H | $CF_3$ | $CF_3$ | H | $CF_3$ | S | $CH(CH_3)$ | O | $CH_2CF_3$ |
| P1458 | H | Cl | H | $CF_3$ | $CF_3$ | H | $CH_3$ | S | $CH(CH_3)$ | O | $CH_2CF_3$ |
| P1459 | H | Cl | H | $CF_3$ | $CF_3$ | H | Br | O | $CH(CH_3)$ | O | $CH_2CHF_2$ |
| P1460 | H | Cl | H | $CF_3$ | $CF_3$ | H | Cl | O | $CH(CH_3)$ | O | $CH_2CHF_2$ |
| P1461 | H | Cl | H | $CF_3$ | $CF_3$ | H | $CF_3$ | O | $CH(CH_3)$ | O | $CH_2CHF_2$ |
| P1462 | H | Cl | H | $CF_3$ | $CF_3$ | H | $CH_3$ | O | $CH(CH_3)$ | O | $CH_2CHF_2$ |
| P1463 | H | Cl | H | $CF_3$ | $CF_3$ | H | Br | O | $CH(CH_3)$ | O | $CH(CH_3)CF_3$ |
| P1464 | H | Cl | H | $CF_3$ | $CF_3$ | H | Cl | O | $CH(CH_3)$ | O | $CH(CH_3)CF_3$ |
| P1465 | H | Cl | H | $CF_3$ | $CF_3$ | H | $CF_3$ | O | $CH(CH_3)$ | O | $CH(CH_3)CF_3$ |
| P1466 | H | Cl | H | $CF_3$ | $CF_3$ | H | $CH_3$ | O | $CH(CH_3)$ | O | $CH(CH_3)CF_3$ |
| P1467 | H | Cl | H | $CF_3$ | $CF_3$ | H | Br | O | $CH(CH_3)$ | O | $CH_2CH_2CF_3$ |
| P1468 | H | Cl | H | $CF_3$ | $CF_3$ | H | Cl | O | $CH(CH_3)$ | O | $CH_2CH_2CF_3$ |
| P1469 | H | Cl | H | $CF_3$ | $CF_3$ | H | $CF_3$ | O | $CH(CH_3)$ | O | $CH_2CH_2CF_3$ |
| P1470 | H | Cl | H | $CF_3$ | $CF_3$ | H | $CH_3$ | O | $CH(CH_3)$ | O | $CH_2CH_2CF_3$ |
| P1471 | H | Cl | H | $CF_3$ | $CF_3$ | H | Br | O | $CH(CH_2CH_3)$ | O | $CH_2CF_3$ |
| P1472 | H | Cl | H | $CF_3$ | $CF_3$ | H | Cl | O | $CH(CH_2CH_3)$ | O | $CH_2CF_3$ |
| P1473 | H | Cl | H | $CF_3$ | $CF_3$ | H | $CF_3$ | O | $CH(CH_2CH_3)$ | O | $CH_2CF_3$ |
| P1474 | H | Cl | H | $CF_3$ | $CF_3$ | H | $CH_3$ | O | $CH(CH_2CH_3)$ | O | $CH_2CF_3$ |
| P1475 | H | Cl | H | $CF_3$ | $CF_3$ | H | Br | O | $C(CH_3)_2$ | O | $CH_2CF_3$ |
| P1476 | H | Cl | H | $CF_3$ | $CF_3$ | H | Cl | O | $C(CH_3)_2$ | O | $CH_2CF_3$ |
| P1477 | H | Cl | H | $CF_3$ | $CF_3$ | H | $CF_3$ | O | $C(CH_3)_2$ | O | $CH_2CF_3$ |
| P1478 | H | Cl | H | $CF_3$ | $CF_3$ | H | $CH_3$ | O | $C(CH_3)_2$ | O | $CH_2CF_3$ |
| P1479 | H | Cl | H | $CF_3$ | $CF_3$ | H | Br | O | $CH_2CH_2$ | O | $CH_2CF_3$ |
| P1480 | H | Cl | H | $CF_3$ | $CF_3$ | H | Cl | O | $CH_2CH_2$ | O | $CH_2CF_3$ |
| P1481 | H | Cl | H | $CF_3$ | $CF_3$ | H | $CF_3$ | O | $CH_2CH_2$ | O | $CH_2CF_3$ |
| P1482 | H | Cl | H | $CF_3$ | $CF_3$ | H | $CH_3$ | O | $CH_2CH_2$ | O | $CH_2CF_3$ |
| P1483 | H | H | F | $CF_3$ | $CF_3$ | H | Br | O | $CH_2$ | O | $CH_2CF_3$ |
| P1484 | H | H | F | $CF_3$ | $CF_3$ | H | Cl | O | $CH_2$ | O | $CH_2CF_3$ |
| P1485 | H | H | F | $CF_3$ | $CF_3$ | H | $CF_3$ | O | $CH_2$ | O | $CH_2CF_3$ |
| P1486 | H | H | F | $CF_3$ | $CF_3$ | H | $CH_3$ | O | $CH_2$ | O | $CH_2CF_3$ |
| P1487 | H | H | F | $CF_3$ | $CF_3$ | H | Br | O | $CH_2$ | S | $CH_2CF_3$ |
| P1488 | H | H | F | $CF_3$ | $CF_3$ | H | Cl | O | $CH_2$ | S | $CH_2CF_3$ |
| P1489 | H | H | F | $CF_3$ | $CF_3$ | H | $CF_3$ | O | $CH_2$ | S | $CH_2CF_3$ |
| P1490 | H | H | F | $CF_3$ | $CF_3$ | H | $CH_3$ | O | $CH_2$ | S | $CH_2CF_3$ |
| P1491 | H | H | F | $CF_3$ | $CF_3$ | H | Br | S | $CH_2$ | O | $CH_2CF_3$ |
| P1492 | H | H | F | $CF_3$ | $CF_3$ | H | Cl | S | $CH_2$ | O | $CH_2CF_3$ |
| P1493 | H | H | F | $CF_3$ | $CF_3$ | H | $CF_3$ | S | $CH_2$ | O | $CH_2CF_3$ |
| P1494 | H | H | F | $CF_3$ | $CF_3$ | H | $CH_3$ | S | $CH_2$ | O | $CH_2CF_3$ |
| P1495 | H | H | F | $CF_3$ | $CF_3$ | H | Br | O | $CH_2$ | O | $CH_2CHF_2$ |
| P1496 | H | H | F | $CF_3$ | $CF_3$ | H | Cl | O | $CH_2$ | O | $CH_2CHF_2$ |
| P1497 | H | H | F | $CF_3$ | $CF_3$ | H | $CF_3$ | O | $CH_2$ | O | $CH_2CHF_2$ |
| P1498 | H | H | F | $CF_3$ | $CF_3$ | H | $CH_3$ | O | $CH_2$ | O | $CH_2CHF_2$ |
| P1499 | H | H | F | $CF_3$ | $CF_3$ | $CF_3$ | Br | O | $CH_2$ | O | $CH_2CF_3$ |
| P1500 | H | H | F | $CF_3$ | $CF_3$ | $CF_3$ | Cl | O | $CH_2$ | O | $CH_2CF_3$ |
| P1501 | H | H | F | $CF_3$ | $CF_3$ | $CF_3$ | $CF_3$ | O | $CH_2$ | O | $CH_2CF_3$ |
| P1502 | H | H | F | $CF_3$ | $CF_3$ | $CF_3$ | $CH_3$ | O | $CH_2$ | O | $CH_2CF_3$ |
| P1503 | H | H | F | $CF_3$ | $CF_2CF_3$ | H | Br | O | $CH_2$ | O | $CH_2CF_3$ |
| P1504 | H | H | F | $CF_3$ | $CF_2CF_3$ | H | Cl | O | $CH_2$ | O | $CH_2CF_3$ |
| P1505 | H | H | F | $CF_3$ | $CF_2CF_3$ | H | $CF_3$ | O | $CH_2$ | O | $CH_2CF_3$ |
| P1506 | H | H | F | $CF_3$ | $CF_2CF_3$ | H | $CH_3$ | O | $CH_2$ | O | $CH_2CF_3$ |
| P1507 | H | H | F | $CF_3$ | $CF_3$ | H | Br | O | $CH_2$ | O | $CH(CH_3)CF_3$ |
| P1508 | H | H | F | $CF_3$ | $CF_3$ | H | Cl | O | $CH_2$ | O | $CH(CH_3)CF_3$ |
| P1509 | H | H | F | $CF_3$ | $CF_3$ | H | $CF_3$ | O | $CH_2$ | O | $CH(CH_3)CF_3$ |
| P1510 | H | H | F | $CF_3$ | $CF_3$ | H | $CH_3$ | O | $CH_2$ | O | $CH(CH_3)CF_3$ |
| P1511 | H | H | F | $CF_3$ | $CF_3$ | $CF_3$ | Br | O | $CH(CH_3)$ | O | $CH_2CF_3$ |
| P1512 | H | H | F | $CF_3$ | $CF_3$ | $CF_3$ | Cl | O | $CH(CH_3)$ | O | $CH_2CF_3$ |
| P1513 | H | H | F | $CF_3$ | $CF_3$ | $CF_3$ | $CF_3$ | O | $CH(CH_3)$ | O | $CH_2CF_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1514 | H | H | F | $CF_3$ | $CF_3$ | $CF_3$ | $CH_3$ | O | $CH(CH_3)$ | O | $CH_2CF_3$ |
| P1515 | H | H | F | $CF_3$ | $CF_2CF_3$ | H | Br | O | $CH(CH_3)$ | O | $CH_2CF_3$ |
| P1516 | H | H | F | $CF_3$ | $CF_2CF_3$ | H | Cl | O | $CH(CH_3)$ | O | $CH_2CF_3$ |
| P1517 | H | H | F | $CF_3$ | $CF_2CF_3$ | H | $CF_3$ | O | $CH(CH_3)$ | O | $CH_2CF_3$ |
| P1518 | H | H | F | $CF_3$ | $CF_2CF_3$ | H | $CH_3$ | O | $CH(CH_3)$ | O | $CH_2CF_3$ |
| P1519 | H | H | F | $CF_3$ | $CF_3$ | H | Br | O | $CH(CH_3)$ | O | $CH_2CF_3$ |
| P1520 | H | H | F | $CF_3$ | $CF_3$ | H | Cl | O | $CH(CH_3)$ | O | $CH_2CF_3$ |
| P1521 | H | H | F | $CF_3$ | $CF_3$ | H | $CF_3$ | O | $CH(CH_3)$ | O | $CH_2CF_3$ |
| P1522 | H | H | F | $CF_3$ | $CF_3$ | H | $CH_3$ | O | $CH(CH_3)$ | O | $CH_2CF_3$ |
| P1523 | H | H | F | $CF_3$ | $CF_3$ | H | Br | O | $CH(CH_3)$ | S | $CH_2CF_3$ |
| P1524 | H | H | F | $CF_3$ | $CF_3$ | H | Cl | O | $CH(CH_3)$ | S | $CH_2CF_3$ |
| P1525 | H | H | F | $CF_3$ | $CF_3$ | H | $CF_3$ | O | $CH(CH_3)$ | S | $CH_2CF_3$ |
| P1526 | H | H | F | $CF_3$ | $CF_3$ | H | $CH_3$ | O | $CH(CH_3)$ | S | $CH_2CF_3$ |
| P1527 | H | H | F | $CF_3$ | $CF_3$ | H | Br | S | $CH(CH_3)$ | O | $CH_2CF_3$ |
| P1528 | H | H | F | $CF_3$ | $CF_3$ | H | Cl | S | $CH(CH_3)$ | O | $CH_2CF_3$ |
| P1529 | H | H | F | $CF_3$ | $CF_3$ | H | $CF_3$ | S | $CH(CH_3)$ | O | $CH_2CF_3$ |
| P1530 | H | H | F | $CF_3$ | $CF_3$ | H | $CH_3$ | S | $CH(CH_3)$ | O | $CH_2CF_3$ |
| P1531 | H | H | F | $CF_3$ | $CF_3$ | H | Br | O | $CH(CH_3)$ | O | $CH_2CHF_2$ |
| P1532 | H | H | F | $CF_3$ | $CF_3$ | H | Cl | O | $CH(CH_3)$ | O | $CH_2CHF_2$ |
| P1533 | H | H | F | $CF_3$ | $CF_3$ | H | $CF_3$ | O | $CH(CH_3)$ | O | $CH_2CHF_2$ |
| P1534 | H | H | F | $CF_3$ | $CF_3$ | H | $CH_3$ | O | $CH(CH_3)$ | O | $CH_2CHF_2$ |
| P1535 | H | H | F | $CF_3$ | $CF_3$ | H | Br | O | $CH(CH_3)$ | O | $CH(CH_3)CF_3$ |
| P1536 | H | H | F | $CF_3$ | $CF_3$ | H | Cl | O | $CH(CH_3)$ | O | $CH(CH_3)CF_3$ |
| P1537 | H | H | F | $CF_3$ | $CF_3$ | H | $CF_3$ | O | $CH(CH_3)$ | O | $CH(CH_3)CF_3$ |
| P1538 | H | H | F | $CF_3$ | $CF_3$ | H | $CH_3$ | O | $CH(CH_3)$ | O | $CH(CH_3)CF_3$ |
| P1539 | H | H | F | $CF_3$ | $CF_3$ | H | Br | O | $CH(CH_3)$ | O | $CH_2CH_2CF_3$ |
| P1540 | H | H | F | $CF_3$ | $CF_3$ | H | Cl | O | $CH(CH_3)$ | O | $CH_2CH_2CF_3$ |
| P1541 | H | H | F | $CF_3$ | $CF_3$ | H | $CF_3$ | O | $CH(CH_3)$ | O | $CH_2CH_2CF_3$ |
| P1542 | H | H | F | $CF_3$ | $CF_3$ | H | $CH_3$ | O | $CH(CH_3)$ | O | $CH_2CH_2CF_3$ |
| P1543 | H | H | F | $CF_3$ | $CF_3$ | H | Br | O | $CH(CH_2CH_3)$ | O | $CH_2CF_3$ |
| P1544 | H | H | F | $CF_3$ | $CF_3$ | H | Cl | O | $CH(CH_2CH_3)$ | O | $CH_2CF_3$ |
| P1545 | H | H | F | $CF_3$ | $CF_3$ | H | $CF_3$ | O | $CH(CH_2CH_3)$ | O | $CH_2CF_3$ |
| P1546 | H | H | F | $CF_3$ | $CF_3$ | H | $CH_3$ | O | $CH(CH_2CH_3)$ | O | $CH_2CF_3$ |
| P1547 | H | H | F | $CF_3$ | $CF_3$ | H | Br | O | $C(CH_3)_2$ | O | $CH_2CF_3$ |
| P1548 | H | H | F | $CF_3$ | $CF_3$ | H | Cl | O | $C(CH_3)_2$ | O | $CH_2CF_3$ |
| P1549 | H | H | F | $CF_3$ | $CF_3$ | H | $CF_3$ | O | $C(CH_3)_2$ | O | $CH_2CF_3$ |
| P1550 | H | H | F | $CF_3$ | $CF_3$ | H | $CH_3$ | O | $C(CH_3)_2$ | O | $CH_2CF_3$ |
| P1551 | H | H | F | $CF_3$ | $CF_3$ | H | Br | O | $CH_2CH_2$ | O | $CH_2CF_3$ |
| P1552 | H | H | F | $CF_3$ | $CF_3$ | H | Cl | O | $CH_2CH_2$ | O | $CH_2CF_3$ |
| P1553 | H | H | F | $CF_3$ | $CF_3$ | H | $CF_3$ | O | $CH_2CH_2$ | O | $CH_2CF_3$ |
| P1554 | H | H | F | $CF_3$ | $CF_3$ | H | $CH_3$ | O | $CH_2CH_2$ | O | $CH_2CF_3$ |
| P1555 | H | Cl | Cl | Cl | $CF_3$ | H | H | O | $CH_2$ | O | $CH_2CF_3$ |
| P1556 | H | Cl | Cl | Cl | $CF_3$ | H | $CF_3$ | O | $CH_2$ | O | $CH_2CF_3$ |
| P1557 | H | Cl | Cl | Cl | $CF_3$ | H | H | O | $CH_2$ | S | $CH_2CF_3$ |
| P1558 | H | Cl | Cl | Cl | $CF_3$ | H | Cl | O | $CH_2$ | S | $CH_2CF_3$ |
| P1559 | H | Cl | Cl | Cl | $CF_3$ | H | $CF_3$ | O | $CH_2$ | S | $CH_2CF_3$ |
| P1560 | H | Cl | Cl | Cl | $CF_3$ | H | $CH_3$ | O | $CH_2$ | S | $CH_2CF_3$ |
| P1561 | H | Cl | Cl | Cl | $CF_3$ | H | H | S | $CH_2$ | O | $CH_2CF_3$ |
| P1562 | H | Cl | Cl | Cl | $CF_3$ | H | Cl | S | $CH_2$ | O | $CH_2CF_3$ |
| P1563 | H | Cl | Cl | Cl | $CF_3$ | H | $CF_3$ | S | $CH_2$ | O | $CH_2CF_3$ |
| P1564 | H | Cl | Cl | Cl | $CF_3$ | H | $CH_3$ | S | $CH_2$ | O | $CH_2CF_3$ |
| P1565 | H | Cl | Cl | Cl | $CF_3$ | H | H | O | $CH_2$ | O | $CH_2CHF_2$ |
| P1566 | H | Cl | Cl | Cl | $CF_3$ | H | $CF_3$ | O | $CH_2$ | O | $CH_2CHF_2$ |
| P1567 | H | Cl | Cl | Cl | $CF_3$ | H | $CH_3$ | O | $CH_2$ | O | $CH_2CHF_2$ |
| P1568 | H | Cl | Cl | Cl | $CF_3$ | H | H | O | $CH_2$ | O | $CH_2CH_2F$ |
| P1569 | H | Cl | Cl | Cl | $CF_3$ | H | Br | O | $CH_2$ | O | $CH_2CH_2F$ |
| P1570 | H | Cl | Cl | Cl | $CF_3$ | H | Cl | O | $CH_2$ | O | $CH_2CH_2F$ |
| P1571 | H | Cl | Cl | Cl | $CF_3$ | H | $CF_3$ | O | $CH_2$ | O | $CH_2CH_2F$ |
| P1572 | H | Cl | Cl | Cl | $CF_3$ | H | $CH_3$ | O | $CH_2$ | O | $CH_2CH_2F$ |
| P1573 | H | Cl | Cl | Cl | $CF_3$ | H | H | O | $CH_2$ | O | $CH_2CH_3$ |
| P1574 | H | Cl | Cl | Cl | $CF_3$ | H | Br | O | $CH_2$ | O | $CH_2CH_3$ |
| P1575 | H | Cl | Cl | Cl | $CF_3$ | H | Cl | O | $CH_2$ | O | $CH_2CH_3$ |
| P1576 | H | Cl | Cl | Cl | $CF_3$ | H | $CF_3$ | O | $CH_2$ | O | $CH_2CH_3$ |
| P1577 | H | Cl | Cl | Cl | $CF_3$ | H | $CH_3$ | O | $CH_2$ | O | $CH_2CH_3$ |
| P1578 | H | Cl | Cl | Cl | $CF_3$ | $CF_3$ | H | O | $CH_2$ | O | $CH_2CF_3$ |
| P1579 | H | Cl | Cl | Cl | $CF_3$ | $CF_3$ | Br | O | $CH_2$ | O | $CH_2CF_3$ |
| P1580 | H | Cl | Cl | Cl | $CF_3$ | $CF_3$ | Cl | O | $CH_2$ | O | $CH_2CF_3$ |
| P1581 | H | Cl | Cl | Cl | $CF_3$ | $CF_3$ | $CF_3$ | O | $CH_2$ | O | $CH_2CF_3$ |
| P1582 | H | Cl | Cl | Cl | $CF_3$ | $CF_3$ | $CH_3$ | O | $CH_2$ | O | $CH_2CF_3$ |
| P1583 | H | Cl | Cl | Cl | $CF_2CF_3$ | H | H | O | $CH_2$ | O | $CH_2CF_3$ |
| P1584 | H | Cl | Cl | Cl | $CF_2CF_3$ | H | Br | O | $CH_2$ | O | $CH_2CF_3$ |
| P1585 | H | Cl | Cl | Cl | $CF_2CF_3$ | H | Cl | O | $CH_2$ | O | $CH_2CF_3$ |
| P1586 | H | Cl | Cl | Cl | $CF_2CF_3$ | H | $CF_3$ | O | $CH_2$ | O | $CH_2CF_3$ |
| P1587 | H | Cl | Cl | Cl | $CF_2CF_3$ | H | $CH_3$ | O | $CH_2$ | O | $CH_2CF_3$ |
| P1588 | H | Cl | Cl | Cl | $CF_3$ | H | H | O | $CH_2$ | O | $CH(CH_3)CF_3$ |
| P1589 | H | Cl | Cl | Cl | $CF_3$ | H | Br | O | $CH_2$ | O | $CH(CH_3)CF_3$ |
| P1590 | H | Cl | Cl | Cl | $CF_3$ | H | Cl | O | $CH_2$ | O | $CH(CH_3)CF_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1591 | H | Cl | Cl | Cl | CF$_3$ | H | CF$_3$ | O | CH$_2$ | O | CH(CH$_3$)CF$_3$ |
| P1592 | H | Cl | Cl | Cl | CF$_3$ | H | CH$_3$ | O | CH$_2$ | O | CH(CH$_3$)CF$_3$ |
| P1593 | H | Cl | Cl | Cl | CF$_3$ | CF$_3$ | H | O | CH(CH$_3$) | O | CH$_2$CF$_3$ |
| P1594 | H | Cl | Cl | Cl | CF$_3$ | CF$_3$ | Br | O | CH(CH$_3$) | O | CH$_2$CF$_3$ |
| P1595 | H | Cl | Cl | Cl | CF$_3$ | CF$_3$ | Cl | O | CH(CH$_3$) | O | CH$_2$CF$_3$ |
| P1596 | H | Cl | Cl | Cl | CF$_3$ | CF$_3$ | CF$_3$ | O | CH(CH$_3$) | O | CH$_2$CF$_3$ |
| P1597 | H | Cl | Cl | Cl | CF$_3$ | CF$_3$ | CH$_3$ | O | CH(CH$_3$) | O | CH$_2$CF$_3$ |
| P1598 | H | Cl | Cl | Cl | CF$_2$CF$_3$ | H | H | O | CH(CH$_3$) | O | CH$_2$CF$_3$ |
| P1599 | H | Cl | Cl | Cl | CF$_2$CF$_3$ | H | Br | O | CH(CH$_3$) | O | CH$_2$CF$_3$ |
| P1600 | H | Cl | Cl | Cl | CF$_2$CF$_3$ | H | Cl | O | CH(CH$_3$) | O | CH$_2$CF$_3$ |
| P1601 | H | Cl | Cl | Cl | CF$_2$CF$_3$ | H | CF$_3$ | O | CH(CH$_3$) | O | CH$_2$CF$_3$ |
| P1602 | H | Cl | Cl | Cl | CF$_2$CF$_3$ | H | CH$_3$ | O | CH(CH$_3$) | O | CH$_2$CF$_3$ |
| P1603 | H | Cl | Cl | Cl | CF$_3$ | H | H | O | CH(CH$_3$) | O | CH$_2$CF$_3$ |
| P1604 | H | Cl | Cl | Cl | CF$_3$ | H | H | O | CH(CH$_3$) | S | CH$_2$CF$_3$ |
| P1605 | H | Cl | Cl | Cl | CF$_3$ | H | H | S | CH(CH$_3$) | O | CH$_2$CF$_3$ |
| P1606 | H | Cl | Cl | Cl | CF$_3$ | H | Br | S | CH(CH$_3$) | O | CH$_2$CF$_3$ |
| P1607 | H | Cl | Cl | Cl | CF$_3$ | H | Cl | S | CH(CH$_3$) | O | CH$_2$CF$_3$ |
| P1608 | H | Cl | Cl | Cl | CF$_3$ | H | CF$_3$ | S | CH(CH$_3$) | O | CH$_2$CF$_3$ |
| P1609 | H | Cl | Cl | Cl | CF$_3$ | H | CH$_3$ | S | CH(CH$_3$) | O | CH$_2$CF$_3$ |
| P1610 | H | Cl | Cl | Cl | CF$_3$ | H | H | O | CH(CH$_3$) | O | CH$_2$CHF$_2$ |
| P1611 | H | Cl | Cl | Cl | CF$_3$ | H | Br | O | CH(CH$_3$) | O | CH$_2$CHF$_2$ |
| P1612 | H | Cl | Cl | Cl | CF$_3$ | H | Cl | O | CH(CH$_3$) | O | CH$_2$CHF$_2$ |
| P1613 | H | Cl | Cl | Cl | CF$_3$ | H | CF$_3$ | O | CH(CH$_3$) | O | CH$_2$CHF$_2$ |
| P1614 | H | Cl | Cl | Cl | CF$_3$ | H | CH$_3$ | O | CH(CH$_3$) | O | CH$_2$CHF$_2$ |
| P1615 | H | Cl | Cl | Cl | CF$_3$ | H | H | O | CH(CH$_3$) | O | CH$_2$CH$_2$F |
| P1616 | H | Cl | Cl | Cl | CF$_3$ | H | Br | O | CH(CH$_3$) | O | CH$_2$CH$_2$F |
| P1617 | H | Cl | Cl | Cl | CF$_3$ | H | Cl | O | CH(CH$_3$) | O | CH$_2$CH$_2$F |
| P1618 | H | Cl | Cl | Cl | CF$_3$ | H | CF$_3$ | O | CH(CH$_3$) | O | CH$_2$CH$_2$F |
| P1619 | H | Cl | Cl | Cl | CF$_3$ | H | CH$_3$ | O | CH(CH$_3$) | O | CH$_2$CH$_2$F |
| P1620 | H | Cl | Cl | Cl | CF$_3$ | H | H | O | CH(CH$_3$) | O | CH$_2$CH$_3$ |
| P1621 | H | Cl | Cl | Cl | CF$_3$ | H | Br | O | CH(CH$_3$) | O | CH$_2$CH$_3$ |
| P1622 | H | Cl | Cl | Cl | CF$_3$ | H | Cl | O | CH(CH$_3$) | O | CH$_2$CH$_3$ |
| P1623 | H | Cl | Cl | Cl | CF$_3$ | H | CF$_3$ | O | CH(CH$_3$) | O | CH$_2$CH$_3$ |
| P1624 | H | Cl | Cl | Cl | CF$_3$ | H | CH$_3$ | O | CH(CH$_3$) | O | CH$_2$CH$_3$ |
| P1625 | H | Cl | Cl | Cl | CF$_3$ | H | H | O | CH(CH$_3$) | O | CH(CH$_3$)CF$_3$ |
| P1626 | H | Cl | Cl | Cl | CF$_3$ | H | Br | O | CH(CH$_3$) | O | CH(CH$_3$)CF$_3$ |
| P1627 | H | Cl | Cl | Cl | CF$_3$ | H | Cl | O | CH(CH$_3$) | O | CH(CH$_3$)CF$_3$ |
| P1628 | H | Cl | Cl | Cl | CF$_3$ | H | CF$_3$ | O | CH(CH$_3$) | O | CH(CH$_3$)CF$_3$ |
| P1629 | H | Cl | Cl | Cl | CF$_3$ | H | CH$_3$ | O | CH(CH$_3$) | O | CH(CH$_3$)CF$_3$ |
| P1630 | H | Cl | Cl | Cl | CF$_3$ | H | H | O | CH(CH$_3$) | O | CH$_2$CH$_2$CF$_3$ |
| P1631 | H | Cl | Cl | Cl | CF$_3$ | H | Br | O | CH(CH$_3$) | O | CH$_2$CH$_2$CF$_3$ |
| P1632 | H | Cl | Cl | Cl | CF$_3$ | H | Cl | O | CH(CH$_3$) | O | CH$_2$CH$_2$CF$_3$ |
| P1633 | H | Cl | Cl | Cl | CF$_3$ | H | CF$_3$ | O | CH(CH$_3$) | O | CH$_2$CH$_2$CF$_3$ |
| P1634 | H | Cl | Cl | Cl | CF$_3$ | H | CH$_3$ | O | CH(CH$_3$) | O | CH$_2$CH$_2$CF$_3$ |
| P1635 | H | Cl | Cl | Cl | CF$_3$ | H | H | O | CH(CH$_2$CH$_3$) | O | CH$_2$CF$_3$ |
| P1636 | H | Cl | Cl | Cl | CF$_3$ | H | H | O | C(CH$_3$)$_2$ | O | CH$_2$CF$_3$ |
| P1637 | H | Cl | Cl | Cl | CF$_3$ | H | H | O | CH$_2$CH$_2$ | O | CH$_2$CF$_3$ |
| P1638 | H | Cl | Cl | Cl | CF$_3$ | H | Br | O | CH$_2$CH$_2$ | O | CH$_2$CF$_3$ |
| P1639 | H | Cl | Cl | Cl | CF$_3$ | H | Cl | O | CH$_2$CH$_2$ | O | CH$_2$CF$_3$ |
| P1640 | H | Cl | Cl | Cl | CF$_3$ | H | CF$_3$ | O | CH$_2$CH$_2$ | O | CH$_2$CF$_3$ |
| P1641 | H | Cl | Cl | Cl | CF$_3$ | H | CH$_3$ | O | CH$_2$CH$_2$ | O | CH$_2$CF$_3$ |
| P1642 | H | Cl | H | Cl | CF$_3$ | H | H | O | CH$_2$ | O | CH$_2$CF$_3$ |
| P1643 | H | Cl | H | Cl | CF$_3$ | H | Br | O | CH$_2$ | O | CH$_2$CF$_3$ |
| P1644 | H | Cl | H | Cl | CF$_3$ | H | CF$_3$ | O | CH$_2$ | O | CH$_2$CF$_3$ |
| P1645 | H | Cl | H | Cl | CF$_3$ | H | H | O | CH$_2$ | S | CH$_2$CF$_3$ |
| P1646 | H | Cl | H | Cl | CF$_3$ | H | Br | O | CH$_2$ | S | CH$_2$CF$_3$ |
| P1647 | H | Cl | H | Cl | CF$_3$ | H | Cl | O | CH$_2$ | S | CH$_2$CF$_3$ |
| P1648 | H | Cl | H | Cl | CF$_3$ | H | CF$_3$ | O | CH$_2$ | S | CH$_2$CF$_3$ |
| P1649 | H | Cl | H | Cl | CF$_3$ | H | CH$_3$ | O | CH$_2$ | S | CH$_2$CF$_3$ |
| P1650 | H | Cl | H | Cl | CF$_3$ | H | H | S | CH$_2$ | O | CH$_2$CF$_3$ |
| P1651 | H | Cl | H | Cl | CF$_3$ | H | Br | S | CH$_2$ | O | CH$_2$CF$_3$ |
| P1652 | H | Cl | H | Cl | CF$_3$ | H | Cl | S | CH$_2$ | O | CH$_2$CF$_3$ |
| P1653 | H | Cl | H | Cl | CF$_3$ | H | CF$_3$ | S | CH$_2$ | O | CH$_2$CF$_3$ |
| P1654 | H | Cl | H | Cl | CF$_3$ | H | CH$_3$ | S | CH$_2$ | O | CH$_2$CF$_3$ |
| P1655 | H | Cl | H | Cl | CF$_3$ | H | H | O | CH$_2$ | O | CH$_2$CHF$_2$ |
| P1656 | H | Cl | H | Cl | CF$_3$ | H | Br | O | CH$_2$ | O | CH$_2$CHF$_2$ |
| P1657 | H | Cl | H | Cl | CF$_3$ | H | Cl | O | CH$_2$ | O | CH$_2$CHF$_2$ |
| P1658 | H | Cl | H | Cl | CF$_3$ | H | CF$_3$ | O | CH$_2$ | O | CH$_2$CHF$_2$ |
| P1659 | H | Cl | H | Cl | CF$_3$ | H | CH$_3$ | O | CH$_2$ | O | CH$_2$CHF$_2$ |
| P1660 | H | Cl | H | Cl | CF$_3$ | H | H | O | CH$_2$ | O | CH$_2$CH$_2$F |
| P1661 | H | Cl | H | Cl | CF$_3$ | H | Br | O | CH$_2$ | O | CH$_2$CH$_2$F |
| P1662 | H | Cl | H | Cl | CF$_3$ | H | Cl | O | CH$_2$ | O | CH$_2$CH$_2$F |
| P1663 | H | Cl | H | Cl | CF$_3$ | H | CF$_3$ | O | CH$_2$ | O | CH$_2$CH$_2$F |
| P1664 | H | Cl | H | Cl | CF$_3$ | H | CH$_3$ | O | CH$_2$ | O | CH$_2$CH$_2$F |
| P1665 | H | Cl | H | Cl | CF$_3$ | H | H | O | CH$_2$ | O | CH$_2$CH$_3$ |
| P1666 | H | Cl | H | Cl | CF$_3$ | H | Br | O | CH$_2$ | O | CH$_2$CH$_3$ |
| P1667 | H | Cl | H | Cl | CF$_3$ | H | Cl | O | CH$_2$ | O | CH$_2$CH$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1668 | H | Cl | H | Cl | CF$_3$ | H | CF$_3$ | O | CH$_2$ | O | CH$_2$CH$_3$ |
| P1669 | H | Cl | H | Cl | CF$_3$ | H | CH$_3$ | O | CH$_2$ | O | CH$_2$CH$_3$ |
| P1670 | H | Cl | H | Cl | CF$_3$ | CF$_3$ | H | O | CH$_2$ | O | CH$_2$CF$_3$ |
| P1671 | H | Cl | H | Cl | CF$_3$ | CF$_3$ | Br | O | CH$_2$ | O | CH$_2$CF$_3$ |
| P1672 | H | Cl | H | Cl | CF$_3$ | CF$_3$ | Cl | O | CH$_2$ | O | CH$_2$CF$_3$ |
| P1673 | H | Cl | H | Cl | CF$_3$ | CF$_3$ | CF$_3$ | O | CH$_2$ | O | CH$_2$CF$_3$ |
| P1674 | H | Cl | H | Cl | CF$_3$ | CF$_3$ | CH$_3$ | O | CH$_2$ | O | CH$_2$CF$_3$ |
| P1675 | H | Cl | H | Cl | CF$_2$CF$_3$ | H | H | O | CH$_2$ | O | CH$_2$CF$_3$ |
| P1676 | H | Cl | H | Cl | CF$_2$CF$_3$ | H | Br | O | CH$_2$ | O | CH$_2$CF$_3$ |
| P1677 | H | Cl | H | Cl | CF$_2$CF$_3$ | H | Cl | O | CH$_2$ | O | CH$_2$CF$_3$ |
| P1678 | H | Cl | H | Cl | CF$_2$CF$_3$ | H | CF$_3$ | O | CH$_2$ | O | CH$_2$CF$_3$ |
| P1679 | H | Cl | H | Cl | CF$_2$CF$_3$ | H | CH$_3$ | O | CH$_2$ | O | CH$_2$CF$_3$ |
| P1680 | H | Cl | H | Cl | CF$_3$ | H | H | O | CH$_2$ | O | CH(CH$_3$)CF$_3$ |
| P1681 | H | Cl | H | Cl | CF$_3$ | H | Br | O | CH$_2$ | O | CH(CH$_3$)CF$_3$ |
| P1682 | H | Cl | H | Cl | CF$_3$ | H | Cl | O | CH$_2$ | O | CH(CH$_3$)CF$_3$ |
| P1683 | H | Cl | H | Cl | CF$_3$ | H | CF$_3$ | O | CH$_2$ | O | CH(CH$_3$)CF$_3$ |
| P1684 | H | Cl | H | Cl | CF$_3$ | H | CH$_3$ | O | CH$_2$ | O | CH(CH$_3$)CF$_3$ |
| P1685 | H | Cl | H | Cl | CF$_3$ | CF$_3$ | H | O | CH(CH$_3$) | O | CH$_2$CF$_3$ |
| P1686 | H | Cl | H | Cl | CF$_3$ | CF$_3$ | Br | O | CH(CH$_3$) | O | CH$_2$CF$_3$ |
| P1687 | H | Cl | H | Cl | CF$_3$ | CF$_3$ | Cl | O | CH(CH$_3$) | O | CH$_2$CF$_3$ |
| P1688 | H | Cl | H | Cl | CF$_3$ | CF$_3$ | CF$_3$ | O | CH(CH$_3$) | O | CH$_2$CF$_3$ |
| P1689 | H | Cl | H | Cl | CF$_3$ | CF$_3$ | CH$_3$ | O | CH(CH$_3$) | O | CH$_2$CF$_3$ |
| P1690 | H | Cl | H | Cl | CF$_2$CF$_3$ | H | H | O | CH(CH$_3$) | O | CH$_2$CF$_3$ |
| P1691 | H | Cl | H | Cl | CF$_2$CF$_3$ | H | Br | O | CH(CH$_3$) | O | CH$_2$CF$_3$ |
| P1692 | H | Cl | H | Cl | CF$_2$CF$_3$ | H | Cl | O | CH(CH$_3$) | O | CH$_2$CF$_3$ |
| P1693 | H | Cl | H | Cl | CF$_2$CF$_3$ | H | CF$_3$ | O | CH(CH$_3$) | O | CH$_2$CF$_3$ |
| P1694 | H | Cl | H | Cl | CF$_2$CF$_3$ | H | CH$_3$ | O | CH(CH$_3$) | O | CH$_2$CF$_3$ |
| P1695 | H | Cl | H | Cl | CF$_3$ | H | H | O | CH(CH$_3$) | O | CH$_2$CF$_3$ |
| P1696 | H | Cl | H | Cl | CF$_3$ | H | Br | O | CH(CH$_3$) | O | CH$_2$CF$_3$ |
| P1697 | H | Cl | H | Cl | CF$_3$ | H | Cl | O | CH(CH$_3$) | O | CH$_2$CF$_3$ |
| P1698 | H | Cl | H | Cl | CF$_3$ | H | CF$_3$ | O | CH(CH$_3$) | O | CH$_2$CF$_3$ |
| P1699 | H | Cl | H | Cl | CF$_3$ | H | CH$_3$ | O | CH(CH$_3$) | O | CH$_2$CF$_3$ |
| P1700 | H | Cl | H | Cl | CF$_3$ | H | H | O | CH(CH$_3$) | S | CH$_2$CF$_3$ |
| P1701 | H | Cl | H | Cl | CF$_3$ | H | Br | O | CH(CH$_3$) | S | CH$_2$CF$_3$ |
| P1702 | H | Cl | H | Cl | CF$_3$ | H | Cl | O | CH(CH$_3$) | S | CH$_2$CF$_3$ |
| P1703 | H | Cl | H | Cl | CF$_3$ | H | CF$_3$ | O | CH(CH$_3$) | S | CH$_2$CF$_3$ |
| P1704 | H | Cl | H | Cl | CF$_3$ | H | CH$_3$ | O | CH(CH$_3$) | S | CH$_2$CF$_3$ |
| P1705 | H | Cl | H | Cl | CF$_3$ | H | H | S | CH(CH$_3$) | O | CH$_2$CF$_3$ |
| P1706 | H | Cl | H | Cl | CF$_3$ | H | Br | S | CH(CH$_3$) | O | CH$_2$CF$_3$ |
| P1707 | H | Cl | H | Cl | CF$_3$ | H | Cl | S | CH(CH$_3$) | O | CH$_2$CF$_3$ |
| P1708 | H | Cl | H | Cl | CF$_3$ | H | CF$_3$ | S | CH(CH$_3$) | O | CH$_2$CF$_3$ |
| P1709 | H | Cl | H | Cl | CF$_3$ | H | CH$_3$ | S | CH(CH$_3$) | O | CH$_2$CF$_3$ |
| P1710 | H | Cl | H | Cl | CF$_3$ | H | H | O | CH(CH$_3$) | O | CH$_2$CHF$_2$ |
| P1711 | H | Cl | H | Cl | CF$_3$ | H | Br | O | CH(CH$_3$) | O | CH$_2$CHF$_2$ |
| P1712 | H | Cl | H | Cl | CF$_3$ | H | Cl | O | CH(CH$_3$) | O | CH$_2$CHF$_2$ |
| P1713 | H | Cl | H | Cl | CF$_3$ | H | CF$_3$ | O | CH(CH$_3$) | O | CH$_2$CHF$_2$ |
| P1714 | H | Cl | H | Cl | CF$_3$ | H | CH$_3$ | O | CH(CH$_3$) | O | CH$_2$CHF$_2$ |
| P1715 | H | Cl | H | Cl | CF$_3$ | H | H | O | CH(CH$_3$) | O | CH$_2$CH$_2$F |
| P1716 | H | Cl | H | Cl | CF$_3$ | H | Br | O | CH(CH$_3$) | O | CH$_2$CH$_2$F |
| P1717 | H | Cl | H | Cl | CF$_3$ | H | Cl | O | CH(CH$_3$) | O | CH$_2$CH$_2$F |
| P1718 | H | Cl | H | Cl | CF$_3$ | H | CF$_3$ | O | CH(CH$_3$) | O | CH$_2$CH$_2$F |
| P1719 | H | Cl | H | Cl | CF$_3$ | H | CH$_3$ | O | CH(CH$_3$) | O | CH$_2$CH$_2$F |
| P1720 | H | Cl | H | Cl | CF$_3$ | H | H | O | CH(CH$_3$) | O | CH$_2$CH$_3$ |
| P1721 | H | Cl | H | Cl | CF$_3$ | H | Br | O | CH(CH$_3$) | O | CH$_2$CH$_3$ |
| P1722 | H | Cl | H | Cl | CF$_3$ | H | Cl | O | CH(CH$_3$) | O | CH$_2$CH$_3$ |
| P1723 | H | Cl | H | Cl | CF$_3$ | H | CF$_3$ | O | CH(CH$_3$) | O | CH$_2$CH$_3$ |
| P1724 | H | Cl | H | Cl | CF$_3$ | H | CH$_3$ | O | CH(CH$_3$) | O | CH$_2$CH$_3$ |
| P1725 | H | Cl | H | Cl | CF$_3$ | H | H | O | CH(CH$_3$) | O | CH(CH$_3$)CF$_3$ |
| P1726 | H | Cl | H | Cl | CF$_3$ | H | Br | O | CH(CH$_3$) | O | CH(CH$_3$)CF$_3$ |
| P1727 | H | Cl | H | Cl | CF$_3$ | H | Cl | O | CH(CH$_3$) | O | CH(CH$_3$)CF$_3$ |
| P1728 | H | Cl | H | Cl | CF$_3$ | H | CF$_3$ | O | CH(CH$_3$) | O | CH(CH$_3$)CF$_3$ |
| P1729 | H | Cl | H | Cl | CF$_3$ | H | CH$_3$ | O | CH(CH$_3$) | O | CH(CH$_3$)CF$_3$ |
| P1730 | H | Cl | H | Cl | CF$_3$ | H | H | O | CH(CH$_3$) | O | CH$_2$CH$_2$CF$_3$ |
| P1731 | H | Cl | H | Cl | CF$_3$ | H | Br | O | CH(CH$_3$) | O | CH$_2$CH$_2$CF$_3$ |
| P1732 | H | Cl | H | Cl | CF$_3$ | H | Cl | O | CH(CH$_3$) | O | CH$_2$CH$_2$CF$_3$ |
| P1733 | H | Cl | H | Cl | CF$_3$ | H | CF$_3$ | O | CH(CH$_3$) | O | CH$_2$CH$_2$CF$_3$ |
| P1734 | H | Cl | H | Cl | CF$_3$ | H | CH$_3$ | O | CH(CH$_3$) | O | CH$_2$CH$_2$CF$_3$ |
| P1735 | H | Cl | H | Cl | CF$_3$ | H | H | O | CH(CH$_2$CH$_3$) | O | CH$_2$CF$_3$ |
| P1736 | H | Cl | H | Cl | CF$_3$ | H | Br | O | CH(CH$_2$CH$_3$) | O | CH$_2$CF$_3$ |
| P1737 | H | Cl | H | Cl | CF$_3$ | H | Cl | O | CH(CH$_2$CH$_3$) | O | CH$_2$CF$_3$ |
| P1738 | H | Cl | H | Cl | CF$_3$ | H | CF$_3$ | O | CH(CH$_2$CH$_3$) | O | CH$_2$CF$_3$ |
| P1739 | H | Cl | H | Cl | CF$_3$ | H | CH$_3$ | O | CH(CH$_2$CH$_3$) | O | CH$_2$CF$_3$ |
| P1740 | H | Cl | H | Cl | CF$_3$ | H | H | O | C(CH$_3$)$_2$ | O | CH$_2$CF$_3$ |
| P1741 | H | Cl | H | Cl | CF$_3$ | H | Br | O | C(CH$_3$)$_2$ | O | CH$_2$CF$_3$ |
| P1742 | H | Cl | H | Cl | CF$_3$ | H | Cl | O | C(CH$_3$)$_2$ | O | CH$_2$CF$_3$ |
| P1743 | H | Cl | H | Cl | CF$_3$ | H | CF$_3$ | O | C(CH$_3$)$_2$ | O | CH$_2$CF$_3$ |
| P1744 | H | Cl | H | Cl | CF$_3$ | H | CH$_3$ | O | C(CH$_3$)$_2$ | O | CH$_2$CF$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1745 | H | Cl | H | Cl | CF$_3$ | H | H | O | CH$_2$CH$_2$ | O | CH$_2$CF$_3$ |
| P1746 | H | Cl | H | Cl | CF$_3$ | H | Br | O | CH$_2$CH$_2$ | O | CH$_2$CF$_3$ |
| P1747 | H | Cl | H | Cl | CF$_3$ | H | Cl | O | CH$_2$CH$_2$ | O | CH$_2$CF$_3$ |
| P1748 | H | Cl | H | Cl | CF$_3$ | H | CF$_3$ | O | CH$_2$CH$_2$ | O | CH$_2$CF$_3$ |
| P1749 | H | Cl | H | Cl | CF$_3$ | H | CH$_3$ | O | CH$_2$CH$_2$ | O | CH$_2$CF$_3$ |
| P1750 | H | H | Cl | Cl | CF$_3$ | H | H | O | CH$_2$ | O | CH$_2$CF$_3$ |
| P1751 | H | H | Cl | Cl | CF$_3$ | H | Br | O | CH$_2$ | O | CH$_2$CF$_3$ |
| P1752 | H | H | Cl | Cl | CF$_3$ | H | Cl | O | CH$_2$ | O | CH$_2$CF$_3$ |
| P1753 | H | H | Cl | Cl | CF$_3$ | H | CF$_3$ | O | CH$_2$ | O | CH$_2$CF$_3$ |
| P1754 | H | H | Cl | Cl | CF$_3$ | H | CH$_3$ | O | CH$_2$ | O | CH$_2$CF$_3$ |
| P1755 | H | H | Cl | Cl | CF$_3$ | H | H | O | CH$_2$ | S | CH$_2$CF$_3$ |
| P1756 | H | H | Cl | Cl | CF$_3$ | H | Br | O | CH$_2$ | S | CH$_2$CF$_3$ |
| P1757 | H | H | Cl | Cl | CF$_3$ | H | Cl | O | CH$_2$ | S | CH$_2$CF$_3$ |
| P1758 | H | H | Cl | Cl | CF$_3$ | H | CF$_3$ | O | CH$_2$ | S | CH$_2$CF$_3$ |
| P1759 | H | H | Cl | Cl | CF$_3$ | H | CH$_3$ | O | CH$_2$ | S | CH$_2$CF$_3$ |
| P1760 | H | H | Cl | Cl | CF$_3$ | H | H | S | CH$_2$ | O | CH$_2$CF$_3$ |
| P1761 | H | H | Cl | Cl | CF$_3$ | H | Br | S | CH$_2$ | O | CH$_2$CF$_3$ |
| P1762 | H | H | Cl | Cl | CF$_3$ | H | Cl | S | CH$_2$ | O | CH$_2$CF$_3$ |
| P1763 | H | H | Cl | Cl | CF$_3$ | H | CF$_3$ | S | CH$_2$ | O | CH$_2$CF$_3$ |
| P1764 | H | H | Cl | Cl | CF$_3$ | H | CH$_3$ | S | CH$_2$ | O | CH$_2$CF$_3$ |
| P1765 | H | H | Cl | Cl | CF$_3$ | H | H | O | CH$_2$ | O | CH$_2$CHF$_2$ |
| P1766 | H | H | Cl | Cl | CF$_3$ | H | Br | O | CH$_2$ | O | CH$_2$CHF$_2$ |
| P1767 | H | H | Cl | Cl | CF$_3$ | H | Cl | O | CH$_2$ | O | CH$_2$CHF$_2$ |
| P1768 | H | H | Cl | Cl | CF$_3$ | H | CF$_3$ | O | CH$_2$ | O | CH$_2$CHF$_2$ |
| P1769 | H | H | Cl | Cl | CF$_3$ | H | CH$_3$ | O | CH$_2$ | O | CH$_2$CHF$_2$ |
| P1770 | H | H | Cl | Cl | CF$_3$ | H | H | O | CH$_2$ | O | CH$_2$CH$_2$F |
| P1771 | H | H | Cl | Cl | CF$_3$ | H | Br | O | CH$_2$ | O | CH$_2$CH$_2$F |
| P1772 | H | H | Cl | Cl | CF$_3$ | H | Cl | O | CH$_2$ | O | CH$_2$CH$_2$F |
| P1773 | H | H | Cl | Cl | CF$_3$ | H | CF$_3$ | O | CH$_2$ | O | CH$_2$CH$_2$F |
| P1774 | H | H | Cl | Cl | CF$_3$ | H | CH$_3$ | O | CH$_2$ | O | CH$_2$CH$_2$F |
| P1775 | H | H | Cl | Cl | CF$_3$ | H | H | O | CH$_2$ | O | CH$_2$CH$_3$ |
| P1776 | H | H | Cl | Cl | CF$_3$ | H | Br | O | CH$_2$ | O | CH$_2$CH$_3$ |
| P1777 | H | H | Cl | Cl | CF$_3$ | H | Cl | O | CH$_2$ | O | CH$_2$CH$_3$ |
| P1778 | H | H | Cl | Cl | CF$_3$ | H | CF$_3$ | O | CH$_2$ | O | CH$_2$CH$_3$ |
| P1779 | H | H | Cl | Cl | CF$_3$ | H | CH$_3$ | O | CH$_2$ | O | CH$_2$CH$_3$ |
| P1780 | H | H | Cl | Cl | CF$_3$ | CF$_3$ | H | O | CH$_2$ | O | CH$_2$CF$_3$ |
| P1781 | H | H | Cl | Cl | CF$_3$ | CF$_3$ | Br | O | CH$_2$ | O | CH$_2$CF$_3$ |
| P1782 | H | H | Cl | Cl | CF$_3$ | CF$_3$ | Cl | O | CH$_2$ | O | CH$_2$CF$_3$ |
| P1783 | H | H | Cl | Cl | CF$_3$ | CF$_3$ | CF$_3$ | O | CH$_2$ | O | CH$_2$CF$_3$ |
| P1784 | H | H | Cl | Cl | CF$_3$ | CF$_3$ | CH$_3$ | O | CH$_2$ | O | CH$_2$CF$_3$ |
| P1785 | H | H | Cl | Cl | CF$_2$CF$_3$ | H | H | O | CH$_2$ | O | CH$_2$CF$_3$ |
| P1786 | H | H | Cl | Cl | CF$_2$CF$_3$ | H | Br | O | CH$_2$ | O | CH$_2$CF$_3$ |
| P1787 | H | H | Cl | Cl | CF$_2$CF$_3$ | H | Cl | O | CH$_2$ | O | CH$_2$CF$_3$ |
| P1788 | H | H | Cl | Cl | CF$_2$CF$_3$ | H | CF$_3$ | O | CH$_2$ | O | CH$_2$CF$_3$ |
| P1789 | H | H | Cl | Cl | CF$_2$CF$_3$ | H | CH$_3$ | O | CH$_2$ | O | CH$_2$CF$_3$ |
| P1790 | H | H | Cl | Cl | CF$_3$ | H | H | O | CH$_2$ | O | CH(CH$_3$)CF$_3$ |
| P1791 | H | H | Cl | Cl | CF$_3$ | H | Br | O | CH$_2$ | O | CH(CH$_3$)CF$_3$ |
| P1792 | H | H | Cl | Cl | CF$_3$ | H | Cl | O | CH$_2$ | O | CH(CH$_3$)CF$_3$ |
| P1793 | H | H | Cl | Cl | CF$_3$ | H | CF$_3$ | O | CH$_2$ | O | CH(CH$_3$)CF$_3$ |
| P1794 | H | H | Cl | Cl | CF$_3$ | H | CH$_3$ | O | CH$_2$ | O | CH(CH$_3$)CF$_3$ |
| P1795 | H | H | Cl | Cl | CF$_3$ | CF$_3$ | H | O | CH(CH$_3$) | O | CH$_2$CF$_3$ |
| P1796 | H | H | Cl | Cl | CF$_3$ | CF$_3$ | Br | O | CH(CH$_3$) | O | CH$_2$CF$_3$ |
| P1797 | H | H | Cl | Cl | CF$_3$ | CF$_3$ | Cl | O | CH(CH$_3$) | O | CH$_2$CF$_3$ |
| P1798 | H | H | Cl | Cl | CF$_3$ | CF$_3$ | CF$_3$ | O | CH(CH$_3$) | O | CH$_2$CF$_3$ |
| P1799 | H | H | Cl | Cl | CF$_3$ | CF$_3$ | CH$_3$ | O | CH(CH$_3$) | O | CH$_2$CF$_3$ |
| P1800 | H | H | Cl | Cl | CF$_2$CF$_3$ | H | H | O | CH(CH$_3$) | O | CH$_2$CF$_3$ |
| P1801 | H | H | Cl | Cl | CF$_2$CF$_3$ | H | Br | O | CH(CH$_3$) | O | CH$_2$CF$_3$ |
| P1802 | H | H | Cl | Cl | CF$_2$CF$_3$ | H | Cl | O | CH(CH$_3$) | O | CH$_2$CF$_3$ |
| P1803 | H | H | Cl | Cl | CF$_2$CF$_3$ | H | CF$_3$ | O | CH(CH$_3$) | O | CH$_2$CF$_3$ |
| P1804 | H | H | Cl | Cl | CF$_2$CF$_3$ | H | CH$_3$ | O | CH(CH$_3$) | O | CH$_2$CF$_3$ |
| P1805 | H | H | Cl | Cl | CF$_3$ | H | H | O | CH(CH$_3$) | O | CH$_2$CF$_3$ |
| P1806 | H | H | Cl | Cl | CF$_3$ | H | Br | O | CH(CH$_3$) | O | CH$_2$CF$_3$ |
| P1807 | H | H | Cl | Cl | CF$_3$ | H | Cl | O | CH(CH$_3$) | O | CH$_2$CF$_3$ |
| P1808 | H | H | Cl | Cl | CF$_3$ | H | CF$_3$ | O | CH(CH$_3$) | O | CH$_2$CF$_3$ |
| P1809 | H | H | Cl | Cl | CF$_3$ | H | CH$_3$ | O | CH(CH$_3$) | O | CH$_2$CF$_3$ |
| P1810 | H | H | Cl | Cl | CF$_3$ | H | H | O | CH(CH$_3$) | S | CH$_2$CF$_3$ |
| P1811 | H | H | Cl | Cl | CF$_3$ | H | Br | O | CH(CH$_3$) | S | CH$_2$CF$_3$ |
| P1812 | H | H | Cl | Cl | CF$_3$ | H | Cl | O | CH(CH$_3$) | S | CH$_2$CF$_3$ |
| P1813 | H | H | Cl | Cl | CF$_3$ | H | CF$_3$ | O | CH(CH$_3$) | S | CH$_2$CF$_3$ |
| P1814 | H | H | Cl | Cl | CF$_3$ | H | CH$_3$ | O | CH(CH$_3$) | S | CH$_2$CF$_3$ |
| P1815 | H | H | Cl | Cl | CF$_3$ | H | H | S | CH(CH$_3$) | O | CH$_2$CF$_3$ |
| P1816 | H | H | Cl | Cl | CF$_3$ | H | Br | S | CH(CH$_3$) | O | CH$_2$CF$_3$ |
| P1817 | H | H | Cl | Cl | CF$_3$ | H | Cl | S | CH(CH$_3$) | O | CH$_2$CF$_3$ |
| P1818 | H | H | Cl | Cl | CF$_3$ | H | CF$_3$ | S | CH(CH$_3$) | O | CH$_2$CF$_3$ |
| P1819 | H | H | Cl | Cl | CF$_3$ | H | CH$_3$ | S | CH(CH$_3$) | O | CH$_2$CF$_3$ |
| P1820 | H | H | Cl | Cl | CF$_3$ | H | H | O | CH(CH$_3$) | O | CH$_2$CHF$_2$ |
| P1821 | H | H | Cl | Cl | CF$_3$ | H | Br | O | CH(CH$_3$) | O | CH$_2$CHF$_2$ |

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1822 | H | H | Cl | Cl | CF₃ | H | Cl | O | CH(CH₃) | O | CH₂CHF₂ |
| P1823 | H | H | Cl | Cl | CF₃ | H | CF₃ | O | CH(CH₃) | O | CH₂CHF₂ |
| P1824 | H | H | Cl | Cl | CF₃ | H | CH₃ | O | CH(CH₃) | O | CH₂CHF₂ |
| P1825 | H | H | Cl | Cl | CF₃ | H | H | O | CH(CH₃) | O | CH₂CH₂F |
| P1826 | H | H | Cl | Cl | CF₃ | H | Br | O | CH(CH₃) | O | CH₂CH₂F |
| P1827 | H | H | Cl | Cl | CF₃ | H | Cl | O | CH(CH₃) | O | CH₂CH₂F |
| P1828 | H | H | Cl | Cl | CF₃ | H | CF₃ | O | CH(CH₃) | O | CH₂CH₂F |
| P1829 | H | H | Cl | Cl | CF₃ | H | CH₃ | O | CH(CH₃) | O | CH₂CH₂F |
| P1830 | H | H | Cl | Cl | CF₃ | H | H | O | CH(CH₃) | O | CH₂CH₃ |
| P1831 | H | H | Cl | Cl | CF₃ | H | Br | O | CH(CH₃) | O | CH₂CH₃ |
| P1832 | H | H | Cl | Cl | CF₃ | H | Cl | O | CH(CH₃) | O | CH₂CH₃ |
| P1833 | H | H | Cl | Cl | CF₃ | H | CF₃ | O | CH(CH₃) | O | CH₂CH₃ |
| P1834 | H | H | Cl | Cl | CF₃ | H | CH₃ | O | CH(CH₃) | O | CH₂CH₃ |
| P1835 | H | H | Cl | Cl | CF₃ | H | H | O | CH(CH₃) | O | CH(CH₃)CF₃ |
| P1836 | H | H | Cl | Cl | CF₃ | H | Br | O | CH(CH₃) | O | CH(CH₃)CF₃ |
| P1837 | H | H | Cl | Cl | CF₃ | H | Cl | O | CH(CH₃) | O | CH(CH₃)CF₃ |
| P1838 | H | H | Cl | Cl | CF₃ | H | CF₃ | O | CH(CH₃) | O | CH(CH₃)CF₃ |
| P1839 | H | H | Cl | Cl | CF₃ | H | CH₃ | O | CH(CH₃) | O | CH(CH₃)CF₃ |
| P1840 | H | H | Cl | Cl | CF₃ | H | H | O | CH(CH₃) | O | CH₂CH₂CF₃ |
| P1841 | H | H | Cl | Cl | CF₃ | H | Br | O | CH(CH₃) | O | CH₂CH₂CF₃ |
| P1842 | H | H | Cl | Cl | CF₃ | H | Cl | O | CH(CH₃) | O | CH₂CH₂CF₃ |
| P1843 | H | H | Cl | Cl | CF₃ | H | CF₃ | O | CH(CH₃) | O | CH₂CH₂CF₃ |
| P1844 | H | H | Cl | Cl | CF₃ | H | CH₃ | O | CH(CH₃) | O | CH₂CH₂CF₃ |
| P1845 | H | H | Cl | Cl | CF₃ | H | H | O | CH(CH₂CH₃) | O | CH₂CF₃ |
| P1846 | H | H | Cl | Cl | CF₃ | H | Br | O | CH(CH₂CH₃) | O | CH₂CF₃ |
| P1847 | H | H | Cl | Cl | CF₃ | H | Cl | O | CH(CH₂CH₃) | O | CH₂CF₃ |
| P1848 | H | H | Cl | Cl | CF₃ | H | CF₃ | O | CH(CH₂CH₃) | O | CH₂CF₃ |
| P1849 | H | H | Cl | Cl | CF₃ | H | CH₃ | O | CH(CH₂CH₃) | O | CH₂CF₃ |
| P1850 | V | H | Cl | Cl | CF₃ | H | H | O | C(CH₃)₂ | O | CH₂CF₃ |
| P1851 | H | H | Cl | Cl | CF₃ | H | Br | O | C(CH₃)₂ | O | CH₂CF₃ |
| P1852 | H | H | Cl | Cl | CF₃ | H | Cl | O | C(CH₃)₂ | O | CH₂CF₃ |
| P1853 | H | H | Cl | Cl | CF₃ | H | CF₃ | O | C(CH₃)₂ | O | CH₂CF₃ |
| P1854 | H | H | Cl | Cl | CF₃ | H | CH₃ | O | C(CH₃)₂ | O | CH₂CF₃ |
| P1855 | H | H | Cl | Cl | CF₃ | H | H | O | CH₂CH₂ | O | CH₂CF₃ |
| P1856 | H | H | Cl | Cl | CF₃ | H | Br | O | CH₂CH₂ | O | CH₂CF₃ |
| P1857 | H | H | Cl | Cl | CF₃ | H | Cl | O | CH₂CH₂ | O | CH₂CF₃ |
| P1858 | H | H | Cl | Cl | CF₃ | H | CF₃ | O | CH₂CH₂ | O | CH₂CF₃ |
| P1859 | H | H | Cl | Cl | CF₃ | H | CH₃ | O | CH₂CH₂ | O | CH₂CF₃ |
| P1860 | H | Cl | F | Cl | CF₃ | H | H | O | CH₂ | O | CH₂CF₃ |
| P1861 | H | Cl | F | Cl | CF₃ | H | Cl | O | CH₂ | O | CH₂CF₃ |
| P1862 | H | Cl | F | Cl | CF₃ | H | CF₃ | O | CH₂ | O | CH₂CF₃ |
| P1863 | H | Cl | F | Cl | CF₃ | H | H | O | CH₂ | S | CH₂CF₃ |
| P1864 | H | Cl | F | Cl | CF₃ | H | Br | O | CH₂ | S | CH₂CF₃ |
| P1865 | H | Cl | F | Cl | CF₃ | H | Cl | O | CH₂ | S | CH₂CF₃ |
| P1866 | H | Cl | F | Cl | CF₃ | H | CF₃ | O | CH₂ | S | CH₂CF₃ |
| P1867 | H | Cl | F | Cl | CF₃ | H | CH₃ | O | CH₂ | S | CH₂CF₃ |
| P1868 | H | Cl | F | Cl | CF₃ | H | H | S | CH₂ | O | CH₂CF₃ |
| P1869 | H | Cl | F | Cl | CF₃ | H | Br | S | CH₂ | O | CH₂CF₃ |
| P1870 | H | Cl | F | Cl | CF₃ | H | Cl | S | CH₂ | O | CH₂CF₃ |
| P1871 | H | Cl | F | Cl | CF₃ | H | CF₃ | S | CH₂ | O | CH₂CF₃ |
| P1872 | H | Cl | F | Cl | CF₃ | H | CH₃ | S | CH₂ | O | CH₂CF₃ |
| P1873 | H | Cl | F | Cl | CF₃ | H | H | O | CH₂ | O | CH₂CHF₂ |
| P1874 | H | Cl | F | Cl | CF₃ | H | Br | O | CH₂ | O | CH₂CHF₂ |
| P1875 | H | Cl | F | Cl | CF₃ | H | Cl | O | CH₂ | O | CH₂CHF₂ |
| P1876 | H | Cl | F | Cl | CF₃ | H | CF₃ | O | CH₂ | O | CH₂CHF₂ |
| P1877 | H | Cl | F | Cl | CF₃ | H | CH₃ | O | CH₂ | O | CH₂CHF₂ |
| P1878 | H | Cl | F | Cl | CF₃ | H | H | O | CH₂ | O | CH₂CH₂F |
| P1879 | H | Cl | F | Cl | CF₃ | H | Br | O | CH₂ | O | CH₂CH₂F |
| P1880 | H | Cl | F | Cl | CF₃ | H | Cl | O | CH₂ | O | CH₂CH₂F |
| P1881 | H | Cl | F | Cl | CF₃ | H | CF₃ | O | CH₂ | O | CH₂CH₂F |
| P1882 | H | Cl | F | Cl | CF₃ | H | CH₃ | O | CH₂ | O | CH₂CH₂F |
| P1883 | H | Cl | F | Cl | CF₃ | H | H | O | CH₂ | O | CH₂CH₃ |
| P1884 | H | Cl | F | Cl | CF₃ | H | Br | O | CH₂ | O | CH₂CH₃ |
| P1885 | H | Cl | F | Cl | CF₃ | H | Cl | O | CH₂ | O | CH₂CH₃ |
| P1886 | H | Cl | F | Cl | CF₃ | H | CF₃ | O | CH₂ | O | CH₂CH₃ |
| P1887 | H | Cl | F | Cl | CF₃ | H | CH₃ | O | CH₂ | O | CH₂CH₃ |
| P1888 | H | Cl | F | Cl | CF₃ | CF₃ | H | O | CH₂ | O | CH₂CF₃ |
| P1889 | H | Cl | F | Cl | CF₃ | CF₃ | Br | O | CH₂ | O | CH₂CF₃ |
| P1890 | H | Cl | F | Cl | CF₃ | CF₃ | Cl | O | CH₂ | O | CH₂CF₃ |
| P1891 | H | Cl | F | Cl | CF₃ | CF₃ | CF₃ | O | CH₂ | O | CH₂CF₃ |
| P1892 | H | Cl | F | Cl | CF₃ | CF₃ | CH₃ | O | CH₂ | O | CH₂CF₃ |
| P1893 | H | Cl | F | Cl | CF₂CF₃ | H | H | O | CH₂ | O | CH₂CF₃ |
| P1894 | H | Cl | F | Cl | CF₂CF₃ | H | Br | O | CH₂ | O | CH₂CF₃ |
| P1895 | H | Cl | F | Cl | CF₂CF₃ | H | Cl | O | CH₂ | O | CH₂CF₃ |
| P1896 | H | Cl | F | Cl | CF₂CF₃ | H | CF₃ | O | CH₂ | O | CH₂CF₃ |
| P1897 | H | Cl | F | Cl | CF₂CF₃ | H | CH₃ | O | CH₂ | O | CH₂CF₃ |
| P1898 | H | Cl | F | Cl | CF₃ | H | H | O | CH₂ | O | CH(CH₃)CF₃ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1899 | H | Cl | F | Cl | $CF_3$ | H | Br | O | $CH_2$ | O | $CH(CH_3)CF_3$ |
| P1900 | H | Cl | F | Cl | $CF_3$ | H | Cl | O | $CH_2$ | O | $CH(CH_3)CF_3$ |
| P1901 | H | Cl | F | Cl | $CF_3$ | H | $CF_3$ | O | $CH_2$ | O | $CH(CH_3)CF_3$ |
| P1902 | H | Cl | F | Cl | $CF_3$ | H | $CH_3$ | O | $CH_2$ | O | $CH(CH_3)CF_3$ |
| P1903 | H | Cl | F | Cl | $CF_3$ | $CF_3$ | H | O | $CH(CH_3)$ | O | $CH_2CF_3$ |
| P1904 | H | Cl | F | Cl | $CF_3$ | $CF_3$ | Br | O | $CH(CH_3)$ | O | $CH_2CF_3$ |
| P1905 | H | Cl | F | Cl | $CF_3$ | $CF_3$ | Cl | O | $CH(CH_3)$ | O | $CH_2CF_3$ |
| P1906 | H | Cl | F | Cl | $CF_3$ | $CF_3$ | $CF_3$ | O | $CH(CH_3)$ | O | $CH_2CF_3$ |
| P1907 | H | Cl | F | Cl | $CF_3$ | $CF_3$ | $CH_3$ | O | $CH(CH_3)$ | O | $CH_2CF_3$ |
| P1908 | H | Cl | F | Cl | $CF_2CF_3$ | H | H | O | $CH(CH_3)$ | O | $CH_2CF_3$ |
| P1909 | H | Cl | F | Cl | $CF_2CF_3$ | H | Br | O | $CH(CH_3)$ | O | $CH_2CF_3$ |
| P1910 | H | Cl | F | Cl | $CF_2CF_3$ | H | Cl | O | $CH(CH_3)$ | O | $CH_2CF_3$ |
| P1911 | H | Cl | F | Cl | $CF_2CF_3$ | H | $CF_3$ | O | $CH(CH_3)$ | O | $CH_2CF_3$ |
| P1912 | H | Cl | F | Cl | $CF_2CF_3$ | H | $CH_3$ | O | $CH(CH_3)$ | O | $CH_2CF_3$ |
| P1913 | H | Cl | F | Cl | $CF_3$ | H | H | O | $CH(CH_3)$ | O | $CH_2CF_3$ |
| P1914 | H | Cl | F | Cl | $CF_3$ | H | Br | O | $CH(CH_3)$ | O | $CH_2CF_3$ |
| P1915 | H | Cl | F | Cl | $CF_3$ | H | Cl | O | $CH(CH_3)$ | O | $CH_2CF_3$ |
| P1916 | H | Cl | F | Cl | $CF_3$ | H | $CF_3$ | O | $CH(CH_3)$ | O | $CH_2CF_3$ |
| P1917 | H | Cl | F | Cl | $CF_3$ | H | $CH_3$ | O | $CH(CH_3)$ | O | $CH_2CF_3$ |
| P1918 | H | Cl | F | Cl | $CF_3$ | H | H | O | $CH(CH_3)$ | S | $CH_2CF_3$ |
| P1919 | H | Cl | F | Cl | $CF_3$ | H | Br | O | $CH(CH_3)$ | S | $CH_2CF_3$ |
| P1920 | H | Cl | F | Cl | $CF_3$ | H | Cl | O | $CH(CH_3)$ | S | $CH_2CF_3$ |
| P1921 | H | Cl | F | Cl | $CF_3$ | H | $CF_3$ | O | $CH(CH_3)$ | S | $CH_2CF_3$ |
| P1922 | H | Cl | F | Cl | $CF_3$ | H | $CH_3$ | O | $CH(CH_3)$ | S | $CH_2CF_3$ |
| P1923 | H | Cl | F | Cl | $CF_3$ | H | H | S | $CH(CH_3)$ | O | $CH_2CF_3$ |
| P1924 | H | Cl | F | Cl | $CF_3$ | H | Br | S | $CH(CH_3)$ | O | $CH_2CF_3$ |
| P1925 | H | Cl | F | Cl | $CF_3$ | H | Cl | S | $CH(CH_3)$ | O | $CH_2CF_3$ |
| P1926 | H | Cl | F | Cl | $CF_3$ | H | $CF_3$ | S | $CH(CH_3)$ | O | $CH_2CF_3$ |
| P1927 | H | Cl | F | Cl | $CF_3$ | H | $CH_3$ | S | $CH(CH_3)$ | O | $CH_2CF_3$ |
| P1928 | H | Cl | F | Cl | $CF_3$ | H | H | O | $CH(CH_3)$ | O | $CH_2CHF_2$ |
| P1929 | H | Cl | F | Cl | $CF_3$ | H | Br | O | $CH(CH_3)$ | O | $CH_2CHF_2$ |
| P1930 | H | Cl | F | Cl | $CF_3$ | H | Cl | O | $CH(CH_3)$ | O | $CH_2CHF_2$ |
| P1931 | H | Cl | F | Cl | $CF_3$ | H | $CF_3$ | O | $CH(CH_3)$ | O | $CH_2CHF_2$ |
| P1932 | H | Cl | F | Cl | $CF_3$ | H | $CH_3$ | O | $CH(CH_3)$ | O | $CH_2CHF_2$ |
| P1933 | H | Cl | F | Cl | $CF_3$ | H | H | O | $CH(CH_3)$ | O | $CH_2CH_2F$ |
| P1934 | H | Cl | F | Cl | $CF_3$ | H | Br | O | $CH(CH_3)$ | O | $CH_2CH_2F$ |
| P1935 | H | Cl | F | Cl | $CF_3$ | H | Cl | O | $CH(CH_3)$ | O | $CH_2CH_2F$ |
| P1936 | H | Cl | F | Cl | $CF_3$ | H | $CF_3$ | O | $CH(CH_3)$ | O | $CH_2CH_2F$ |
| P1937 | H | Cl | F | Cl | $CF_3$ | H | $CH_3$ | O | $CH(CH_3)$ | O | $CH_2CH_2F$ |
| P1938 | H | Cl | F | Cl | $CF_3$ | H | H | O | $CH(CH_3)$ | O | $CH_2CH_3$ |
| P1939 | H | Cl | F | Cl | $CF_3$ | H | Br | O | $CH(CH_3)$ | O | $CH_2CH_3$ |
| P1940 | H | Cl | F | Cl | $CF_3$ | H | Cl | O | $CH(CH_3)$ | O | $CH_2CH_3$ |
| P1941 | H | Cl | F | Cl | $CF_3$ | H | $CF_3$ | O | $CH(CH_3)$ | O | $CH_2CH_3$ |
| P1942 | H | Cl | F | Cl | $CF_3$ | H | $CH_3$ | O | $CH(CH_3)$ | O | $CH_2CH_3$ |
| P1943 | H | Cl | F | Cl | $CF_3$ | H | H | O | $CH(CH_3)$ | O | $CH(CH_3)CF_3$ |
| P1944 | H | Cl | F | Cl | $CF_3$ | H | Br | O | $CH(CH_3)$ | O | $CH(CH_3)CF_3$ |
| P1945 | H | Cl | F | Cl | $CF_3$ | H | Cl | O | $CH(CH_3)$ | O | $CH(CH_3)CF_3$ |
| P1946 | H | Cl | F | Cl | $CF_3$ | H | $CF_3$ | O | $CH(CH_3)$ | O | $CH(CH_3)CF_3$ |
| P1947 | H | Cl | F | Cl | $CF_3$ | H | $CH_3$ | O | $CH(CH_3)$ | O | $CH(CH_3)CF_3$ |
| P1948 | H | Cl | F | Cl | $CF_3$ | H | H | O | $CH(CH_3)$ | O | $CH_2CH_2CF_3$ |
| P1949 | H | Cl | F | Cl | $CF_3$ | H | Br | O | $CH(CH_3)$ | O | $CH_2CH_2CF_3$ |
| P1950 | H | Cl | F | Cl | $CF_3$ | H | Cl | O | $CH(CH_3)$ | O | $CH_2CH_2CF_3$ |
| P1951 | H | Cl | F | Cl | $CF_3$ | H | $CF_3$ | O | $CH(CH_3)$ | O | $CH_2CH_2CF_3$ |
| P1952 | H | Cl | F | Cl | $CF_3$ | H | $CH_3$ | O | $CH(CH_3)$ | O | $CH_2CH_2CF_3$ |
| P1953 | H | Cl | F | Cl | $CF_3$ | H | H | O | $CH(CH_2CH_3)$ | O | $CH_2CF_3$ |
| P1954 | H | Cl | F | Cl | $CF_3$ | H | Br | O | $CH(CH_2CH_3)$ | O | $CH_2CF_3$ |
| P1955 | H | Cl | F | Cl | $CF_3$ | H | Cl | O | $CH(CH_2CH_3)$ | O | $CH_2CF_3$ |
| P1956 | H | Cl | F | Cl | $CF_3$ | H | $CF_3$ | O | $CH(CH_2CH_3)$ | O | $CH_2CF_3$ |
| P1957 | H | Cl | F | Cl | $CF_3$ | H | $CH_3$ | O | $CH(CH_2CH_3)$ | O | $CH_2CF_3$ |
| P1958 | H | Cl | F | Cl | $CF_3$ | H | H | O | $C(CH_3)_2$ | O | $CH_2CF_3$ |
| P1959 | H | Cl | F | Cl | $CF_3$ | H | Br | O | $C(CH_3)_2$ | O | $CH_2CF_3$ |
| P1960 | H | Cl | F | Cl | $CF_3$ | H | Cl | O | $C(CH_3)_2$ | O | $CH_2CF_3$ |
| P1961 | H | Cl | F | Cl | $CF_3$ | H | $CF_3$ | O | $C(CH_3)_2$ | O | $CH_2CF_3$ |
| P1962 | H | Cl | F | Cl | $CF_3$ | H | $CH_3$ | O | $C(CH_3)_2$ | O | $CH_2CF_3$ |
| P1963 | H | Cl | F | Cl | $CF_3$ | H | H | O | $CH_2CH_2$ | O | $CH_2CF_3$ |
| P1964 | H | Cl | F | Cl | $CF_3$ | H | Br | O | $CH_2CH_2$ | O | $CH_2CF_3$ |
| P1965 | H | Cl | F | Cl | $CF_3$ | H | Cl | O | $CH_2CH_2$ | O | $CH_2CF_3$ |
| P1966 | H | Cl | F | Cl | $CF_3$ | H | $CF_3$ | O | $CH_2CH_2$ | O | $CH_2CF_3$ |
| P1967 | H | Cl | F | Cl | $CF_3$ | H | $CH_3$ | O | $CH_2CH_2$ | O | $CH_2CF_3$ |
| P1968 | H | Br | H | Br | $CF_3$ | H | H | O | $CH_2$ | O | $CH_2CF_3$ |
| P1969 | H | Br | H | Br | $CF_3$ | H | Br | O | $CH_2$ | O | $CH_2CF_3$ |
| P1970 | H | Br | H | Br | $CF_3$ | H | Cl | O | $CH_2$ | O | $CH_2CF_3$ |
| P1971 | H | Br | H | Br | $CF_3$ | H | $CF_3$ | O | $CH_2$ | O | $CH_2CF_3$ |
| P1972 | H | Br | H | Br | $CF_3$ | H | $CH_3$ | O | $CH_2$ | O | $CH_2CF_3$ |
| P1973 | H | Br | H | Br | $CF_3$ | H | H | O | $CH_2$ | S | $CH_2CF_3$ |
| P1974 | H | Br | H | Br | $CF_3$ | H | Br | O | $CH_2$ | S | $CH_2CF_3$ |
| P1975 | H | Br | H | Br | $CF_3$ | H | Cl | O | $CH_2$ | S | $CH_2CF_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P1976 | H | Br | H | Br | CF$_3$ | H | CF$_3$ | O | CH$_2$ | S | CH$_2$CF$_3$ |
| P1977 | H | Br | H | Br | CF$_3$ | H | CH$_3$ | O | CH$_2$ | S | CH$_2$CF$_3$ |
| P1978 | H | Br | H | Br | CF$_3$ | H | H | S | CH$_2$ | O | CH$_2$CF$_3$ |
| P1979 | H | Br | H | Br | CF$_3$ | H | Br | S | CH$_2$ | O | CH$_2$CF$_3$ |
| P1980 | H | Br | H | Br | CF$_3$ | H | Cl | S | CH$_2$ | O | CH$_2$CF$_3$ |
| P1981 | H | Br | H | Br | CF$_3$ | H | CF$_3$ | S | CH$_2$ | O | CH$_2$CF$_3$ |
| P1982 | H | Br | H | Br | CF$_3$ | H | CH$_3$ | S | CH$_2$ | O | CH$_2$CF$_3$ |
| P1983 | H | Br | H | Br | CF$_3$ | H | H | O | CH$_2$ | O | CH$_2$CHF$_2$ |
| P1984 | H | Br | H | Br | CF$_3$ | H | Br | O | CH$_2$ | O | CH$_2$CHF$_2$ |
| P1985 | H | Br | H | Br | CF$_3$ | H | Cl | O | CH$_2$ | O | CH$_2$CHF$_2$ |
| P1986 | H | Br | H | Br | CF$_3$ | H | CF$_3$ | O | CH$_2$ | O | CH$_2$CHF$_2$ |
| P1987 | H | Br | H | Br | CF$_3$ | H | CH$_3$ | O | CH$_2$ | O | CH$_2$CHF$_2$ |
| P1988 | H | Br | H | Br | CF$_3$ | H | H | O | CH$_2$ | O | CH$_2$CH$_2$F |
| P1989 | H | Br | H | Br | CF$_3$ | H | Br | O | CH$_2$ | O | CH$_2$CH$_2$F |
| P1990 | H | Br | H | Br | CF$_3$ | H | Cl | O | CH$_2$ | O | CH$_2$CH$_2$F |
| P1991 | H | Br | H | Br | CF$_3$ | H | CF$_3$ | O | CH$_2$ | O | CH$_2$CH$_2$F |
| P1992 | H | Br | H | Br | CF$_3$ | H | CH$_3$ | O | CH$_2$ | O | CH$_2$CH$_2$F |
| P1993 | H | Br | H | Br | CF$_3$ | H | H | O | CH$_2$ | O | CH$_2$CH$_3$ |
| P1994 | H | Br | H | Br | CF$_3$ | H | Br | O | CH$_2$ | O | CH$_2$CH$_3$ |
| P1995 | H | Br | H | Br | CF$_3$ | H | Cl | O | CH$_2$ | O | CH$_2$CH$_3$ |
| P1996 | H | Br | H | Br | CF$_3$ | H | CF$_3$ | O | CH$_2$ | O | CH$_2$CH$_3$ |
| P1997 | H | Br | H | Br | CF$_3$ | H | CH$_3$ | O | CH$_2$ | O | CH$_2$CH$_3$ |
| P1998 | H | Br | H | Br | CF$_3$ | CF$_3$ | H | O | CH$_2$ | O | CH$_2$CF$_3$ |
| P1999 | H | Br | H | Br | CF$_3$ | CF$_3$ | Br | O | CH$_2$ | O | CH$_2$CF$_3$ |
| P2000 | H | Br | H | Br | CF$_3$ | CF$_3$ | Cl | O | CH$_2$ | O | CH$_2$CF$_3$ |
| P2001 | H | Br | H | Br | CF$_3$ | CF$_3$ | CF$_3$ | O | CH$_2$ | O | CH$_2$CF$_3$ |
| P2002 | H | Br | H | Br | CF$_3$ | CF$_3$ | CH$_3$ | O | CH$_2$ | O | CH$_2$CF$_3$ |
| P2003 | H | Br | H | Br | CF$_2$CF$_3$ | H | H | O | CH$_2$ | O | CH$_2$CF$_3$ |
| P2004 | H | Br | H | Br | CF$_2$CF$_3$ | H | Br | O | CH$_2$ | O | CH$_2$CF$_3$ |
| P2005 | H | Br | H | Br | CF$_2$CF$_3$ | H | Cl | O | CH$_2$ | O | CH$_2$CF$_3$ |
| P2006 | H | Br | H | Br | CF$_2$CF$_3$ | H | CF$_3$ | O | CH$_2$ | O | CH$_2$CF$_3$ |
| P2007 | H | Br | H | Br | CF$_2$CF$_3$ | H | CH$_3$ | O | CH$_2$ | O | CH$_2$CF$_3$ |
| P2008 | H | Br | H | Br | CF$_3$ | H | H | O | CH$_2$ | O | CH(CH$_3$)CF$_3$ |
| P2009 | H | Br | H | Br | CF$_3$ | H | Br | O | CH$_2$ | O | CH(CH$_3$)CF$_3$ |
| P2010 | H | Br | H | Br | CF$_3$ | H | Cl | O | CH$_2$ | O | CH(CH$_3$)CF$_3$ |
| P2011 | H | Br | H | Br | CF$_3$ | H | CF$_3$ | O | CH$_2$ | O | CH(CH$_3$)CF$_3$ |
| P2012 | H | Br | H | Br | CF$_3$ | H | CH$_3$ | O | CH$_2$ | O | CH(CH$_3$)CF$_3$ |
| P2013 | H | Br | H | Br | CF$_3$ | CF$_3$ | H | O | CH(CH$_3$) | O | CH$_2$CF$_3$ |
| P2014 | H | Br | H | Br | CF$_3$ | CF$_3$ | Br | O | CH(CH$_3$) | O | CH$_2$CF$_3$ |
| P2015 | H | Br | H | Br | CF$_3$ | CF$_3$ | Cl | O | CH(CH$_3$) | O | CH$_2$CF$_3$ |
| P2016 | H | Br | H | Br | CF$_3$ | CF$_3$ | CF$_3$ | O | CH(CH$_3$) | O | CH$_2$CF$_3$ |
| P2017 | H | Br | H | Br | CF$_3$ | CF$_3$ | CH$_3$ | O | CH(CH$_3$) | O | CH$_2$CF$_3$ |
| P2018 | H | Br | H | Br | CF$_2$CF$_3$ | H | H | O | CH(CH$_3$) | O | CH$_2$CF$_3$ |
| P2019 | H | Br | H | Br | CF$_2$CF$_3$ | H | Br | O | CH(CH$_3$) | O | CH$_2$CF$_3$ |
| P2020 | H | Br | H | Br | CF$_2$CF$_3$ | H | Cl | O | CH(CH$_3$) | O | CH$_2$CF$_3$ |
| P2021 | H | Br | H | Br | CF$_2$CF$_3$ | H | CF$_3$ | O | CH(CH$_3$) | O | CH$_2$CF$_3$ |
| P2022 | H | Br | H | Br | CF$_2$CF$_3$ | H | CH$_3$ | O | CH(CH$_3$) | O | CH$_2$CF$_3$ |
| P2023 | H | Br | H | Br | CF$_3$ | H | H | O | CH(CH$_3$) | O | CH$_2$CF$_3$ |
| P2024 | H | Br | H | Br | CF$_3$ | H | Cl | O | CH(CH$_3$) | O | CH$_2$CF$_3$ |
| P2025 | H | Br | H | Br | CF$_3$ | H | H | O | CH(CH$_3$) | S | CH$_2$CF$_3$ |
| P2026 | H | Br | H | Br | CF$_3$ | H | Br | O | CH(CH$_3$) | S | CH$_2$CF$_3$ |
| P2027 | H | Br | H | Br | CF$_3$ | H | Cl | O | CH(CH$_3$) | S | CH$_2$CF$_3$ |
| P2028 | H | Br | H | Br | CF$_3$ | H | CF$_3$ | O | CH(CH$_3$) | S | CH$_2$CF$_3$ |
| P2029 | H | Br | H | Br | CF$_3$ | H | CH$_3$ | O | CH(CH$_3$) | S | CH$_2$CF$_3$ |
| P2030 | H | Br | H | Br | CF$_3$ | H | H | S | CH(CH$_3$) | O | CH$_2$CF$_3$ |
| P2031 | H | Br | H | Br | CF$_3$ | H | Br | S | CH(CH$_3$) | O | CH$_2$CF$_3$ |
| P2032 | H | Br | H | Br | CF$_3$ | H | Cl | S | CH(CH$_3$) | O | CH$_2$CF$_3$ |
| P2033 | H | Br | H | Br | CF$_3$ | H | CF$_3$ | S | CH(CH$_3$) | O | CH$_2$CF$_3$ |
| P2034 | H | Br | H | Br | CF$_3$ | H | CH$_3$ | S | CH(CH$_3$) | O | CH$_2$CF$_3$ |
| P2035 | H | Br | H | Br | CF$_3$ | H | H | O | CH(CH$_3$) | O | CH$_2$CHF$_2$ |
| P2036 | H | Br | H | Br | CF$_3$ | H | Br | O | CH(CH$_3$) | O | CH$_2$CHF$_2$ |
| P2037 | H | Br | H | Br | CF$_3$ | H | Cl | O | CH(CH$_3$) | O | CH$_2$CHF$_2$ |
| P2038 | H | Br | H | Br | CF$_3$ | H | CF$_3$ | O | CH(CH$_3$) | O | CH$_2$CHF$_2$ |
| P2039 | H | Br | H | Br | CF$_3$ | H | CH$_3$ | O | CH(CH$_3$) | O | CH$_2$CHF$_2$ |
| P2040 | H | Br | H | Br | CF$_3$ | H | H | O | CH(CH$_3$) | O | CH$_2$CH$_2$F |
| P2041 | H | Br | H | Br | CF$_3$ | H | Br | O | CH(CH$_3$) | O | CH$_2$CH$_2$F |
| P2042 | H | Br | H | Br | CF$_3$ | H | Cl | O | CH(CH$_3$) | O | CH$_2$CH$_2$F |
| P2043 | H | Br | H | Br | CF$_3$ | H | CF$_3$ | O | CH(CH$_3$) | O | CH$_2$CH$_2$F |
| P2044 | H | Br | H | Br | CF$_3$ | H | CH$_3$ | O | CH(CH$_3$) | O | CH$_2$CH$_2$F |
| P2045 | H | Br | H | Br | CF$_3$ | H | H | O | CH(CH$_3$) | O | CH$_2$CH$_3$ |
| P2046 | H | Br | H | Br | CF$_3$ | H | Br | O | CH(CH$_3$) | O | CH$_2$CH$_3$ |
| P2047 | H | Br | H | Br | CF$_3$ | H | Cl | O | CH(CH$_3$) | O | CH$_2$CH$_3$ |
| P2048 | H | Br | H | Br | CF$_3$ | H | CF$_3$ | O | CH(CH$_3$) | O | CH$_2$CH$_3$ |
| P2049 | H | Br | H | Br | CF$_3$ | H | CH$_3$ | O | CH(CH$_3$) | O | CH$_2$CH$_3$ |
| P2050 | H | Br | H | Br | CF$_3$ | H | H | O | CH(CH$_3$) | O | CH(CH$_3$)CF$_3$ |
| P2051 | H | Br | H | Br | CF$_3$ | H | Br | O | CH(CH$_3$) | O | CH(CH$_3$)CF$_3$ |
| P2052 | H | Br | H | Br | CF$_3$ | H | Cl | O | CH(CH$_3$) | O | CH(CH$_3$)CF$_3$ |

-continued

| Cmpd No. | R1 | R2 | R3 | R4 | R6 | R8 | R10 | W1 | (C1-C8) alkyl | W2 | R15 |
|---|---|---|---|---|---|---|---|---|---|---|---|
| P2053 | H | Br | H | Br | $CF_3$ | H | $CF_3$ | O | $CH(CH_3)$ | O | $CH(CH_3)CF_3$ |
| P2054 | H | Br | H | Br | $CF_3$ | H | $CH_3$ | O | $CH(CH_3)$ | O | $CH(CH_3)CF_3$ |
| P2055 | H | Br | H | Br | $CF_3$ | H | H | O | $CH(CH_3)$ | O | $CH_2CH_2CF_3$ |
| P2056 | H | Br | H | Br | $CF_3$ | H | Br | O | $CH(CH_3)$ | O | $CH_2CH_2CF_3$ |
| P2057 | H | Br | H | Br | $CF_3$ | H | Cl | O | $CH(CH_3)$ | O | $CH_2CH_2CF_3$ |
| P2058 | H | Br | H | Br | $CF_3$ | H | $CF_3$ | O | $CH(CH_3)$ | O | $CH_2CH_2CF_3$ |
| P2059 | H | Br | H | Br | $CF_3$ | H | $CH_3$ | O | $CH(CH_3)$ | O | $CH_2CH_2CF_3$ |
| P2060 | H | Br | H | Br | $CF_3$ | H | H | O | $CH(CH_2CH_3)$ | O | $CH_2CF_3$ |
| P2061 | H | Br | H | Br | $CF_3$ | H | Br | O | $CH(CH_2CH_3)$ | O | $CH_2CF_3$ |
| P2062 | H | Br | H | Br | $CF_3$ | H | Cl | O | $CH(CH_2CH_3)$ | O | $CH_2CF_3$ |
| P2063 | H | Br | H | Br | $CF_3$ | H | $CF_3$ | O | $CH(CH_2CH_3)$ | O | $CH_2CF_3$ |
| P2064 | H | Br | H | Br | $CF_3$ | H | $CH_3$ | O | $CH(CH_2CH_3)$ | O | $CH_2CF_3$ |
| P2065 | H | Br | H | Br | $CF_3$ | H | H | O | $C(CH_3)_2$ | O | $CH_2CF_3$ |
| P2066 | H | Br | H | Br | $CF_3$ | H | Br | O | $C(CH_3)_2$ | O | $CH_2CF_3$ |
| P2067 | H | Br | H | Br | $CF_3$ | H | Cl | O | $C(CH_3)_2$ | O | $CH_2CF_3$ |
| P2068 | H | Br | H | Br | $CF_3$ | H | $CF_3$ | O | $C(CH_3)_2$ | O | $CH_2CF_3$ |
| P2069 | H | Br | H | Br | $CF_3$ | H | $CH_3$ | O | $C(CH_3)_2$ | O | $CH_2CF_3$ |
| P2070 | H | Br | H | Br | $CF_3$ | H | H | O | $CH_2CH_2$ | O | $CH_2CF_3$ |
| P2071 | H | Br | H | Br | $CF_3$ | H | Br | O | $CH_2CH_2$ | O | $CH_2CF_3$ |
| P2072 | H | Br | H | Br | $CF_3$ | H | Cl | O | $CH_2CH_2$ | O | $CH_2CF_3$ |
| P2073 | H | Br | H | Br | $CF_3$ | H | $CF_3$ | O | $CH_2CH_2$ | O | $CH_2CF_3$ |
| P2074 | H | Br | H | Br | $CF_3$ | H | $CH_3$ | O | $CH_2CH_2$ | O | $CH_2CF_3$ |

Example A

Bioassays on Beet Armyworm ("BAW") and Corn Earwom ("CEW") and Cabbage Looper ("CL")

BAW has few effective parasites, diseases, or predators to lower its population. BAW infests many weeds, trees, grasses, legumes, and field crops. In various places, it is of economic concern upon asparagus, cotton, corn, soybeans, tobacco, alfalfa, sugar beets, peppers, tomatoes, potatoes, onions, peas, sunflowers, and citrus, among other plants. CEW is known to attack corn and tomatoes, but it also attacks artichoke, asparagus, cabbage, cantaloupe, collards, cowpeas, cucumbers, eggplant, lettuce, lima beans, melon, okra, peas, peppers, potatoes, pumpkin, snap beans, spinach, squash, sweet potatoes, and watermelon, among other plants. CEW is also known to be resistant to certain insecticides. CL is also known to be resistant to certain insecticides. Consequently, because of the above factors control of these pests is important. Furthermore, molecules that control these pests are useful in controlling other pests.

Certain molecules disclosed in this document were tested against BAW, CEW and CL using procedures described in the following examples. In the reporting of the results, the "BAW & CEW & CL Rating Table" was used (See Table Section).

Bioassays ON BAW (*Spodoptera exigua*)

Bioassays on BAW were conducted using a 128-well diet tray assay. One to five second instar BAW larvae were placed in each well (3 mL) of the diet tray that had been previously filled with 1 mL of artificial diet to which 50 µg/cm² of the test compound (dissolved in 50 µL of 90:10 acetone-water mixture) had been applied (to each of eight wells) and then allowed to dry. Trays were covered with a clear self-adhesive cover, and held at 25° C., 14:10 light-dark for five to seven days. Percent mortality was recorded for the larvae in each well; activity in the eight wells was then averaged. The results are indicated in the tables entitled "Table 3: Assay Results Part 1" and "Table 4: Assay Results Part 2" (See Table Section).

Bioassays ON CEW (*Helicoverpa zea*)

Bioassays on CEW were conducted using a 128-well diet tray assay. One to five second instar CEW larvae were placed in each well (3 mL) of the diet tray that had been previously filled with 1 mL of artificial diet to which 50 µg/cm² of the test compound (dissolved in 50 µL of 90:10 acetone—water mixture) had been applied (to each of eight wells) and then allowed to dry. Trays were covered with a clear self-adhesive cover, and held at 25° C., 14:10 light-dark for five to seven days. Percent mortality was recorded for the larvae in each well; activity in the eight wells was then averaged. The results are indicated in the table entitled "Table 3: Assay Results Part 1" (See Table Section).

Bioassays on CL (*Trichoplusia ni*)

Bioassays on CL were conducted using a 128-well diet tray assay. One to five second instar CL larvae were placed in each well (3 mL) of the diet tray that had been previously filled with 1 mL of artificial diet to which 50 µg/cm² of the test compound (dissolved in 50 µL of 90:10 acetone-water mixture) had been applied (to each of eight wells) and then allowed to dry. Trays were covered with a clear self-adhesive cover, and held at 25° C., 14:10 light-dark for five to seven days. Percent mortality was recorded for the larvae in each well; activity in the eight wells was then averaged. The results are indicated in the table entitled "Table 4: Assay Results Part 2" (See Table Section).

Example B

Bioassays on Green Peach Aphid ("GPA") (*Myzus persicae*)

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, *papaya*, peppers, sweet potatoes, tomatoes, watercress, and zucchini, among other plants. GPA also attacks many ornamental crops such as carnation, *chrysanthemum*, flowering white cabbage, poinsettia, and roses. GPA has developed resistance to many pesticides.

Certain molecules disclosed in this document were tested against GPA using procedures described in the following example. In the reporting of the results, the "GPA Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/MeOH (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/MeOH (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

$$\text{Corrected \% Control} = 100*(X-Y)/X$$

where

X=No. of live aphids on solvent check plants and

Y=No. of live aphids on treated plants

The results are indicated in the tables entitled "Table 3: Assay Results Part 1" and "Table 4: Assay Results Part 2" (See Table Section).

Pesticidally Acceptable Acid Addition Salts, Salt Derivatives, Solvates, Ester Derivatives, Polymorphs, Isotopes and Radionuclides Molecules of Formula One may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous NaOH, potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the invention disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) in place of $^1H$.

Molecules of Formula One may be made with different radionuclides. Of particular importance are molecules having $^{14}C$.

Stereoisomers

Molecules of Formula One may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

Molecules of Formula One may also be used in combination (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, or virucidal properties. Additionally, the molecules of Formula One may also be used in combination (such as, in a compositional mixture, or a simultaneous or sequential application) with compounds that are antifeedants, bird repellents, chemosterilants, herbicide safeners, insect attractants, insect repellents, mammal repellents, mating disrupters, plant activators, plant growth regulators, or synergists. Examples of such compounds in the above groups that may be used with the Molecules of Formula One are—(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlomidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxaprid, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nomicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid. For more information consult the "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council, or its prior or more recent editions.

Biopesticides

Molecules of Formula One may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g. *Metarhizium anisopliae*);
2. entomopathogenic nematodes (e.g. *Steinemema feltiae*); and
3. entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the Biopesticide Manual) 3rd Edition. British Crop Production Council (BCPC), Farnham, Surrey UK.

Other Active Compounds

Molecules of Formula One may also be used in combination (such as in a compositional mixture, or a simultaneous or sequential application) with one or more of the following:
1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl) hydrazone;
15. N-ethyl-2,2-dichloro-1-methylcyclopropane-carboxamide-2-(2,6-dichloro-α,α,α-trifluoro-p-tolyl) hydrazone nicotine;
16. O-{(E-)-[2-(4-chloro-phenyl)-2-cyano-1-(2-trifluoromethylphenyl)-vinyl]}S-methyl thiocarbonate;
17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl]] phenyl mesylate; and
20. N-Ethyl-2,2-dichloro-1-methylcyclopropanecarboxamide-2-(2,6-dichloro-alpha,alpha,alpha-trifluoro-p-tolyl) hydrazone.

Synergistic Mixtures

Molecules of Formula One may be used with certain active compounds to form synergistic mixtures where the mode of action of such compounds compared to the mode of action of the molecules of Formula One are the same, similar, or different. Examples of modes of action include, but are not limited to: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs). Generally, weight ratios of the molecules of Formula One in a synergistic mixture with another compound are from about 10:1 to about 1:10, in another embodiment from about 5:1 to about 1:5, and in another embodiment from about 3:1, and in another embodiment about 1:1.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions. For further information on formulation types see "Catalogue of Pesticide Formulation Types and International Coding System" Technical Monograph n° 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra-low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources.

Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula One may be used to control pests e.g. beetles, earwigs, cockroaches, flies. aphids, scales, whiteflies, leafhoppers, ants, wasps, termites, moths, butterflies, lice, grasshoppers, locusts, crickets, fleas, *thrips*, bristletails, mites, ticks, nematodes, and symphylans.

In another embodiment, the molecules of Formula One may be used to control pests in the Phyla Nematoda and/or Arthropoda.

In another embodiment, the molecules of Formula One may be used to control pests in the Subphyla Chelicerata, Myriapoda, and/or Hexapoda.

In another embodiment, the molecules of Formula One may be used to control pests in the Classes of Arachnida, Symphyla, and/or Insecta.

In another embodiment, the molecules of Formula One may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus,* and *Pthirus pubis.*

In another embodiment, the molecules of Formula One may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fiiscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile,* and *Zabrus tenebrioides.*

In another embodiment, the molecules of Formula One may be used to control pests of the Order Dermaptera.

In another embodiment, the molecules of Formula One may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis,* and *Supella longipalpa.*

In another embodiment, the molecules of Formula One may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana,* and *Stomoxys calcitrans.*

In another embodiment, the molecules of Formula One may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris califomicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

In another embodiment, the molecules of Formula One may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richteri, Solenopsis xyloni*, and *Tapinoma sessile*.

In another embodiment, the molecules of Formula One may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., *and Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis*, and *Reticulitermes virginicus*.

In another embodiment, the molecules of Formula One may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae*, and *Zeuzera pyrina*.

In another embodiment, the molecules of Formula One may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae*, and *Trichodectes canis*.

In another embodiment, the molecules of Formula One may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria*, and *Scudderia furcata*.

In another embodiment, the molecules of Formula One may be used to control pests of the Order Siphonaptera. A non-exhaustive list of particular species includes, but is not limited to, *Ceratophyllus gallinae, Ceratophyllus niger, Ctenocephalides canis, Ctenocephalides felis*, and *Pulex irritans*.

In another embodiment, the molecules of Formula One may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fiisca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis*, and *Taeniothrips rhopalantennalis, Thrips hawaiiensis, Thrips nigropilosus, Thrips orientalis, Thrips tabaci*.

In another embodiment, the molecules of Formula One may be used to control pests of the Order Thysanura. A non-exhaustive list of particular genera includes, but is not limited to, *Lepisma* spp. and *Thermobia* spp.

In another embodiment, the molecules of Formula One may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae*, and *Varroa destructor*.

In another embodiment, the molecules of Formula One may be used to control pest of the Order Symphyla. A non-exhaustive list of particular sp. includes, but is not limited to, *Scutigerella immaculata*.

In another embodiment, the molecules of Formula One may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis*.

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Molecules of Formula One are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which a molecule of Formula One is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a molecule of Formula One when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The molecules of Formula One may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The molecules of Formula One can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula One can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One.

The molecules of Formula One can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula One may be desirable to control newly emerged larvae.

Systemic movement of pesticides in plants may be utilized to control pests on one portion of the plant by applying (for example by spraying an area) the molecules of Formula One to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula One may further enhance the ability of a plant to better withstand stressful growing conditions. This results in a healthier, more vigorous plant, which can lead to higher yields at harvest time. Generally, about 1 gram of the molecules of Formula One to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula One may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The molecules of Formula One may be used for controlling endoparasites and ectoparasites in the veterinary medicine sector or in the field of non-human animal keeping. The molecules of Formula One are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The molecules of Formula One may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The molecules of Formula One may also be used for controlling parasitic worms, especially of the intestine, in the animals listed above.

The molecules of Formula One may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The molecules of Formula One may also be used on such new invasive species to control them in such new environment.

The molecules of Formula One may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A molecule according to Formula One can be tested to determine its efficacy against pests. Furthermore, mode of action studies can be conducted to determine if said molecule has a different mode of action than other pesticides. Thereafter, such acquired data can be disseminated, such as by the internet, to third parties.

The headings in this document are for convenience only and must not be used to interpret any portion hereof.

Table Section

| BAW, CEW & CL Rating Table | |
|---|---|
| % Control (or Mortality) | Rating |
| 50-100 | A |
| More than 0-Less than 50 | B |
| Not Tested | C |
| No activity noticed in this bioassay | D |

| GPA Rating Table | |
|---|---|
| % Control (or Mortality) | Rating |
| 80-100 | A |
| More than 0-Less than 80 | B |
| Not Tested | C |
| No activity noticed in this bioassay | D |

TABLE 1

Structures for Compounds

| Compound Number | Structure |
|---|---|
| AI34 | 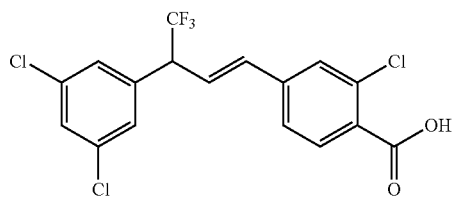 [SMILES: O=C(O)c1ccc(/C=C/C(c2cc(Cl)cc(Cl)c2)C(F)(F)F)cc1Cl] |
| AI36 | 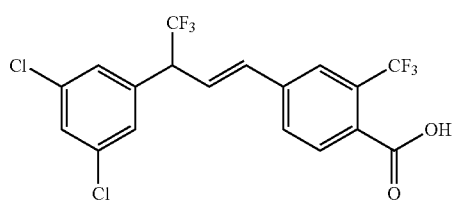 [SMILES: O=C(O)c1ccc(/C=C/C(c2cc(Cl)cc(Cl)c2)C(F)(F)F)cc1C(F)(F)F] |

TABLE 1-continued

| Compound Number | Structure |
|---|---|
| AI37 | 3,5-dichlorophenyl-CH(CF₃)-CH=CH-(2-cyano-4-yl)benzoic acid |
| AI38 | 3,4-dichlorophenyl-CH(CF₃)-CH=CH-(2-chloro-4-yl)benzoic acid |
| AI39 | 3,4-dichlorophenyl-CH(CF₃)-CH=CH-(2-bromo-4-yl)benzoic acid |
| AI40 | 3,4-dichlorophenyl-CH(CF₃)-CH=CH-(2-trifluoromethyl-4-yl)benzoic acid |
| AI41 | 3,4-dichlorophenyl-CH(CF₃)-CH=CH-(2-cyano-4-yl)benzoic acid |
| AI44 | 3,5-dichloro-4-fluorophenyl-CH(CF₃)-CH=CH-(2-trifluoromethyl-4-yl)benzoic acid |
| AI45 | 3,5-dichloro-4-fluorophenyl-CH(CF₃)-CH=CH-(2-cyano-4-yl)benzoic acid |

TABLE 1-continued

Structures for Compounds

| Compound Number | Structure |
|---|---|
| AC1 | 3,5-dichlorophenyl-CH(CF$_3$)-CH=CH-C$_6$H$_4$-C(=O)NHCH$_3$ |
| AC2 | 3,5-dichlorophenyl-CH(CF$_3$)-CH=CH-C$_6$H$_4$-C(=O)NH$_2$ |
| AC3 | 3,5-dichlorophenyl-CH(CF$_3$)-CH=CH-C$_6$H$_4$-C(=O)N(CH$_3$)$_2$ |
| AC4 | 3,5-dichlorophenyl-CH(CF$_3$)-CH=CH-C$_6$H$_4$-C(=O)NH-CH$_2$CF$_3$ |
| AC5 | 3,5-dichlorophenyl-CH(CF$_3$)-CH=CH-C$_6$H$_4$-C(=O)-morpholine |
| AC6 | 3,5-dichlorophenyl-CH(CF$_3$)-CH=CH-(2-methyl-C$_6$H$_3$)-C(=O)NH-CH$_2$CF$_3$ |
| AC7 | 3,5-dichlorophenyl-CH(CF$_3$)-CH=CH-(2-methyl-C$_6$H$_3$)-C(=O)NH-CH$_2$-(6-chloropyridin-3-yl) |

TABLE 1-continued

Structures for Compounds

| Compound Number | Structure |
|---|---|
| AC8 | *(3,5-dichlorophenyl)(CF₃)CH-CH=CH-(2-methylphenyl)-C(=O)-N(2-oxopyrrolidin-1-yl)* |
| AC9 | *(3,5-dichlorophenyl)(CF₃)CH-CH=CH-(2-methylphenyl)-C(=O)NH-CH₂-(2-fluorophenyl)* |
| AC10 | *(3,5-dichlorophenyl)(CF₃)CH-CH=CH-(2-methylphenyl)-C(=O)NH-(thietan-3-yl)* |
| AC11 | *(3,5-dichlorophenyl)(CF₃)CH-CH=CH-(2-methylphenyl)-C(=O)NH-CH₂-phenyl* |
| AC12 | *(3,5-dichlorophenyl)(CF₃)CH-CH=CH-(2-methylphenyl)-C(=O)NH-CH₂-(pyridin-2-yl)* |
| AC13 | *(3,5-dichlorophenyl)(CF₃)CH-CH=CH-(2-methylphenyl)-C(=O)NH-(1,1-dioxothietan-3-yl)* |
| AC14 | *(3,5-dichlorophenyl)(CF₃)CH-CH=CH-(2-methylphenyl)-C(=O)NH-CH₂-(pyridin-3-yl)* |

TABLE 1-continued

Structures for Compounds

| Compound Number | Structure |
|---|---|
| AC15 | 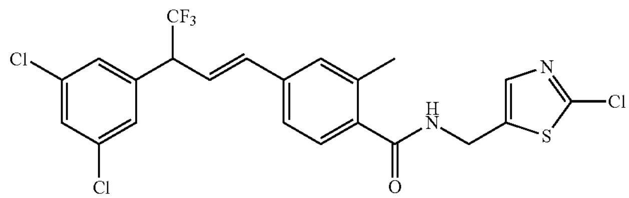 [SMILES: Cc1cc(/C=C/C(c2cc(Cl)cc(Cl)c2)C(F)(F)F)ccc1C(=O)NCc1cnc(Cl)s1] |
| AC16 | 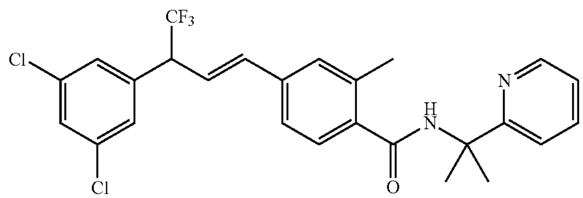 [SMILES: Cc1cc(/C=C/C(c2cc(Cl)cc(Cl)c2)C(F)(F)F)ccc1C(=O)NC(C)(C)c1ccccn1] |
| AC17 | 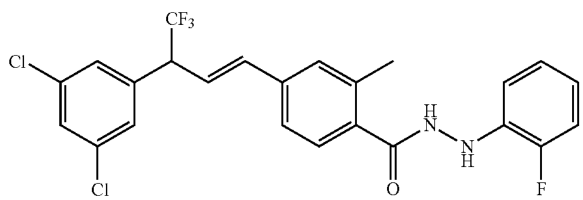 [SMILES: Cc1cc(/C=C/C(c2cc(Cl)cc(Cl)c2)C(F)(F)F)ccc1C(=O)NNc1ccccc1F] |
| AC18 | 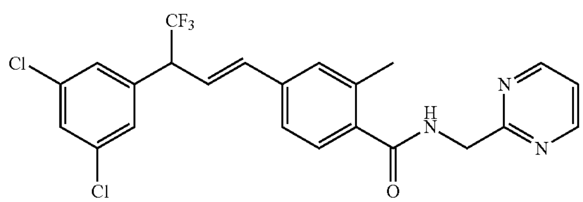 [SMILES: Cc1cc(/C=C/C(c2cc(Cl)cc(Cl)c2)C(F)(F)F)ccc1C(=O)NCc1ncccn1] |
| AC19 | 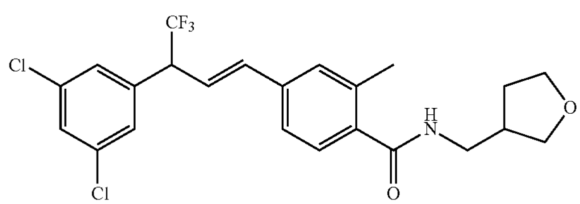 [SMILES: Cc1cc(/C=C/C(c2cc(Cl)cc(Cl)c2)C(F)(F)F)ccc1C(=O)NCC1CCOC1] |
| AC20 | 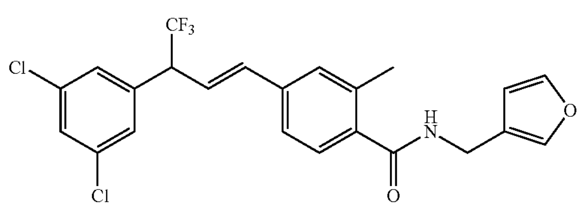 [SMILES: Cc1cc(/C=C/C(c2cc(Cl)cc(Cl)c2)C(F)(F)F)ccc1C(=O)NCc1ccoc1] |
| AC21 | 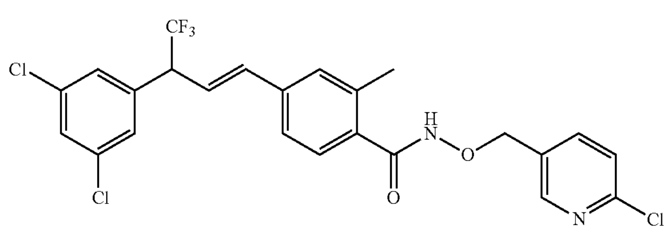 [SMILES: Cc1cc(/C=C/C(c2cc(Cl)cc(Cl)c2)C(F)(F)F)ccc1C(=O)NOCc1ccc(Cl)nc1] |

TABLE 1-continued
Structures for Compounds
| Compound Number | Structure |
|---|---|
| AC22 | 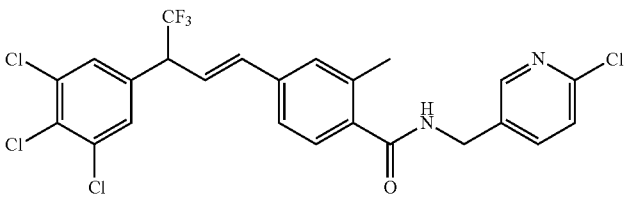 [SMILES: Cc1cc(/C=C/C(c2cc(Cl)c(Cl)c(Cl)c2)C(F)(F)F)ccc1C(=O)NCc1ccc(Cl)nc1] |
| AC23 | 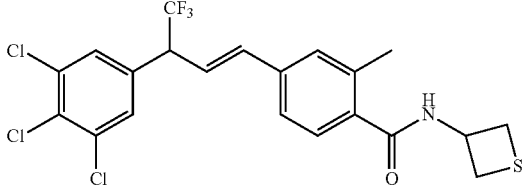 [SMILES: Cc1cc(/C=C/C(c2cc(Cl)c(Cl)c(Cl)c2)C(F)(F)F)ccc1C(=O)NC1CSC1] |
| AC24 | 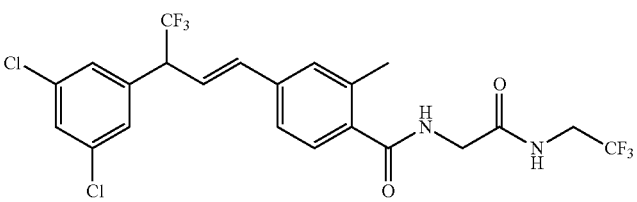 [SMILES: Cc1cc(/C=C/C(c2cc(Cl)cc(Cl)c2)C(F)(F)F)ccc1C(=O)NCC(=O)NCC(F)(F)F] |
| AC25 | 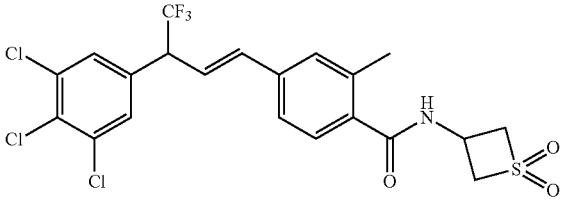 [SMILES: Cc1cc(/C=C/C(c2cc(Cl)c(Cl)c(Cl)c2)C(F)(F)F)ccc1C(=O)NC1CS(=O)(=O)C1] |
| AC26 | 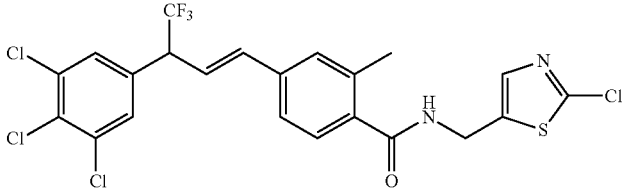 [SMILES: Cc1cc(/C=C/C(c2cc(Cl)c(Cl)c(Cl)c2)C(F)(F)F)ccc1C(=O)NCc1cnc(Cl)s1] |
| AC27 | 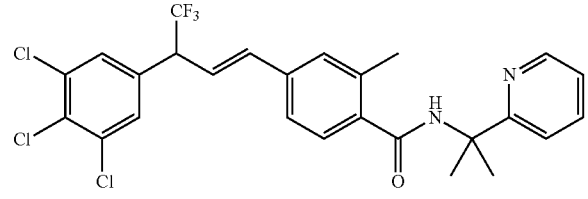 [SMILES: Cc1cc(/C=C/C(c2cc(Cl)c(Cl)c(Cl)c2)C(F)(F)F)ccc1C(=O)NC(C)(C)c1ccccn1] |
| AC28 | 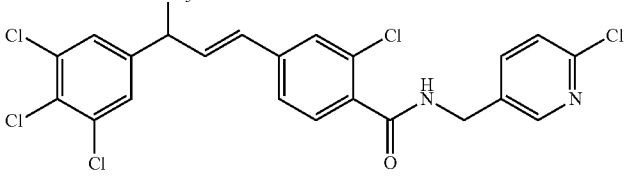 |

TABLE 1-continued
Structures for Compounds
| Compound Number | Structure |
|---|---|
| AC29 | 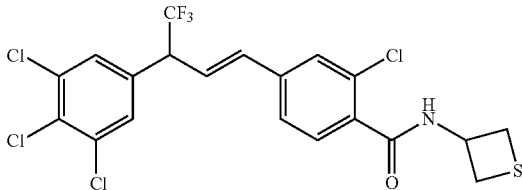 [SMILES: O=C(NC1CSC1)c1ccc(/C=C/C(c2cc(Cl)c(Cl)c(Cl)c2)C(F)(F)F)cc1Cl] |
| AC30 | 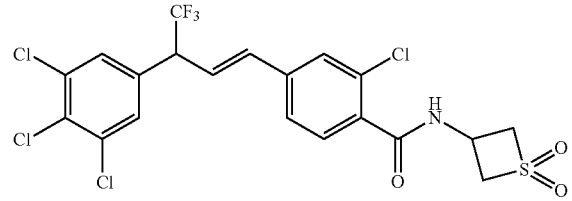 [SMILES: O=C(NC1CS(=O)(=O)C1)c1ccc(/C=C/C(c2cc(Cl)c(Cl)c(Cl)c2)C(F)(F)F)cc1Cl] |
| AC31 | 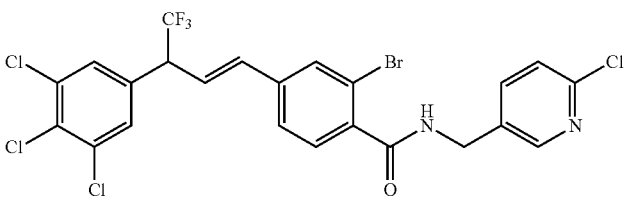 [SMILES: O=C(NCc1ccc(Cl)nc1)c1ccc(/C=C/C(c2cc(Cl)c(Cl)c(Cl)c2)C(F)(F)F)cc1Br] |
| AC32 | 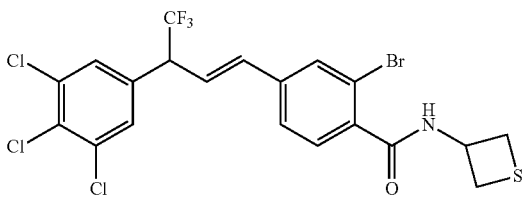 [SMILES: O=C(NC1CSC1)c1ccc(/C=C/C(c2cc(Cl)c(Cl)c(Cl)c2)C(F)(F)F)cc1Br] |
| AC33 | 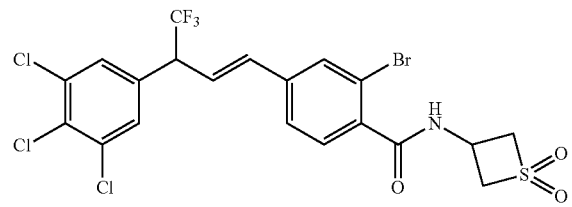 [SMILES: O=C(NC1CS(=O)(=O)C1)c1ccc(/C=C/C(c2cc(Cl)c(Cl)c(Cl)c2)C(F)(F)F)cc1Br] |
| AC34 | 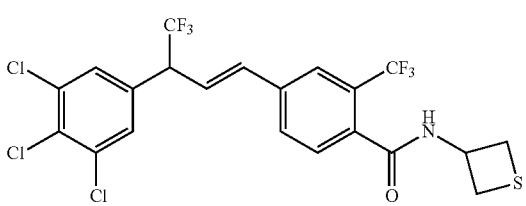 |
| AC35 | 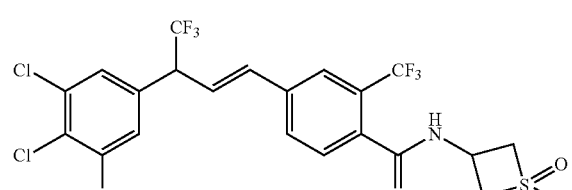 |

TABLE 1-continued

Structures for Compounds

| Compound Number | Structure |
|---|---|
| AC36 | 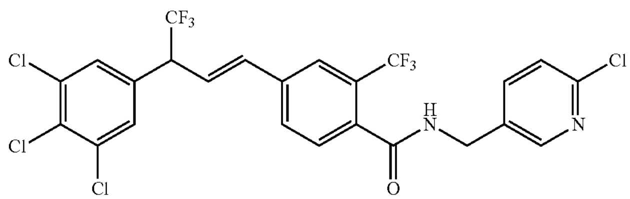 |
| AC37 | 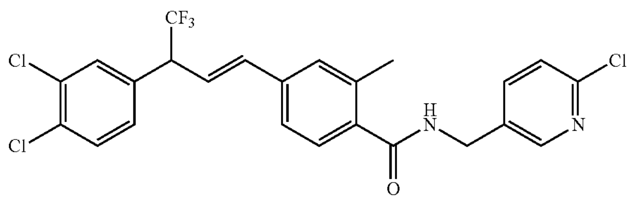 [SMILES: Cc1cc(/C=C/C(c2ccc(Cl)c(Cl)c2)C(F)(F)F)ccc1C(=O)NCc1ccc(Cl)nc1] |
| AC38 | 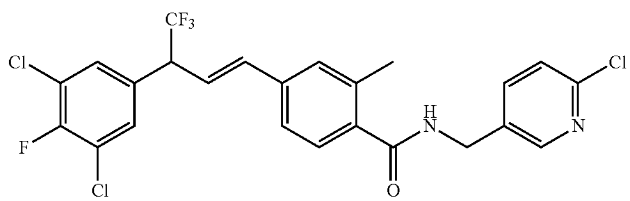 [SMILES: Cc1cc(/C=C/C(c2cc(Cl)c(F)c(Cl)c2)C(F)(F)F)ccc1C(=O)NCc1ccc(Cl)nc1] |
| AC39 | 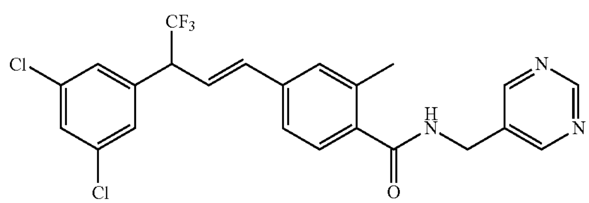 [SMILES: Cc1cc(/C=C/C(c2cc(Cl)cc(Cl)c2)C(F)(F)F)ccc1C(=O)NCc1cncnc1] |
| AC40 | 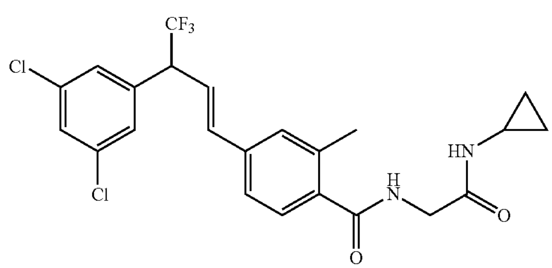 [SMILES: Cc1cc(/C=C/C(c2cc(Cl)cc(Cl)c2)C(F)(F)F)ccc1C(=O)NCC(=O)NC1CC1] |
| AC41 | 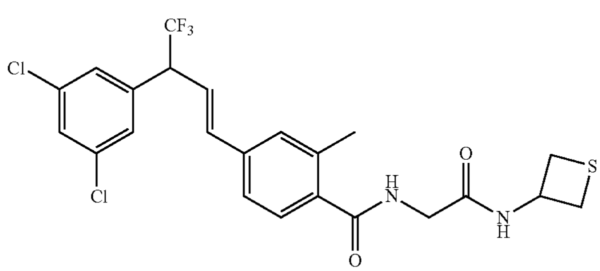 [SMILES: Cc1cc(/C=C/C(c2cc(Cl)cc(Cl)c2)C(F)(F)F)ccc1C(=O)NCC(=O)NC1CSC1] |

TABLE 1-continued

Structures for Compounds

| Compound Number | Structure |
|---|---|
| AC42 | 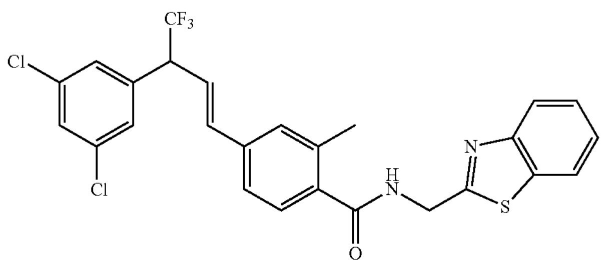 [SMILES: Cc1cc(/C=C/C(c2cc(Cl)cc(Cl)c2)C(F)(F)F)ccc1C(=O)NCc1nc2ccccc2s1] |
| AC43 | 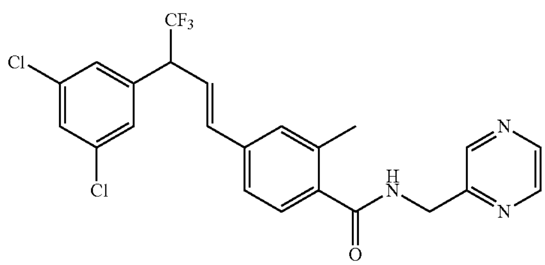 [SMILES: Cc1cc(/C=C/C(c2cc(Cl)cc(Cl)c2)C(F)(F)F)ccc1C(=O)NCc1cnccn1] |
| AC44 | 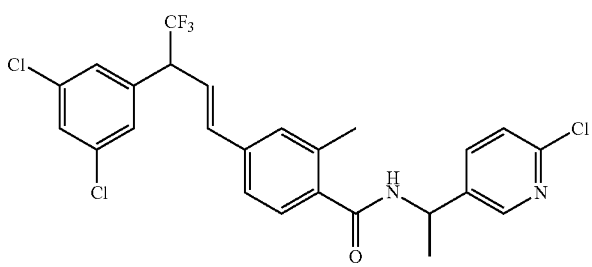 [SMILES: Cc1cc(/C=C/C(c2cc(Cl)cc(Cl)c2)C(F)(F)F)ccc1C(=O)NC(C)c1ccc(Cl)nc1] |
| AC45 | 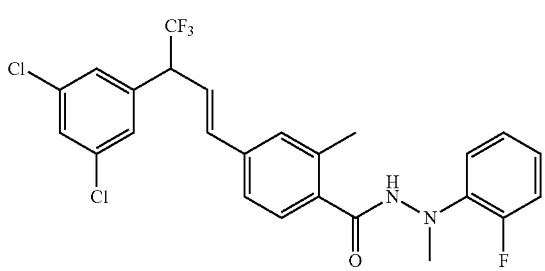 [SMILES: Cc1cc(/C=C/C(c2cc(Cl)cc(Cl)c2)C(F)(F)F)ccc1C(=O)NN(C)c1ccccc1F] |
| AC46 | 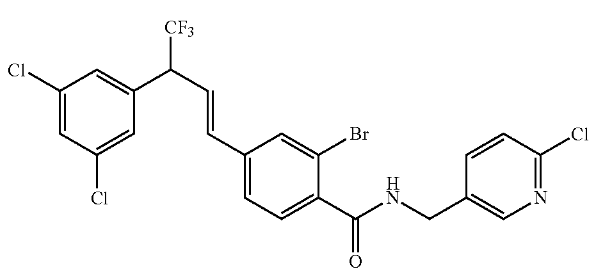 [SMILES: O=C(NCc1ccc(Cl)nc1)c1ccc(/C=C/C(c2cc(Cl)cc(Cl)c2)C(F)(F)F)cc1Br] |

313 314
TABLE 1-continued
Structures for Compounds
| Compound Number | Structure |
|---|---|
| AC47 | 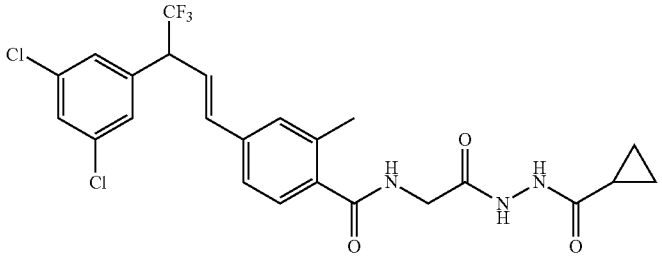 [SMILES: Cc1cc(/C=C/C(c2cc(Cl)cc(Cl)c2)C(F)(F)F)ccc1C(=O)NCC(=O)NNC(=O)C1CC1] |
| AC48 | 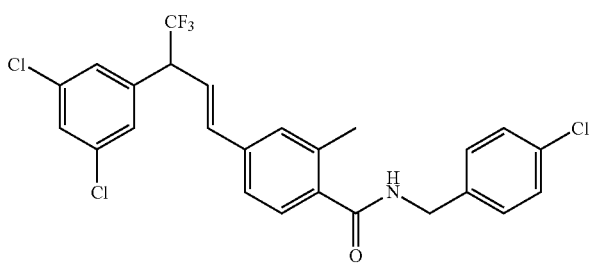 [SMILES: Cc1cc(/C=C/C(c2cc(Cl)cc(Cl)c2)C(F)(F)F)ccc1C(=O)NCc1ccc(Cl)cc1] |
| AC49 | 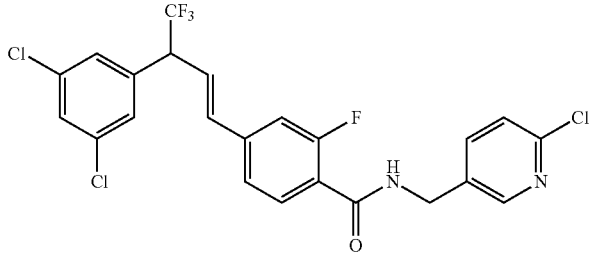 [SMILES: O=C(NCc1ccc(Cl)nc1)c1ccc(/C=C/C(c2cc(Cl)cc(Cl)c2)C(F)(F)F)cc1F] |
| AC50 | 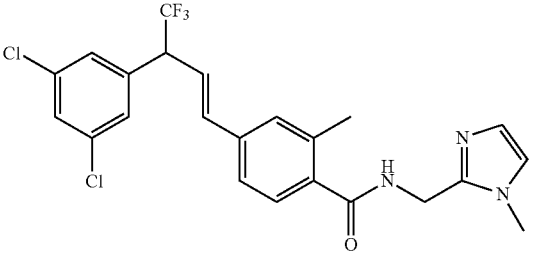 [SMILES: Cc1cc(/C=C/C(c2cc(Cl)cc(Cl)c2)C(F)(F)F)ccc1C(=O)NCc1nccn1C] |
| AC51 | 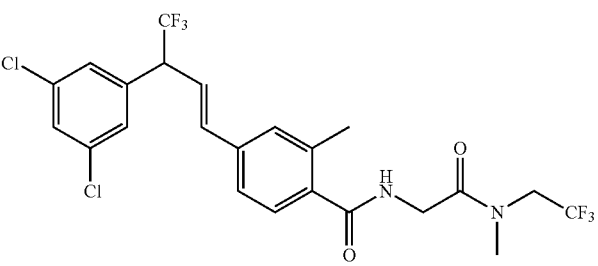 [SMILES: Cc1cc(/C=C/C(c2cc(Cl)cc(Cl)c2)C(F)(F)F)ccc1C(=O)NCC(=O)N(C)CC(F)(F)F] |

TABLE 1-continued

Structures for Compounds

| Compound Number | Structure |
|---|---|
| AC52 | 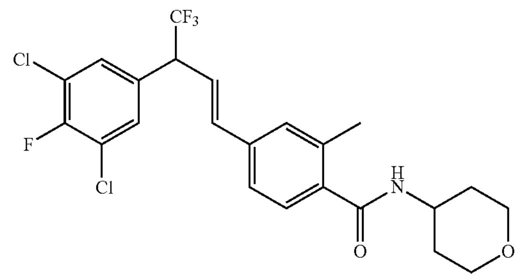 [SMILES: Cc1cc(/C=C/C(c2cc(Cl)c(F)c(Cl)c2)C(F)(F)F)ccc1C(=O)NC1CCOCC1] |
| AC53 | 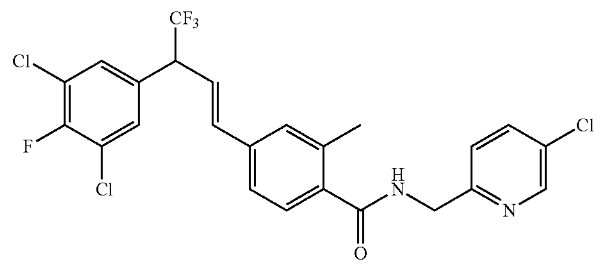 [SMILES: Cc1cc(/C=C/C(c2cc(Cl)c(F)c(Cl)c2)C(F)(F)F)ccc1C(=O)NCc1ccc(Cl)cn1] |
| AC54 | 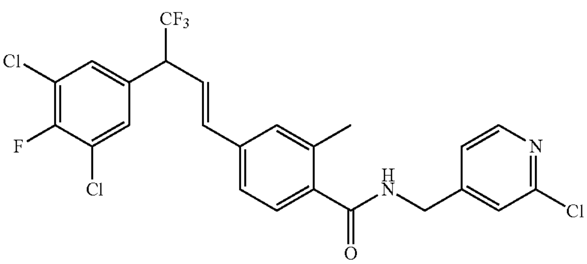 [SMILES: Cc1cc(/C=C/C(c2cc(Cl)c(F)c(Cl)c2)C(F)(F)F)ccc1C(=O)NCc1ccnc(Cl)c1] |
| AC57 | 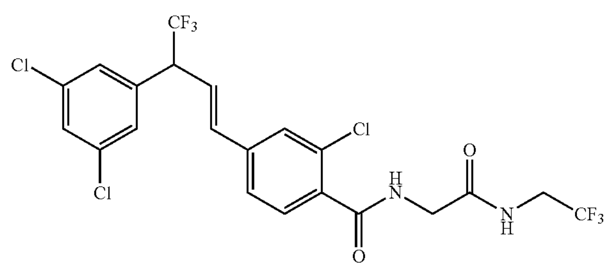 [SMILES: O=C(CNC(=O)c1ccc(/C=C/C(c2cc(Cl)cc(Cl)c2)C(F)(F)F)cc1Cl)NCC(F)(F)F] |
| AC58 | 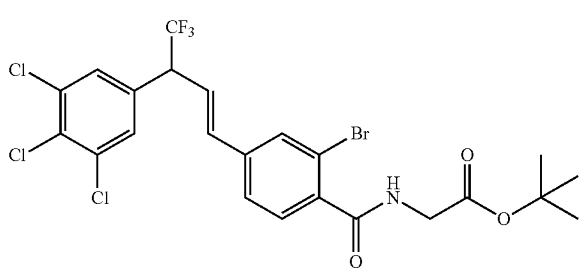 [SMILES: CC(C)(C)OC(=O)CNC(=O)c1ccc(/C=C/C(c2cc(Cl)c(Cl)c(Cl)c2)C(F)(F)F)cc1Br] |

TABLE 1-continued

Structures for Compounds

| Compound Number | Structure |
|---|---|
| AC59 | 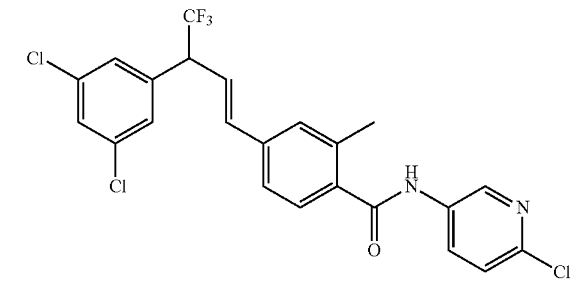 [SMILES: Cc1cc(/C=C/C(c2cc(Cl)cc(Cl)c2)C(F)(F)F)ccc1C(=O)Nc1ccc(Cl)nc1] |
| AC60 | 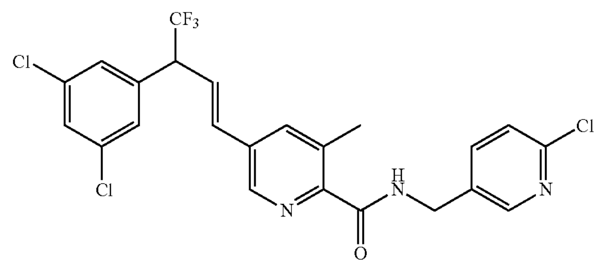 [SMILES: Cc1cc(/C=C/C(c2cc(Cl)cc(Cl)c2)C(F)(F)F)cnc1C(=O)NCc1ccc(Cl)nc1] |
| AC61 | 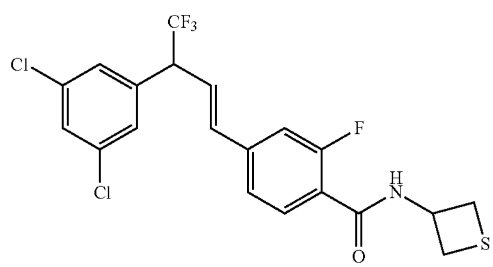 [SMILES: O=C(NC1CSC1)c1ccc(/C=C/C(c2cc(Cl)cc(Cl)c2)C(F)(F)F)cc1F] |
| AC62 | 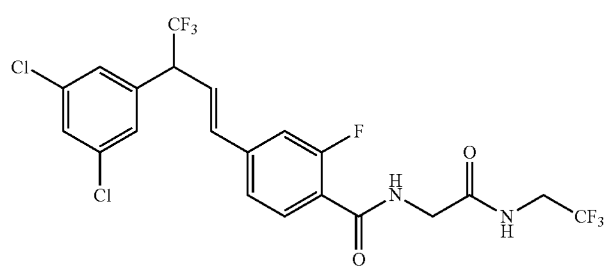 [SMILES: O=C(CNC(=O)c1ccc(/C=C/C(c2cc(Cl)cc(Cl)c2)C(F)(F)F)cc1F)NCC(F)(F)F] |
| AC63 | 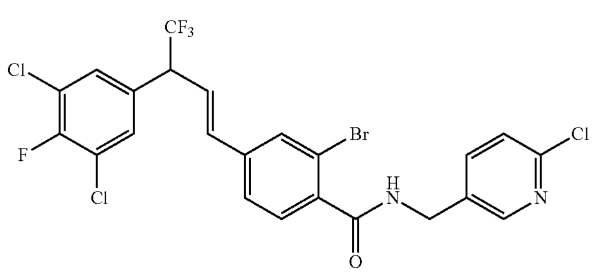 [SMILES: O=C(NCc1ccc(Cl)nc1)c1ccc(/C=C/C(c2cc(Cl)c(F)c(Cl)c2)C(F)(F)F)cc1Br] |

TABLE 1-continued
Structures for Compounds
| Compound Number | Structure |
|---|---|
| AC64 | 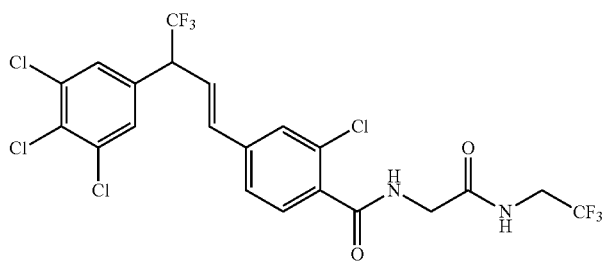 [SMILES: O=C(CNC(=O)c1ccc(/C=C/C(c2cc(Cl)c(Cl)c(Cl)c2)C(F)(F)F)cc1Cl)NCC(F)(F)F] |
| AC65 | 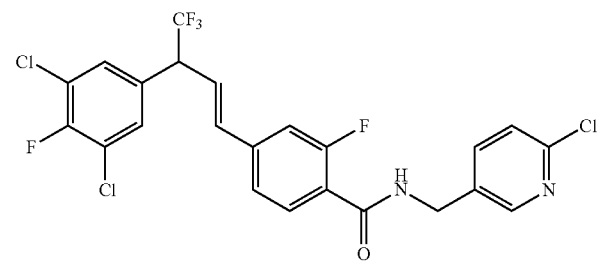 [SMILES: O=C(NCc1ccc(Cl)nc1)c1ccc(/C=C/C(c2cc(Cl)c(F)c(Cl)c2)C(F)(F)F)cc1F] |
| AC66 | 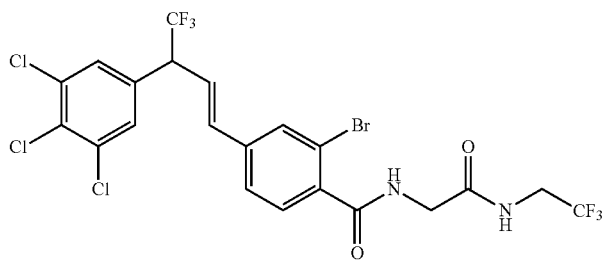 [SMILES: O=C(CNC(=O)c1ccc(/C=C/C(c2cc(Cl)c(Cl)c(Cl)c2)C(F)(F)F)cc1Br)NCC(F)(F)F] |
| AC67 | 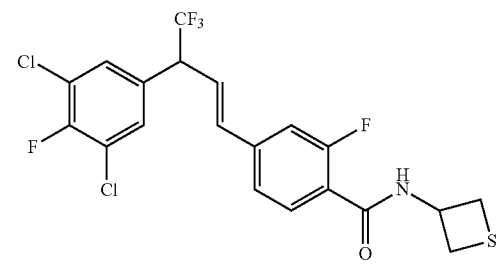 [SMILES: O=C(NC1CSC1)c1ccc(/C=C/C(c2cc(Cl)c(F)c(Cl)c2)C(F)(F)F)cc1F] |
| AC68 | 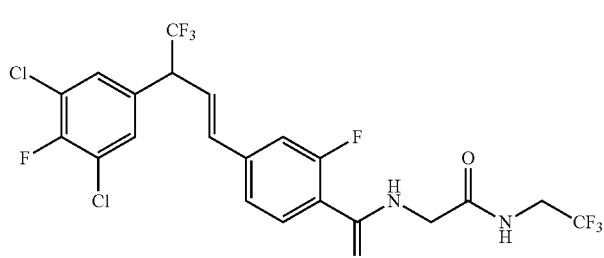 |

TABLE 1-continued

Structures for Compounds

| Compound Number | Structure |
|---|---|
| AC69 | 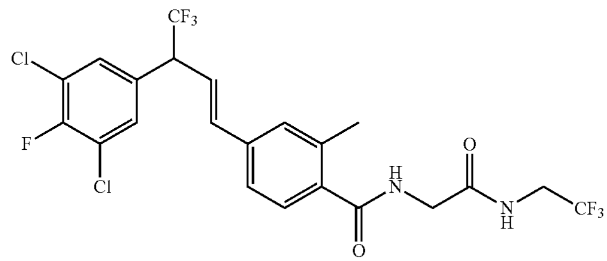 [SMILES: Cc1cc(/C=C/C(c2cc(Cl)c(F)c(Cl)c2)C(F)(F)F)ccc1C(=O)NCC(=O)NCC(F)(F)F] |
| AC70 | 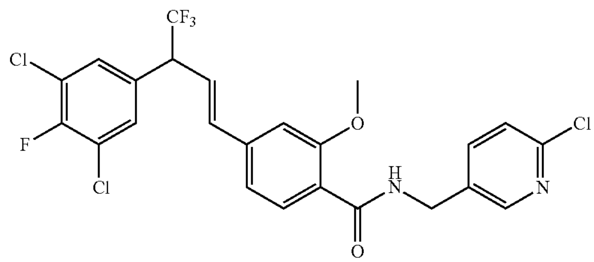 [SMILES: COc1cc(/C=C/C(c2cc(Cl)c(F)c(Cl)c2)C(F)(F)F)ccc1C(=O)NCc1ccc(Cl)nc1] |
| AC71 | 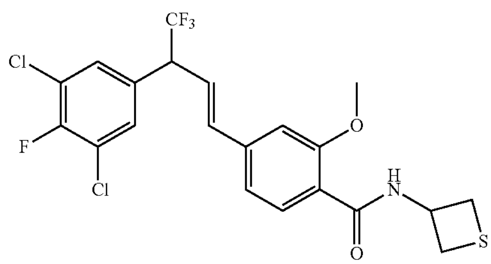 [SMILES: COc1cc(/C=C/C(c2cc(Cl)c(F)c(Cl)c2)C(F)(F)F)ccc1C(=O)NC1CSC1] |
| AC72 | 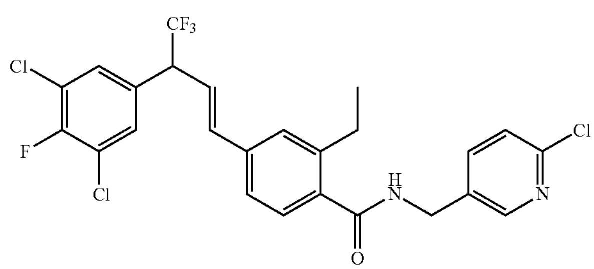 [SMILES: CCc1cc(/C=C/C(c2cc(Cl)c(F)c(Cl)c2)C(F)(F)F)ccc1C(=O)NCc1ccc(Cl)nc1] |
| AC75 | 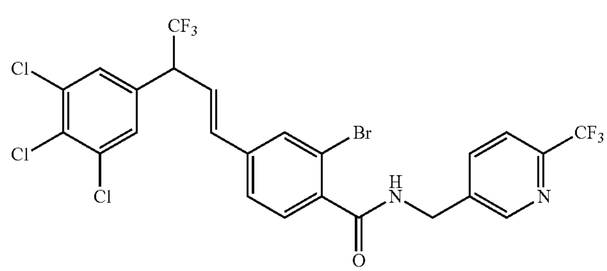 [SMILES: O=C(NCc1ccc(C(F)(F)F)nc1)c1ccc(/C=C/C(c2cc(Cl)c(Cl)c(Cl)c2)C(F)(F)F)cc1Br] |

US 9,622,477 B2
TABLE 1-continued
Structures for Compounds
| Compound Number | Structure |
|---|---|
| AC76 | 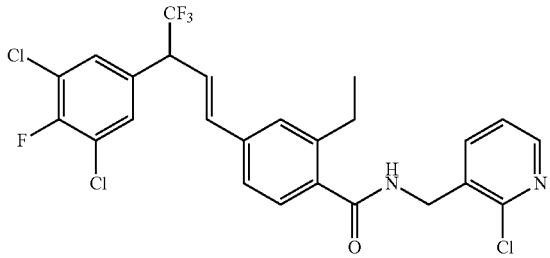 [SMILES: CCc1cc(/C=C/C(c2cc(Cl)c(F)c(Cl)c2)C(F)(F)F)ccc1C(=O)NCc1cccnc1Cl] |
| AC77 | 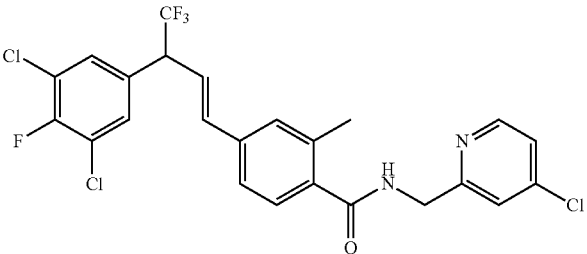 [SMILES: Cc1cc(/C=C/C(c2cc(Cl)c(F)c(Cl)c2)C(F)(F)F)ccc1C(=O)NCc1cc(Cl)ccn1] |
| AC78 | 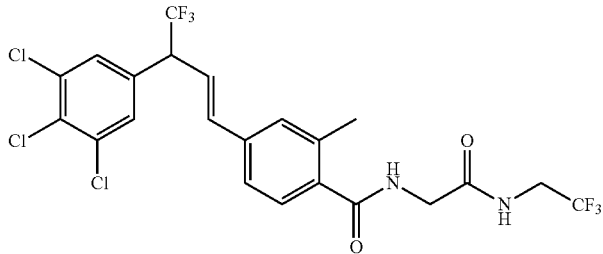 |
| AC79 | 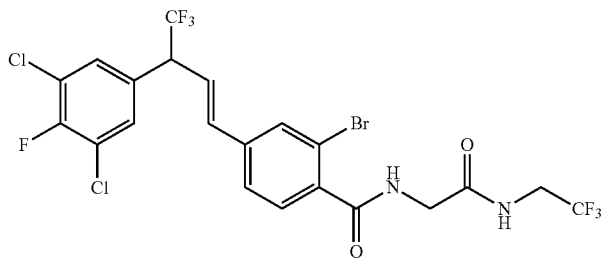 |
| AC80 | 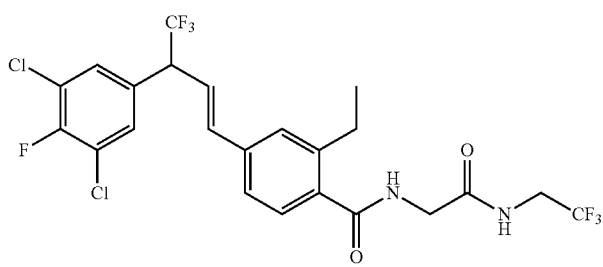 [SMILES: CCc1cc(/C=C/C(c2cc(Cl)c(F)c(Cl)c2)C(F)(F)F)ccc1C(=O)NCC(=O)NCC(F)(F)F] |

TABLE 1-continued

Structures for Compounds

| Compound Number | Structure |
|---|---|
| AC81 | 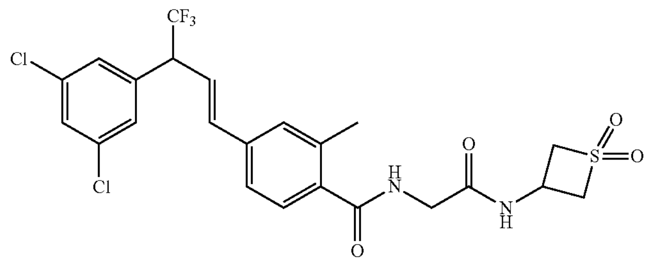 [SMILES: Cc1cc(/C=C/C(c2cc(Cl)cc(Cl)c2)C(F)(F)F)ccc1C(=O)NCC(=O)NC1CS(=O)(=O)C1] |
| AC82 | 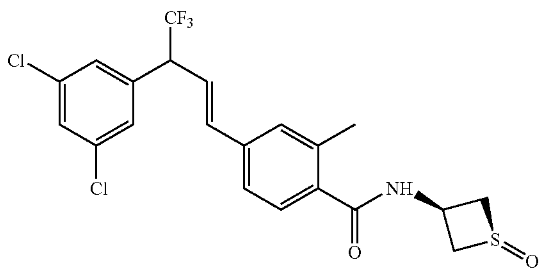 [SMILES: Cc1cc(/C=C/C(c2cc(Cl)cc(Cl)c2)C(F)(F)F)ccc1C(=O)N[C@H]1C[S@@](=O)C1] |
| AC83 | 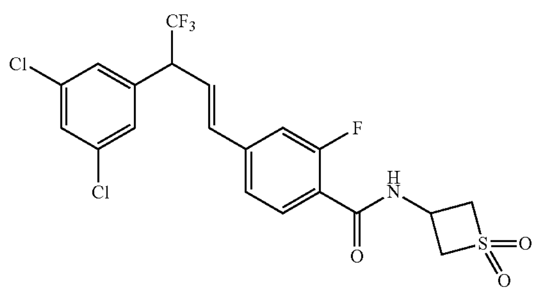 [SMILES: O=C(NC1CS(=O)(=O)C1)c1ccc(/C=C/C(c2cc(Cl)cc(Cl)c2)C(F)(F)F)cc1F] |
| AC84 | 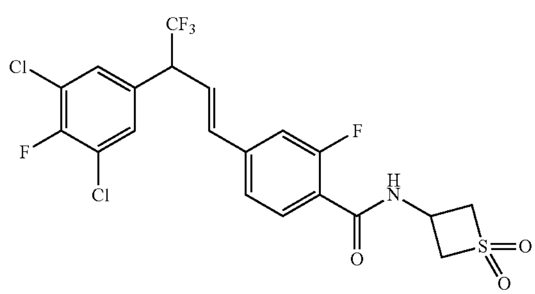 [SMILES: O=C(NC1CS(=O)(=O)C1)c1ccc(/C=C/C(c2cc(Cl)c(F)c(Cl)c2)C(F)(F)F)cc1F] |
| AC85 | 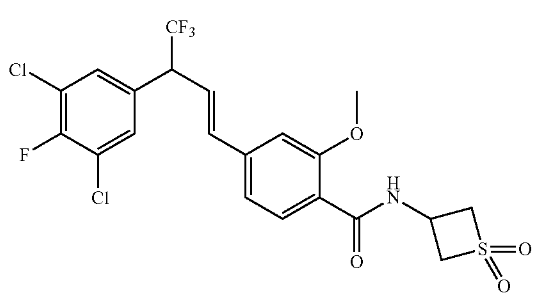 [SMILES: COc1cc(/C=C/C(c2cc(Cl)c(F)c(Cl)c2)C(F)(F)F)ccc1C(=O)NC1CS(=O)(=O)C1] |

TABLE 1-continued
Structures for Compounds
| Compound Number | Structure |
|---|---|
| AC86 | 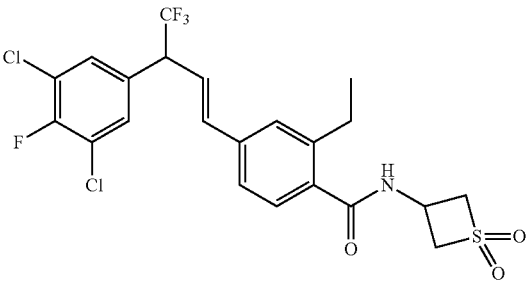 [SMILES: CCc1cc(/C=C/C(c2cc(Cl)c(F)c(Cl)c2)C(F)(F)F)ccc1C(=O)NC1CS(=O)(=O)C1] |
| AC87 | 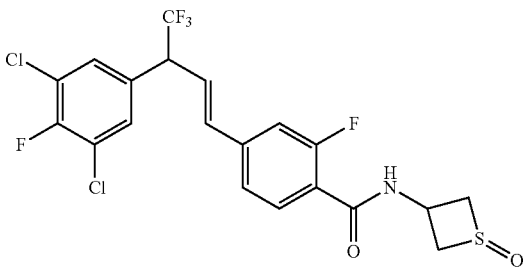 [SMILES: O=C(NC1CS(=O)C1)c1ccc(/C=C/C(c2cc(Cl)c(F)c(Cl)c2)C(F)(F)F)cc1F] |
| AC89 | 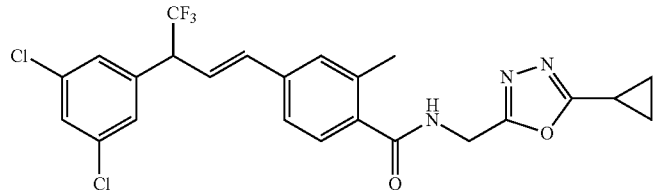 [SMILES: Cc1cc(/C=C/C(c2cc(Cl)cc(Cl)c2)C(F)(F)F)ccc1C(=O)NCc1nnc(C2CC2)o1] |
| AC90 | 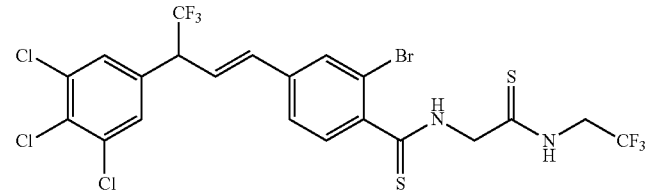 [SMILES: FC(F)(F)CNC(=S)CNC(=S)c1ccc(/C=C/C(c2cc(Cl)c(Cl)c(Cl)c2)C(F)(F)F)cc1Br] |
| AC91 | 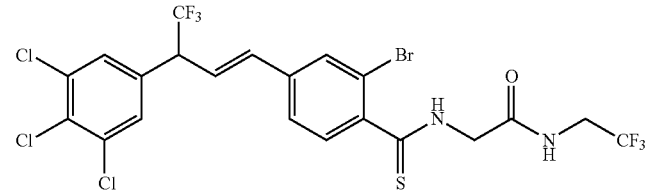 [SMILES: O=C(CNC(=S)c1ccc(/C=C/C(c2cc(Cl)c(Cl)c(Cl)c2)C(F)(F)F)cc1Br)NCC(F)(F)F] |
| AC92 | 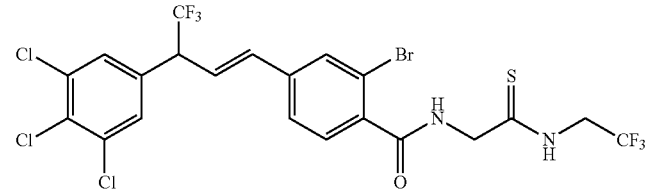 [SMILES: O=C(NCC(=S)NCC(F)(F)F)c1ccc(/C=C/C(c2cc(Cl)c(Cl)c(Cl)c2)C(F)(F)F)cc1Br] |

TABLE 1-continued
Structures for Compounds
| Compound Number | Structure |
|---|---|
| AC93 | 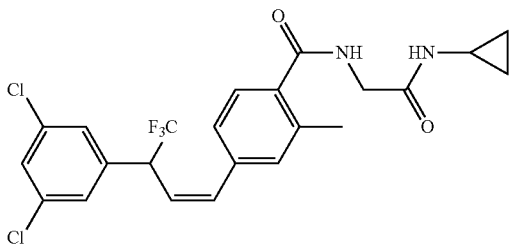 [SMILES: Cc1cc(/C=C\C(c2cc(Cl)cc(Cl)c2)C(F)(F)F)ccc1C(=O)NCC(=O)NC1CC1] |
| AC94 | 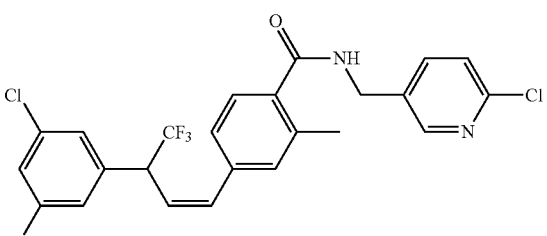 |
| AC95 | 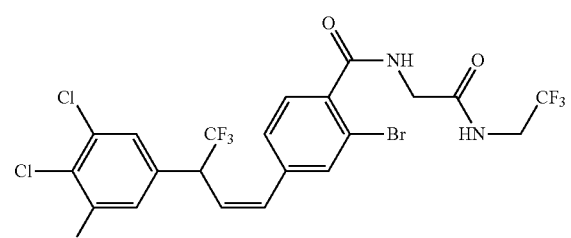 |
| AC96 | 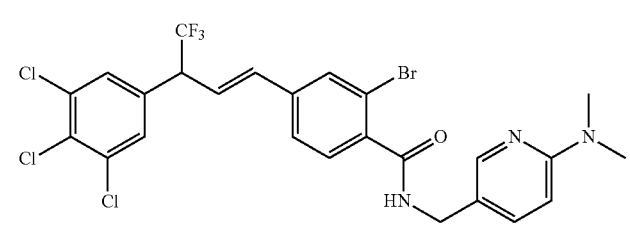 [SMILES: CN(C)c1ccc(CNC(=O)c2ccc(/C=C/C(c3cc(Cl)c(Cl)c(Cl)c3)C(F)(F)F)cc2Br)cn1] |
| AC97 | 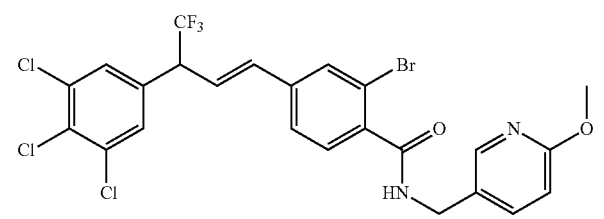 [SMILES: COc1ccc(CNC(=O)c2ccc(/C=C/C(c3cc(Cl)c(Cl)c(Cl)c3)C(F)(F)F)cc2Br)cn1] |
| AC98 | 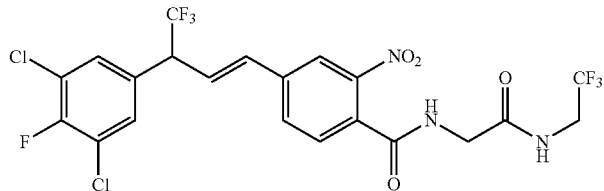 [SMILES: O=C(CNC(=O)c1ccc(/C=C/C(c2cc(Cl)c(F)c(Cl)c2)C(F)(F)F)cc1[N+](=O)[O-])NCC(F)(F)F] |

TABLE 1-continued

Structures for Compounds

| Compound Number | Structure |
| --- | --- |
| AC99 | 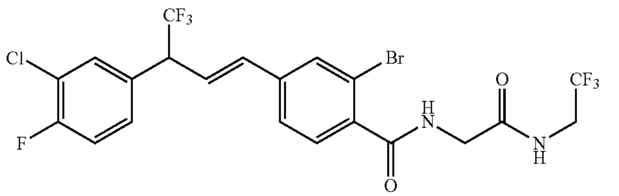 [SMILES: O=C(CNC(=O)c1ccc(/C=C/C(c2ccc(F)c(Cl)c2)C(F)(F)F)cc1Br)NCC(F)(F)F] |
| AC100 | 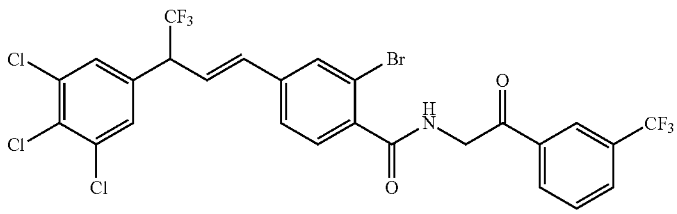 [SMILES: O=C(CNC(=O)c1ccc(/C=C/C(c2cc(Cl)c(Cl)c(Cl)c2)C(F)(F)F)cc1Br)c1cccc(C(F)(F)F)c1] |
| AC101 | 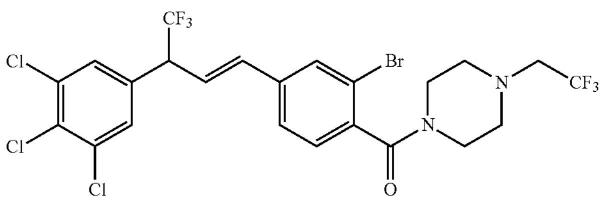 [SMILES: O=C(c1ccc(/C=C/C(c2cc(Cl)c(Cl)c(Cl)c2)C(F)(F)F)cc1Br)N1CCN(CC(F)(F)F)CC1] |
| AC102 | 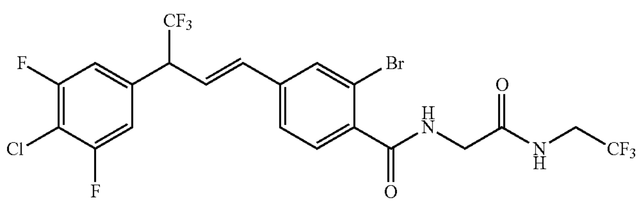 [SMILES: O=C(CNC(=O)c1ccc(/C=C/C(c2cc(F)c(Cl)c(F)c2)C(F)(F)F)cc1Br)NCC(F)(F)F] |
| AC103 | 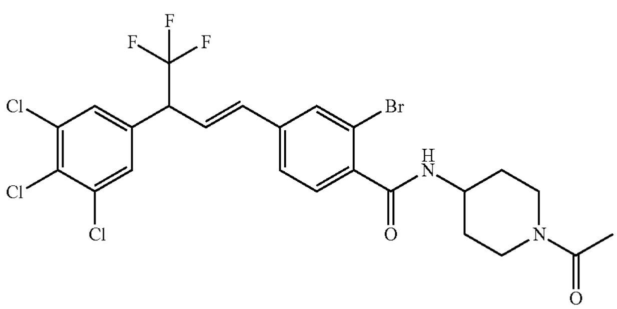 [SMILES: CC(=O)N1CCC(NC(=O)c2ccc(/C=C/C(c3cc(Cl)c(Cl)c(Cl)c3)C(F)(F)F)cc2Br)CC1] |
| AC104 | 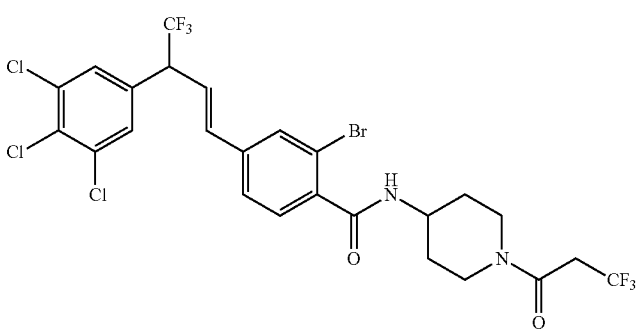 [SMILES: O=C(NC1CCN(C(=O)CC(F)(F)F)CC1)c1ccc(/C=C/C(c2cc(Cl)c(Cl)c(Cl)c2)C(F)(F)F)cc1Br] |

TABLE 1-continued
Structures for Compounds
| Compound Number | Structure |
|---|---|
| AC105 | 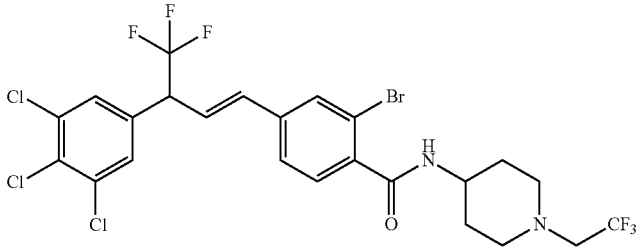 [SMILES: O=C(NC1CCN(CC(F)(F)F)CC1)c1ccc(/C=C/C(c2cc(Cl)c(Cl)c(Cl)c2)C(F)(F)F)cc1Br] |
| AC106 | 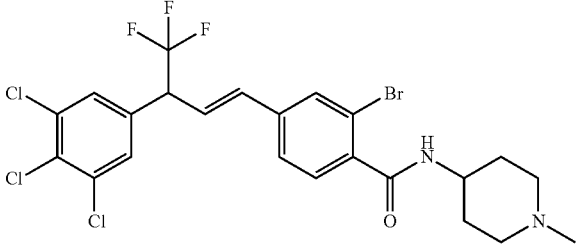 [SMILES: CN1CCC(NC(=O)c2ccc(/C=C/C(c3cc(Cl)c(Cl)c(Cl)c3)C(F)(F)F)cc2Br)CC1] |
| AC107 | 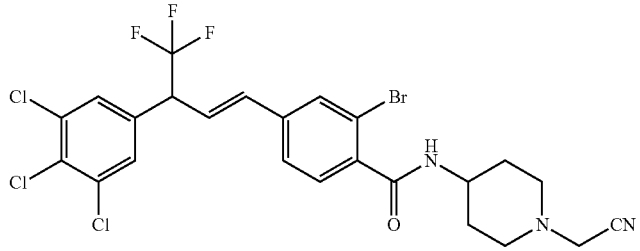 [SMILES: N#CCN1CCC(NC(=O)c2ccc(/C=C/C(c3cc(Cl)c(Cl)c(Cl)c3)C(F)(F)F)cc2Br)CC1] |
| AC108 | 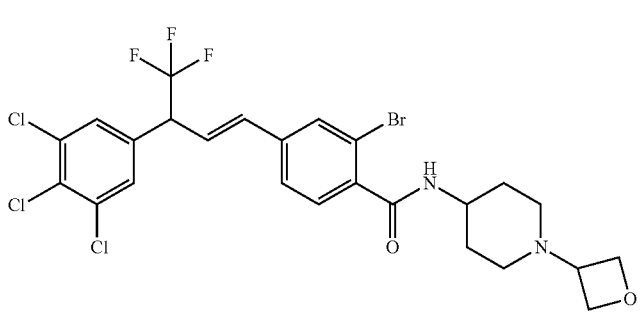 [SMILES: O=C(NC1CCN(C2COC2)CC1)c1ccc(/C=C/C(c2cc(Cl)c(Cl)c(Cl)c2)C(F)(F)F)cc1Br] |
| AC109 | 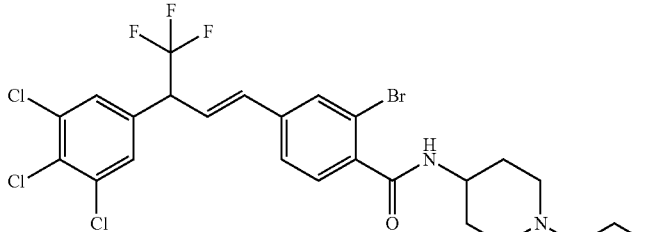 |

TABLE 1-continued
Structures for Compounds
| Compound Number | Structure |
|---|---|
| AC110 | 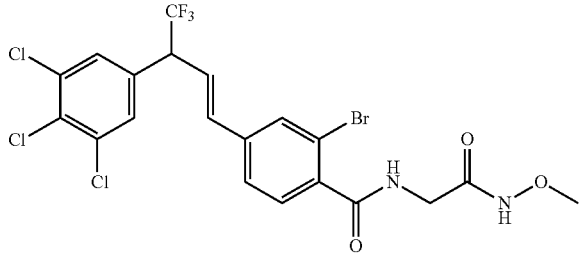 [SMILES: CONC(=O)CNC(=O)c1ccc(/C=C/C(c2cc(Cl)c(Cl)c(Cl)c2)C(F)(F)F)cc1Br] |
| AC111 | 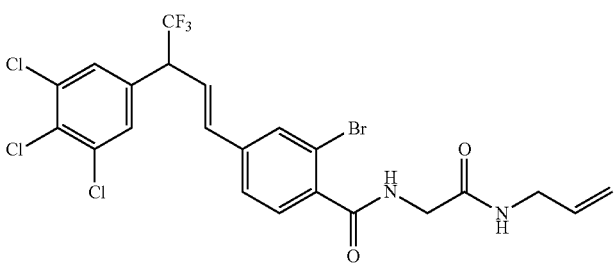 [SMILES: C=CCNC(=O)CNC(=O)c1ccc(/C=C/C(c2cc(Cl)c(Cl)c(Cl)c2)C(F)(F)F)cc1Br] |
| AC112 | 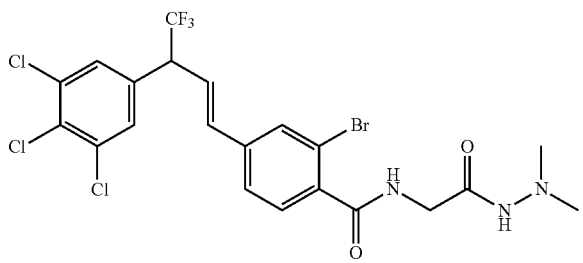 [SMILES: CN(C)NC(=O)CNC(=O)c1ccc(/C=C/C(c2cc(Cl)c(Cl)c(Cl)c2)C(F)(F)F)cc1Br] |
| AC113 | 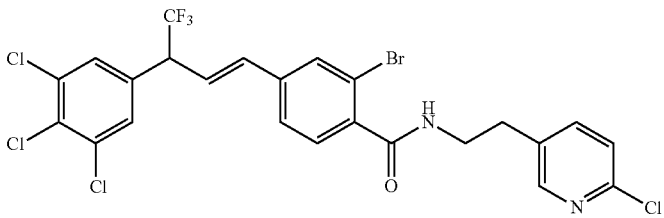 [SMILES: O=C(NCCc1ccc(Cl)nc1)c1ccc(/C=C/C(c2cc(Cl)c(Cl)c(Cl)c2)C(F)(F)F)cc1Br] |
| AC114 | 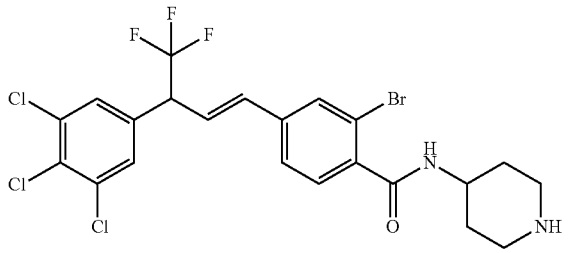 [SMILES: O=C(NC1CCNCC1)c1ccc(/C=C/C(c2cc(Cl)c(Cl)c(Cl)c2)C(F)(F)F)cc1Br] |
| AC115 | 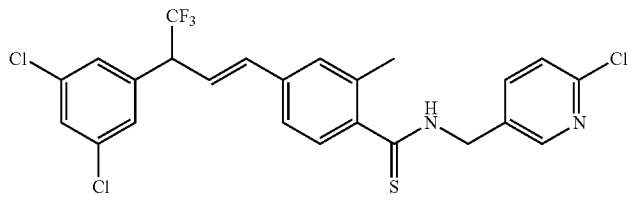 [SMILES: Cc1cc(/C=C/C(c2cc(Cl)cc(Cl)c2)C(F)(F)F)ccc1C(=S)NCc1ccc(Cl)nc1] |

TABLE 1-continued

Structures for Compounds

| Compound Number | Structure |
|---|---|
| AC116 | 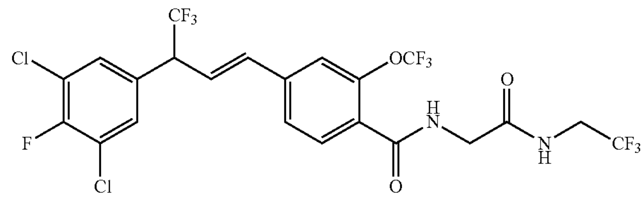 [SMILES: O=C(CNC(=O)c1ccc(/C=C/C(c2cc(Cl)c(F)c(Cl)c2)C(F)(F)F)cc1OC(F)(F)F)NCC(F)(F)F] |
| AC117 | 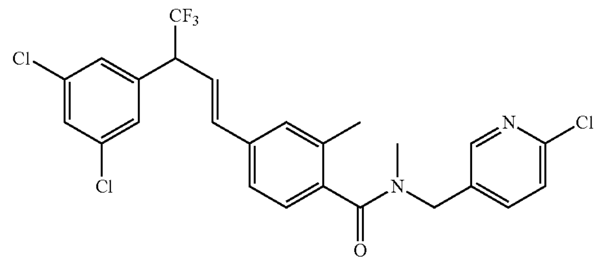 [SMILES: Cc1cc(/C=C/C(c2cc(Cl)cc(Cl)c2)C(F)(F)F)ccc1C(=O)N(C)Cc1ccc(Cl)nc1] |
| AC118 | 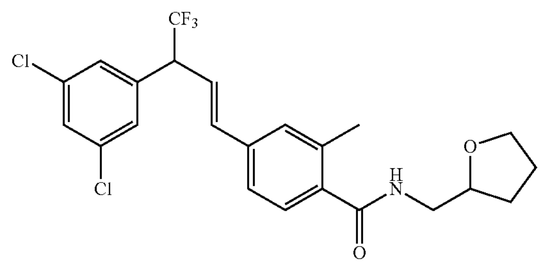 [SMILES: Cc1cc(/C=C/C(c2cc(Cl)cc(Cl)c2)C(F)(F)F)ccc1C(=O)NCC1CCCO1] |
| BC1 | 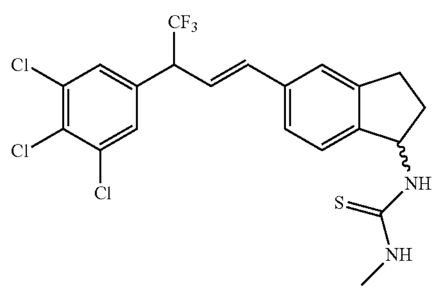 [SMILES: CNC(=S)NC1CCc2cc(/C=C/C(c3cc(Cl)c(Cl)c(Cl)c3)C(F)(F)F)ccc21] |
| BC2 | 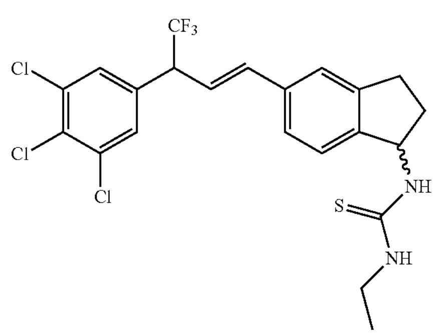 [SMILES: CCNC(=S)NC1CCc2cc(/C=C/C(c3cc(Cl)c(Cl)c(Cl)c3)C(F)(F)F)ccc21] |

TABLE 1-continued

Structures for Compounds

| Compound Number | Structure |
|---|---|
| BC3 | (3,4,5-trichlorophenyl)-CH(CF3)-CH=CH-(indan-5-yl), indan-1-yl-NH-C(=S)-NH-CH2-CH=CH2 |
| BC4 | (3,4,5-trichlorophenyl)-CH(CF3)-CH=CH-(indan-5-yl), indan-1-yl-NH-C(=O)-CH2-CF3 |
| BC5 | (3,4,5-trichlorophenyl)-CH(CF3)-CH=CH-(tetralin-6-yl), tetralin-1-yl-NH-C(=O)-CH2-CF3 |
| BC6 | (3,4,5-trichlorophenyl)-CH(CF3)-CH=CH-(indan-5-yl), indan-1-yl-NH-C(=O)-cyclopropyl |
| BC7 | (3,4,5-trichlorophenyl)-CH(CF3)-CH=CH-(tetralin-6-yl), tetralin-1-yl-NH-C(=O)-cyclopropyl |

TABLE 1-continued

Structures for Compounds

| Compound Number | Structure |
|---|---|
| BC8 | 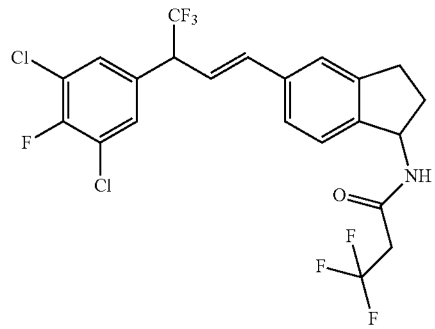 [SMILES: O=C(CC(F)(F)F)NC1CCc2cc(/C=C/C(c3cc(Cl)c(F)c(Cl)c3)C(F)(F)F)ccc21] |
| BC9 | 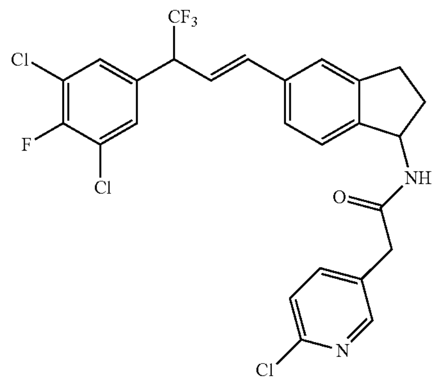 [SMILES: O=C(Cc1ccc(Cl)nc1)NC1CCc2cc(/C=C/C(c3cc(Cl)c(F)c(Cl)c3)C(F)(F)F)ccc21] |
| BC10 | 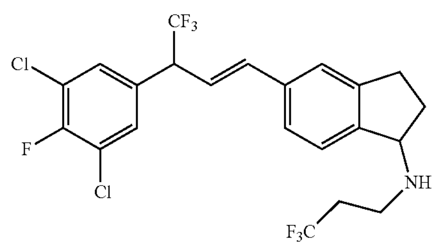 [SMILES: Fc1c(Cl)cc(C(/C=C/c2ccc3c(c2)CCC3NCCC(F)(F)F)C(F)(F)F)cc1Cl] |
| BC11 | 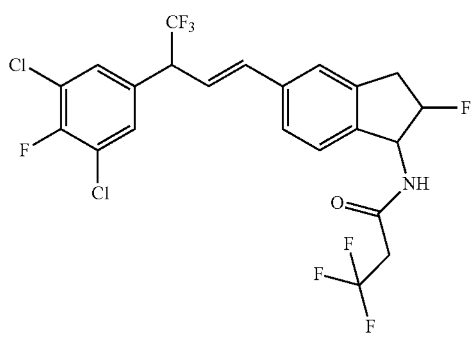 [SMILES: O=C(CC(F)(F)F)NC1c2ccc(/C=C/C(c3cc(Cl)c(F)c(Cl)c3)C(F)(F)F)cc2CC1F] |
| BC12 | 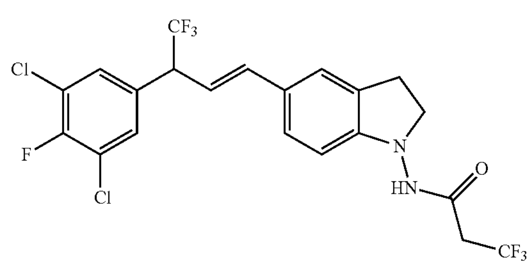 [SMILES: O=C(CC(F)(F)F)NN1CCc2cc(/C=C/C(c3cc(Cl)c(F)c(Cl)c3)C(F)(F)F)ccc21] |

TABLE 1-continued

Structures for Compounds

| Compound Number | Structure |
|---|---|
| BC13 | (structure) |
| BC14 | (structure) |
| CI4 | (structure) |
| CI5 | (structure) |
| CI8 | (structure) |
| CI9 | (structure) |
| CI34 | (structure) |

TABLE 1-continued

Structures for Compounds

| Compound Number | Structure |
|---|---|
| CI35 | 1-(3,4-dichlorophenyl)-2,2,2-trifluoroethyl group connected via CH=CH to 4-(phthalimidomethyl)-2-(trifluoromethyl)phenyl |
| CI36 | 1-(3,5-dichlorophenyl)-2,2,2-trifluoroethyl group connected via CH=CH to 4-(phthalimidomethyl)-2-bromophenyl |
| CI37 | 1-(3,5-dichloro-4-fluorophenyl)-2,2,2-trifluoroethyl group connected via CH=CH to 4-(phthalimidomethyl)-2-bromophenyl |
| CI38 | 1-(3,4-dichlorophenyl)-2,2,2-trifluoroethyl group connected via CH=CH to 4-(phthalimidomethyl)-2-bromophenyl |

TABLE 1-continued
| Compound Number | Structure |
|---|---|
| CI39 | 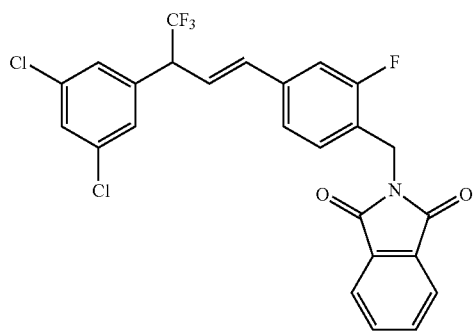 |
| CI40 | 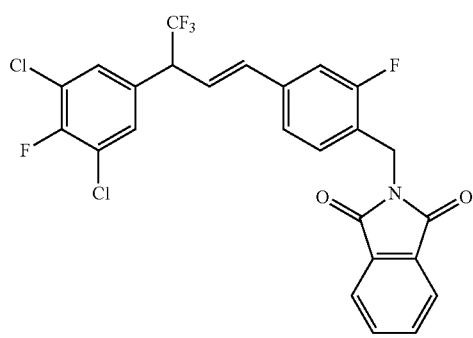 [SMILES: O=C1c2ccccc2C(=O)N1Cc1ccc(/C=C/C(c2cc(Cl)c(F)c(Cl)c2)C(F)(F)F)cc1F] |
| CI41 | 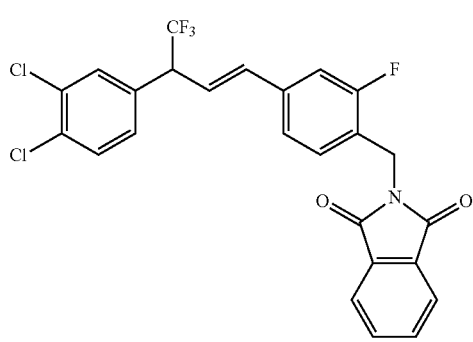 |
| CI49 | 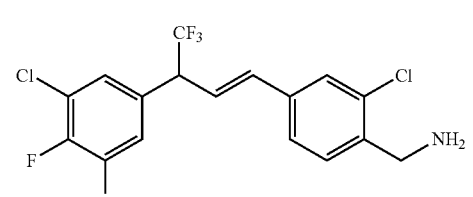 |
| CI50 | 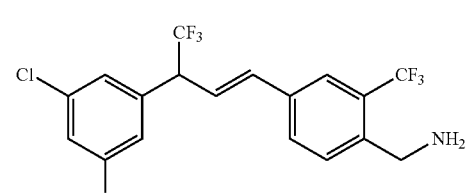 |

TABLE 1-continued

Structures for Compounds

| Compound Number | Structure |
|---|---|
| CI51 | 3,5-dichloro-4-fluorophenyl-C(CF$_3$)H-CH=CH-(2-CF$_3$-4-CH$_2$NH$_2$-phenyl) |
| CI52 | 3,4-dichlorophenyl-C(CF$_3$)H-CH=CH-(2-CF$_3$-4-CH$_2$NH$_2$-phenyl) |
| CI53 | 3,5-dichloro-4-fluorophenyl-C(CF$_3$)H-CH=CH-(2-Br-4-CH$_2$NH$_2$-phenyl) |
| CI54 | 3,4-dichlorophenyl-C(CF$_3$)H-CH=CH-(2-Br-4-CH$_2$NH$_2$-phenyl) |
| CI55 | 3,5-dichlorophenyl-C(CF$_3$)H-CH=CH-(2-F-4-CH$_2$NH$_2$-phenyl) |
| CI56 | 3,5-dichloro-4-fluorophenyl-C(CF$_3$)H-CH=CH-(2-F-4-CH$_2$NH$_2$-phenyl) |
| CI57 | 3,4-dichlorophenyl-C(CF$_3$)H-CH=CH-(2-F-4-CH$_2$NH$_2$-phenyl) |
| CC1 | 3,5-dichlorophenyl-C(CF$_3$)H-CH=CH-(4-CH$_2$NHC(O)CH$_3$-phenyl) |

TABLE 1-continued
Structures for Compounds
| Compound Number | Structure |
|---|---|
| CC2 | 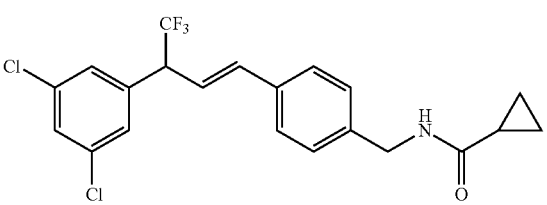 [SMILES: O=C(NCc1ccc(/C=C/C(c2cc(Cl)cc(Cl)c2)C(F)(F)F)cc1)C1CC1] |
| CC3 | 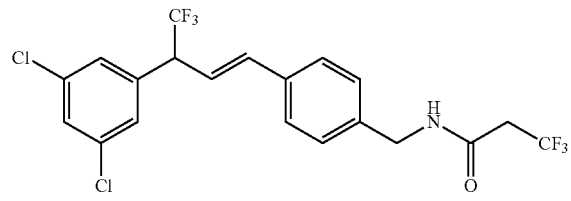 [SMILES: O=C(CC(F)(F)F)NCc1ccc(/C=C/C(c2cc(Cl)cc(Cl)c2)C(F)(F)F)cc1] |
| CC4 | 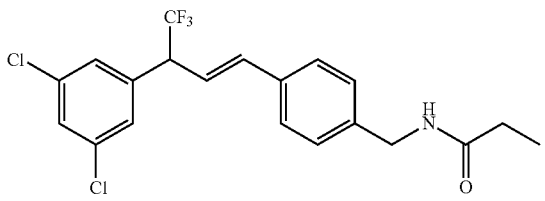 [SMILES: CCC(=O)NCc1ccc(/C=C/C(c2cc(Cl)cc(Cl)c2)C(F)(F)F)cc1] |
| CC5 | 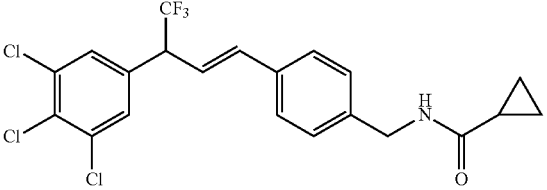 [SMILES: O=C(NCc1ccc(/C=C/C(c2cc(Cl)c(Cl)c(Cl)c2)C(F)(F)F)cc1)C1CC1] |
| CC6 | 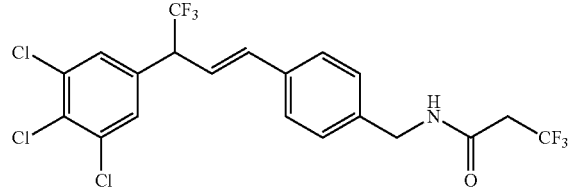 [SMILES: O=C(CC(F)(F)F)NCc1ccc(/C=C/C(c2cc(Cl)c(Cl)c(Cl)c2)C(F)(F)F)cc1] |
| CC7 | 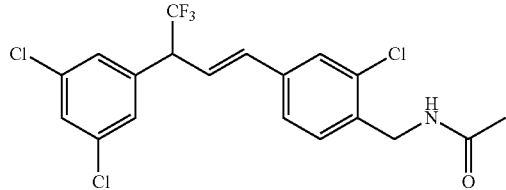 [SMILES: CC(=O)NCc1ccc(/C=C/C(c2cc(Cl)cc(Cl)c2)C(F)(F)F)cc1Cl] |
| CC8 | 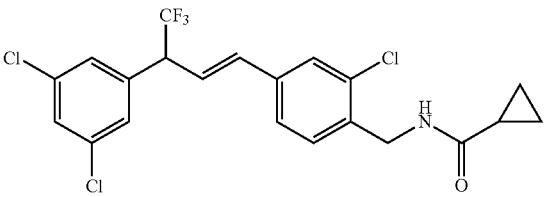 [SMILES: O=C(NCc1ccc(/C=C/C(c2cc(Cl)cc(Cl)c2)C(F)(F)F)cc1Cl)C1CC1] |

TABLE 1-continued

Structures for Compounds

| Compound Number | Structure |
|---|---|
| CC9 | 3,5-dichlorophenyl-C(CF3)H-CH=CH-(2-chloro-4-yl)phenyl-CH2-NH-C(O)-CH2-CF3 |
| CC10 | 3,4,5-trichlorophenyl-C(CF3)H-CH=CH-(2-chloro-4-yl)phenyl-CH2-NH-C(O)-CH2-CF3 |
| CC11 | 3,4,5-trichlorophenyl-C(CF3)H-CH=CH-(2-chloro-4-yl)phenyl-CH2-NH-C(O)-cyclopropyl |
| CC12 | 3,4,5-trichlorophenyl-C(CF3)H-CH=CH-(2-chloro-4-yl)phenyl-CH2-NH-C(O)-C(CH3)3 |
| CC13 | 3,4,5-trichlorophenyl-C(CF3)H-CH=CH-phenyl-CH2-NH-C(O)-(2-chloropyridin-4-yl) |
| CC14 | 3,4,5-trichlorophenyl-C(CF3)H-CH=CH-(2-chloro-4-yl)phenyl-CH2-NH-C(O)-CH2-(6-chloropyridin-3-yl) |
| CC15 | 3,5-dichloro-4-fluorophenyl-C(CF3)H-CH=CH-(2-chloro-4-yl)phenyl-CH2-NH-C(O)-cyclopropyl |

TABLE 1-continued

| Compound Number | Structure |
|---|---|
| CC16 | 3,5-dichloro-4-fluorophenyl-C(CF₃)H-CH=CH-(4-phenyl)-CH₂-NH-C(=O)-CH₂CF₃ |
| CC17 | 3,4-dichlorophenyl-C(CF₃)H-CH=CH-(2-chloro-4-phenyl)-CH₂-NH-C(=O)-cyclopropyl |
| CC18 | 3,4-dichlorophenyl-C(CF₃)H-CH=CH-(2-chloro-4-phenyl)-CH₂-NH-C(=O)-CH₂CF₃ |
| CC19 | 3,4,5-trichlorophenyl-C(CF₃)H-CH=CH-(2-chloro-4-phenyl)-CH₂-NH-C(=O)-CH₂CH₂-S-CH₃ |
| CC20 | 3,4,5-trichlorophenyl-C(CF₃)H-CH=CH-(2-chloro-4-phenyl)-CH₂-NH-C(=S)-cyclopropyl |
| CC21 | 3,5-dichlorophenyl-C(CF₃)H-CH=CH-(2-trifluoromethyl-4-phenyl)-CH₂-NH-C(=O)-cyclopropyl |
| CC22 | 3,4,5-trichlorophenyl-C(CF₃)H-CH=CH-(2-trifluoromethyl-4-phenyl)-CH₂-NH-C(=O)-cyclopropyl |

TABLE 1-continued

Structures for Compounds

| Compound Number | Structure |
|---|---|
| CC23 | 3,4,5-trichlorophenyl-CH(CF$_3$)-CH=CH-[2-(CF$_3$)-4-(CH$_2$NHC(O)-3-pyridyl)phenyl] |
| CC24 | 3,4,5-trichlorophenyl-CH(CF$_3$)-CH=CH-[2-(CF$_3$)-4-(CH$_2$NHC(O)CH$_2$CF$_3$)phenyl] |
| CC25 | 3,4,5-trichlorophenyl-CH(CF$_3$)-CH=CH-[2-Br-4-(CH$_2$NHC(O)CH$_2$CF$_3$)phenyl] |
| CC26 | 3,4,5-trichlorophenyl-CH(CF$_3$)-CH=CH-[2-Br-4-(CH$_2$NHC(O)-cyclopropyl)phenyl] |
| CC27 | 3,4,5-trichlorophenyl-CH(CF$_3$)-CH=CH-[2-F-4-(CH$_2$NHC(O)CH$_2$CF$_3$)phenyl] |
| CC28 | 3,4,5-trichlorophenyl-CH(CF$_3$)-CH=CH-[2-F-4-(CH$_2$NHC(O)-cyclopropyl)phenyl] |

TABLE 1-continued

Structures for Compounds

| Compound Number | Structure |
|---|---|
| CC29 | 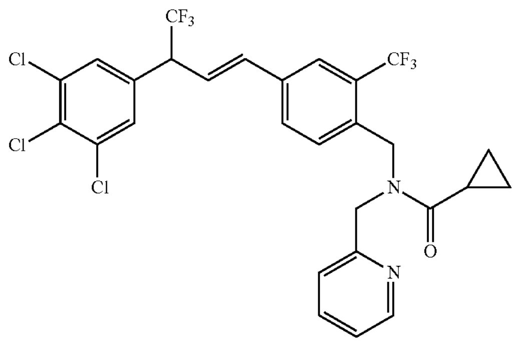 [SMILES: O=C(C1CC1)N(Cc1ccccn1)Cc1ccc(/C=C/C(c2cc(Cl)c(Cl)c(Cl)c2)C(F)(F)F)cc1C(F)(F)F] |
| CC30 | 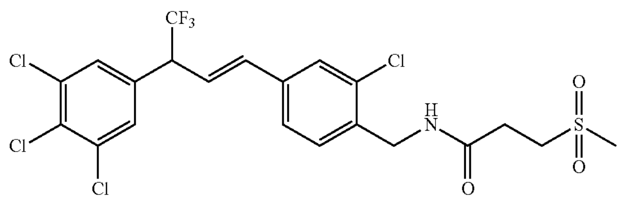 [SMILES: CS(=O)(=O)CCC(=O)NCc1ccc(/C=C/C(c2cc(Cl)c(Cl)c(Cl)c2)C(F)(F)F)cc1Cl] |
| CC31 | 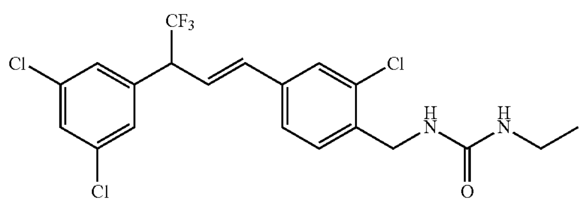 [SMILES: CCNC(=O)NCc1ccc(/C=C/C(c2cc(Cl)cc(Cl)c2)C(F)(F)F)cc1Cl] |
| CC32 | 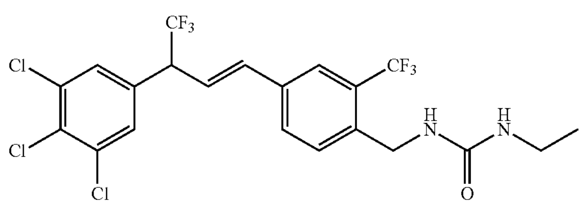 |
| CC33 | 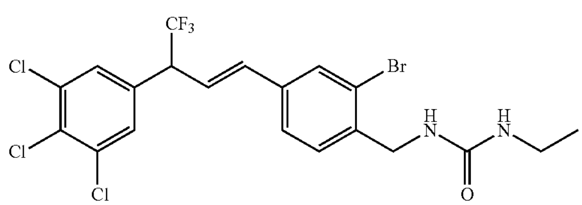 [SMILES: CCNC(=O)NCc1ccc(/C=C/C(c2cc(Cl)c(Cl)c(Cl)c2)C(F)(F)F)cc1Br] |
| CC34 | 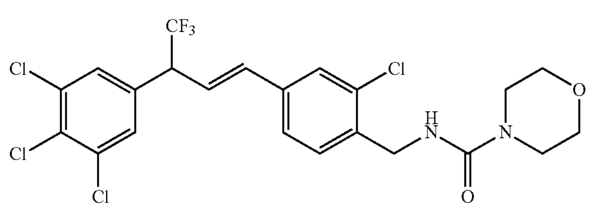 [SMILES: O=C(NCc1ccc(/C=C/C(c2cc(Cl)c(Cl)c(Cl)c2)C(F)(F)F)cc1Cl)N1CCOCC1] |

US 9,622,477 B2
361                                                                             362
TABLE 1-continued
Structures for Compounds
| Compound Number | Structure |
|---|---|
| CC35 | 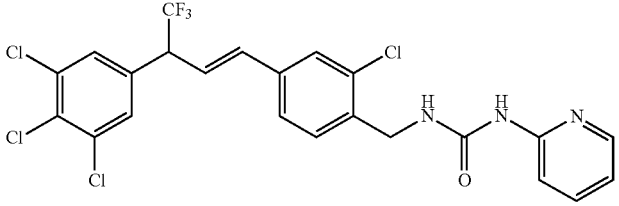 [SMILES: O=C(NCc1ccc(/C=C/C(c2cc(Cl)c(Cl)c(Cl)c2)C(F)(F)F)cc1Cl)Nc1ccccn1] |
| CC36 | 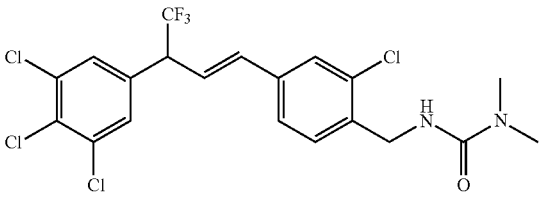 [SMILES: CN(C)C(=O)NCc1ccc(/C=C/C(c2cc(Cl)c(Cl)c(Cl)c2)C(F)(F)F)cc1Cl] |
| CC37 | 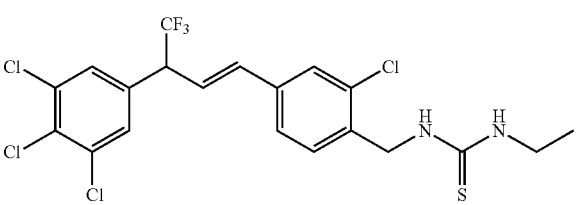 [SMILES: CCNC(=S)NCc1ccc(/C=C/C(c2cc(Cl)c(Cl)c(Cl)c2)C(F)(F)F)cc1Cl] |
| CC38 | 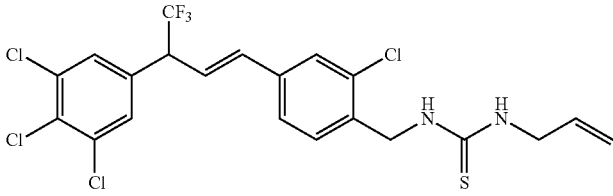 [SMILES: C=CCNC(=S)NCc1ccc(/C=C/C(c2cc(Cl)c(Cl)c(Cl)c2)C(F)(F)F)cc1Cl] |
| CC39 | 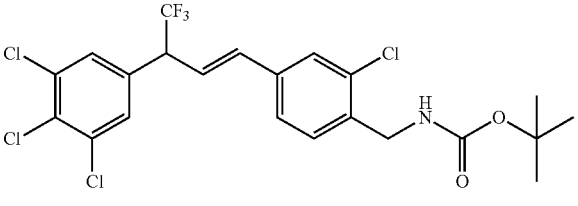 [SMILES: CC(C)(C)OC(=O)NCc1ccc(/C=C/C(c2cc(Cl)c(Cl)c(Cl)c2)C(F)(F)F)cc1Cl] |
| CC40 | 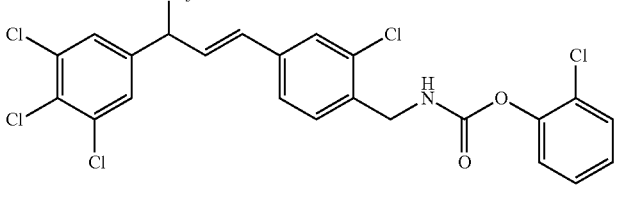 |
| CC41 | 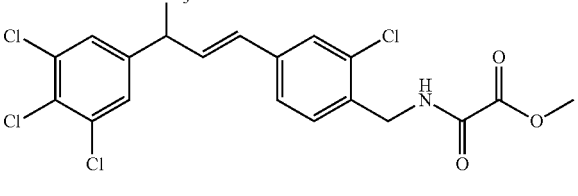 |

TABLE 1-continued
Structures for Compounds
| Compound Number | Structure |
|---|---|
| CC42 | 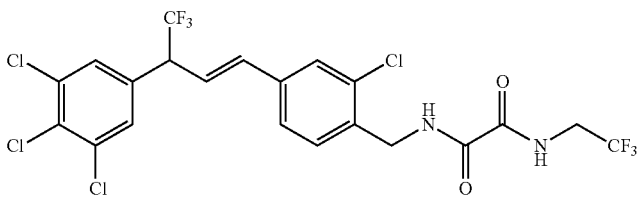 [SMILES: O=C(NCc1ccc(/C=C/C(c2cc(Cl)c(Cl)c(Cl)c2)C(F)(F)F)cc1Cl)C(=O)NCC(F)(F)F] |
| CC43 | 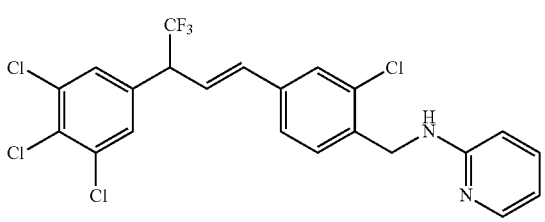 [SMILES: FC(F)(F)C(/C=C/c1ccc(CNc2ccccn2)c(Cl)c1)c1cc(Cl)c(Cl)c(Cl)c1] |
| CC44 | 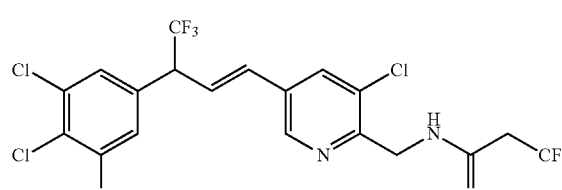 |
| CC45 | 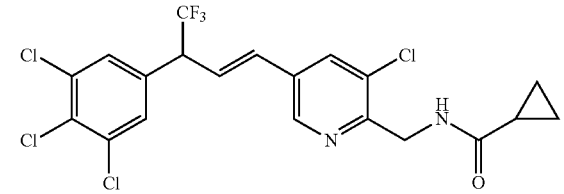 [SMILES: O=C(NCc1ncc(/C=C/C(c2cc(Cl)c(Cl)c(Cl)c2)C(F)(F)F)cc1Cl)C1CC1] |
| CC46 | 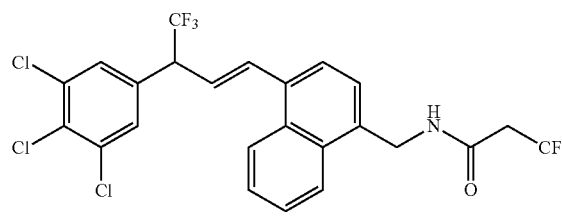 |
| CC47 | 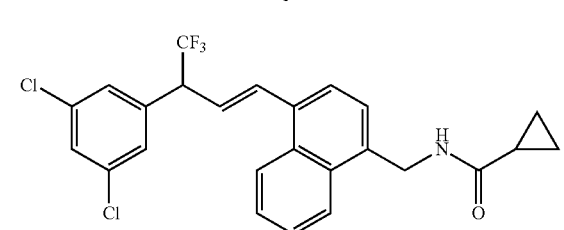 |
| CC48 | 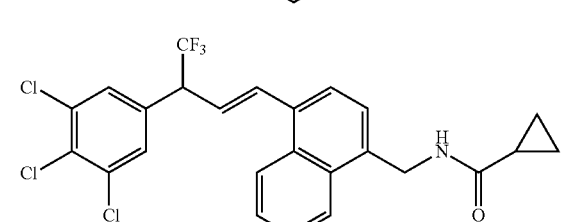 |

US 9,622,477 B2
365
366
TABLE 1-continued
Structures for Compounds
| Compound Number | Structure |
|---|---|
| CC49 | 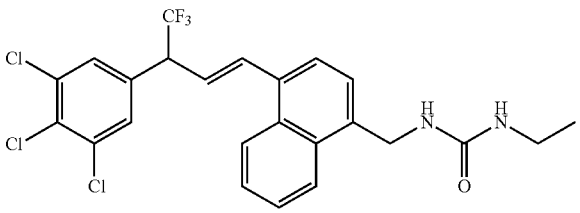 [SMILES: CCNC(=O)NCc1ccc(/C=C/C(c2cc(Cl)c(Cl)c(Cl)c2)C(F)(F)F)c2ccccc12] |
| CC50 | 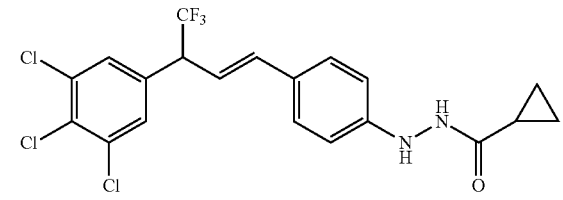 [SMILES: O=C(NNc1ccc(/C=C/C(c2cc(Cl)c(Cl)c(Cl)c2)C(F)(F)F)cc1)C1CC1] |
| CC51 | 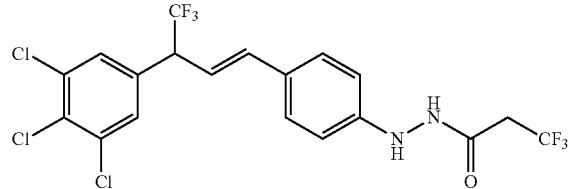 [SMILES: O=C(CC(F)(F)F)NNc1ccc(/C=C/C(c2cc(Cl)c(Cl)c(Cl)c2)C(F)(F)F)cc1] |
| CC52 | 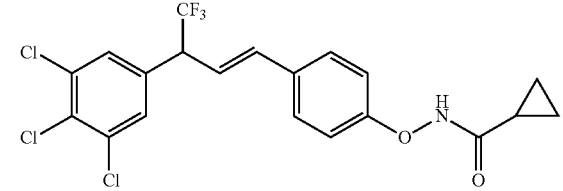 [SMILES: O=C(NOc1ccc(/C=C/C(c2cc(Cl)c(Cl)c(Cl)c2)C(F)(F)F)cc1)C1CC1] |
| CC53 | 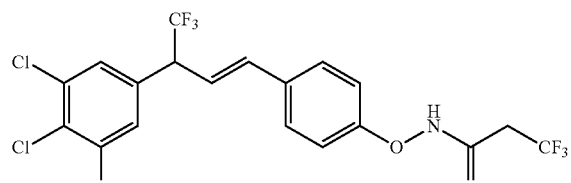 |
| CC54 | 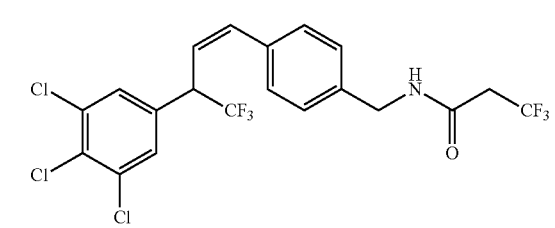 [SMILES: O=C(CC(F)(F)F)NCc1ccc(/C=C\C(c2cc(Cl)c(Cl)c(Cl)c2)C(F)(F)F)cc1] |
| DC1 | 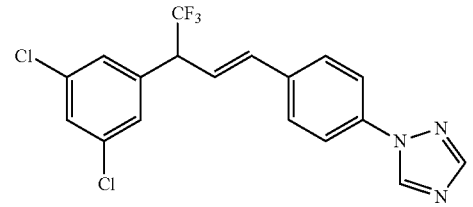 |

TABLE 1-continued
Structures for Compounds
| Compound Number | Structure |
|---|---|
| DC2 | 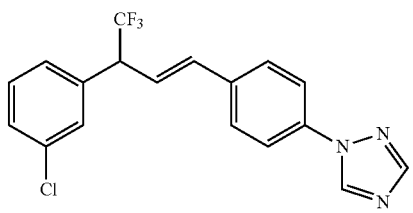 [SMILES: FC(F)(F)C(/C=C/c1ccc(-n2cncn2)cc1)c1cccc(Cl)c1] |
| DC3 | 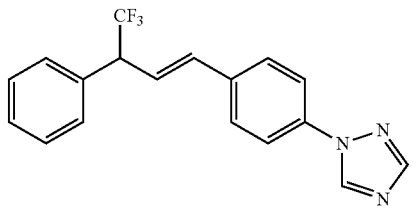 [SMILES: FC(F)(F)C(/C=C/c1ccc(-n2cncn2)cc1)c1ccccc1] |
| DC4 | 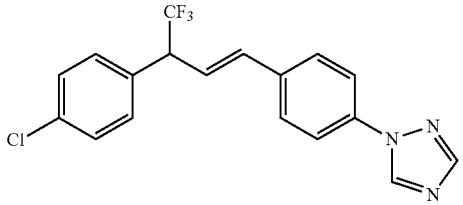 [SMILES: FC(F)(F)C(/C=C/c1ccc(-n2cncn2)cc1)c1ccc(Cl)cc1] |
| DC5 | 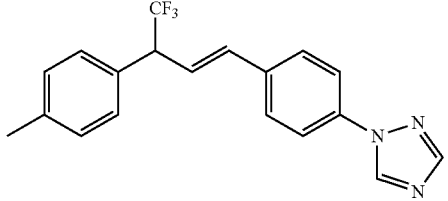 [SMILES: Cc1ccc(C(/C=C/c2ccc(-n3cncn3)cc2)C(F)(F)F)cc1] |
| DC6 | 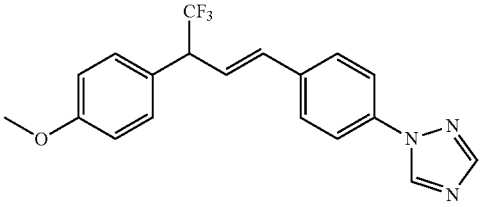 [SMILES: COc1ccc(C(/C=C/c2ccc(-n3cncn3)cc2)C(F)(F)F)cc1] |
| DC7 | 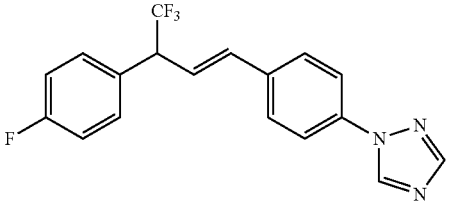 [SMILES: Fc1ccc(C(/C=C/c2ccc(-n3cncn3)cc2)C(F)(F)F)cc1] |
| DC8 | 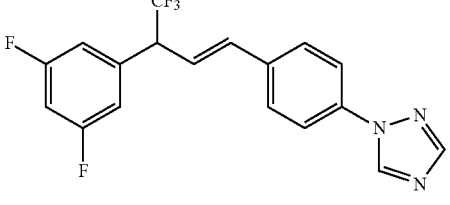 |

TABLE 1-continued

Structures for Compounds

| Compound Number | Structure |
|---|---|
| DC9 | 3-fluorophenyl-CH(CF₃)-CH=CH-(4-(1,2,4-triazol-1-yl)phenyl) |
| DC10 | 2-fluorophenyl-CH(CF₃)-CH=CH-(4-(1,2,4-triazol-1-yl)phenyl) |
| DC11 | 3,5-dimethylphenyl-CH(CF₃)-CH=CH-(4-(1,2,4-triazol-1-yl)phenyl) |
| DC12 | 3,4-dichlorophenyl-CH(CF₃)-CH=CH-(4-(1,2,4-triazol-1-yl)phenyl) |
| DC13 | 2,4-dichlorophenyl-CH(CF₃)-CH=CH-(4-(1,2,4-triazol-1-yl)phenyl) |
| DC14 | 2,3-dichlorophenyl-CH(CF₃)-CH=CH-(4-(1,2,4-triazol-1-yl)phenyl) |
| DC15 | 2,6-dichlorophenyl-CH(CF₃)-CH=CH-(4-(1,2,4-triazol-1-yl)phenyl) |

TABLE 1-continued

Structures for Compounds

| Compound Number | Structure |
|---|---|
| DC16 | 3,5-bis(trifluoromethyl)phenyl–CH(CF$_3$)–CH=CH–(4-(1,2,4-triazol-1-yl)phenyl) |
| DC17 | 2,3,5-trichlorophenyl–CH(CF$_3$)–CH=CH–(4-(1,2,4-triazol-1-yl)phenyl) |
| DC18 | 3,4,5-trichlorophenyl–CH(CF$_3$)–CH=CH–(4-(1,2,4-triazol-1-yl)phenyl) |
| DC19 | 3-chloro-5-(trifluoromethyl)phenyl–CH(CF$_3$)–CH=CH–(4-(1,2,4-triazol-1-yl)phenyl) |
| DC20 | 3,5-dichloro-4-methoxyphenyl–CH(CF$_3$)–CH=CH–(4-(1,2,4-triazol-1-yl)phenyl) |
| DC21 | 3,5-dichlorophenyl–CH(CF$_3$)–CH=CH–(4-(3-methyl-1,2,4-triazol-1-yl)phenyl) |
| DC22 | 3,5-dichlorophenyl–CH(CF$_3$)–CH=CH–(4-(3-nitro-1,2,4-triazol-1-yl)phenyl) |

TABLE 1-continued

| Compound Number | Structure |
|---|---|
| DC23 | 3,5-dichlorophenyl-CH(CF$_3$)-CH=CH-(4-phenyl)-(5-methyl-1,2,4-triazol-1-yl) |
| DC24 | 3,5-dichlorophenyl-CH(CF$_3$)-CH=CH-(4-phenyl)-(5-acetyl-1,2,4-triazol-1-yl) |
| DC25 | 3,5-dichlorophenyl-CH(CF$_3$)-CH=CH-(4-phenyl)-(5-methylthio-1,2,4-triazol-1-yl) |
| DC26 | 3,5-dichlorophenyl-CH(CF$_3$)-CH=CH-(4-phenyl)-(5-cyclopropylcarbonyl-1,2,4-triazol-1-yl) |
| DC27 | 3,5-dichlorophenyl-CH(CF$_3$)-CH=CH-(4-phenyl)-(5-methylsulfonyl-1,2,4-triazol-1-yl) |
| DC28 | 3,4-dichlorophenyl-CH(CF$_3$)-CH=CH-(3-cyano-4-(1,2,4-triazol-1-yl)phenyl) |

TABLE 1-continued

Structures for Compounds

| Compound Number | Structure |
|---|---|
| DC29 | 3,5-dichlorophenyl-CH(CF$_3$)-CH=CH-(3-cyano-4-(1H-1,2,4-triazol-1-yl)phenyl) |
| DC30 | 3,5-bis(trifluoromethyl)phenyl-CH(CF$_3$)-CH=CH-(3-cyano-4-(1H-1,2,4-triazol-1-yl)phenyl) |
| DC31 | 3,4,5-trichlorophenyl-CH(CF$_3$)-CH=CH-(3-cyano-4-(1H-1,2,4-triazol-1-yl)phenyl) |
| DC32 | 3-chlorophenyl-CH(CF$_3$)-CH=CH-(3-cyano-4-(1H-1,2,4-triazol-1-yl)phenyl) |
| DC33 | 3-chloro-5-(trifluoromethyl)phenyl-CH(CF$_3$)-CH=CH-(3-cyano-4-(1H-1,2,4-triazol-1-yl)phenyl) |
| DC34 | 3,5-dichloro-4-methoxyphenyl-CH(CF$_3$)-CH=CH-(3-cyano-4-(1H-1,2,4-triazol-1-yl)phenyl) |
| DC35 | 3,5-dichloro-4-fluorophenyl-CH(CF$_3$)-CH=CH-(3-cyano-4-(1H-1,2,4-triazol-1-yl)phenyl) |

TABLE 1-continued

Structures for Compounds

| Compound Number | Structure |
|---|---|
| DC36 | 3,5-dichlorophenyl-C(CF$_3$)H-CH=CH-(4-(3-methyl-1,2,4-triazol-1-yl)-3-cyanophenyl) |
| DC37 | 3,5-dichlorophenyl-C(CF$_3$)H-CH=CH-(4-(3-nitro-1,2,4-triazol-1-yl)-3-cyanophenyl) |
| DC38 | 3,5-dichlorophenyl-C(CF$_3$)H-CH=CH-(4-(3-amino-1,2,4-triazol-1-yl)-3-cyanophenyl) |
| DC39 | 3,5-dichlorophenyl-C(CF$_3$)H-CH=CH-(4-(3-acetamido-1,2,4-triazol-1-yl)-3-cyanophenyl) |
| DC40 | 3,4,5-trichlorophenyl-C(CF$_3$)H-CH=CH-(4-(3-nitro-1,2,4-triazol-1-yl)-3-cyanophenyl) |
| DC41 | 3,4,5-trichlorophenyl-C(CF$_3$)H-CH=CH-(4-(3-amino-1,2,4-triazol-1-yl)-3-cyanophenyl) |
| DC42 | 3,4,5-trichlorophenyl-C(CF$_3$)H-CH=CH-(4-(3-(N,N-bis(cyclopropylcarbonyl)amino)-1,2,4-triazol-1-yl)-3-cyanophenyl) |

TABLE 1-continued

Structures for Compounds

| Compound Number | Structure |
|---|---|
| DC43 | 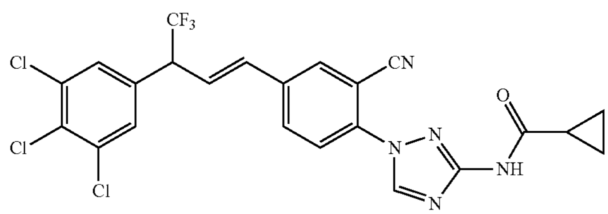 [SMILES: N#Cc1cc(/C=C/C(c2cc(Cl)c(Cl)c(Cl)c2)C(F)(F)F)ccc1-n1cnc(NC(=O)C2CC2)n1] |
| DC44 | 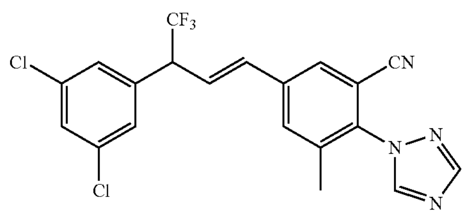 [SMILES: Cc1cc(/C=C/C(c2cc(Cl)cc(Cl)c2)C(F)(F)F)cc(C#N)c1-n1cncn1] |
| DC45 | 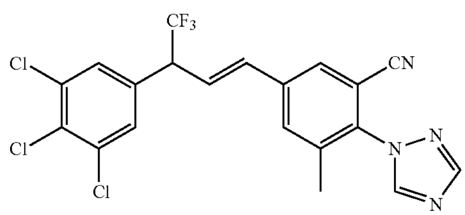 [SMILES: Cc1cc(/C=C/C(c2cc(Cl)c(Cl)c(Cl)c2)C(F)(F)F)cc(C#N)c1-n1cncn1] |
| DC46 | 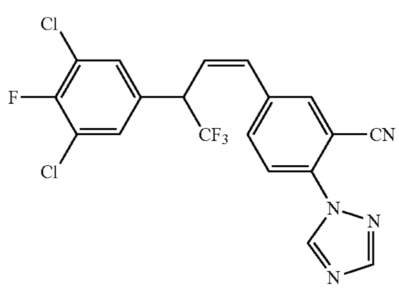 [SMILES: N#Cc1cc(/C=C\C(c2cc(Cl)c(F)c(Cl)c2)C(F)(F)F)ccc1-n1cncn1] |
| DC47 | 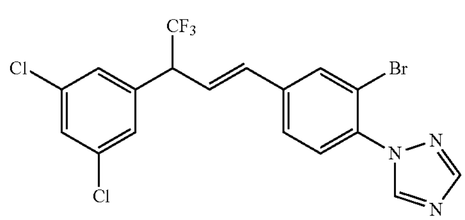 [SMILES: FC(F)(F)C(/C=C/c1ccc(-n2cncn2)c(Br)c1)c1cc(Cl)cc(Cl)c1] |
| DC48 | 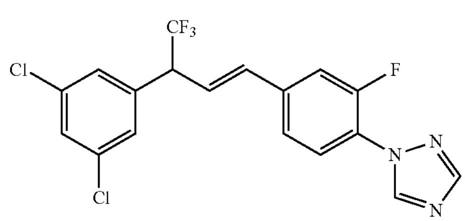 [SMILES: Fc1cc(/C=C/C(c2cc(Cl)cc(Cl)c2)C(F)(F)F)ccc1-n1cncn1] |

TABLE 1-continued
Structures for Compounds
| Compound Number | Structure |
|---|---|
| DC49 | 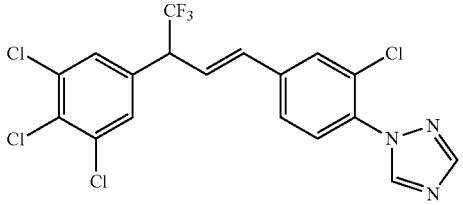 |
| DC50 | 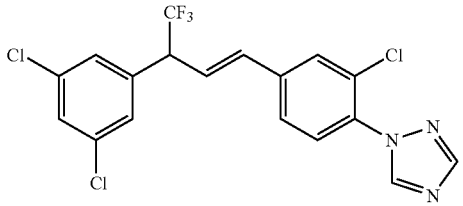 [SMILES: FC(F)(F)C(/C=C/c1ccc(-n2cncn2)c(Cl)c1)c1cc(Cl)cc(Cl)c1] |
| DC51 | 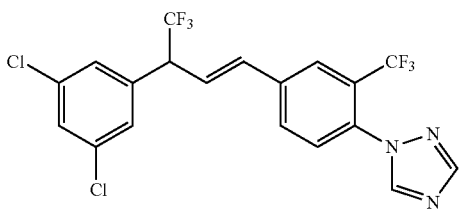 |
| DC52 | 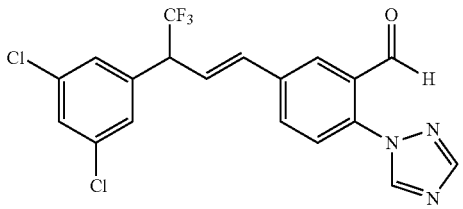 [SMILES: O=Cc1cc(/C=C/C(c2cc(Cl)cc(Cl)c2)C(F)(F)F)ccc1-n1cncn1] |
| DC53 | 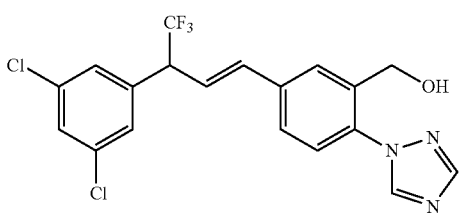 [SMILES: OCc1cc(/C=C/C(c2cc(Cl)cc(Cl)c2)C(F)(F)F)ccc1-n1cncn1] |
| DC54 | 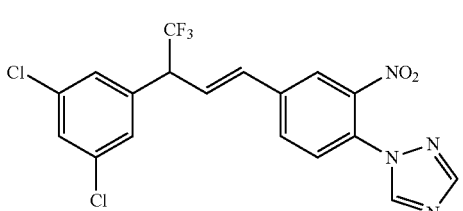 |
| DC55 | 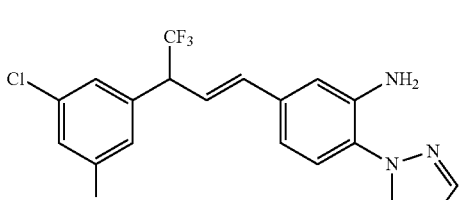 |

TABLE 1-continued
Structures for Compounds
| Compound Number | Structure |
|---|---|
| DC56 | 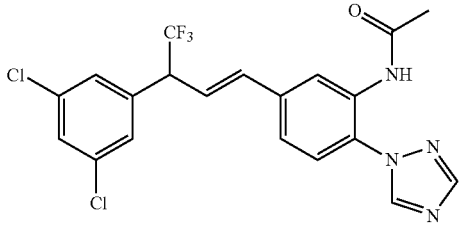 [SMILES: CC(=O)Nc1cc(/C=C/C(c2cc(Cl)cc(Cl)c2)C(F)(F)F)ccc1-n1cncn1] |
| DC57 | 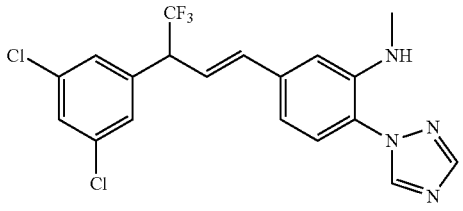 [SMILES: CNc1cc(/C=C/C(c2cc(Cl)cc(Cl)c2)C(F)(F)F)ccc1-n1cncn1] |
| DC58 | 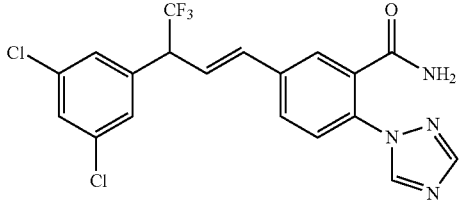 [SMILES: NC(=O)c1cc(/C=C/C(c2cc(Cl)cc(Cl)c2)C(F)(F)F)ccc1-n1cncn1] |
| DC59 | 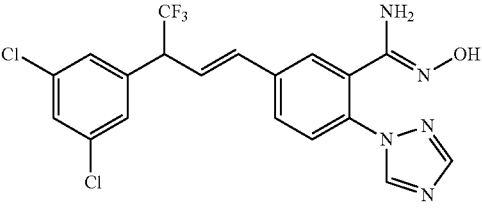 [SMILES: N/C(=N\O)c1cc(/C=C/C(c2cc(Cl)cc(Cl)c2)C(F)(F)F)ccc1-n1cncn1] |
| DC60 | 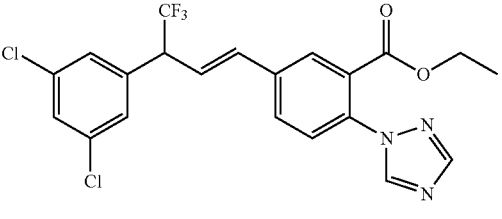 [SMILES: CCOC(=O)c1cc(/C=C/C(c2cc(Cl)cc(Cl)c2)C(F)(F)F)ccc1-n1cncn1] |
| DC61 | 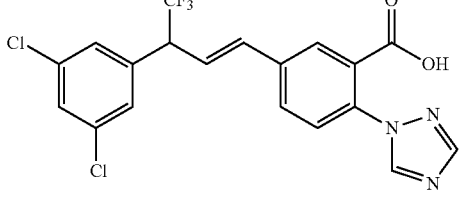 |
| DC62 | 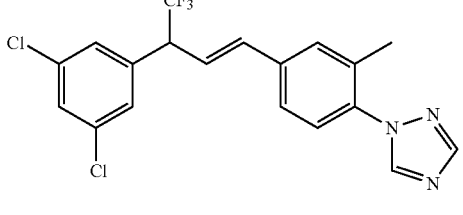 |

TABLE 1-continued

Structures for Compounds

| Compound Number | Structure |
|---|---|
| DC63 | 3,4,5-trichlorophenyl-CH(CF₃)-CH=CH-(4-(1,2,4-triazol-1-yl)-3-methylphenyl) |
| DC64 | 3,5-dichlorophenyl-CH(CF₃)-CH=CH-(4-(1,2,4-triazol-1-yl)-3-(pyridin-4-yl)phenyl) |
| DC65 | 3,5-dichlorophenyl-CH(CF₃)-CH=CH-(4-(1,2,4-triazol-1-yl)-2-methylphenyl) |
| DC66 | 3,4,5-trichlorophenyl-CH(CF₃)-CH=CH-(4-(1,2,4-triazol-1-yl)-2-chlorophenyl) |
| DC67 | 3,5-dichlorophenyl-CH(CF₃)-CH=CH-(4-(1,2,4-triazol-1-yl)-2-chlorophenyl) |
| DC68 | 3,5-dichlorophenyl-CH(CF₃)-CH=C(CH₃)-(4-(1,2,4-triazol-1-yl)phenyl) |
| DC69 | 3,5-dichlorophenyl-C(OH)(CF₃)-CH=CH-(4-(1,2,4-triazol-1-yl)phenyl) |

TABLE 1-continued

Structures for Compounds

| Compound Number | Structure |
|---|---|
| DC70 | 3,5-dichlorophenyl-C(CF3)(OMe)-CH=CH-(4-(1,2,4-triazol-1-yl)phenyl) |

TABLE 1A

Structures for F Compounds

| Compound Number | Structure | Appearance | Prepared as in Example: |
|---|---|---|---|
| F1 | 3,4,5-trichlorophenyl-CH(CF3)-CH=CH-(2-bromo-phenyl)-C(=O)NH-C(CH3)2-C(=O)NH-CH2CF3 | white foam | 135 |
| F2 | 3,4,5-trichlorophenyl-CH(CF3)-CH=CH-(2-chloro-phenyl)-C(=O)NH-C(CH3)2-C(=O)NH-CH2CF3 | brown gum | 15 |
| F3 | 3,4,5-trichlorophenyl-CH(CF3)-CH=CH-(2-methyl-phenyl)-C(=O)NH-C(CH3)2-C(=O)NH-CH2CF3 | pale yellow gum | 15 |
| F4 | 3,4,5-trichlorophenyl-CH(CF3)-CH=CH-(2-trifluoromethyl-phenyl)-C(=O)NH-C(CH3)2-C(=O)NH-CH2CF3 | yellow solid | 15 |

TABLE 1A-continued

Structures for F Compounds

| Compound Number | Structure | Appearance | Prepared as in Example: |
|---|---|---|---|
| F5 | 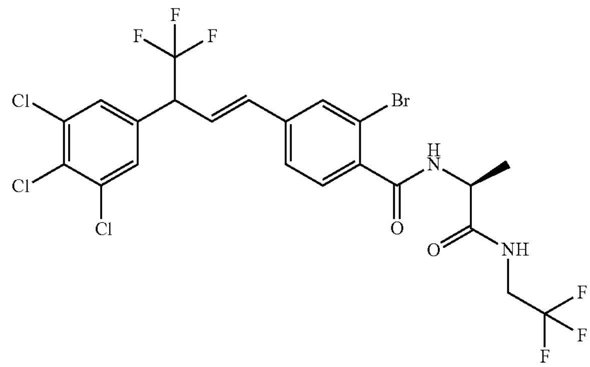 [SMILES: C[C@H](NC(=O)c1ccc(/C=C/C(c2cc(Cl)c(Cl)c(Cl)c2)C(F)(F)F)cc1Br)C(=O)NCC(F)(F)F] | | 108 |
| F6 | 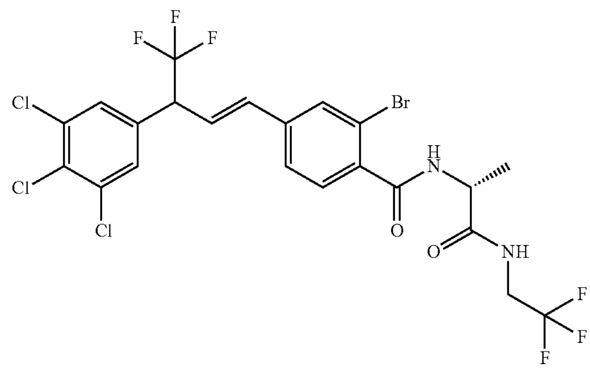 [SMILES: C[C@@H](NC(=O)c1ccc(/C=C/C(c2cc(Cl)c(Cl)c(Cl)c2)C(F)(F)F)cc1Br)C(=O)NCC(F)(F)F] | | 108 |
| F7 | 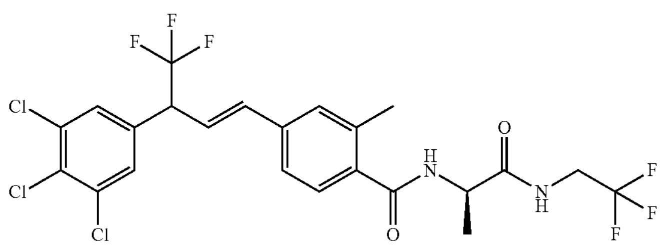 [SMILES: Cc1cc(/C=C/C(c2cc(Cl)c(Cl)c(Cl)c2)C(F)(F)F)ccc1C(=O)N[C@H](C)C(=O)NCC(F)(F)F] | yellow solid | 15 |
| F8 | 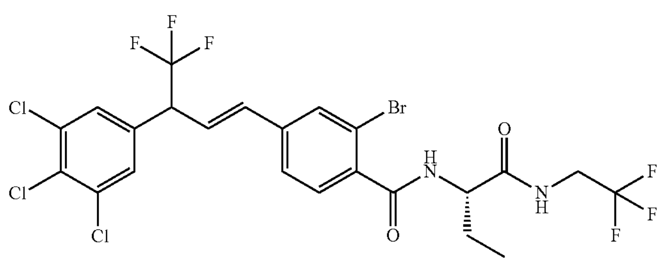 [SMILES: CC[C@H](NC(=O)c1ccc(/C=C/C(c2cc(Cl)c(Cl)c(Cl)c2)C(F)(F)F)cc1Br)C(=O)NCC(F)(F)F] | off-white solid | 15 |
| F8A | 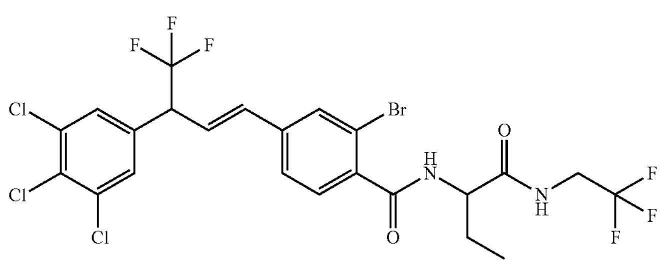 | pale yellow solid | 15 |

TABLE 1A-continued

Structures for F Compounds

| Compound Number | Structure | Appearance | Prepared as in Example: |
|---|---|---|---|
| F9 | [Structure: 3,4,5-trichlorophenyl-CH(CF3)-CH=CH-(2-methylphenyl)-C(=O)NH-CH(CH3)-C(=O)NH-CH2CF3] | yellow solid | 15 |
| F10 | [Structure: (+)- 3,4,5-trichlorophenyl-CH(CF3)-CH=CH-(2-bromophenyl)-C(=O)NH-CH(CH3)-C(=O)NH-CH2CF3] | off-white solid | 132 |
| F11 | [Structure: (-)- 3,4,5-trichlorophenyl-CH(CF3)-CH=CH-(2-bromophenyl)-C(=O)NH-CH(CH3)-C(=O)NH-CH2CF3] | off-white solid | 132 |
| F12 | [Structure: (+)- 3,4,5-trichlorophenyl-CH(CF3)-CH=CH-(2-bromophenyl)-C(=O)NH-CH(CH3)-C(=O)NH-CH2CF3, with stereochemistry on alanine] | off-white solid | 133 |
| F13 | [Structure: (-)- 3,4,5-trichlorophenyl-CH(CF3)-CH=CH-(2-bromophenyl)-C(=O)NH-CH(CH3)-C(=O)NH-CH2CF3, with stereochemistry on alanine] | off-white solid | 133 |
| F14 | [Structure: 3,5-bis(trifluoromethyl)phenyl-CH(CF3)-CH=CH-(2-bromophenyl)-C(=O)NH-CH(CH3)-C(=O)NH-CH2CF3] | pale yellow solid | 15 |

TABLE 1A-continued

Structures for F Compounds

| Compound Number | Structure | Appearance | Prepared as in Example: |
|---|---|---|---|
| F15 | 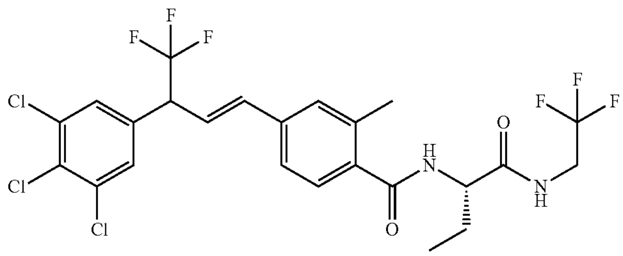 [SMILES: CC[C@H](NC(=O)c1ccc(/C=C/C(c2cc(Cl)c(Cl)c(Cl)c2)C(F)(F)F)cc1C)C(=O)NCC(F)(F)F] | yellow solid | 15 |
| F15A | 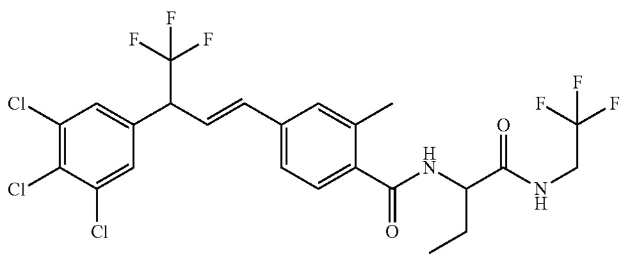 | yellow solid | 15 |
| F16 | 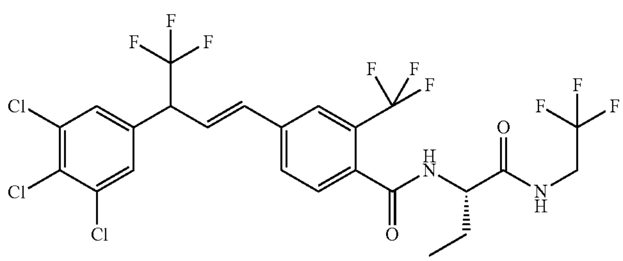 [SMILES: CC[C@H](NC(=O)c1ccc(/C=C/C(c2cc(Cl)c(Cl)c(Cl)c2)C(F)(F)F)cc1C(F)(F)F)C(=O)NCC(F)(F)F] | pale yellow solid | 15 |
| F16A | 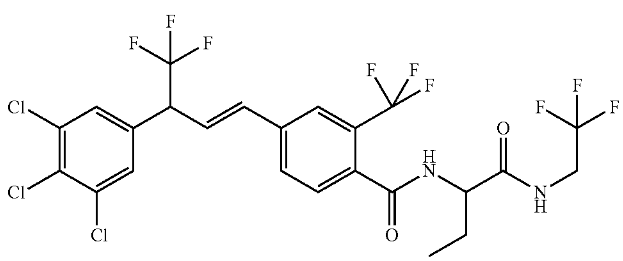 [SMILES: CCC(NC(=O)c1ccc(/C=C/C(c2cc(Cl)c(Cl)c(Cl)c2)C(F)(F)F)cc1C(F)(F)F)C(=O)NCC(F)(F)F] | yellow solid | 15 |
| F17 | 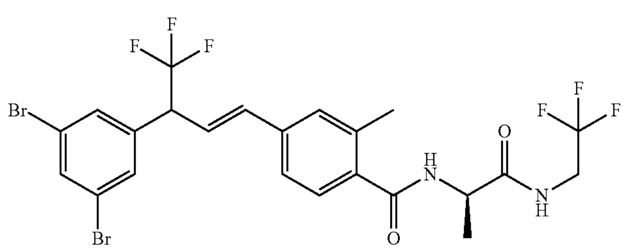 [SMILES: Cc1cc(/C=C/C(c2cc(Br)cc(Br)c2)C(F)(F)F)ccc1C(=O)N[C@H](C)C(=O)NCC(F)(F)F] | off-white solid | 15 |
| F18 | 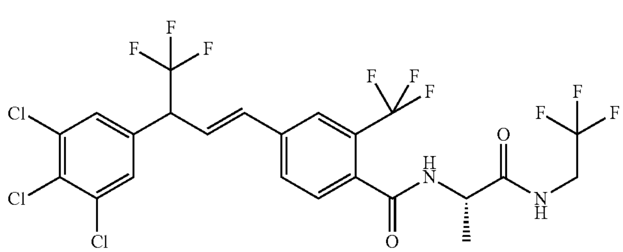 [SMILES: C[C@H](NC(=O)c1ccc(/C=C/C(c2cc(Cl)c(Cl)c(Cl)c2)C(F)(F)F)cc1C(F)(F)F)C(=O)NCC(F)(F)F] | yellow solid | 15 |

TABLE 1A-continued

Structures for F Compounds

| Compound Number | Structure | Appearance | Prepared as in Example: |
|---|---|---|---|
| F19 | 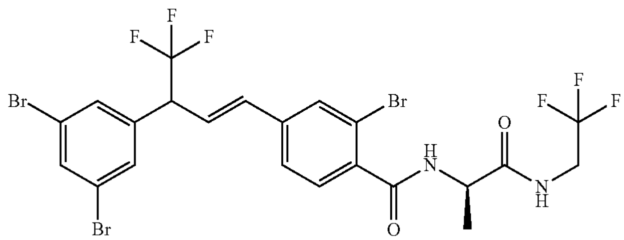 [SMILES: C[C@@H](NC(=O)c1ccc(/C=C/C(c2cc(Br)cc(Br)c2)C(F)(F)F)cc1Br)C(=O)NCC(F)(F)F] | yellow gum | 15 |
| F20 | 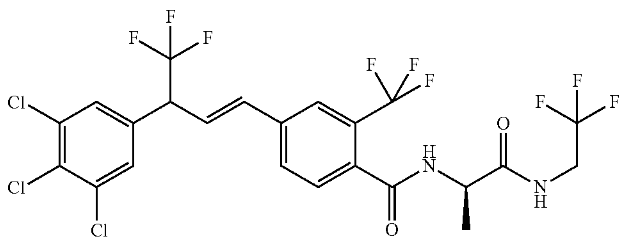 [SMILES: C[C@@H](NC(=O)c1ccc(/C=C/C(c2cc(Cl)c(Cl)c(Cl)c2)C(F)(F)F)cc1C(F)(F)F)C(=O)NCC(F)(F)F] | yellow solid | 15 |
| F20A | 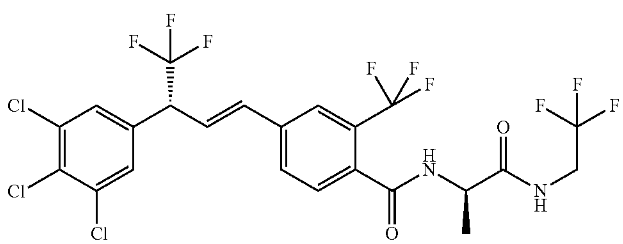 [SMILES: C[C@@H](NC(=O)c1ccc(/C=C/[C@H](c2cc(Cl)c(Cl)c(Cl)c2)C(F)(F)F)cc1C(F)(F)F)C(=O)NCC(F)(F)F] | off-white solid | 133 |
| F20B | 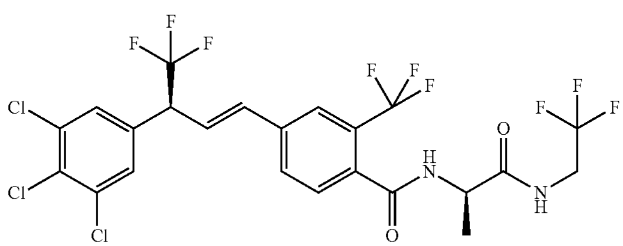 [SMILES: C[C@@H](NC(=O)c1ccc(/C=C/[C@@H](c2cc(Cl)c(Cl)c(Cl)c2)C(F)(F)F)cc1C(F)(F)F)C(=O)NCC(F)(F)F] | off-white solid | 133 |
| F20C | 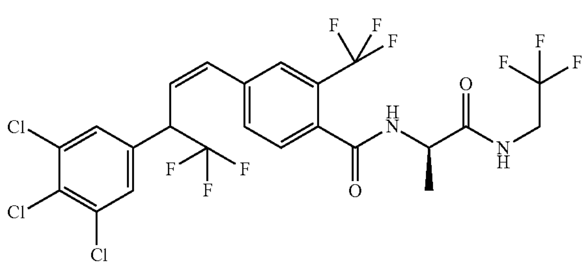 [SMILES: C[C@@H](NC(=O)c1ccc(/C=C\C(c2cc(Cl)c(Cl)c(Cl)c2)C(F)(F)F)cc1C(F)(F)F)C(=O)NCC(F)(F)F] | white solid | 88 |
| F21 | 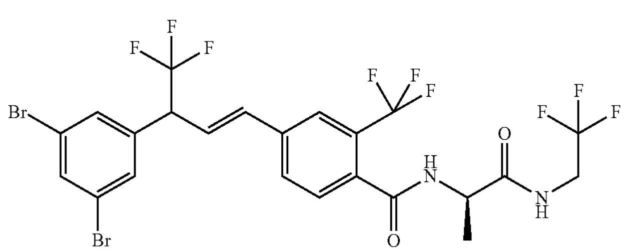 [SMILES: C[C@@H](NC(=O)c1ccc(/C=C/C(c2cc(Br)cc(Br)c2)C(F)(F)F)cc1C(F)(F)F)C(=O)NCC(F)(F)F] | yellow gum | 15 |

TABLE 1A-continued

Structures for F Compounds

| Compound Number | Structure | Appearance | Prepared as in Example: |
|---|---|---|---|
| F22 | 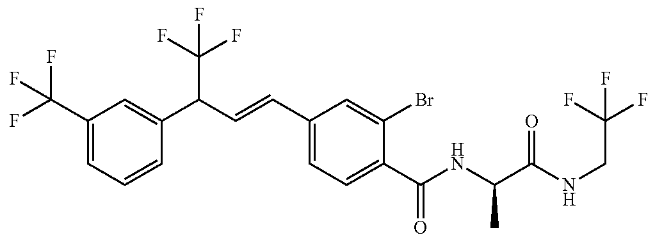 [SMILES: C[C@@H](NC(=O)c1ccc(/C=C/C(c2cccc(C(F)(F)F)c2)C(F)(F)F)cc1Br)C(=O)NCC(F)(F)F] | light brown gum | 15 |
| F23 | 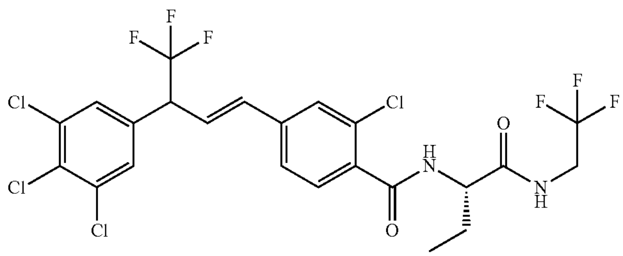 [SMILES: CC[C@H](NC(=O)c1ccc(/C=C/C(c2cc(Cl)c(Cl)c(Cl)c2)C(F)(F)F)cc1Cl)C(=O)NCC(F)(F)F] | pale yellow liquid | 15 |
| F23A | 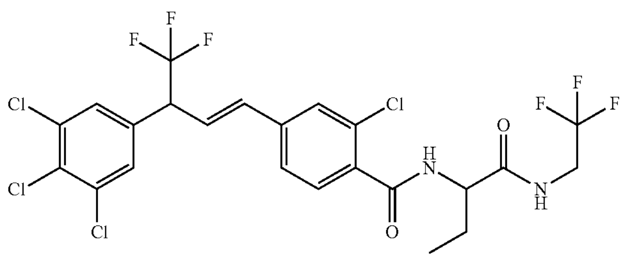 [SMILES: CCC(NC(=O)c1ccc(/C=C/C(c2cc(Cl)c(Cl)c(Cl)c2)C(F)(F)F)cc1Cl)C(=O)NCC(F)(F)F] | yellow solid | 15 |
| F24 | 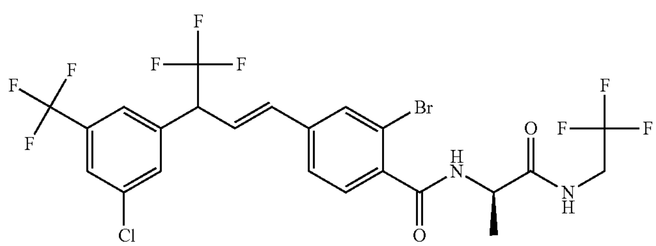 [SMILES: C[C@@H](NC(=O)c1ccc(/C=C/C(c2cc(Cl)cc(C(F)(F)F)c2)C(F)(F)F)cc1Br)C(=O)NCC(F)(F)F] | pale yellow liquid | 15 |
| F25 | 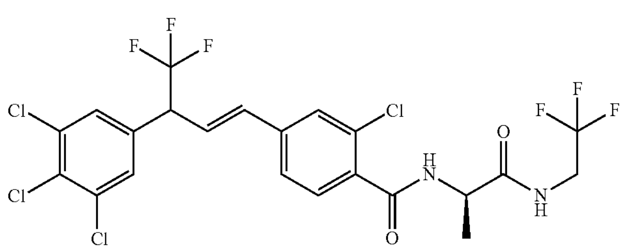 [SMILES: C[C@@H](NC(=O)c1ccc(/C=C/C(c2cc(Cl)c(Cl)c(Cl)c2)C(F)(F)F)cc1Cl)C(=O)NCC(F)(F)F] | yellow solid | 15 |
| F26 | 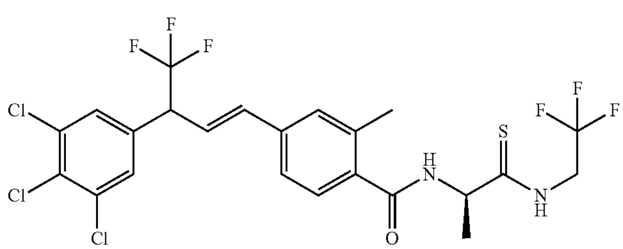 [SMILES: Cc1cc(/C=C/C(c2cc(Cl)c(Cl)c(Cl)c2)C(F)(F)F)ccc1C(=O)N[C@H](C)C(=S)NCC(F)(F)F] | brown gum | 15 |

TABLE 1A-continued

Structures for F Compounds

| Compound Number | Structure | Appearance | Prepared as in Example: |
|---|---|---|---|
| F27 | 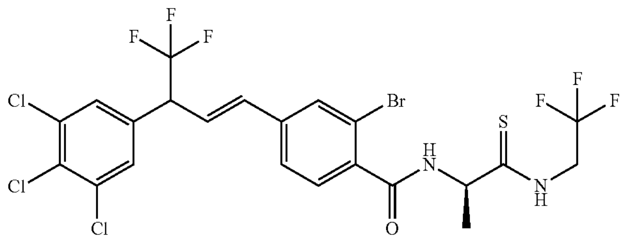 | pale yellow gum | 15 |
| F28 | 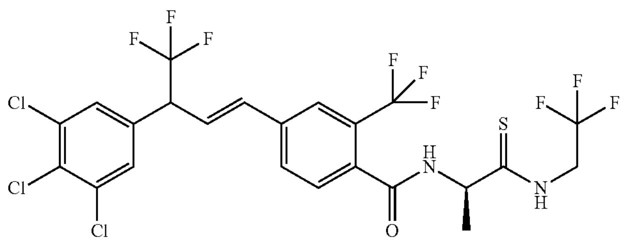 [SMILES: C[C@@H](NC(=O)c1ccc(/C=C/C(c2cc(Cl)c(Cl)c(Cl)c2)C(F)(F)F)cc1C(F)(F)F)C(=S)NCC(F)(F)F] | brown gum | 15 |
| F29 | 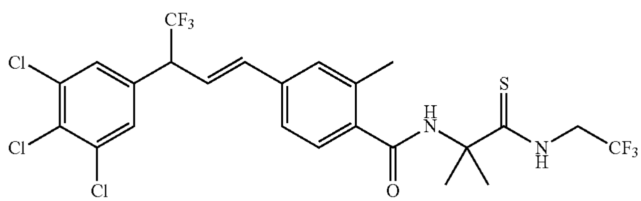 | pale yellow gum | 19 |
| F30 | 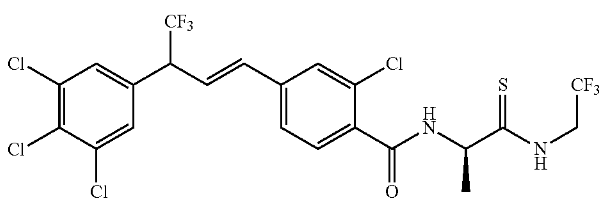 | brown gum | 15 |
| F31 | 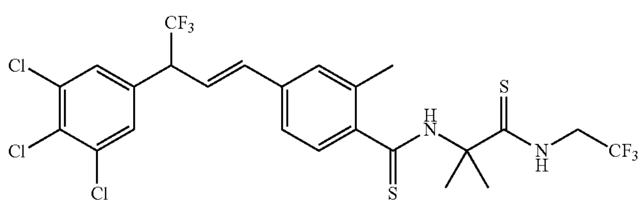 [SMILES: Cc1cc(/C=C/C(c2cc(Cl)c(Cl)c(Cl)c2)C(F)(F)F)ccc1C(=O)NC(C)(C)C(=S)NCC(F)(F)F] | pale yellow gum | 134 |

TABLE 1B

Structures of Prophetic Compounds Subsequently Exemplified

| Compound Number | Structure | Appearance | Prepared as in Example: |
|---|---|---|---|
| P1 | 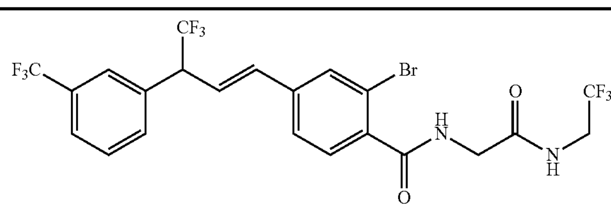 | Yellow solid | 15 |

TABLE 1B-continued
Structures of Prophetic Compounds Subsequently Exemplified
| Compound Number | Structure | Appearance | Prepared as in Example: |
|---|---|---|---|
| P2 | 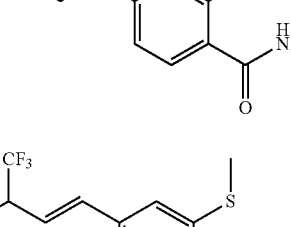 | Brown gum | 15 |
| P12 | 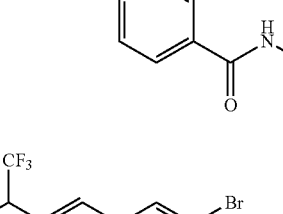 | Off white solid | 15 |
| P14 | 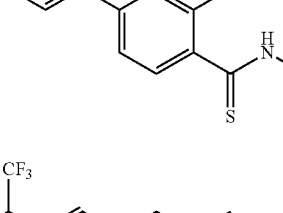 | Light yellow gum | 19 |
| P15 | 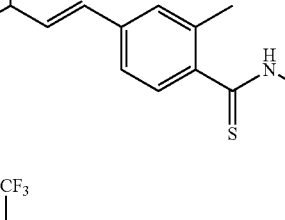 | Light yellow gum | 19 |
| P82 | 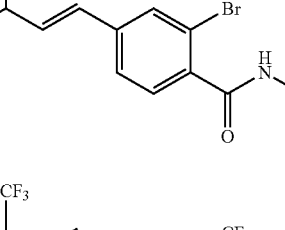 | Brown semi solid | 15 |
| P84 | 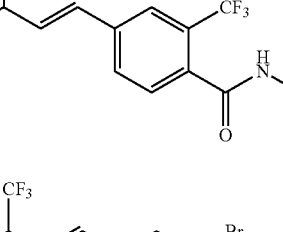 | Pale yellow solid | 15 |
| P156 | 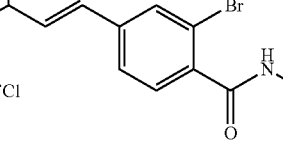 | Green liquid | 15 |

TABLE 1B-continued

Structures of Prophetic Compounds Subsequently Exemplified

| Compound Number | Structure | Appearance | Prepared as in Example: |
|---|---|---|---|
| P226 | 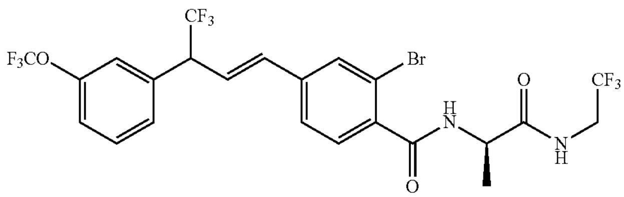 [SMILES: C[C@@H](NC(=O)c1ccc(/C=C/C(c2cccc(OC(F)(F)F)c2)C(F)(F)F)cc1Br)C(=O)NCC(F)(F)F] | Brown semi solid | 15 |
| P228 | 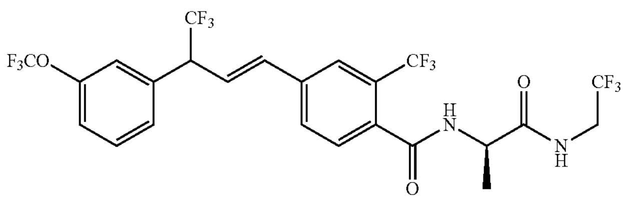 [SMILES: C[C@@H](NC(=O)c1ccc(/C=C/C(c2cccc(OC(F)(F)F)c2)C(F)(F)F)cc1C(F)(F)F)C(=O)NCC(F)(F)F] | Brown semi solid | 15 |
| P298 | 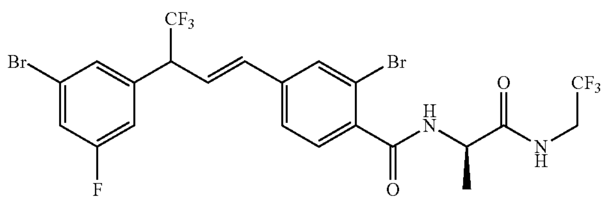 | Yellow solid | 15 |
| P300 | 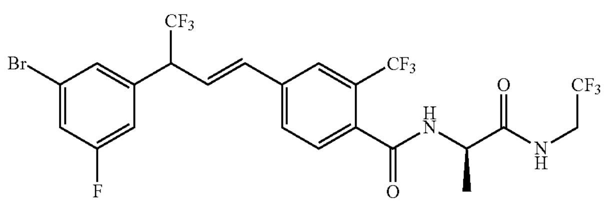 [SMILES: C[C@@H](NC(=O)c1ccc(/C=C/C(c2cc(F)cc(Br)c2)C(F)(F)F)cc1C(F)(F)F)C(=O)NCC(F)(F)F] | Brown gum | 15 |
| P442 | 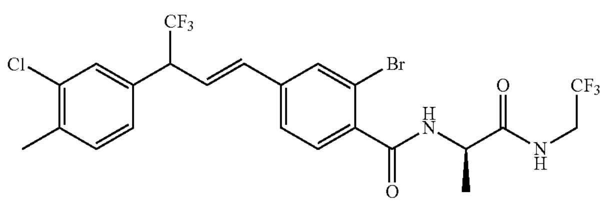 [SMILES: Cc1ccc(C(/C=C/c2ccc(C(=O)N[C@H](C)C(=O)NCC(F)(F)F)c(Br)c2)C(F)(F)F)cc1Cl] | Pale yellow solid | 15 |
| P444 | 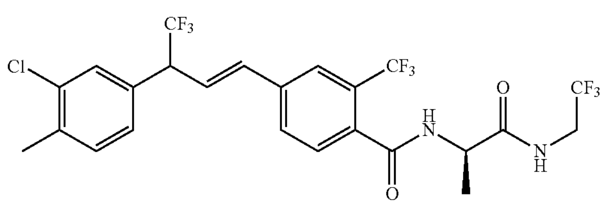 | Pale yellow solid | 15 |
| P514 | 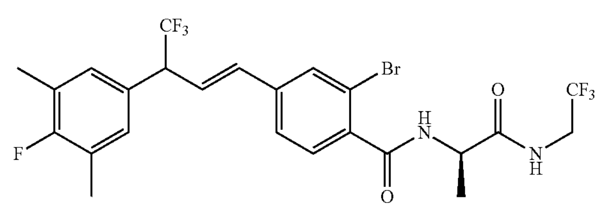 [SMILES: Cc1cc(C(/C=C/c2ccc(C(=O)N[C@H](C)C(=O)NCC(F)(F)F)c(Br)c2)C(F)(F)F)cc(C)c1F] | Off white solid | 15 |

TABLE 1B-continued
Structures of Prophetic Compounds Subsequently Exemplified
| Compound Number | Structure | Appearance | Prepared as in Example: |
|---|---|---|---|
| P516 | 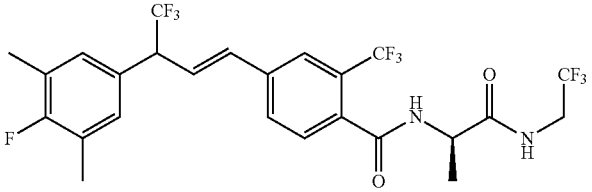 [SMILES: Cc1cc(C(/C=C/c2ccc(C(=O)N[C@H](C)C(=O)NCC(F)(F)F)c(C(F)(F)F)c2)C(F)(F)F)cc(C)c1F] | Brown solid | 15 |
| P568 | 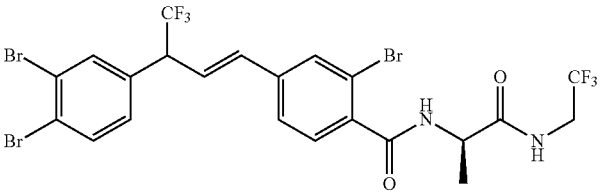 [SMILES: C[C@@H](NC(=O)c1ccc(/C=C/C(c2ccc(Br)c(Br)c2)C(F)(F)F)cc1Br)C(=O)NCC(F)(F)F] | Brown semi solid | 15 |
| P586 | 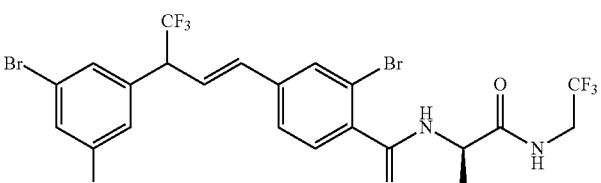 | Brown semi solid | 15 |
| P588 | 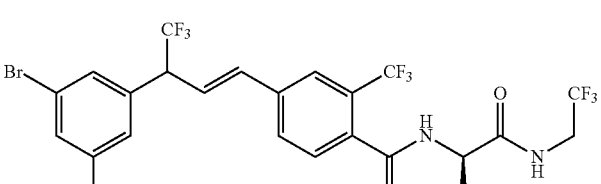 | Brown semi solid | 15 |
| P660 | 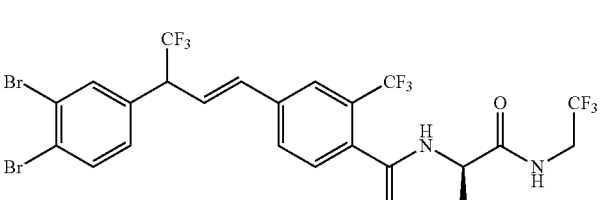 | Pale yellow solid | 15 |
| P730 | 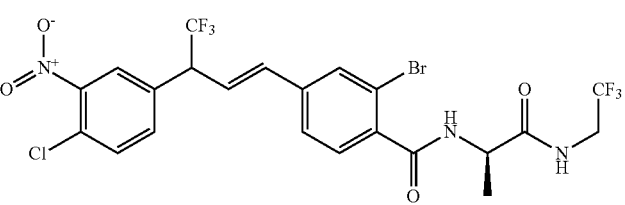 [SMILES: C[C@@H](NC(=O)c1ccc(/C=C/C(c2ccc(Cl)c([N+](=O)[O-])c2)C(F)(F)F)cc1Br)C(=O)NCC(F)(F)F] | Yellow solid | 15 |
| P732 | 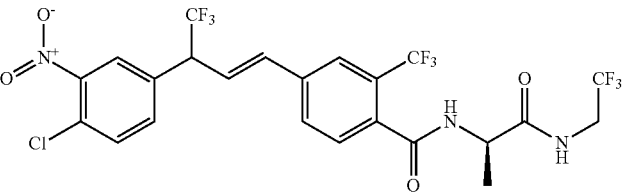 [SMILES: C[C@@H](NC(=O)c1ccc(/C=C/C(c2ccc(Cl)c([N+](=O)[O-])c2)C(F)(F)F)cc1C(F)(F)F)C(=O)NCC(F)(F)F] | Brown semi solid | 15 |

TABLE 1B-continued

Structures of Prophetic Compounds Subsequently Exemplified

| Compound Number | Structure | Appearance | Prepared as in Example: |
|---|---|---|---|
| P802 | 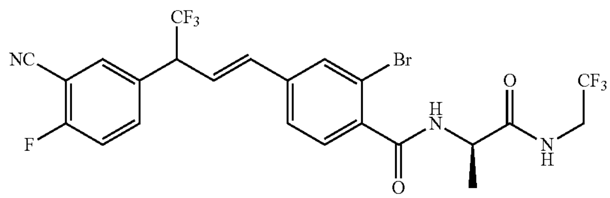 [SMILES: C[C@@H](NC(=O)c1ccc(/C=C/C(c2ccc(F)c(C#N)c2)C(F)(F)F)cc1Br)C(=O)NCC(F)(F)F] | Brown gum | 15 |
| P804 | 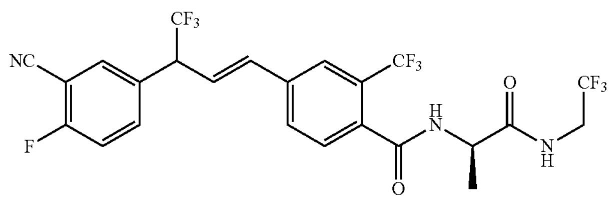 [SMILES: C[C@@H](NC(=O)c1ccc(/C=C/C(c2ccc(F)c(C#N)c2)C(F)(F)F)cc1C(F)(F)F)C(=O)NCC(F)(F)F] | Brown gum | 15 |
| P1090 | 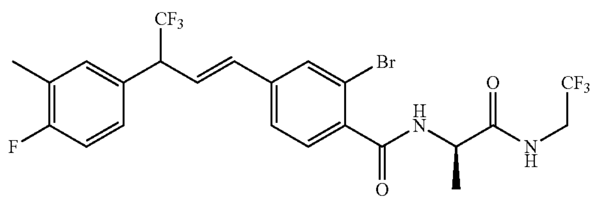 [SMILES: Cc1cc(C(/C=C/c2ccc(C(=O)N[C@H](C)C(=O)NCC(F)(F)F)c(Br)c2)C(F)(F)F)ccc1F] | Light brown solid | 15 |
| P1092 | 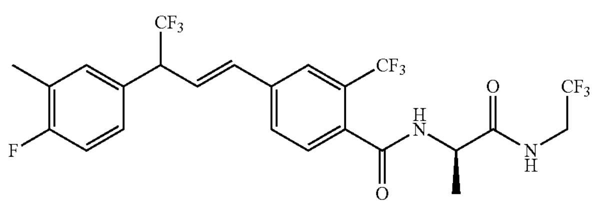 [SMILES: Cc1cc(C(/C=C/c2ccc(C(=O)N[C@H](C)C(=O)NCC(F)(F)F)c(C(F)(F)F)c2)C(F)(F)F)ccc1F] | Brown semi solid | 15 |
| P1197 | 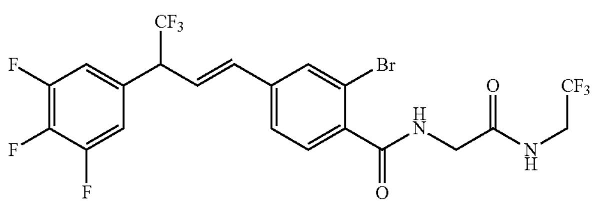 [SMILES: O=C(CNC(=O)c1ccc(/C=C/C(c2cc(F)c(F)c(F)c2)C(F)(F)F)cc1Br)NCC(F)(F)F] | Off white solid | 15 |
| P1269 | 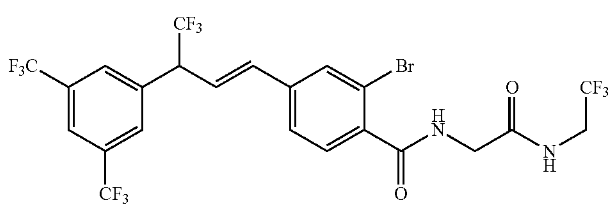 [SMILES: O=C(CNC(=O)c1ccc(/C=C/C(c2cc(C(F)(F)F)cc(C(F)(F)F)c2)C(F)(F)F)cc1Br)NCC(F)(F)F] | Pale yellow solid | 15 |
| P1340 | 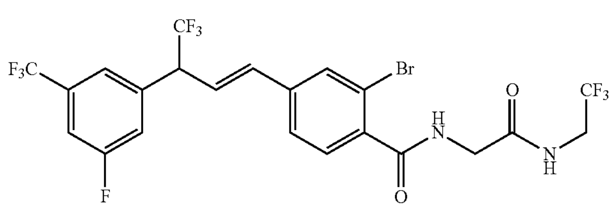 | Pale yellow liquid | 15 |

TABLE 1B-continued

Structures of Prophetic Compounds Subsequently Exemplified

| Compound Number | Structure | Appearance | Prepared as in Example: |
|---|---|---|---|
| P1411 | 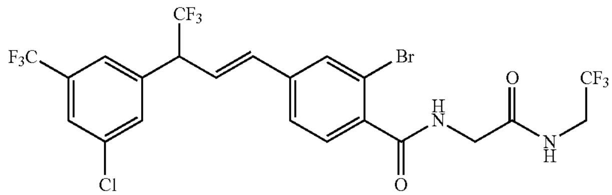 [SMILES: O=C(CNC(=O)c1ccc(/C=C/C(c2cc(Cl)cc(C(F)(F)F)c2)C(F)(F)F)cc1Br)NCC(F)(F)F] | Pale yellow liquid | 15 |
| P1483 | 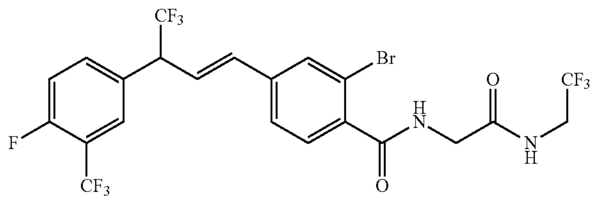 [SMILES: O=C(CNC(=O)c1ccc(/C=C/C(c2ccc(F)c(C(F)(F)F)c2)C(F)(F)F)cc1Br)NCC(F)(F)F] | Off white solid | 15 |
| P1556 | 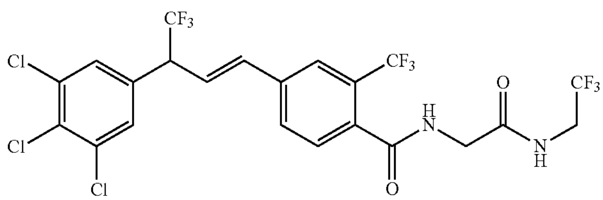 | Brown solid | 15 |
| P1558 | 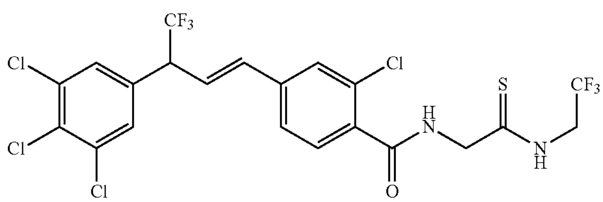 [SMILES: O=C(NCC(=S)NCC(F)(F)F)c1ccc(/C=C/C(c2cc(Cl)c(Cl)c(Cl)c2)C(F)(F)F)cc1Cl] | Brown solid | 134 |
| P1559 | 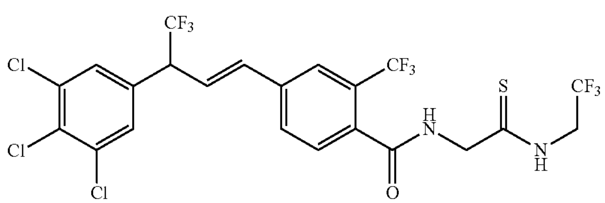 [SMILES: O=C(NCC(=S)NCC(F)(F)F)c1ccc(/C=C/C(c2cc(Cl)c(Cl)c(Cl)c2)C(F)(F)F)cc1C(F)(F)F] | Brown gum | 134 |
| P1560 | 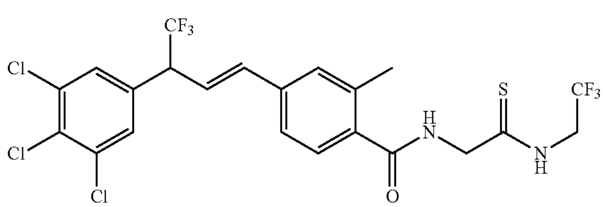 | Off white solid | 19 |
| P1564 | 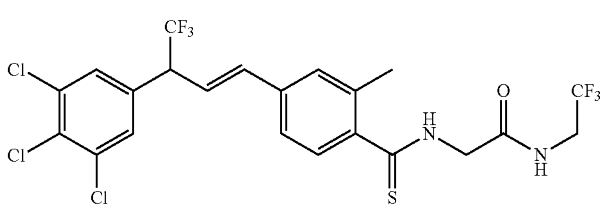 [SMILES: Cc1cc(/C=C/C(c2cc(Cl)c(Cl)c(Cl)c2)C(F)(F)F)ccc1C(=S)NCC(=O)NCC(F)(F)F] | Yellow solid | 19 |

TABLE 1B-continued

Structures of Prophetic Compounds Subsequently Exemplified

| Compound Number | Structure | Appearance | Prepared as in Example: |
|---|---|---|---|
| P1566 | 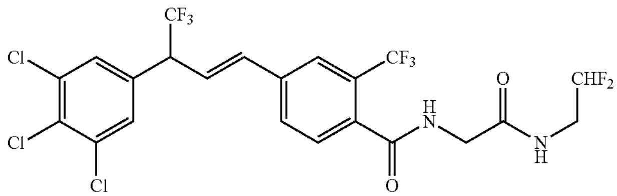 | Brown solid | 15 |
| P1589 | 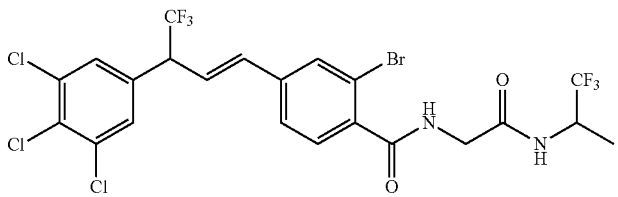 [SMILES: CC(NC(=O)CNC(=O)c1ccc(/C=C/C(c2cc(Cl)c(Cl)c(Cl)c2)C(F)(F)F)cc1Br)C(F)(F)F] | Pale yellow gum | 15 |
| P1591 | 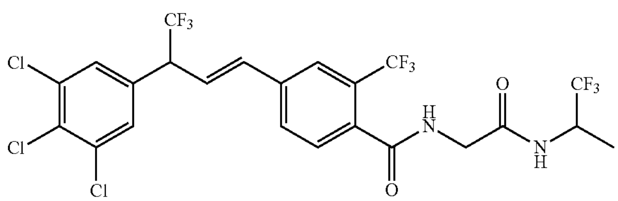 [SMILES: CC(NC(=O)CNC(=O)c1ccc(/C=C/C(c2cc(Cl)c(Cl)c(Cl)c2)C(F)(F)F)cc1C(F)(F)F)C(F)(F)F] | Brown gum | 15 |
| P1592 | 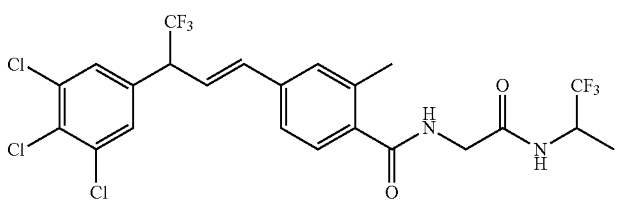 [SMILES: Cc1cc(/C=C/C(c2cc(Cl)c(Cl)c(Cl)c2)C(F)(F)F)ccc1C(=O)NCC(=O)NC(C)C(F)(F)F] | Pale yellow gum | 15 |
| P1599 | 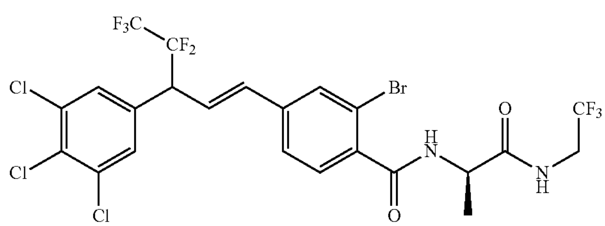 [SMILES: C[C@@H](NC(=O)c1ccc(/C=C/C(c2cc(Cl)c(Cl)c(Cl)c2)C(F)(F)C(F)(F)F)cc1Br)C(=O)NCC(F)(F)F] | Brown semi solid | 12 |
| P1601 | 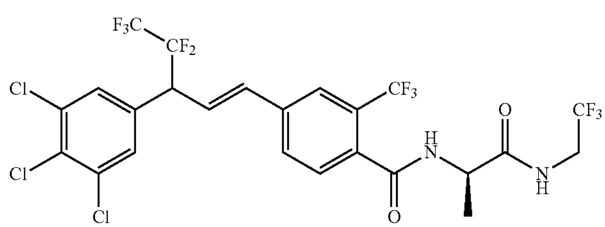 | Brown viscous liquid | 15 |
| P1603 | 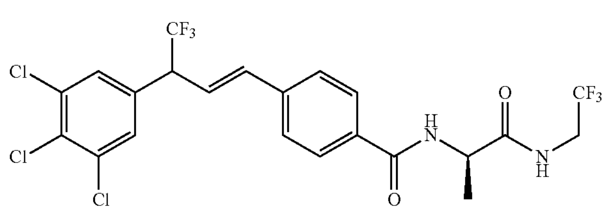 [SMILES: C[C@@H](NC(=O)c1ccc(/C=C/C(c2cc(Cl)c(Cl)c(Cl)c2)C(F)(F)F)cc1)C(=O)NCC(F)(F)F] | Off white solid | 135 |

TABLE 1B-continued

Structures of Prophetic Compounds Subsequently Exemplified

| Compound Number | Structure | Appearance | Prepared as in Example: |
|---|---|---|---|
| P1611A | 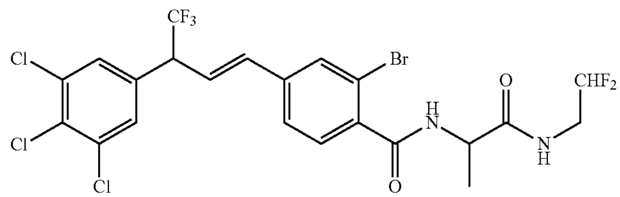 [SMILES: CC(NC(=O)c1ccc(/C=C/C(c2cc(Cl)c(Cl)c(Cl)c2)C(F)(F)F)cc1Br)C(=O)NCC(F)F] | Pale yellow solid | 137 |
| P1613A | 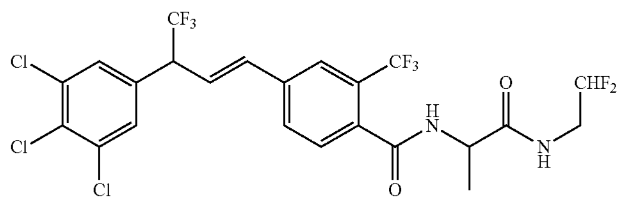 [SMILES: CC(NC(=O)c1ccc(/C=C/C(c2cc(Cl)c(Cl)c(Cl)c2)C(F)(F)F)cc1C(F)(F)F)C(=O)NCC(F)F] | Brown solid | 137 |
| P1616 | 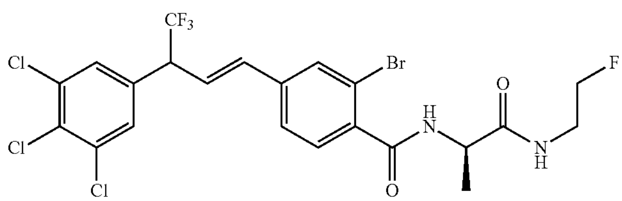 [SMILES: C[C@@H](NC(=O)c1ccc(/C=C/C(c2cc(Cl)c(Cl)c(Cl)c2)C(F)(F)F)cc1Br)C(=O)NCCF] | Brown gum | 15 |
| P1616A | 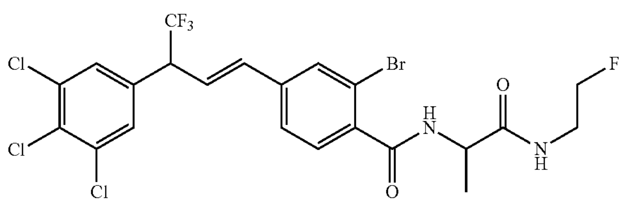 [SMILES: CC(NC(=O)c1ccc(/C=C/C(c2cc(Cl)c(Cl)c(Cl)c2)C(F)(F)F)cc1Br)C(=O)NCCF] | Pale yellow semi solid | 137 |
| P1618A | 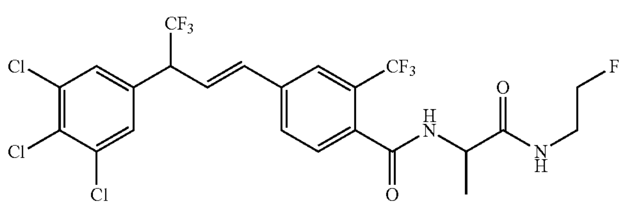 [SMILES: CC(NC(=O)c1ccc(/C=C/C(c2cc(Cl)c(Cl)c(Cl)c2)C(F)(F)F)cc1C(F)(F)F)C(=O)NCCF] | Brown solid | 137 |
| P1621 | 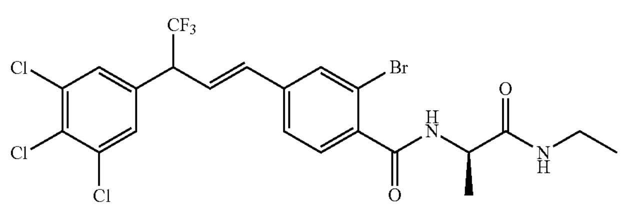 [SMILES: CCNC(=O)[C@@H](C)NC(=O)c1ccc(/C=C/C(c2cc(Cl)c(Cl)c(Cl)c2)C(F)(F)F)cc1Br] | Brown viscous liquid | 12 |
| P1623 | 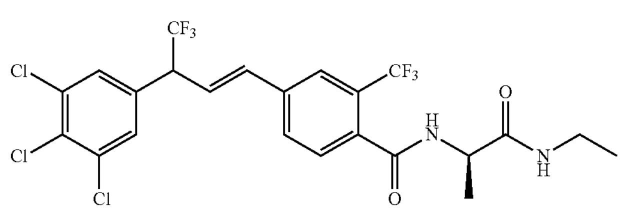 | Brown liquid | 12 |

TABLE 1B-continued

Structures of Prophetic Compounds Subsequently Exemplified

| Compound Number | Structure | Appearance | Prepared as in Example: |
|---|---|---|---|
| P1624 | 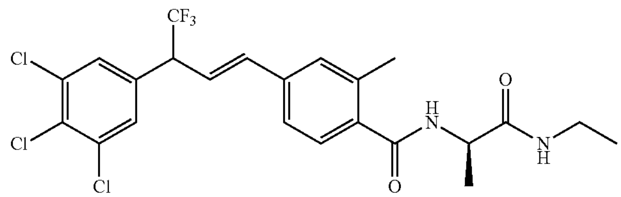 [SMILES: CCNC(=O)[C@@H](C)NC(=O)c1ccc(/C=C/C(c2cc(Cl)c(Cl)c(Cl)c2)C(F)(F)F)cc1C] | Brown semi solid | 12 |
| P1631A | 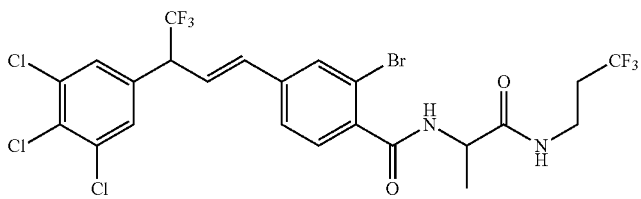 [SMILES: CC(NC(=O)c1ccc(/C=C/C(c2cc(Cl)c(Cl)c(Cl)c2)C(F)(F)F)cc1Br)C(=O)NCCC(F)(F)F] | Brown viscous liquid | 137 |
| P1633A | 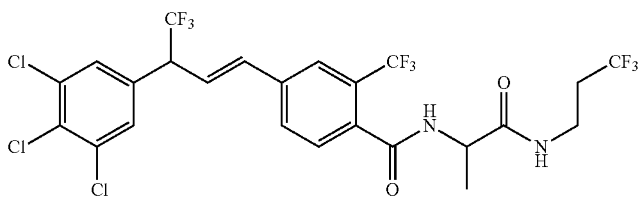 [SMILES: CC(NC(=O)c1ccc(/C=C/C(c2cc(Cl)c(Cl)c(Cl)c2)C(F)(F)F)cc1C(F)(F)F)C(=O)NCCC(F)(F)F] | Brown solid | 137 |
| P1636 | 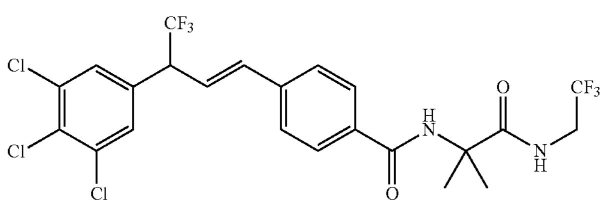 [SMILES: CC(C)(NC(=O)c1ccc(/C=C/C(c2cc(Cl)c(Cl)c(Cl)c2)C(F)(F)F)cc1)C(=O)NCC(F)(F)F] | Off white solid | 135 |
| P1638 | 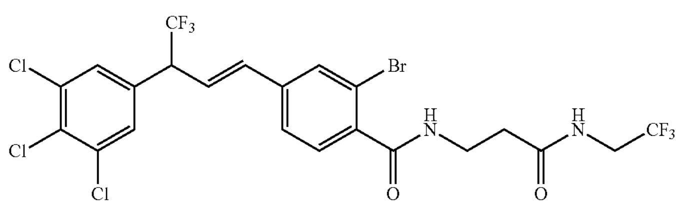 [SMILES: O=C(CCNC(=O)c1ccc(/C=C/C(c2cc(Cl)c(Cl)c(Cl)c2)C(F)(F)F)cc1Br)NCC(F)(F)F] | Pale yellow solid | 15 |
| P1640 | 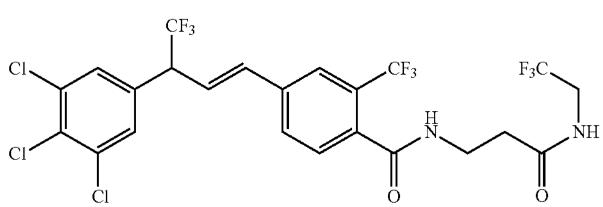 [SMILES: O=C(CCNC(=O)c1ccc(/C=C/C(c2cc(Cl)c(Cl)c(Cl)c2)C(F)(F)F)cc1C(F)(F)F)NCC(F)(F)F] | Brown semi solid | 15 |
| P1641 | 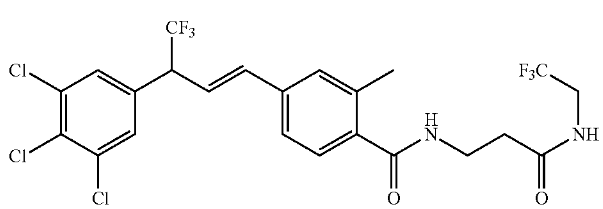 [SMILES: Cc1cc(/C=C/C(c2cc(Cl)c(Cl)c(Cl)c2)C(F)(F)F)ccc1C(=O)NCCC(=O)NCC(F)(F)F] | Brown solid | 15 |

TABLE 1B-continued

Structures of Prophetic Compounds Subsequently Exemplified

| Compound Number | Structure | Appearance | Prepared as in Example: |
|---|---|---|---|
| P1691 | 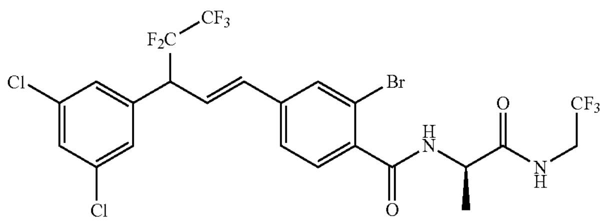 [SMILES: C[C@@H](NC(=O)c1ccc(/C=C/C(c2cc(Cl)cc(Cl)c2)C(F)(F)C(F)(F)F)cc1Br)C(=O)NCC(F)(F)F] | Brown gum | 15 |
| P1693 | 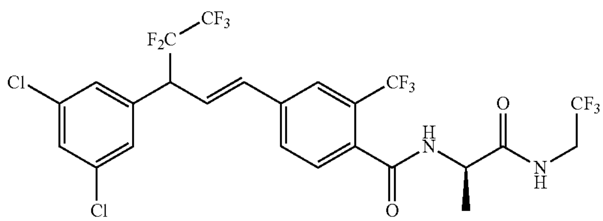 [SMILES: C[C@@H](NC(=O)c1ccc(/C=C/C(c2cc(Cl)cc(Cl)c2)C(F)(F)C(F)(F)F)cc1C(F)(F)F)C(=O)NCC(F)(F)F] | Pale yellow semi solid | 15 |
| P1696 | 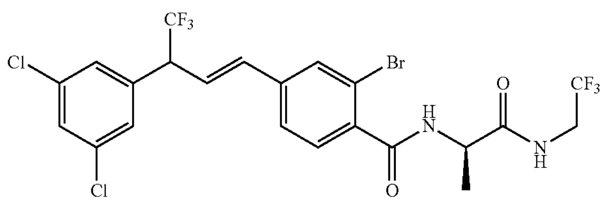 | Yellow solid | 15 |
| P1698 | 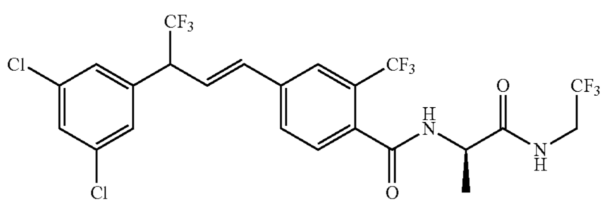 [SMILES: C[C@@H](NC(=O)c1ccc(/C=C/C(c2cc(Cl)cc(Cl)c2)C(F)(F)F)cc1Br)C(=O)NCC(F)(F)F] | Yellow semi solid | 15 |
| P1776 | 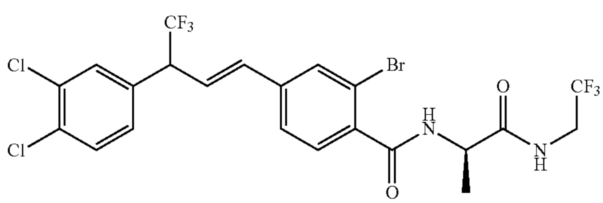 [SMILES: C[C@@H](NC(=O)c1ccc(/C=C/C(c2ccc(Cl)c(Cl)c2)C(F)(F)F)cc1Br)C(=O)NCC(F)(F)F] | White solid | 15 |
| P1781 | 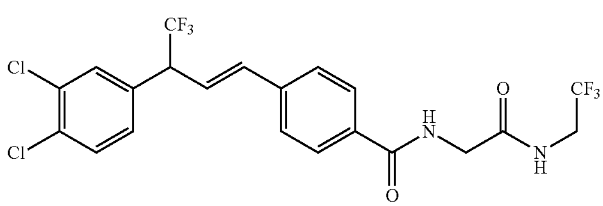 [SMILES: O=C(CNC(=O)c1ccc(/C=C/C(c2ccc(Cl)c(Cl)c2)C(F)(F)F)cc1)NCC(F)(F)F] | White solid | 15 |
| P1806 | 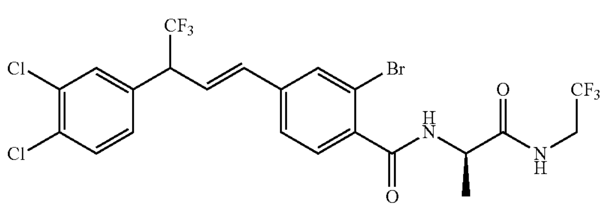 [SMILES: C[C@@H](NC(=O)c1ccc(/C=C/C(c2ccc(Cl)c(Cl)c2)C(F)(F)F)cc1Br)C(=O)NCC(F)(F)F] | Brown gum | 15 |

TABLE 1B-continued

Structures of Prophetic Compounds Subsequently Exemplified

| Compound Number | Structure | Appearance | Prepared as in Example: |
|---|---|---|---|
| P1808 | 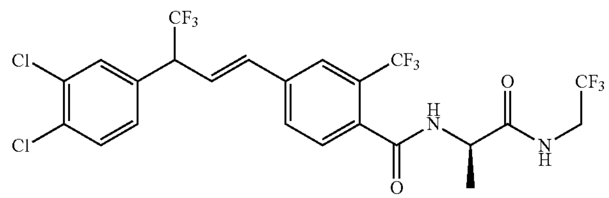 [SMILES: C[C@@H](NC(=O)c1ccc(/C=C/C(c2ccc(Cl)c(Cl)c2)C(F)(F)F)cc1C(F)(F)F)C(=O)NCC(F)(F)F] | Pale yellow gum | 15 |
| P1862 | 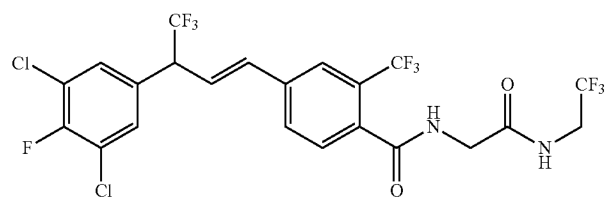 | Off white gum | 15 |
| P1864 | 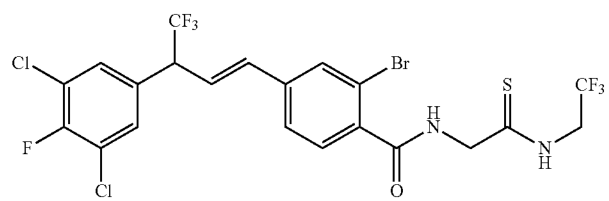 | Brown gum | 19 |
| P1866 | 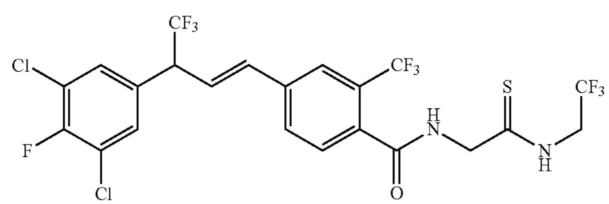 [SMILES: O=C(NCC(=S)NCC(F)(F)F)c1ccc(/C=C/C(c2cc(Cl)c(F)c(Cl)c2)C(F)(F)F)cc1C(F)(F)F] | Brown liquid | 19 |
| P1969 | 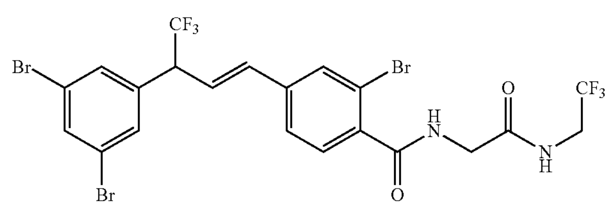 | Brown solid | 15 |
| P1970 | 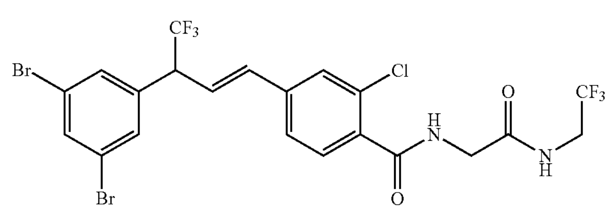 [SMILES: O=C(CNC(=O)c1ccc(/C=C/C(c2cc(Br)cc(Br)c2)C(F)(F)F)cc1Cl)NCC(F)(F)F] | Brown gum | 15 |
| P1971 | 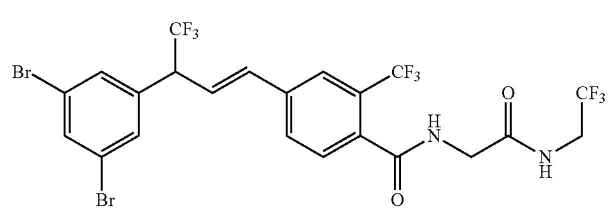 | Pale yellow solid | 15 |

TABLE 1B-continued

Structures of Prophetic Compounds Subsequently Exemplified

| Compound Number | Structure | Appearance | Prepared as in Example: |
|---|---|---|---|
| P1972 | 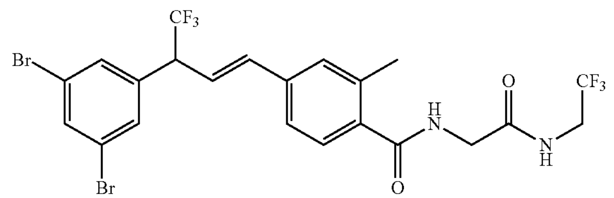 [SMILES: Cc1cc(/C=C/C(c2cc(Br)cc(Br)c2)C(F)(F)F)ccc1C(=O)NCC(=O)NCC(F)(F)F] | Light brown solid | 15 |
| P2009 | 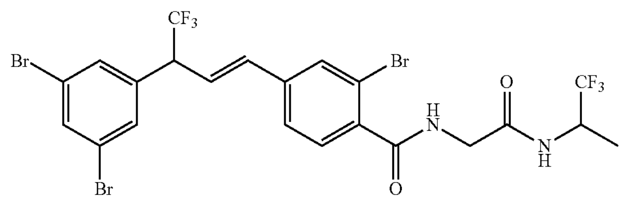 [SMILES: CC(NC(=O)CNC(=O)c1ccc(/C=C/C(c2cc(Br)cc(Br)c2)C(F)(F)F)cc1Br)C(F)(F)F] | Yellow solid | 15 |
| P2010 | 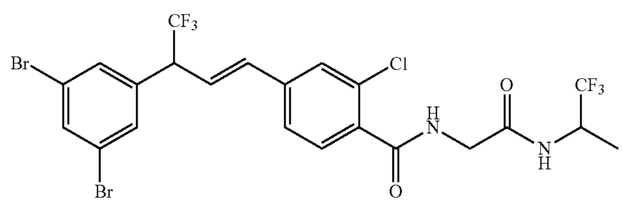 [SMILES: CC(NC(=O)CNC(=O)c1ccc(/C=C/C(c2cc(Br)cc(Br)c2)C(F)(F)F)cc1Cl)C(F)(F)F] | Yellow gum | 15 |
| P2011 | 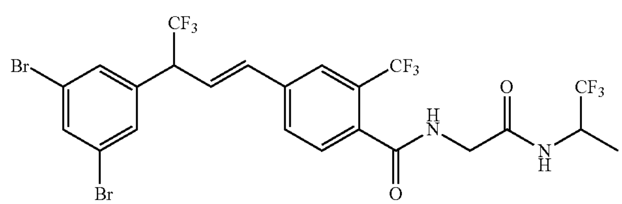 [SMILES: CC(NC(=O)CNC(=O)c1ccc(/C=C/C(c2cc(Br)cc(Br)c2)C(F)(F)F)cc1C(F)(F)F)C(F)(F)F] | Yellow solid | 15 |
| P2012 | 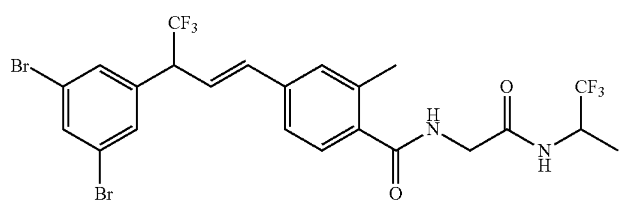 [SMILES: Cc1cc(/C=C/C(c2cc(Br)cc(Br)c2)C(F)(F)F)ccc1C(=O)NCC(=O)NC(C)C(F)(F)F] | Off white solid | 15 |
| P2036 | 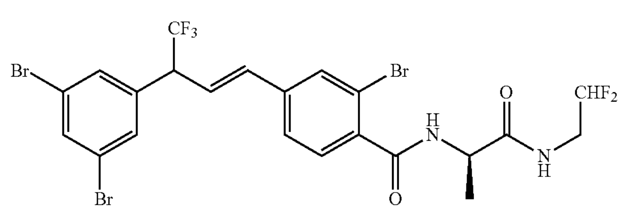 [SMILES: C[C@@H](NC(=O)c1ccc(/C=C/C(c2cc(Br)cc(Br)c2)C(F)(F)F)cc1Br)C(=O)NCC(F)F] | Brown solid | 15 |
| P2038 | 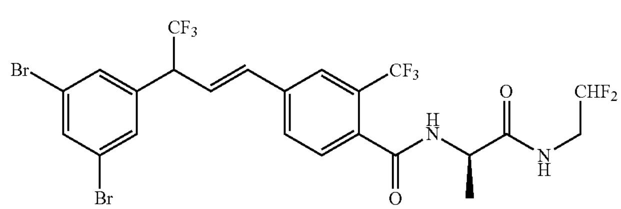 | Yellow liquid | 15 |

TABLE 1B-continued

Structures of Prophetic Compounds Subsequently Exemplified

| Compound Number | Structure | Appearance | Prepared as in Example: |
|---|---|---|---|
| P2041 | 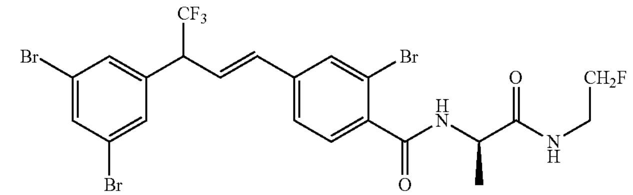 | Brown solid | 15 |
| P2043 | 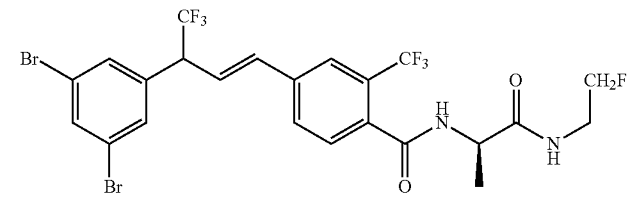 | Dark green solid | 15 |
| P2056 | 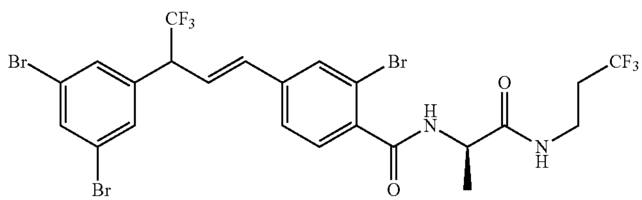 [SMILES: C[C@@H](NC(=O)c1ccc(/C=C/C(c2cc(Br)cc(Br)c2)C(F)(F)F)cc1Br)C(=O)NCCC(F)(F)F] | Brown solid | 15 |
| P2058 | 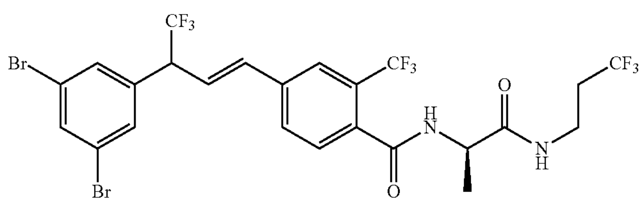 [SMILES: C[C@@H](NC(=O)c1ccc(/C=C/C(c2cc(Br)cc(Br)c2)C(F)(F)F)cc1C(F)(F)F)C(=O)NCCC(F)(F)F] | Pale yellow semi solid | 15 |

TABLE 1C

Structures for FA Compounds

| Compound Number | Structure | Appearance | Prepared as in Example: |
|---|---|---|---|
| FA1 | 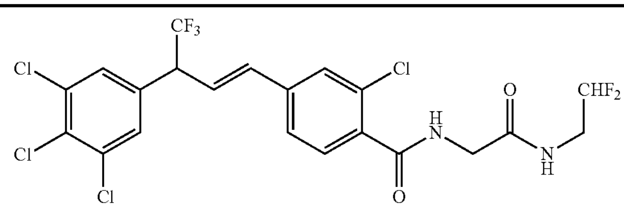 | Pale yellow gum | 15 |
| FA2 | 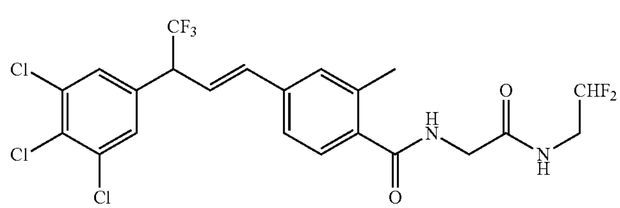 [SMILES: Cc1cc(/C=C/C(c2cc(Cl)c(Cl)c(Cl)c2)C(F)(F)F)ccc1C(=O)NCC(=O)NCC(F)F] | Light green liquid | 15 |

TABLE 1C-continued

Structures for FA Compounds

| Compound Number | Structure | Appearance | Prepared as in Example: |
|---|---|---|---|
| FA3 | 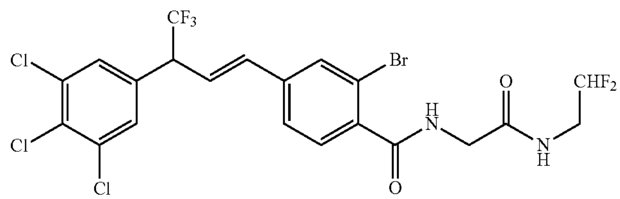 [SMILES: O=C(CNC(=O)c1ccc(/C=C/C(c2cc(Cl)c(Cl)c(Cl)c2)C(F)(F)F)cc1Br)NCC(F)F] | Brown gum | 15 |
| FA4 | 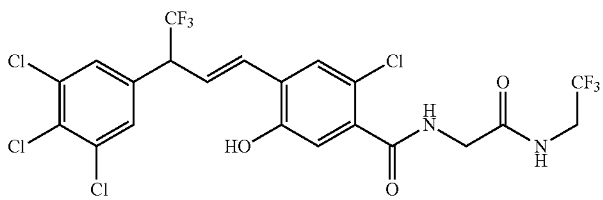 [SMILES: O=C(CNC(=O)c1cc(O)c(/C=C/C(c2cc(Cl)c(Cl)c(Cl)c2)C(F)(F)F)cc1Cl)NCC(F)(F)F] | White foam | 138 |
| FA5 | 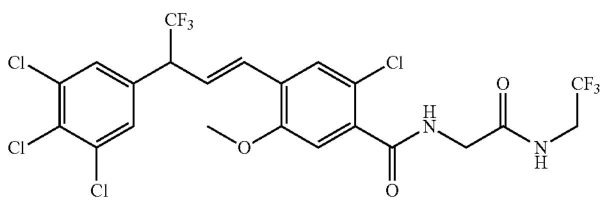 [SMILES: COc1cc(C(=O)NCC(=O)NCC(F)(F)F)c(Cl)cc1/C=C/C(c1cc(Cl)c(Cl)c(Cl)c1)C(F)(F)F] | White foam | 138 |
| FA6 | 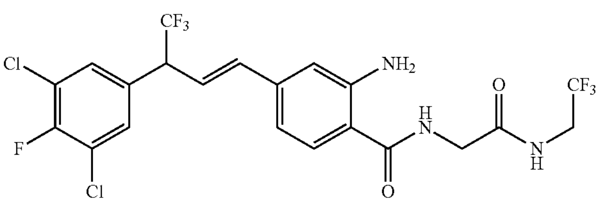 [SMILES: Nc1cc(/C=C/C(c2cc(Cl)c(F)c(Cl)c2)C(F)(F)F)ccc1C(=O)NCC(=O)NCC(F)(F)F] | Yellow solid | 146 |
| FA7 | 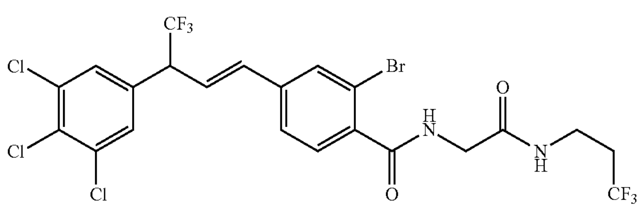 [SMILES: O=C(CNC(=O)c1ccc(/C=C/C(c2cc(Cl)c(Cl)c(Cl)c2)C(F)(F)F)cc1Br)NCCC(F)(F)F] | Pale yellow solid | 137 |
| FA8 | 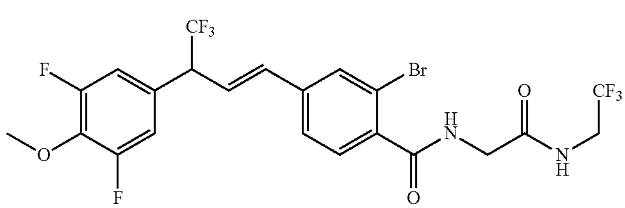 [SMILES: COc1c(F)cc(C(/C=C/c2ccc(C(=O)NCC(=O)NCC(F)(F)F)c(Br)c2)C(F)(F)F)cc1F] | Pale yellow gum | 15 |
| FA9 | 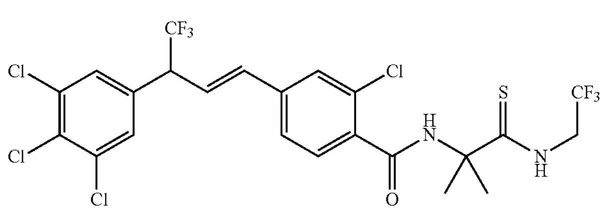 | Yellow gum | 134 |

TABLE 1C-continued

Structures for FA Compounds

| Compound Number | Structure | Appearance | Prepared as in Example: |
|---|---|---|---|
| FA10 | 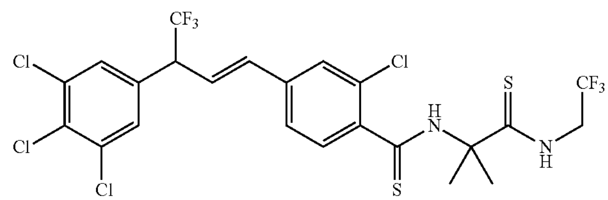 [SMILES: CC(C)(NC(=O)c1ccc(/C=C/C(c2cc(Cl)c(Cl)c(Cl)c2)C(F)(F)F)cc1Cl)C(=S)NCC(F)(F)F] | Yellow gum | 134 |
| FA11 | 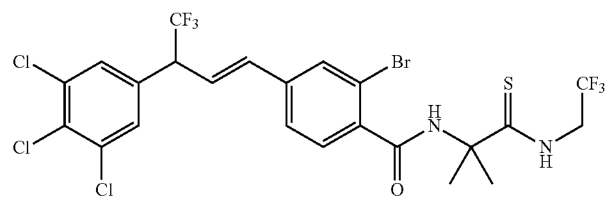 | Brown semi solid | 134 |
| FA12 | 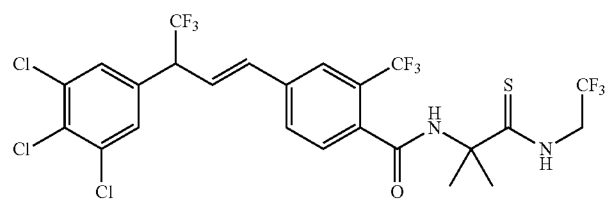 | Brown semi solid | 134 |
| FA13 | 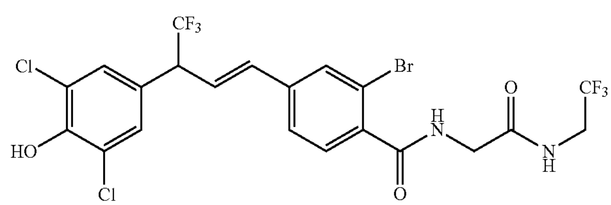 | Light green solid | 147 |
| FA14 | 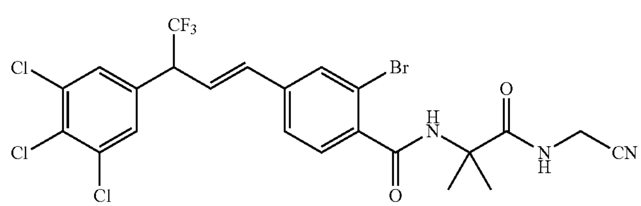 [SMILES: CC(C)(NC(=O)c1ccc(/C=C/C(c2cc(Cl)c(Cl)c(Cl)c2)C(F)(F)F)cc1Br)C(=O)NCC#N] | White foam | 142 |
| FA15 | 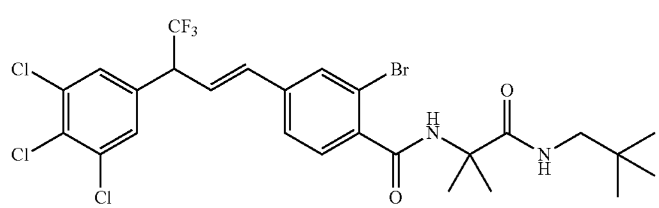 [SMILES: CC(C)(C)CNC(=O)C(C)(C)NC(=O)c1ccc(/C=C/C(c2cc(Cl)c(Cl)c(Cl)c2)C(F)(F)F)cc1Br] | White foam | 142 |
| FA16 | 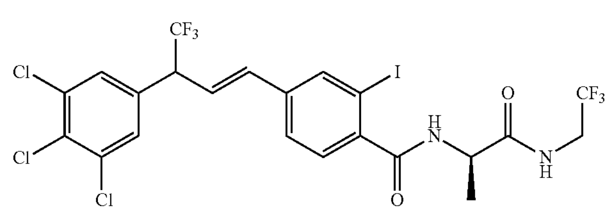 [SMILES: C[C@@H](NC(=O)c1ccc(/C=C/C(c2cc(Cl)c(Cl)c(Cl)c2)C(F)(F)F)cc1I)C(=O)NCC(F)(F)F] | Pale yellow solid | 15 |

TABLE 1C-continued

Structures for FA Compounds

| Compound Number | Structure | Appearance | Prepared as in Example: |
|---|---|---|---|
| FA17 | 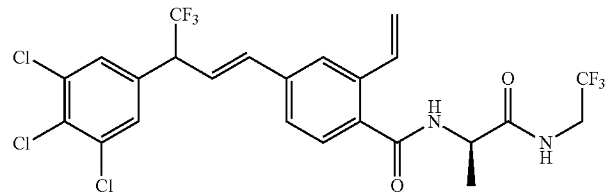 [SMILES: C=Cc1cc(/C=C/C(c2cc(Cl)c(Cl)c(Cl)c2)C(F)(F)F)ccc1C(=O)N[C@H](C)C(=O)NCC(F)(F)F] | Off white solid | 15 |
| FA18 | 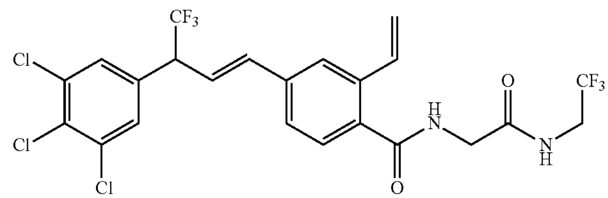 [SMILES: C=Cc1cc(/C=C/C(c2cc(Cl)c(Cl)c(Cl)c2)C(F)(F)F)ccc1C(=O)NCC(=O)NCC(F)(F)F] | Yellow semi solid | 15 |
| FA19 | 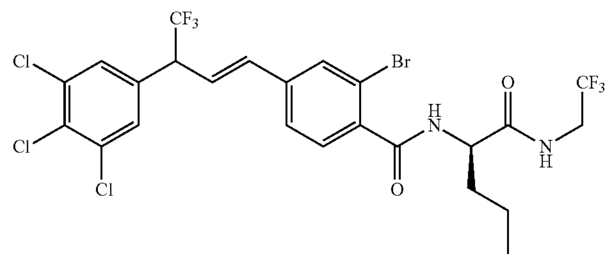 [SMILES: CCC[C@@H](NC(=O)c1ccc(/C=C/C(c2cc(Cl)c(Cl)c(Cl)c2)C(F)(F)F)cc1Br)C(=O)NCC(F)(F)F] | Pale yellow solid | 15 |
| FA20 | 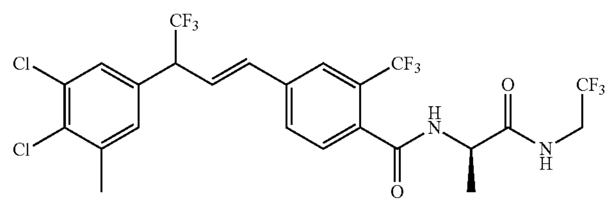 [SMILES: Cc1cc(C(/C=C/c2ccc(C(=O)N[C@H](C)C(=O)NCC(F)(F)F)c(C(F)(F)F)c2)C(F)(F)F)cc(Cl)c1Cl] | Pale yellow solid | 15 |
| FA21 | 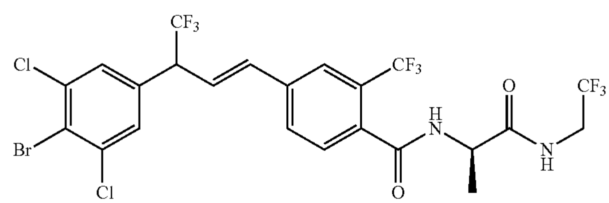 | Brown gum | 15 |
| FA22 | 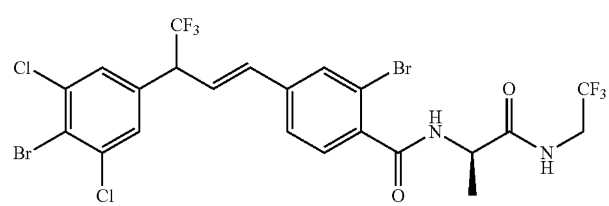 | Yellow gum | 15 |
| FA23 | 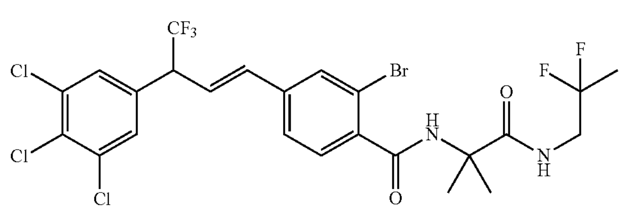 [SMILES: CC(F)(F)CNC(=O)C(C)(C)NC(=O)c1ccc(/C=C/C(c2cc(Cl)c(Cl)c(Cl)c2)C(F)(F)F)cc1Br] | Light yellow oil | 142 |

TABLE 1C-continued

Structures for FA Compounds

| Compound Number | Structure | Appearance | Prepared as in Example: |
|---|---|---|---|
| FA24 | 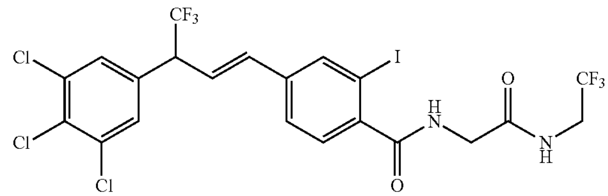 | Off white solid | 15 |
| FA25 | 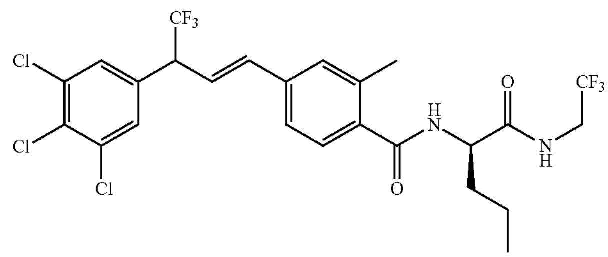 [SMILES: CCC[C@@H](NC(=O)c1ccc(/C=C/C(c2cc(Cl)c(Cl)c(Cl)c2)C(F)(F)F)cc1C)C(=O)NCC(F)(F)F] | Yellow solid | 15 |
| FA26 | 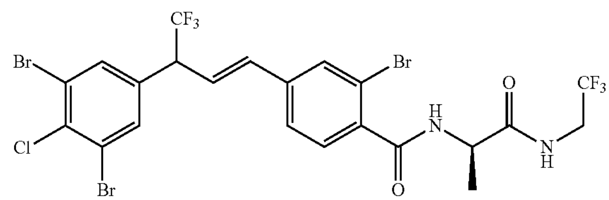 | Light green solid | 12 |
| FA27 | 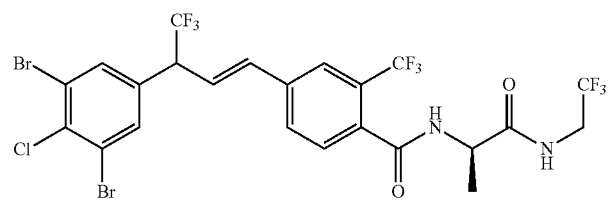 | Pale green solid | 12 |
| FA28 | 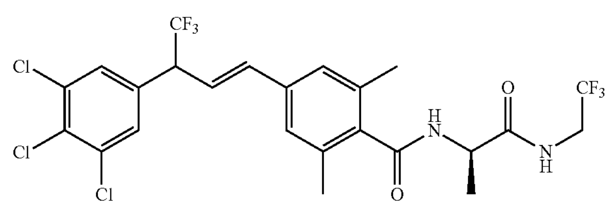 [SMILES: Cc1cc(/C=C/C(c2cc(Cl)c(Cl)c(Cl)c2)C(F)(F)F)cc(C)c1C(=O)N[C@H](C)C(=O)NCC(F)(F)F] | Brown solid | 15 |
| FA29 | 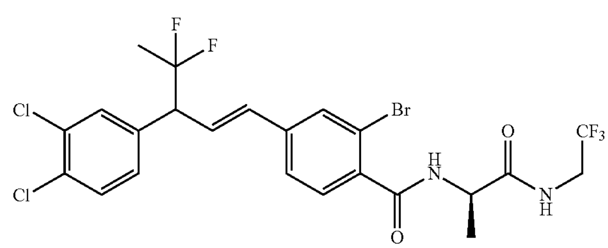 [SMILES: C[C@@H](NC(=O)c1ccc(/C=C/C(c2ccc(Cl)c(Cl)c2)C(C)(F)F)cc1Br)C(=O)NCC(F)(F)F] | Brown liquid | 15 |
| FA30 | 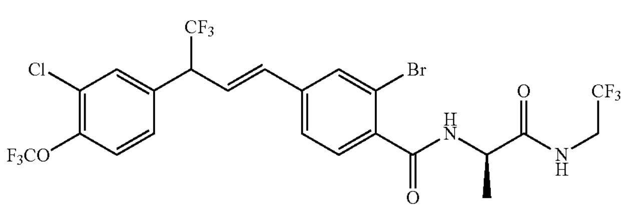 [SMILES: C[C@@H](NC(=O)c1ccc(/C=C/C(c2ccc(OC(F)(F)F)c(Cl)c2)C(F)(F)F)cc1Br)C(=O)NCC(F)(F)F] | Brown gum | 12 |

TABLE 1C-continued

Structures for FA Compounds

| Compound Number | Structure | Appearance | Prepared as in Example: |
|---|---|---|---|
| FA31 | 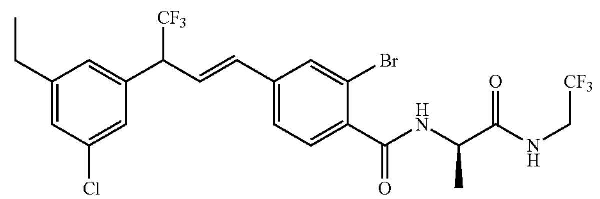 [SMILES: CCc1cc(Cl)cc(C(/C=C/c2ccc(C(=O)N[C@H](C)C(=O)NCC(F)(F)F)c(Br)c2)C(F)(F)F)c1] | Pale yellow solid | 12 |
| FA32 | 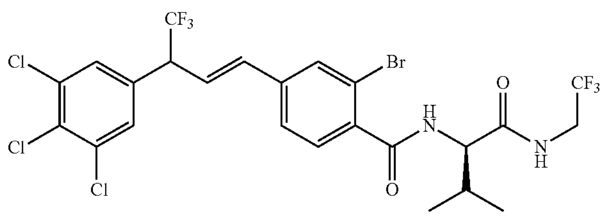 [SMILES: CC(C)[C@@H](NC(=O)c1ccc(/C=C/C(c2cc(Cl)c(Cl)c(Cl)c2)C(F)(F)F)cc1Br)C(=O)NCC(F)(F)F] | Yellow solid | 15 |
| FA33 | 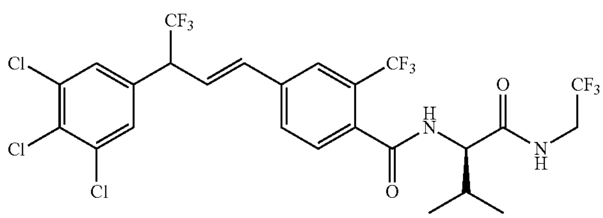 | Yellow solid | 135 |
| FA34 | 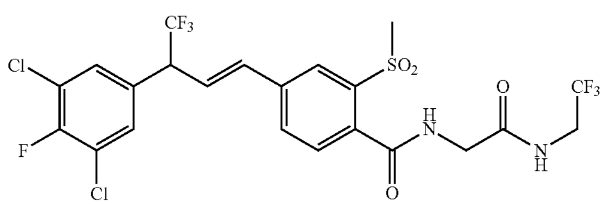 [SMILES: CS(=O)(=O)c1cc(/C=C/C(c2cc(Cl)c(F)c(Cl)c2)C(F)(F)F)ccc1C(=O)NCC(=O)NCC(F)(F)F] | Off white solid | 149 |

TABLE 2

Analytical Data for Compounds in Table 1.

| Compound Number | mp (° C.) | ESIMS | $^1$H NMR (δ)$^a$ | IR (cm$^{-1}$) |
|---|---|---|---|---|
| AC1 | 156-161 | 386.09 ([M − H]$^-$) | 7.83 (m, 2H), 7.68-7.63 (m, 5H), 6.93 (dd, J = 15.6, 8.0 Hz, 1H), 6.81 (d J = 15.6 Hz, 1H,), 4.15 (m, 1H), 2.80 (s, 3H) | |
| AC2 | 110-112 | 374 ([M + H]$^+$) | 7.80 (d, J = 8.4 Hz, 2H), 7.48 (d, J = 8.0 Hz, 2H), 7.38 (m, 1H), 7.30 (s, 2H), 6.65 (d, J = 16.0 Hz, 1H), 6.46 (dd, J = 16.0, 8.0 Hz, 1H), 4.15 (m, 1H) | |
| AC3 | 162-166 | 402.24 ([M + H]$^+$) | 7.42 (m, 4H), 7.37 (t, J = 1.8 Hz, 1H), 7.28 (s, 2H), 6.63 (d, J = 16.0 Hz, 1H), 6.41 (dd, J = 16.0, 8.4 Hz, 1H), 4.15 (m, 1H), 3.20 (s, 3H), 3.00 (s, 3H) | |
| AC4 | 122-126 | 454 ([M − H]$^-$) | 7.79 (d, J = 1.2 Hz, 2H), 7.48 (d, J = 8.4 Hz, 2H), 7.38 (t, J = 1.8 Hz, 1H), | |

TABLE 2-continued

Analytical Data for Compounds in Table 1.

| Compound Number | mp (° C.) | ESIMS | ¹H NMR (δ)ᵃ | IR (cm⁻¹) |
|---|---|---|---|---|
| | | | 7.30 (s, 2H), 6.64 (d, J = 15.6 Hz, 1H), 6.40 (dd, J = 15.6, 8.0 Hz, 1H), 6.30 (m, 1H), 4.15 (m, 3H) | |
| AC5 | | 444.12 ([M + H]⁺) | 7.67 (s, 3H), 7.64 (d, J = 8.0 Hz, 2H), 7.42 (d, J = 8.0 Hz, 2H), 6.91 (dd, J = 15.6, 8.0 Hz, 1H), 6.80 (d, J = 15.6 Hz, 1H), 4.80 (m, 1H), 3.60 (br s, 8H) | |
| AC6 | | 468.40 ([M − H]⁻) | 7.40 (m, 2H), 7.26 (m, 3H), 6.56 (d, J = 16.0 Hz, 1H), 6.48 (dd, J = 16.0, 8.0 Hz, 1H), 5.82 (br s, 1H), 4.08 (m, 3H), 2.52 (s, 3H) | 1657, 1113, 804 |
| AC7 | | 511.02 ([M − H]⁻) | 8.39 (s, 1H), 7.74 (m, 1H), 7.39 (m, 3H), 7.24 (m, 4H), 6.58 (d, J = 16.0 Hz, 1H), 6.38 (dd, J = 16.0, 8.0 Hz, 1H), 6.16 (br s, 1H), 4.63 (m, 2H), 4.12 (m, 1H), 2.41 (s, 3H) | 3276, 1645, 1111, 801 |
| AC8 | | 454.11 ([M − H]⁻) | 7.39 (s, 1H), 7.22 (m, 2H), 7.19 (m, 3H), 6.53 (d, J = 16.0 Hz, 1H), 6.39-6.34 (dd, J = 16.0, 8.0 Hz, 1H), 4.22 (m, 1H), 3.95 (t, J = 7.0 Hz, 2H), 2.62 (t, J = 8.0 Hz, 2H), 2.30 (s, 3H), 2.18 (m, 2H) | 1748, 1112, 801 |
| AC9 | | 494.02 ([M − H]⁻) | 7.45 (t, J = 7.6 Hz, 1H), 7.36 (m, 2H), 7.21 (m, 3H), 7.15 (m, 4H), 6.56 (d, J = 16.0 Hz, 1H), 6.38 (dd, J = 16.0, 8.4 Hz, 1H), 6.08 (br s, 1H), 4.68 (d, J = 5.6 Hz, 2H), 4.11 (m, 1H), 2.44 (s, 3H) | 3276, 1645, 1112, 801 |
| A10 | 140-143 | 458.00 ([M − H]⁻) | 7.38 (t, J = 1.6 Hz, 1H), 7.34 (d, J = 7.6 Hz, 1H), 7.27 (m, 2H), 7.24 (m, 2H), 6.57 (d, J = 16.0 Hz, 1H), 6.40 (dd, J = 16.0, 8.0 Hz, 1H), 6.16 (m 1H), 5.44 (m, 1H), 4.12 (m, 1H), 3.51 (m, 2H), 3.40 (m, 2H), 2.44 (s, 3H) | |
| AC11 | | 476.17 ([M − H]⁻) | 7.39-7.29 (m, 9H), 7.24 (m, 2H), 6.56 (d, J = 16.0 Hz, 1H), 6.38 (dd, J = 16.0, 8.0 Hz, 1H), 5.99 (br s, 1H), 4.63 (d, J = 6.0 Hz, 1H), 4.11 (m, 1H), 2.47 (s, 3H) | 3287, 1644, 1112, 801 |
| AC12 | | 479.30 ([M + H]⁺) | 8.63 (d, J = 4.4 Hz, 1H), 7.71 (m, 1H), 7.47 (d, J = 8.4 Hz, 1H), 7.37 (m, 2H), 7.32 (m, 2H), 7.23 (m, 2H), 7.13 (m, 1H), 6.58 (d, J = 16.0 Hz, 1H), 6.40 (dd, J = 16.0, 8.0 Hz, 1H), 4.75 (d, J = 4.8 Hz, 2H), 4.12 (m, 1H), 2.49 (s, 3H) | 3293, 1653, 1112, 800 |
| AC13 | 75-78 | 490.04 ([M − H]⁻) | 7.38 (m, 2H), 7.27 (m, 3H), 7.23 (br s, 1H), 6.58 (d, J = 16.0 Hz, 1H), 6.45 (m 1H), 6.42 | |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| AC14 | | 480.99 ([M + 2H]$^+$) | (dd, J = 16.0, 8.4 Hz, 1H), 4.91 (m 1H), 4.64 (m, 2H), 4.14 (m, 1H), 4.04 (m, 2H), 2.46 (s, 3H) 8.63 (s, 2H), 7.76 (d, J = 8.0 Hz, 1H), 7.36 (m, 3H), 7.22 (m, 1H), 7.13 (m, 2H), 6.57 (d, J = 16.0 Hz, 1H), 6.39 (dd, J = 16.0, 8.0 Hz, 1H), 6.13 (br s, 1H), 4.66 (d, J = 5.6 Hz, 2H), 4.11 (m, 1H), 2.46 (s, 3H) | 3293, 1645, 1113, 800 |
| AC15 | 59-61 | 516.86 ([M − H]$^-$) | 7.45 (s, 1H), 7.37 (m, 1H), 7.34 (m, 1H), 7.26 (m, 3H), 7.22 (m, 1H), 6.57 (d, J = 16.0 Hz, 1H), 6.40 (dd, J = 16.0, 8.0 Hz, 1H), 6.18 (m, 1H), 4.71 (d, J = 6.4 Hz, 2H), 4.11 (m, 1H), 2.46 (s, 3H) | 3246, 1635, 1112, 801 |
| AC16 | | 506.93 ([M + H]$^+$) | 8.47 (m, 1H), 8.19 (s, 1H), 7.76 (m, 1H), 7.47 (m, 2H), 7.37 (m, 1H), 7.28 (m, 2H), 7.24 (m, 1H), 7.21 (m, 1H), 6.59 (d, J = 16.0 Hz, 1H), 6.39 (dd, J = 16.0, 8.4 Hz, 1H), 4.12 (m, 1H), 2.48 (s, 3H), 1.88 (s, 6H) | 1657, 1113, 801 |
| AC17 | 70-73 | 494.98 ([M − H]$^-$) | 7.49 (m, 2H), 7.38 (m, 1H), 7.29 (m, 4H), 7.08 (m, 3H), 6.91 (m, 1H), 6.61 (d, J = 16.0 Hz, 1H), 6.48 (m, 1H), 6.43 (dd, J = 16.0, 8.0 Hz, 1H), 4.13 (m, 1H), 2.49 (s, 3H) | |
| AC18 | 155-158 | 480.44 ([M + H]$^+$) | 8.73 (d, J = 4.8 Hz, 2H), 7.53 (d, J = 8.4 Hz, 1H), 7.37 (m, 1H), 7.27 (m, 4H), 7.23 (m, 1H), 7.11 (m, 1H), 6.60 (d, J = 16.0 Hz, 1H), 6.41 (dd, J = 16.0, 8.0 Hz, 1H), 4.90 (d, J = 4.8 Hz, 2H), 4.13 (m, 1H), 2.52 (s, 3H) | |
| AC19 | 55-57 | 471.66 ([M + H]$^+$) | 7.37 (m, 1H), 7.33 (d, J = 7.6 Hz, 1H), 7.27 (m, 2H), 7.22 (m, 2H), 6.57 (d, J = 16.0 Hz, 1H), 6.39 (dd, J = 16.0, 8.0 Hz, 1H), 6.10 (brs, 1H), 4.13 (m, 2H), 3.94 (m, 1H), 3.79 (m, 2H), 3.35 (m, 1H), 2.45 (s, 3H), 2.14 (m, 1H), 1.71 (m, 2H), 1.65 (m, 1H). | |
| AC20 | | 467.68 ([M + H]$^+$) | 7.37 (m, 2H), 7.27 (m, 2H), 7.23 (m, 2H), 6.57 (d, J = 16.0 Hz, 1H), 6.38 (m, 3H), 6.01 (m, 1H), 4.63 (d, J = 5.6 Hz, 2H), 4.13 (m, 1H), 2.45 (s, 3H) | 3437, 1664, 1265, 1114, 746 |
| AC21 | 61-64 | 528.78 ([M + H]$^+$) | 8.44 (s, 1H), 8.18 (s, 1H), 7.83 (br s, 1H), 7.38 (m, 2H), 7.27 (m, 2H), 7.25 (m, 2H), 7.21 (m, 1H), 6.57 (d, J = 16.0 Hz, 1H), 6.40 (dd, J = 16.0, 8.0 Hz, 1H), 5.01 (s, 2H), 4.11 (m, 1H), 2.43 (s, 3H) | |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| AC22 | | 545.08 ([M − H]$^-$) | 8.39 (s, 1H), 7.73 (m, 1H), 7.40 (s, 1H), 7.35 (m, 2H), 7.22 (m, 3H), 6.57 (d, J = 16.0 Hz, 1H), 6.38 (dd, J = 16.0, 7.6 Hz, 1H), 6.14 (br s, 1H), 4.62 (d, J = 6.0 Hz, 2H), 4.13 (m, 1H), 2.45 (s, 3H) | 3270, 1642, 1111, 809 |
| AC23 | | 492.35 ([M − H]$^-$) | 7.42 (s, 2H), 7.36 (m, 1H), 7.24 (m, 2H), 6.59 (d, J = 16.0 Hz, 1H), 6.40 (dd, J = 16.0, 8.0 Hz, 1H), 6.20 (br s, 1H), 5.46 (m, 1H), 4.15 (m, 1H), 3.52 (m, 2H), 3.41 (m, 2H), 2.45 (s, 3H) | 3273, 1641, 1250, 1113, 807 |
| AC24 | 129-132 | 526.98 ([M + H]$^+$) | 7.40 (m, 2H), 7.27 (m, 2H), 7.25 (m, 2H), 6.92 (br s, 2H), 6.60 (m, 1H), 6.48 (dd, J = 16.0, 8.0 Hz, 1H), 4.19 (d, J = 5.2, 2H), 4.08 (m, 1H), 3.99 (m, 2H), 2.46 (s, 3H) | 3298, 1664, 1113, 803 |
| AC25 | | 542.24 ([M − H]$^-$) | 7.41 (m, 3H), 7.27 (m, 2H), 6.58 (d, J = 15.6 Hz, 1H), 6.42 (m, 2H), 4.92 (m, 1H), 4.65 (m, 2H), 4.14 (m, 1H), 4.09 (m, 2H), 2.46 (s, 3H) | 3257, 1652, 1316, 1109, 807 |
| AC26 | | 550.69 ([M − H]$^-$) | 7.45 (s, 1H), 7.40 (s, 2H), 7.34 (d, J = 8.0 Hz, 1H), 7.22 (m, 2H), 6.54 (d, J = 16.0 Hz, 1H), 6.38 (dd, J = 16.0, 8.0 Hz, 1H), 4.71 (d, J = 6.0 Hz, 2H), 4.11 (m, 1H), 2.46 (s, 3H) | 3255, 1638, 1113, 809 |
| AC27 | | 541.00 ([M − H]$^-$) | 8.46 (d, J = 4.0 Hz, 1H), 8.20 (s, 1H), 7.76 (m, 1H), 7.47 (m, 2H), 7.41 (s, 2H), 7.23 (m, 2H), 7.21 (m, 1H), 6.59 (d, J = 16.0 Hz, 1H), 6.37 (dd, J = 16.0, 8.4 Hz, 1H), 4.11 (m, 1H), 2.48 (s, 3H), 1.88 (s, 6H) | 1653, 1113, 809 |
| AC28 | 65-67 | 564.84 ([M − H]$^-$) | 8.40 (s, 1H), 7.74 (m, 2H), 7.42 (m, 3H), 7.36 (m, 2H), 6.72 (br s, 1H), 6.52 (d, J = 16.0 Hz, 1H), 6.43 (dd, J = 16.0, 8.0 Hz, 1H), 4.66 (d, J = 6.4 Hz, 2H), 4.12 (m, 1H) | 3267, 1650, 1112, 809 |
| AC29 | 75-78 | 511.78 ([M − H]$^-$) | 7.71 (d, J = 8.4 Hz, 1H), 7.42 (m, 3H), 7.35 (m, 1H), 6.75 (br s, 1H), 6.56 (d, J = 16.0 Hz, 1H), 6.43 (dd, J = 16.0, 8.0 Hz, 1H), 5.49 (m, 1H), 4.14 (m, 1H), 3.50 (m, 4H) | |
| AC30 | 110-113 | 543.72 ([M − H]$^-$) | 7.42 (d, J = 8.4 Hz, 1H), 7.44 (s, 1H), 7.40 (s, 1H), 7.38 (m, 1H), 7.06 (br s, 1H), 6.58 (d, J = 15.6 Hz, 1H), 6.45 (dd, J = 15.6, 8.0 Hz, 1H), 4.93 (m, 1H), 4.65 (m, 2H), 4.13 (m, 3H) | |
| AC31 | 68-70 | 610.73 ([M + H]$^+$) | 8.42 (s, 1H), 7.76 (m, 1H), 7.61 (m, 2H), 7.39 (m, 4H), 6.54-6.39 (m, 3H), 4.66 (d, J = 6.0 Hz, 2H), 4.12 (m, 1H) | |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| AC32 | 78-80 | 555.89 ([M − H]$^-$) | 7.61 (m, 2H), 7.40 (m, 3H), 6.54 (m, 2H), 6.40 (dd, J = 16.0, 8.0 Hz, 1H), 5.46 (m, 1H), 4.14 (m, 1H), 3.50 (m, 4H) | |
| AC33 | 182-184 | 587.68 ([M − H]$^-$) | 7.62 (s, 1H), 7.58 (d, J = 8.0 Hz, 1H), 7.40 (m, 3H), 6.84 (br s, 1H), 6.55 (d, J = 15.6 Hz, 1H), 6.45 (dd, J = 15.6, 7.6 Hz, 1H), 4.93 (m 1H), 4.65 (m, 2H), 4.13 (m, 4H) | |
| AC34 | 151-153 | 545.83 ([M − H]$^-$) | 7.67 (s, 1H), 7.61 (d, J = 6.0 Hz, 1H), 7.53 (m, 1H), 7.41 (s, 2H), 6.64 (d, J = 16.0 Hz, 1H), 6.40 (dd, J = 16.0, 8.0 Hz, 1H), 6.18 (br s, 1H), 5.44 (m, 1H), 4.14 (m, 1H), 3.50 (m, 2H), 3.40 (m, 2H) | |
| AC35 | 100-102 | 577.71 ([M − H]$^-$) | 7.70 (s, 1H), 7.63 (m, 1H), 7.53 (d, J = 7.6 Hz, 1H), 7.41 (s, 2H), 6.53 (d, J = 16.0 Hz, 1H), 6.49 (m, 2H), 4.93 (m, 1H), 4.64 (m, 2H), 4.13 (m, 1H), 4.03 (m, 2H) | 3257, 1655, 1113, 808 |
| AC36 | 81-83 | 600.83 ([M + H]$^+$) | 8.40 (s, 1H), 7.73 (m, 2H), 7.61 (d, J = 8.4 Hz, 1H), 7.52 (d, J = 8.0 Hz, 1H), 7.40 (s, 2H), 7.35 (d, J = 8.0 Hz, 1H), 6.63 (d, J = 16.0 Hz, 1H), 6.46 (dd, J = 16.0, 7.6 Hz, 1H), 6.14 (m, 1H), 4.63 (d, J = 6.0 Hz, 2H), 4.14 (m, 1H) | |
| AC37 | | 512.68 ([M + H]$^+$) | 8.39 (s, 1H), 7.73 (m, 1H), 7.48 (m, 2H), 7.34 (d, J = 7.6 Hz, 1H), 7.24 (m, 3H), 6.55 (d, J = 16.0 Hz, 1H), 6.41 (dd, J = 16.0, 7.6 Hz, 1H), 6.12 (m, 1H), 4.62 (d, J = 6.0 Hz, 2H), 4.13 (m, 1H), 2.45 (s, 3H) | 3268, 1644, 1109, 820 |
| AC38 | 79-80 | 528.85 ([M − H]$^-$) | 8.46 (m, 1H), 7.73 (m, 1H), 7.35 (m, 4H), 7.22 (m, 2H), 6.56 (d, J = 16.0 Hz, 1H), 6.38 (dd, J = 16.0, 8.0 Hz, 1H), 4.62 (d, J = 6.0 Hz, 2H), 4.10 (m, 1H), 2.45 (s, 3H) | |
| AC39 | 141-144 | 477.83 ([M − H]$^-$) | 9.19 (s, 1H), 8.79 (s, 2H), 7.37 (m, 2H), 7.23 (m, 2H), 7.21 (m, 1H), 6.57 (d, J = 16.0 Hz, 1H), 6.40 (dd, J = 16.0, 7.6 Hz 1H), 6.21 (m, 1H), 4.65 (s, 2H), 4.11 (m, 1H), 2.46 (s, 3H) | |
| AC40 | 69-72 | 484.67 ([M + H]$^+$) | 8.33 (t, J = 5.6 Hz, 1H), 8.61 (m, 1H), 7.68 (m, 3H), 7.48 (m, 2H), 6.86 (dd, J = 15.6, 8.2 Hz 1H), 6.74 (d, J = 15.6 Hz, 1H), 4.44 (m, 1H), 3.76 (d, J = 6.0 Hz, 2H), 2.54 (m, 1H), 2.67 (s, 3H), 0.59 (m, 2H), 0.54 (m, 2H) | |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| AC41 | 196-199 | 515.00 ([M − H]$^-$) | 8.66 (d, J = 7.6 Hz, 1H), 8.39 (t, J = 5.6 Hz, 1H), 7.65 (s, 3H), 7.45 (m, 3H), 6.86 (dd, J = 15.6, 8.8 Hz, 1H), 6.74 (d, J = 15.6 Hz, 1H), 5.01 (m, 1H), 4.99 (m, 1H), 3.78 (d, J = 6.0 Hz, 2H), 3.40 (m, 2H), 3.22 (m, 2H), 2.37 (m, 3H) | |
| AC42 | 79-82 | 534.72 ([M + H]$^+$) | 7.99 (d, J = 8.0 Hz, 1H), 7.89 (d, J = 8.0 Hz, 1H), 7.51 (m, 2H), 7.44 (m, 2H), 7.27 (m, 4H), 6.71 (t, J = 5.2 Hz, 1H), 6.59 (d, J = 16.0 Hz, 1H), 6.41 (dd, J = 16.0, 8.0 Hz, 1H), 5.05 (d, J = 1.6 Hz, 2H), 4.12 (m, 1H), 2.52 (m, 3H) | |
| AC43 | | 481.75 ([M + H]$^+$) | 8.69 (s, 1H), 8.52 (s, 2H), 7.45 (d, J = 7.6 Hz, 1H), 7.37 (d, J = 2.0 Hz, 1H), 7.26 (m, 2H), 7.21 (m, 1H), 6.83 (s, 1H), 6.58 (d, J = 16.0 Hz, 1H), 6.40 (dd, J = 16.0, 8.4 Hz, 1H), 4.81 (d, J = 5.6 Hz, 2H), 4.12 (t, J = 8.4 Hz 1H), 2.45 (s, 3H) | 1663, 1608, 1168, 1114, 801 |
| AC44 | | 528.01 ([M + H]$^+$) | 8.44 (d, J = 2.4 Hz, 1H), 7.69 (d, J = 2.4 Hz, 1H), 7.37 (m, 1H), 7.33 (s, 1H), 7.31 (s, 1H), 7.26 (m, 1H), 7.24 (m, 3H), 6.57 (d, J = 16.0 Hz, 1H), 6.39 (dd, J = 16.0, 8.0 Hz, 1H), 5.96 (d, J = 7.2 Hz, 1H), 5.32 (t, J = 7.2 Hz, 1H), 4.11 (t, J = 8.4 Hz, 1H), 2.41 (s, 3H), 1.61 (d, J = 7.2 Hz, 3H) | 1640, 1166, 1112, 800 |
| AC45 | | 512.88 ([M + H]$^+$) | 7.66 (s, 1H), 7.37 (d, J = 6.8 Hz, 2H), 7.26 (m, 3H), 7.18 (m, 1H), 7.11 (m, 2H), 6.99 (m, 1H), 6.57 (d, J = 15.6 Hz, 1H), 6.39 (dd, J = 15.6, 8.0 Hz, 1H), 4.11 (t, J = 8.4 Hz, 1H), 3.36 (s, 3H), 2.43 (s, 3H) | 1657, 1167, 1106, 800 |
| AC46 | 61-64 | 575.93 ([M + H]$^+$) | 8.42 (d, J = 2.0 Hz, 1H), 7.76 (d, J = 2.4 Hz, 1H), 7.61 (m, 2H), 7.39 (m, 3H), 7.26 (s, 2H), 6.54 (d, J = 16.0 Hz, 1H), 6.42 (dd, J = 16.0, 7.6 Hz, 1H), 4.65 (d, J = 6.0 Hz, 2H), 4.14 (m, 1H) | |
| AC47 | | 525.89 ([M − H]$^-$) | 10.02 (s, 1H), 9.87 (s, 1H), 8.47 (t, J = 6.0 Hz, 1H), 7.66 (s, 3H), 7.44 (s, 1H), 7.40 (d, J = 3.6 Hz, 2H), 6.86 (dd, J = 15.6, 9.2 Hz, 1H), 6.74 (d, J = 15.6 Hz, 1H), 4.82 (t, J = 9.6 Hz, 2H), 3.88 (d, J = 6.0 Hz, 2H), 2.36 (s, 3H), 1.63 (m, 1H), 0.76 (m, 4H) | 3280, 1640 |
| AC48 | | 509.96 ([M − H]$^-$) | 7.37 (m, 7H), 7.34 (m, 3H), , 6.57 (d, J = 16.0 Hz, 1H), 6.39 (dd, J = 16.0, 8.0 Hz, 1H), 6.01 | 3275, 1642 |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| | | | (m, 1H), 4.60 (d, J = 6.0 Hz, 2H), 4.13 (m, 1H), 2.46 (s, 3H) | |
| AC49 | | 518.85 ([M + H]$^+$) | 8.39 (d, J = 2.0 Hz, 1H), 8.11 (m, 1H), 7.71 (d, J = 2.4 Hz, 1H), 7.41 (m, 3H), 7.17 (m, 3H), 6.59 (d, J = 16.0 Hz, 1H), 6.47 (dd, J = 16.0, 8.0 Hz, 1H), 4.66 (d, J = 5.6 Hz, 2H), 4.14 (m, 1H) | 1658, 1112, 1025, 2219 |
| AC50 | | 481.88 ([M + H]$^+$) | 8.72 (m, 1H), 7.67 (s, 3H), 7.46 (s, 1H), 7.40 (m, 2H), 7.08 (s, 1H), 6.82 (m, 2H), 6.55 (d, J = 7.6 Hz, 1H), 4.82 (m, 1H), 4.48 (s, 2H), 3.65 (s, 3H), 2.38 (s, 3H) | 1654, 1112, 800, 3069 |
| AC51 | | 540.83 ([M + H]$^+$) | 7.45 (d, J = 7.6 Hz, 1H), 7.38 (m, 1H), 7.27 (m, 2H), 7.22 (m, 2H), 6.85 (m, 1H), 6.58 (d, J = 16.0 Hz, 1H), 6.40 (dd, J = 16.0, 8.0 Hz, 1H), 4.33 (m, 2H), 4.14 (m, 3H), 3.18 (s, 3H), 2.48 (s, 3H) | 1652, 1571, 802, 1114, 2926 |
| AC52 | | 488.29 ([M − H]$^-$) | 7.33 (m, 2H), 7.25 (m, 3H), 6.56 (d, J = 15.6 Hz, 1H), 6.37 (dd, J = 15.6, 8.0 Hz, 1H), 5.61 (d, J = 8.0 Hz, 1H), 4.21 (m, 1H), 4.01 (m, 1H), 4.08 (m, 2H), 3.56 (t, J = 10.0 Hz, 2H), 2.48 (m, 2H), 2.08 (m, 2H), 1.5 (m, 3H) | 1635, 11134, 813, 2927 |
| AC53 | | 532.92 ([M + H]$^+$) | 8.49 (d, J = 2.0 Hz, 1H), 7.69 (d, J = 2.4 Hz, 1H), 7.43 (d, J = 8.0 Hz, 1H), 7.34 (m, 3H), 7.26 (m, 2H), 6.95 (m, 1H), 6.58 (d, J = 16.0 Hz, 1H), 6.38 (dd, J = 16.0, 8.0 Hz, 1H), 4.72 (d, J = 5.2 Hz, 2H), 4.09 (m, 1H), 2.47 (s, 3H) | 1651, 3027, 815, 1113 |
| AC54 | | 529.06 ([M − H]$^-$) | 8.37 (d, J = 5.2 Hz, 1H), 7.41 (d, J = 8.0 Hz, 1H), 7.36 (m, 3H), 7.31 (m, 1H), 7.26 (m, 2H), 6.58 (d, J = 16.0 Hz, 1H), 6.40 (dd, J = 16.0, 7.6 Hz, 1H), 5.20 (t, J = 5.6 Hz, 1H), 4.63 (d, J = 6.0 Hz, 2H), 4.13 (m, 1H), 2.18 (s, 3H) | 1654, 3434, 814, 1112 |
| AC57 | | 464.96 ([M + H]$^+$) | 8.69 (t, J = 6.0 Hz, 1H), 8.58 (t, J = 6.0 Hz, 1H), 7.92 (s, 1H), 7.87 (d, J = 6.4 Hz, 2H), 7.62 (d, J = 8.4 Hz, 1H), 7.45 (d, J = 8.4 Hz, 1H), 7.0 (m, 1H), 6.76 (d, J = 15.6 Hz, 1H), 6.76 (dd, J = 15.6, 8.0 Hz, 1H), 4.01 (m, J = 8.0 Hz, 1H), 3.71 (m, 2H), 3.49 (m, 2H) | 3417, 1658, 1165, 817 |
| AC58 | 124.4-126.9 | 599.76 ([M + H]$^+$) | 7.62 (m, 2H), 7.40 (s, 2H), 7.37 (d, J = 1.6 Hz, 1H), 6.61 (t, J = 4.8 Hz, 1H), 6.55 (d, J = 16.0 Hz, 1H), 6.41 (dd, J = 16.0, 7.6 Hz, 1H), 4.16 | |

TABLE 2-continued

Analytical Data for Compounds in Table 1.

| Compound Number | mp (° C.) | ESIMS | ¹H NMR (δ)ᵃ | IR (cm⁻¹) |
|---|---|---|---|---|
| AC59 | 80-83 | 497.40 ([M − H]⁻) | (d, J = 6.0 Hz, 2H), 4.01 (m, 1H), 1.56 (s, 9H) 8.42 (d, J = 2.1 Hz, 1H), 8.29 (d, J = 7.5 Hz, 1H), 7.51 (m, 2H), 7.39 (m, 1H), 7.36 (m, 4H), 7.28 (m, 1H), 6.61 (d, J = 15.9 Hz, 1H), 6.45 (dd, J = 15.9, 7.8 Hz 1H), 4.14 (t, J = 8.4 Hz, 1H), 2.51 (s, 3H) | |
| AC60 | | 515.09 ([M + H]−) | 8.52 (s, 1H), 8.39 (d, J = 1.8 Hz, 2H), 7.70 (d, J = 2.1 Hz, 1H), 7.62 (s, 1H), 7.43 (s, 1H), 7.35 (m, 3H), 6.62 (d, J = 16.2 Hz, 1H), 6.52 (dd, J = 16.2, 7.5 Hz, 1H), 4.62 (d, J = 6.3 Hz, 2H), 4.19 (m, 1H), 2.76 (s, 3H) | 1668, 1589, 1167, 1113, 802 |
| AC61 | | 461.90 ([M − H]⁻) | 8.07 (t, J = 8.0 Hz, 1H), 7.39 (t, J = 2.0 Hz, 1H), 7.28 (d, J = 1.2 Hz, 3H), 7.17 (d, J = 1.6 Hz, 1H), 7.11 (m, 1H), 6.59 (d, J = 15.6 Hz, 1H), 6.47 (dd, J = 15.6, 7.6 Hz, 1H), 5.49 (m, 1H), 4.14 (t, J = 8.4 Hz, 1H), 3.48 (m, 4H) | 1658, 1114, 801 |
| AC62 | 105-108 | 528.88 ([M − H]⁻) | 8.62 (t, J = 6.4 Hz, 1H), 8.46 (m, 1H), 7.73 (m, 5H), 7.48 (d, J = 7.6 Hz, 1H), 7.03 (dd, J = 15.6, 9.2 Hz, 1H), 6.81 (d, J = 15.6 Hz, 1H), 4.86 (m, 1H), 3.97 (m, 4H) | |
| AC63 | 77-80 | 594.67 ([M + H]⁺) | 8.43 (s, 1H), 7.76 (d, J = 2.4 Hz, 1H), 7.60 (m, 2H), 7.38 (d, J = 7.6 Hz, 1H), 7.33 (d, J = 6.4 Hz, 3H), 6.54 (d, J = 16.0 Hz, 1H), 6.46 (m, 1H), 6.41 (dd, J = 16.0 8.0 Hz, 1H), 4.65 (d, J = 6.0 Hz, 2H), 4.15 (m, 1H) | 3257, 1653 |
| AC64 | 83-85 | 580.72 ([M − H]⁻) | 7.72 (d, J = 8.0 Hz, 1H), 7.44 (s, 1H), 7.40 (s, 2H), 7.36 (d, J = 6.8 Hz, 1H), 7.05 (t, J = 5.2 Hz, 1H), 6.70 (t, J = 5.2 Hz, 1H), 6.57 (d, J = 15.6 Hz, 1H), 6.44 (dd, J = 15.6, 8.0 Hz, 1H), 4.23 (d, J = 5.6 Hz, 2H), 4.15 (m, 1H), 4.01 (m, 2H) | |
| AC65 | | 534.72 ([M − H]⁻) | 8.39 (d, J = 2.0 Hz, 1H), 8.12 (t, J = 8.4 Hz, 1H), 7.71 (d, J = 2.4 Hz, 1H), 7.34 (m, 3H), 7.26 (m, 1H), 7.11 (m, 2H), 6.59 (d, J = 16.0 Hz, 1H), 6.46 (dd, J = 16.0, 8.0 Hz, 1H), 4.66 (d, J = 5.2 Hz, 2H), 4.13 (m, 1H) | 1658, 1113, 817, 2925 |
| AC66 | 73-75 | 624.61 ([M − H]⁻) | 7.88 (s, 1H), 7.63 (d, J = 1.6 Hz, 1H), 7.57 (d, J = 8.0 Hz, 1H), 7.40 (m, 2H), 6.80 (t, J = 5.6 Hz, 1H), 6.70 (t, J = 5.6 Hz, 1H), 6.56 (d, J = 16.0 Hz, 1H), 6.44 (dd, J = 16.0, 8.0 Hz, 1H), 4.22 (m, 2H), 4.12 (m, 1H), 4.01 (m, 2H) | |

TABLE 2-continued

Analytical Data for Compounds in Table 1.

| Compound Number | mp (° C.) | ESIMS | ¹H NMR (δ)$^a$ | IR (cm$^{-1}$) |
|---|---|---|---|---|
| AC67 | | 479.82 ([M − H]$^-$) | 8.07 (t, J = 8.0 Hz, 1H), 7.34 (d, J = 6.0 Hz, 2H), 7.28 (s, 1H), 7.17(s, 2H), 6.59 (d, J = 15.6 Hz, 1H), 6.46 (dd, J = 15.6, 8.0 Hz, 1H), 5.49 (m, 1H), , 4.12 (m, 1H), 3.49 (m, 4H). | 3272, 1644 |
| AC68 | 90-93 | 546.80 ([M − H]$^-$) | 8.6 (t, J = 6.4 Hz, 1H), 8.45 (m, 1H), 7.86 (d, J = 6.4 Hz, 2H), 7.75 (t, J = 8.0 Hz, 1H), 7.63 (d, J = 12.0 Hz, 1H), 7.48 (d, J = 8.0 Hz, 1H), 7.03 (dd, J = 15.6, 9.6 Hz, 1H), 6.80 (d, J = 15.6 Hz, 1H), 4.88 (m, 1H), 3.96 (m, 4H) | 3315, 1684 |
| AC69 | | 542.82 ([M − H]$^-$) | 7.41 (d, J = 8.0 Hz, 1H), 7.34 (d, J = 5.6 Hz, 2H), 7.26 (m, 1H), 7.23 (m, 1H), 6.81 (s, 1H), 6.57 (d, J = 15.6 Hz, 1H), 6.55 (s, 1H), 6.39 (dd, J = 15.6, 8.0 Hz, 1H), 4.18 (m, 2H), 4.13 (m, 1H), 3.97 (m, 2H), 2.46 (s, 3H) | 3294, 1685 |
| AC70 | 176-178 | 545.23 ([M − H]$^-$) | 8.38 (d, J = 2.4 Hz, 1H), 8.22 (d, J = 6.8 Hz, 2H), 7.71 (d, J = 2.4 Hz, 1H), 7.35 (d, J = 6.0 Hz, 2H), 7.30 (d, J = 7.6 Hz, 1H), 7.15 (d, J = 1.6 Hz, 1H), 6.93 (d, J = 1.2 Hz, 1H), 6.60 (d, J = 15.6 Hz, 1H), 6.43 (dd, J = 15.6, 7.6 Hz, 1H), 4.66 (d, J = 6.0 Hz, 2H), 4.13 (m, 1H), 3.98 (s, 3H) | |
| AC71 | | 492.20 ([M − H]$^-$) | 8.24 (d, J = 7.6 Hz, 1H), 8.15 (d, J = 8.4 Hz, 1H), 7.35 (d, J = 6.0 Hz, 2H), 7.13 (d, J = 1.2 Hz, 1H), 6.92 (s, 1H), 6.61 (d, J = 16.0 Hz, 1H), 6.43 (dd, J = 16.0, 7.6 Hz, 1H), 5.48 (m, 1H), 4.13 (m, 1H), 4.03 (s, 3H), 3.48 (m, 4H) | 1639, 3079, 858 |
| AC72 | | 543.05 ([M − H]$^-$) | 8.42 (d, J = 2.4 Hz, 1H), 7.75 (d, J = 2.4 Hz, 1H), 7.34 (m, 4H), 7.20 (m, 2H), 6.60 (d, J = 16.0 Hz, 1H), 6.36 (dd, J = 16.0, 8.0 Hz, 1H), 6.12 (t, J = 5.6 Hz, 1H), 4.62 (d, J = 6.0 Hz, 2H), 4.20 (m, 1H), 2.82 (m, 2H), 1.45 (t, J = 5.6 Hz, 3H) | 1642, 3246, 814, 1113 |
| AC75 | | 644.78 ([M + H]$^+$) | 8.72 (s, 1H), 7.97 (d, J = 7.2 Hz, 1H), 7.70 (d, J = 8.4 Hz, 1H), 7.61 (m, 2H), 7.40 (m, 2H), 6.55 (m, 2H), 6.42 (dd, J = 16.0, 8.0 Hz, 1H), 4.76 (d, J = 6.0 Hz, 2H), 4.12 (m, 1H) | 3431, 1652, 1171, 809 |
| AC76 | | 531.34 ([M + H]$^+$) | 8.87 (t, J = 6.0 Hz, 1H), 8.34 (d, J = 2.1 Hz, 1H), 7.85 (d, J = 6.3 Hz, 3H), 7.48 (m, 4H), 6.57 (d, J = 15.6 Hz, 1H), 6.45 (dd, J = 15.6, 9.0 Hz, 1H), 4.84 (m, 1H), 4.49 | 3120, 1708, 1171 |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| | | | (d, J = 5.7 Hz, 2H), 2.82 (m, 2H), 2.36 (t, J = 5.6 Hz, 3H) | |
| AC77 | | 531.1 ([M + H]$^+$) | 8.87 (t, J = 6.0 Hz, 1H), 8.34 (d, J = 2.1 Hz, 1H), 7.85 (d, J = 6.3 Hz, 3H), 7.48 (m, 4H), 6.57 (d, J = 15.6 Hz, 1H), 6.45 (dd, J = 15.6, 8.0 Hz, 1H), 4.84 (m, 1H), 4.49 (d, J = 5.7 Hz, 2H), 2.36 (s, 3H) | 3444, 1648, 1114, 814 |
| AC78 | | 561.06 ([M + H]$^+$) | 8.59 (t, J = 6.4 Hz, 1H), 8.47 (t, J = 5.6 Hz, 1H), 7.89 (s, 2H), 7.45 (m, 3H), 6.87 (m, 1H), 6.75 (d, J = 15.6 Hz, 1H), 4.85 (t, J = 8.0 Hz 1H), 3.98 (m, 4H), 2.58 (s, 3H) | 3432, 1631, 1161, 840 |
| AC79 | | 610.97 ([M + H]$^+$) | 8.69 (t, J = 6.0 Hz, 1H), 8.58 (t, J = 6.0 Hz, 1H), 7.92 (s, 1H), 7.87 (d, J = 6.4 Hz, 2H), 7.62 (d, J = 8.4 Hz, 1H), 7.45 (d, J = 8.4 Hz, 1H), 7.0 (m, 1H), 6.76 (d, J = 15.6 Hz, 1H) 4.83 (t, J = 8.0 Hz, 1H), 3.98 (m, 4H) | 3303, 1658, 1166, 817 |
| AC80 | | 561.06 ([M + H]$^+$) | 7.37 (m, 3H), 7.26 (m, 1H), 7.24 (m, 1H), 6.59 (d, J = 15.6 Hz, 1H), 6.39 (dd, J = 15.6, 8.0 Hz, 1H), 4.24 (m, 4H), 3.90 (m, 1H), 2.83 (m, 2H), 1.26 (m, 3H) | 3412, 1624, 1157, 825 |
| AC81 | 9-92 | 546.93 ([M − H]$^-$) | 8.73 (d, J = 5.6 Hz, 1H), 8.45 (t, J = 6.0 Hz, 1H), 7.76 (s, 3H), 7.45 (m, 3H), 6.86 (dd, J = 16.0, 9.2 Hz, 1H), 4.83 (m, 1H), 4.56 (m, 2H), 4.51 (m, 1H), 4.10 (m, 2H), 3.85 (d, J = 6.0 Hz, 2H), 2.50 (m, 3H) | |
| AC82 | | 477.69 ([M + H]$^+$) | 7.38 (d, J = 1.8 Hz, 2H), 7.33 (s, 1H), 7.27 (s, 3H), 6.58 (d, J = 16.0 Hz, 1H), 6.42 (d, J = 8.1 Hz, 1H), 6.36 (dd, J = 16.0, 7.8 Hz, 1H), 4.71 (m, 1H), 4.23 (m, 3H), 3.26 (m, 2H), 2.45 (s, 3H) | 1646, 1353, 1196, 1112, 800 |
| AC83 | | 493.83 ([M − H]$^-$) | 8.07 (t, J = 8.4 Hz, 1H), 7.39 (t, J = 1.6 Hz, 1H), 7.31 (d, J = 1.2 Hz, 1H), 7.26 (m, 2H), 7.23 (m, 1H), 7.19 (d, J = 1.6 Hz, 1H), 6.60 (d, J = 16.8 Hz, 1H), 6.49 (dd, J = 16.8, 7.6 Hz, 1H), 4.90 (m, 1H), 4.64 (m, 2H), 4.14 (m, 2H), 4.10 (m, 1H) | 1527, 1113, 801, 1167, 1321 |
| AC84 | | 511.75 ([M − H]$^-$) | 8.07 (t, J = 8.0 Hz, 1H), 7.34 (m, 3H), 7.19 (d, J = 13.2 Hz, 1H), 6.60 (d, J = 16.4 Hz, 1H), 6.48 (dd, J = 16.4, 8.0 Hz, 1H), 4.88 (m, 1H), 4.62 (m, 2H), 4.12 (m, 3H) | 1645, 1113, 804, 3030, 1245 |
| AC85 | | 523.83 ([M − H]$^-$) | 8.60 (d, J = 6.8 Hz, 1H), 8.15 (d, J = 8.4 Hz, 1H), 7.35 (d, J = 6.0 Hz, 1H), 7.15 (d, J = 7.2 Hz, 1H), 6.94 (s, 1H), 6.60 (d, J = | 1652, 3039, 802, 1114 |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| | | | 15.6 Hz, 1H), 6.44 (dd, J = 7.6, 7.6 Hz, 1H), 4.93 (m, 1H), 4.62 (m, 2H), 4.13 (m, 6H) | |
| AC86 | | 524.36 ([M + H]$^+$) | 7.35 (d, J = 6.3 Hz, 3H), 7.26 (m, 2H), 7.20 (m, 1H), 6.60 (d, J = 15.9 Hz, 1H), 6.47 (dd, J = 15.9, 6.6 Hz, 1H), 4.86 (m, 1H), 4.65 (m, 2H), 4.13 (m, 3H), 2.84 (q, 2.8 Hz, 2H), 1.26 (m, 3H) | 3333, 1651, 815 |
| AC87 | | 495.82 ([M − H]$^-$) | 8.07 (t, J = 8.0 Hz, 1H), 7.52 (m, 3H), 7.19 (d, J = 13.2 Hz, 1H), 6.59 (d, J = 16.4 Hz, 1H), 6.47 (dd, J = 16.4, 8.0 Hz, 1H), 4.69 (m, 1H), 4.23 (m, 3H), 3.29 (m, 2H) | 1623, 1114, 816 |
| AC89 | | 509.89 ([M + H]$^+$) | 7.43 (m, 2H), 7.27 (m, 2H), 7.23 (m, 2H), 6.58 (d, J = 16.0 Hz, 1H), 6.41 (dd, J = 16.0, 7.6 Hz, 1H), 4.79 (d, J = 5.6 Hz, 2H), 4.14 (m, 1H), 2.48 (s, 3H), 2.18 (m, 1H), 1.16 (m, 4H) | 1666, 1166, 1112, 800 |
| AC90 | | 656.9 ([M − H]$^-$) | 8.34 (m, 1H), 8.27 (m, 1H), 7.60 (d, J = 1.6 Hz, 1H), 7.49 (d, J = 8.0 Hz, 2H), 7.40 (s, 2H), 7.36 (dd, J = 8.2, 1.7 Hz, 1H), 6.53 (d, J = 16.0 Hz, 1H), 6.38 (dd, J = 15.9, 7.9 Hz, 1H), 4.89 (d, J = 8.4 Hz, 2H), 4.48 (d, J = 9.0 Hz, 2H), 4.11 (m, 1H) | |
| AC91 | | 640.9 ([M − H]$^-$) | 8.18 (t, J = 5.0 Hz, 1H), 7.58 (d, J = 1.6 Hz, 1H), 7.47 (d, J = 8.0 Hz, 1H), 7.40 (s, 2H), 7.34 (dd, J = 8.1, 1.6 Hz, 1H), 6.52 (m, 2H), 6.37 (dd, J = 15.9, 7.9 Hz, 1H), 4.54 (d, J = 4.9 Hz, 2H), 4.12 (m, 1H), 3.99 (qd, J = 8.9, 6.5 Hz, 2H) | |
| AC92 | | 640.9 ([M − H]$^-$) | 9.16 (d, J = 6.1 Hz, 1H), 7.65 (d, J = 1.6 Hz, 1H), 7.57 (d, J = 8.0 Hz, 1H), 7.41 (m, 3H), 7.21 (t, J = 5.6 Hz, 1H), 6.55 (d, J = 15.9 Hz, 1H), 6.41 (dd, J = 15.9, 7.8 Hz, 1H), 4.59 (d, J = 5.6 Hz, 2H), 4.45 (qd, J = 9.0, 6.0 Hz, 2H), 4.12 (q, J = 7.2 Hz, 1H) | |
| AC93 | | 485.5 ([M + H]$^+$) | 7.52-7.41 (d, J = 8.2 Hz, 1H), 7.39-7.34 (m, 1H), 7.24-7.17 (d, J = 1.8 Hz, 2H), 7.02-6.92 (m, 2H), 6.90-6.83 (d, J = 11.4 Hz, 1H), 6.71 (br s, 1H), 6.17 (br s, 1H), 6.12-6.01 (dd, J = 11.4, 10.3 Hz, 1H), 4.44-4.38 (d, J = 4.2 Hz, 1H), 4.35-4.27 (m, 1H), 4.10-3.99 (d, J = 5.1 Hz, 2H), 2.78-2.67 (m, 1H), 2.44 (s, 3H), 0.88-0.78 (m, 2H), 0.60-0.45 (m, 2H) | $^1$C NMR (δ)$^3$ 169.91, 169.84, 138.23, 137.41, 136.84, 134.79, 134.69, 131.07, 128.69, 127.49, 127.43, 126.72, 126.61 (q, J = 212.10 Hz), 125.61, 123.76, 47.89 (q, J = 28.28 Hz), 43.46, 22.65, 19.97, 8.21 |

TABLE 2-continued

Analytical Data for Compounds in Table 1.

| Compound Number | mp (° C.) | ESIMS | ¹H NMR (δ)ᵃ | IR (cm⁻¹) |
|---|---|---|---|---|
| AC94 | | 511.6 ([M]−) | 8.36-8.24 (d, J = 2.4 Hz, 1H), 7.75-7.64 (m, 1H), 7.38-7.24 (m, 3H), 7.24-7.09 (d, J = 1.8 Hz, 2H), 6.99-6.90 (m, 2H), 6.89-6.74 (d, J = 11.4 Hz, 1H), 6.63-6.43 (m, 1H), 6.14-5.98 (m, 1H), 4.69-4.51 (d, J = 6.1 Hz, 2H), 4.37-4.20 (m, 1H), 2.46-2.31 (s, 3H) | 3262, 1607, 1247, 1164, 1111 |
| AC95 | 48-61 | 626.9 ([M + H]⁺) | 7.58 (d, J = 7.9 Hz, 1H), 7.44-7.29 (m, 3H), 7.14 (dd, J = 7.9, 1.6 Hz, 1H), 6.86 (d, J = 11.4 Hz, 1H), 6.76 (t, J = 5.9 Hz, 1H), 6.59 (br s, 1H), 6.21-6.04 (m, 1H), 4.23 (d, J = 5.5 Hz, 1H), 3.98 (qd, J = 9.0, 6.5 Hz, 2H) | |
| AC96 | | 619.6 ([M + H]⁺) | 8.83 (s, 1H), 8.06 (br, 1H), 7.90 (s, 2H), 7.63 (d, J = 8.1 Hz, 2H), 7.53 (m, 1H), 6.94 (m, 1H), 6.77 (d, J = 15.3 Hz, 1H), 6.63 (d, J = 9.3 Hz, 1H), 4.84 (m, 1H), 4.30 (d, J = 5.6 Hz, 2H), 2.99 (s, 6H) | 1616, 1114 |
| AC97 | | 606.6 ([M + H]⁺) | 8.20 (d, J = 2.1 Hz, 1H), 7.73 (d, J = 2.7 Hz, 1H), 7.60 (m, 2H), 7.39 (s, 2H), 7.29 (m, 1H), 6.79 (d, J = 8.4 Hz, 1H), 6.55 (d, J = 15.9 Hz, 1H), 6.40 (m, 2H), 4.60 (d, J = 2.7 Hz, 2H), 4.13 (m, 1H), 3.95 (s, 3H) | 1644, 1113 |
| AC98 | | 577.87 ([M + H]⁺) | 9.04 (t, J = 6.0 Hz, 1H), 8.60 (t, J = 6.6 Hz, 1H), 8.25 (s, 1H), 7.97 (d, J = 8.1 Hz, 1H), 7.87 (d, J = 6.3 Hz, 2H), 7.69 (d, J = 7.5 Hz, 1H), 7.15 (dd, J = 15.9, 9.3 Hz, 1H), 6.89 (d, J = 15.9 Hz, 1H), 4.86 (m, 1H), 3.98 (m, 4H). | 1663, 1168 |
| AC99 | | 574.81 ([M + H]⁺) | 8.69 (t, J = 6.0 Hz, 1H), 8.58 (t, J = 6.6 Hz, 1H), 7.91 (s, 1H), 7.85 (m, 1H), 7.61 (m, 2H), 7.52 (m, 2H), 6.98 (dd, J = 15.3, 9.0 Hz, 1H), 6.76 (d, J = 15.3 Hz, 1H), 4.81 (m, 1H), 4.01 (m, 4H) | 1650, 1164 |
| AC100 | | 673.80 ([M + H]⁺) | 8.29 (s, 1H), 8.22 (d, J = 8.1 Hz, 1H), 7.93 (d, J = 7.8 Hz, 1H), 7.72 (m, 1H), 7.65 (m, 2H), 7.40 (s, 2H), 7.18 (br, 1H), 6.59 (d, J = 16.0 Hz, 1H), 6.43 (dd, J = 16.0, 7.6 Hz, 1H), 5.02 (d, J = 1.2 Hz, 2H), 4.12 (m, 1H) | 3403, 1659 |
| AC101 | | 636.83 ([M + H]⁺) | 7.56 (d, J = 9.0 Hz, 1H), 7.39 (d, J = 6.0 Hz, 2H), 7.26 (m, 2H), 6.54 (d, J = 15.9 Hz, 1H), 6.37 (dd, J = 8.0, 15.9 Hz, | 1637, 1113 |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| | | | 1H), 4.01 (m, 1H), 3.84 (m, 2H), 3.33 (m, 2H), 3.04 (m, 2H), 2.84 (m, 3H), 2.62 (m, 1H) | |
| AC102 | | 592.84 ([M + H]$^+$) | 7.60 (m, 2H), 7.32 (m, 1H), 7.03 (d, J = 7.2 Hz, 2H), 6.74 (br, 1H), 6.62 (br, 1H), 6.56 (d, J = 16.2 Hz, 1H), 6.41 (dd, J = 16.2, 7.8 Hz, 1H), 4.22 (d, J = 5.4 Hz, 2H), 4.14 (m, 1H), 4.01 (m, 2H) | 1668, 1167 |
| AC103 | 99.2-105.0 | 612.7 ([M + H]$^+$) | 8.40 (d, J = 8.0 Hz, 1H), 7.92 (d, J = 5.2 Hz, 1H), 7.59 (d, J = 8.0 Hz, 1H), 7.35 (d, J = 8.0 Hz, 1H), 6.99 (dd, J = 16.0, 7.6 Hz, 1H), 6.76 (d, J = 16.0 Hz, 1H), 4.84 (m, 1H), 4.23 (d, J = 13.2 Hz, 1H), 3.97 (m, 1H), 3.79 (d, J = 13.6 Hz, 1H), 3.16 (t, J = 11.2 Hz, 1H), 2.77 (t, J = 11.2 Hz, 1H), 1.99 (s, 3H), 1.88 (m, 2H), 1.45 (m, 2H) | 1634, 1113, 809 |
| AC104 | | 680.97 ([M + H]$^+$) | 7.60 (m, 2H), 7.40 (m 3H), 6.55 (d, J = 15.6 Hz, 1H), 6.41 (dd, J = 15.6, 7.8 Hz, 1H), 4.24 (m, 1H), 3.34 (m, 2H), 2.90 (m, 1H), 2.24 (m, 2H), 1.52(m, 2H), 1.34 (m, 4H) | 3437, 1644, 1113, 807, 511 |
| AC105 | | 609.9 ([M + H]$^+$) | 7.59 (s, 1H), 7.55 (m, 1H), 7.50 (m, 1H), 7.40 (m, 2H), 6.54(d, J = 16.0 Hz, 1H), 6.50 (J = 16.0, 8.0 Hz, 1H), 4.14 (m, 2H), 3.08 (m, 4H), 2.67 (m, 2H), 2.12 (m, 2H), 1.70 (m, 2H). | 3303, 1649, 1115, 2242, 809, 506 |
| AC106 | | 584.95 ([M + H]$^+$) | 7.59 (s, 1H), 7.51 (d, J = 8.4 Hz, 1H), 7.40 (s, 2H), 7.36 (d, J = 6.8 Hz, 1H), 6.54 (d, J = 16.0 Hz, 1H), 6.40 (dd, J = 16.0, 8.0 Hz, 1H), 6.03 (d, J = 8.0 Hz, 1H), 4.11 (m, 2H), 3.10 (m, 2H), 2.50 (m, 2H ), 2.50 (s, 3H) (m, 2H), 1.94 (m, 2H) | 3417, 1648, 1112, 805, 555 |
| AC107 | | 609.9 ([M + H]$^+$) | 8.41 (d, J = 7.8 Hz, 1H), 7.90 (s, 2H), 7.62 (m, 2H), 7.51(m, 1H), 6.92 (dd, J = 15.9, 9.0 Hz, 1H), 6.77 (d, J = 15.9 Hz, 1H), 4.81 (m, 1H), 3.73 (s, 2H), 3.31 (m, 1H), 3.28 (m, 1H), 2.82 (t, J = 11.4 Hz, 2H), 2.82 (m, 2H), 2.30 (m, 2H), 1.88 (m, 2H), 1.57 (m, 2H) | 3303, 1645, 1115, 2243, 810, 507 |
| AC108 | | 626.9 ([M + H]$^+$) | 7.60 (m, 2H) 7.39 (s, 2H), 7.28 (m, 1H), 6.56 (d, J = 15.6 Hz, 1H), 6.40 (dd, J = 15.6, 7.8 Hz, 1H), 5.91 (m, 1H), 4.65 (m, 2H), 4.10 (m, 1H), 4.07 (m, 2H), 3.59 (m, 1H), 2.74 (m, 2H), 2.13 (m, 4H), 2.07 (m, 1H) | 3420, 1649, 1113, 809, 554 |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| AC109 | | 614.6 ([M + H]$^+$) | 7.56 (m, 2H), 7.39 (s, 2H), 7.29 (s, 1H), 6.50 (d, J = 15.9 Hz, 1H), 6.41 (dd, J = 15.9, 8.0 Hz 1H), 4.09 (m, 1H), 3.88 (m, 2H), 3.49 (m, 2H), 2.92 (m, 2H), 2.81 (m, 1H), 2.74 (m, 2H), 2.25 (m, 4H) | 1647, 1113 |
| AC110 | | 572.6 ([M + H]$^+$) | 11.20 (s, 1H), 8.66 (br, 1H), 7.92 (m, 3H), 7.62 (d, J = 8.0 Hz, 1H), 7.45 (d, J = 8.0 Hz, 1H), 6.77 (dd, J = 15.6, 9.2 Hz, 1H), 6.77 (d, J = 15.6 Hz, 1H), 4.85 (m, 1H), 3.74 (d, J = 5.2 Hz, 2H), 3.61 (s, 3H) | 3412, 1690, 1114, 846, 559 |
| AC111 | | 582.79 ([M + H]$^+$) | 8.63 (t, J = 6.0 Hz, 1H), 8.04 (t, J = 6.0 Hz, 1H), 7.92 (m, 3H), 7.62 (d, J = 1.2 Hz, 1H), 7.47 (d, J = 7.6 Hz, 1H), 7.00 (dd, J = 15.6, 8.8 Hz, 1H), 6.77 (d, J = 15.6 Hz, 1H), 5.19 (d, J = 1.6 Hz, 1H), 5.01 (d, J = 1.2 Hz, 1H), 4.85 (m, 1H), 3.86 (d, J = 5.6 Hz, 2H), 3.75 (t, J = 5.6 Hz, 2H) | 3419, 1659, 843, 557 |
| AC112 | | 582.79 ([M + H]$^+$) | 8.84 (br, 1H), 8.58 (m, 1H), 8.30 (m, 1H), 7.91 (s, 2H), 7.61 (d, J = 8.1 Hz, 1H), 7.42 (d, J = 7.8 Hz, 1H), 7.00 (dd, J = 15.6, 9.3 Hz, 1H), 6.77 (d, J = 15.6 Hz, 1H), 4.85 (m, 1H), 4.11 (d, J = 5.6 Hz, 1H), 3.73 (d, J = 5.6 Hz, 1H), 3.04 (s, 6H) | 3399, 1662, 1114, 807, 582 |
| AC113 | | 626.88 ([M + H]$^+$) | 8.48 (t, J = 5.2 Hz, 1H), 8.3 (s, 1H), 7.90 (s, 2H), 7.79 (dd, J = 2.0, 2.0 Hz 2H), 7.58 (d, J = 8.4 Hz, 1H) 7.46 (d, J = 7.6 Hz, 1H) 7.26 (d, J = 7.6 Hz, 1H), 6.98 (m, 1H), 6.75 (d, J = 15.6 Hz, 1H), 4.85 (m, 1H), 3.49 (d, J = 6.4 Hz, 2H) 2.87 (t, J = 6.4 Hz, 2H) | 3431, 1651, 1113, 808, 554 |
| AC114 | 113.7-117.5 | 570.7 ([M + H]$^+$) | 8.77 (s, 1H), 8.58 (d, J = 7.2 Hz, 2H), 7.93 (d, J = 7.2 Hz, 2H), 7.60 (dd, J = 1.2, 0.8 Hz, 1H), 7.37 (d, J = 7.6 Hz, 1H), 6.99 (m, 1H), 6.77 (d, J = 16 Hz, 1H), 4.85 (m, 1H), 4.10 (m, 1H) 3.29 (m, 2H), 3.05 (m, 2H), 2.0 (m, 2H), 1.76 (m, 2H) | |
| AC115 | | 529.00 ([M + H]$^+$) | 8.43 (s, 1H), 7.79 (d, J = 8.0 Hz, 1H), 7.51 (m, 1H), 7.36 (d, J = 8.4 Hz, 3H), 7.21 (m, 3H), 6.55 (d, J = 15.6 Hz, 1H), 6.36 (dd, J = 15.6, 8.0 Hz, 1H), 5.04 (d, J = 5.6 Hz, 2H), 4.10 (m, 1H), 2.35 (s, 3H) | 1589, 3459, 801, 1110 |
| AC116 | | 614.87 ([M + H]$^+$) | 7.99 (d, J = 8.4 Hz, 1H), 7.46 (d, J = 1.6 Hz, 1H), 7.34 (d, J = 6.4 Hz, 2H), 7.28 (m, 2H), 6.62 (m, 2H), 6.47 (dd, J = 16.0, | 3424, 1657, 1165 |

TABLE 2-continued

Analytical Data for Compounds in Table 1.

| Compound Number | mp (° C.) | ESIMS | ¹H NMR (δ)$^a$ | IR (cm$^{-1}$) |
|---|---|---|---|---|
| | | | 7.2 Hz, 1H), 4.23 (m, 2H), 4.12 (m, 1H), 4.00 (m, 2H) | |
| AC117 | | 525.42 ([M − H]$^-$) | 8.39 (br, 1H), 7.85 (br, 1H), 7.62 (m, 3H), 7.53 (d, J = 8.0 Hz, 1H), 7.46 (s, 1H), 7.40 (d, J = 8.0 Hz, 1H), 7.17 (m, 1H), 6.78 (dd, J = 16.0, 8.8 Hz, 1H), 6.70 (m, 1H), 4.77 (m, 1H), 4.66 (s, 1H), 4.32 (s, 1H), 2.97 (s, 3H), 2.16 (s, 3H) | 3401, 1636, 1113, 750 |
| AC118 | | 471.79 ([M + H]$^+$) | 7.36 (d, J = 8.0 Hz, 2H), 7.27 (m, 2H), 7.22 (m, 2H), 6.57 (d, J = 16.0 Hz, 1H), 6.38 (dd, J = 16.0, 8.0 Hz, 1H), 6.10 (br, 1H), 4.15 (m, 2H), 3.89 (m, 1H), 3.80 (m, 2H), 3.35 (m, 1H), 2.46 (s, 3H), 2.06 (s, 1H), 1.96 (m, 2H), 1.65 (m, 1H) | 3437, 1655, 1262, 1105, 802 |
| BC1 | | 492.17 ([M + H]$^+$) | 7.39 (s, 2H), 7.25-7.18 (m, 3H), 6.58 (d, J = 16.0 Hz, 1H), 6.30 (dd, J = 16.0, 8.4 Hz, 1H), 5.91-5.70 (br, 2H), 4.05 (m, 1H), 3.05-2.80 (m, 6H), 2.70 (m, 1H), 1.81 (m, 1H) | 3211, 1569, 1113, 806 |
| BC2 | | 506.4 ([M + H]$^+$) | 8.80 (s, 1H), 8.20 (s, 1H), 7.82 (m, 3H), 7.4 (s, 2H), 6.62 (d, J = 16.0 Hz, 1H), 6.52 (dd, J = 16.0, 8.0 Hz, 1H), 4.18(m, 1H), 3.38 (m, 2H), 2.98 (m, 2H), 2.71 (m, 1H), 2.04 (m, 2H), 1.54 (s, 3H). | 2923, 1542, 1033, 805 |
| BC3 | | 518.04 ([M − H]$^-$) | 7.40 (s, 2H), 7.33-7.22 (m, 3H), 6.61 (d, J = 16.0 Hz, 1H), 6.34-6.28 (dd, J = 16.0, 8.0 Hz, 1H), 5.96-5.80 (m, 3H), 5.22 (m, 4H), 4.01 (m, 2H), 2.84-2.99 (m, 2H), 2.71 (m, 1H), 1.86 (m, 1H) | 3120, 1592, 1146, 895 |
| BC4 | | 529.02 ([M + H]$^+$) | 7.39 (s, 2H), 7.25-7.20 (m, 3H), 6.34 (d, J = 16.0 Hz, 1H), 6.30 (dd, J = 16.0, 8.0 Hz, 1H), 5.81 (br, 1H), 5.48 (m, 1H), 4.10 (m, 1H), 3.10 (m, 2H), 2.86-3.07 (m, 2H), 2.86 (m, 1H), 1.81 (m, 1H); | 3283, 1652, 1241, 811 |
| BC5 | | 544.25 ([M − H]$^-$) | 7.40 (s, 2H), 7.21 (s, 1H), 7.12 (m, 1H), 6.56 (d, J = 16.0 Hz, 1H), 6.32 (dd, J = 16.0, 8.4 Hz, 1H), 5.85 (br s, 1H), 5.23 (br s, 1H), 4.12 (m, 1H), 3.18 (m, 3H), 2.80 (m, 3H), 2.08 (m, 2H), 1.83 (m, 5H), 1.25 (m, 2H), 1.01 (m, 3H), 0.78 (m, 2H) | 3489, 3291, 1655, 1112, 808 |
| BC6 | | 485.96 ([M − H]$^-$) | 7.40 (s, 2H), 7.31-7.18 (m, 3H), 6.58 (d, J = 16.0 Hz, 1H), 6.24-6.28 (dd, J = 16.0, 8.0 Hz, 1H), 5.40 (br, 1H), 4.01 (m, 2H), 2.78- | 3429, 1114, 804 |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| BC7 | | 500.01 ([M − H]$^-$) | 3.01 (m, 2H), 2.51 (s, 1H), 1.86 (m, 1H), 1.20 (m, 2H), 1.01 (m, 2H), 0.78 (m, 2H) 7.40 (s, 2H), 7.31 (s, 1H), 7.18 (m, 1H), 7.18 (s, 1H), 6.58 (d, J = 16.0 Hz, 1H), 6.32 (dd, J = 16.0, 8.0 Hz, 1H), 5.78 (br s, 1H), 5.21 (br s, 1H), 4.01 (m, 1H), 2.78 (m, 2H), 2.01 (m, 1H), 1.86 (m, 4H), 1.25 (m, 2H), 1.01 (m, 3H), 0.78 (m, 2H) | 3296, 1115, 806 |
| BC8 | | 511.88 ([M − H]$^-$) | 7.38-7.20 (m, 5H), 6.62 (d, J = 16.0 Hz, 1H), 6.34 (dd, J = 16.0, 8.0 Hz, 1H), 5.83 (br, 1H), 5.52 (m, 1H), 4.12 (m, 1H), 3.12 (m, 2H), 3.06-2.82 (m, 2H), 2.75 (m, 1H), 1.85 (m, 1H) | 1657, 1113, 855 |
| BC9 | 179-181 | 556.83 ([M − H]$^-$) | 8.30 (s, 1H), 7.68 (d, J = 6.4 Hz, 1H), 7.38-7.20 (m, 5H), 6.60 (d, J = 16.0 Hz, 1H), 6.34 (dd, J = 16.0, 8.0 Hz, 1H), 5.63 (br, 1H), 5.52 (m, 1H), 4.12 (m, 1H), 3.56 (s, 2H), 3.06-2.82 (m, 2H), 2.70 (m, 1H), 1.82 (m, 1H) | |
| BC10 | | 497.98 ([M − H]$^-$) | 7.38-7.20 (m, 5H), 6.62 (d, J = 16.0 Hz, 1H), 6.34 (dd, J = 16.0, 8.0 Hz, 1H), 5.83 (br, 1H), 5.52 (m, 1H), 4.12 (m, 1H), 3.02 (m, 3H), 2.82 (m, 1H), 2.50 (m, 3H), 1.82 (m, 1H), 1.42 (m, 1H) | 3027, 1654, 815 |
| BC11 | | 530.09 ([M − H]$^-$) | 7.80 (m, 1H), 7.48 (m, 2H), 7.32 6.65 (d, J = 16.0 Hz, 1H), 6.54 (dd, J = 16.0, 8.0 Hz, 1H), 5.38 (m, 1H), 4.18 (m, 1H), 3.62 (m, 1H), 3.32 (m, 1H), 2.86 (m, 1H), 1.81 (m, 1H) | 1715, 1113, 816 |
| BC12 | | 514.86 ([M + H]$^+$) | 7.32, (d, J = 6.0 Hz, 2H) 7.28 (m, 1H), 7.20 (d, J = 8.0, 1H), 7.14 (d, J = 8.8, 1H), 6.70 (d, J = 8.0 Hz, 1H), 6.60 (m, 2H), 4.15 (m, 1H), 3.85 (m, 1H), 3.65 (m, 1H), 3.46 (m, 2H), 3.19 (m, 2H); | 3428, 1112, 857 |
| BC13 | 121-126 | 553.06 ([M − H]$^-$) | 8.33 (br, 1H), 7.59 (s, 1H), 7.45 (m, 3H), 6.72 (d, J = 3.6, 1H), 6.39 (m, 1H), 4.71 (t, J = 7.2 Hz, 2H), 4.15 (m, 2H) | |
| BC14 | 172-175 | 554.0 ([M − H]$^-$) | 8.83 (t, J = 6.6 Hz, 1H), 8.42 (t, J = 14.7 Hz, 1H), 8.22 (d, J = 8.1 Hz, 1H), 8.13 (t, J = 6.3 Hz, 1H), 7.98-7.86 (m, 2H), 7.16-7.07 (m, 1H), 7.01-6.93 (m, 1H), 4.96-4.81 (m, 3H), 4.00-3.88 (m, 2H) | |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| CC1 | 107-109 | 402.00 ([M + H]$^+$) | 7.37 (m, 3H), 7.28 (m, 4H), 6.60 (d, J = 16.0 Hz, 1H), 6.36 (dd, J = 16.0, 8.0 Hz, 1H), 5.75 (br s, 1H), 4.46 (d, J = 6 Hz, 2H), 4.01 (m, 1H), 2.11 (s, 3H) | |
| CC2 | 118-120 | 428.11 ([M + H]$^+$) | 7.37 (m, 3H), 7.28 (m, 4H), 6.60 (d, J = 16.0 Hz, 1H), 6.35 (dd, J = 16.0, 8.0 Hz, 1H), 5.83 (br s, 1H), 4.46 (d, J = 6.0 Hz, 2H), 4.11 (m, 1H), 1.40 (m, 1H), 1.02 (m, 2H), 0.77 (m, 2H) | |
| CC3 | 119-122 | 468.20 ([M − H]$^-$) | 7.38 (m, 3H), 7.27 (m, 3H), 6.60 (d, J = 16.0 Hz, 1H), 6.36 (dd, J = 16.0, 8.4 Hz, 1H), 5.00 (br s, 1H), 4.48 (d, J = 5.6 Hz, 2H), 4.11 (m, 1H), 3.15 (q, J = 10.4 Hz, 2H) | |
| CC4 | | 414.16 ([M − H]$^-$) | 7.37 (m, 3H), 7.28 (m, 3H), 6.60 (d, J = 16.0 Hz, 1H), 6.35 (dd, J = 16.0, 8.0 Hz, 1H), 5.69 (br s, 1H), 4.46 (d, J = 6.0 Hz, 2H), 4.21 (m, 1H), 2.29 (q, J = 5.8 Hz, 2H), 1.30 (t, J = 7.2 Hz, 3H) | |
| CC5 | | 460.28 ([M − H]$^-$) | 7.40 (m, 3H), 7.28 (m, 2H), 6.60 (d, J = 15.6 Hz, 1H), 6.33 (dd, J = 15.6, 8.0 Hz, 1H), 5.84 (br s, 1H), 4.46 (d, J = 5.6 Hz, 2H), 4.10 (m, 1H), 1.36 (m, 1H), 1.02 (m, 2H), 0.77 (m, 2H) | |
| CC6 | 106-108 | 504.08 ([M − H]$^-$) | 7.40 (m, 3H), 7.26 (m, 1H), 6.60 (d, J = 16.0 Hz, 1H), 6.34 (dd, J = 16.0, 8.0 Hz, 1H), 5.96 (br s, 1H), 4.49 (d, J = 5.6 Hz, 2H), 4.10 (m, 1H), 3.15 (q, J = 10.8 Hz, 2H) | |
| CC7 | 127-128 | 436.03 ([M + H]$^+$) | 7.42 (m, 4H), 7.24 (m, 2H), 6.53 (d, J = 16.0 Hz, 1H), 6.36 (dd, J = 16.0, 8.0 Hz, 1H), 5.86 (br s, 1H), 4.51 (d, J = 6.0 Hz, 2H), 4.05 (m, 1H), 2.02 (s, 3H) | |
| CC8 | 129-131 | 462.15 ([M + H]$^+$) | 8.58 (t, J = 5.6 Hz, 1H), 7.72 (m, 1H), 7.66 (m, 3H), 7.49 (d, J = 8.0 Hz, 1H), 7.30 (d, J = 8.0 Hz, 1H), 6.90 (dd, J = 16.0, 8.0 Hz, 1H), 6.73 (d, J = 16 Hz, 1H), 4.81 (m, 1H), 4.33 (d, J = 6.0 Hz, 1H), 1.64 (m, 1H), 0.68 (m, 4H) | |
| CC9 | 132-134 | 504.25 ([M + H]$^+$) | 7.41 (m, 3H), 7.26 (m, 3H), 6.54 (d, J = 16.0 Hz, 1H), 6.37 (dd, J = 16.0, 8.0 Hz, 1H), 6.13 (br s, 1H), 4.56 (d, J = 6.0 Hz, 2H), 4.11 (m, 1H), 3.13 (m, 2H) | |

TABLE 2-continued

Analytical Data for Compounds in Table 1.

| Compound Number | mp (° C.) | ESIMS | ¹H NMR (δ)$^a$ | IR (cm$^{-1}$) |
|---|---|---|---|---|
| CC10 | | 538.03 ([M + 2H]$^+$) | 7.38 (m, 4H), 6.56 (d, J = 16.0 Hz, 1H), 6.38 (dd, J = 16.0, 8.0 Hz, 1H), 6.18 (m, 1H), 4.58 (m, 2H), 4.08 (m, 1H), 3.08 (m, 2H) | 1651, 1112, 807 |
| CC11 | 111-112 | 494.12 ([M − H]$^-$) | 7.42 (m, 3H), 7.24 (m, 1H), 6.54 (d, J = 15.6 Hz, 1H), 6.34 (dd, J = 16.0, 8.0 Hz, 1H), 6.03 (m, 1H), 4.53 (d, J = 6.0 Hz, 1H), 4.10 (m, 1H), 1.39 (m, 1H), 1.00 (m, 2H), 0.77 (m, 2H) | |
| CC12 | 76-78 | 510.07 ([M − H]$^-$) | 7.39 (s, 4H), 7.34 (d, J = 8.0 Hz, 1H), 7.26 (m, 1H), 6.57 (d, J = 16.0 Hz, 1H), 6.35 (dd, J = 16.0, 8.0 Hz, 1H), 6.10 (br s, 1H), 4.49 (d, J = 6.0 Hz, 2H), 4.10 (m, 1H), 1.20 (s, 9H) | |
| CC13 | 73-76 | 563.37 ([M − H]$^-$) | 8.51 (d, J = 5.2 Hz, 1H), 7.63 (s, 1H), 7.51 (m, 1H), 7.45 (m, 2H), 7.39 (s, 2H), 7.28 (m, 1H), 6.58 (m, 2H), 6.37 (dd, J = 16.0, 8.0 Hz, 1H), 4.71 (d, J = 6.0 Hz, 1H), 4.11 (m, 1H) | |
| CC14 | | 581.45 ([M+1H]$^+$) | 8.51 (m, 1H), 8.30 (d, J = 2.4 Hz, 1H), 7.73 (m, 1H), 7.61 (s, 2H), 7.51 (s, 1H), 7.32 (m, 3H), 6.66 (d, J = 16.0 Hz, 1H), 6.56 (dd, J = 16.0, 8.4 Hz, 1H), 4.50 (m, 1H), 4.45 (d, J = 5.6 Hz, 1H), 3.56 (s, 2H) | 3430, 1656, 1109, 806 |
| CC15 | | 480.24 ([M + H]$^+$) | 7.40 (m, 3H), 7.33 (m, 1H), 7.22 (m, 2H), 6.54 (d, J = 15.6 Hz, 1H), 6.34 (dd, J = 16.0, 8.0 Hz, 1H), 6.03 (br s, 1H), 4.53 (d, J = 6.0 Hz, 2H), 4.13 (m, 1H), 1.41 (m, 1H), 1.00 (m, 2H), 0.77 (m, 2H) | 3293, 1651, 1543, 1114, 812 |
| CC16 | | 520.33 ([M − H]$^-$) | 7.42 (s, 1H), 7.37 (m, 3H), 7.22 (m, 1H), 6.54 (d, J = 16.0 Hz, 1H), 6.36 (dd, J = 16.0, 8.0 Hz, 1H), 6.19 (br s, 1H), 4.51 (d, J = 6.0 Hz, 2H), 4.21 (m, 1H), 3.33 (m, 2H) | 3307, 1665, 1114, 813 |
| CC17 | 117-119 | 459.83 ([M − H]$^-$) | 7.51 (m, 2H), 7.39 (m, 2H), 7.24 (m, 2H), 6.52 (d, J = 15.6 Hz, 1H), 6.38 (dd, J = 15.6, 7.6 Hz, 1H), 6.02 (br s, 1H), 4.53 (d, J = 6.0 Hz, 2H), 4.14 (m, 1H), 1.38 (m, 1H)), 1.00 (m, 2H), 0.77 (m, 2H) | 3293, 1633, 1110, 820 |
| CC18 | 119-123 | 501.88 ([M − H]$^-$) | 7.48 (m, 2H), 7.41 (s, 1H), 7.36 (d, J = 8.0 Hz, 1H), 7.23 (m, 2H), 6.52 (d, J = 16.0 Hz, 1H), 6.39 (dd, J = 16.0, 8.0 Hz, 1H), 6.13 (br s, 1H), 4.56 (d, J = 6.0 Hz, 2H), 4.15 (m, 1H), 3.13 (m, 2H) | 3435, 1644, 1111, 817 |
| CC19 | | 530 ([M + H]$^+$) | 7.41 (m, 2H), 7.24 (m, 1H), 6.53 (d, J = 16.0 Hz, 1H), 6.35 (dd, J = | 3435, 1644, 1111, 817 |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| CC20 | | 512 ([M + H]$^+$) | 16.0, 8.0 Hz, 1H), 4.53 (m, 2H), 4.10 (m, 1H), 3.42 (m, 2H), 2.97 (s, 3H), 2.78 (m, 2H) 7.42 (m, 3H), 7.24 (m, 1H), 6.54 (d, J = 15.6 Hz, 1H), 6.34 (dd, J = 15.6, 8.0 Hz, 1H), 6.03 (m 1H), 4.53 (d, J = 6.0 Hz, 1H), 4.10 (m, 1H), 1.19 (m, 1H), 1.00 (m, 2H), 0.77 (m, 2H) | 3293, 1633, 1110, 820 |
| CC21 | 55-58 | 493.99 ([M − H]$^-$) | (DMSO-d$_6$) 8.62 (m, 1H), 7.95 (s, 1H), 7.85 (m, 1H), 7.66 (m, 3H), 7.47 (d, J = 8.0 Hz, 1H), 6.98 (dd, J = 16.0, 8.0 Hz, 1H), 6.84 (d, J = 16.0 Hz, 1H), 4.83 (m, 1H), 4.44 (s, 2H), 1.68 (m, 1H), 0.71 (m, 4H) | |
| CC22 | 67-69 | 530.01 ([M + H]$^+$) | 8.62 (m, 1H), 7.90 (s, 3H), 7.82 (m, 1H), 7.45 (m, 1H), 6.98 (m, 1H), 6.84 (d, J = 16.0 Hz, 1H), 4.82 (m, 1H), 4.4 (s, 2H), 1.66 (m, 1H), 0.72 (m, 4H) | |
| CC23 | 69-71 | 564.99 ([M − H]$^-$) | 9.02 (br s, 1H), 8.54 (br s, 1H), 8.26 (br s, 1H), 7.48-7.54 (m, 3H), 7.22-7.42 (m, 3H), 6.59-6.62 (m, 2H), 6.38-6.42 (m, 1H), 4.82 (m, 2H), 4.19 (s, 1H) | |
| CC24 | 125-127 | 570.26 ([M − H]$^-$) | 7.64 (s, 1H), 7.54 (s, 2H), 7.46 (s, 2H), 6.62 (d, J = 16.0 Hz, 1H), 6.41 (dd, J = 16.0, 8.4 Hz, 1H), 6.03 (m, 1H), 4.65 (d, J = 6.4 Hz, 2H), 4.14 (m, 1H, ), 3.13 (q, J = 10.6 Hz, 2H) | |
| CC25 | | 579.86 ([M − H]$^-$) | 7.60 (s, 1H), 7.40 (s, 2H), 7.37 (d, J = 8.0 Hz, 1H), 7.31 (d, J = 8.0 Hz, 1H), 6.53 (d, 1H, J = 16.0 Hz), 6.35 (dd, J = 16.0, 8.0 Hz, 1H), 6.17 (br s, 1H), 4.56 (d, J = 6.4 Hz, 2H), 4.12 (m, 1H), 3.15 (q, J = 10.6 Hz, 2H) | 3297, 1663, 1114, 809 |
| CC26 | 129-131 | 539.89 ([M + H]$^+$) | 7.59 (s, 1H), 7.39 (m, 2H), 7.30 (s, 1H), 6.53 (d, J = 16.0 Hz, 1H), 6.35 (dd, J = 16.0, 8.0 Hz, 1H), 6.06 (br s, 1H), 4.42 (d, J = 4.4 Hz, 2H), 4.12 (m, 1H), 1.35 (br s, 1H), 0.95 (br s, 2H), 0.75 (m, 2H) | |
| CC27 | | 519.95 ([M − H]$^-$) | 7.39 (s, 2H), 7.33 (t, J = 7.6 Hz, 1H), 7.14 (m, 2H), 6.56 (d, J = 16.0 Hz, 1H), 6.35 (dd, J = 16.0, 7.6 Hz, 1H), 6.06 (br s, 1H), 4.52 (d, J = 16.0 Hz, 2H), 4.08 (m, 1H), 3.90 (s, 2H), 3.13 (m, 2H) | 3306, 1786 |
| CC28 | | 477.93 ([M − H]$^-$) | 7.39 (s, 2H), 7.35 (m, 1H), 7.14 (m, 2H), 6.55 (d, J = 15.6 Hz, 1H), 6.33 (dd, J = 15.6, 8.0 | 3625, 1747 |

TABLE 2-continued

Analytical Data for Compounds in Table 1.

| Compound Number | mp (° C.) | ESIMS | ¹H NMR (δ)[a] | IR (cm⁻¹) |
|---|---|---|---|---|
| | | | Hz, 1H), 5.93 (br s, 1H), 4.49 (d, J = 16.0 Hz, 2H), 4.10 (m, 1H), 1.36 (m, 1H), 1.00 (m, 2H), 0.77 (m, 2H) | |
| CC29 | | 620.86 ([M − H]⁻) | 8.58 (d, J = 4.6 Hz, 1H), 7.74 (m, 1H), 7.62 (m, 2H), 7.52 (m, 1H), 7.4 (s, 2H), 7.3 (m, 1H), 7.2 (m, 2H), 6.60 (d, J = 16.0 Hz, 1H), 6.38 (dd, J = 16.0, 8.0 Hz, 1H), 5.02 (s, 1H), 4.8 (s, 1H), 4.8 (d, J = 10 Hz, 2H), 4.10 (m, 1H), 1.8 (m, 1H), 1.2 (m, 2H), 0.6 (m, 2H) | 1645, 1115, 808 |
| CC30 | 101-104 | 559.75 ([M − H]⁻) | 7.41 (m, 4H), 7.24 (m, 1H), 6.53 (d, J = 16.0 Hz, 1H), 6.35 (dd, J = 16.0, 8.0 Hz, 1H), 6.12 (br s, 1H), 4.53 (m, 2H), 4.10 (m, 1H), 3.42 (m, 2H), 2.91 (s, 3H), 2.78 (m, 2H) | |
| CC31 | 177-178 | 463 ([M − H]⁻) | 7.58 (m, 2H), 7.41 (m, 3H), 7.24 (m, 1H), 6.53 (d, J = 16.0 Hz, 1H), 6.35 (dd, J = 16.0, 8.0 Hz, 1H), 4.70 (br s, 1H), 4.43 (s, 2H), 4.08 (m, 1H), 3.21 (m, 2H), 1.25 (m, 3H); | |
| CC32 | 141-142 | 532.99 ([M + H]⁺) | 7.66 (m, 2H), 7.54 (m, 1H), 7.41 (s, 2H), 6.62 (d, J = 16.0 Hz, 1H), 6.40 (dd, J = 16.0, 8.0 Hz, 1H), 4.59 (s, 3H), 4.19 (m, 1H), 3.25 (m, 2H), 1.15 (m, 2H) | |
| CC33 | | 540.88 ([M − H]⁻) | 7.57 (s, 1H), 7.40 (m, 2H), 7.30 (s, 1H), 7.20 (br s, 1H), 6.53 (d, J = 16.0 Hz, 1H), 6.33 (dd, J = 16.0, 8.0 Hz, 1H), 6.06 (br s, 1H), 4.75 (br s, 1H), 4.42 (s, 2H), 4.20 (br s, 1H), 4.15 (m, 2H), 3.20 (m, 2H), 1.15 (m, 3H) | 3338, 1631, 1578, 1114, 809 |
| CC34 | 118-120 | 541.40 ([M + H]⁺) | 7.42 (m, 3H), 7.28 (m, 2H), 6.54 (d, J = 16.0 Hz, 1H), 6.36 (dd, J = 16.0, 8.0 Hz, 1H), 4.96 (m, 1H), 4.51 (d, J = 5.6 Hz, 2H), 4.12 (m, 1H), 3.69 (t, J = 4.8 Hz, 4H), 3.35 (t, J = 4.8 Hz, 1H) | |
| CC35 | 78-79 | 547.82 ([M + H]⁺) | 9.95 (br s, 1H), 8.17 (d, J = 4.8 Hz, 1H), 7.61 (d, J = 6.4 Hz), 7.43 (m, 3H), 7.24 (m, 2H), 6.90 (t, J = 5.6 Hz, 1H), 6.66 (d, J = 8.4 Hz, 1H), 6.54 (d, J = 16.0 Hz, 1H), 6.33 (dd, J = 16.0, 8.0 Hz, 1H), 4.65 (d, J = 6.0 Hz, 1H), 4.09 (m, 1H) | |
| CC36 | | 497 ([M − H]⁻) | 7.39 (m, 4H), 7.28 (m, 1H), 6.54 (d, J = 16.0 Hz, 1H), 6.34 (dd, J = 16.0, 8.0 Hz, 1H), 4.97 (br s, 1H), 4.38 (d, J = 6.0 Hz, 2H), 4.10 (m, 1H), 2.9 (s, 3H), 2.7 (s, 3H) | 3350, 1705, 1114, 808 |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| CC37 | 88-91 | 515.01 ([M + H]$^+$) | 7.49 (d, J = 8 Hz, 1H), 7.41 (d, J = 7.2 Hz, 2H), 7.26 (m, 2H), 6.50 (d, J = 16 Hz, 1H), 6.35 (dd, J = 16.0, 8.0 Hz, 1H), 6.0 (brs, 1H), 5.73 (br s, 1H), 4.80 (br s, 2H), 4.09 (m, 1H), 1.23 (m, 3H) | |
| CC38 | 63-66 | 526.97 ([M + H]$^+$) | 7.48 (d, J = 8 Hz, 1H), 7.39 (m, 3H), 7.27 (m, 1H), 6.54 (d, J = 16 Hz, 1H), 6.33 (dd, J = 6.0, 8.0 Hz, 1H), 6.17 (br s, 1H), 5.92 (br s, 1H), 5.83 (m, 2H), 5.29 (t, J = 15.4 Hz, 2H), 4.80 (br s, 2H), 4.12 (m, 1H), 4.02 (br s, 2H) | |
| CC39 | | 526.09 ([M − H]$^-$) | 7.39 (m, 4H), 7.28 (m, 1H), 6.54 (d, J = 16.0 Hz, 1H), 6.34 (dd, J = 16.0, 8.0 Hz, 1H), 4.97 (br s, 1H), 4.38 (d, J = 6.0 Hz, 2H), 4.10 (m, 1H), 1.53 (s, 9H) | 3350, 1705, 1114, 808 |
| CC40 | 159-160 | 580.25 ([M − H]$^-$) | 7.46 (m, 5H), 7.29 (m, 1H), 7.20 (m, 3H), 6.55 (d, J = 16.0 Hz, 1H), 6.37 (dd, J = 16.0, 8.0 Hz, 1H), 5.62 (br s, 1H), 4.55 (d, J = 6.4 Hz, 2H), 4.11 (m, 1H) | |
| CC41 | | 512.22 ([M − H]$^-$) | 7.48 (m, 1H), 7.43 (m, 3H), 7.38 (m, 1H), 7.23 (s, 1H), 6.55 (d, J = 16.0 Hz, 1H), 6.36 (d, J = 16.0 Hz, 1H), 4.60 (d, 2H), 4.18 (m, 1H), 3.85 (s, 3H) | 1740, 1701, 1114, 808 |
| CC42 | 161-163 | 578.96 ([M − H]$^-$) | (DMSO-d$_6$) 9.45 (br s, 2H), 7.90 (s, 2H), 7.75 (s, 1H), 7.46 (br s, 1H), 7.28 (br s, 1H), 6.93 (m, 1H), 6.75 (br s, 1H), 4.80 (m, 1H), 4.40 (br s, 2H), 3.90 (br s, 2H) | |
| CC43 | 140-142 | 505.39 ([M + H]$^+$) | 8.11 (d, J = 4.0 Hz, 1H), 7.40 (m, 5H), 7.22 (m, 1H), 6.61 (m, 2H), 6.35 (m, 2H), 4.94 (br s, 1H) 4.61 (d, J = 6.4 Hz, 2H), 4.11 (m, 1H) | |
| CC44 | | 536.88 ([M − H]$^-$) | 8.41 (s, 1H), 7.77 (s, 1H), 7.47 (br s, 1H), 7.40 (s, 2H), 6.58 (d, J = 16.0 Hz, 1H), 6.45 (dd, J = 16.0, 8.0 Hz, 1H), 4.68 (d, J = 4.0 Hz, 2H), 4.14 (m, 1H), 3.24 (q, J = 10.8 Hz, 2H) | 3320, 1674, 1114, 808 |
| CC45 | | 494.88 ([M − H]$^-$) | 8.41 (s, 1H), 7.76 (s, 1H), 7.40 (s, 2H), 7.15 (br s, 1H), 6.58 (d, J = 16.0 Hz, 1H), 6.44 (dd, J = 16.0, 8.0 Hz, 1H), 4.67 (d, J = 4.4 Hz, 2H), 4.16 (m, 1H), 1.57 (m, 1H), 1.04 (m, 2H), 0.87 (m, 2H) | 3309, 1659, 1115, 808 |
| CC46 | 151-153 | 554.04 ([M − H]$^-$) | 8.06 (m, 1H), 7.61 (m, 4H), 7.48 (s, 2H), 7.44 (d, J = 8.0 Hz, 1H), 7.38 (m, 1H), 6.42 (m, 1H), | |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| | | | 5.92 (br s, 1H), 4.92 (m, 2H), 4.24 (m, 1H), 3.12 (m, 2H) | |
| CC47 | | 478.09 ([M + H]$^+$) | 8.06 (m, 2H), 7.61 (m, 4H), 7.48 (s, 2H), 7.44 (d, J = 8.0 Hz, 1H), 7.38 (m, 2H), 6.42 (m, 1H), 4.92 (s, 2H), 1.36 (m, 1H), 1.00 (m, 2H), 0.77 (m, 2H) | 3309, 1659, 1115, 808 |
| CC48 | | 511.05 ([M + H]$^+$) | 8.06 (m, 2H), 7.61 (m, 3H), 7.48 (s, 2H), 7.44 (d, J = 8.0 Hz, 1H), 7.38 (m, 2H), 6.42 (m, 1H), 4.92 (s, 2H), 1.36 (m, 1H), 1.00 (m, 2H), 0.77 (m, 2H) | 3309, 1659, 1115, 808 |
| CC49 | 84-87 | 515.33 ([M + H]$^+$). | 8.06 (m, 1H), 7.98 (m, 1H), 7.61 (m, 3H), 7.48 (s, 2H), 7.44 (d, J = 8.0 Hz, 1H), 7.38 (m, 2H), 6.42 (m, 1H), 4.92 (s, 2H), 4.6 (br s, 1H), 4.24 (m, 1H), 3.21 (m, 2H), 1.2 (t, J = 4.6 Hz, 3H) | |
| CC50 | 138-140 | 461.32 ([M − 1H]$^-$)) | 9.81 (s, 1H), 7.90 (s, 1H), 7.84 (s, 2H), 7.34 (d, J = 8.4 Hz, 2H), 6.65 (d, J = 15.6 Hz, 1H), 6.61 (m, 1H), 6.57 (s, 1H), 6.48 (dd, J = 15.6, 8.8 Hz, 1H), 4.74 (m, 1H), 1.64 (m, 1H), 0.75 (m, 4H); | |
| CC51 | 149-150 | 505.31 ([M − H]$^-$) | 7.56 (br s, 1H), 7.4 (s, 3H), 7.3 (m, 3H), 7.05 (br s, 1H), 6.8 (d, J = 6 Hz, 2H), 6.57 (m, 2H), 6.20 (m, 2H), 4.05 (m, 1H), 3.2 (q, J = 10.4 Hz, 2H) | |
| CC52 | | 464.87 ([M − H]$^-$) | 7.40 (s, 2H), 7.18 (s, 1H), 7.08 (s, 1H), 6.85 (m, 1H), 6.45 (m, 1H), 6.20 (m, 1H), 5.55 (s, 1H), 4.08 (m, 1H), 1.30-1.10 (m, 4H), 1.90 (m, 1H) | 3309, 1659, 1115, 808 |
| CC53 | | 506 ([M + H]$^+$) | 7.40 (s, 2H), 7.18 (s, 1H), 7.08 (s, 1H), 6.85 (m, 1H), 6.45 (m, 1H), 6.20 (m, 1H), 5.55 (s, 1H), 4.08 (m, 1H), 3.21 (m, 2H) | 3309, 1659, 1115, 808 |
| CC54 | | 504 ([M + H]$^+$) | 7.28 (s, 2H), 7.25 (m, 2H), 7.10 (d, J = 8.0 Hz, 2H), 6.89 (d, J = 11.4 Hz, 1H), 6.07 (br s, 1H), 6.01 (m, 1H), 4.51 (d, J = 5.8 Hz, 2H), 4.34 (m, 1H), 3.12 (q, J = 7.5 Hz, 2H) | |
| DC1 | 93-97 | 398.05 ([M + H]$^+$) | 8.56 (s, 1H), 8.11 (s, 1H), 7.68 (d, J = 8.4 Hz, 2H), 7.54 (d, J = 8.4 Hz, 2H), 7.38 (t, J = 1.8 Hz, 1H), 7.29 (s, 2H), 6.62 (d, J = 15.6 Hz, 1H), 6.42 (dd, J = 15.6, 8.2 Hz, 1H), 4.15 (m, 1H) | |
| DC2 | | 363.0746 (363.075) | 8.59 (s, 1H), 8.13 (s, 1H), 7.69 (d, J = 8.5 Hz, 2H), 7.55 (d, J = 8.5 Hz, 2H), 7.41-7.29 (m, 4H), 6.64 (d, J = 15.7 | 3121, 1524, 1251, 1165, 1119 |

TABLE 2-continued

Analytical Data for Compounds in Table 1.

| Compound Number | mp (° C.) | ESIMS | $^1$H NMR ($\delta$)$^a$ | IR (cm$^{-1}$) |
|---|---|---|---|---|
| | | | Hz, 1H), 6.47 (dd, J = 15.9, 8.0 Hz, 1H), 4.17 (m, 1H) | |
| DC3 | | 329.1144 (329.114) | 8.56 (s, 1H), 8.11 (s, 1H), 7.65 (d, J = 8.4 Hz, 2H), 7.52 (d, J = 8.3 Hz, 2H), 7.40 (m, 5H), 6.61 (d, J = 15.8 Hz, 1H), 6.51 (dd, J = 15.9, 7.7 Hz, 1H), 4.18 (m, 1H) | 1521, 1246, 1219, 1162, 1152, 1107 |
| DC4 | | 364.11 ([M + H]$^+$) | 8.56 (s, 1H), 8.10 (s, 1H), 7.66 (d, J = 2.0 Hz, 2H), 7.52 (d, J = 8.8 Hz, 2H), 7.38 (d, J = 2.4 Hz, 2H), 7.34 (d, J = 8.4 Hz, 2H), 6.61 (d, J = 16.0 Hz, 1H), 6.40 (dd, J = 16.0, 7.6 Hz, 1H), 4.15 (m, 1H) | 3147, 1528, 1494, 1246, 1165, 1108 |
| DC5 | | 344.25 ([M + H]$^+$) | 8.54 (s, 1H), 8.10 (s, 1H), 7.62 (d, J = 8.3 Hz, 2H), 7.50 (d, J = 8.4 Hz, 2H), 7.25 (d, J = 8.3 Hz, 2H), 7.20 (d, J = 8.0 Hz, 2H), 6.60 (d, J = 16.0 Hz, 1H), 6.51 (dd, J = 16.0, 8.0 Hz, 1H), 4.15 (m, 1H), 2.37 (s, 3H) | 3122, 3047, 1523, 1252, 1160, 1107 |
| DC6 | | 360.28 ([M + H]$^+$) | 8.55 (s, 1H), 8.10 (s, 1H), 7.65 (d, J = 8.8 Hz, 2H), 7.52 (d, J = 8.8 Hz, 2H), 7.32 (d, J = 8.8 Hz, 2H), 6.95 (d, J = 8.8 Hz, 2H), 6.60 (d, J = 16.0 Hz, 1H), 6.56 (dd, J = 16.0, 7.4 Hz, 1H), 4.15 (m, 1H), 3.82 (s, 3H) | 3124, 2936, 1522, 1249, 1160 |
| DC7 | | 348 ([M + H]$^+$) | 8.55 (s, 1H), 8.10 (s, 1H), 7.62 (d, J = 8.8 Hz, 2H), 7.5 (d, J = 8.4 Hz, 2H), 7.38 (m, 2H), 7.12 (m, 2H), 6.61 (d, J = 16.0 Hz, 1H), 6.40 (dd, J = 16.0, 7.6 Hz, 1H), 4.15 (m, 1H) | 3141, 1512, 1246, 1118 |
| DC8 | | 366.13 ([M + H]$^+$) | 8.57 (s, 1H), 8.11 (s, 1H), 7.65 (d, J = 7.2 Hz, 2H), 7.52 (d, J = 8.0 Hz, 2H), 6.95 (m, 2H), 6.82 (m, 1H), 6.65 (d, J = 16.0 Hz, 1H), 6.50 (dd, J = 16.0, 8.0 Hz, 1H), 4.15 (m, 1H) | 3116, 1628, 1524, 1252, 1168, 1118 |
| DC9 | | 348.11 ([M + H]$^+$) | 8.71 (s, 1H), 8.20 (s, 1H), 7.70 (d, J = 8.0 Hz, 2H), 7.57 (d, J = 8.0 Hz, 2H), 7.40 (m, 1H), 7.19 (m, 3H), 6.60 (d, J = 16.0 Hz, 1H), 6.40 (dd, J = 16.0, 8.4 Hz, 1H), 4.15 (m, 1H) | 3115, 1525, 1248, 1174 |
| DC10 | | 348.11 ([M + H]$^+$) | 8.75 (s, 1H), 8.20 (s, 1H), 7.72 (d, J = 8.4 Hz, 2H), 7.6 (d, J = 8.4 Hz, 2H), 7.20-7.40 (m, 4H), 6.60 (d, J = 16.0 Hz, 1H), 6.40 (dd, J = 16.0, 8.0 Hz, 1H,) 4.60 (m, 1H) | 3114, 1526, 1259, 1238, 1193, 1114 |
| DC11 | 75.5-78.5 | 358.14 ([M + H]$^+$) | 8.55 (s, 1H), 8.10 (s, 1H), 7.65 (d, J = 8.8 Hz, 2H), 7.52 (d, J = 8.4 Hz, 2H), 7.01 (s, 3H), 6.60 (d, J = 16.0 Hz, 1H), 6.51 (dd, J = 16.0, 7.8 | |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| | | | Hz, 1H), 4.15 (m, 1H), 2.34 (s, 6H) | |
| DC12 | | 398.05 ([M + H]$^+$) | 8.58 (s, 1H), 8.10 (s, 1H), 7.68 (d, J = 8.4 Hz, 2H), 7.53 (m, 4H), 7.2 (s, 1H) 6.62 (d, J = 15.6 Hz, 1H), 6.44 (dd, J = 15.6, 8.0 Hz, 1H), 4.15 (m, 1H) | 3055, 2930, 1523, 1250, 1165 |
| DC13 | | 396.16 ([M + H]$^+$) | 8.58 (s, 1H), 8.10 (s, 1H), 7.62 (d, J = 8.4 Hz, 2H), 7.55 (m, 4H), 7.25 (m, 1H), 6.64 (d, J = 16.0 Hz, 1H), 6.40 (dd, J = 16.0, 8.0 Hz, 1H), 4.90 (m, 1H) | 3108, 1523, 1249, 1166, 1127 |
| DC14 | | 398.05 ([M + H]$^+$) | 8.58 (s, 1H), 8.10 (s, 1H), 7.62 (d, J = 8.4 Hz, 2H), 7.55 (m, 4H), 7.25 (m, 1H), 6.67 (d, J = 16.0 Hz, 1H), 6.40 (dd, J = 16.0, 8.0 Hz, 1H), 5.00 (m, 1H) | 3117, 2925, 1526, 1246, 1172, 1117 |
| DC15 | | 397.95 ([M + H]$^+$) | 8.58 (s, 1H), 8.10 (s, 1H), 7.66 (d, J = 8.0 Hz, 2H), 7.52 (m, 3H), 7.40 (d, J = 8.0 Hz, 1H), 7.30 (dd, J = 8.4, 2.9 Hz, 1H), 6.64 (d, J = 16.0 Hz, 1H), 6.40 (dd, J = 16.0, 8.0 Hz, 1H), 4.90 (m, 1H) | 3120, 1524, 1267, 1176, 1112 |
| DC16 | | 466 ([M + H]$^+$) | 8.61 (s, 1H), 8.13 (s, 1H), 7.92 (s, 1H), 7.86 (s, 2H), 7.70 (d, J = 7.0 Hz, 2H), 7.54 (d, J = 7.0 Hz, 2H), 6.67 (d, J = 16.0 Hz, 1H), 6.46 (dd, J = 16.0, 8.0 Hz, 1H), 4.35 (m, 1H) | |
| DC17 | | 430.06 ([M + H]$^+$) | 8.58 (s, 1H), 8.1 (s, 1H), 7.68 (d, J = 8.4 Hz, 2H), 7.54 (d, J = 8.4 Hz, 2H), 7.51 (s, 1H), 7.42 (s, 1H), 6.68 (d, J = 16.0 Hz, 1H), 6.35 (dd, J = 16.0, 8.0, Hz, 1H), 4.98 (m, 1H) | 3122, 3076, 2929, 1523, 1250, 1168, 1114 |
| DC18 | 92-95 | 429.91 ([M + H]$^+$) | 8.57 (s, 1H), 8.11 (s, 1H), 7.69 (d, J = 8.8 Hz, 2H), 7.54 (d, J = 8.4 Hz, 2H), 7.42 (s, 2H), 6.65 (d, J = 16.0 Hz, 1H), 6.40 (dd, J = 16.0, 8.0 Hz, 1H), 4.10 (m, 1H) | |
| DC19 | 97-99 | 430.321 ([M + H]$^+$) | 8.58 (s, 1H), 8.12 (s, 1H), 7.68 (d, J = 8.0 Hz, 2H), 7.64 (s, 1H), 7.59 (s, 1H), 7.55 (m, 3H), 6.60 (d, J = 16.0 Hz, 1H), 6.40 (dd, J = 16.0, 8.0 Hz, 1H), 4.22 (m, 1H) | |
| DC20 | | 427.0463 (427.0466) | 8.58 (s, 1H), 8.15 (s, 1H), 7.70 (d, J = 8.4 Hz, 2H), 7.58 (d, J = 8.4 Hz, 2H), 7.36 (s, 2H), 6.62 (d, J = 16.0 Hz, 1H), 6.43 (dd, J = 16.0, 8.0 Hz, 1H), 4.12 (m, 1H), 3.88 (s, 3H) | 2937, 1524, 1482, 1278, 1249, 1166, 1112 |
| DC21 | | 412.04 ([M + H]$^+$) | 8.42 (s, 1H), 7.60 (d, J = 8.0 Hz, 2H), 7.50 (d, J = 8.0 Hz, 2H), 7.40 (s, 1H), 7.22 (s, 2H), 6.60 (d, J = 16.0 Hz, 1H), | 3108, 1572, 1531, 1242, 1172, 1104 |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| | | | 6.42 (dd, J = 16.0, 8.0 Hz, 1H), 4.15 (m, 1H), 2.5 (s, 3H) | |
| DC22 | 147-149 | 441.01 ([M − H]$^-$) | 8.62 (s, 1H), 7.78 (d, J = 8.0 Hz, 2H), 7.60 (d, J = 8.0 Hz, 2H), 7.40 (s, 1H), 7.30 (s, 2H), 6.67 (d, J = 16.0 Hz, 1H), 6.48 (dd, J = 16.0, 8.0 Hz, 1H), 4.15 (m, 1H) | |
| DC23 | | 412.05 ([M + H]$^+$) | 7.95 (s, 1H), 7.35 (d, J = 8.0 Hz, 2H), 7.46 (d, J = 8.0 Hz, 2H), 7.39 (s, 1H), 7.29 (s, 2H), 6.67 (d, J = 16.0 Hz, 1H), 6.45 (dd, J = 16.0, 8.0 Hz, 1H), 4.12 (m, 1H), 2.51 (s, 3H) | 1112, 799 |
| DC24 | 133-134 | 440.03 ([M + H]$^+$) | 8.10 (s, 1H), 7.52 (d, J = 8.0 Hz, 2H), 7.42-7.38 (m, 3H), 7.28 (s, 2H), 6.67 (d, J = 16.0 Hz, 1H), 6.45 (dd, J = 16.0, 8.0 Hz, 1H), 4.16 (m, 1H), 2.79 (s, 3H) | |
| DC25 | | 442.02 ([M − H]$^-$) | 7.97 (s, 1H), 7.59 (d, J = 8.0 Hz, 2H), 7.53 (d, J = 8.0 Hz, 2H), 7.38 (m, 1H), 7.29 (s, 2H), 6.65 (d, J = 16.0 Hz, 1H), 6.42 (dd, J = 16.0, 8.0 Hz, 1H), 4.17 (m, 1H), 2.74 (s, 3H) | 1167, 1114, 800 |
| DC26 | | 464.03 ([M − H]$^-$) | 8.12 (s, 1H), 7.49 (d, J = 8.0 Hz, 2H), 7.40-7.37 (m 3H), 7.28 (s, 2H), 6.66 (d, J = 16.0 Hz, 1H), 6.44 (dd, J = 16.0, 8.0 Hz, 1H), 4.14 (m, 1H), 3.22 (m, 1H), 1.09-1.16 (m, 4H) | 1689, 1253, 1166, 1114, 979, 964 |
| DC27 | | 473.94 ([M − H]$^-$) | 8.19 (s, 1H), 7.64 (d, J = 7.2 Hz, 2H), 7.55 (d, 7.2 Hz, 2H), 7.39 (s, 1H), 7.30 (s, 2H), 6.62 (d, J = 16.0 Hz, 1H), 6.42 (dd, J = 8.0, 16.0 Hz, 1H), 4.18 (m, 1H), 3.58 (s, 3H) | 1571, 1331, 1170, 1113, 764 |
| DC28 | | 421.22 ([M + H]$^+$) | 8.79 (s, 1H), 8.18 (s, 1H), 7.80 (m, 3H), 7.52 (m, 2H), 7.24 (m, 1H), 6.63 (d, J = 16.0 Hz, 1H), 6.54 (d, J = 16.0, 7.6 Hz, 1H), 4.19 (m, 1H) | 3126, 2233, 1516, 1250, 1165, 1109 |
| DC29 | | 421.22 ([M + H]$^+$) | 8.80 (s, 1H), 8.2 (s, 1H), 7.75-7.82 (m, 3H), 7.41 (t, J = 2 Hz, 1H), 7.26 (m, 2H), 6.65 (d, J = 16.0 Hz, 1H), 6.52 (dd, J = 16.0, 7.6 Hz, 1H), 4.16 (m, 1H) | 3005, 1716, 1363, 1223 |
| DC30 | | 489.17 ([M + H]$^+$) | 8.81 (s, 1H), 8.20 (s, 1H), 7.94 (s, 1H), 7.85 (m, 3H), 7.79 (m, 2H), 6.70 (d, J = 16.0 Hz, 1H), 6.58 (dd, J = 16.0, 8.0 Hz, 1H), 4.35 (m, 1H) | 2964, 2234, 1289, 1166, 1136 |
| DC31 | 117-118 | 455.27 ([M + H]$^+$) | 8.80 (s, 1H), 8.20 (s, 1H), 7.82 (m, 3H), 7.4 (s, 2H), 6.62 (d, J = 16.0 Hz, 1H), 6.52 (dd, J = 16.0, 8.0 Hz, 1H), 4.18 (m, 1H) | |
| DC32 | | 388.0705 (388.0703) | 8.82 (s, 1H), 8.22 (s, 1H), 7.82-7.78 (m, 3H), 7.38-7.30 (m, 3H), 6.62 | 3126, 2234, 1520, 1280, 1164, 1112 |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| | | | (d, J = 16.1 Hz, 1H), 6.56 (dd, J = 16.1, 6.8 Hz, 1H), 4.18 (m, 1H) | |
| DC33 | | 455.22 ([M − H]$^-$) | 8.80 (s, 1H), 8.20 (s, 1H), 7.82-7.80 (m, 3H), 7.70-7.50 (m, 3H), 6.65 (d, J = 16.9 Hz, 1H), 6.54 (dd, J = 16.9, 6.8 Hz, 1H), 4.25 (m, 1H) | 3122, 3086, 2234, 1517, 1327, 1168, 1113 |
| DC34 | | 452.0412 (452.0419) | 8.85 (s, 1H), 8.23 (br s, 1H), 7.83-7.78 (m, 3H), 7.33 (s, 2H), 6.69 (d, J = 14.9 Hz, 1H), 6.50 (dd, J = 14.9, 7.2 Hz, 1H), 4.15 (m, 1H), 3.90 (s, 3H) | 3122, 2934, 2231, 1516, 1480, 1248, 1211, 1165, 1111 |
| DC35 | | 439.01 ([M − H]$^-$) | 8.60 (s, 1H), 8.20 (s, 1H), 7.82 (m, 3H), 7.28 (m, 2H), 6.65 (d, J = 16.0 Hz, 1H), 6.48 (dd, J = 16.0, 8.0 Hz, 1H), 4.20 (m, 1H) | 2233, 1518, 1250, 1169, 1035, 817 |
| DC36 | | 437.25 ([M + H]$^+$) | 8.70 (s, 1H), 7.80 (m, 3H), 7.40 (s, 1H), 7.28 (s, 2H), 6.63 (d, J = 16.0 Hz, 1H), 6.50 (dd, J = 16.0, 8.0 Hz, 1H), 4.18 (m, 1H), 2.50 (s, 1H) | 2927, 2233, 1572, 1531, 1248, 1166, 1112 |
| DC37 | 109-111 | 466.10 ([M − H]$^-$) | 8.86 (s, 1H), 7.89 (m, 3H), 7.40 (s, 1H), 7.30 (s, 2H), 6.68 (d, J = 16.0 Hz, 1H), 6.57 (dd, J = 16.0, 8.0 Hz, 1H), 4.18 (m, 1H) | |
| DC38 | 96-98 | 436.11 ([M − H]$^-$) | 8.58 (s, 1H), 7.75 (m, 3H), 7.40 (s, 1H), 7.28 (s, 2H), 6.61 (d, J = 16.0 Hz, 1H), 6.42 (dd, J = 16.0, 8.2 Hz, 1H), 4.40 (br s, 2H), 4.15 (m, 1H) | |
| DC39 | 224-226 | 480.30 ([M + H]$^+$) | 8.65 (s, 1H), 8.18 (br s, 1H), 7.80-7.70 (m, 3H), 7.40 (s, 1H), 7.27 (s, 2H), 7.36 (m, 1H), 7.28 (m, 2H), 6.60 (d, J = 16.8 Hz, 1H), 6.47 (m, 1H), 4.16 (m, 1H), 2.40 (br s, 3H) | 3352, 2237, 1707, 1163, 841 |
| DC40 | 70-73 | 436.11 ([M − 2H]$^-$) | 8.86 (s, 1H), 7.88 (m, 3H), 7.44 (s, 2H), 6.67 (d, J = 16.0 Hz, 1H), 6.56 (dd, J = 16.0 7.6 Hz, 1H), 4.19 (m, 1H) | |
| DC41 | 72-75 | 469.95 ([M − H]$^-$) | (DMSO-d$_6$) 8.72 (s, 1H), 8.26 (s, 1H), 8.01 (d, J = 8.4 Hz, 1H), 7.91 (s, 2H), 7.77 (d, J = 8.4 Hz, 1H), 6.42 (dd, J = 15.6, 9.2 Hz, 1H), 6.83 (d, J = 15.6 Hz, 1H), 5.87 (s, 2H), 4.89 (m, 1H) | |
| DC42 | 104-107 | 609.98 ([M + H]$^+$) | 8.78 (s, 2H), 7.83 (s, 1H), 7.80 (m, 2H), 7.42 (s, 2H), 6.65 (d, J = 16.4 Hz, 1H), 6.51 (dd, J = 16.4, 7.8 Hz, 1H), 4.17 (m, 1H), 4 2.16 (m, 2H), 1.25 (m, 4H), 1.00 (m, 4H) | 2234, 1714, 1114, 807 |
| DC43 | 109-112 | 540.04 ([M + H]$^+$) | (DMSO-d$_6$) 10.94 (br s, 1H), 8.36 (s, 1H), 8.08 (m, J = 8.4 Hz, 1H), 7.91 (s, 2H), 7.84 (d, J = 8.4 Hz, 1H), 7.13 (dd, J = 15.6, 9.2 Hz, 1H), | 3233, 2233, 1699, 1114, 807 |

TABLE 2-continued

Analytical Data for Compounds in Table 1.

| Compound Number | mp (° C.) | ESIMS | $^1$H NMR (δ)$^a$ | IR (cm$^{-1}$) |
|---|---|---|---|---|
| | | | 6.87 (d, J = 15.6 Hz, 1H), 4.92 (m, 1H), 1.99 (br s, 1H), 0.82 (s, 4H) | |
| DC44 | | 435.26 [M − H]$^-$ | 8.33 (s, 1H), 8.23 (s, 1H), 7.66 (s, 1H), 7.60 (s, 1H), 7.41 (m, 1H), 7.28 (m, 2H), 6.62 (d, J = 16.0 Hz, 1H), 6.51 (dd, J = 16.0, 7.8 Hz, 1H), 4.16 (m, 1H), 2.20 (s, 3H) | 2236, 1510, 1114, 801 |
| DC45 | 75-78 | 468.87 [M − H]$^-$ | 8.36 (s, 1H), 8.23 (s, 1H), 7.66 (s, 1H), 7.60 (s, 1H), 7.41 (s, 2H), 6.62 (d, J = 16.4 Hz, 1H), 6.51 (dd, J = 16.4, 7.6 Hz, 1H), 4.16 (m, 1H), 2.20 (s, 3H) | |
| DC46 | | 411.4 ([M]$^+$) | 8.83 (s, 1H), 8.21 (s, 1H), 7.83 (d, J = 8.5 Hz, 1H), 7.61 (d, J = 1.9 Hz, 1H), 7.52 (dd, J = 8.4, 1.9 Hz, 1H), 7.28 (d, J = 3.8 Hz, 2H), 6.93 (d, J = 11.5 Hz, 1H), 6.26-6.20 (m, 1H), 4.22 (m, 1H) | $^{13}$C NMR (δ)$^3$ 155.63, 153.27, 153.12, 143.01, 137.89, 136.25, 134.03, 133.88, 132.23, 131.23, 131.18, 129.20, 126.17, 125.04, 124.99 |
| DC47 | 139-141 | 474.16 ([M − H]$^-$) | 8.51 (s, 1H), 8.14 (s, 1H), 7.75 (s, 1H), 7.5 (m, 2H), 7.4 (s, 1H), 7.30 (m, 2H), 6.60 (d, J = 16.0 Hz, 1H), 6.50 (dd, J = 16.0, 8.0 Hz, 1H), 4.15 (m, 1H) | |
| DC48 | 124-126 | 414.05 [M − H]$^-$ | 8.69 (s, 1H), 8.14 (s, 1H), 7.96 (d, J = 4.8 Hz, 1H), 7.39-7.27 (m, 5H), 6.95 (d, J = 16.0 Hz, 1H), 6.51 (dd, J = 16.0, 7.6 Hz, 1H), 4.13 (m, 1H) | |
| DC49 | 81-83 | 463.96 [M − H]$^-$ | 8.57 (s, 1H), 8.14 (s, 1H), 7.60 (m, 2H), 7.44 (m, 3H), 6.95 (d, J = 16.0 Hz, 1H), 6.51 (dd, J = 16.0, 7.6 Hz, 1H), 4.13 (m, 1H) | |
| DC50 | 140-143 | 430.07 [M − H]$^-$) | 8.56 (s, 1H), 8.13 (s, 1H), 7.59 (d, J = 1.2 Hz, 2H), 7.44 (m, 2H), 7.28 (m, 2H), 6.61 (d, J = 16.0 Hz, 1H), 6.47 (dd, J = 16.0, 8.0 Hz, 1H), 4.15 (m, 1H) | 1110, 803 |
| DC51 | 118-121 | 464.22 ([M − H]$^-$) | 8.32 (s, 1H), 8.15 (s, 1H), 7.82 (s, 1H), 7.73 (d, J = 8.4 Hz, 1H), 7.53 (d, J = 8.4 Hz, 1H), 7.41 (s, 1H), 7.29 (s, 2H), 6.70 (d, J = 15.6 Hz, 1H), 6.50 (dd, J = 15.6, 8.0 Hz, 1H), 4.20 (m, 1H) | |
| DC52 | | | 9.99 (s, 1H), 8.42 (s, 1H), 8.12 (s, 1H), 8.01 (s, 1H), 7.68 (m, 1H), 7.44 (m, 1H), 7.33 (m, 1H), 7.22 (s, 2H), 6.62 (d, J = 16.7 Hz, 1H), 6.45 (dd, J = 16.7, 9.3 Hz, 1H), 4.10 (m, 1H) | 3123, 3079, 2925, 1692, 1571, 1512, 1253, 1164, 1111 |
| DC53 | | | 8.30 (m, 1H), 8.00 (br s, 1H), 7.75 (m, 1H), 7.68 (m, 1H), 7.55 (m, 1H), 7.36 (m, 1H), 7.28 (m, | 3250, 3043, 1683, 1116 |

TABLE 2-continued

Analytical Data for Compounds in Table 1.

| Compound Number | mp (° C.) | ESIMS | ¹H NMR (δ)$^a$ | IR (cm$^{-1}$) |
|---|---|---|---|---|
| | | | 2H), 6.70 (m, 1H), 6.58 (br s, 1H), 6.33 (m, 1H), 5.88 (m, 2H), 4.10 (m, 1H) | |
| DC54 | 56-58 | 441.07 ([M − H]$^−$) | 8.40 (s, 1H), 8.13 (s, 1H), 8.02 (s, 1H), 7.76 (d, J = 8.4 Hz, 1H), 7.59 (d, J = 8.0 Hz, 1H), 7.4 (s, 1H), 7.29 (m, 2H), 6.69 (d, J = 15.6 Hz, 1H), 6.57 (dd, J = 15.6, 7.8 Hz, 1H), 4.15 (m, 1H) | |
| DC55 | | 412.97 ([M + H]$^+$) | 8.37 (s, 1H), 8.18 (s, 1H), 7.39 (s, 1H), 7.30 (m, 2H), 7.19 (d, J = 8.0 Hz, 1H), 6.90 (m, 2H), 6.55 (d, J = 15.6 Hz, 1H), 6.38 (dd, J = 15.6, 8.2 Hz, 1H), 4.20 (m, 1H), 2.50 (br s, 2H) | |
| DC56 | 175-177 | 453 ([M − H]$^−$) | 9.59 (br s, 1H), 8.55 (s, 1H), 8.47 (s, 2H), 8.23 (s, 1H), 7.30 (m, 4H), 6.62 (d, J = 16.0 Hz, 1H), 6.40 (dd, J = 16.0, 8.0 Hz, 1H), 4.15 (m, 1H), 2.20 (s, 3H) | |
| DC57 | | 426.0627 (426.0626) | 8.33 (s, 1H), 8.16 (s, 1H), 7.38 (s, 1H), 7.29 (s, 2H), 7.15 (d, J = 7.6 Hz, 1H), 6.80 (d, J = 7.6 Hz, 1H), 6.74 (m, 1H), 6.60 (d, J = 15.6 Hz, 1H), 6.35 (dd, J = 15.6, 8.4 Hz, 1H), 5.40 (br s, 1H), 4.15 (m, 1H), 2.90 (s, 3H) | 3342, 3112, 2931, 1606, 1583, 1574, 1528, 1153 |
| DC58 | 94-97 | 440.0424 (440.0419) | (DMSO-d$_6$) 8.76 (s, 1H), 8.16 (s, 1H), 7.90 (br s, 1H), 7.83 (s, 1H), 7.70 (d, J = 7.9 Hz, 1H), 7.71-7.67 (m, 3H), 7.58 (d, J = 7.9 Hz, 1H), 7.52 (br s, 1H), 7.00 (dd, J = 15.8, 8.7 Hz, 1H), 6.85 (d, J = 15.8 Hz, 1H), 4.85 (m, 1H) | 3403, 3304, 3178, 1674, 1571, 1169, 1108 |
| DC59 | 87-90 | | (DMSO-d$_6$) 9.00 (s, 1H), 8.63 (s, 1H), 8.17 (s, 1H), 7.70-7.59 (m, 5H), 7.00 (dd, J = 16.2, 9.7 Hz, 1H), 6.85 (d, J = 16.2 Hz, 1H), 5.90 (br s 2H), 4.83 (m, 1H) | |
| DC60 | | 469.0577 (469.0572) | 8.32 (s, 1H), 8.10 (s, 1H), 7.97 (s, 1H), 7.65 (d, J = 8.1 Hz, 1H), 7.47 (d, J = 8.1 Hz, 1H), 7.40 (m, 1H), 7.28 (s, 2H), 6.62 (d, J = 16.5 Hz, 1H), 6.49 (dd, J = 16.5, 7.7 Hz, 1H), 4.23-4.04 (m, 3H), 1.15 (t, J = 8.0 Hz, 3H) | 2987, 1725, 1518, 1275, 1166, 1113 |
| DC61 | 130-132 | 442.15 ([M + H]$^+$) | (DMSO-d$_6$) 9.90 (s, 1H), 8.17 (s, 1H), 8.15 (m, 1H), 7.90 (m, 1H), 7.71 (m, 2H), 7.67 (m, 1H), 7.62 (d, J = 7.3 Hz, 1H), 7.03 (dd, J = 16.5, 8.3 Hz, 1H), 6.62 (d, J = 16.5 Hz, 1H), 4.87 (m, 1H) | |
| DC62 | | 412.10 ([M + H]$^+$) | 8.27 (s, 1H), 8.23 (s, 1H), 7.40 (m, 3H), 7.30 (m, 3H), 6.64 (d, J = 16.0 Hz, 1H), 6.45 (dd, | 1513, 1252, 1166, 1112, 801 |

TABLE 2-continued

Analytical Data for Compounds in Table 1.

| Compound Number | mp (° C.) | ESIMS | ¹H NMR (δ)[a] | IR (cm⁻¹) |
|---|---|---|---|---|
| DC63 |  | 446.01 ([M + H]⁺) | J = 16.0, 8.0 Hz, 1H), 4.19 (m, 1H), 2.21 (s, 3H) 8.26 (s, 1H), 8.12 (s, 1H), 7.42 (s, 2H), 7.18-7.28 (m, 3H), 6.62 (d, J = 15.6 Hz, 1H), 6.39 (dd, J = 15.6, 9.4 Hz, 1H), 4.10 (m, 1H), 2.25 (s, 3H) | 2928, 2525, 1249, 1169, 1114, 809 |
| DC64 |  | 475.03 ([M + H]⁺) | 8.84 (d, J = 5.8 Hz, 2H), 8.33 (s, 1H), 8.20 (s, 1H), 7.75 (m, 1H), 7.60 (d, J = 28.6 Hz, 1H), 7.58-7.48 (m, 3H), 7.42 (m, 1H), 7.28 (s, 2H), 6.71 (d, J = 16.9 Hz, 1H), 6.39 (dd, J = 16.9, 8.2 Hz, 1H), 4.15 (m, 1H) | 1683, 1167, 650, 479 |
| DC65 |  | 412.05 ([M + H]⁺) | 8.55 (s, 1H), 8.12 (s, 1H), 7.55 (m, 3H), 7.39 (m, 1H), 7.30 (d, J = 1.6 Hz, 1H), 6.85 (d, J = 16.0 Hz, 1H), 6.41 (dd, J = 16.0, 8.0 Hz, 1H), 4.17 (m, 1H), 2.40 (s, 3H) | 722, 111 |
| DC66 | 60-61 | 468.26 ([M + H]⁺) | 8.59 (s, 1H), 8.14 (s, 1H), 7.94 (s, 1H), 7.70 (d, J = 8.0 Hz, 1H), 7.61 (d, J = 8.0 Hz, 1H), 7.43 (s, 2H), 7.23 (d, J = 16.0 Hz, 1H), 6.41 (dd, J = 16.0, 8.0 Hz, 1H), 4.20 (m, 1H) |  |
| DC67 | 133-134 | 432.30 ([M + H]⁺) | 8.59 (s, 1H), 8.12 (s, 1H), 7.78 (br s, 1H), 7.71 (m, 1H), 7.62 (m, 1H), 7.39 (s, 1H), 7.32 (s, 2H), 7.03 (d, J = 16.0 Hz, 1H), 6.43 (dd, J = 16.0, 8.0 Hz, 1H), 0.21 (m, 1H) | 800, 114 |
| DC68 |  | 412.03 ([M + H]⁺) | 8.71 (s, 1H), 8.18 (s, 1H), 7.71 (d, J = 8.0 Hz, 2H), 7.55 (d, J = 8.0 Hz, 2H), 7.37 (s, 1H), 7.28 (m, 2H), 6.08 (d, J = 16.0 Hz, 1H), 4.26 (m, 1H), 2.05 (s, 3H) |  |
| DC69 | 162-168 | 414.03 ([M + H]⁺) | 8.56 (s, 1H), 8.11 (s, 1H), 7.70 (d, J = 8.5 Hz, 2H), 7.56 (d, J = 8.5 Hz, 2H), 7.54 (m, 2H), 7.40 (m, 1H), 6.91 (d, J = 16.5 Hz, 1H), 6.66 (d, J = 16.5 Hz, 1H) |  |
| DC70 | 99-103 | 428.05 ([M + H]⁺) | 8.58 (s, 1H), 8.13 (s, 1H), 7.73 (d, J = 8.7 Hz, 2H), 7.60 (d, J = 8.7 Hz, 2H), 7.46 (m, 2H), 7.42 (m, 1H), 6.85 (d, J = 16.2 Hz, 1H), 6.40 (d, J = 16.2 Hz, 1H), 3.42 (s, 3H) |  |

[a]¹H NMR spectral data were acquired using a 400 MHz instrument in CDCl₃ except where noted. HRMS data are noted observed value (theoretical value).

TABLE 2A

Analytical Data for Compounds in Table 1A.

| Compound Number | mp (° C.); $[\alpha]_D^{25}$ | ESIMS | $^1$H NMR (δ)$^a$ | IR (cm$^{-1}$); $^{19}$F NMR (δ) |
|---|---|---|---|---|
| F1 | 53-64 | 655 ([M + H]$^+$) | rotomers δ 7.61 (d, J = 1.6 Hz, 1H), 7.50 (d, J = 7.9 Hz, 1H), 7.45 (dd, J = 6.4, 3.0 Hz, 0.5H), 7.41 (s, 2H), 7.37 (dd, J = 8.0, 1.6 Hz, 1H), 7.33 (t, J = 6.2 Hz, 0.5H), 6.53 (d, J = 15.9 Hz, 1H), 6.45 (s, 1H), 6.39 (dd, J = 15.9, 7.8 Hz, 1H), 4.21-4.01 (m, 1H), 3.96 (qd, J = 9.1, 6.4 Hz, 1.5H), 3.85 (td, J = 9.2, 6.5 Hz, 0.5 H) 1.69 (s, 6H), | |
| F2 | | 608.92 ([M + H]$^+$) | (300 MHz, CDCl$_3$) δ 7.65 (d, J = 7.6 Hz, 1H), 7.43-7.40 (m, 2H), 7.36 (d, J = 8.4 Hz, 1H), 7.29 (m, 1H), 6.56 (d, J = 15.6 Hz, 1H), 6.43 (dd, J = 15.6, 7.2 Hz, 1H), 4.12-4.08 (m, 1H), 3.97-3.94 (m, 2H), 1.70 (s, 6H) | 3368, 1682, 1162, 808 |
| F3 | | 588.90 ([M + H]$^+$) | (300 MHz, DMSO-d$_6$) δ 8.23 (s, 1H), 8.17 (broad s, 1H), 7.89 (s, 2H), 7.48-7.38 (m, 3H), 6.82 (dd, J = 15.6, 7.8 Hz, 1H), 6.74 (d, J = 15.6 Hz, 1H), 4.90-4.80 (m, 1H), 3.89-3.84 (m, 2H), 2.30 (s, 3H), 1.42 (s, 6H) | 3394, 1678, 1163, 807 |
| F4 | | 642.99 ([M + H]$^+$) | (300 MHz, DMSO-d$_6$) δ 8.58 (s, 1H), 8.20 (t, J = 6.6 Hz, 1H), 7.98-7.89 (m, 4H), 7.80 (d, J = 8.1 Hz, 1H), 7.04 (dd, J = 15.6, 8.7 Hz, 1H), 6.88 (d, J = 15.6 Hz, 1H), 4.88-4.78 (m, 1H), 3.89-3.82 (m, 2H), 1.40 (s, 6H) | 3460, 1677, 1165, 557 |
| F5 | | 640.9 ([M + H]$^+$) | 7.62 (d, J = 1.7 Hz, 1H), 7.53 (d, J = 7.8 Hz, 1H), 7.42-7.29 (m, 3H), 6.91 (t, J = 6.7 Hz, 1H), 6.54 (bs, 1H) 6.53 (d, J = 15.9 Hz, 1H), 6.39 (dd, J = 15.9, 7.8 Hz, 1H), 4.74 (q, J = 7.1 Hz, 1H), 4.10 (m, 1H), 4.05-3.72 (m, 2H), 1.53 (d, J = 7.0 Hz, 3H) | 3288, 1644, 1162 |
| F6 | | 640.9 ([M + H]$^+$) | 7.62 (d, J = 1.6 Hz, 1H), 7.53 (d, J = 8.0 Hz, 1H), 7.41 (s, 2H), 7.38 (dd, J = 8.0, 1.7 Hz, 1H), 6.86 (t, J = 6.2 Hz, 1H), 6.57-6.49 (m, 2H), 6.40 (dd, J = 15.9, 7.8 Hz, 1H), 4.74 (m, 1H), 4.15-4.04 (m, 1H), 4.00-3.81 (m, 2H), 1.53 (d, J = 7.1 Hz, 3H) | 3288, 1645, 1164 |
| F7 | | 574.92 ([M + H]$^+$) | (300 MHz, DMSO-d$_6$) δ 8.56 (t, J = 6.3 Hz, 1H), 8.43 (d, J = 4.5 Hz, 1H), 7.89 (s, 2H), 7.44-7.34 (m, 3H), 6.88 (dd, J = 15.6, 8.4 Hz, 1H), 6.75 (d, J = 15.6 Hz, 1H), 4.85-4.79 (m, 1H), 4.49-4.44 (m, 1H), 3.99-3.83 (m, 2H), 2.33 (s, 3H), 1.34 (d, J = 7.2 Hz, 3H) | 3412, 1685, 1163, 809 |
| F8 | | 652.95 ([M + H]$^+$) | (400 MHz, DMSO-d$_6$) δ 8.62 (t, J = 6.0 Hz, 1H), 8.59 (d, J = 7.6 Hz, 1H), 7.92-7.91 (m, 3H), 7.60 (d, J = 7.6 Hz, 1H), 7.38 (d, J = 8.1 Hz, 1H), 6.99 (dd, J = 15.6, 9.2 Hz, 1H), 6.77 (d, J = 15.6 Hz, 1H), 4.85-4.80 (m, 1H), 4.41-4.36 (m, 1H), 4.05-3.99 (m, 1H), 3.91-3.84 (m, 1H), 1.73-1.63 (m, 2H), 0.99 (t, J = 7.6 Hz, 3H) | 3291, 1647, 1165, 808, 565 |
| F8A | | 650.99 ([M − H]$^-$) | (300 MHz, DMSO-d$_6$) δ 8.64-8.57 (m, 2H), 7.92-7.91 (m, 3H), 7.60 (d, J = 7.5 Hz, 1H), 7.38 (d, J = 7.5 Hz, 1H), 7.01 (dd, J = 15.6, 9.0 Hz, 1H), 6.78 (d, J = 15.6 Hz, 1H), 4.86-4.80 (m, 1H), 4.42-4.35 (m, 1H), 4.06-3.84 (m, 2H), 1.76-1.62 (m, 2H), 0.93 (t, J = 7.2 Hz, 3H). | 3289, 1646, 1164, 808. 725, 649 |
| F9 | | 575.04 ([M + H]$^+$) | (400 MHz, DMSO-d$_6$) δ 8.56 (t, J = 6.0 Hz, 1H), 8.44 (d, J = 7.2 Hz, 1H), 7.89 (s, 2H), 7.45 (s, 1H), 7.41-7.35 (m, 2H), 6.87 (dd, J = 16.0, 9.2 Hz, 1H), 6.74 (d, J = 15.2 Hz, 1H), 4.85-4.80 (m, 1H), 4.48-4.44 (m, 1H), 4.03-3.85 (m, 2H), 2.33 (s, 3H), 1.31 (d, J = 7.2 Hz, 3H) | 3407, 1685, 1161, 808 |
| F10 | | 638.84 ([M + H]$^+$) | (400 MHz, DMSO-d$_6$) δ 8.61 (d, J = 7.2 Hz, 1H), 8.52 (t, J = 6.0 Hz, 1H), 7.88-7.87 (m, 3H), 7.56 (d, J = 7.6 Hz, 1H), 7.38 (d, J = 8.0 Hz, 1H), 6.96 (dd, J = 16.6, 9.2 Hz, 1H), 6.73 (d, J = 15.6 Hz, 1H), 4.81-4.77 (m, 1H), 4.46-4.42 (m, 1H), 4.00-3.81 (m, 2H), 1.27 (d, J = 7.2 Hz, 3H) | 3415, 1652, 1162, 807, 561 |
| F11 | | 638.90 ([M + H]$^+$) | (400 MHz, DMSO-d$_6$) δ 8.61 (d, J = 7.2 Hz, 1H), 8.52 (t, J = 6.0 Hz, 1H), 7.88-7.87 (m, 3H), 7.56 (d, J = 7.6 Hz, 1H), 7.38 (d, J = 8.0 Hz, 1H), 6.96 (dd, J = 16.6, 9.2 Hz, 1H), 6.73 (d, J = 15.6 Hz, 1H), 4.81-4.77 (m, 1H), 4.46-4.42 (m, 1H), 4.00-3.81 (m, 2H), 1.27 (d, J = 7.2 Hz, 3H) | 3415, 1652, 1162, 807, 561 |

TABLE 2A-continued

Analytical Data for Compounds in Table 1A.

| Compound Number | mp (° C.); $[\alpha]_D^{25}$ | ESIMS | $^1$H NMR (δ)$^a$ | IR (cm$^{-1}$); $^{19}$F NMR (δ) |
|---|---|---|---|---|
| F12 | | 638.90 ([M + H]$^+$) | (400 MHz, DMSO-d$_6$) δ 8.65 (d, J = 7.2 Hz, 1H), 8.56 (t, J = 8.0 Hz, 1H), 7.92 (s, 1H), 7.91 (s, 2H), 7.60-7.58 (m, 1H), 7.42 (d, J = 7.6 Hz, 1H), 6.99 (dd, J = 15.6, 8.0 Hz, 1H), 6.77 (d, J = 15.6 Hz, 1H), 4.83-4.76 (m, 1H), 4.52-4.45 (m, 1H), 4.06-3.82 (m, 2H), 1.33 (d, J = 8.0 Hz, 3H) | 3418, 1646, 1163, 808, 564 |
| F13 | | 638.96 ([M + H]$^+$) | (400 MHz, DMSO-d$_6$) δ 8.65 (d, J = 7.2 Hz, 1H), 8.56 (t, J = 8.0 Hz, 1H), 7.92 (s, 1H), 7.91 (s, 2H), 7.60-7.58 (m, 1H), 7.42 (d, J = 7.6 Hz, 1H), 6.99 (dd, J = 15.6, 8.0 Hz, 1H), 6.77 (d, J = 15.6 Hz, 1H), 4.83-4.76 (m, 1H), 4.52-4.45 (m, 1H), 4.06-3.82 (m, 2H), 1.33 (d, J = 8.0 Hz, 3H) | 3418, 1646, 1163, 808, 564 |
| F14 | | 673.31 ([M + H]$^+$) | (300 MHz, CDCl$_3$) δ 7.91 (s, 1H), 7.82 (s, 2H), 7.62 (s, 1H), 7.53 (d, J = 7.5 Hz, 1H), 7.40 (d, J = 8.1 Hz, 1H), 6.80 (bs, 1H), 6.62 (s, 1H), 6.55 (d, J = 16.0 Hz, 1H), 6.50 (dd, J = 16.0, 8.0 Hz, 1H), 4.73-4.70 (m, 1H), 4.40-4.25 (m, 1H), 3.95-3.92 (m, 2H), 1.56 (d, J = 7.5 Hz, 3H) | 3422, 1640, 1169, 528 |
| F15 | | 589.00 ([M + H]$^+$) | (400 MHz, DMSO-d$_6$) δ 8.58 (t, J = 8.8 Hz, 1H), 8.32 (d, J = 8.0 Hz, 1H), 7.85 (s, 2H), 7.42 (s, 1H), 7.37 (d, J = 8.0 Hz, 1H), 7.31 (d, J = 7.6 Hz, 1H), 6.83 (dd, J = 15.6, 8.8 Hz, 1H), 6.71 (d, J = 15.6 Hz, 1H), 4.77-4.81 (m, 1H), 4.30-4.35 (m, 1H), 3.94-4.00 (m, 1H), 3.80-3.86 (m, 1H), 2.29 (s, 3H), 1.71-1.60 (m, 2H), 0.88 (t, J = 7.6 Hz, 3H) | 3295, 1682, 1164, 80 |
| F15A | | 588.9 ([M + H]$^+$) | (300 MHz, DMSO-d$_6$) δ 8.61 (t, J = 6.0 Hz, 1H), 8.35 (d, J = 7.5 Hz, 1H), 7.89 (s, 2H), 7.45 (s, 1H), 7.41 (d, J = 8.4 Hz, 1H), 7.34 (d, J = 7.8 Hz, 1H), 6.88 (dd, J = 15.9, 8.7 Hz, 1H), 6.75 (d, J = 15.9 Hz, 1H), 4.85-4.79 (m, 1H), 4.40-4.32 (m, 1H), 4.04-3.82 (m, 2H), 2.33 (s, 3H), 1.76-1.62 (m, 2H), 0.91 (t, J = 7.5 Hz, 3H) | 3290, 1646, 1165, 808. 725, 651 |
| F16 | | 643.06 ([M + H]$^+$) | (400 MHz, DMSO-d$_6$) δ 8.65-8.60 (m, 2H), 7.95 (s, 1H), 7.89-7.82 (m, 3H), 7.47 (d, J = 8.0 Hz, 1H), 7.04 (dd, J = 15.6, 9.2 Hz, 1H), 6.85 (d, J = 15.9 Hz, 1H), 4.85-4.80 (m, 1H), 4.38-4.33 (m, 1H), 4.01 (m, 2H), 1.72-1.58 (m, 2H), 0.86 (t, J = 7.6 Hz, 3H) | 3292, 1652, 1167, 809 |
| F16A | | 640.9 ([M − H]$^-$) | (300 MHz, DMSO-d$_6$) δ 8.66-8.62 (m, 2H), 7.98 (s, 1H), 7.92-7.87 (m, 3H), 7.51 (d, J = 7.8 Hz, 1H), 7.04 (dd, J = 15.6, 9.0 Hz, 1H), 6.89 (d, J = 15.6 Hz, 1H), 4.86-4.79 (m, 1H), 4.41-4.37 (m, 1H), 4.05-3.87 (m, 2H), 1.72-1.63 (m, 2H), 0.90 (t, J = 6.9 Hz, 3H) | 3290, 1651, 1166, 809 |
| F17 | | 628.95 ([M + H]$^+$) | (400 MHz, DMSO-d$_6$) δ 8.55 (t, J = 6.4 Hz, 1H), 8.42 (d, J = 7.6 Hz, 1H), 7.89 (s, 1H), 7.82 (s, 2H), 7.45 (s, 1H), 7.41-7.35 (m, 2H), 6.85 (dd, J = 16.0, 8.8 Hz, 1H), 6.74 (d, J = 15.6 Hz, 1H), 4.81-4.76 (m, 1H), 4.48-4.44 (m, 1H), 3.99-3.84 (m, 2H), 2.33 (s, 3H), 1.30 (d, J = 7.6 Hz, 3H) | 3299, 1686, 1165, 568 |
| F18 | | 629.0 ([M + H]$^+$) | (300 MHz, DMSO-d$_6$) δ 8.76 (d, J = 7.8 Hz, 1H), 8.61 (t, J = 12.9 Hz, 1H), 7.98 (s, 1 H), 7.92-7.88 (m, 3H), 7.56 (d, J = 8.1 Hz, 1H), 7.10 (dd, J = 16.2, 9.3 Hz, 1H), 6.89 (d, J = 16.0 Hz, 1H), 4.89-4.83 (m, 1H), 4.51-4.47 (m, 1H), 4.01-3.88 (m, 2H), 1.29 (d, J = 7.2 Hz, 3H) | 3407, 1713, 1160, 807 |
| F19 | | 692.88 ([M + H]$^+$) | (400 MHz, DMSO-d$_6$) δ 8.61 (d, J = 7.2 Hz, 1H), 8.52 (t, J = 12.8 Hz, 1H), 7.88 (s, 1H), 7.85 (s, 1H), 7.80 (s, 2H), 7.56 (d, J = 6.8 Hz, 1H), 7.38 (d, J = 8.0 Hz, 1H), 6.95 (dd, J = 15.6, 9.2 Hz, 1H), 6.72 (d, J = 15.6 Hz, 1H), 4.77-4.72 (m, 1H), 4.46-4.42 (m, 1H), 3.98-3.82 (m, 2H), 1.27 (d, J = 6.8 Hz, 3H) | 3404, 1646, 1165, 565 |
| F20 | | 629.29 ([M + H]$^+$) | (400 MHz, DMSO-d$_6$) δ 8.75 (d, J = 7.8 Hz, 1H), 8.59 (t, J = 6.6 Hz, 1H), 7.98-7.88 (m, 4H), 7.56 (d, J = 8.1 Hz, 1H), 7.09 (dd, J = 15.6, 8.7 Hz, 1H), 6.89 (d, J = 15.9 Hz, 1H), 4.89-4.83 (m, 1H), 4.52-4.47 (m, 1H), 4.01-3.88 (m, 2H), 1.30 (d, J = 6.9 Hz, 3H) | 3407, 1679, 1165, 808 |

TABLE 2A-continued

Analytical Data for Compounds in Table 1A.

| Compound Number | mp (° C.); [α]$_D^{25}$ | ESIMS | $^1$H NMR (δ)$^a$ | IR (cm$^{-1}$); $^{19}$F NMR (δ) |
|---|---|---|---|---|
| F20A | [α]$_D^{25}$ = +49.2 (c, 1% in CH$_2$Cl$_2$) | 628.89 ([M + H]$^+$) | (400 MHz, DMSO-d$_6$) δ 8.74 (d, J = 7.6 Hz, 1H), 7.98 (s, 1H), 7.92-7.89 (m, 3H), 7.56 (d, J = 8.4 Hz, 1H), 7.08 (dd, J = 15.6, 8.8 Hz, 1H), 6.88 (d, J = 15.6 Hz, 1H), 4.88-4.83 (m, 1H), 4.51-4.48 (m, 1H), 3.99-3.86 (m, 2H), 1.49 (d, J = 6.8 Hz, 3H) | 3315, 1657, 1167, 700 |
| F20B | [α]$_D^{25}$ = −38.8 (c, 1% in CH$_2$Cl$_2$) | 628.89 ([M + H]$^+$) | (400 MHz, DMSO-d$_6$) δ 8.74 (d, J = 7.6 Hz, 1H), 7.98 (s, 1H), 7.92-7.89 (m, 3H), 7.56 (d, J = 8.4 Hz, 1H), 7.08 (dd, J = 15.6, 8.8 Hz, 1H), 6.88 (d, J = 15.6 Hz, 1H), 4.88-4.83 (m, 1H), 4.51-4.48 (m, 1H), 3.99-3.86 (m, 2H), 1.49 (d, J = 6.8 Hz, 3H) | 3315, 1657, 1167, 700 |
| F20C | 61-70 | 629 ([M + H]$^+$) | 7.64 (t, J = 6.4 Hz, 1H), 7.52 (d, J = 7.9 Hz, 1H), 7.42 (s, 1H), 7.34 (d, J = 2.9 Hz, 3H), 6.64 (m, 1H), 6.91 (d, J = 11.4 Hz, 1H), 6.19 (dd, J = 11.4, 10.3 Hz, 1H), 4.94 (p, J = 7.1 Hz, 1H), 4.18 (q, J = 8.8 Hz, 1H), 3.95-3.71 (m, 2H), 1.52 (d, J = 6.9 Hz, 3H) | $^{19}$F NMR (376 MHz, CDCl3) δ-59.22, amide rotamers −69.43 and −69.45, −72.60 |
| F21 | | 682.98 ([M + H]$^+$) | (400 MHz, DMSO-d$_6$) δ 8.70 (d, J = 7.2 Hz, 1H), 8.55 (t, J = 6.4 Hz, 1H), 7.94 (s, 1H), 7.87-7.81 (m, 4H), 7.52 (d, J = 8.4 Hz, 1H), 7.04 (dd, J = 15.6, 9.2 Hz, 1H), 6.84 (d, J = 15.6 Hz, 1H), 4.80-4.75 (m, 1H), 4.47-4.44 (m, 1H), 3.97-3.78 (m, 2H), 1.29 (d, J = 7.6 Hz, 3H) | 3302, 1656, 1166, 557 |
| F22 | | 605.32 ([M + H]$^+$) | (300 MHz, DMSO-d$_6$) δ 8.65 (d, J = 7.5 Hz, 1H), 8.55 (t, J = 8.1 Hz, 1H), 7.93-7.87 (m, 3H), 7.78 (d, J = 8.1 Hz, 1H), 7.71-7.66 (m, 1H), 7.61 (d, J = 8.1 Hz, 1H), 7.41 (d, J = 6.0 Hz, 1H), 7.03 (dd, J = 15.6, 9.2 Hz, 1H), 6.79 (d, J = 15.9 Hz, 1H), 4.93-4.86 (m, 1H), 4.50-4.45 (m, 1H), 4.00-3.85 (m, 2H), 1.33 (d, J = 7.2 Hz, 3H) | 3412, 1645, 1164, 597 |
| F23 | | 609.00 ([M + H]$^+$) | 7.66 (d, J = 8.4 Hz, 1H), 7.43 (s, 1H), 7.40 (s, 2H), 7.34 (d, J = 7.6 Hz, 1H), 6.79 (s, 1H), 6.73 (s, 1H), 6.56 (d, J = 16.4 Hz, 1H), 6.43 (dd, J = 16.4, 8.0 Hz, 1H), 4.64-4.60 (m, 1H), 4.13-4.06 (m, 1H), 4.00-3.85 (m, 2H), 2.09 (m, 1H), 1.87-1.78 (m, 2H), 1.37 (t, J = 7.2 Hz, 3H) | 3291, 1645, 1165, 749 |
| F23A | | 608.99 ([M + H]$^+$) | (400 MHz, DMSO-d$_6$) δ 8.63 (t, J = 6.4 Hz, 1H), 8.59 (d, J = 8.0 Hz, 1H), 7.91 (s, 2H), 7.77 (s, 1H), 7.56 (d, J = 8.0 Hz, 1H), 7.42 (d, J = 8.0 Hz, 1H), 7.00 (dd, J = 15.6, 9.2 Hz, 1H), 6.78 (d, J = 15.6 Hz, 1H), 4.86-4.81 (m, 1H), 4.42-4.37 (m, 1H), 4.05-3.84 (m, 2H), 1.75-1.61 (m, 2H), 0.92 (t, J = 7.2 Hz, 3H) | 3292, 1646, 1165, 808 |
| F24 | | 622.97 ([M + H]$^+$) | (300 MHz, DMSO-d$_6$) δ 8.65 (d, J = 7.5 Hz, 1H), 8.56 (bs, 1H), 7.92-7.85 (m, 3H), 7.76-7.73 (m, 1H), 7.61 (d, J = 7.8 Hz, 1H), 7.42 (d, J = 7.8 Hz, 1H), 7.04 (dd, J = 15.6, 9.0 Hz, 1H), 6.08 (d, J = 15.9 Hz, 1H), 4.98-4.92 (m, 1H), 4.50-4.46 (m, 1H), 4.00-3.88 (m, 2H), 1.31 (d, J = 7.2 Hz, 3H) | 3421, 1646, 1168 |
| F25 | | 594.94 ([M + H]$^+$) | (300 MHz, DMSO-d$_6$) δ 8.66 (d, J = 7.2 Hz, 1H), 8.57 (t, J = 6.0 Hz, 1H), 7.91 (s, 2H), 7.77 (s, 1H), 7.57 (d, J = 6.9 Hz, 1H), 7.46 (d, J = 7.8 Hz, 1H), 7.02 (dd, J = 15.6, 9.0 Hz, 1H), 6.78 (d, J = 15.6 Hz, 1H), 4.87-4.80 (m, 1H), 4.51-4.47 (m, 1H), 4.04-3.88 (m, 2H), 1.31 (d, J = 7.2 Hz, 3H) | 3299, 1687, 1164, 808 |
| F26 | | 588.96 ([M − H]$^−$) | (300 MHz, DMSO-d$_6$) δ 10.54 (bs, 1H), 8.53 (d, J = 6.9 Hz, 1H), 7.89 (s, 2H), 7.45-7.38 (m, 3H), 6.88 (dd, J = 15.9, 8.4 Hz, 1H), 6.75 (d, J = 15.9 Hz, 1H), 4.87-4.79 (m, 2H), 4.67-4.65 (m, 1H), 4.53-4.50 (m, 1H), 2.33 (s, 3H), 1.37 (d, J = 6.9 Hz, 3H) | 3429, 1645, 1165, 750 |
| F27 | | 655.27 ([M + H]$^+$) | (300 MHz, DMSO-d$_6$) δ 10.52 (bs, 1H), 8.74 (d, J = 5.7 Hz, 1H), 7.93-7.91 (m, 3H), 7.62 (d, J = 8.7 Hz, 1H), 7.48 (d, J = 7.8 Hz, 1H), 6.98 (dd, J = 15.0, 6.3 Hz, 1H), 6.77 (d, J = 15.6 Hz, 1H), 4.88-4.80 (m, 2H), 4.52-4.43 (m, 2H), 1.37 (d, J = 6.9 Hz, 3H) | 3422, 1657, 1161, 806, 557 |
| F28 | | 644.94 ([M + H]$^+$) | (300 MHz, DMSO-d$_6$) δ 10.57 (bs, 1H), 8.85 (d, J = 7.5 Hz, 1H), 7.99-7.70 (m, 4H), 7.65 (d, J = 8.1 Hz, 1H), | 3257, 1663, 1170, 809, 552 |

TABLE 2A-continued

Analytical Data for Compounds in Table 1A.

| Compound Number | mp (° C.); [α]$_D^{25}$ | ESIMS | $^1$H NMR (δ)$^a$ | IR (cm$^{-1}$); $^{19}$F NMR (δ) |
|---|---|---|---|---|
| | | | 7.07 (dd, J = 15.9, 6.9 Hz, 1H), 6.89 (d, J = 15.6 Hz, 1H), 4.88-4.84 (m, 2H), 4.67-4.50 (m, 2H), 1.36 (d, J = 6.9 Hz, 3H) | |
| F29 | | 602.94 ([M − H]$^-$) | (300 MHz, DMSO-d$_6$) δ 9.87 (bs, 1H), 8.40 (bs, 1H), 7.89 (s, 2H), 7.54 (d, J = 8.1 Hz, 1H), 7.45 (s, 1H), 7.41 (d, J = 7.8 Hz, 1H), 6.88 (dd, J = 15.9, 8.7 Hz, 1H), 6.75 (d, J = 15.3 Hz, 1H), 4.85-4.79 (m, 1H), 4.55-4.50 (m, 2H), 2.32 (s, 3H), 1.60 (s, 6H) | 3420, 1645, 1164, 750 |
| F30 | | 611.0 ([M + H]$^+$) | (300 MHz, DMSO-d$_6$) δ 10.65 (bs, 1H), 8.75 (d, J = 6.9 Hz, 1H), 7.90 (s, 2H), 7.78 (s, 1H), 7.58-7.49 (m, 2H), 6.98 (dd, J = 14.7 Hz, 8.0 Hz, 1H), 6.78 (d, J = 15.3 Hz, 1H), 4.89-4.84 (m, 2H), 4.78-4.60 (m, 1H), 4.59-4.49 (m, 1H), 1.37 (d, J = 6.9 Hz, 3H) | 3432, 1651, 1259, 750 |
| F31 | | 618.87 ([M − H]$^-$) | (300 MHz, DMSO-d$_6$) δ 10.14 (s, 1H), 9.72 (broad s, 1H), 7.88 (s, 2H), 7.40-7.34 (m, 2H), 7.24 (d, J = 7.8 Hz, 1H), 6.81 (dd, J = 16.0, 8.0 Hz, 1H) 6.69 (d, J = 16.0 Hz, 1H), 4.84-4.78 (m, 1H), 4.55-4.50 (m, 2H), 2.29 (s, 3H), 1.76 (s, 6H) | 3436, 1261, 750 |

$^a$$^1$H NMR spectral data were acquired using a 400 MHz instrument in CDCl$_3$ except where noted. HRMS data are noted observed value (theoretical value).

TABLE 2B

Analytical Data for Compounds in Table 1B.

| Compound Number | mp (° C.) | ESIMS | $^1$H NMR (δ)$^a$ | IR (cm$^{-1}$); $^{19}$F NMR (δ) |
|---|---|---|---|---|
| P1 | | 590.91 ([M + H]$^+$) | (400 MHz, DMSO-d$_6$) δ 8.69 (t, J = 5.6 Hz, 1H), 8.56 (t, J = 6.4 Hz, 1H), 7.93-7.88 (m, 3H), 7.77-7.75 (m, 1H), 7.70-7.66 (m, 1H), 7.62-7.60 (m, 1H), 7.45 (d, J = 8.0 Hz, 1H), 7.03 (dd, J = 15.6, 8.8 Hz, 1H), 6.78 (d, J = 15.6 Hz, 1H), 4.92-4.87 (m, 1H), 3.97-3.90 (m, 4H) | 3327, 1703, 1164, 595 |
| P2 | | 581.91 ([M − H]$^-$) | 7.63-7.62 (m, 1H), 7.58 (d, J = 8.4 Hz, 1H), 7.39-7.37 (m, 1H), 7.12 (d, J = 8.0 Hz, 2H), 6.78 (t, J = 4.8 Hz, 1H), 6.65 (bs, 1H), 6.59 (d, J = 16.0 Hz, 1H), 6.39 (dd, J = 15.6, 7.6 Hz, 1H), 4.24-4.20 (m, 3H), 4.00-3.92 (m, 2H) | 3280, 2243, 1637, 1166 |
| P12 | | 577.07 ([M + H]$^+$) | (400 MHz, DMSO-d$_6$) δ 8.61-8.54 (m, 2H), 7.86 (d, J = 6.4 Hz, 2H), 7.53 (d, J = 8.0 Hz, 1H), 7.45-7.42 (m, 2H), 6.95 (dd, J = 15.6, 9.6 Hz, 1H), 6.80 (d, J = 15.6 Hz, 1H), 4.86-4.76 (m, 1H), 3.98-3.89 (m, 4H), 2.43 (s, 3H) | 3311, 1646, 1164, 714 |
| P14 | | 638.80 ([M − H]$^-$) | (300 MHz, DMSO-d$_6$) δ 10.55 (t, J = 6.0 Hz, 1H), 10.53 (t, J = 5.2 Hz, 1H), 7.90 (s, 1H), 7.87 (d, J = 8.8 Hz, 2H), 7.59-7.56 (m, 1H), 7.37-7.35 (m, 1H), 6.98 (dd, J = 15.6, 9.0 Hz, 1H), 6.76 (d, J = 15.9 Hz, 1H), 4.84-4.77 (m, 1H), 4.70-4.58 (m, 4H) | 3435, 1166, 749, 597 |
| P15 | | 590.8 ([M − H]$^-$) | (400 MHz, DMSO-d$_6$) δ 10.62 (t, J = 6.0 Hz, 1H), 10.54 (t, J = 5.2 Hz, 1H), 7.89 (s, 2H), 7.42 (s, 1H), 7.39-7.37 (m, 1H), 7.24 (d, J = 7.6 Hz, 1H), 6.84 (dd, J = 15.6, 8.8 Hz, 1H), 6.74 (d, J = 15.6 Hz, 1H), 4.84-4.80 (m, 1H), 4.71 (d, J = 6.0 Hz, 2H), 4.65-4.56 (m, 2H), 2.35 (s, 3H) | 3243, 2923, 1106, 614 |
| P82 | | 590.9 ([M + H]$^+$) | (300 MHz, DMSO-d$_6$) δ 8.65 (d, J = 7.2 Hz, 1H), 8.56 (t, J = 6.6 Hz, 1H), 7.88 (s, 1H), 7.59-7.56 (m, 2H), 7.47-7.40 (m, 2H), 6.90-6.88 (m, 2H), 4.97-4.94 (m, 1H), 4.50-4.46 (m, 1H), 4.00-3.88 (m, 2H), 1.31 (d, J = 7.2 Hz, 3H) | 3298, 1643, 1162 |
| P84 | 82-85 | 581.1 ([M + H]$^+$) | (300 MHz, DMSO-d$_6$) δ 8.74 (d, J = 7.2 Hz, 1H), 8.59 (t, J = 6.6 Hz, 1H), 7.96 (s, 1H), 7.89 (d, J = 7.5 Hz, 1H), 7.61-7.44 (m, 3H) 6.99 (m, 2H), 4.98-4.95 (m, 1H), 4.51-4.47 (m, 1H), 3.99-3.88 (m, 2H), 1.29 (d, J = 6.8 Hz, 3H) | |
| P156 | | 639.0 ([M + H]$^+$) | (400 MHz, DMSO-d$_6$) δ 8.66 (d, J = 8.0 Hz, 1H), 8.56 (t, J = 5.6 Hz, 1H), 7.95-7.93 (m, 2H), 7.60 (d, J = 7.6 Hz, 1H), 7.42 (d, J = 8.0 Hz, 1H), 7.03 (dd, J = 15.6, 8.8 Hz, 1H), 6.94 (d, J = 15.6 Hz, 1H), 5.09-5.04 (m, 1H), 4.53-4.43 (m, 1H), 4.02-3.86 (m, 2H), 1.31 (t, J = 6.8 Hz, 3H) | 3436, 2924, 1662, 1162, 750 |
| P226 | | 620.95 ([M + H]$^+$) | (300 MHz, DMSO-d$_6$) δ 8.65 (d, J = 7.5 Hz 1H), 8.57 (t, J = 6.3 Hz, 1H), 7.90 (s, 1H), 7.60-7.55 | 3413, 1668, 1161 |

TABLE 2B-continued

Analytical Data for Compounds in Table 1B.

| Compound Number | mp (° C.) | ESIMS | $^1$H NMR (δ)$^a$ | IR (cm$^{-1}$); $^{19}$F NMR (δ) |
|---|---|---|---|---|
| P228 | | 610.94 ([M + H]$^+$) | (m, 4H), 7.41(d, J = 7.8 Hz, 2H), 6.99 (dd, J = 15.6, 9.0 Hz, 1H), 6.78 (d, J = 15.9 Hz, 1H), 4.85-4.79 (m, 1H), 4.50-4.43 (m, 1H), 4.00-3.85 (m, 2H), 1.33 (d, J = 7.8 Hz, 3H) (300 MHz, DMSO-d$_6$) δ 8.74 (d, J = 7.5 Hz, 1H), 8.61 (t, J = 6.6 Hz, 1H), 7.96 (s, 1H), 7.91 (d, J = 8.1 Hz, 1H), 7.63-7.53 (m, 4H), 7.41 (d, J = 7.5 Hz, 1H), 7.08 (dd, J = 15.6, 8.7 Hz, 1H), 6.89 (d, J = 15.6 Hz, 1H), 4.84-4.81 (m, 1H), 4.51-4.43 (m, 1H), 3.99-3.85 (m, 2H), 1.29 (d, J = 7.5 Hz, 3H) | 3413, 1668, 1161, 564 |
| P298 | | 634.8 ([M + H]$^+$) | (400 MHz, DMSO-d$_6$) δ 8.65 (d, J = 7.6 Hz, 1H), 8.55 (t, J = 6.4 Hz, 1H), 7.92-7.91 (d, J = 1.6 Hz, 1H), 7.67 (s, 1H), 7.62-7.58 (m, 2H), 7.54 (d, J = 9.6 Hz, 1H), 7.41 (d, J = 8.0 Hz, 1H), 6.97 (dd, J = 15.6, 9.2 Hz, 1H), 6.77 (d, J = 15.6 Hz, 1H), 4.82-4.77 (m, 1H), 4.50-4.46 (m, 1H), 4.00-3.82 (m, 2H), 1.31 (t, J = 7.2 Hz, 3H) | 3307, 2925, 1652, 1164 |
| P300 | | 623.2 ([M + H]$^+$) | (400 MHz, DMSO-d$_6$) δ 8.74 (d, J = 7.6 Hz, 1H), 8.60 (d, J = 16.0 Hz, 1H), 7.97 (s, 1H), 7.90 (d, J = 8.0 Hz, 1H), 7.68 (s, 1H), 7.62-7.59 (m, 1H), 7.56-7.53 (m, 2H), 7.06 (dd, J = 15.6, 9.2 Hz, 1H), 6.88 (d, J = 15.6 Hz, 1H), 4.84-4.80 (m, 1H), 4.51-4.47 (m, 1H), 4.03-3.85 (m, 2H), 1.29 (d, J = 7.2 Hz, 3H) | 3296, 1652, 1167 |
| P442 | | 584.87 ([M + H]$^+$) | (400 MHz, DMSO-d$_6$) δ 8.64 (d, J = 7.2 Hz, 1H), 8.57 (t, J = 12.8 Hz, 1H), 7.87 (d, J = 1.2 Hz, 1H), 7.58-7.52 (m, 2H), 7.48 (d, J = 8.4 Hz, 1H), 7.41-7.37 (m, 2H), 6.90 (dd, J = 16.0, 8.8 Hz, 1H), 6.74 (d, J = 15.6 Hz, 1H), 4.68-4.63 (m, 1H), 4.49-4.46 (m, 1H), 3.99-3.86 (m, 2H), 2.35 (s, 3H), 1.28 (d, J = 7.2 Hz, 3H) | 3410, 1692, 1163, 769, 565 |
| P444 | | 574.98 ([M + H]$^+$) | (400 MHz, DMSO-d$_6$) δ 8.73 (d, J = 8.0 Hz, 1H), 8.60 (t, J = 6.0 Hz, 1H), 7.92 (s, 1H), 7.88 (d, J = 8.4 Hz, 1H), 7.55-7.53 (m, 2H), 7.48 (d, J = 8.4 Hz, 1H), 7.40 (d, J = 8.4 Hz, 1H), 6.98 (dd, J = 15.8, 8.8 Hz, 1H), 6.86 (d, J = 15.6 Hz, 1H), 4.70-4.66 (m, 1H), 4.50-4.47 (m, 1H), 3.99-3.82 (m, 2H), 2.35 (s, 3H), 1.27 (d, J = 7.2 Hz, 3H) | 3292, 1661, 1158, 741 |
| P514 | | 583.0 ([M + H]$^+$) | (300 MHz, DMSO-d$_6$) δ 8.64 (d, J = 7.2 Hz, 1H), 8.57 (t, J = 6.3 Hz, 1H), 7.86 (s, 1H), 7.58 (d, J = 7.5 Hz, 1H), 7.41 (d, J = 8.1 Hz, 1H), 7.26 (d, J = 6.6 Hz, 2H), 6.88 (dd, J = 15.9, 8.4 Hz, 1H), 6.73 (d, J = 15.9 Hz, 1H), 4.58-4.46 (m, 2H), 4.00-3.85 (m, 2H), 2.24 (s, 6H), 1.31 (d, J = 7.5 Hz, 3H) | 3276, 1638, 1167, 598 |
| P516 | | 573.37 ([M + H]$^+$) | (300 MHz, DMSO-d$_6$) δ 8.73 (d, J = 7.8 Hz, 1H), 8.61 (t, J = 6.3 Hz, 1H), 7.88 (d, J = 8.4 Hz, 2H), 7.55 (d, J = 8.1 Hz, 1H), 7.27 (d, J = 6.9 Hz, 2H), 6.98 (dd, J = 15.6, 8.4 Hz, 1H), 6.85 (d, J = 15.6 Hz, 1H), 4.57-4.46 (m, 2H), 3.99-3.85 (m, 2H), 2.24 (s, 6H), 1.29 (d, J = 7.2 Hz, 3H) | 3299, 1654, 1165 |
| P568 | | 692.88 ([M + H]$^+$) | (300 MHz, DMSO-d$_6$) δ 8.65 (d, J = 7.8 Hz, 1H), 8.55 (t, J = 7.8 Hz, 1H), 7.98 (s, 1H), 7.90 (s, 1H), 7.85 (d, J = 8.7 Hz, 1H), 7.60-7.57 (m, 1H), 7.51-7.48 (m, 1H), 7.41-7.39 (m, 1H), 6.96 (dd, J = 15.6, 8.7 Hz, 1H), 6.76 (d, J = 15.9 Hz, 1H), 4.81-4.72 (m, 1H), 4.50-4.46 (m, 1H), 4.01-3.82 (m, 2H), 1.31 (d, J = 6.9 Hz, 3H) | 3306, 1646, 1164 |
| P586 | | 646.9 ([M − H]$^−$) | 7.64 (s, 1H), 7.56-7.54 (m, 2H), 7.43-7.39 (m, 2H), 7.33 (s, 2H), 6.81 (bs, 1H), 6.57 (d, J = 16.0 Hz, 1H), 6.50 (d, J = 8.0 Hz, 1H), 6.45 (dd, J = 16.0, 7.6 Hz, 1H), 4.75-4.72 (m, 1H), 4.14-4.10 (m, 1H), 4.00-3.90 (m, 2H), 1.30 (d, J = 7.2 Hz, 3H) | 3384, 1647, 1164, 749, 566 |
| P588 | | 638.84 ([M + H]$^+$) | (300 MHz, CDCl$_3$) δ 7.69 (s, 1H), 7.62-7.59 (m, 1H), 7.55-7.49 (m, 2H), 7.42 (s, 1H), 7.32 (s, 1H), 6.88 (bs, 1H), 6.65 (d, J = 16.2 Hz, 1H), 6.49 (dd, J = 16.2, 8.1 Hz, 1H), 6.34 (d, J = 7.2 Hz, 1H), 4.76-4.71 (m, 1H), 4.15-4.12 (m, 1H), 3.96-3.89 (m, 2H), 1.49 (d, J = 7.3 Hz, 3H) | 3304, 2928, 1650, 1165, 673, 558 |
| P660 | | 682.8 ([M + H]$^+$) | (400 MHz, DMSO-d$_6$) δ 8.74 (d, J = 8.0 Hz, 1H), 8.60 (t, J = 8.8 Hz, 1H), 7.99-7.96 (m, 2H), 7.90 (d, J = 8.3 Hz, 1H), | 3310, 1650, 1166, 558 |

TABLE 2B-continued

Analytical Data for Compounds in Table 1B.

| Compound Number | mp (° C.) | ESIMS | ¹H NMR (δ)ᵃ | IR (cm⁻¹); ¹⁹F NMR (δ) |
|---|---|---|---|---|
| | | | 7.85 (d, J = 8.3 Hz, 1H), 7.55-7.50 (m, 2H), 7.04 (dd, J = 15.6, 8.8 Hz, 1H), 6.86 (d, J = 16.0 Hz, 1H), 4.83-4.78 (m, 1H), 4.51-4.47 (m, 1H), 3.99-3.86 (m, 2H), 1.29 (d, J = 5.1 Hz, 3H) | |
| P730 | | 615.85 ([M + H]⁺) | (300 MHz, DMSO-d₆) δ 8.67 (d, J = 7.8 Hz, 1H), 8.55 (t, J = 6.6 Hz, 1H), 8.31 (s, 1H), 7.90-7.86 (m, 3H), 7.60 (d, J = 9.2 Hz, 1H), 7.42 (d, J = 8.1 Hz, 1H), 6.98 (dd, J = 15.6, 8.7 Hz, 1H), 6.79 (d, J = 15.6 Hz, 1H), 4.96-4.95 (m, 1H), 4.50-4.45 (m, 1H), 3.96-3.88 (m, 2H), 1.31 (d, J = 9.3 Hz, 3H) | 3299, 1651, 1166, 739 |
| P732 | | 605.96 ([M + H]⁺) | (300 MHz, CDCl₃) δ 7.91 (s, 1H), 7.69 (s, 1H), 7.64-7.50 (m, 4H), 6.71 (bs, 1H), 6.67 (d, J = 16.2 Hz, 1H), 6.52 (dd, J = 15.9, 7.8 Hz, 1H), 6.30 (d, J = 6.9 Hz, 1H), 4.73-4.69 (m, 1H), 4.30-4.24 (m, 1H), 3.96-3.91 (m, 2H), 1.49 (d, J = 7.2 Hz, 3H) | 3297, 1651, 1167, 749 |
| P802 | | 578.1 ([M − H]⁻) | (300 MHz, DMSO-d₆) δ 8.65 (d, J = 7.2 Hz, 1H), 8.56 (t, J = 6.3 Hz, 1H), 8.20-8.18 (m, 1H), 8.00-7.90 (m, 2H), 7.66-7.54 (m, 2H), 7.42 (d, J = 8.1 Hz, 1H), 6.99 (dd, J = 15.9, 9.3 Hz, 1H), 6.77 (d, J = 15.9 Hz, 1H), 4.88-4.82 (m, 1H), 4.51-4.46 (m, 1H), 4.00-3.88 (m, 2H), 1.29 (d, J = 7.2 Hz, 3H) | 3307, 2927, 2238, 1659, 1166 |
| P804 | | 570.3 ([M + H]⁺) | (300 MHz, DMSO-d₆) δ 8.74 (d, J = 7.8 Hz, 1H), 8.59 (t, J = 6.6 Hz, 1H), 8.21-8.19 (m, 1H), 8.01-7.96 (m, 2H), 7.90 (d, J = 8.1 Hz, 1H), 7.66-7.60 (m, 1H), 7.56 (d, J = 8.1 Hz, 1H), 7.08 (dd, J = 15.9, 8.7 Hz, 1H), 6.88 (d, J = 15.6 Hz, 1H), 4.91-4.85 (m, 1H), 4.52-4.47 (m, 1H), 3.99-3.88 (m, 2H), 1.29 (d, J = 6.9 Hz, 3H) | 3301, 3078, 2239, 1657, 1167 |
| P1090 | | 569.89 ([M + H]⁺) | (300 MHz, DMSO-d₆) δ 8.64 (d, J = 7.5 Hz, 1H), 8.55 (t, J = 6.3 Hz, 1H), 7.86 (s, 1H), 7.58 (d, J = 7.2 Hz, 1H), 7.47 (d, J = 6.9 Hz, 1H), 7.41-7.36 (m, 3H), 7.21-7.15 (m, 1H), 6.91 (dd, J = 15.6, 8.7 Hz, 1H), 6.74 (d, J = 15.9 Hz, 1H), 4.66-4.60 (m, 1H), 4.50-4.45 (m, 1H), 4.03-3.85 (m, 2H), 2.26 (s, 3H), 1.31 (d, J = 7.2 Hz, 3H) | 3277, 1698, 1167, 518 |
| P1092 | | 559.05 ([M + H]⁺) | (300 MHz, DMSO-d₆) δ 8.74 (d, J = 7.8 Hz, 1H), 8.59 (t, J = 6.3 Hz, 1H), 7.92 (s, 1H), 7.89 (d, J = 8.1 Hz, 1H), 7.56 (d, J = 8.1 Hz, 1H), 7.48 (d, J = 7.2 Hz, 1H), 7.42-7.38 (m, 1H), 7.19 (t, J = 9.3 Hz, 1H), 7.00 (dd, J = 15.9, 8.7 Hz, 1H), 6.85 (d, J = 15.9 Hz, 1H), 4.69-4.62 (m, 1H), 4.51-4.47 (m, 1H), 4.02-3.85 (m, 2H), 2.26 (s, 3H), 1.29 (d, J = 7.2 Hz, 3H) | 3437, 1643, 1165 |
| P1197 | | 576.83 ([M + H]⁺) | (300 MHz, CDCl₃) δ 7.62-7.56 (m, 2H), 7.40-7.37 (m, 1H), 7.05-7.00 (m, 2H), 6.72 (bs, 1H), 6.56 (bs, 1H), 6.51 (d, J = 16.2 Hz, 1H), 6.52 (dd, J = 15.9, 7.5 Hz, 1H), 4.21 (d, J = 5.4 Hz, 2H), 4.13-4.08 (m, 1H), 4.02-3.91 (m, 2H) | 3311, 1655, 1166 |
| P1269 | | 659.07 ([M + H]⁺) | (300 MHz, CDCl₃) δ 7.91 (s, 1H), 7.83 (s, 2H), 7.64-7.56 (m, 2H), 7.42-7.39 (m, 1H), 6.74 (bs, 1H), 6.62 (bs, 1H), 6.61 ( d, J = 15.9 Hz, 1H), 6.50 (dd, J = 15.7, 7.8 Hz, 1H), 4.35-4.30 (m, 1H), 4.21 (d, J = 6.0 Hz, 2H), 4.02-3.90 (m, 2H) | 3317, 1706, 1175, 559 |
| P1340 | | 607.00 ([M − H]⁻) | (300 MHz, DMSO-d₆) δ 8.68 (t, J = 5.7 Hz, 1H), 8.56 (t, J = 6.3 Hz, 1H), 7.93 (s, 1H), 7.87-7.83 (m, 2H), 7.76-7.75 (m, 1H), 7.62-7.55 (m, 1H), 7.45 (d, J = 7.8 Hz, 1H), 7.05 (dd, J = 15.6, 9.0 Hz, 1H), 6.88 (d, J = 15.3 Hz, 1H), 4.99-4.92 (m, 1H), 4.01-3.90 (m, 4H) | 3411, 1652, 1166 |
| P1411 | | 624.92 ([M + H]⁺) | (300 MHz, CDCl₃) δ 7.64 (s, 1H), 7.58-7.55 (m, 3H), 7.51 (s, 1H), 7.41-7.38 (m, 1H), 6.77 (bs, 1H), 6.72 (bs, 1H), 6.59 (d, J = 15.9 Hz, 1H), 6.48 (dd, J = 15.9, 7.5 Hz, 1H), 4.24-4.19 (m, 4H), 4.01-3.90 (m, 1H) | 3098, 1721, 1214, 723, 513 |
| P1483 | | 608.78 ([M + H]⁺) | (300 MHz, CDCl3) δ 7.62-7.54 (m, 3H), 7.39 (d, J = 8.1 Hz, 1H), 7.29-7.24 (m, 1H), 6.84-6.82 (m, 2H), 6.56 (d, J = 15.6 Hz, 1H), 6.49 (dd, J = 15.6, 6.6 Hz, 1H), 4.23-4.19 (m, 2H), 4.01-3.93 (m, 2H) | 3300, 1657, 1164, 560 |
| P1556 | | 614.84 ([M + H]⁺) | 7.70 (s, 1H), 7.63-7.61 (m, 1H), 7.56-7.51 (m, 1H), 7.41 (s, 2H), 6.65 (d, J = 15.6 Hz, 1H), 6.60 (bs, 2H), 6.50 (dd, | 3369, 1719, 1164, 807. |

TABLE 2B-continued

Analytical Data for Compounds in Table 1B.

| Compound Number | mp (° C.) | ESIMS | ¹H NMR (δ)ᵃ | IR (cm⁻¹); ¹⁹F NMR (δ) |
|---|---|---|---|---|
| P1558 | | 595.00 ([M − H]⁻) | (300 MHz, CDCl₃) δ 8.89 (bs, 1H), 7.72-7.69 (d, J = 8.1 Hz, 1H), 7.45-7.35 (m, 4H), 7.25-7.19 (m, 1H), 6.58 (d, J = 15.9 Hz, 1H), 6, 45 (dd, J = 15.9, 7.8 Hz, 1H), 4.57 (d, J = 5.7 Hz, 2H), 4.49-4.38 (m, 2H), 4.16-4.03 (m, 1H) J = 15.2, 6.8 Hz, 1H), 4.19-4.13 (m, 3H), 3.98-3.94 (m, 2H) | 3351, 1660, 1161, 700 |
| P1559 | | 628.95 ([M − H]⁻) | (300 MHz, DMSO-d₆) δ 10.45 (t, J = 6.4 Hz, 1H), 8.97 (t, J = 6.0 Hz, 1H), 8.02-7.92 (m, 4H), 7.77 (d, J = 7.5 Hz, 1H), 7.10 (dd, J = 15.6, 9.0 Hz, 1H), 6.90 (d, J = 15.6 Hz, 1H), 4.90-4.82 (m, 1H), 4.63-4.58 (m, 2H), 4.23 (d, J = 6.0 Hz, 2H) | 3398, 1664, 1163, 808 |
| P1560 | | 574.88 ([M − H]⁻) | (400 MHz, DMSO-d₆) δ 10.38 (t, J = 6.0 Hz, 1H), 8.65 (t, J = 5.6 Hz, 1H), 7.88 (s, 2H), 7.50-7.42 (m, 3H), 6.88 (dd, J = 15.6, 8.8 Hz, 1H), 6.75 (d, J = 15.6 Hz, 1H), 4.85-4.81 (m, 1H), 4.63-4.54 (m, 2H), 4.24 (d, J = 6.2 Hz, 2H), 2.36 (s, 3H) | 3246, 1646, 1161, 808 |
| P1564 | | 576.6 ([M + H]⁺) | (400 MHz, DMSO-d₆) δ 10.48 (t, J = 6.0 Hz, 1H), 8.74 (t, J = 6.2 Hz, 1H), 7.89 (s, 2H), 7.41-7.36 (m, 2H), 7.19 (d, J = 8.0 Hz, 1H), 6.84 (dd, J = 15.6, 8.8 Hz, 1H), 6.73 (d, J = 15.6 Hz, 1H), 4.84-4.79 (m, 1H), 4.42 (d, J = 6.0 Hz, 2H), 3.98-3.92 (m, 2H), 2.32 (s, 3H) | 3351, 1684, 1163, 808 |
| P1566 | | 597.00 ([M + H]⁺) | (400 MHz, DMSO-d₆) δ 8.74 (t, J = 5.6 Hz, 1H), 8.30 (t, J = 6.0 Hz, 1H), 8.03-7.84 (m, 4H), 7.61 (d, J = 8.4 Hz, 1H), 7.09 (dd, J = 15.6, 8.8 Hz, 1H), 6.89 (d, J = 16.4 Hz, 1H), 4.88-4.81 (m, 1H), 3.89 (d, J-5.6 Hz, 2H), 3.59-3.48 (m, 3H) | 3323, 1654, 1115, 808 |
| P1589 | | 638.9 ([M + H]⁺) | (300 MHz, DMSO-d₆) δ 8.63 (t, J = 5.7 Hz, 1H), 8.50 (d, J = 9.0 Hz, 1H), 7.93-7.91 (m, 3H), 7.62-7.60 (m, 1H), 7.42 (d, J = 7.8 Hz, 1H), 7.01 (dd, J = 15.6, 9.6 Hz, 1H), 6.77 (d, J = 15.6 Hz, 1H), 4.88-4.80 (m, 1H), 4.66-4.60 (m, 1H), 4.00-3.97 (m, 1H), 3.87-3.80 (m, 1H), 1.27 (d, J = 6.9 Hz, 3H) | 3412, 1657, 1169, 749, 565 |
| P1591 | | 628.95 ([M + H]⁺) | (300 MHz, DMSO-d₆) δ 8.74 (t, J = 6.0 Hz, 1H), 8.51 (d, J = 8.7 Hz, 1H), 7.99 (s, 1H), 7.92-7.90 (m, 3H), 7.58 (d, J = 8.1 Hz, 1H), 7.10 (dd, J = 15.6, 8.7 Hz, 1H), 6.89 (d, J = 15.9 Hz, 1H), 4.89-4.86 (m, 1H), 4.66-4.58 (m, 1H), 4.00-3.92 (m, 1H), 3.88-3.80 (m, 1H), 1.27 (d, J = 7.2 Hz, 3H) | 3436, 1667, 1261, 749 |
| P1592 | | 574.98 ([M + H]⁺) | (300 MHz, DMSO-d₆) δ 8.51 (d, J = 8.7 Hz, 1H), 8.41 (t, J = 6.0 Hz, 1H), 7.89 (s, 2H), 7.45-7.35 (m, 3H), 6.83 (dd, J = 15.6, 8.5 Hz, 1H), 6.75 (d, J = 15.6 Hz, 1H), 4.86-4.79 (m, 1H), 4.65-4.60 (m, 1H), 3.98-3.91 (m, 1H), 3.85-3.78 (m, 1H), 2.36 (s, 3H), 1.26 (d, J = 6.9 Hz, 3H) | 3418, 1651, 1163, 748 |
| P1599 | | 689.9 ([M + H]⁺) | (300 MHz, DMSO-d₆) δ 8.67 (bs, 1H), 8.60 (t, J = 6.0 Hz, 1H), 7.95 (d, J = 9.9 Hz, 2H), 7.91 (s, 1H), 7.78 (d, J = 6.6 Hz, 1H), 7.42 (d, J = 7.8 Hz, 1H) 7.12 (dd, J = 15.6, 9.9 Hz, 1H), 6.78 (d, J = 15.3 Hz, 1H), 4.94-4.91 (m, 1H), 4.52-4.45 (m, 1H), 4.00-3.85 (m, 2H), 1.33 (d, J = 6.9 Hz, 3H) | 3415, 1599, 1162, 748 |
| P1601 | | 678.6 ([M + H]⁺) | (300 MHz, DMSO-d₆) δ 8.73 (bs, 1H), 8.59 (t, J = 6.0 Hz, 1H), 7.95 (d, J = 9.9 Hz, 2H), 7.88-7.83 (m, 2H), 7.56 (d, J = 7.2 Hz, 1H), 7.12 (dd, J = 15.6, 10.5 Hz, 1H), 6.78 (d, J = 15.3 Hz, 1H), 4.94-4.91 (m, 1H), 4.51-4.43 (m, 1H), 3.99-3.88 (m, 2H), 1.31 (d, J = 6.9 Hz, 3H) | 3423, 1646, 1141, 807 |
| P1603 | 113-117 | 563 ([M + H]⁺) | 7.80-7.72 (m, 2H), 7.48-7.44 (m, 2H), 7.42 (s, 2H), 6.92 (t, J = 6.4 Hz, 1H), 6.62 (m, 1H), 6.42 (dd, J = 15.9, 8.0 Hz, 1H), 4.75 (p, J = 7.1 Hz, 1H), 4.11 (p, J = 8.5 Hz, 1H), 4.07-3.79 (m, 2H), 1.54 (d, J = 7.0 Hz, 3H) | ¹⁹F NMR (376 MHz, CDCl₃) δ −68.66, −72.52 |
| P1611A | | 621.0 ([M + H]⁺) | (300 MHz, DMSO-d₆) δ 8.60 (d, J = 7.8 Hz, 1H), 8.28 (t, J = 5.7 Hz, 1H), 7.91 (s, 3H), 7.61-7.58 (m, 1H), 7.43 (d, J = 8.1 Hz, 1H), 7.01 (dd, J = 15.6, 9.0 Hz, 1H), 6.77 (d, J = 15.9 Hz, 1H), 4.86-4.79 (m, 1H), 4.49-4.44 (m, 1H), 3.55-3.31 (m, 2H), 1.30 (d, J = 6.9 Hz, 3H) | 3410, 2925, 1645, 1115, 748, 561 |
| P1613A | | 611.1 ([M + H]⁺) | (300 MHz, DMSO-d₆) δ 8.70 (d, J = 7.8 Hz, 1H), 8.31 (t, J = 5.7 Hz, 1H), 7.98 (s, 1H), 7.92-7.88 (m, 3H), 7.57-7.55 (m, | 3297, 1651, 1115, 808 |

TABLE 2B-continued

Analytical Data for Compounds in Table 1B.

| Compound Number | mp (° C.) | ESIMS | ¹H NMR (δ)$^a$ | IR (cm$^{-1}$); ¹⁹F NMR (δ) |
|---|---|---|---|---|
| | | | 1H), ), 7.09 (dd, J = 15.3, 9.0 Hz, 1H), 6.89 (d, J = 15.9 Hz, 1H), 4.89-4.82 (m, 1H), 4.52-4.43 (m, 1H), 3.57-3.47 (m, 2H), 1.29 (d, J = 7.5 Hz, 3H) | |
| P1616 | | 602.8 ([M + H]⁺) | (300 MHz, DMSO-d₆) δ 8.64 (d, J = 7.5 Hz, 1H), 8.11 (t, J = 5.4 Hz, 1H), 7.91 (s, 3H), 7.60-7.58 (m, 1H), 7.43 (d, J = 8.2 Hz, 1H), 7.00 (dd, J = 15.6, 9.0 Hz, 1H), 6.77 (d, J = 15.9 Hz, 1H), 4.86-4.53 (m, 1H), 4.51-4.42 (m, 2H), 4.35 (t, J = 5.1 Hz, 1H), 3.45-3.31 (m, 2H), 1.31 (d, J = 7.2 Hz, 3H) | 3305, 1650, 1169, 749, 559 |
| P1616A | | 602.8 ([M + H]⁺) | (400 MHz, DMSO-d₆) δ 8.53 (d, J = 7.60 Hz, 1H), 8.08 (t, J = 6.0 Hz, 1H), 7.91-7.90 (m 3H), 7.59 (d, J = 7.6 Hz, 1H), 7.43 (d, J = 8.0 Hz, 1H), 6.98 (dd, J = 16.0, 9.2 Hz, 1H), 6.77 (d, J = 16.0 Hz, 1H), 4.84-4.80 (m, 1H), 4.50-4.36 (m, 3H), 3.44-3.24 (m, 2H), 1.30 (d, J = 7.2 Hz, 3H) | 3407, 1651, 1169, 744, 559 |
| P1618A | | 593.1 ([M + H]⁺) | (300 MHz, DMSO-d₆) δ 8.64 (d, J = 7.8 Hz, 1H), 8.17 (t, J = 5.4 Hz, 1H), 8.03-7.87 (m, 3H), 7.60 (d, J = 7.8 Hz, 1H), 7.09 (dd, J = 15.9, 9.0 Hz, 1H), 6.89 (d, J = 15.9 Hz, 1H), 4.89-4.53 (m, 1H), 4.53-4.42 (m, 2H), 4.35 (t, J = 5.1 Hz, 1H), 3.44-3.42 (m, 2H), 1.28 (d, J = 6.9 Hz, 3H) | 3411, 1651, 1115, 809 |
| P1621 | | 585.0 ([M + H]⁺) | (300 MHz, DMSO-d₆) δ 8.50 (bs, 1H), 7.91 (s, 3H), 7.83-7.81 (m, 1H), 7.60 (d, J = 8.1 Hz, 1H), 7.43. (d, J = 8.1 Hz, 1H), 7.00 (dd, J = 15.9, 9.9 Hz, 1H), 6.77 (d, J = 15.9 Hz, 1H), 4.86-4.80 (m, 1H), 4.40-4.36 (m, 1H), 3.14-3.06 (m, 2H), 1.28 (d, J = 6.9 Hz, 3H), 1.03 (t, J = 6.0 Hz, 3H) | 3411, 1649, 1168, 806, 559 |
| P1623 | | 575.1 ([M + H]⁺) | (300 MHz, DMSO-d₆) δ 8.59 (bs, 1H), 7.97 (s, 1H), 7.92-7.85 (m, 4H), 7.57 (d, J = 7.8 Hz, 1H), 7.09 (dd, J = 16.2, 9.3 Hz, 1H), 6.88 (d, J = 15.9 Hz, 1H), 4.89-4.82 (m, 1H), 4.43-4.36 (m, 1H), 3.12-3.05 (m, 2H), 1.26 (d, J = 7.2 Hz, 3H), 1.05 (t, J = 7.5 Hz, 3H) | 3412, 1645, 1115, 749 |
| P1624 | | 521.2 ([M + H]⁺) | (300 MHz, DMSO-d₆) δ 8.26 (bs, 1H), 7.89 (s, 1H), 7.85-7.81 (m, 2H), 7.47-7.37 (m, 2H), 7.34 (d, J = 7.5 Hz, 1H), 6.88 (dd, J = 15.9, 8.7 Hz, 1H), 6.75 (d, J = 15.9 Hz, 1H), 4.85-4.79 (m, 1H), 4.39-4.34 (m, 1H), 3.13-3.04 (m, 2H), 2.48 (s, 3H), 1.28 (d, J = 7.5 Hz, 3H), 1.04 (t, J = 7.5 Hz, 3H) | 3307, 1642, 1114, 749 |
| P1631A | | 652.8 ([M + H]⁺) | (400 MHz, DMSO-d₆) δ 8.54 (d, J = 7.60 Hz, 1H), 8.07 (t, J = 5.4 Hz, 1H), 7.91-7.90 ( m 3H), 7.60 (d, J = 9.2 Hz, 1H), 7.43 (d, J = 8.0 Hz, 1H), 6.98 (dd, J = 16.0, 9.0 Hz, 1H), 6.77 (d, J = 16.0 Hz, 1H), 4.85-4.80 (m, 1H), 4.41-4.37 (m, 1H), 3.40-3.26 (m, 2H), 2.50-2.38 (m, 2H), 1.28 (d, J = 7.6 Hz, 3H) | 3297, 1646, 1161, 742, 555 |
| P1633A | | 640.7 ([M − H]⁻) | (300 MHz, DMSO-d₆) δ 8.66 (d, J = 7.2 Hz, 1H), 8.13 (t, J = 5.4 Hz, 1H), 7.97 (s, 1H), 7.92-7.88 (m, 3H), 7.58 (d, J = 8.2 Hz, 1H), 7.09 (dd, J = 16.3, 9.0 Hz, 1H), 6.89 (d, J = 15.9 Hz, 1H), 4.89-4.82 (m, 1H), 4.42-4.37 (m, 1H), 3.38-3.24 (m, 2H), 2.44-2.36 (m, 2H), 1.27 (d, J = 7.2 Hz, 3H) | 3299, 1651, 1139, 808 |
| P1636 | 176-184 | 575 ([M − H]⁻) | 7.76-7.72 (m, 2H), 7.48-7.44 (m, 2H), 7.42 (s, 2H), 6.62 (d, J = 15.9 Hz, 1H), 6.54 (s, 1H), 6.42 (dd, J = 15.9, 7.9 Hz, 1H), 4.89 (s, 1H), 4.11 (p, J = 8.7 Hz, 1H), 3.92 (dqd, J = 22.9, 9.0, 6.5 Hz, 1H), 1.71 (s, 6H) | ¹⁹F NMR (376 MHz, CDCl₃) rotomers 6 −68.65, −72.57, −73.24 |
| P1638 | | 638.64 ([M + H]⁺) | (300 MHz, DMSO-d₆) δ 8.60 (bs, 1H), 8.44 (t, J = 6.0 Hz, 1H), 7.90 (s, 3H), 7.59 (d, J = 6.9 Hz,1H), 7.33 (d, J = 7.8 Hz, 1H), 7.00 (dd, J = 16.2, 9.6 Hz, 1H), 6.76 (d, J = 15.3 Hz, 1H), 4.88-4.4.80 (m, 1H), 3.92-3.87 (m, 2H), 3.42-3.40 (m, 2H), 2.50-2.49 (m, 2H) | 3427, 2924, 1651, 1162, 680 |
| P1640 | | 628.9 ([M + H]⁺) | (300 MHz, DMSO-d₆) δ 8.61 (bs, 1H), 8.53 (t, J = 6.0 Hz, 1H), 7.96 (s, 1H), 7.92-7.86 (m, 3H), 7.47 (d, J = 9.0 Hz, 1H), 7.18 (dd, J = 15.6, 8.1 Hz, 1H), 6.88 (d, J = 15.6 Hz, 1H), 4.91-4.78 (m, 1H), 3.96-3.84 (m, 2H), 3.45-3.38 (m, 2H), 2.50-2.43 (m, 2H) | 3445, 1644, 1163, 749 |
| P1641 | | 574.8 ([M + H]⁺) | (300 MHz, DMSO-d₆) δ 8.61 (bs, 1H), 8.27 (t, J = 5.4 Hz, 1H), 7.89 (s, 2H), 7.47-7.37 (m, 2H), 7.28 (d, J = 8.1 Hz, | 3427, 2926, 1645, 1162, 809 |

TABLE 2B-continued

Analytical Data for Compounds in Table 1B.

| Compound Number | mp (° C.) | ESIMS | $^1$H NMR (δ)$^a$ | IR (cm$^{-1}$); $^{19}$F NMR (δ) |
|---|---|---|---|---|
| P1691 | | 654.8 ([M + H]$^+$) | 1H), 6.88 (dd, J = 15.6, 9.0 Hz, 1H), 6.74 (d, J = 15.9 Hz, 1H), 4.88-4.81 (m, 1H), 3.92-3.86 (m, 2H), 3.45-3.38 (m, 2H), 2.51-2.44 (m, 2H), 2.32 (s, 3H) (300 MHz, DMSO-d$_6$) δ 8.64 (d, J = 7.2 Hz, 1H), 8.57 (t, J = 6.3 Hz, 1H), 7.91 (s, 1H), 7.71 (s, 2H), 7.66 (s, 1H), 7.57 (d, J = 8.1 Hz, 1H), 7.41 (d, J = 7.5 Hz, 1H), 7.03 (dd, J = 15.6, 9.6 Hz, 1H), 6.78 (d, J = 15.6 Hz, 1H), 4.91-4.71 (m, 1H), 4.50-4.45 (m, 1H), 4.02-3.82 (m, 2H), 1.30 (d, J = 7.2 Hz, 3H) | 3301, 1647, 1164, 746 |
| P1693 | | 645.1 ([M + H]$^+$) | (300 MHz, DMSO-d$_6$) δ 8.73 (d, J = 7.2 Hz, 1H), 8.61 (d, J = 6.3 Hz, 1H), 7.96 (s, 1H), 7.86-7.80 (m, 1H), 7.71 (s, 2H), 7.67 (d, J = 8.1 Hz, 1H), 7.56 (d, J = 7.8 Hz, 1H), 7.00 (dd, J = 15.6, 9.3 Hz, 1H), 6.90 (d, J = 15.9 Hz, 1H), 4.92-4.71 (m, 1H), 4.51-4.49 (m, 1H), 3.99-3.85 (m, 2H), 1.29 (d, J = 7.2 Hz, 3H) | 3309, 1650, 1165, 677 |
| P1696 | | 604.2 ([M + H]$^+$) | (300 MHz, DMSO-d$_6$) δ 8.65 (d, J = 7.2 Hz, 1H), 8.55 (t, J = 6.0 Hz, 1H), 7.92 (d, J = 1.5 Hz, 1H), 7.68 (t, J = 3.3 Hz, 3H), 7.60 (d, J = 6.9Hz, 1H), 7.42 (d, J = 7.8 Hz, 1H), 7.00 (dd, J = 15.3, 8.7 Hz, 1H), 6.76 (d, J = 15.6 Hz, 1H), 4.83 (t, J = 7.2 Hz, 1H), 4.51 (t, J = 7.2 Hz, 1H), 4.01-3.88 (m, 2H), 1.29 (d, J = 7.2 Hz, 3H) | 3418, 1645, 1165, 750, 562 |
| P1698 | | 595.1 ([M + H]$^+$) | (300 MHz, DMSO-d$_6$) δ 8.74 (d J = 7.5 Hz, 1H), 8.59 (t, J = 6.6 Hz, 1H), 7.98 (s, 1H), 7.91 (d, J = 8.4 Hz, 1H), 7.69-7.62 (m, 2H), 7.56 (d, J = 7.5 Hz, 1H), 7.09 (dd, J = 15.3, 8.7 Hz, 1H), 6.88 (d, J = 15.6 Hz, 1H), 4.83-4.80 (m, 1H), 4.51-4.47 (m, 1H), 3.99-3.86 (m, 2H), 1.29 (d, J = 7.2 Hz, 3H) | 3294, 2928, 1646, 1166, 750 |
| P1776 | | 593.2 ([M + H]$^+$) | (400 MHz, DMSO-d$_6$) δ 8.69 (t, J = 6.0 Hz, 1H), 8.57 (t, J = 6.4 Hz, 1H), 7.90 (dd, J = 13.3, 1.8 Hz, 2H), 7.72 (d, J = 8.4 Hz, 1H), 7.58 (ddd, J = 18.0, 8.2, 1.8 Hz, 2H), 7.44 (d, J = 7.9 Hz, 1H), 6.94 (dd, J = 15.7, 9.0 Hz, 1H), 6.74 (d, J = 15.7 Hz, 1H), 4.81 (p, J = 9.4 Hz, 1H), 4.02-3.87 (m, 4H) | $^{19}$F NMR (376 MHz, DMSO-d$_6$) δ -67.98, -70.71 |
| P1781 | | 513.2 ([M + H]$^+$) | 7.85-7.74 (m, 2H), 7.53-7.41 (m, 4H), 7.30 (t, J = 6.2 Hz, 1H), 7.23 (dd, J = 8.4, 2.0 Hz, 1H), 7.19 (t, J = 5.2 Hz, 1H), 6.61 (d, J = 15.9 Hz, 1H), 6.46 (dd, J = 15.9, 7.8 Hz, 1H), 4.26 (d, J = 5.1 Hz, 2H), 4.21-4.07 (m, 1H), 3.95 (qd, J = 9.1, 6.4 Hz, 2H) | $^{19}$F NMR (376 MHz, CDCl$_3$) δ -68.78, -72.44 |
| P1806 | | 605.0 ([M + H]$^+$) | (300 MHz, DMSO-d$_6$) δ 8.67 (d, J = 7.2 Hz, 1H), 8.57 (t, J = 6.3 Hz, 1H), 7.91-7.88 (m, 2H), 7.74 (d, J = 8.7 Hz, 1H), 7.64-7.59 (m, 2H), 7.41 (d, J = 8.1 Hz, 1H), 6.98 (dd, J = 15.9, 9.3 Hz, 1H), 6.76 (d, J = 15.9 Hz, 1H), 4.83-4.77 (m, 1H), 4.52-4.43 (m, 1H), 4.05-3.83 (m, 2H), 1.30 (d, J = 7.2 Hz, 3H) | 3411, 2925, 1650, 1163, 747 |
| P1808 | | 695.1 ([M + H]$^+$) | (400 MHz, DMSO-d$_6$) δ 8.74 (d, J = 7.2 Hz, 1H), 8.59 (s, 1H), 7.96-7.89 (m, 3H), 7.73 (d, J = 8.4 Hz, 1H), 7.55 (t, J = 8.8 Hz, 2H), 7.05 (dd, J = 16.0, 8.8 Hz, 1H), 6.87 (d, J = 16.0 Hz, 1H), 4.85-4.80 (m, 1H), 4.51-4.47 (m, 1H), 3.99-3.88 (m, 2H), 1.28 (d, J = 6.8 Hz, 3H) | 3297, 1652, 1165, 745 |
| P1862 | | 598.89 ([M + H]$^+$) | 7.70 (s, 1H), 7.62-7.60 (m, 1H), 7.55-7.53 (m, 1H), 7.35 (d, J = 5.6 Hz, 2H), 7.89 (t, J = 6.0 Hz, 1H), 6.67 (t, J = 5.6 Hz, 1H), 6.64 (d, J = 16.0 Hz, 1H), 6.48 (dd, J = 16.4, 8.0 Hz, 1H), 4.23 (d, J = 5.6 Hz, 2H), 4.17-4.08 (m, 1H), 3.97-3.89 (m, 2H) | 3324, 1673, 1164, 772 |
| P1864 | | 622.88 ([M − H]$^−$) | (400 MHz, DMSO-d$_6$) δ 10.39 (bs, 1H), 8.85 (t, J = 6.0 Hz, 1H), 7.94 (s, 1H), 7.87 (d, J = 6.4 Hz, 2H), 7.64 (d, J = 8.4 Hz, 1H), 7.58 (d, J = 8.0 Hz, 1H), 7.00 (dd, J = 15.6, 8.8 Hz, 1H), 6.77 (d, J = 15.6 Hz, 1H), 4.81-4.79 (m, 1H), 4.63-4.59 (m, 2H), 4.24 (d, J = 6.0 Hz, 2H) | 3256, 1657, 1166, 749, 591 |
| P1866 | | 614.91 ([M + H]$^+$) | (400 MHz, DMSO-d$_6$) δ 10.43 (bs, 1H), 8.96 (t, J = 6.0 Hz, 1H), 8.00 (s, 1H), 7.94 (d, J = 7.6 Hz, 1H), 7.88 (d, J = 6.4 Hz, 2H), 7.76 (d, J = 8.0 Hz, 1H), 7.09 (dd, J = 15.6, 9.2 Hz, 1H), 6.88 (d, J = 16.0 Hz, 1H), 4.86-4.78 | 3447, 1655, 1167, 816 |

TABLE 2B-continued

Analytical Data for Compounds in Table 1B.

| Compound Number | mp (° C.) | ESIMS | ¹H NMR (δ)ᵃ | IR (cm⁻¹); ¹⁹F NMR (δ) |
|---|---|---|---|---|
| | | | (m, 1H), 4.62-4.58 (m, 2H), 4.23 (d, J = 5.6 Hz, 2H) | |
| P1969 | | 678.77 ([M + H]⁺) | (300 MHz, DMSO-d₆) δ 8.65 (t, J = 5.4 Hz, 1H), 8.54 (t, J = 6.3 Hz, 1H), 7.90-7.86 (m, 2H), 7.82 (s, 2H), 7.60 (d, J = 7.2 Hz, 1H), 7.43 (d, J = 7.8 Hz, 1H), 6.99 (dd, J = 15.6, 9.0 Hz, 1H), 6.75 (d, J = 15.6 Hz, 1H), 4.83-4.76 (m, 1H), 4.01-3.91 (m, 4H) | 3296, 1697, 1164, 596 |
| P1970 | | 634.87 ([M + H]⁺) | (300 MHz, DMSO-d₆) δ 8.68 (t, J = 6.0 Hz, 1H), 8.57 (t, J = 6.0 Hz, 1H), 7.89-7.78 (m, 4H), 7.59-7.56 (m, 1H), 7.49-7.46 (m, 1H), 7.02 (dd, J = 15.9, 8.1 Hz, 1H), 6,78 (d, J = 15.6 Hz, 1H), 4.83-4.76 (m, 1H), 4.01-3.91 (m, 4H) | 3299, 1658, 1164, 745, 543 |
| P1971 | | 668.87 ([M + H]⁺) | (300 MHz, DMSO-d₆) δ 8.77 (t, J = 6.0 Hz, 1H), 8.59 (t, J = 6.3 Hz, 1H), 7.99 (s, 1H), 7.93-7.85 (m, 4H), 7.60 (d, J = 8.1 Hz, 1H), 7.10 (dd, J = 15.9, 9.3 Hz, 1H), 6.89 (d, J = 15.9 Hz, 1H), 4.85-4.79 (m, 1H), 3.98-3.90 (m, 4H) | 3351, 1705, 1165, 551 |
| P1972 | | 614.84 ([M + H]⁺) | (400 MHz, DMSO-d₆) δ 8.57 (t, J = 6.4 Hz, 1H), 8.47 (t, J = 6.0 Hz, 1H), 7.88-7.80 (m, 3H), 7.45 (s, 1H), 7.43-7.37 (m, 2H), 6.86 (dd, J = 15.6, 8.8 Hz, 1H), 6.74 (d, J = 15.6 Hz, 1H), 4.83-4.74 (m, 1H), 3.98-3.88 (m, 4H), 2.37 (s, 3H) | 3311, 1650, 1163, 543 |
| P2009 | | 692.88 ([M + H]⁺) | (300 MHz, DMSO-d₆) δ 8.62 (t, J = 5.7 Hz, 1H), 8.50 (d, J = 8.7 Hz, 1H), 7.93-7.92 (m, 1H), 7.89-7.88 (m, 1H), 7.84 (s, 2H), 7.62-7.59 (m, 1H), 7.42 (d, J = 8.1 Hz, 1H), 7.01 (dd, J = 15.9, 9.2 Hz, 1H), 6.77 (d, J = 15.6 Hz, 1H), 4.82-4.76 (m, 1H), 4.65-4.58 (m, 1H), 4.00-3.92 (m, 1H), 3.87-3.80 (m, 1H), 1.27 (d, J = 6.9 Hz, 3H) | 3402, 1659, 1165, 560 |
| P2010 | | 646.84 ([M − H]⁻) | (300 MHz, DMSO-d₆) δ 8.63 (t, J = 6.0 Hz, 1H), 8.50 (d, J = 8.7 Hz, 1H), 7.89-7.88 (m, 1H), 7.84 (s, 2H), 7.78 (s, 1H), 7.59-7.56 (m, 1H), 7.46 (d, J = 7.5 Hz, 1H), 7.00 (dd, J = 15.6, 9.0 Hz, 1H), 6.78 (d, J = 15.3 Hz, 1H), 4.79-4.76 (m, 1H), 4.63-4.60 (m, 1H), 3.95-3.86 (m, 2H), 1.27 (d, J = 7.2 Hz, 3H) | 3406, 1658, 1165, 746, 583 |
| P2011 | | 682.93 ([M + H]⁺) | (400 MHz, DMSO-d₆) δ 8.73 (t, J = 5.6 Hz, 1H), 8.50 (d, J = 8.8 Hz, 1H), 7.98 (s, 1H), 7.90-7.89 (m, 2H), 7.85 (s, 2H), 7.57 (d, J = 8.4 Hz, 1H), 7.09 (dd, J = 15.6, 9.2 Hz, 1H), 6.88 (d, J = 15.6 Hz, 1H), 4.84-4.79 (m, 1H), 4.65-4.59 (m, 1H), 4.03-3.95 (m, 1H), 3.87-3.81 (m, 1H), 1.25 (d, J = 6.0 Hz, 3H) | 3417, 1666, 1115, 558 |
| P2012 | | 628.89 ([M + H]⁺) | (300 MHz, DMSO-d₆) δ 8.51 (d, J = 8.7 Hz, 1H), 8.41 (t, J = 6.0 Hz, 1H), 7.88 (s, 1H), 7.82 (s, 1H), 7.45-7.34 (m, 3H), 6.87 (dd, J = 15.9, 8.7 Hz, 1H), 6.74 (d, J = 15.6 Hz, 1H), 4.82-4.75 (m, 1H), 4.65-4.57 (m, 1H), 3.98-3.78 (m, 2H), 2.36 (s, 3H), 1.26 (d, J = 7.2 Hz, 3H) | 3406, 1643, 1163, 583 |
| P2036 | | 674.7 ([M + H]⁺) | (300 MHz, DMSO-d₆) δ 8.61 (d, J = 7.8 Hz, 1H), 8.26 (t, J = 5.7 Hz, 1H), 7.92-7.88 (m, 2H), 7.84 (s, 2H), 7.61 (d, J = 7.8 Hz, 1H), 7.42 (d, J = 7.8 Hz, 1H), 7.00 (dd, J = 15.9, 9.3 Hz, 1H), 6.77 (d, J = 15.9 Hz, 1H), 6.20-5.80 (m, 1H), 4.83-4.74 (m, 1H), 4.51-4.42 (m, 1H), 3.61-3.31 (m, 2H), 1.31 (d, J = 7.5 Hz, 3H) | 3296, 1651, 1113, 534 |
| P2038 | | 662.7 ([M − H]⁺) | (300 MHz, DMSO-d₆) δ 8.69 (d, J = 7.2 Hz, 1H), 8.30 (bs, 1H), 7.98 (s, 1H), 7.89-7.85 (m, 4H), 7.57 (d, J = 8.1 Hz, 1H), 7.42 (d, J = 7.8 Hz, 1H), 7.09 (dd, J = 15.9, 9.6 Hz, 1H), 6.88 (d, J = 15.9 Hz, 1H), 6.18-5.81 (m, 1H), 4.84-4.78 (m, 1H), 4.50-4.45 (m, 1H), 3.50-3.45 (m, 2H), 1.29 (d, J = 7.2 Hz, 3H) | 3292, 1650, 1115, 747, 681 |
| P2041 | | 656.6 ([M + H]⁺) | (400 MHz, DMSO-d₆) δ 8.56 (d, J = 7.2 Hz, 1H), 8.10 (t, J = 5.2 Hz, 1H), 7.92-7.88 (m, 2H), 7.84 (s, 2H), 7.60 (d, J = 8.0 Hz, 1H), 7.42 (d, J = 8.0 Hz, 1H), 6.99 (dd, J = 16.0, 9.6 Hz, 1H), 6.76 (d, J = 16.0 Hz, 1H), 4.81-4.74 (m, 1H), 4.50-4.36 (m, 1H), 3.56-3.36 (m, 2H), 1.29 (d, J = 6.8 Hz, 3H) | 3305, 1645, 1167, 559 |
| P2043 | | 646.9 ([M + H]⁺) | (300 MHz, DMSO-d₆) δ 8.64 (d, J = 7.8 Hz, 1H), 8.15 (t, J = 5.7 Hz, 1H), 7.97 (s, 1H) 7.90-7.85 (m, 4H), 7.57 (d, J = 8.0 Hz, 1H), 7.09 (dd, J = | 3291, 1651, 1115, 588 |

TABLE 2B-continued

Analytical Data for Compounds in Table 1B.

| Compound Number | mp (° C.) | ESIMS | ¹H NMR (δ)[a] | IR (cm⁻¹); ¹⁹F NMR (δ) |
|---|---|---|---|---|
| P2056 | 91-94 | 706.8 ([M + H]⁺) | (400 MHz, DMSO-d₆) δ 8.57 (d, J = 7.2 Hz, 1H), 8.09 (t, J = 5.2 Hz, 1H), 7.92-7.88 (m, 2H), 7.84 (s, 2H), 7.60 (d, J = 7.6 Hz, 1H), 7.43 (d, J = 7.6 Hz, 1H), 6.99 (dd, J = 15.6, 9.1 Hz, 1H), 6.76 (d, J = 15.6 Hz, 1H), 4.81-4.77 (m, 1H), 4.40-4.36 (m, 1H), 3.40-3.25 (m, 2H) 2.44-2.32 (m, 2H), 1.28 (d, J = 6.8 Hz, 3H) | |
| P2058 | | 696.8 ([M + H]⁺) | (300 MHz, DMSO-d₆) δ 8.66 (s, 1H), 8.14 (s, 2H), 7.97 (s, 1H), 7.89-7.85 (m, 3H) 7.57 (d, J = 8.1 1H), 7.06 (dd, J = 16.2, 9.0 Hz, 1H), 6.88 (d, J = 16.2 Hz, 1H), 4.82-4.81 (m, 1H), 4.41-4.37 (m, 1H) 3.38-2.99 (m, 2H), 2.44-2.36 (m, 2H) 1.27 (d, J = 7.2 Hz, 3H) | 3309, 1650, 1141 |

[a]¹H NMR spectral data were acquired using a 400 MHz instrument in CDCl₃ except where noted. HRMS data are noted observed value (theoretical value).

TABLE 2C

Analytical Data for Compounds in Table 1C.

| Compound Number | mp (° C.) | ESIMS | ¹H NMR (δ)[a] | IR (cm⁻¹); ¹⁹F NMR (δ) |
|---|---|---|---|---|
| FA1 | | 562.89 ([M + H]⁺) | (400 MHz, DMSO-d₆) δ 8.65 (t, J = 5.2 Hz, 1H), 8.28 (t, J = 6.0 Hz, 1H), 7.91 (s, 2H), 7.78 (s, 1H), 7.58 (d, J = 8.0 Hz, 1H), 7.50 (d, J = 8.0 Hz, 1H), 7.01 (dd, J = 15.6, 9.2 Hz, 1H), 6.78 (d, J = 15.6 Hz, 1H), 4.86-4.79 (m, 1H), 3.90 (d, J = 6.0 Hz, 2H), 3.59-3.48 (m, 3H) | 3418, 1658, 1114, 749 |
| FA2 | | 542.93 ([M + H]⁺) | (400 MHz, DMSO-d₆) δ 8.45 (t, J = 6.0 Hz, 1H), 8.29 (t, J = 4.5 Hz, 1H), 7.89 (s, 2H), 7.45-7.34 (m, 3H), 6.87 (dd, J = 15.7, 6.9 Hz, 1H), 6.75 (d, J = 15.8 Hz, 1H), 4.85-4.80 (m, 1H), 3.87 (d, J = 4.8 Hz, 2H), 3.57-3.47 (m, 3H), 2.42 (s, 3H) | 3430, 1646, 1113, 749 |
| FA3 | | 606.78 ([M + H]⁺) | (400 MHz, DMSO-d₆) δ 8.65 (t, J = 5.6 Hz, 1H), 8.27 (t, J = 5.6 Hz, 1H), 7.93-7.91 (m, 2H), 7.62-7.58 (m, 2H), 7.46 (d, J = 8.0 Hz, 1H), 7.00 (dd, J = 15.2, 9.2 Hz, 1H), 6.77 (d, J = 15.6 Hz, 1H), 4.85-4.81 (m, 1H), 3.89 (d, J = 6.0 Hz, 1H), 3.59-3.48 (m, 2H), 3.17-3.08 (m, 2H) | 3420, 1654, 114, 749, 558 |
| FA4 | | 599.00 ([M + H]⁺) | (400 MHz, CDCl₃) δ 9.81 (s, 1H), 8.06 (d, J = 7.1 Hz, 1H), 7.70 (d, J = 5.5 Hz, 1H), 7.44 (s, 1H), 7.37 (t, J = 2.7 Hz, 2H), 7.20 (s, 1H), 6.82 (d, J = 15.9 Hz, | |

TABLE 2C-continued

Analytical Data for Compounds in Table 1C.

| Compound Number | mp (° C.) | ESIMS | $^1$H NMR ($\delta$)$^a$ | IR (cm$^{-1}$); $^{19}$F NMR ($\delta$) |
|---|---|---|---|---|
| | | | 1H), 6.50 (dd, J = 16.0, 8.5 Hz, 1H), 4.14 (m, 3H), 3.89 (m, 2H) | |
| FA5 | | 613.10 ([M + H]$^+$) | (400 MHz, CDCl$_3$) $\delta$ 7.45 (s, 1H), 7.41 (s, 2H), 7.29 (s, 1H), 7.28 (s, 1H), 6.84 (m, 2H), 6.43 (dd, J = 16.0, 8.3 Hz, 1H), 4.25 (d, J = 5.4 Hz, 2H), 4.10 (m, 1H), 3.97 (qd, J = 9.0, 6.4 Hz, 2H), 3.87 (s, 3H) | |
| FA6 | | 545.92 ([M + H]$^+$) | (400 MHz, DMSO-d$_6$) $\delta$ 8.56 (t, J = 6.4 Hz, 1H), 8.51 (t, J = 5.6 Hz, 1H), 7.82 (d, J = 6.4 Hz, 2H), 7.56 (d, J = 8.0 Hz, 1H), 6.81 (d, J = 8.4 Hz, 1H), 6.75 (s, 1H), 6.72 (dd, J = 15.6, 6.8 Hz, 1H), 6.62 (d, J = 15.6 Hz, 1H), 6.51 (bs, 2H), 4.82-4.78 (m, 1H), 3.96-3.85 (m, 4H) | 3369, 1694, 1164, 713 |
| FA7 | | 638.78 ([M + H]$^+$) | (300 MHz, CDCl$_3$) $\delta$ 7.62-7.56 (m, 2H), 7.46-7.37 (m, 2H), 6.77-6.76 (m, 1H), 6.56 (d, J = 14.1 Hz, 1H), 6.43 (dd, J = 15.9, 7.8 Hz, 1H), 4.14-4.07 (m, 3H), 3.61-3.54 (m, 2H), 2.42-2.34 (m, 2H) | 3284, 1667, 1166, 744, 591 |
| FA8 | | 588.87 ([M + H]$^+$) | (300 MHz, DMSO-d$_6$) $\delta$ 8.68 (t, J = 5.7 Hz, 1H), 8.56 (t, J = 6.6 Hz, 1H), 7.91 (s, 1H), 7.61-7.58 (m, 1H), 7.45-7.39 (m, 3H), 6.95 (dd, J = 15.9, 9.3 Hz, 1H), 6.75 (d, J = 15.9 Hz, 1H), 4.76-4.64 (m, 1H), 4.06-3.92 (m, 4H), 3.90 (s, 3H) | 3297, 1658, 1165 |
| FA9 | | 624.92 ([M + H]$^+$) | (300 MHz, DMSO-d$_6$) $\delta$ 9.81 (bs, 1H), 8.69 (s, 1H), 7.90 (s, 2H), 7.78 (s, 1H), 7.59-7.58 (m, 2H), 7.02 (dd, J = 15.8, 9.3 Hz, 1H), 6.78 (d, J = 15.8 Hz, 1H), 4.86-4.79 (m, 1H), 4.57-4.52 (m, 2H), 1.60 (s, 6H) | 3430, 1651, 1166, 750 |
| FA10 | | 640.9 ([M + H]$^+$) | (300 MHz, DMSO-d$_6$) $\delta$ 10.41 (s, 1H), 9.68 (bs, 1H), 7.90 (s, 2H), 7.76-7.67 (m, 1H), 7.53 (d, J = 8.1 Hz, 1H), 7.42 (d, J = 7.8 Hz, 1H), 6.97 (dd, J = 15.6, 8.7 Hz, 1H), 6.77 (d, J = 15.6 Hz, 1H), 4.86 (t, J = 9.3 Hz, 1H), 4.55-4.47 (m, 2H), 1.75 (s, 6H) | 3434, 1260, 750 |
| FA11 | | 668.8 ([M + H]$^+$) | (300 MHz, DMSO-d$_6$) $\delta$ 9.80 (bs, 1H), 8.69 (s, 1H), 7.92-7.90 (m, 3H), 7.60-7.55 (m, 2H), 7.01 (dd, J = 15.5, 9.1 Hz, 1H), | 3425, 1651, 1261, 750 |

TABLE 2C-continued

Analytical Data for Compounds in Table 1C.

| Compound Number | mp (° C.) | ESIMS | ¹H NMR (δ)$^a$ | IR (cm$^{-1}$); ¹⁹F NMR (δ) |
|---|---|---|---|---|
| | | | 6.77 (d, J = 15.6 Hz, 1H), 4.84-4.30 (m, 1H), 4.57-4.52 (m, 2H), 1.60 (s, 6H) | |
| FA12 | | 660.8 ([M + 2H]$^+$) | (300 MHz, DMSO-d$_6$) δ 9.87 (bs, 1H), 8.76 (bs, 1H), 7.98 (s, 1H), 7.95-7.91 (m, 3H), 7.83 (d, J = 8.1 Hz, 1H), 7.09 (dd, J = 15.9, 9.3 Hz, 1H), 6.89 (d, J = 15.9, 1H), 4.89 (t, J = 9.6 Hz, 1H), 4.57-4.51 (m, 2H), 1.58 (s, 6H) | 3430, 1651, 1261, 750 |
| FA13 | | 606.8 ([M + H]$^+$) | (300 MHz, DMSO-d$_6$) δ 10.36 (s, 1H), 8.67 (bs, 1H), 8.56 (bs, 1H), 7.92 (s, 1H), 7.61-7.58 (m, 3H), 7.44 (d, J = 7.8 Hz, 1H), 6.96 (dd, J = 15.4, 8.8 Hz, 1H), 6.74 (d, J = 15.7 Hz, 1H), 4.61-4.70 (m, 1H), 4.04-3.90 (m, 4H) | 3418, 1651, 1164, 749 |
| FA14 | | 611.9 ([M + H]$^+$) | (400 MHz, CDCl$_3$) δ 7.69 (s, 1H), 7.62 (d, J = 1.6 Hz, 1H), 7.53 (d, J = 8.0 Hz, 1H), 7.39 (m, 3H), 6.54 (d, J = 15.9 Hz, 1H), 6.40 (dd, J = 15.9, 7.8 Hz, 1H), 6.28 (s, 1H), 4.21 (d, J = 5.7 Hz, 2H), 4.12 (m, 1H), 1.69 (s, 6H) | ¹⁹F NMR (376 MHz, CDCl$_3$) δ -68.59 |
| FA15 | | 643.19 ([M + H]$^+$) | (400 MHz, CDCl$_3$) δ 7.60 (d, J = 1.6 Hz, 1H), 7.51 (d, J = 8.0 Hz, 1H), 7.40 (s, 2H), 7.36 (dd, J = 8.1, 1.6 Hz, 1H), 6.66 (d, J = 10.0 Hz, 2H), 6.53 (d, J = 15.9 Hz, 1H), 6.38 (dd, J = 15.9, 7.8 Hz, 1H), 4.11 (m, 1H), 3.12 (d, J = 6.2 Hz, 2H), 1.72 (s, 6H), 0.93 (s, 9H) | ¹⁹F NMR (376 MHz, CDCl$_3$) δ -68.62 |
| FA16 | | 687.0 ([M + H]$^+$) | (300 MHz, DMSO-d$_6$) δ 8.61-8.53 (m, 2H), 8.11 (s, 1H), 7.91 (s, 2H), 7.62 (d, J = 8.4 Hz, 1H), 7.36 (d, J = 8.1 Hz, 1H), 6.98 (dd, J = 15.9, 9.3 Hz, 1H), 6.74 (d, J = 15.9 Hz, 1H), 4.85-4.82 (m, 1H), 4.50-4.45 (m, 1H), 4.00-3.88 (m, 2H), 1.36 (d, J = 7.5 Hz, 3H) | 3433, 1640, 1163, 749 |
| FA17 | | 587.1 ([M + H]$^+$) | (300 MHz, DMSO-d$_6$) δ 8.60-8.53 (m, 2H), 7.91-7.85 (m, 3H), 7.54 (d, J = 8.1 Hz, 1H), 7.40 (d, J = 8.1 Hz, 1H), 7.02 (dd, J = 17.4, 11.1 Hz, 1H), 6.92 (dd, J = 15.9, 9.0 Hz, 1H), 6.81 (d, J = 15.9 Hz, 1H), 5.95 (d, J = 17.1 Hz, 1H), 5.33 (d, J = 11.7 Hz, 1H), 4.87-4.80 (m, 1H), | 3419, 1644, 1162, 748 |

TABLE 2C-continued

Analytical Data for Compounds in Table 1C.

| Compound Number | mp (° C.) | ESIMS | ¹H NMR (δ)ᵃ | IR (cm⁻¹); ¹⁹F NMR (δ) |
|---|---|---|---|---|
| FA18 | | 573.2 ([M + H]⁺) | 4.47-4.43 (m, 1H), 4.01-3.87 (m, 2H), 1.31 (d, J = 6.9 Hz, 3H) (300 MHz, DMSO-d₆) δ 8.62-8.56 (m, 2H), 7.91-7.86 (m, 3H), 7.56 (d, J = 9.3 Hz, 1H), 7.42 (d, J = 8.1 Hz, 1H), 7.11 (dd, J = 17.4, 11.1 Hz, 1H), 6.98 (dd, J = 15.9, 9.3 Hz, 1H), 6.82 (d, J = 15.9 Hz, 1H), 5.96 (d, J = 16.8 Hz, 1H), 5.34 (d, J = 12.0 Hz, 1H), 4.87-4.81 (m, 1H), 4.01-3.89 (m, 4H) | 3422, 1649, 1164, 809 |
| FA19 | | 667.0 ([M + H]⁺) | (300 MHz, DMSO-d₆) δ 8.64-8.58 (m, 2H), 7.92-7.89 (m, 3H), 7.60 (d, J = 8.1 Hz, 1H), 7.37 (d, J = 7.8 Hz, 1H), 7.00 (dd, J = 15.3, 8.7 Hz, 1H), 6.77 (d, J = 15.6 Hz, 1H), 4.86-4.79 (m, 1H), 4.49-4.42 (m, 1H), 4.07-3.81 (m, 2H), 1.65-1.59 (m, 2H), 1.40-1.30 (m, 2H), 0.89 (t, J = 6.9 Hz, 3H) | 3288, 1645, 1164, 743, 563 |
| FA20 | | 609.1 ([M + H]⁺) | (400 MHz, DMSO-d₆) δ 8.74 (d J = 7.6 Hz, 1H), 8.59 (t, J = 6.4 Hz, 1H), 7.95 (s, 1H), 7.89 (d, J = 7.2 Hz, 1H), 7.72 (s, 1H), 7.55 (d, J = 7.2 Hz, 2H), 7.02 (dd, J = 16.0, 8.8 Hz, 1H), 6.87 (d, J = 15.6 Hz, 1H), 4.76-4.72 (m, 1H), 4.51-4.47 (m, 1H), 3.99-3.88 (m, 2H), 2.42 (s, 3H), 1.29 (d, J = 7.2 Hz, 3H) | 3422, 2926, 1651, 1165, 783 |
| FA21 | | 673.0 ([M + H]⁺) | (300 MHz, DMSO-d₆) δ 8.74 (d, J = 7.5 Hz, 1H), 8.59 (t, J = 6.3 Hz, 1H), 7.98 (s, 1H), 7.91-7.85 (m, 3H), 7.56 (d, J = 8.1 Hz, 1H), 7.09 (dd, J = 15.9, 9.3 Hz, 1H), 6.88 (d, J = 15.6 Hz, 1H), 4.88-4.81 (m, 1H), 4.52-4.57 (m, 1H), 4.04-3.85 (m, 2H), 1.29 (t, J = 6.9 Hz, 3H) | 3429, 1650, 1165, 804 |
| FA22 | | 681.0 ([M − H]⁻) | (300 MHz, DMSO-d₆) δ 8.65 (d, J = 7.5 Hz, 1H), 8.55 (t, J = 5.7 Hz, 1H), 7.91-7.85 (m, 2H), 7.48-7.39 (m, 2H), 7.31-7.26 (m, 1H), 7.00 (dd, J = 15.9, 9.3 Hz, 1H), 6.77 (d, J = 15.6 Hz, 1H), 4.86-4.82 (m, 1H), 4.50-4.46 (m, 1H), 4.00-3.88 (m, 2H), 1.31 (t, J = 7.2 Hz, 3H) | 3298, 1651, 1164, 689, 536 |

TABLE 2C-continued

Analytical Data for Compounds in Table 1C.

| Compound Number | mp (° C.) | ESIMS | ¹H NMR (δ)$^a$ | IR (cm$^{-1}$); ¹⁹F NMR (δ) |
|---|---|---|---|---|
| FA23 | | 651.2 ([M + H]$^+$) | (400 MHz, CDCl$_3$) δ 7.61 (d, J = 1.6 Hz, 1H), 7.51 (d, J = 8.0 Hz, 1H), 7.40 (s, 2H), 7.37 (dd, J = 8.1, 1.6 Hz, 1H), 6.85 (t, J = 6.2 Hz, 1H), 6.53 (d, J = 15.9 Hz, 1H), 6.42 (s, 1H), 6.38 (dd, J = 15.9, 7.8 Hz, 1H), 4.11 (m, 1H), 3.70 (td, J = 13.3, 6.3 Hz, 2H), 1.67 (m, 9H) | ¹⁹F NMR (376 MHz, CDCl$_3$) δ −68.61, −96.22 |
| FA24 | | 672.9 ([M + H]$^+$) | (400 MHz, DMSO-d$_6$) δ 8.49 (t, J = 6.0 Hz, 1H), 8.42 (t, J = 6.4 Hz, 1H), 7.98 (s, 1H), 7.76 (s, 2H), 7.49-7.47 (m, 1H), 7.24 (d, J = 8.0 Hz, 1H), 6.82 (dd, J = 15.6, 9.2 Hz, 1H), 6.59 (d, J = 16.4 Hz, 1H), 4.70-4.65 (m, 1H), 3.89-3.75 (m, 4H) | 3410, 1653, 1164, 812 |
| FA25 | | 603.0 ([M + H]$^+$) | (400 MHz, DMSO-d$_6$) δ 8.61 (t, J = 6.4 Hz, 1H), 8.37 (d, J = 8.0 Hz, 1H), 7.89 (s, 2H), 7.45 (s, 1H), 7.40 (d, J = 8.4 Hz, 1H), 7.33 (d, J = 8.0 Hz, 1H), 6.86 (dd, J = 16.0, 8.8 Hz, 1H), 6.75 (d, J = 15.6 Hz, 1H), 4.85-4.80 (m, 1H), 4.47-4.41 (m, 1H), 4.02-3.96 (m, 1H), 3.90-3.83 (m, 1H), 2.32 (s, 3H), 1.67-1.61 (m, 2H), 1.42-1.28 (m, 2H), 0.89 (t, J = 7.6 Hz, 3H) | 3288, 1676, 1164, 809 |
| FA26 | 108-111 | 726.9 ([M + H]$^+$) | (300 MHz, DMSO-d$_6$) δ 8.65 (d, J = 7.2 Hz, 1H), 8.55 (t, J = 6.3 Hz, 1H), 8.04 (s, 1H), 7.92 (s, 1H), 7.84-7.76 (m, 1H), 7.61 (d, J = 7.8 Hz, 1H), 7.42 (d, J = 7.8 Hz, 1H), 7.01 (dd, J = 15.6, 9.0 Hz, 1H), 6.77 (d, J = 15.9 Hz, 1H), 4.84-4.78 (m, 1H), 4.51-4.46 (m, 1H), 4.00-3.88 (m, 2H), 1.31 (d, J = 7.5 Hz, 3H) | |
| FA27 | 103-107 | 717.1 ([M + H]$^+$) | (300 MHz, DMSO-d$_6$) δ 8.74 (d, J = 6.9 Hz, 1H), 8.59 (t, J = 6.0 Hz, 1H), 8.06 (s, 1H), 7.91-7.79 (m, 3H), 7.56 (d, J = 8.1 Hz, 1H), 7.09 (dd, J = 15.9, 8.6 Hz, 1H), 6.88 (d, J = 15.3 Hz, 1H), 4.84-4.81 (m, 1H), 4.52-4.47 (m, 1H), 3.99-3.88 (m, 2H), 1.29 (d, J = 6.9 Hz, 3H) | |
| FA28 | | 588.9 ([M + H]$^+$) | (300 MHz, DMSO-d$_6$) δ 8.59 (t, J = 6.6 Hz, 1H), 8.51 (d, J = 6.9 Hz, 1H), 7.88 (s, 2H), 7.22 (s, 2H), 6.75-6.63 (m, 2H), | 3361, 2960, 1690, 1166, 819 |

TABLE 2C-continued

Analytical Data for Compounds in Table 1C.

| Compound Number | mp (° C.) | ESIMS | ¹H NMR (δ)$^a$ | IR (cm$^{-1}$); ¹⁹F NMR (δ) |
|---|---|---|---|---|
| | | | 4.83-4.77 (m, 1H), 4.50-4.49 (m, 1H), 4.00-3.87 (m, 2H), 2.21 (s, 6H), 1.33-1.22 (m, 3H) | |
| FA29 | | 600.8 ([M + H]$^+$) | (400 MHz, DMSO-d$_6$) δ 8.63 (d, J = 7.2 Hz, 1H), 8.55 (t, J = 6.4 Hz, 1H), 7.86 (s, 2H), 7.77 (d, J = 2.0 Hz, 1H), 7.66 (d, J = 8.4 Hz, 1H), 7.54 (d, J = 7.2 Hz, 1H), 7.47 (dd, J = 10.0, 8.0 Hz, 1H), 7.39 (d, J = 7.6 Hz, 1H), 6.94 (dd, J = 15.6, 9.3 Hz, 1H), 6.63 (d, J = 15.6 Hz, 1H), 4.48-4.43 (m, 1H), 4.05-3.92 (m, 2H), 1.64 (t, J = 19.2 Hz, 3H), 1.30 (d, J = 6.8 Hz, 3H) | 3288, 1687, 1164, 748, 568 |
| FA30 | | 655.0 ([M + H]$^+$) | (300 MHz, DMSO-d$_6$) δ 8.64 (d, J = 7.5 Hz, 1H), 8.58 (t, J = 6.3 Hz, 1H), 7.95-7.91 (m, 2H), 7.66 (s, 2H), 7.60 (d, J = 8.1 Hz, 1H), 7.42 (d, J = 7.8 Hz, 1H), 6.99 (dd, J = 15.9, 9.3 Hz, 1H), 6.78 (d, J = 15.9 Hz, 1H), 4.88-4.82 (m, 1H), 4.50-4.46 (m, 1H), 4.00-3.85 (m, 2H), 1.31 (d, J = 7.5 Hz, 3H) | 3418, 1717, 1165, 748, 525 |
| FA31 | | 598.9 ([M + H]$^+$) | (300 MHz, DMSO-d$_6$) δ 8.65 (d, J = 7.5 Hz, 1H), 8.55 (t, J = 5.7 Hz, 1H), 7.89 (s, 1H), 7.60 (d, J = 8.1 Hz, 1H), 7.46 (s, 1H), 7.41 (d, J = 7.8 Hz, 2H), 7.31 (s, 1H), 6.96 (dd, J = 15.9, 8.7 Hz, 1H), 6.76 (d, J = 15.9 Hz, 1H), 4.71 (t, J = 9.3 Hz, 1H), 4.50 (t, J = 7.5 Hz, 1H), 4.00-3.88 (m, 2H), 2.67-2.60 (m, 2H), 1.31 (d, J = 7.2 Hz, 3H), 1.21 (t, J = 7.5 Hz, 3H) | 3406, 1645, 1163, 749, 597 |
| FA32 | | 666.9 ([M + H]$^+$) | (300 MHz, DMSO-d$_6$) δ 8.68 (s, 1H), 8.54 (d, J = 8.4 Hz, 1H), 7.96-7.91 (m, 3H), 7.59 (d, J = 8.1 Hz, 1H), 7.33 (d, J = 6.6 Hz, 1H), 6.98 (dd, J = 15.6, 8.0 Hz, 1H), 6.77 (d, J = 15.9, 1H), 4.88-4.72 (m, 1H), 4.36-4.31 (m, 1H), 4.07-3.81 (m, 2H), 2.06-1.99 (m, 1H), 0.95-0.85 (m, 6H) | 3288, 1645, 1165, 750 |
| FA33 | | 656.9 ([M + H]$^+$) | (300 MHz, DMSO-d$_6$) δ 8.71 (d, J = 6.3 Hz 1H), 8.65 (d, J = 8.4 Hz, 1H), 7.98 (s, 1H), 7.92-7.87 (m, 3H), 7.45 (d, J = 8.1 Hz, 1H), 7.03 (dd, J = 1 6 Hz, 8.0 Hz, 1H), 6.89 (d, J = 15.9 Hz, | 3294, 1650, 1165, 810 |

TABLE 2C-continued

Analytical Data for Compounds in Table 1C.

| Compound Number | mp (° C.) | ESIMS | $^1$H NMR (δ)$^a$ | IR (cm$^{-1}$); $^{19}$F NMR (δ) |
|---|---|---|---|---|
| FA34 | | 608.85 [(M + H)$^+$] | 1H), 4.88-4.82 (m, 1H), 4.35-4.10 (m, 1H), 4.07-3.81 (m, 2H), 2.06-1.99 (m, 1H), 0.95-0.85 (m, 6H) (300 MHz, DMSO-d$_6$) δ 9.01 (t, J = 6.0, 1H), 8.37 (t, J = 6.4 Hz, 1H), 8.08 (s, 1H), 8.01-7.96 (m, 1H), 7.88-7.86 (m, 2H), 7.64 (d, J = 7.6 Hz, 1H), 7.05 (dd, J = 16.4, 8.8 Hz, 1H), 6.91 (d, J = 15.6 Hz, 1H), 4.87-4.80 (m, 1H), 3.98-3.91 (m, 4H), 3.38 (s, 3H) | 768, 721, 416, 337, 164 |

$^a$$^1$H NMR spectral data were acquired using a 400 MHz instrument in CDCl$_3$ except where noted. HRMS data are noted observed value (theoretical value).

TABLE 3

Assays Results Part 1

| Compound Number | BAW Rating | CEW Rating | GPA Rating |
|---|---|---|---|
| AC1 | D | D | B |
| AC2 | C | C | C |
| AC3 | D | D | B |
| AC4 | D | A | B |
| AC5 | D | D | B |
| AC6 | D | A | B |
| AC7 | A | A | B |
| AC8 | D | B | B |
| AC9 | A | A | B |
| AC10 | A | A | B |
| AC11 | A | A | D |
| AC12 | A | A | D |
| AC13 | A | A | B |
| AC14 | A | B | D |
| AC15 | A | A | B |
| AC16 | A | A | C |
| AC17 | A | A | B |
| AC18 | A | A | B |
| AC19 | D | D | B |
| AC20 | A | A | C |
| AC21 | D | D | C |
| AC22 | A | A | D |
| AC23 | A | A | B |
| AC24 | A | A | D |
| AC25 | A | A | D |
| AC26 | A | A | B |
| AC27 | A | A | B |
| AC28 | A | A | B |
| AC29 | A | A | B |
| AC30 | A | A | B |
| AC31 | A | A | B |
| AC32 | A | A | B |
| AC33 | A | A | B |
| AC34 | A | A | B |
| AC35 | A | A | C |
| AC36 | A | A | B |
| AC37 | A | A | B |
| AC38 | A | A | C |
| AC39 | A | A | C |
| AC40 | A | A | D |
| AC41 | A | D | D |
| AC42 | A | D | D |
| AC43 | A | A | B |
| AC44 | A | A | B |
| AC45 | A | A | D |
| AC46 | A | A | D |
| AC47 | D | D | B |
| AC48 | A | A | B |
| AC49 | A | A | B |
| AC50 | A | D | B |
| AC51 | A | A | B |
| AC52 | A | A | B |
| AC53 | A | A | B |
| AC54 | A | A | B |
| AC57 | A | A | B |
| AC58 | A | A | B |
| AC59 | A | A | B |
| AC60 | A | A | B |
| AC61 | A | A | B |
| AC62 | A | A | D |
| AC63 | A | A | B |
| AC64 | A | A | B |
| AC65 | A | A | B |
| AC66 | A | A | B |
| AC67 | A | A | B |
| AC68 | A | A | D |
| AC69 | A | A | A |
| AC70 | D | D | B |
| AC71 | A | A | B |
| AC72 | A | A | B |
| AC75 | A | A | B |
| AC76 | A | A | D |
| AC77 | A | A | B |
| AC78 | A | A | A |
| AC79 | A | A | A |
| AC80 | A | A | B |
| AC81 | A | D | D |
| AC82 | A | A | B |
| AC83 | A | A | B |
| AC84 | A | A | D |
| AC85 | A | A | B |
| AC86 | A | A | D |
| AC87 | A | A | B |
| AC89 | A | A | B |
| AC90 | A | A | C |
| AC91 | A | A | C |
| AC92 | A | A | C |
| AC93 | A | D | C |
| AC94 | D | B | B |
| AC95 | A | A | C |

TABLE 3-continued

Assays Results Part 1

| Compound Number | BAW Rating | CEW Rating | GPA Rating |
|---|---|---|---|
| AC96 | D | D | C |
| AC97 | D | D | C |
| AC98 | A | A | C |
| AC99 | A | A | C |
| AC100 | C | C | C |
| AC101 | D | D | C |
| AC102 | D | A | C |
| AC103 | A | A | D |
| AC104 | A | A | B |
| AC105 | A | A | D |
| AC106 | A | A | B |
| AC107 | B | A | D |
| AC108 | B | D | D |
| AC109 | D | D | C |
| AC110 | A | A | C |
| AC111 | A | A | C |
| AC112 | A | A | C |
| AC113 | B | A | D |
| AC114 | A | B | D |
| AC115 | A | A | D |
| AC116 | C | C | C |
| AC117 | A | D | B |
| AC118 | A | D | D |
| BC1 | A | A | D |
| BC2 | A | A | D |
| BC3 | A | A | D |
| BC4 | A | A | B |
| BC5 | A | A | B |
| BC6 | A | A | D |
| BC7 | A | A | D |
| BC8 | A | A | B |
| BC9 | A | A | D |
| BC10 | A | A | B |
| BC11 | C | C | C |
| BC12 | C | C | C |
| BC13 | A | A | D |
| BC14 | A | D | D |
| CC1 | D | D | D |
| CC2 | A | A | B |
| CC3 | A | A | D |
| CC4 | A | B | B |
| CC5 | A | A | B |
| CC6 | A | A | B |
| CC7 | A | A | B |
| CC8 | A | A | D |
| CC9 | A | A | B |
| CC10 | A | A | B |
| CC11 | A | A | B |
| CC12 | D | D | B |
| CC13 | A | A | B |
| CC14 | A | D | D |
| CC15 | A | A | B |
| CC16 | A | A | B |
| CC17 | A | A | B |
| CC18 | A | A | B |
| CC19 | A | A | B |
| CC20 | A | A | D |
| CC21 | A | A | D |
| CC22 | A | A | B |
| CC23 | A | A | B |
| CC24 | A | A | D |
| CC25 | A | A | B |
| CC26 | A | D | B |
| CC27 | A | A | D |
| CC28 | A | A | D |
| CC29 | A | A | B |
| CC30 | A | A | D |
| CC31 | B | D | C |
| CC32 | A | A | B |
| CC33 | A | A | B |
| CC34 | A | A | B |
| CC35 | D | D | D |
| CC36 | A | A | D |
| CC37 | A | A | D |
| CC38 | A | A | D |
| CC39 | D | D | B |
| CC40 | D | A | D |
| CC41 | D | D | B |
| CC42 | D | D | D |
| CC43 | A | B | B |
| CC44 | A | A | B |
| CC45 | A | A | D |
| CC46 | D | A | C |
| CC47 | D | D | C |
| CC48 | D | D | C |
| CC49 | D | D | D |
| CC50 | A | A | D |
| CC51 | A | A | D |
| CC52 | A | D | D |
| CC53 | D | D | B |
| CC54 | A | A | C |
| DC1 | A | A | D |
| DC2 | D | D | C |
| DC3 | B | D | C |
| DC4 | A | D | C |
| DC5 | D | D | C |
| DC6 | D | D | C |
| DC7 | A | D | C |
| DC8 | A | D | C |
| DC9 | D | D | C |
| DC10 | D | D | C |
| DC11 | A | D | C |
| DC12 | A | A | B |
| DC13 | A | A | C |
| DC14 | D | D | C |
| DC15 | D | D | C |
| DC16 | A | A | C |
| DC17 | A | A | C |
| DC18 | A | A | C |
| DC19 | A | A | C |
| DC20 | A | D | C |
| DC21 | D | D | C |
| DC22 | D | D | C |
| DC23 | D | A | C |
| DC24 | D | D | C |
| DC25 | D | D | C |
| DC26 | D | D | C |
| DC27 | D | D | C |
| DC28 | A | A | B |
| DC29 | A | A | C |
| DC30 | A | A | C |
| DC31 | A | A | B |
| DC32 | D | D | C |
| DC33 | A | A | C |
| DC34 | A | A | B |
| DC35 | A | A | B |
| DC36 | D | D | C |
| DC37 | A | A | C |
| DC38 | A | A | C |
| DC39 | A | A | C |
| DC40 | A | A | C |
| DC41 | A | A | C |
| DC42 | A | A | C |
| DC43 | A | A | C |
| DC44 | A | A | C |
| DC45 | A | A | C |
| DC46 | A | A | C |
| DC47 | A | A | C |
| DC48 | A | A | C |
| DC49 | A | A | C |
| DC50 | A | A | C |
| DC51 | A | A | C |
| DC52 | D | D | C |
| DC53 | D | A | C |
| DC54 | D | D | C |
| DC55 | D | D | C |
| DC56 | D | D | C |
| DC57 | A | A | C |
| DC58 | D | D | C |
| DC59 | D | D | C |

TABLE 3-continued

Assays Results Part 1

| Compound Number | BAW Rating | CEW Rating | GPA Rating |
|---|---|---|---|
| DC60 | A | A | C |
| DC61 | D | D | C |
| DC62 | A | A | C |
| DC63 | A | A | C |
| DC64 | D | D | C |
| DC65 | D | A | C |
| DC66 | A | A | C |
| DC67 | A | A | C |
| DC68 | A | A | C |
| DC69 | D | D | C |
| DC70 | A | A | C |

TABLE 4

Assays Results F Compounds

| Compound Number | BAW Rating | CL Rating | GPA Rating |
|---|---|---|---|
| F1 | A | A | B |
| F2 | A | A | C |
| F3 | A | A | C |
| F4 | A | A | C |
| F5 | A | A | C |
| F6 | C | C | C |
| F7 | A | A | C |
| F8 | A | A | C |
| F8A | A | A | C |
| F9 | A | A | C |
| F10 | A | A | C |
| F11 | A | A | C |
| F12 | A | A | C |
| F13 | A | A | C |
| F14 | A | A | C |
| F15 | A | A | C |
| F15A | A | A | C |
| F16 | A | A | C |
| F16A | A | A | C |
| F17 | A | A | C |
| F18 | A | A | C |
| F19 | A | A | C |
| F20 | A | A | C |
| F20A | A | A | A |
| F20B | A | A | C |
| F20C | A | A | C |
| F21 | A | A | C |
| F22 | A | A | C |
| F23 | D | A | C |
| F23A | A | A | C |
| F24 | A | A | C |
| F25 | A | A | C |
| F26 | A | A | C |
| F27 | A | A | C |
| F28 | A | A | C |
| F29 | A | A | C |
| F30 | A | A | C |
| F31 | A | A | C |

TABLE 5

Assay Results Prophetic Compounds Subsequently Exemplified

| Compound Number | BAW Rating | CL Rating | GPA Rating |
|---|---|---|---|
| P1 | A | A | C |
| P2 | D | A | C |
| P12 | A | A | C |
| P14 | B | A | C |
| P15 | A | A | C |
| P82 | A | A | C |
| P84 | A | A | C |
| P156 | A | A | C |
| P226 | A | A | C |
| P228 | A | A | C |
| P298 | D | A | B |
| P300 | A | A | C |
| P442 | A | A | C |
| P444 | A | A | C |
| P514 | A | A | C |
| P516 | A | A | C |
| P568 | A | A | C |
| P586 | A | A | C |
| P588 | A | A | C |
| P660 | A | A | C |
| P730 | A | A | C |
| P732 | A | A | C |
| P802 | A | A | C |
| P804 | A | A | C |
| P1090 | A | A | C |
| P1092 | A | A | C |
| P1197 | A | A | C |
| P1269 | A | A | C |
| P1340 | A | A | C |
| P1411 | A | A | B |
| P1483 | A | A | C |
| P1556 | A | A | C |
| P1558 | A | A | C |
| P1559 | A | A | C |
| P1560 | A | A | C |
| P1564 | A | A | C |
| P1566 | A | A | A |
| P1589 | A | A | C |
| P1591 | A | A | C |
| P1592 | A | A | C |
| P1599 | A | A | C |
| P1601 | A | A | B |
| P1603 | A | A | C |
| P1611A | A | A | C |
| P1613A | A | A | C |
| P1616 | A | A | C |
| P1616A | A | A | C |
| P1618A | A | A | C |
| P1621 | A | A | C |
| P1623 | A | A | C |
| P1624 | A | A | A |
| P1631A | A | A | B |
| P1633A | A | A | C |
| P1636A | A | A | C |
| P1638 | A | A | C |
| P1640 | D | A | D |
| P1641 | A | A | C |
| P1691 | A | A | C |
| P1693 | A | A | C |
| P1696 | A | A | C |
| P1698 | A | A | C |
| P1776 | A | A | C |
| P1781 | A | A | C |
| P1806 | A | A | C |
| P1808 | A | A | C |
| P1862 | A | A | C |
| P1864 | A | A | C |
| P1866 | A | A | C |
| P1969* | A | A | C |
| P1970 | A | A | C |
| P1971 | A | A | C |
| P1972 | A | A | C |
| P2009 | A | A | C |
| P2010 | A | A | C |
| P2011 | A | A | C |
| P2012 | A | A | C |
| P2036 | A | A | C |
| P2038 | A | A | C |
| P2041 | A | A | C |
| P2043 | A | A | C |

TABLE 5-continued

Assay Results Prophetic Compounds Subsequently Exemplified

| Compound Number | BAW Rating | CL Rating | GPA Rating |
|---|---|---|---|
| P2056 | A | A | C |
| P2058 | A | A | C |

*Performed at 12.5 ug/cm$^2$

TABLE 6

Assay Results FA Compounds

| Compound Number | BAW Rating | CL Rating | GPA Rating |
|---|---|---|---|
| FA1 | A | A | C |
| FA2 | A | A | C |
| FA3 | A | A | C |
| FA4 | A | A | C |
| FA5 | A | A | C |
| FA6 | A | A | C |
| FA7 | A | A | C |
| FA8 | B | A | C |
| FA9 | A | A | C |
| FA10 | B | B | C |
| FA11 | B | A | D |
| FA12 | A | A | C |
| FA13 | D | A | C |
| FA14 | A | A | C |
| FA15 | A | A | C |
| FA16 | A | A | A |
| FA17 | A | A | C |
| FA18 | A | A | C |
| FA19 | A | A | C |
| FA20 | A | A | C |
| FA21 | A | A | C |
| FA22 | A | A | C |
| FA23 | A | A | C |
| FA24 | A | A | C |
| FA25 | A | A | C |
| FA26 | A | A | C |
| FA27 | A | A | C |
| FA28 | A | A | C |
| FA29 | A | A | C |
| FA30 | A | A | C |
| FA31 | A | A | C |
| FA32 | A | A | C |
| FA33 | A | A | C |
| FA34 | D | A | C |

We claim:

1. A composition comprising a molecule according to Formula One:

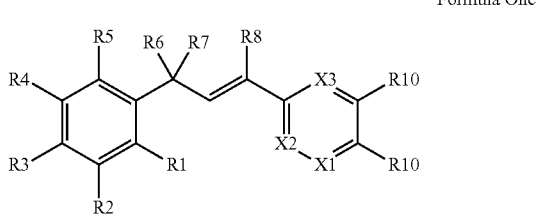

Formula One wherein:
(a) R1 is H;
(b) R2 is selected from the group consisting of H, F, Cl, Br, and (C$_1$-C$_8$)alkyl;
(c) R3 is selected from the group consisting of H, F, Cl, Br, (C$_1$-C$_8$)alkoxy, and halo(C$_1$-C$_8$)alkoxy;
(d) R4 is selected from the group consisting of F, Cl, Br, and (C$_1$-C$_8$)alkyl;
(e) R5 is H;
(f) R6 is (C$_1$-C$_8$)haloalkyl;
(g) R7 is H;
(h) R8 is H;
(i) R9 is H;
(j) R10 is selected from the group consisting of Cl, Br, I, (C$_1$-C$_8$)alkyl, halo(C$_1$-C$_8$)alkyl, S(O)$_2$(C$_1$-C$_8$)alkyl, NR14R15, and (C$_2$-C$_8$)alkenyl;
(k) R11 is C(=X5)N(R14)((C$_1$-C$_8$)alkylC(=X5)N(R14)(R15)) wherein each X5 is independently selected from the group consisting of O and S;
(l) R12 is selected from the group consisting of H and (C$_1$-C$_8$)alkyl;
(m) R13 is selected from the group consisting of H and (C$_1$-C$_8$)alkoxy;
(n) R14 is H;
(o) R15 is selected from the group consisting of H, (C$_1$-C$_8$)alkyl, substituted (C$_1$-C$_8$)alkyl, and halo(C$_1$-C$_8$)alkyl, wherein each said substituted (C$_1$-C$_8$)alkyl is substituted with one or more CN substituents;
(r) X1 is CR12;
(s) X2 is CR13; and
(t) X3 is CR9.

2. A composition according to claim 1 wherein said molecule said R11 is selected from the group consisting of C(=O)N(H)(CH(CH$_3$))C(=O)N(H)(CH$_2$CF$_3$)), C(=O)N(H)(C(CH$_3$)$_2$)C(=O)N(H)(CH$_2$CN)),
C(=O)N(H)(C(CH$_3$)$_2$)C(=O)N(H)(CH$_2$C(CH$_3$)$_3$)),
C(=O)N(H)(C(CH$_3$)$_2$)C(=O)N(H)(CH$_2$CF$_2$CH$_3$)),
C(=O)N(H)(CH(CH$_2$CH$_2$CH$_3$))C(=O)N(H)CH$_2$CF$_3$)),
C(=O)N(H)(CH(CH(CH(CH$_3$)$_2$))C(=O)N(H)(CH$_2$CF$_3$)),
C(=O)N(H)(C((CH$_3$)$_2$)C(=S)N(H)(CH$_2$CF$_3$)), and
C(=S)N(H)(C((CH$_3$)$_2$)C(=S)N(H)(CH$_2$CF$_3$)).

3. A composition according to claim 1 wherein said molecule said R11 is C(=(O or S))N(H)(((C$_1$-C$_8$)alkyl)C(=(O or S))N(H)(halo(C$_1$-C$_8$)alkyl)).

4. A composition according to claim 1 further comprising a biopesticide.

5. A composition according to claim 1 further comprising one or more of the following compounds:
(a) 3-(4-chloro-2,6-dimethylphenyl)-4-hydroxy-8-oxa-1-azaspiro[4,5]dec-3-en-2-one;
(b) 3-(4'-chloro-2,4-dimethyl[1,1'-biphenyl]-3-yl)-4-hydroxy-8-oxa-1-azaspiro[4,5]dec-3-en-2-one;
(c) 4-[[(6-chloro-3-pyridinyl)methyl]methylamino]-2(5H)-furanone;
(d) 4-[[(6-chloro-3-pyridinyl)methyl]cyclopropylamino]-2(5H)-furanone;
(e) 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
(f) 2-cyano-N-ethyl-4-fluoro-3-methoxy-benenesulfonamide;
(g) 2-cyano-N-ethyl-3-methoxy-benzenesulfonamide;
(h) 2-cyano-3-difluoromethoxy-N-ethyl-4-fluoro-benzenesulfonamide;
(i) 2-cyano-3-fluoromethoxy-N-ethyl-benzenesulfonamide;
(j) 2-cyano-6-fluoro-3-methoxy-N,N-dimethyl-benzenesulfonamide;
(k) 2-cyano-N-ethyl-6-fluoro-3-methoxy-N-methyl-benzenesulfonamide;
(l) 2-cyano-3-difluoromethoxy-N,N-dimethylbenzenesulfon-amide;

(m) 3-(difluoromethyl)-N-[2-(3,3-dimethylbutyl)phenyl]-1-methyl-1H-pyrazole-4-carboxamide;
(n) N-ethyl-2,2-dimethylpropionamide-2-(2,6-dichloro-α,α,α-trifluoro-p-tolyl) hydrazone;
(o) N-ethyl-2,2-dichloro-1-methylcyclopropane-carboxamide-2-(2,6-dichloro-α,α,α-trifluoro-p-tolyl) hydrazone nicotine;
(p) O-{(E-)-[2-(4-chloro-phenyl)-2-cyano-1-(2-trifluoromethylphenyl)-vinyl]}S-methyl thiocarbonate;
(q) (E)-N1-[(2-chloro-1,3-thiazol-5-ylmethyl)]-N2-cyano-N1-methylacetamidine;
(r) 1-(6-chloropyridin-3-ylmethyl)-7-methyl-8-nitro-1,2,3,5,6,7-hexahydro-imidazo[1,2-a]pyridin-5-ol;
(s) 4-[4-chlorophenyl-(2-butylidine-hydrazono)methyl)] phenyl mesylate; and
(t)N-Ethyl-2,2-dichloro-1-methylcyclopropanecarboxamide-2-(2,6-dichloro-alpha,alpha,alpha-trifluoro-p-tolyl)hydrazone.

6. A composition according to claim 1 further comprising:
(a) one or more compounds having acaricidal, algicidal, avicidal, bactericidal, fungicidal, herbicidal, insecticidal, molluscicidal, nematicidal, rodenticidal, or virucidal properties; or
(b) one or more compounds that are antifeedants, bird repellents, chemosterilants, herbicide safeners, insect attractants, insect repellents, mammal repellents, mating disrupters, plant activators, plant growth regulators, or synergists; or
(c) both (a) and (b).

7. A composition according to claim 1 further comprising a compound having one or more of the following modes of action: acetylcholinesterase inhibitor; sodium channel modulator, chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor, nicotinic acetylcholine receptor; Midgut membrane disrupter; oxidative phosphorylation disrupter, and ryanodine receptor (RyRs).

8. A composition according to claim 1 further comprising one or more compounds selected from the group consisting of: (3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris (2-hydroxypropyl)ammonium, amiprofos-methyl, amiprophos, amisulbrom, amiton, amiton oxalate, amitraz, amitrole, ammonium sulfamate, ammonium a-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxaprid, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarp, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdepallethrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl a-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium a-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid.

9. A composition according to claim 1 further comprising an agriculturally acceptable carrier.

10. A composition according to claim 1 wherein said molecule is in the form of a pesticidally acceptable acid addition salt.

11. A composition according to claim 1 wherein said molecule is in the form of a salt derivative.

12. A composition according to claim 1 wherein said molecule is in the form a hydrate.

13. A composition according to claim 1 wherein said molecule is in the form an ester derivative.

14. A composition according to claim 1 wherein said molecule is in the form a crystal polymorph.

15. A composition according to claim 1 wherein said molecule has a $^2H$ in place of $^1H$.

16. A composition according to claim 1 wherein said molecule has a $^{14}C$ in place of a $^{12}C$.

17. A composition according to claim 1 further comprising a seed.

18. A composition according to claim 1 further comprising a seed that has been genetically modified to express one or more specialized traits.

19. A composition according to claim 1 wherein said composition is encapsulated inside, or placed on the surface of, a capsule.

20. A composition according to claim 1 wherein said composition is encapsulated inside, or placed on the surface of, a capsule, wherein said capsule has a diameter of about 100-900 nanometers or about 10-900 microns.

21. A process of controlling pests comprising applying a composition according to claim 1, to an area to control a pest, in an amount sufficient to control such pest.

22. A process according to claim 21 wherein said pest is selected from the group consisting of beetles, earwigs, cockroaches, flies, aphids, scales, whiteflies, leafhoppers, ants, wasps, termites, moths, butterflies, lice, grasshoppers, locusts, crickets, fleas, *thrips*, bristletails, mites, ticks, nematodes, and symphylans.

23. A process according to claim 21 wherein said pest is from phyla Nematoda or Arthropoda.

24. A process according to claim 21 wherein said pest is from subphyla Chelicerata, Myripoda, or Hexapoda.

25. A process according to claim 21 wherein said pest is from class of Arachnida, Symphyla, or Insecta.

26. A process according to claim 21 wherein said pest is from order Anoplura, order Coleoptera, order Dermaptera, order Blattaria, order Diptera, order Hemiptera, order Hymenoptera, order Isoptera, order Lepidoptera, order Mallophaga, order Orthoptera, order Siphonaptera, order Thysanoptera, order Thysanura, order Acarina, or order Symphyla.

27. A process according to claim 21 wherein said pest is BAW, CL, or CEW.

28. A process according to claim 21 wherein said amount is from about 0.01 grams per hectare to about 5000 grams per hectare.

29. A process according to claim 21 wherein said amount is from about 0.1 grams per hectare to about 500 grams per hectare.

30. A process according to claim 1 wherein said amount is from about 1 gram per hectare to about 50 grams per hectare.

31. A process according to claim 21 wherein said area is an area where apples, corn, cotton, soybeans, canola, wheat, rice, sorghum, barley, oats, potatoes, oranges, alfalfa, lettuce, strawberries, tomatoes, peppers, crucifers, pears, tobacco, almonds, sugar beets, or beans, are growing, or the seeds thereof are going to be planted.

32. A process according to claim 21 further comprising applying said composition to a genetically modified plant that has been genetically modified to express one or more specialized traits.

33. A process according to claim 1 further comprising ammonium sulfate.

34. A process to control endoparasites, ectoparasites, or both, comprising orally administering or topically applying a composition according to claim 1 to a non-human animal.

35. A process to enhance plant health, yield, vigor, quality, or tolerance comprising applying a composition according to claim 1 to a plant at a time when pest activity is low.

* * * * *